US012540141B2

(12) United States Patent
Wang et al.

(10) Patent No.: US 12,540,141 B2
(45) Date of Patent: *Feb. 3, 2026

(54) SPIROPYRROLIDINE DERIVED ANTIVIRAL AGENTS

(71) Applicant: Enanta Pharmaceuticals, Inc., Watertown, MA (US)

(72) Inventors: Guoqiang Wang, Belmont, MA (US); Ruichao Shen, Belmont, MA (US); Yong He, Lexington, MA (US); Jun Ma, Wayland, MA (US); Xuechao Xing, Wilmington, MA (US); Hui Cao, Belmont, MA (US); Xuri Gao, Newtonville, MA (US); Xiaowen Peng, Sudbury, MA (US); Jiang Long, Wayland, MA (US); Wei Li, Lexington, MA (US); Jiajun Zhang, Cambridge, MA (US); Joseph D. Panarese, Newton, MA (US); Nathaniel Thomas Kenton, Watertown, MA (US); Samuel Bartlett, Brighton, MA (US); Yat Sun Or, Waltham, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 962 days.

This patent is subject to a terminal disclaimer.

(21) Appl. No.: 17/531,874

(22) Filed: Nov. 22, 2021

(65) Prior Publication Data

US 2023/0103494 A1 Apr. 6, 2023

Related U.S. Application Data

(63) Continuation-in-part of application No. 17/479,244, filed on Sep. 20, 2021, now Pat. No. 11,384,090, and a continuation-in-part of application No. 17/479,530, filed on Sep. 20, 2021, now Pat. No. 11,352,363.

(60) Provisional application No. 63/142,663, filed on Jan. 28, 2021, provisional application No. 63/117,170, filed on Nov. 23, 2020.

(51) Int. Cl.

| | |
|---|---|
| ***C07D 487/10*** | (2006.01) |
| ***A61P 31/14*** | (2006.01) |
| ***C07D 471/20*** | (2006.01) |
| ***C07D 519/00*** | (2006.01) |

(52) U.S. Cl.

CPC ............ *C07D 487/10* (2013.01); *A61P 31/14* (2018.01); *C07D 471/20* (2013.01); *C07D 519/00* (2013.01)

(58) Field of Classification Search

CPC ... C07D 487/10; C07D 471/20; C07D 519/00

See application file for complete search history.

(56) References Cited

U.S. PATENT DOCUMENTS

| | | | |
|---|---|---|---|
| 8,222,288 | B2 | 7/2012 | Wang et al. |
| 8,222,425 | B2 | 7/2012 | Britt et al. |
| 8,372,802 | B2 | 2/2013 | Gai et al. |
| 8,546,416 | B2 | 10/2013 | Ambarkhane et al. |
| 9,290,757 | B2 | 3/2016 | Madison |
| 9,309,284 | B2 | 4/2016 | Chang et al. |
| 9,328,147 | B2 | 5/2016 | Wu et al. |
| 9,347,044 | B2 | 5/2016 | Brown et al. |
| 9,428,739 | B2 | 8/2016 | Colt et al. |
| 9,447,382 | B2 | 9/2016 | Mack |
| 9,474,759 | B2 | 10/2016 | Chang et al. |
| 9,512,443 | B2 | 12/2016 | Richmond et al. |
| 9,587,235 | B2 | 3/2017 | Buechler et al. |
| 9,591,858 | B2 | 3/2017 | Valles et al. |
| 9,688,978 | B2 | 6/2017 | Buechler et al. |
| 9,772,328 | B2 | 9/2017 | Stein et al. |
| 9,791,436 | B2 | 10/2017 | Alexandrov et al. |

(Continued)

FOREIGN PATENT DOCUMENTS

| | | |
|---|---|---|
| CN | 114057624 A | 2/2022 |
| CN | 115894504 A | 4/2023 |

(Continued)

OTHER PUBLICATIONS

U.S. Appl. No. 17/379,409, filed Jul. 19, 2021.

(Continued)

*Primary Examiner* — Rebecca L Anderson

(74) *Attorney, Agent, or Firm* — Edgar W. Harlan; Carolyn S. Elmore; Elmore Patent Law Group, P.C.

(57) ABSTRACT

The present invention discloses compounds of Formula (Ia), and pharmaceutically acceptable salts, thereof:

(Ia)

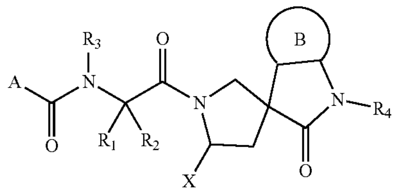

which inhibit coronavirus replication activity. The invention further relates to pharmaceutical compositions comprising a compound of Formula (Ia) or a pharmaceutically acceptable salt thereof, and methods of treating or preventing a coronavirus infection in a subject in need thereof, comprising administering to the subject a therapeutically effective amount of a compound of Formula (Ia) or a pharmaceutically acceptable salt thereof.

13 Claims, No Drawings

(56) References Cited

U.S. PATENT DOCUMENTS

| | | | |
|---|---|---|---|
| 9,828,342 B2 | 11/2017 | Home et al. | |
| 9,975,885 B2 | 5/2018 | St John et al. | |
| 10,017,463 B2 | 7/2018 | Hedstrom et al. | |
| 10,023,879 B2 | 7/2018 | Flynn et al. | |
| 10,093,915 B2 | 10/2018 | Wu et al. | |
| 10,130,701 B2 | 11/2018 | Bickerton et al. | |
| 10,196,444 B2 | 2/2019 | Jarjour et al. | |
| 10,221,396 B2 | 3/2019 | Brown et al. | |
| 10,260,048 B2 | 4/2019 | Mack | |
| 10,383,929 B2 | 8/2019 | Morgan et al. | |
| 10,428,142 B2 | 10/2019 | Jarjour et al. | |
| 10,457,731 B2 | 10/2019 | Jarjour et al. | |
| 10,472,618 B2 | 11/2019 | Wu et al. | |
| 10,479,975 B2 | 11/2019 | Friedman | |
| 10,590,084 B2 | 3/2020 | Buckman et al. | |
| 10,624,960 B2 | 4/2020 | Morgan et al. | |
| 10,639,358 B2 | 5/2020 | Morgan et al. | |
| 10,639,359 B2 | 5/2020 | Morgan et al. | |
| 10,646,558 B2 | 5/2020 | Morgan et al. | |
| 10,711,260 B2 | 7/2020 | Wu et al. | |
| 10,774,343 B2 | 9/2020 | Morgan et al. | |
| 10,784,994 B2 | 9/2020 | Yi et al. | |
| 10,793,843 B2 | 10/2020 | Jarjour et al. | |
| 10,927,367 B2 | 2/2021 | Jarjour et al. | |
| 10,934,261 B2 | 3/2021 | Buckman et al. | |
| 10,934,575 B2 | 3/2021 | Grosveld et al. | |
| 10,954,529 B2 | 3/2021 | Flynn et al. | |
| 10,959,969 B1 | 3/2021 | Johnson | |
| 10,986,848 B2 | 4/2021 | Holz-Schietinger et al. | |
| 11,013,779 B2 | 5/2021 | Chang et al. | |
| 11,020,466 B2 | 6/2021 | Morgan et al. | |
| 11,021,513 B2 | 6/2021 | Schinazi et al. | |
| 11,033,600 B2 | 6/2021 | Chang et al. | |
| 11,045,546 B1 | 6/2021 | Kelly et al. | |
| 11,058,763 B2 | 7/2021 | Zhang et al. | |
| 11,058,779 B2 | 7/2021 | Lu et al. | |
| 11,072,787 B2 | 7/2021 | Wu et al. | |
| 11,124,497 B1 | 9/2021 | Arnold et al. | |
| 11,174,231 B1 | 11/2021 | Arnold et al. | |
| 11,207,370 B2 | 12/2021 | Schinazi et al. | |
| 11,319,325 B1 | 5/2022 | Zhang et al. | |
| 11,325,916 B1 * | 5/2022 | Shen | C07D 487/10 |
| 11,339,170 B1 * | 5/2022 | Gao | A61P 31/14 |
| 11,352,363 B1 | 6/2022 | Wang et al. | |
| 11,358,953 B2 | 6/2022 | Panarese et al. | |
| 11,384,090 B2 | 7/2022 | Wang et al. | |
| 11,858,945 B2 | 1/2024 | Panarese et al. | |
| 11,912,714 B2 * | 2/2024 | Cao | C07D 471/04 |
| 11,919,910 B2 | 3/2024 | Wang et al. | |
| 2005/0143320 A1 | 6/2005 | Yang et al. | |
| 2006/0014821 A1 | 1/2006 | He et al. | |
| 2008/0125430 A1 | 5/2008 | Wang et al. | |
| 2009/0137818 A1 | 5/2009 | Hilgenfeld et al. | |
| 2010/0272681 A1 | 10/2010 | Farmer et al. | |
| 2010/0317661 A1 | 12/2010 | Wang et al. | |
| 2013/0072500 A1 | 3/2013 | Banka et al. | |
| 2013/0072686 A1 | 3/2013 | Cadieux et al. | |
| 2014/0148494 A1 | 5/2014 | Wang et al. | |
| 2014/0243341 A1 | 8/2014 | Chang et al. | |
| 2014/0378680 A1 | 12/2014 | Wang et al. | |
| 2015/0133368 A1 | 5/2015 | Chang et al. | |
| 2015/0336928 A1 | 11/2015 | Fang et al. | |
| 2017/0044183 A1 | 2/2017 | Lim et al. | |
| 2020/0230198 A1 | 7/2020 | Chang et al. | |
| 2021/0355111 A1 | 11/2021 | Arnold et al. | |
| 2022/0033383 A1 | 2/2022 | Panarese et al. | |
| 2022/0041652 A1 | 2/2022 | Panarese et al. | |
| 2022/0048944 A1 | 2/2022 | Panarese et al. | |
| 2022/0162216 A1 | 5/2022 | Wang et al. | |
| 2022/0162231 A1 | 5/2022 | Wang et al. | |
| 2022/0380377 A1 | 12/2022 | Zhang et al. | |
| 2022/0402926 A1 | 12/2022 | Zhang et al. | |
| 2023/0103494 A1 | 4/2023 | Wang et al. | |
| 2023/0115107 A1 | 4/2023 | Gao et al. | |
| 2023/0122228 A1 | 4/2023 | Shen et al. | |
| 2023/0151019 A1 | 5/2023 | Cao et al. | |
| 2023/0159545 A1 | 5/2023 | Panarese et al. | |
| 2023/0159546 A1 | 5/2023 | Kass et al. | |
| 2023/0174531 A1 | 6/2023 | Panarese et al. | |
| 2023/0174542 A1 | 6/2023 | Panarese et al. | |
| 2023/0203048 A1 | 6/2023 | Wang et al. | |
| 2023/0295175 A1 | 9/2023 | Zhu et al. | |
| 2023/0331734 A1 | 10/2023 | Cao et al. | |
| 2024/0132512 A1 | 4/2024 | Zhu et al. | |

FOREIGN PATENT DOCUMENTS

| | | | |
|---|---|---|---|
| EP | 4159211 | A1 | 4/2023 |
| EP | 4209494 | A1 | 7/2023 |
| WO | 0059929 | A1 | 10/2000 |
| WO | 0208244 | A2 | 1/2002 |
| WO | 2004101742 | A3 | 6/2005 |
| WO | 2005113580 | A1 | 12/2005 |
| WO | 2006061714 | A2 | 6/2006 |
| WO | 2006061714 | A3 | 8/2006 |
| WO | 2007038138 | A2 | 4/2007 |
| WO | 2008144507 | A2 | 11/2008 |
| WO | 2012099454 | A1 | 7/2012 |
| WO | 2013049382 | A3 | 5/2013 |
| WO | 2013166319 | A1 | 11/2013 |
| WO | 2017222935 | A1 | 12/2017 |
| WO | 2018023054 | A1 | 2/2018 |
| WO | 2018042343 | A2 | 3/2018 |
| WO | 2020081636 | A1 | 4/2020 |
| WO | 2021205296 | A1 | 10/2021 |
| WO | 2021206876 | A1 | 10/2021 |
| WO | 2021206877 | A1 | 10/2021 |
| WO | 2021207409 | A2 | 10/2021 |
| WO | 2021226546 | A1 | 11/2021 |
| WO | 2021250648 | A1 | 12/2021 |
| WO | 2021252491 | A1 | 12/2021 |
| WO | 2021252644 | A1 | 12/2021 |
| WO | 2022013684 | A1 | 1/2022 |
| WO | 2022020242 | A1 | 1/2022 |
| WO | 2022020711 | A1 | 1/2022 |
| WO | 2022021841 | A1 | 2/2022 |
| WO | 2022070048 | A1 | 4/2022 |
| WO | 2022109363 | A1 | 5/2022 |
| WO | 2022159644 | A1 | 7/2022 |
| WO | 2022235605 | A1 | 11/2022 |
| WO | 2022251615 | A1 | 12/2022 |
| WO | 2022256434 | A1 | 12/2022 |
| WO | 2023086350 | A1 | 5/2023 |
| WO | 2024076680 | A1 | 4/2024 |

OTHER PUBLICATIONS

U.S. Appl. No. 17/479,244, filed Sep. 20, 2021.
U.S. Appl. No. 17/479,248, filed Sep. 20, 2021.
U.S. Appl. No. 17/479,455, filed Sep. 20, 2021.
U.S. Appl. No. 17/479,530, filed Sep. 20, 2021.
U.S. Appl. No. 17/479,669, filed Sep. 20, 2021.
U.S. Appl. No. 17/506,981, filed Oct. 21, 2021.
Efremov, I. et al., "Discovery and Optimization of a Novel Spiropyrrolidine Inhibitor of B-Secretase (BACE1) through Fragment-Based Drug Design", J. Med. Chem., vol. 55, Apr. 2, 2012, 9069-9088.
Halford, B., "Pfizer unveils its oral SARS-00V-2 inhibitor-The antiviral candidate is the first orally administered compound to enter clinical trials that targets the virus's main protease", Chem. & Eng. News, online at https://cen.acs.org/acs-news/acs-meeting-news/Pfizer-unveils-oral-SARS-CoV/99/i13, (a version appeared in 99(13)), Apr. 7, 2021, 2 pgs.
Halford, B., "Pfizer's novel COVID-19 antiviral heads to clinical trials-The small molecule targets coronavirus 3CL protease and is active against multiple coronaviruses in cell studies", Chem. & Eng. News, online at https://cen.acs.org/pharmaceuticals/drug-discovery/Pfizers-novel-COVID-19-antiviral/98/web/2020/09, Sep. 17, 2020, 2 pgs.
Konno, S. et al., "3CL Protease Inhibitors with an Electrophilic Arylketone Moiety as Anti-SARS-CoV-2 Agents", J. Medicinal Chemistry, https://doi.org/10.1021/acs.jmedchem.1c00665, Jul. 27, 2021, pp. 1-14.

(56) References Cited

OTHER PUBLICATIONS

Lee., C. et al., "Structural Basis of Inhibition Specificities of 3C and 3C-like Proteases by Zinc-coordinating and Peptidomimetic Compounds", J. Biological Chem., vol. 284, No. 12, Mar. 20, 2009, 7646-7655.
Xu, J. et al., "Green Oxidation of Indoles Using Halide Catalysis", Nature Communications, 10:4754, https://doi.org/10.1038/s41467-019-12768-4, Oct. 18, 2019, 1-11.
Yang, S. et al., "Synthesis, Crystal Structure, Structure-Activity Relationships, and Antiviral Activity of a Potent SARS Coronavirus 3CL Protease Inhibitor", J. Med. Chem., vol. 49, Jul. 14, 2006, 4971-4980.
Chen, L. , et al., "Design, Synthesis, Characterization, and Biological Activities of Novel Spirooxindole Analogues Containing Hydantoin, Thiohydantoin, Urea, and Thiourea Moieties", J. Agric. Food Chem., 68(39)https://doi.org/10.1021/acs.jafc.0c04488, 10618-10625, 2020.
Panarese, Joseph D et al., U.S. Appl. No. 18/372,732, filed Sep. 25, 2023.
PubChem, SID 160923150, deposited Mar. 4, 2013.
PubChem, SID 267351747, deposited Dec. 11, 2015.
PubChem, SID 332063528, Deposited Apr. 10, 2017.
PubChem, SID 326247498, deposited Jan. 25, 2017.
1-(2-oxospiro[1H-indole-3,3'-pyrrolidine]-1'-yl)-4-pyridin-2-ylbutane-1,4-dione, Pubchem CID 145894940. Create Date: Feb. 12, 2020. Date Accessed: Jun. 9, 2023, 2 pgs.
Anonymous , "Nirmatrelvir", Cortellis Database, Retrieved from the Internet: URL:https://www.cortellis.com/drugdiscovery/entity/drug/1126756/product?ent=qR5ruNw5 &updateHistoryPage=5 &orderBy=_score:desc, Nov. 8, 2022, 3 pgs.
Anonymous , "Pfizer Initiates Phase 1 Study of Novel Oral Antiviral Therapeutic Agent Against SARS-CoV-2 Science Products Stories Newsroom About", Retrieved from the Internet: URL:https://www.pfizer.com/news/press-release/press-release-detail/pfizer-initiatesphase-1-study-novel-oral-antiviral [retrieved on Nov. 11, 2022].
Bafna, K. , "Structural Similarity of SARS-CoV2 Mpro and HCV NS3/4A Proteases Suggests New Approaches for Identifying Existing Drugs Useful as COVID-19 Therapeutics", , ChemRxiv online at DOI: 10.26434/chem rxiv.12153615. v1, Apr. 21, 2020.
Baker, J. D, "A drug repurposing screen identifies hepatitis C antivirals as inhibitors of the SARS-CoV-2 main 1 protease", BioRxiv. Preprint. avail at https://doi.org/10.1101/2020.07.10.197889, Jul. 10, 2020.
Chia, C.S. Brian, "Novel Coronavirus Main Protease Di- and Tripeptide Inhibitors for Treating COVID-19", ACS Med. Chem. Lett., 13(9), , URL:https://pubs.acs.org/doi/pdf/10.1021/acsmedchemlett.2c00332, Aug. 8, 2022, 1388-1389.
Chuck, C-P , "Design, synthesis and crystallographic analysis of nitrile-based broad-spectrum peptidomimetic inhibitors for coronavirus 3C-like proteases", Euro. J. Med. Chem., 59, , https://doi.org/10.1016/j.ejmech.2012.10.053, Jan. 2013, 1-6.
Dai, W. , "Structure-based design of antiviral drug candidates targeting the SARS-CoV-2 main protease", Science, 368(6497), DOI: 10.1126/science. abb4489, Jun. 19, 2020, 1331-1334.
Kelemen, A. , "Spiro[pyrrolidine-3,3'-oxindoles] and Their Indoline Analogues as New 5-HT6 Receptor Chemotypes", Molecules, 22, , DOI: 10.3390/molecules22122221, Dec. 14, 2017, 1-25.
Mandadapu, S. , "Macrocyclic Inhibitors of 3c and 3C-Like Proteases of Picornavirus, Norovirus, and Coronavirus", Bioorg. & Med. Chem. Lett., 23, , http:Ifdx.doi.org/10.1016/j.bmcl.2013.05.021, May 16, 2013, 3709-3712.
Marti, C. , "Novel Approach to Spiro-Pyrrolidine-Oxindoles and its Application to the Synthesis of (+-)-Horsfiline and (-)-Spirotryprostatin", ETH Library, Doctoral Thesis, , https://doi.org/10.3929/ethz-a-004489068, 2003, 1-2, 23-25.
Owen, D. , "Oral inhibitors of the SARS-CoV-2 main protease for the treatment of COVID-19", 261ST Am. Chem. Soc. (ACS) Natl Meet (virtual), Apr. 16, 2021, 1 pg.
Owen, D. R, "An oral SARS-CoV-2 Mpro inhibitor clinical candidate for the treatment of COVID-19", Science, 374(6575), doi: 10.1126/science.abl4784, Dec. 24, 2021, 1586-1593.
Vandyck, K. , "Considerations for the discovery and development of 3-chymotrypsin-like cysteine protease inhibitors targeting SARS-CoV-2 infection", Current Opinion in Virology, 49, DOI: 10.1016/j.coviro.2021.04.006, Apr. 27, 2021, 36-40.
Wang, Y. , "Inhibition of Enterovirus 71 Replication by an a-Hydroxy-Nitrile Derivative NK-1.9k", Antiviral Res., 141, Jan. 5, 2017, 91-100.
Zhai, Y. , "Cyanohydrin as an Anchoring Group for Potent and Selective Inhibitors of Enterovirus 71 3C Protease", J. Med. Chem., 58, 2015, 9414-9420.
Zhang, L. , "a-Ketoamides as Broad-Spectrum Inhibitors of Coronavirus and Enterovirus Replication: Structue-Based Design, Synthesis, and Activity Assessment", J. Med. Chem., 63, , https://dx.doi.org/10.1021/acs.jmedchem.9b01828, 2020, 4562-4578.
Ziarani, G. , "Synthesis of Spiro-Fused Heterocyclic Scaffolds Through Multicomponent Reactions Involving Isatin", ARKIVOC, 2016 (i), , http://dx.doi.org/10.3998/ark.5550190.p009.385, 2016, 1, 14-16.
Pubchem, SID 367622864, May 25, 2018.
Thanigaimalai, P. et al., "Design, synthesis, and biological evaluation of novel dipeptide-type Sars-CoV 3CL protease inhibitors: Structure-activity relationship study", Euro J. Med. Chem., 65, DOI: 10.1016/J.EJMECH.2013.05.005, May 20, 2013, 436-447.
Zhou, L. et al., "An Overview of Spirooxindole as a Promising Scaffold for Novel Drug Discovery", Expert Opinion on Drug Discovery, vol. 15, Iss. 5, Feb. 2020, 603-625.
U.S. Appl. No. 18/654,530, filed May 3, 2024.
U.S. Appl. No. 18/402,901, filed Jan. 3, 2024.
U.S. Appl. No. 18/390,287, filed Dec. 20, 2023.

* cited by examiner

SPIROPYRROLIDINE DERIVED ANTIVIRAL AGENTS

RELATED APPLICATIONS

This application is a continuation-in-part of U.S. application Ser. No. 17/479,244, filed on Sep. 20, 2021 and a continuation-in-part of U.S. application Ser. No. 17/479,530, filed on Sep. 20, 2021. This application also claims the benefit of U.S. Provisional Application No. 63/142,663, filed on Jan. 28, 2021 and U.S. Provisional Application No. 63/117,170, filed on Nov. 23, 2020. The entire teachings of the above applications are incorporated herein by reference.

TECHNICAL FIELD

The invention relates to compounds and methods of inhibiting coronavirus replication activity by targeting the 3C-Like protease (sometimes referred to as "3CLpro", "Main protease", or "Mpro") with a therapeutically effective amount of a 3C-Like protease inhibitor. The invention further relates to pharmaceutical compositions containing the coronavirus 3C-Like protease inhibitor in a mammal by administering effective amounts of such coronavirus 3C-Like protease inhibitor.

BACKGROUND OF THE INVENTION

Coronaviruses are family of single-stranded, positive-strand RNA viruses with viral envelopes, classified within the Nidovirales order. The coronavirus family comprises pathogens of many animal species, including humans, horses, cattle, pigs, birds, cats and monkeys, and have been known for more than 60 years. The isolation of the prototype murine coronavirus strain JHM, for example, was reported in 1949. Coronaviruses are common viruses that generally cause mild to moderate upper-respiratory tract illnesses in humans and are named for the crown-like spikes on their envelope surface. There are four major sub-groups known as alpha, beta, gamma and delta coronaviruses, with the first coronaviruses identified in the mid-1960s. The coronaviruses known to infect humans include alpha coronaviruses 229E and NL63; and beta coronaviruses OC43, HKU1, SARS-CoV (the coronavirus that causes severe acute respiratory syndrome, or SARS), and MERS-CoV (the coronavirus that causes Middle East Respiratory Syndrome, or MERS). People are commonly infected with human coronaviruses 229E, NL63, OC43 and HKU1, and symptoms usually include mild to moderate upper-respiratory tract illnesses of short duration, such as runny nose, cough, sore throat and fever. Occasionally human coronaviruses result in lower-respiratory tract illnesses, such as pneumonia, although this is more common in people with cardiopulmonary disease or compromised immune systems, or in the elderly. Transmission of the common human coronaviruses is not fully understood. However, it is likely that human coronaviruses spread from an infected person to others through the air by coughing and sneezing, and through close personal contact, such as touching or shaking hands. These viruses may also spread by touching contaminated objects or surfaces then touching the mouth, nose, or eyes.

Coronaviruses are enveloped, positive-sense, single-stranded RNA viruses. The genomic RNA of CoVs has a 5'-cap structure and 3'-poly-A tail and contains at least 6 open reading frames (ORFs). The first ORF (ORF 1a/b) directly translates two polyproteins: pp1a and pp1ab. These polyproteins are processed by a 3C-Like protease (3CLpro), also known as the main protease (Mpro), into 16 non-structural proteins. These non-structural proteins engage in the production of subgenomic RNAs that encode four structural proteins, namely envelope, membrane, spike, and nucleocapsid proteins, among other accessory proteins. As a result, it is understood that 3C-Like protease has a critical role in the coronavirus life cycle.

3CLpro is a cysteine protease involved in most cleavage events within the precursor polyprotein. Active 3CLpro is a homodimer containing two protomers and features a Cys-His dyad located in between domains I and II. 3CLpro is conserved among coronaviruses and several common features are shared among the substrates of 3CLpro in different coronaviruses. As there is no human homolog of 3CLpro, it is an ideal antiviral target. Although compounds have been reported to inhibit 3CLpro activity, they have not been approved as coronavirus therapies. (Refer to WO 2004101742 A2, US 2005/0143320 A1, US 2006/0014821 A1, US 2009/0137818 A1, WO 2013/049382 A2, WO 2013/166319 A1, WO2018042343, WO2018023054, WO2005113580, and WO2006061714).

More effective therapies for coronavirus infections are needed due to this high unmet clinical need. This invention provides compounds which inhibit the coronavirus lifecycle and methods for preparation and use of these compounds. These compounds are useful for treating or preventing coronavirus infections and decreasing occurrence of disease complications such as organ failure or death.

SUMMARY OF THE INVENTION

The present invention relates to novel antiviral compounds, pharmaceutical compositions comprising such compounds, as well as methods to treat or prevent viral (particularly coronavirus) infection in a subject in need of such therapy with said compounds. Compounds of the present invention inhibit the protein(s) encoded by a coronavirus or interfere with the life cycle of a coronavirus and are also useful as antiviral agents. In addition, the present invention provides processes for the preparation of said compounds.

In certain embodiments, the present invention provides compounds represented by Formula (Ia), and pharmaceutically acceptable salts, esters and prodrugs thereof, (Ia)

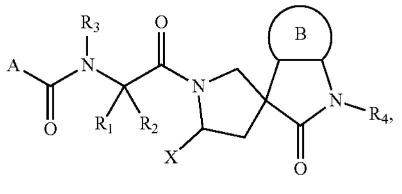

wherein:

A is selected from:
1) $—R_{11}$;
2) $—OR_{12}$; and
3) $—NR_{13}R_{14}$;

B is an optionally substituted aryl or optionally substituted heteroaryl;

X is selected from:
1) —CN;
2) $—C(O)R_{15}$;
3) $—CH(OH)SO_3R_{16}$;
4) $—C(O)NR_{13}R_{14}$; and
5) $—C(O)C(O)NR_{13}R_{14}$;

$R_1$, $R_2$, and $R_3$ are each independently selected from:
1) Hydrogen;
2) Optionally substituted —$C_1$-$C_8$ alkyl;
3) Optionally substituted —$C_2$-$C_8$ alkenyl;
4) Optionally substituted —$C_2$-$C_8$ alkynyl;
5) Optionally substituted —$C_3$-$C_8$ cycloalkyl;
6) Optionally substituted 3- to 8-membered heterocycloalkyl;
7) Optionally substituted aryl;
8) Optionally substituted arylalkyl;
9) Optionally substituted heteroaryl; and
10) Optionally substituted heteroarylalkyl;

alternatively, $R_1$ and $R_2$ are taken together with the carbon atom to which they are attached to form an optionally substituted 3- to 8-membered carbocyclic ring or an optionally substituted 3- to 8-membered heterocyclic ring.

$R_4$ is hydrogen, optionally substituted —$C_1$-$C_4$ alkyl, optionally substituted $C_2$-$C_4$-alkenyl, or optionally substituted —$C_3$-$C_6$ cycloalkyl.

$R_{11}$ and $R_{12}$ are each independently selected from:
1) Optionally substituted —$C_1$-$C_8$ alkyl;
2) Optionally substituted —$C_2$-$C_8$ alkenyl;
3) Optionally substituted —$C_2$-$C_8$ alkynyl;
4) Optionally substituted —$C_3$-$C_8$ cycloalkyl;
5) Optionally substituted 3- to 8-membered heterocycloalkyl;
6) Optionally substituted aryl;
7) Optionally substituted arylalkyl;
8) Optionally substituted heteroaryl; and
9) Optionally substituted heteroarylalkyl;

$R_{13}$ and $R_{14}$ each independently selected from:
1) Hydrogen;
2) Optionally substituted —$C_1$-$C_8$ alkyl;
3) Optionally substituted —$C_2$-$C_8$ alkenyl;
4) Optionally substituted —$C_2$-$C_8$ alkynyl;
5) Optionally substituted —$C_3$-$C_8$ cycloalkyl;
6) Optionally substituted 3- to 8-membered heterocycloalkyl;
7) Optionally substituted aryl;
8) Optionally substituted arylalkyl;
9) Optionally substituted heteroaryl; and
10) Optionally substituted heteroarylalkyl;

alternatively, $R_{13}$ and $R_{14}$ are taken together with the nitrogen atom to which they are attached to form an optionally substituted 3- to 8-membered heterocyclic ring;

$R_{15}$ is hydrogen, hydroxy, or optionally substituted —$C_1$-$C_8$ alkyl; and $R_{16}$ is hydrogen or $Na^+$.

In certain embodiments, the present invention provides compounds represented by Formula (I), and pharmaceutically acceptable salts, esters and prodrugs thereof, (I)

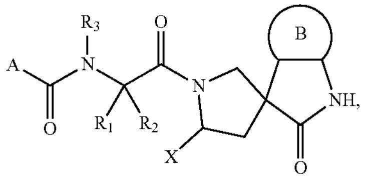

wherein:

A is selected from:
1) —$R_{11}$;
2) —$OR_{12}$; and
3) —$NR_{13}R_{14}$;

B is an optionally substituted aryl or optionally substituted heteroaryl;

X is selected from:
1) —CN;
2) —$C(O)R_{15}$;
3) —$CH(OH)SO_3R_{16}$;
4) —$C(O)NR_{13}R_{14}$; and
5) —$C(O)C(O)NR_{13}R_{14}$;

$R_1$, $R_2$, and $R_3$ are each independently selected from:
1) Hydrogen;
2) Optionally substituted —$C_1$-$C_8$ alkyl;
3) Optionally substituted —$C_2$-$C_8$ alkenyl;
4) Optionally substituted —$C_2$-$C_8$ alkynyl;
5) Optionally substituted —$C_3$-$C_8$ cycloalkyl;
6) Optionally substituted 3- to 8-membered heterocycloalkyl;
7) Optionally substituted aryl;
8) Optionally substituted arylalkyl;
9) Optionally substituted heteroaryl; and
10) Optionally substituted heteroarylalkyl;

alternatively, $R_1$ and $R_2$ are taken together with the carbon atom to which they are attached to form an optionally substituted 3- to 8-membered carbocyclic ring or an optionally substituted 3- to 8-membered heterocyclic ring.

$R_{11}$ and $R_{12}$ are each independently selected from:
1) Optionally substituted —$C_1$-$C_8$ alkyl;
2) Optionally substituted —$C_2$-$C_8$ alkenyl;
3) Optionally substituted —$C_2$-$C_8$ alkynyl;
4) Optionally substituted —$C_3$-$C_8$ cycloalkyl;
5) Optionally substituted 3- to 8-membered heterocycloalkyl;
6) Optionally substituted aryl;
7) Optionally substituted arylalkyl;
8) Optionally substituted heteroaryl; and
9) Optionally substituted heteroarylalkyl;

$R_{13}$ and $R_{14}$ each independently selected from:
1) Hydrogen;
2) Optionally substituted —$C_1$-$C_8$ alkyl;
3) Optionally substituted —$C_2$-$C_8$ alkenyl;
4) Optionally substituted —$C_2$-$C_8$ alkynyl;
5) Optionally substituted —$C_3$-$C_8$ cycloalkyl;
6) Optionally substituted 3- to 8-membered heterocycloalkyl;
7) Optionally substituted aryl;
8) Optionally substituted arylalkyl;
9) Optionally substituted heteroaryl; and
10) Optionally substituted heteroarylalkyl;

alternatively, $R_{13}$ and $R_{14}$ are taken together with the nitrogen atom to which they are attached to form an optionally substituted 3- to 8-membered heterocyclic ring;

$R_{15}$ is hydrogen, hydroxy, or optionally substituted —$C_1$-$C_8$ alkyl; and $R_{16}$ is hydrogen or $Na^+$.

DETAILED DESCRIPTION OF THE INVENTION

In one embodiment of the present invention is a compound of Formula (I) or Formula (Ia) as described above, or a pharmaceutically acceptable salt thereof.

In one embodiment of the present invention, the compound of Formula (Ia) is represented by Formula (Ia-A) or Formula (Ia-B), or a pharmaceutically acceptable salt, ester or prodrug thereof:

(Ia-A)

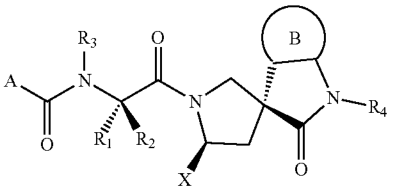

(Ia-B)

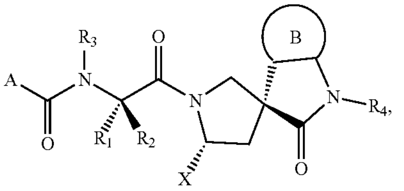

wherein A, B, X, $R_1$, $R_2$, $R_3$, and $R_4$ are as previously defined.

In a preferred embodiment, the compound of Formula (Ia) has the stereochemistry shown in Formula (Ia-A).

In one embodiment of the present invention, the compound of Formula (I) is represented by Formula (I-A) or Formula (I-B), or a pharmaceutically acceptable salt, ester or prodrug thereof:

(I-A)

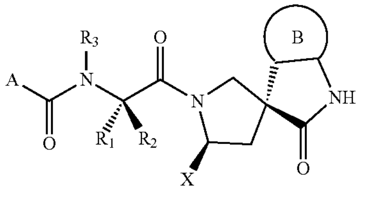

(I-B)

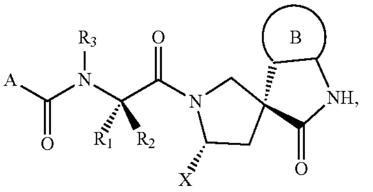

wherein A, B, X, $R_1$, $R_2$, and $R_3$ are as previously defined.

In a preferred embodiment, the compound of Formula (I) has the stereochemistry shown in Formula (I-A).

In certain embodiments of the compounds of Formula (I) or Formula (Ia), $R_1$ is hydrogen or optionally substituted —$C_1$-$C_4$ alkyl; optionally substituted —$C_3$-$C_6$ cycloalkyl; optionally substituted aryl; optionally substituted arylalkyl; optionally substituted heteroarylalkyl. In certain embodiments of the compounds of Formula (I) or Formula (Ia), $R_1$ is optionally substituted —$C_1$-$C_6$ alkyl; optionally substituted —$C_3$-$C_6$ cycloalkyl; optionally substituted $C_3$-$C_6$ cycloalkyl-$C_1$-$C_2$-alkyl-; optionally substituted aryl; optionally substituted arylalkyl; optionally substituted heteroarylalkyl.

In certain embodiments of the compounds of Formula (I) or Formula (Ia), $R_2$ is hydrogen or optionally substituted —$C_1$-$C_4$ alkyl; optionally substituted —$C_3$-$C_6$ cycloalkyl; optionally substituted aryl; optionally substituted arylalkyl; optionally substituted heteroarylalkyl.

In certain embodiments of the compounds of Formula (I) or Formula (Ia), $R_3$ is hydrogen or optionally substituted —$C_1$-$C_4$ alkyl; $R_4$ is hydrogen or or optionally substituted —$C_1$-$C_4$ alkyl. In certain embodiments of the compounds of Formula (I) or Formula (Ia), $R_3$ is hydrogen, -Me, -Et, —Pr, -i-Pr, -allyl, —$CF_3$, —$CD_3$ or cyclopropyl.

In certain embodiments of the compounds of Formula (Ia), $R_4$ is hydrogen, -Me, -Et, —Pr, -i-Pr, -allyl, —$CF_3$ or cyclopropyl.

In certain embodiments of the compounds of Formula (I) or Formula (Ia), X is —CN.

In certain embodiments of the compounds of Formula (I) or Formula (Ia), X is —C(O)H.

In certain embodiments of the compounds of Formula (I) or Formula (Ia), X is —$C(O)CH_2OH$, —$C(O)CH_2C_1$ or —$C(O)CH_2F$.

In certain embodiments of the compounds of Formula (I) or Formula (Ia), X is —$C(O)C(O)NR_{13}R_{14}$, wherein $R_{13}$ and $R_{14}$ are previously defined.

In certain embodiments of the compounds of Formula (I) or Formula (Ia), A is derived from one of the following by removal of a hydrogen atom and is optionally substituted:

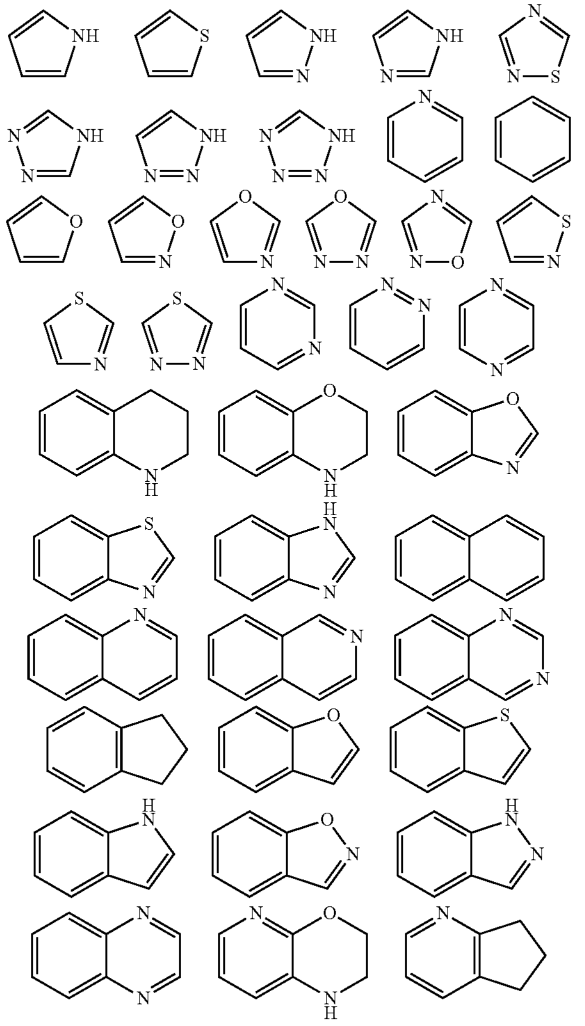

-continued

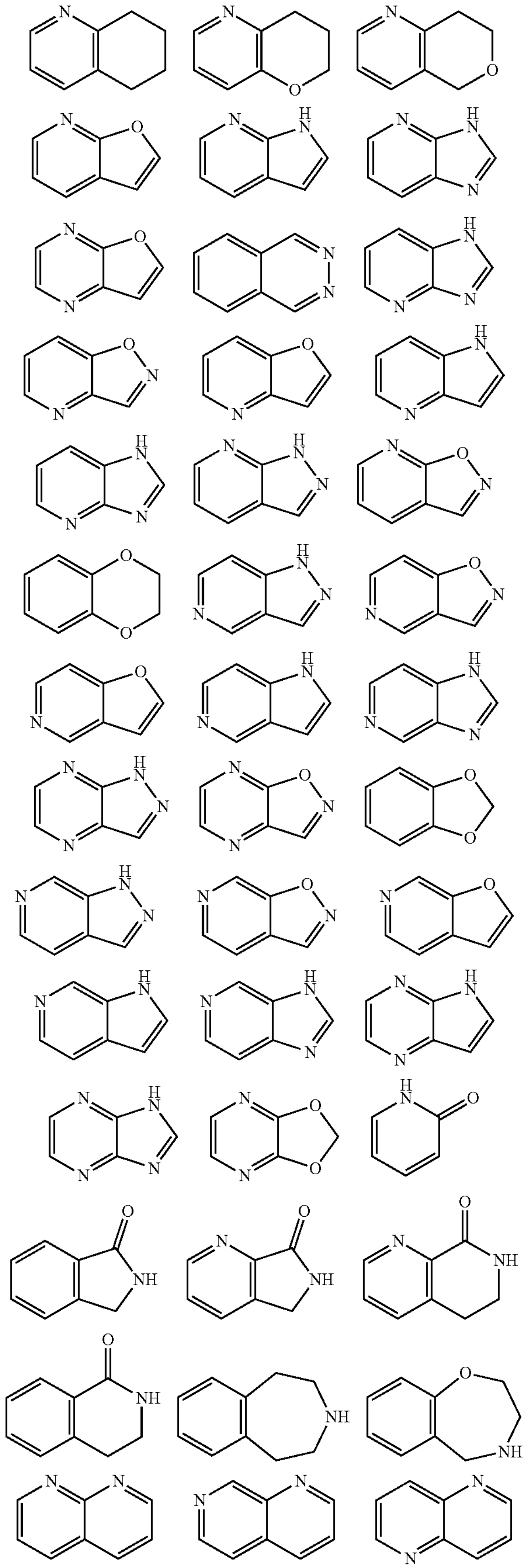

-continued

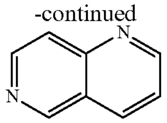

In certain embodiments of the compounds of Formula (I) or Formula (Ia), A is selected from the following groups, and A is optionally substituted:

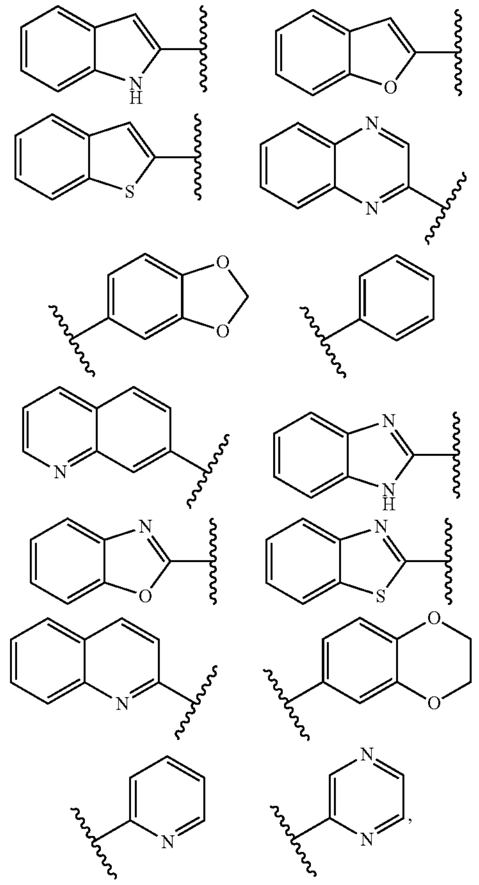

preferably the substituents are independently selected from halogen, CN, $NH_2$, optionally substituted —$C_1$-$C_3$ alkoxy, optionally substituted —$C_1$-$C_3$ alkyl, optionally substituted —$C_3$-$C_6$ cycloalkyl, optionally substituted aryl, and optionally substituted heteroaryl. Preferably the number of substituents is 0 to 3.

In certain embodiments of the compounds of Formula (I) or Formula (Ia), A is selected from the following groups, and A is optionally substituted:

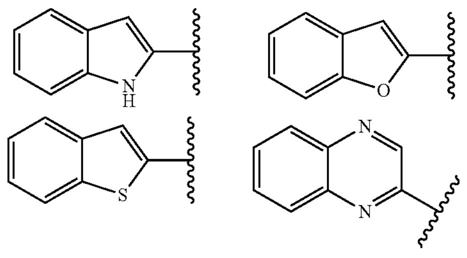

-continued

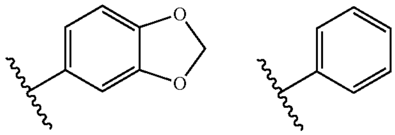

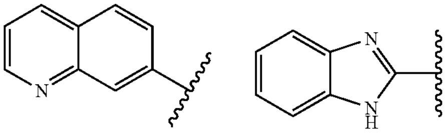

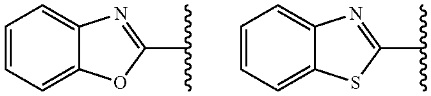

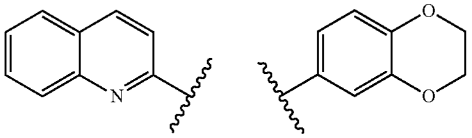

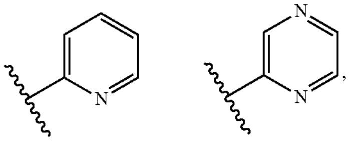
,

In certain embodiments of the compounds of Formula (I) or Formula (Ia), A is selected from the following groups, and A is optionally substituted:

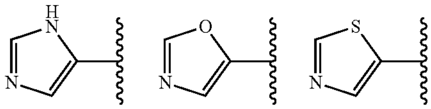

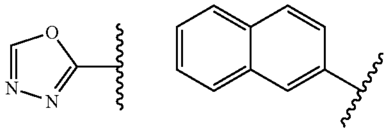

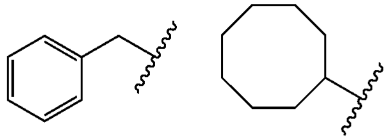

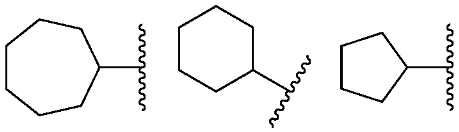

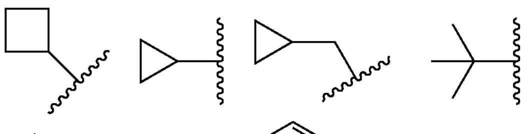

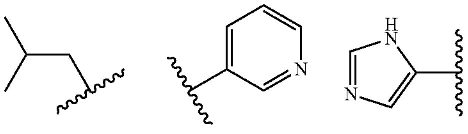

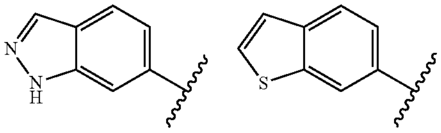

-continued

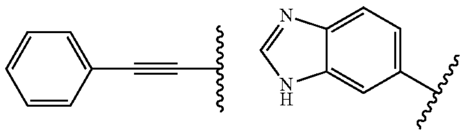

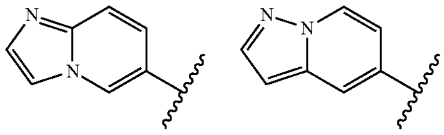

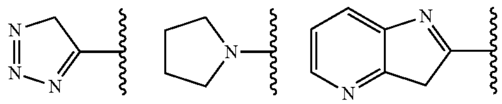

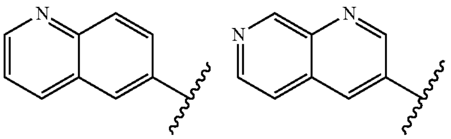

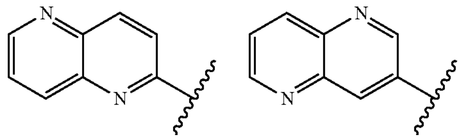

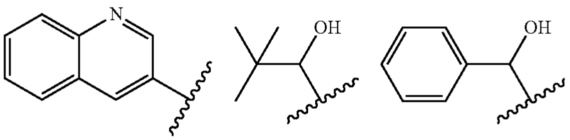

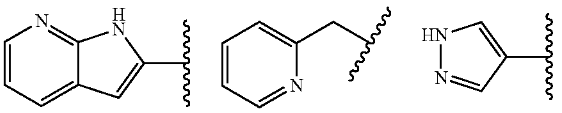

Preferably the substituents of A are independently selected from halogen, CN, $NH_2$, optionally substituted —$C_1$-$C_3$ alkoxy, optionally substituted —$C_1$-$C_3$ alkyl, optionally substituted —$C_3$-$C_6$ cycloalkyl, optionally substituted aryl, and optionally substituted heteroaryl. Preferably the number of substituents is 0 to 3.

In certain embodiments of the compounds of Formula (I) or Formula (Ia), A is selected from the following groups, and A is optionally substituted:

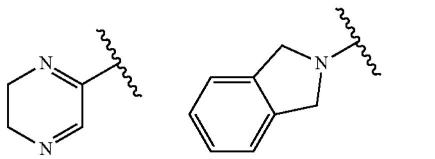

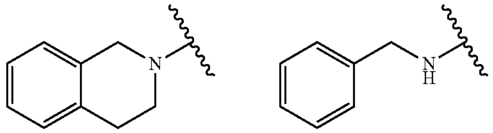

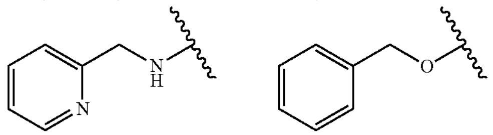

-continued

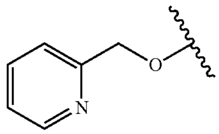
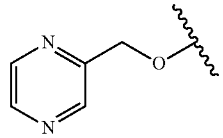
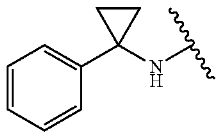
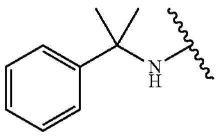
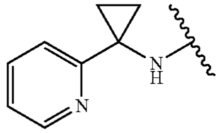
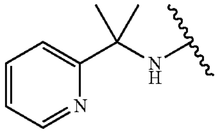
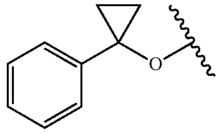
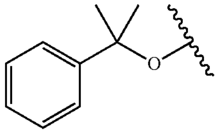
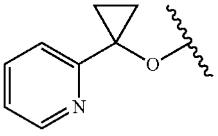
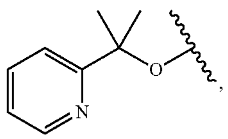

preferably the substituents are independently selected from halogen, CN, $NH_2$, optionally substituted —$C_1$-$C_3$ alkoxy, optionally substituted —$C_1$-$C_3$ alkyl, optionally substituted —$C_3$-$C_6$ cycloalkyl, optionally substituted aryl, and optionally substituted heteroaryl. Preferably the number of substituents is 0 to 3.

In certain embodiments of the compounds of Formula (I) or Formula (Ia), B is selected from the following groups, and B is optionally substituted:

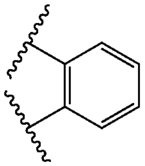
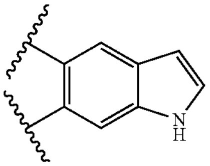
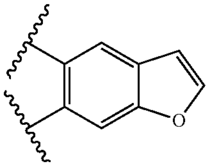
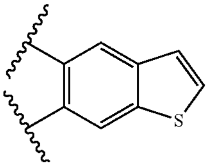
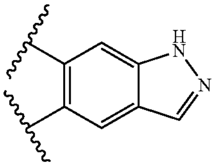
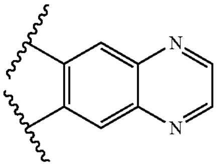
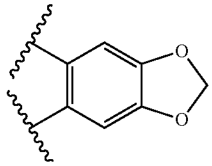
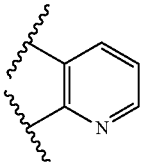

-continued

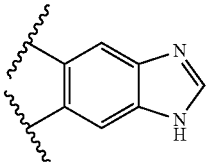
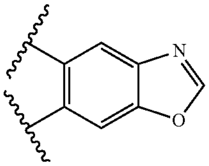
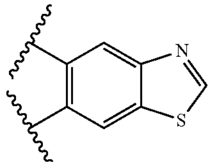
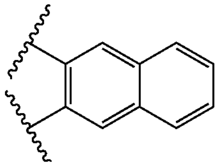
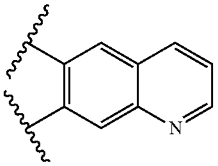
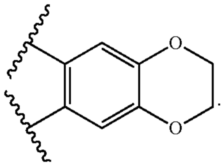

In certain embodiments, the compound of Formula (Ia), is represented by Formula (Ia-1):

(Ia-1)

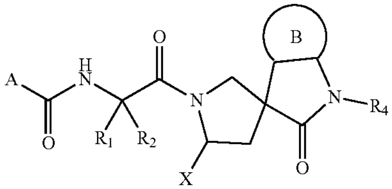

wherein A, B, $R_1$, $R_2$, $R_4$, and X are as previously defined.

In certain embodiments, the compound of Formula (Ia) is represented by Formula (Ia-2):

(Ia-2)

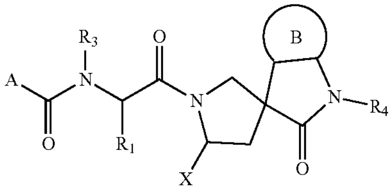

wherein A, B, $R_1$, $R_3$, $R_4$, and X are as previously defined.

In certain embodiments, the compound of Formula (Ia) is represented by Formula (Ia-3):

(Ia-3)

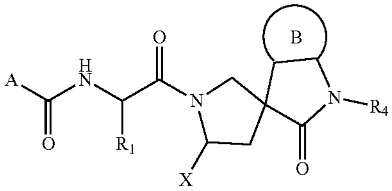

wherein A, B, $R_1$, $R_4$, and X are as previously defined.

In certain embodiments, the compound of Formula (I), is represented by Formula (I-1):

(I-1)

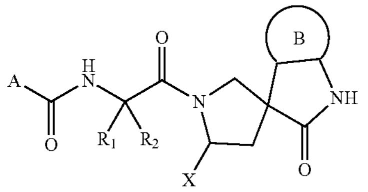

wherein A, B, $R_1$, $R_2$, and X are as previously defined.

In certain embodiments, the compound of Formula (I) is represented by Formula (I-2):

(I-2)

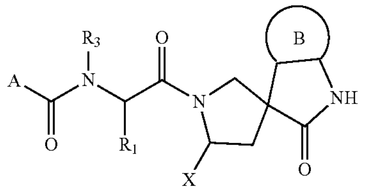

wherein A, B, $R_1$, $R_3$, and X are as previously defined.

In certain embodiments, the compound of Formula (I) is represented by Formula (I-3):

(I-3)

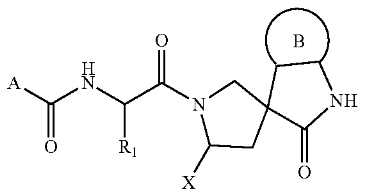

wherein A, B, $R_1$, and X are as previously defined.

In certain embodiments, the compound of Formula (Ia) is represented by Formula (IIa):

(IIa)

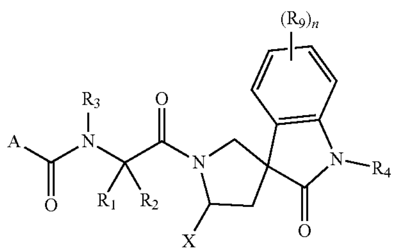

wherein A, $R_1$, $R_2$, $R_3$, $R_4$, and X are as previously defined and each $R_9$ is independently selected from:

1) Halogen;
2) —CN;
3) —$OR_{13}$;
4) —$SR_{13}$;
5) —$NR_{13}R_{14}$;
6) —$OC(O)NR_{13}R_{14}$;
7) Optionally substituted —$C_1$-$C_6$ alkyl;
8) Optionally substituted —$C_3$-$C_8$ cycloalkyl;
9) Optionally substituted 3- to 8-membered heterocycloalkyl;
10) Optionally substituted aryl; and
11) Optionally substituted heteroaryl;

and n is 0, 1, 2, 3, or 4.

In certain embodiments, the compound of Formula (I) is represented by Formula (II):

(II)

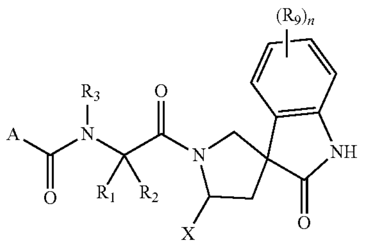

wherein A, $R_1$, $R_2$, $R_3$, and X are as previously defined and each $R_9$ is independently selected from:

1) Halogen;
2) —CN;
3) —$OR_{13}$;
4) —$SR_{13}$;
5) —$NR_{13}R_{14}$;
6) —$OC(O)NR_{13}R_{14}$;
7) Optionally substituted —$C_1$-$C_6$ alkyl;
8) Optionally substituted —$C_3$-$C_8$ cycloalkyl;
9) Optionally substituted 3- to 8-membered heterocycloalkyl;
10) Optionally substituted aryl; and
11) Optionally substituted heteroaryl;

and n is 0, 1, 2, 3, or 4.

In certain embodiments, each $R_9$ is independently selected from chloro, fluoro, methoxy and trifluoromethoxy.

In certain embodiments, the compound of Formula (Ia) is represented by Formula (IIIa-1):

(IIIa-1)

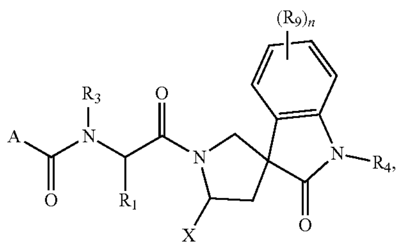

wherein A, $R_1$, $R_3$, $R_4$, $R_9$, n and X are as previously defined.

In certain embodiments, the compound of Formula (Ia) is represented by Formula (IIIa-2):

(IIIa-2)

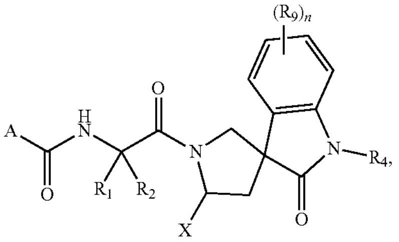

wherein A, $R_1$, $R_2$, $R_4$, $R_9$, n and X are as previously defined.

In certain embodiments, the compound of Formula (I) is represented by Formula (III):

(III)

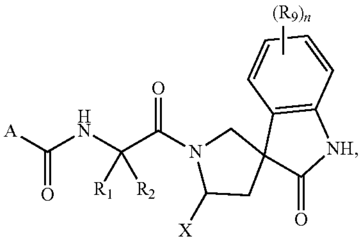

wherein A, $R_1$, $R_2$, $R_9$, n and X are as previously defined.

In certain embodiments, the compound of Formula (Ia) is represented by one of Formulae (IVa-1) to (IVa-6):

(IVa-1)

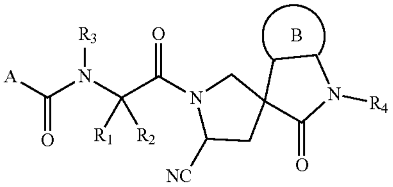

(IVa-2)

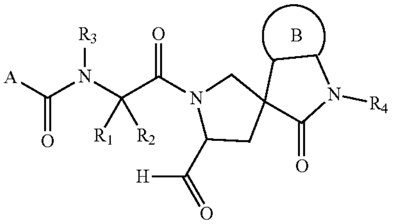

(IVa-3)

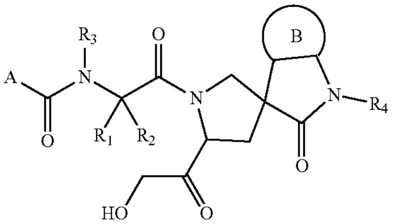

-continued (IVa-4)

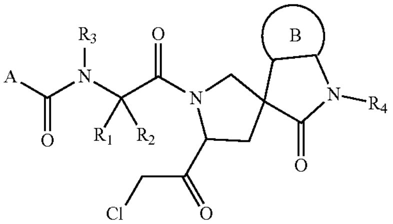

(IVa-5)

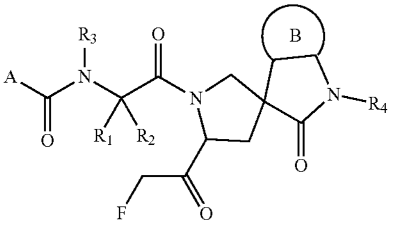

(IVa-6)

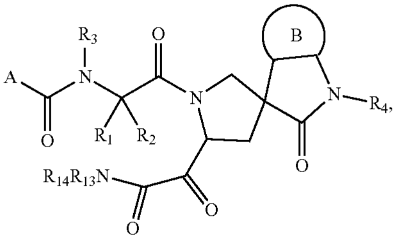

wherein A, B, $R_1$, $R_2$, $R_3$, $R_4$, $R_{13}$ and $R_{14}$ are as previously defined.

In certain embodiments, the compound of Formula (I) is represented by one of Formulae (IV-1) to (IV-6):

(IV-1)

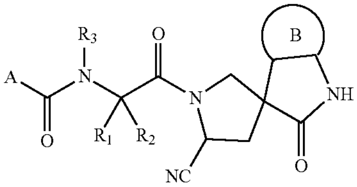

(IV-2)

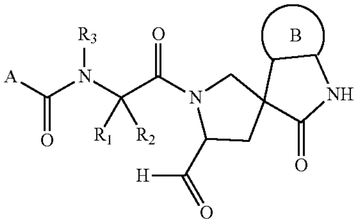

(IV-3)

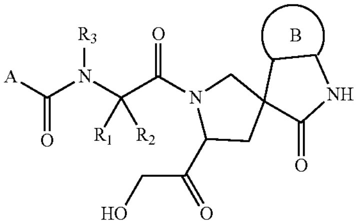

-continued
(IV-4)
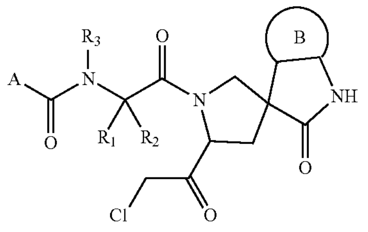
(IV-5)
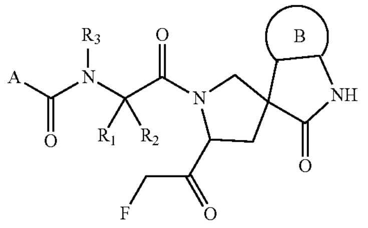
(IV-6)
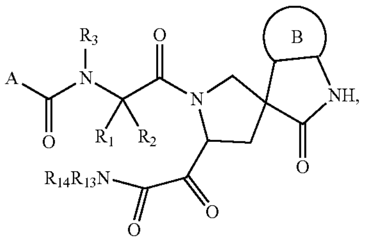
wherein A, B, $R_1$, $R_2$, $R_3$, $R_{13}$ and $R_{14}$ are as previously defined.
In certain embodiments, the compound of Formula (Ia), is represented by one of Formulae (Va-1) to (Va-6):
(Va-1)
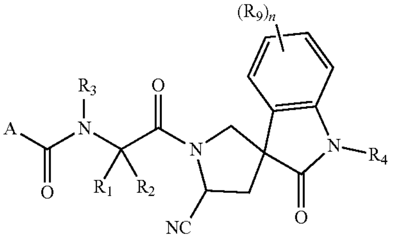
(Va-2)
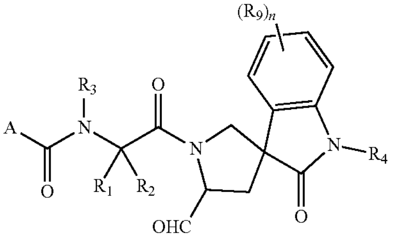
-continued
(Va-3)
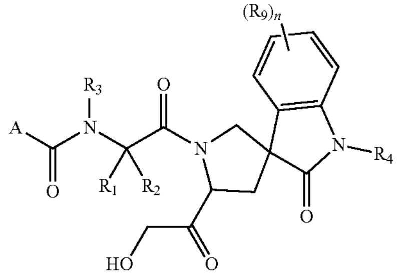
(Va-4)
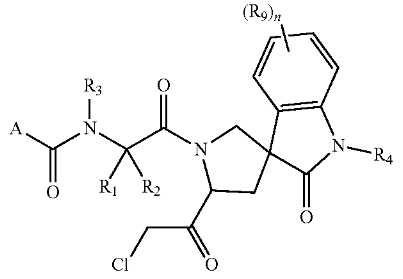
(Va-5)
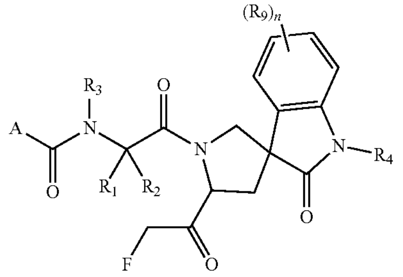
(Va-6)
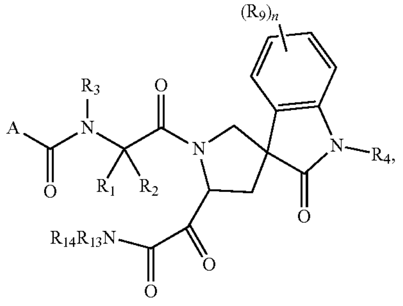
wherein A, $R_1$, $R_2$, $R_3$, $R_4$, $R_9$, $R_{13}$, $R_{14}$ and n are as previously defined.
In certain embodiments, the compound of Formula (I) is represented by one of Formulae (V-1) to (V-6):
(V-1)
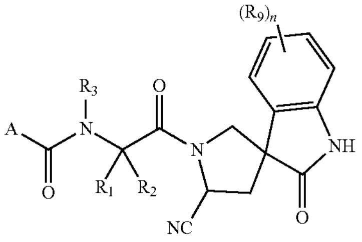

-continued
(V-2)
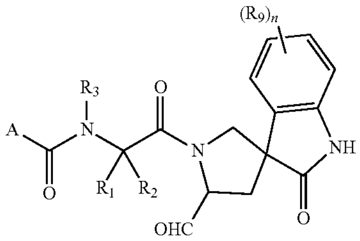
(V-3)
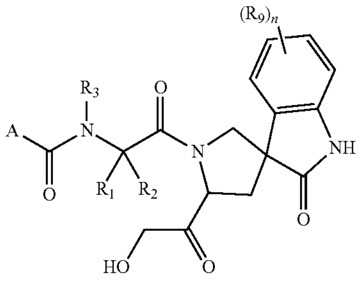
(V-4)
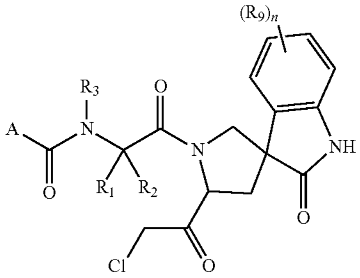
(V-5)
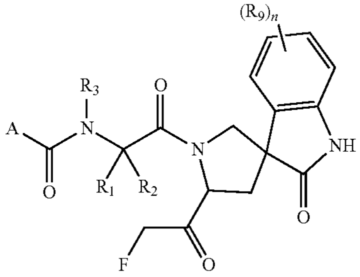
(V-6)
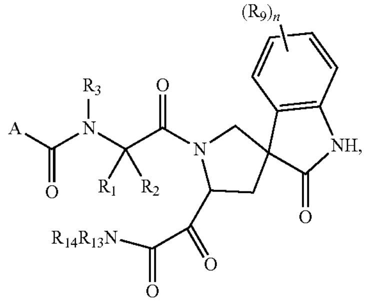
wherein A, $R_1$, $R_2$, $R_3$, $R_9$, $R_{13}$, $R_{14}$ and n are as previously defined.
In certain embodiments, the compound of Formula (Ia) is represented by one of Formulae (VIa-1) to (Via-6):
(VIa-1)
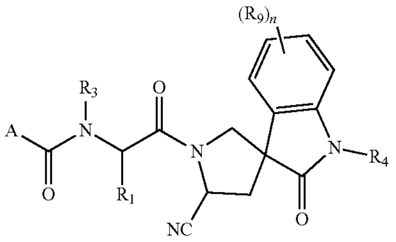
(VIa-2)
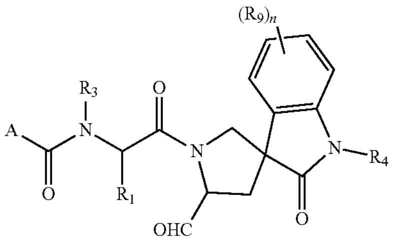
(VIa-3)
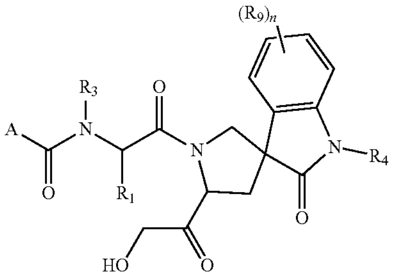
(VIa-4)
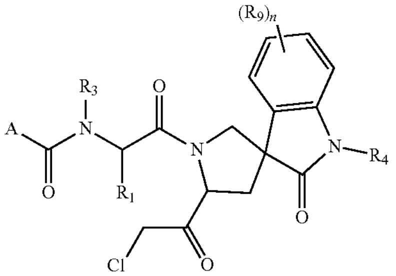
(VIa-5)
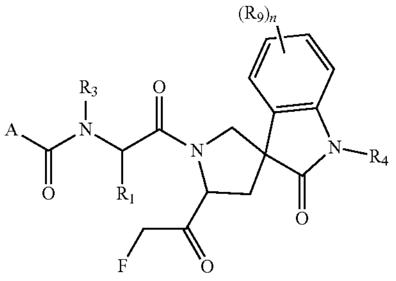

-continued
(VIa-6)
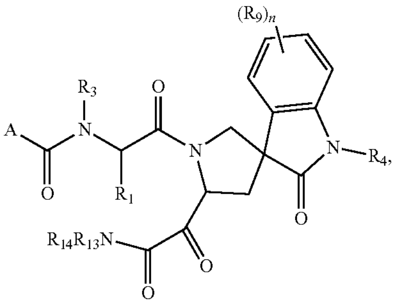
wherein A, $R_1$, $R_3$, $R_4$, $R_9$, $R_{13}$, $R_{14}$ and n are as previously defined.
In certain embodiments, the compound of Formula (I) is represented by one of Formulae (VI-1) to (VI-6):
(VI-1)
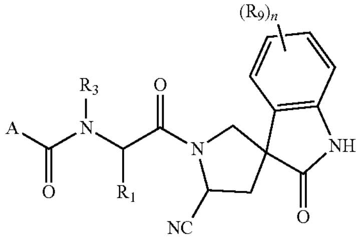
(VI-2)
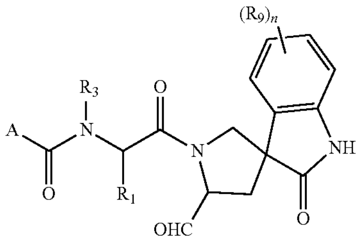
(VI-3)
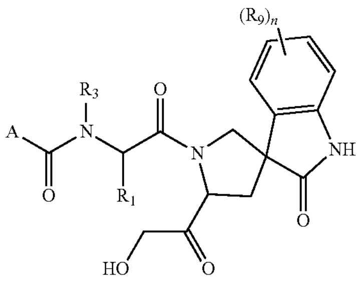
(VI-4)
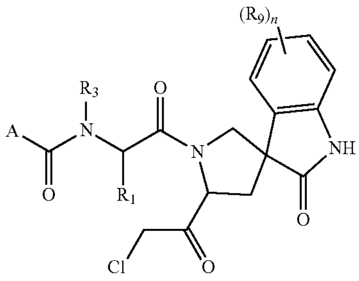
-continued
(VI-5)
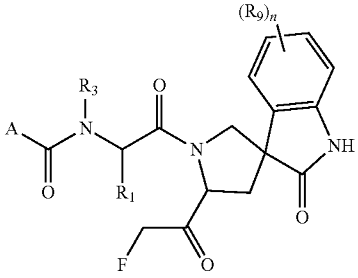
(VI-6)
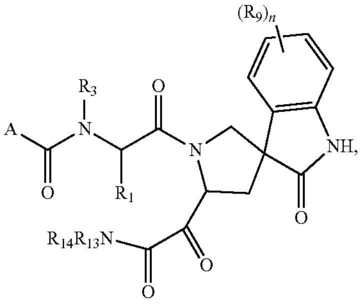
wherein A, $R_1$, $R_3$, $R_9$, $R_{13}$, $R_{14}$ and n are as previously defined.
In certain embodiments, the compound of Formula (I) is represented by one of Formulae (VII-1) to (VII-5):
(VII-1)
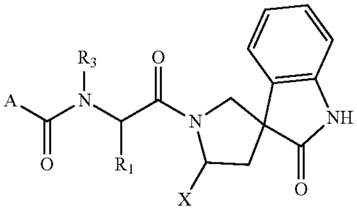
(VII-2)
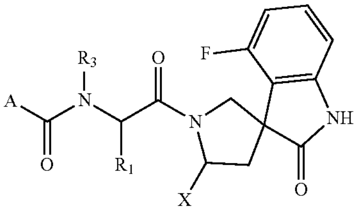
(VII-3)
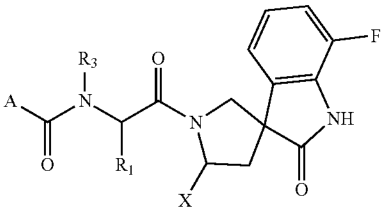

-continued
(VII-4)
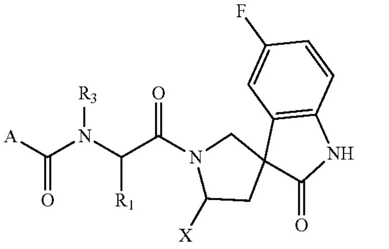
(VII-5)
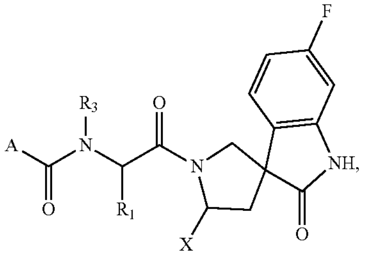
wherein A, $R_1$, $R_3$, and X are as previously defined. Preferably, A is selected from the following:
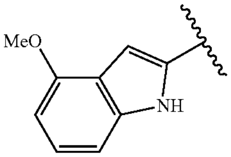
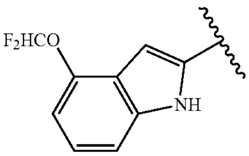
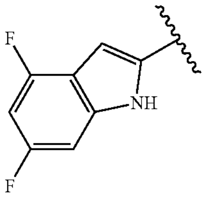
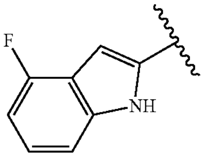
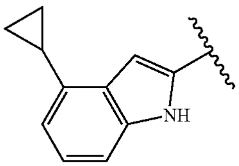
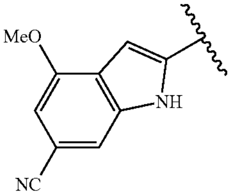
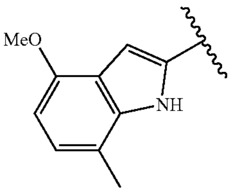
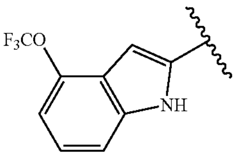
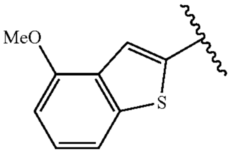
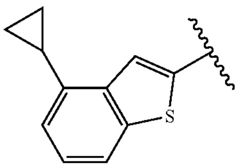
-continued
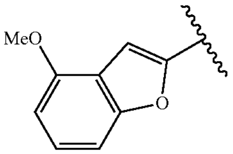
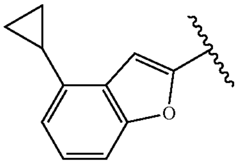
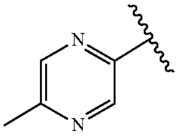
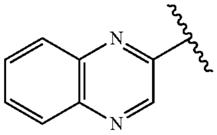
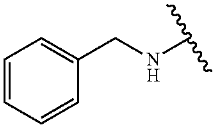
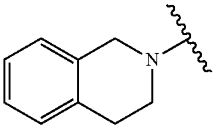
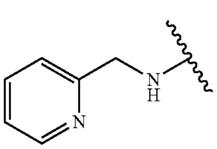
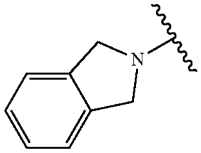
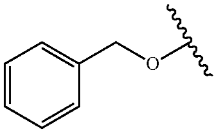
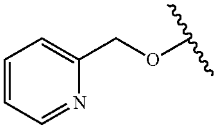
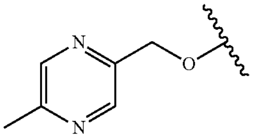
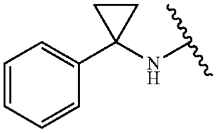
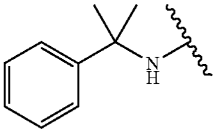
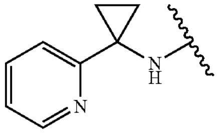
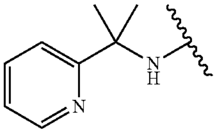
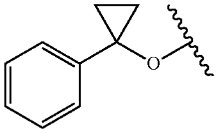
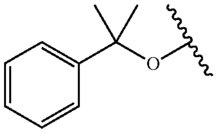
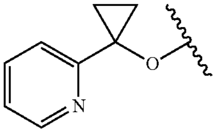
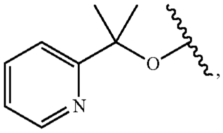,
$R_1$ is selected from the following:
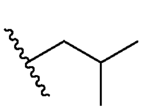
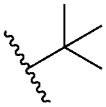
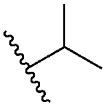
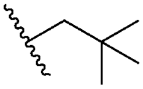
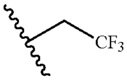
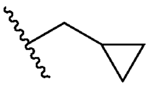

-continued
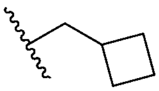
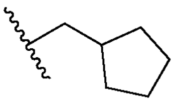
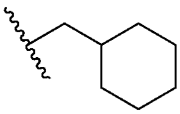
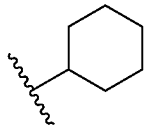
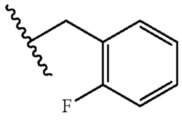
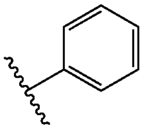
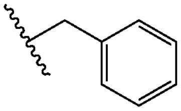
and X is selected from the following:
—CN —CHO 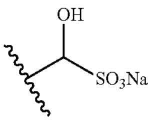
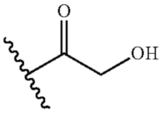
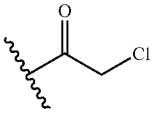
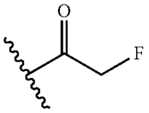
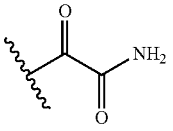
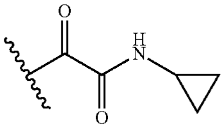
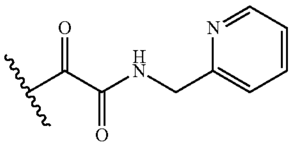
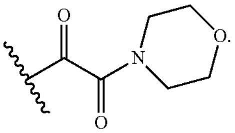
In certain embodiments, the compound of Formula (I) is represented by one of Formulae (VII-6) to (VII-9):
(VII-6)
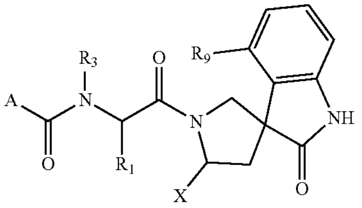
(VII-7)
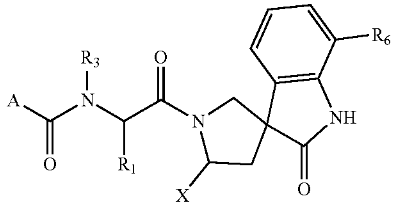
-continued
(VII-8)
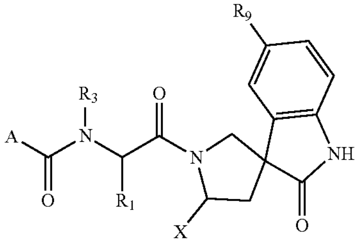
(VII-9)
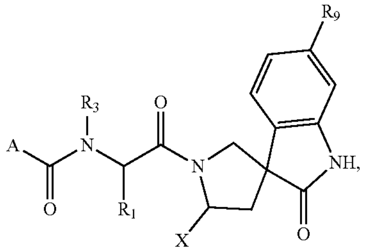
wherein A, $R_1$, $R_3$, $R_9$, and X are as previously defined.
Preferably, A is selected from the following:
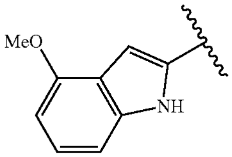
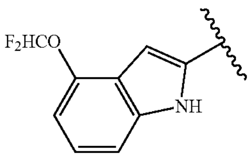
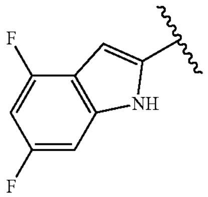
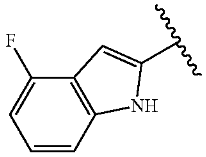
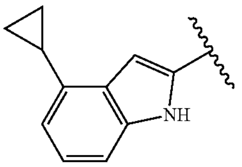
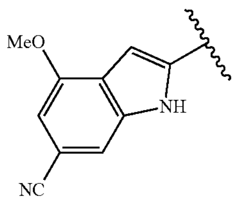
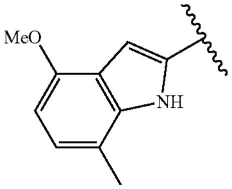
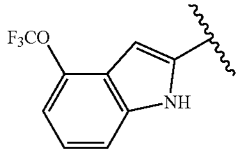
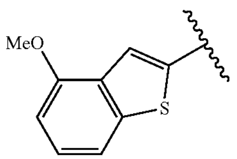
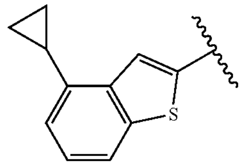

-continued
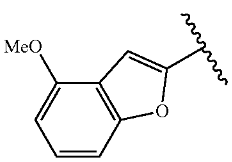
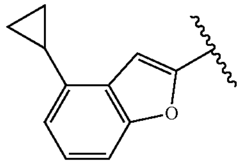
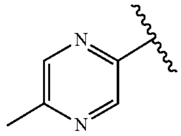
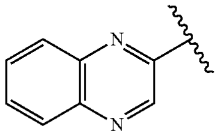
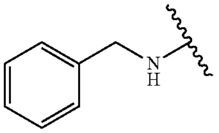
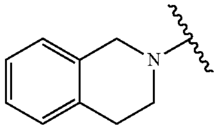
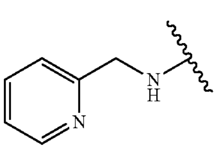
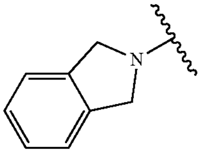
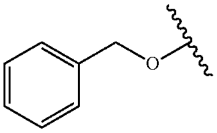
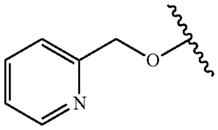
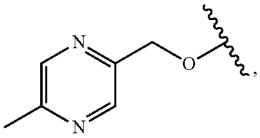
,
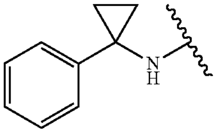
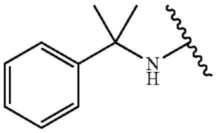
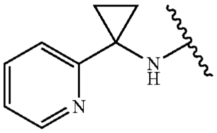
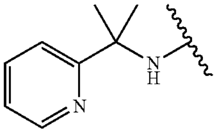
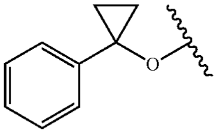
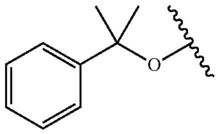
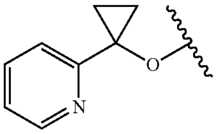
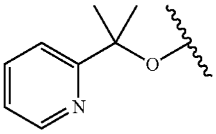
$R_1$ is selected from the following:
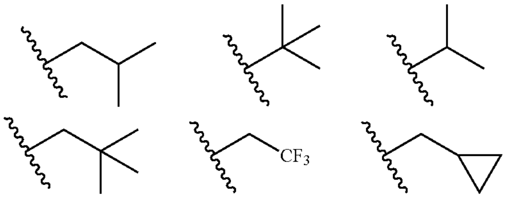
-continued
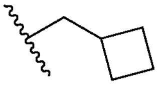
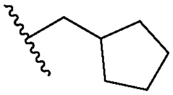
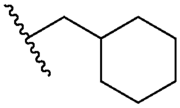
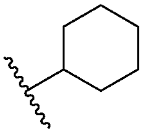
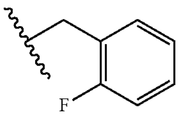
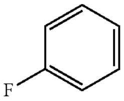
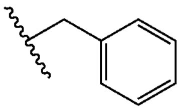
and X is selected from the following:
—CN —CHO
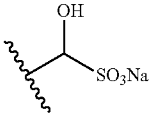
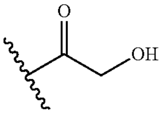
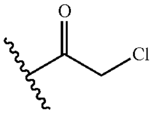
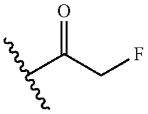
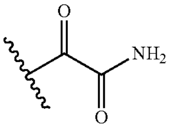
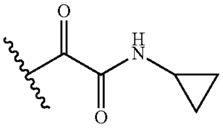
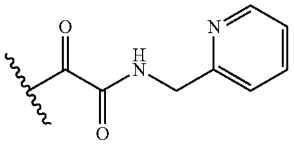
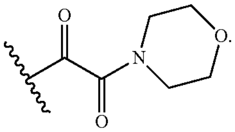
In certain embodiments, the compound of Formula (I) is represented by one of Formulae (VII-1a)~(VII-5a):
(VII-1a)
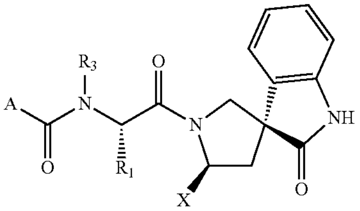
(VII-2a)
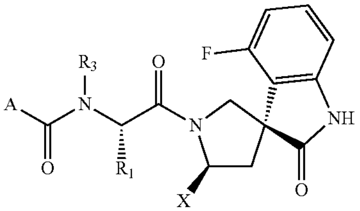

-continued
(VII-3a)
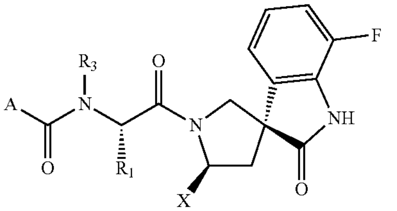
(VII-4a)
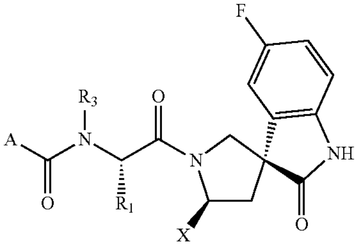
(VII-5a)
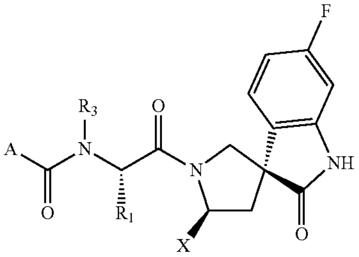
wherein A, $R_1$, $R_3$, and X are as previously defined. Preferably, A is selected from the following:
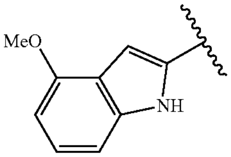
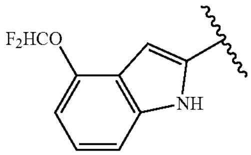
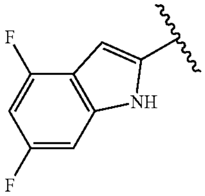
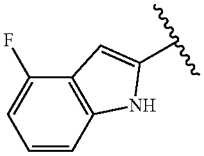
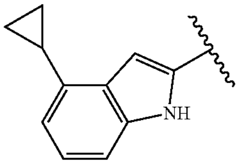
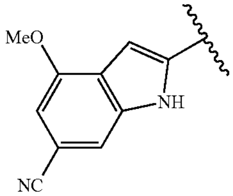
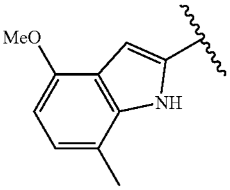
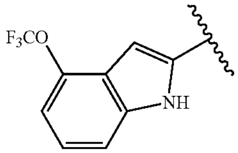
-continued
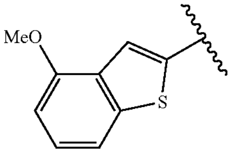
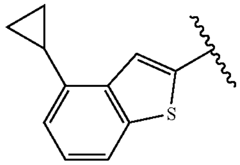
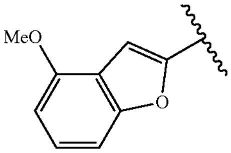
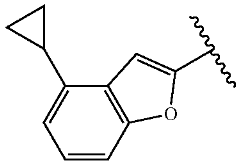
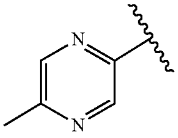
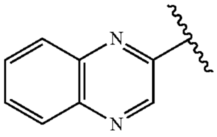
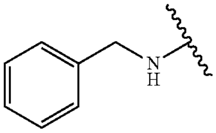
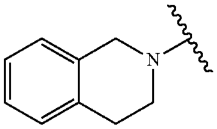
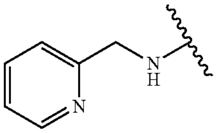
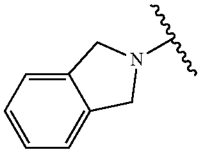
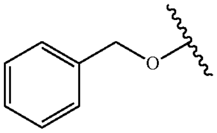
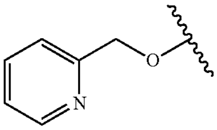
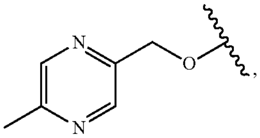,
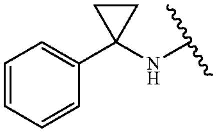
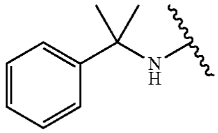
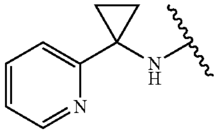
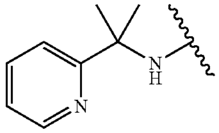
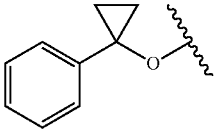
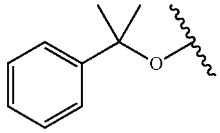
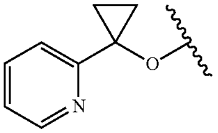
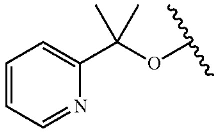

$R_1$ is selected from the following:
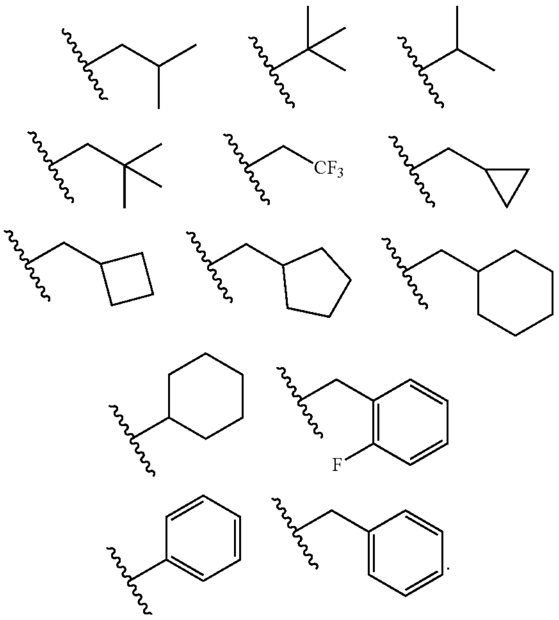
and X is selected from the following:
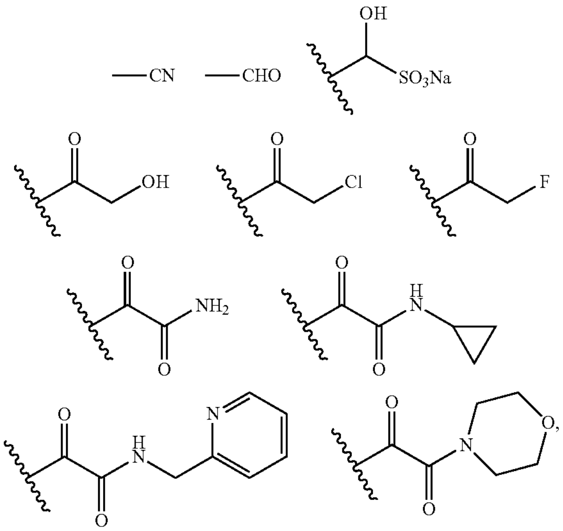
In certain embodiments, the compound of Formula (I) is represented by one of Formulae (VII-6a) (VII-9a):
(VII-6a)
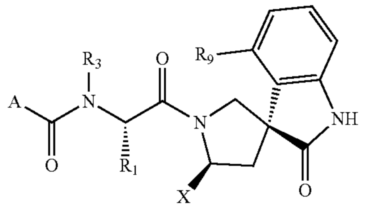
-continued
(VII-7a)
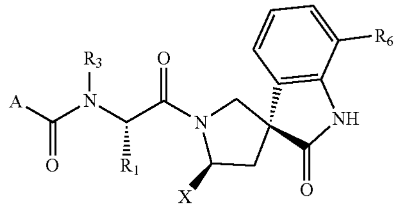
(VII-8a)
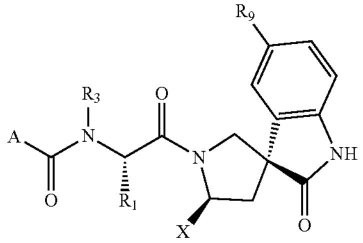
(VII-9a)
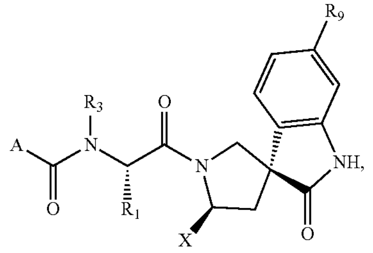
wherein A, $R_1$, $R_3$, $R_9$, and X are as previously defined.
Preferably, A is selected from the following:
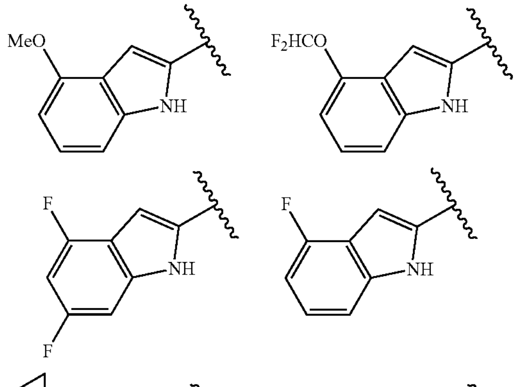
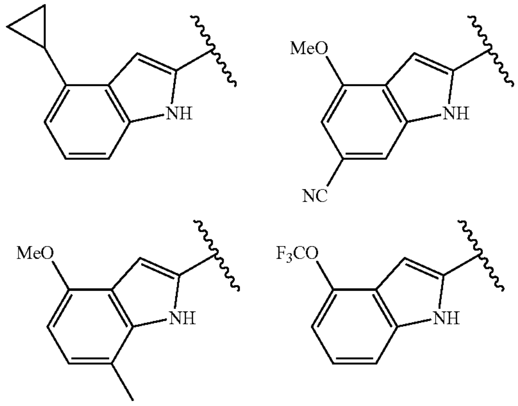

-continued
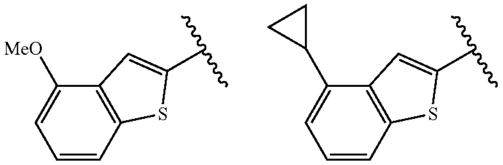
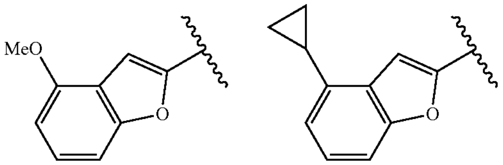
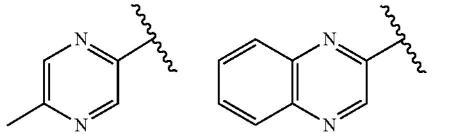
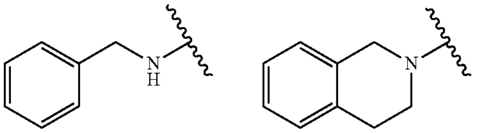
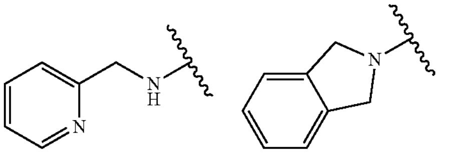
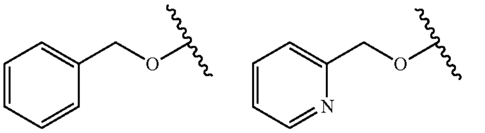
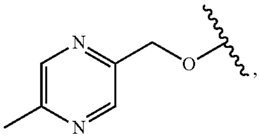,
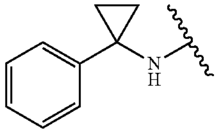
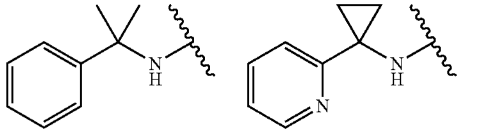
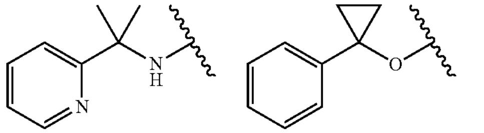
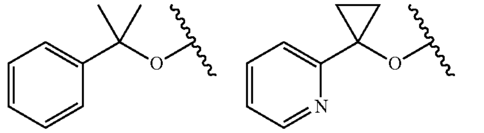
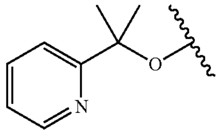
$R_1$ is selected from the following:
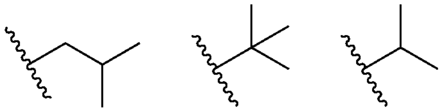
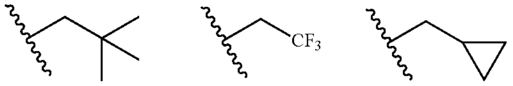
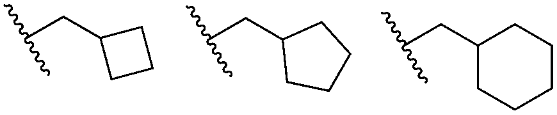
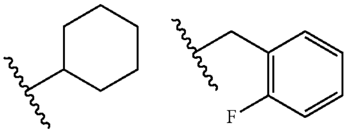
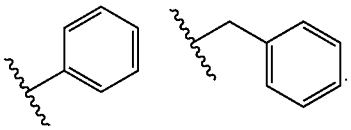.
and X is selected from the following:
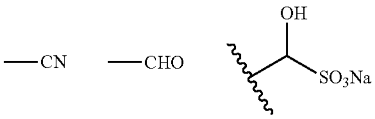
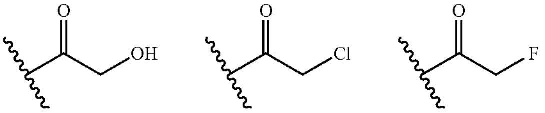
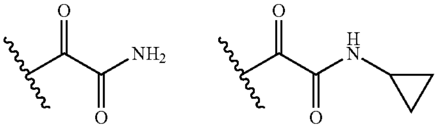
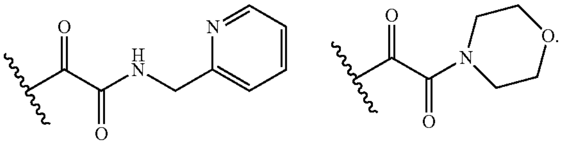.
In certain embodiments, the compound of Formula (I) is represented by one of Formulae (VII-1) to (VII-9) and Formulae (VII-1a) to (VII-9a), wherein A is selected from, the following:
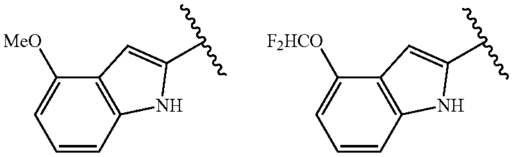

-continued
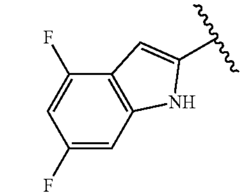
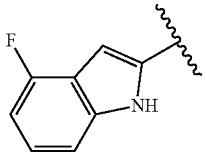
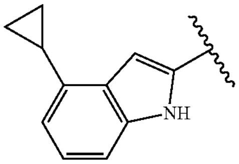
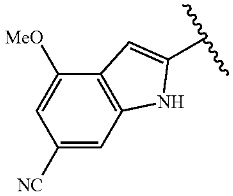
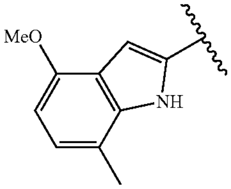
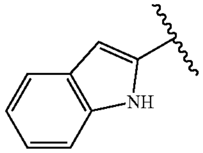
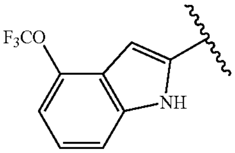
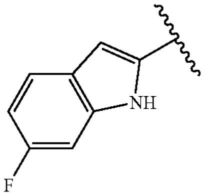
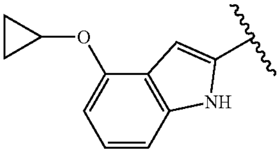
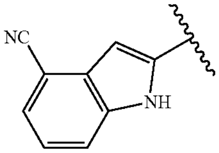
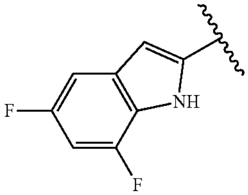
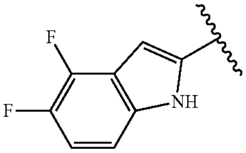
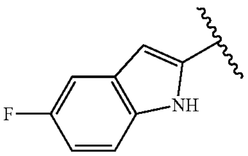
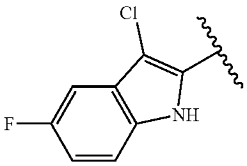
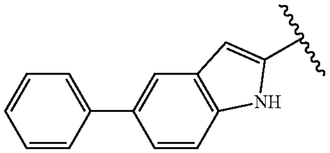
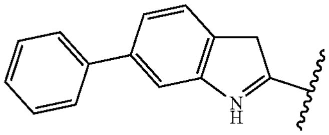
-continued
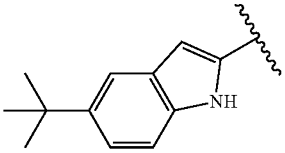
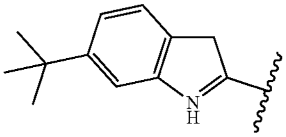
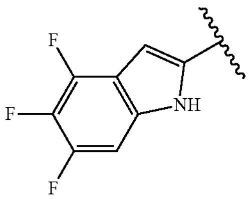
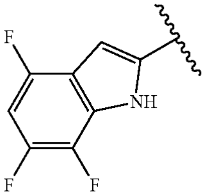
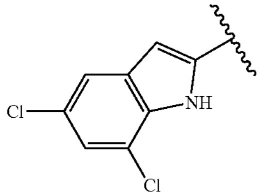
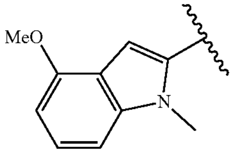
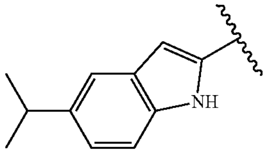
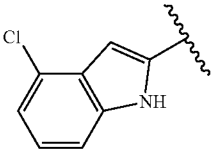
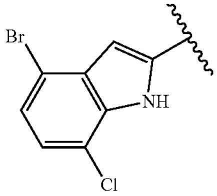
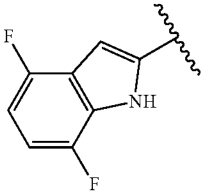
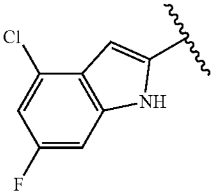
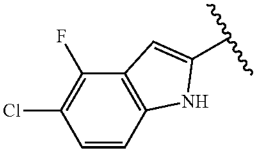
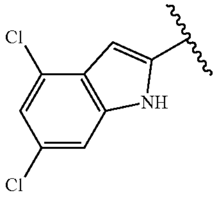
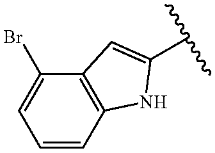
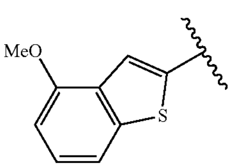
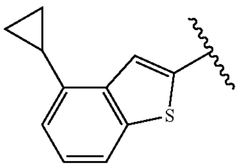
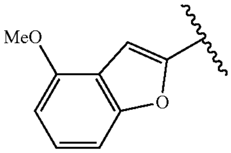
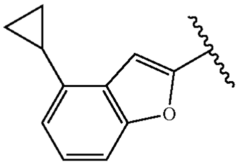

-continued
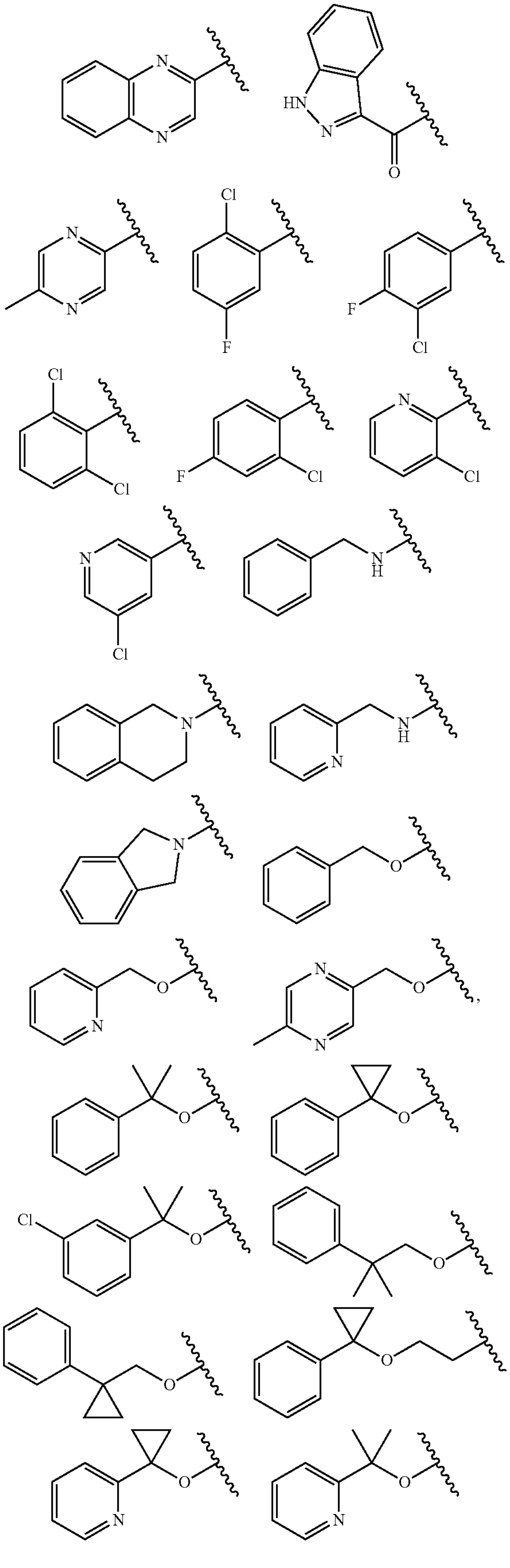
-continued
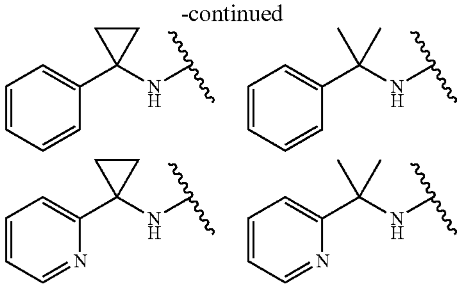
X is selected from the following:
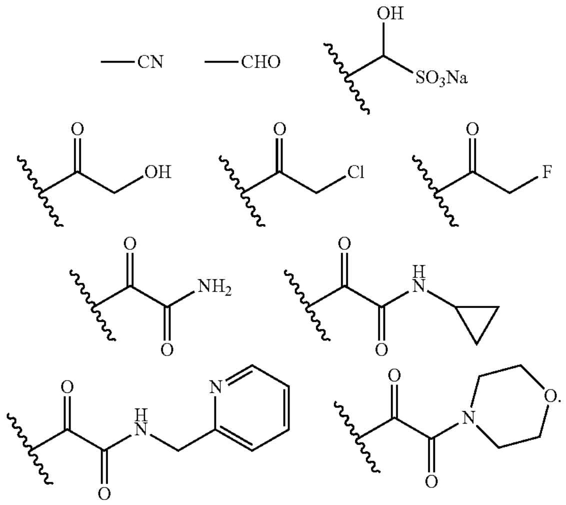
and $R_1$ is selected from the following:
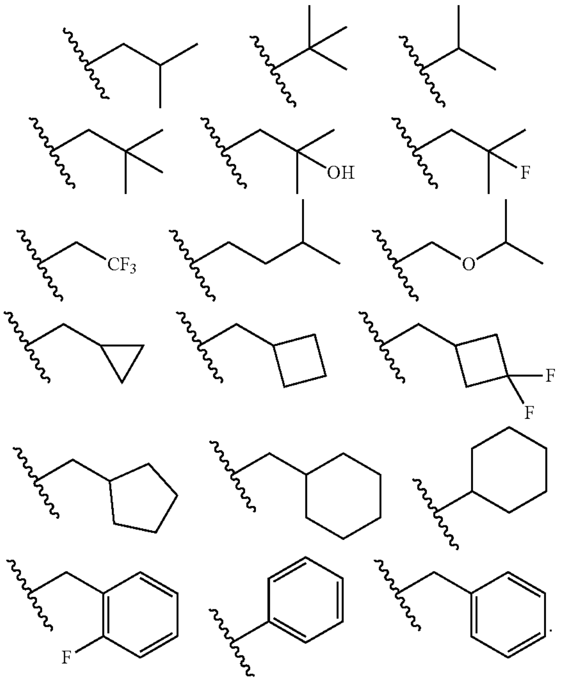

In certain embodiments, the compound of Formula (Ia) is represented by one of Formulae (VIII-1) to (VIII-5):

(VIII-1)

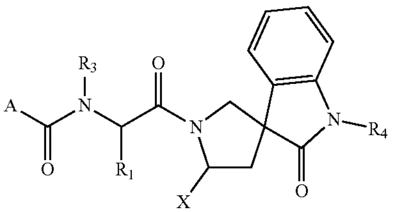

(VIII-2)

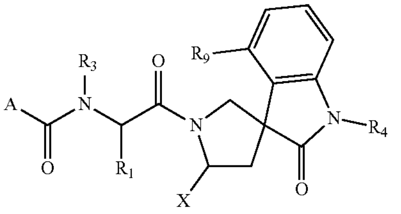

(VIII-3)

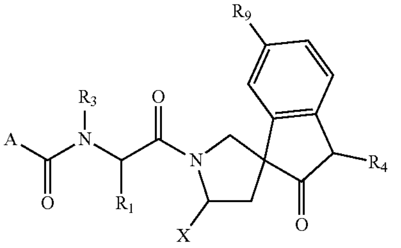

(VIII-4)

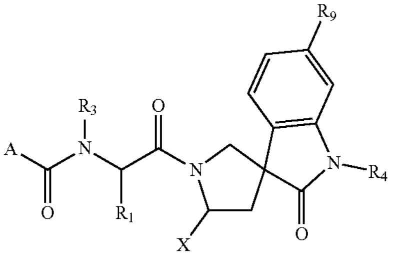

(VIII-5)

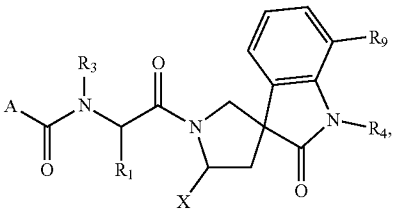

wherein A, X, $R_1$, $R_3$, $R_4$, and $R_9$ are as previously defined.

In certain embodiments, the compound of Formula (Ia) is represented by one of Formulae (VIII-1a) to (VIII-5a):

(VIII-1a)

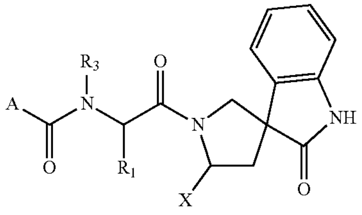

(VIII-2a)

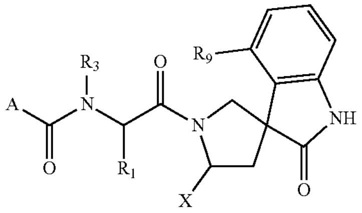

(VIII-3a)

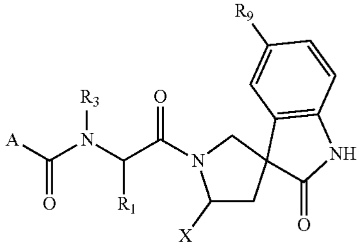

(VIII-4a)

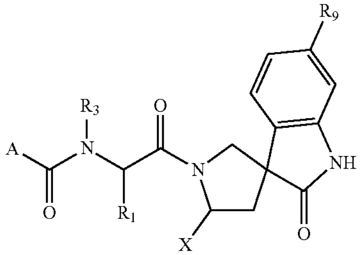

(VIII-5a)

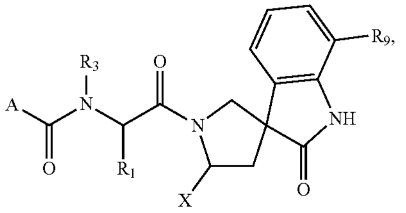

wherein A, $R_1$, $R_3$, and $R_9$ are as previously defined.

In certain embodiments, the compound of Formula (Ia) is represented by one of Formulae (IX-1) to (IX-5):

(IX-1)

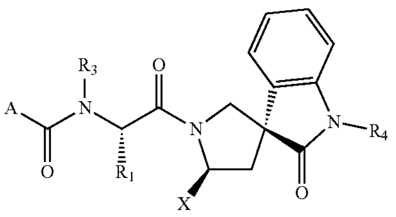

-continued (IX-2)

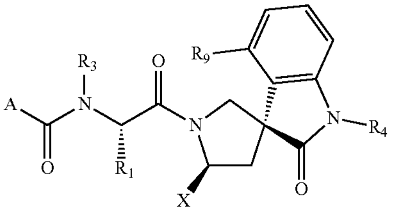

(IX-3)

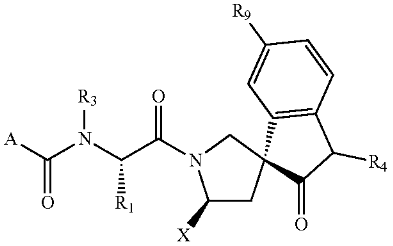

(IX-4)

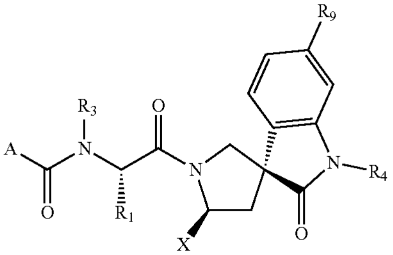

(IX-5)

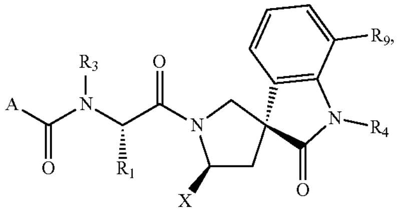

wherein A, X, $R_1$, $R_3$, $R_4$, and $R_9$ are as previously defined.

In certain embodiments, the compound of Formula (Ia) is represented by one of Formulae (IX-1a) to (IX-5a):

(IX-1a)

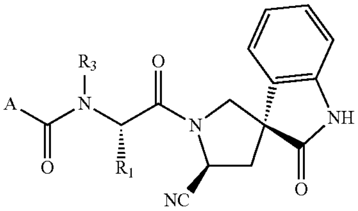

(IX-2a)

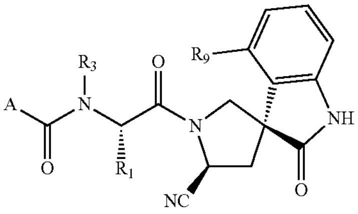

-continued (IX-3a)

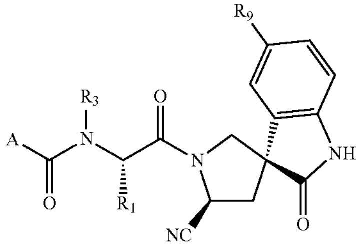

(IX-4a)

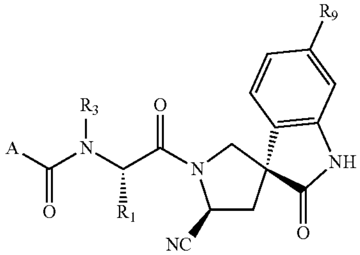

(IX-5a)

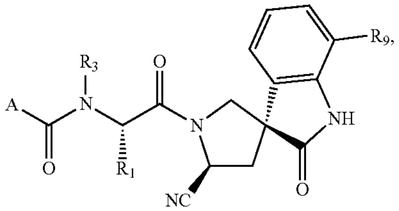

wherein A, $R_1$, $R_3$, and $R_9$ are as previously defined.

In certain embodiments, the compound of Formula (Ia) is represented by one of Formulae (VIII-1) to (VIII-5) and Formulae (IX-1) to (IX-5), wherein $R_3$ is hydrogen, -Me, -Et, —Pr, -i-Pr, -allyl, —$CF_3$, -$CD_3$, or cyclopropyl; $R_4$ is hydrogen, -Me, -Et, —Pr, -i-Pr, -allyl, —$CF_3$ or cyclopropyl; $R_9$ is halogen, —$OCH_3$, —$NH_2$, —$CH_3$, or —$CF_3$; A is selected from the following

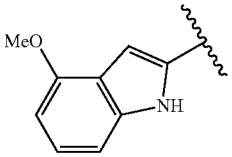
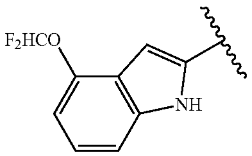
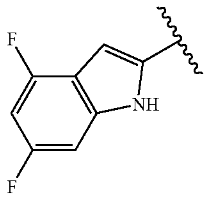
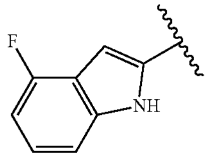
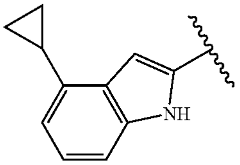
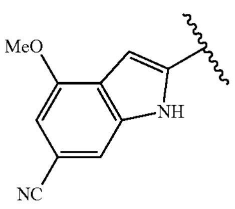

-continued
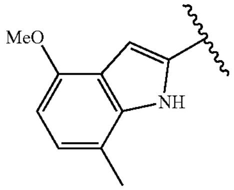
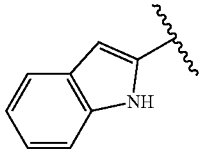
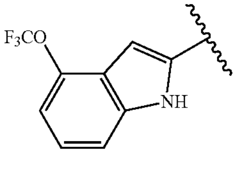
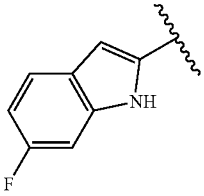
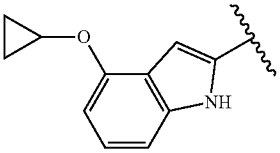
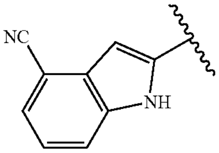
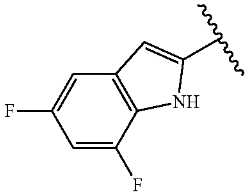
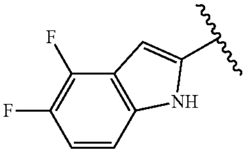
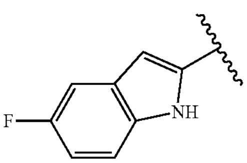
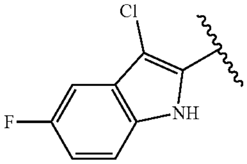
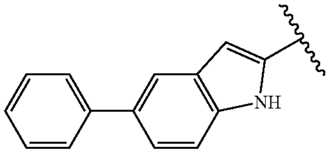
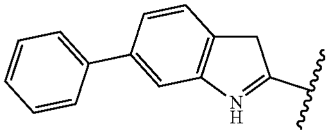
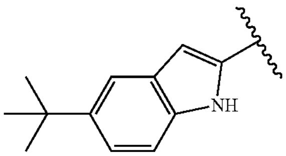
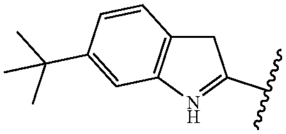
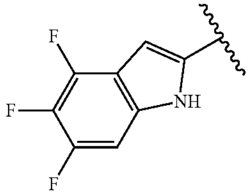
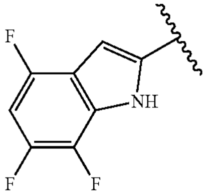
-continued
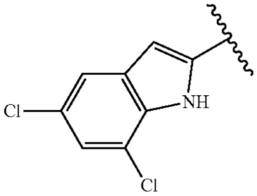
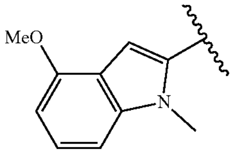
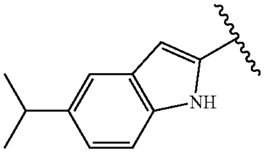
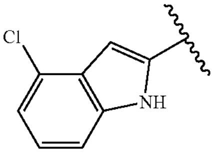
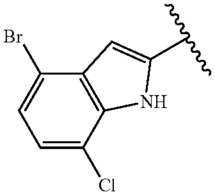
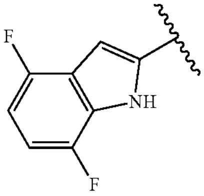
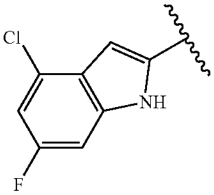
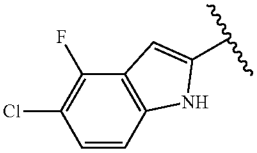
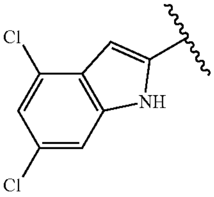
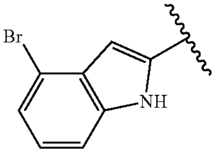
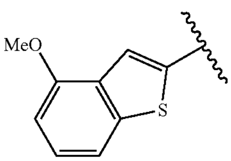
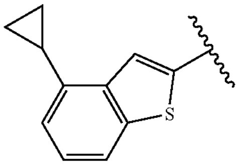
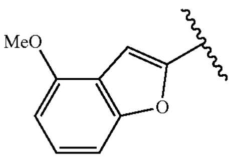
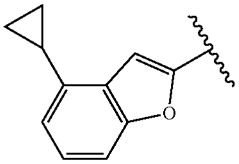
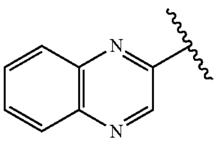
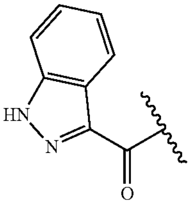
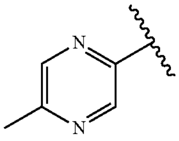
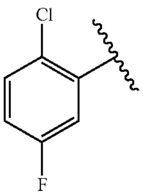
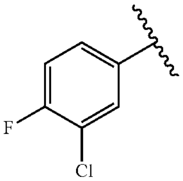

-continued
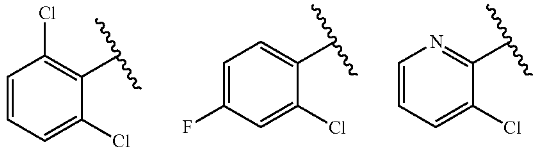
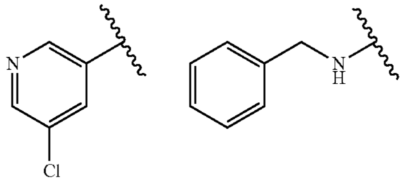
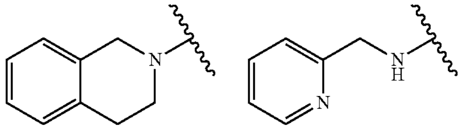
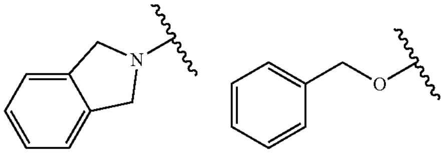
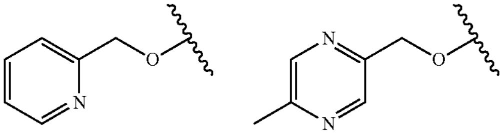,
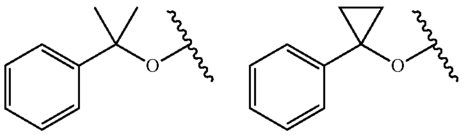
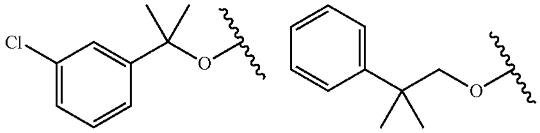
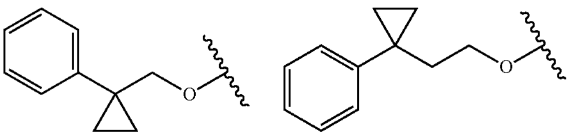
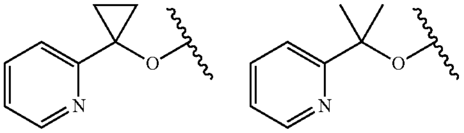
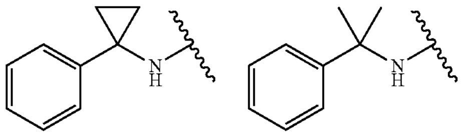
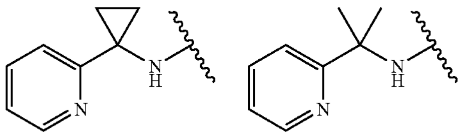
X is selected from the following:
—CN —CHO 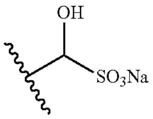
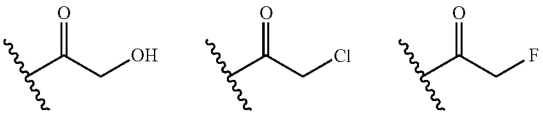
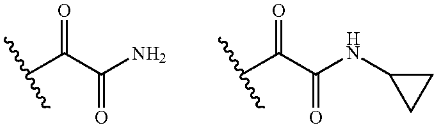
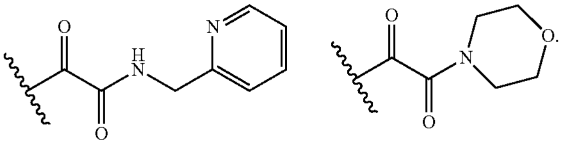
and $R_1$ is selected from the following:
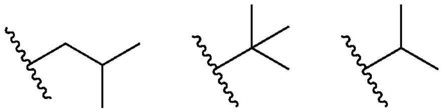
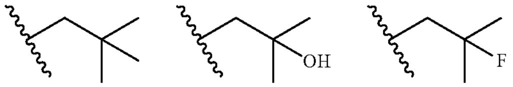
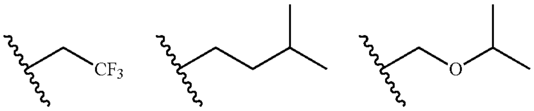
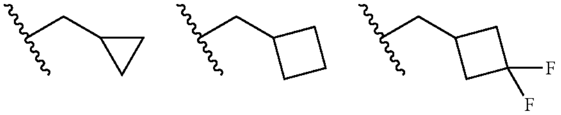
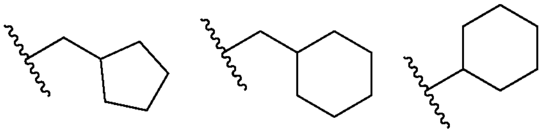
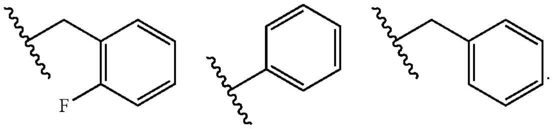.
In certain embodiments, the compound of Formula (Ia) is represented by one of Formulae (X-1) to (X-3):
(X-1)
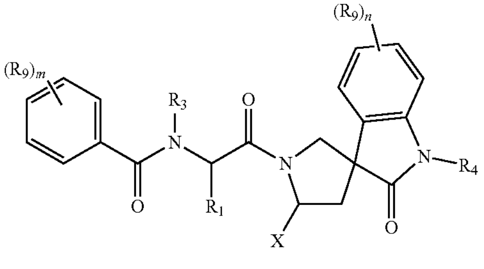

-continued (X-2)

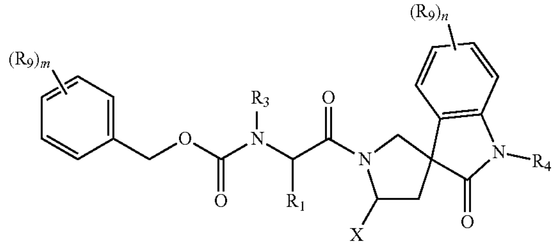

(X-3)

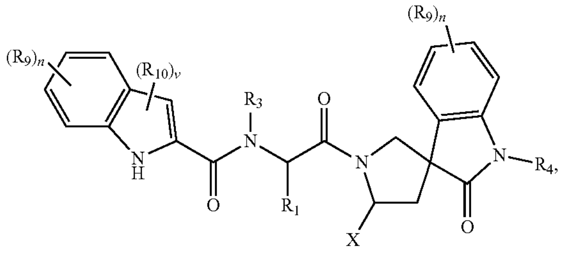

wherein m is 0, 1, 2, 3, 4 or 5; v is 0, 1 or 2; $R_{10}$ is optionally substituted —$C_1$-$C_4$ alkyl or optionally substituted —$C_3$-$C_6$ cycloalkyl; X, $R_1$, $R_3$, $R_4$, $R_9$, and n are as previously defined.

In certain embodiments, the compound of Formula (Ia) is represented by one of Formulae (XI-1) to (XI-3):

(XI-1)

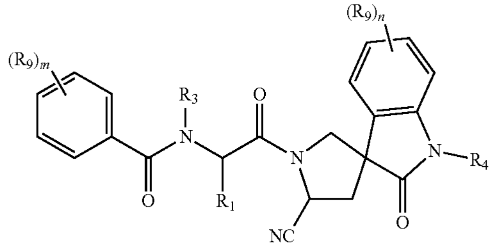

(XI-2)

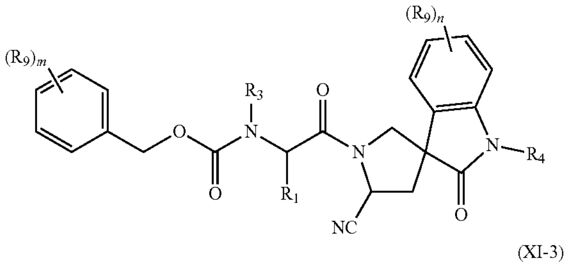

(XI-3)

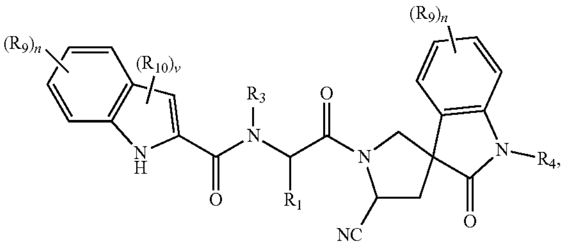

wherein $R_1$, $R_3$, $R_4$, $R_9$, $R_{10}$, m, n, and v are as previously defined.

In certain embodiments, the compound of Formula (Ia) is represented by one of Formulae (XI-1a) to (XI-3a):

(XI-1a)

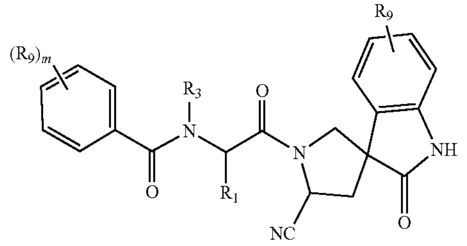

(XI-2a)

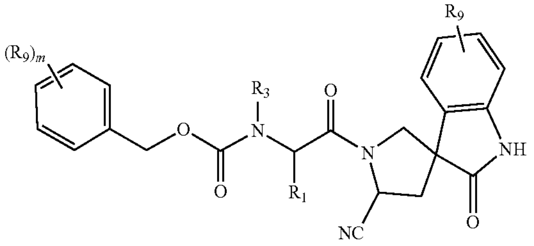

(XI-3a)

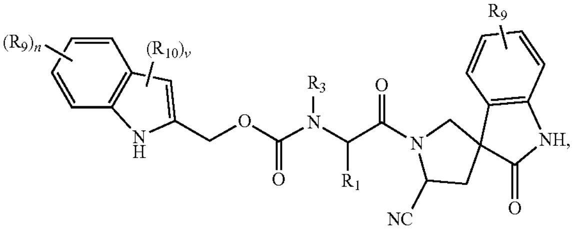

wherein $R_1$, $R_3$, $R_9$, $R_{10}$, m, n, and v are as previously defined.

In certain embodiments, the compound of Formula (Ia) is represented by one of Formulae (XI-1b) to (XI-3b):

(XI-1b)

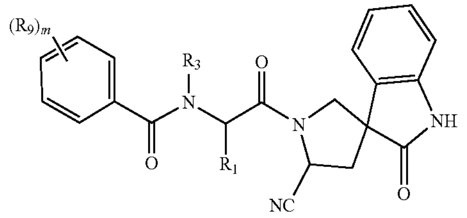

(XI-2b)

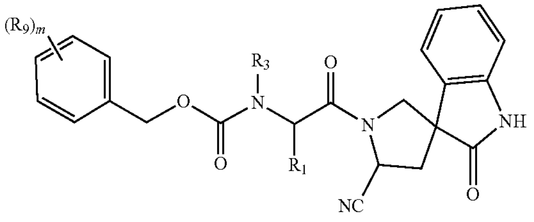

-continued (XI-3b)

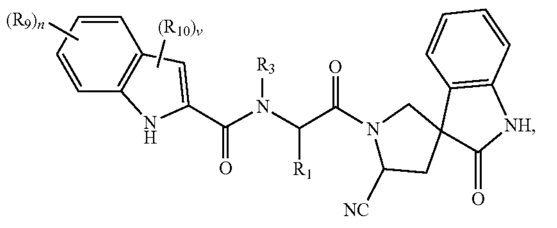

wherein $R_1$, $R_3$, $R_9$, $R_{10}$, m, n, and v are as previously defined.

In certain embodiments, the compound of Formula (Ia) is represented by one of Formulae (XII-1) to (XII-6):

(XII-1)

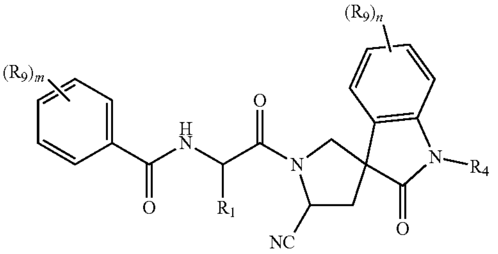

(XII-2)

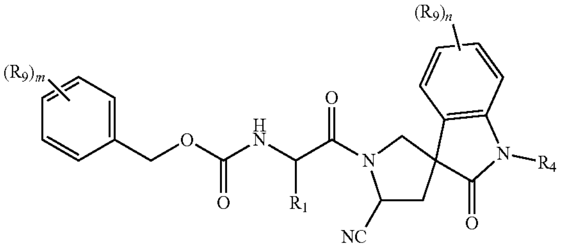

(XII-3)

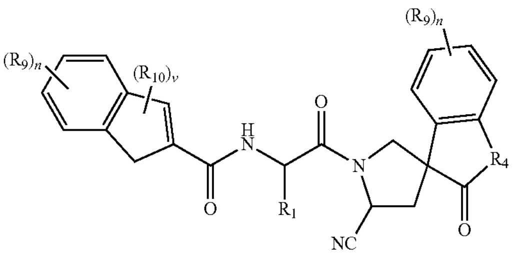

(XII-4)

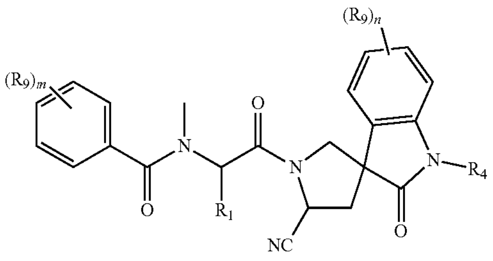

-continued (XII-5)

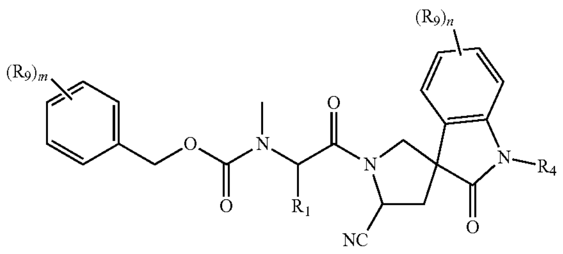

(XII-6)

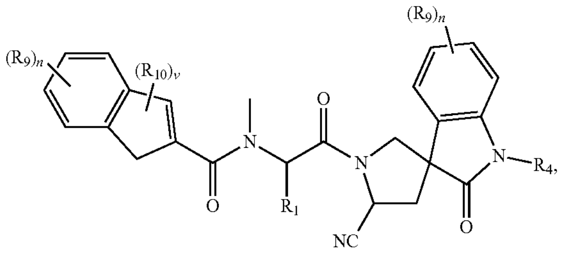

wherein wherein $R_1$, $R_4$, $R_9$, $R_{10}$, m, n, and v are as previously defined.

In certain embodiments, the compound of Formula (Ia) is represented by one of Formulae (XII-1a) to (XII-6a):

(XII-1a)

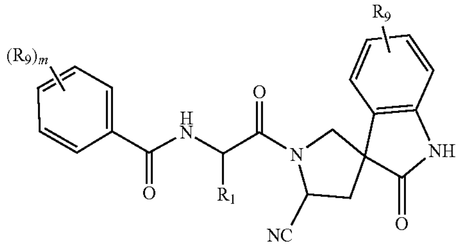

(XII-2a)

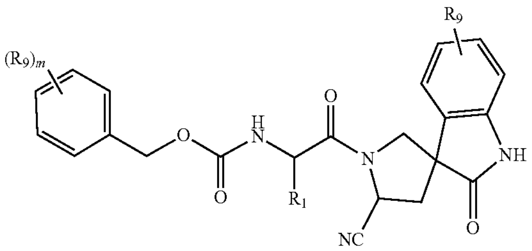

(XII-3a)

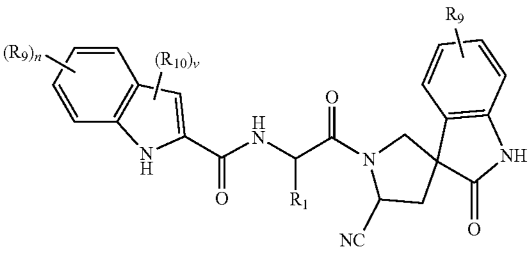

-continued (XII-4a)

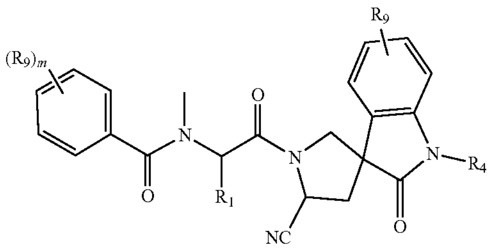

(XII-5a)

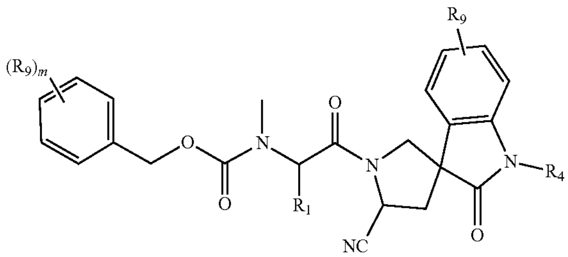

(XII-6a)

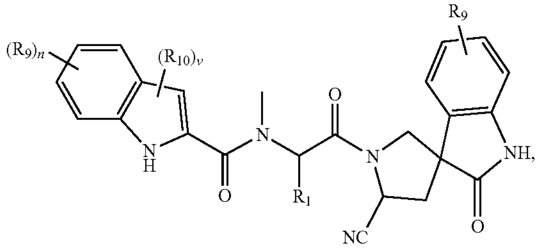

wherein wherein $R_1$, $R_9$, $R_{10}$, m, n, and v are as previously defined.

In certain embodiments, the compound of Formula (Ia) is represented by one of Formulae (XII-1b) to (XII-6b):

(XII-1b)

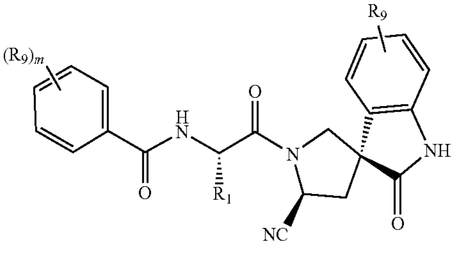

(XII-2b)

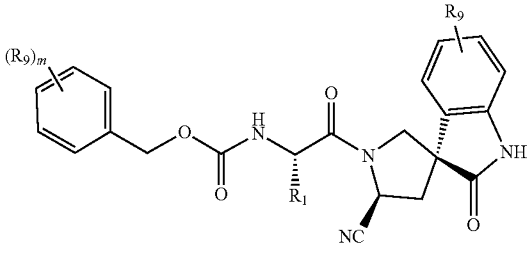

-continued (XII-3b)

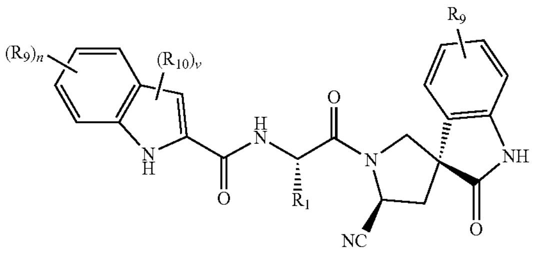

(XII-4b)

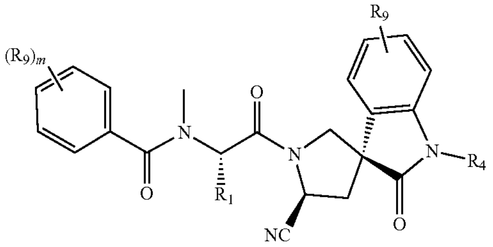

(XII-5b)

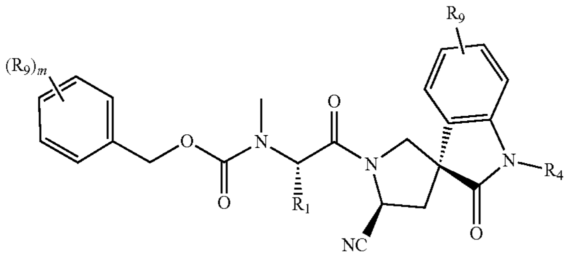

(XII-6b)

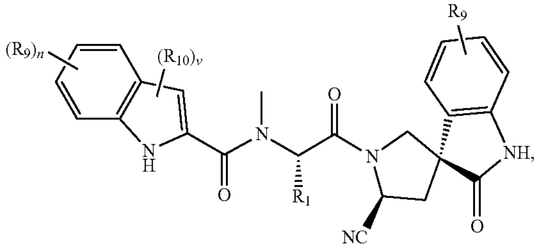

wherein wherein $R_1$, $R_9$, $R_{10}$, m, n, and v are as previously defined.

In certain embodiments, the compound of Formula (Ia) is represented by one of Formulae (XII-1c) to (XII-6c):

(XII-1c)

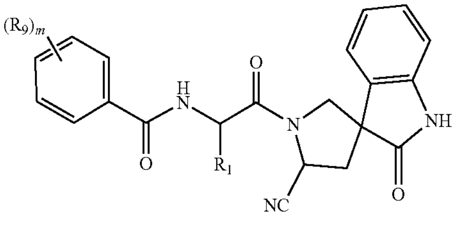

-continued
(XII-2c)
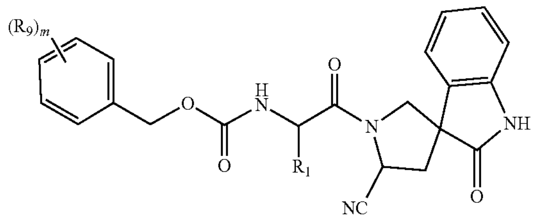
(XII-3c)
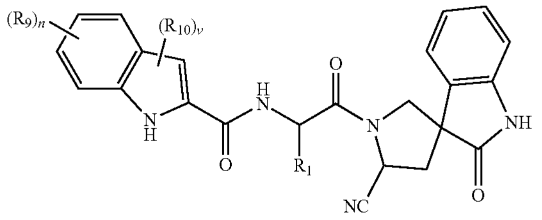
(XII-4c)
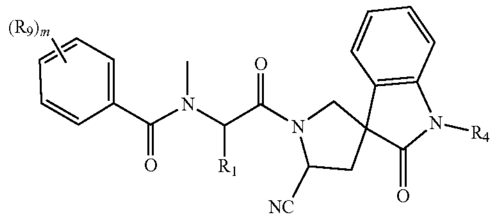
(XII-5c)
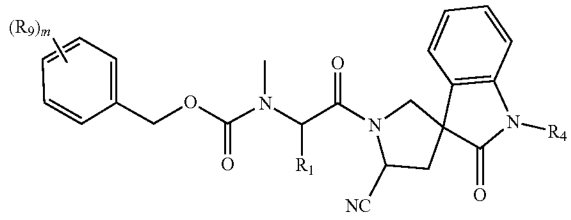
(XII-6c)
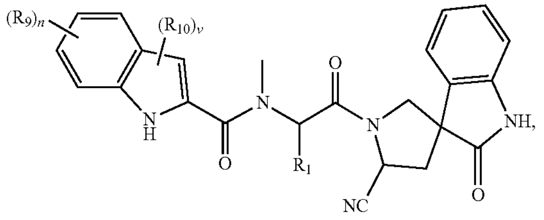
wherein wherein $R_1$, $R_9$, $R_{10}$, m, n, and v are as previously defined.
In certain embodiments, the compound of Formula (Ia) is represented by one of Formulae (XII-1c) to (XII-6d):
(XII-1d)
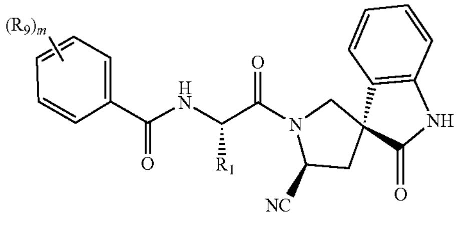
-continued
(XII-2d)
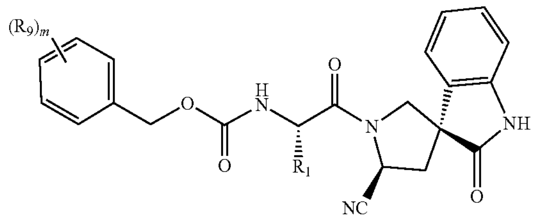
(XII-3d)
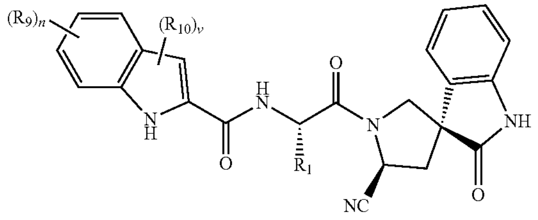
(XII-4d)
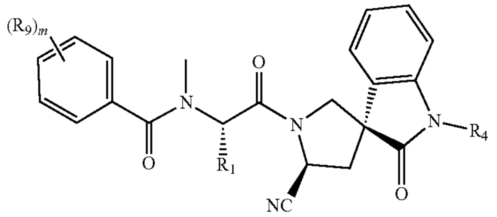
(XII-5d)
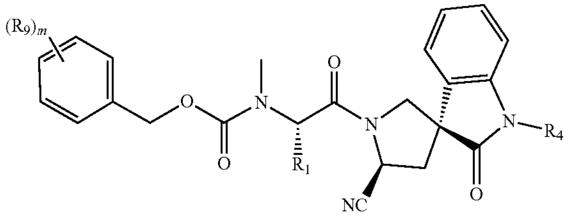
(XII-6d)
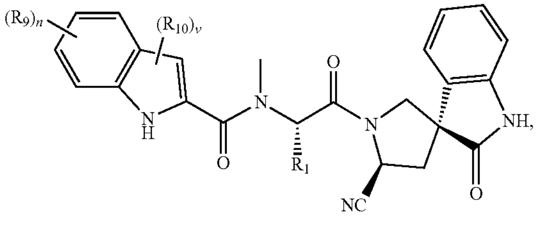
wherein wherein $R_1$, $R_9$, $R_{10}$, m, n, and v are as previously defined.

In certain embodiments, the compound of Formula (Ia) is represented by one of Formulae (XIII-1) to (XIII-6):
(XIII-1)
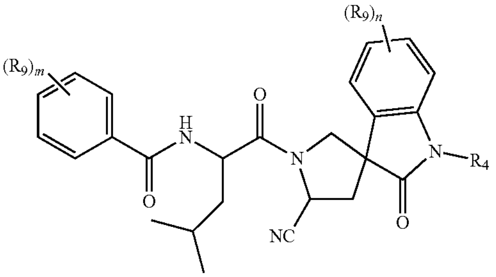
(XII-2)
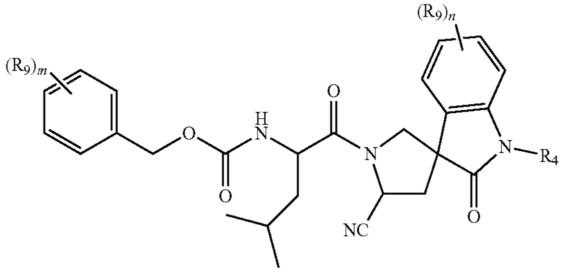
(XII-3)
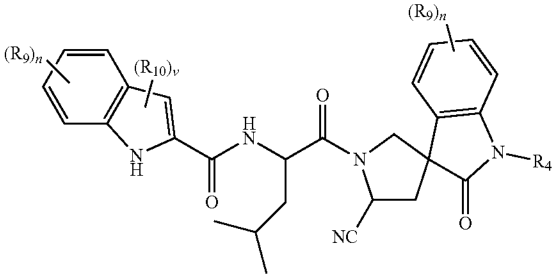
(XIII-4)
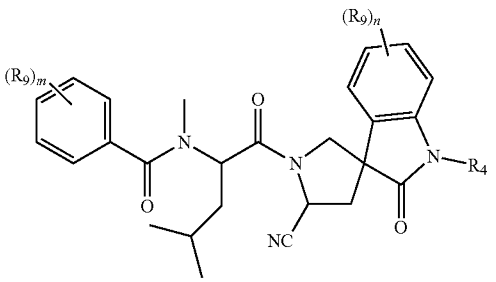
(XII-5)
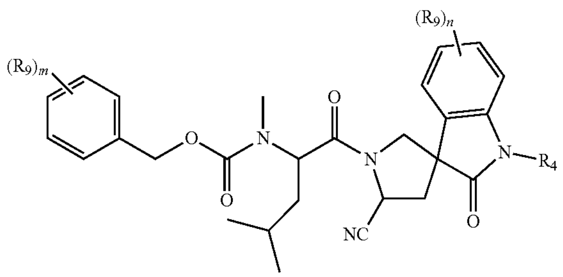
-continued
(XII-6)
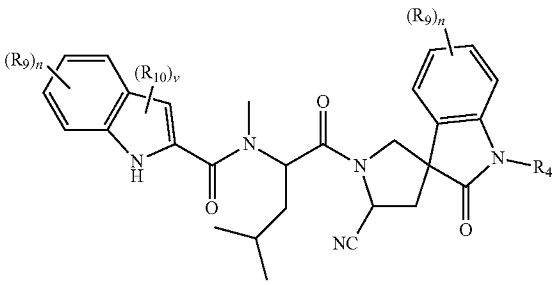
wherein $R_4$, $R_9$, $R_{10}$, m, n, and v are as previously defined.
In certain embodiments, the compound of Formula (Ia) is represented by one of Formulae (XIII-1a) to (XIII-6a):
(XIII-1)
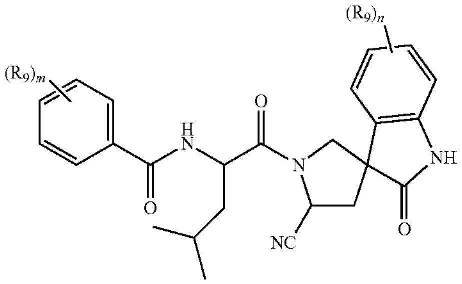
(XII-2)
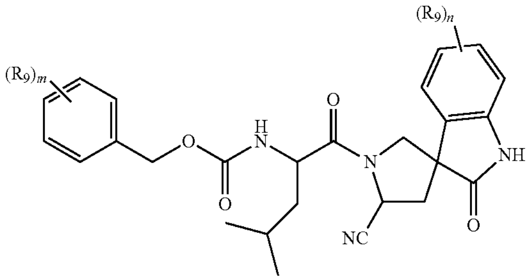
(XII-3)
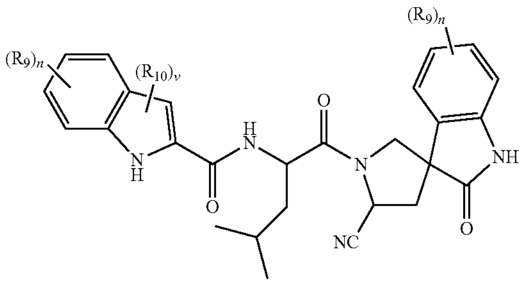

-continued
(XIII-4)
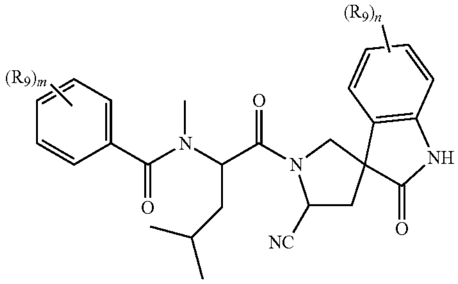
(XII-5)
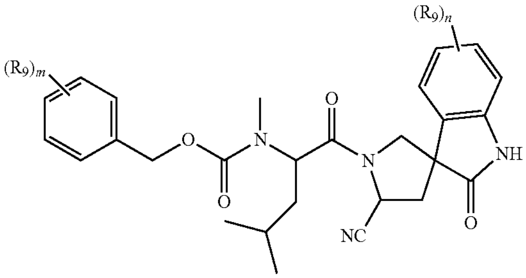
(XII-6a)
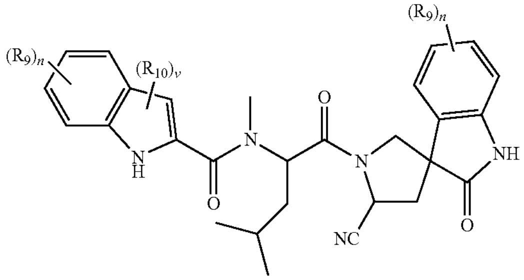
wherein $R_9$, $R_{10}$, m, n, and v are as previously darned.
In certain embodiments, the compound of Formula (Ia) is represented by one of Formulae (XIV-1) to (XIV-6):
(XIV-1)
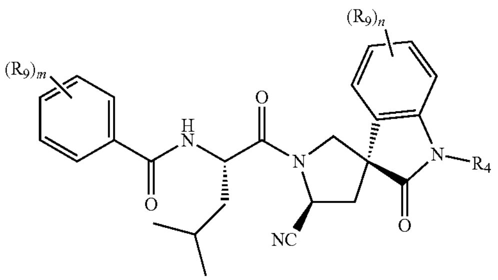
-continued
(XIV-2)
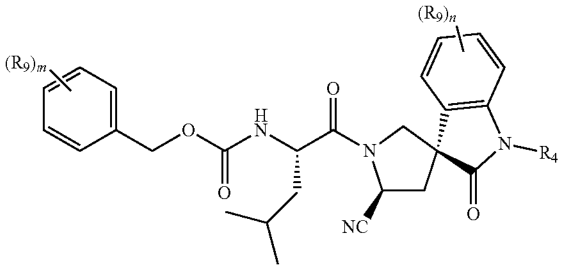
(XIV-3)
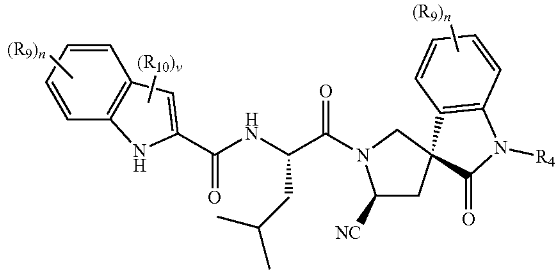
(XIV-4)
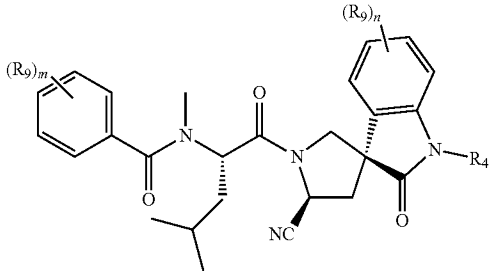
(XIV-5)
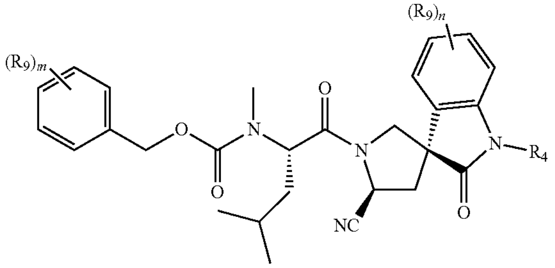
(XIV-6)
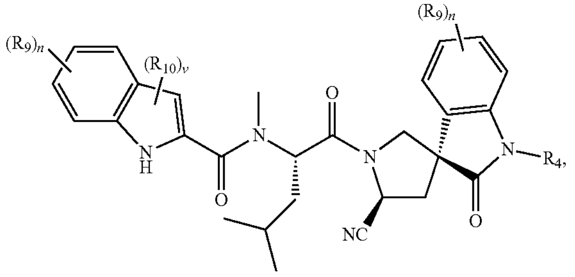
wherein $R_4$, $R_9$, $R_{10}$, m, n, and v are as previously defined.

In certain embodiments, the compound of Formula (Ia) is represented by one of Formulae (XIV-1a) to (XIV-6a):

(XIV-1a)

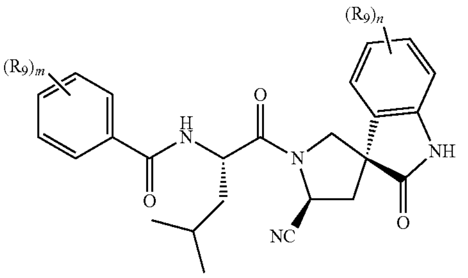

(XIV-2a)

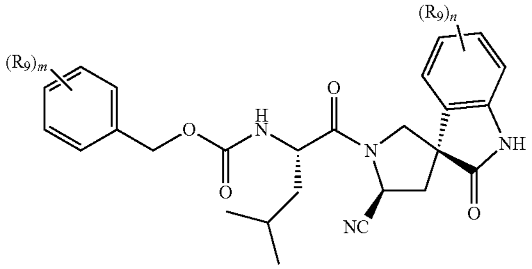

(XIV-3a)

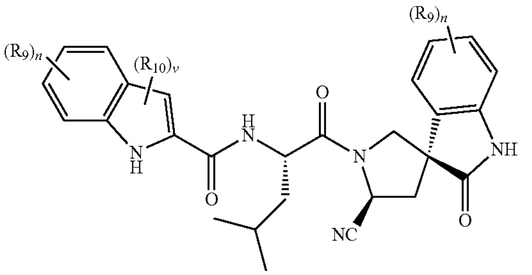

(XIV-4a)

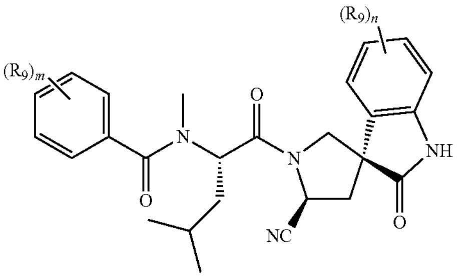

(XIV-5a)

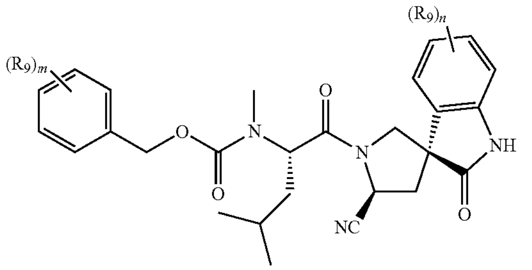

-continued (XIV-6a)

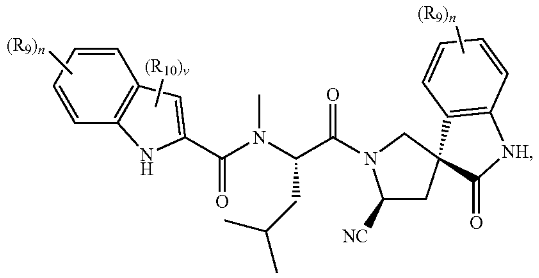

wherein $R_9$, $R_{10}$, m, n, and v are as previously defined.

In certain embodiments, the compound of Formula (Ia) is represented by Formula (XV):

(XV)

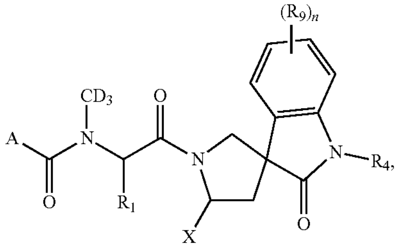

wherein A, $R_1$, $R_4$, $R_9$, n and X are as previously defined.

In certain embodiments, the compound of Formula (Ia) is represented by one of Formulae (XVI-1) to (XVI-3):

(XVI-1)

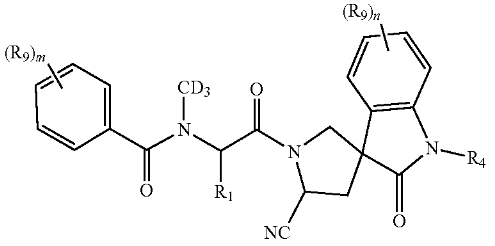

(XVI-2)

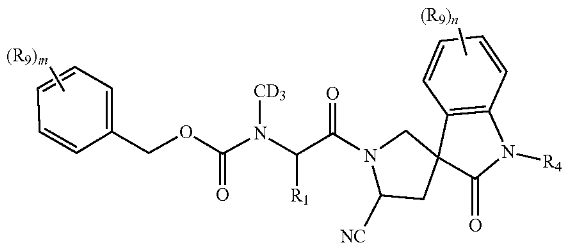

-continued (XVI-3)

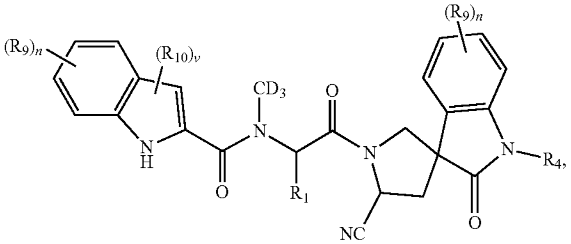

wherein wherein $R_1$, $R_4$, $R_9$, $R_{10}$, m, n, and v are as previously defined.

In certain embodiments, the compound of Formula (Ia) is represented by one of Formulae (XVII-1) to (XVII-3):

(XVII-1)

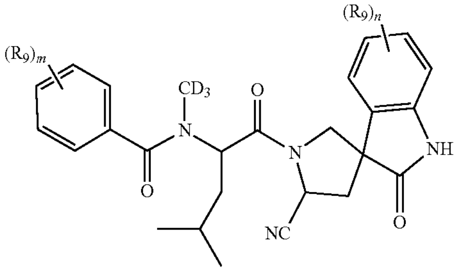

(XVII-2)

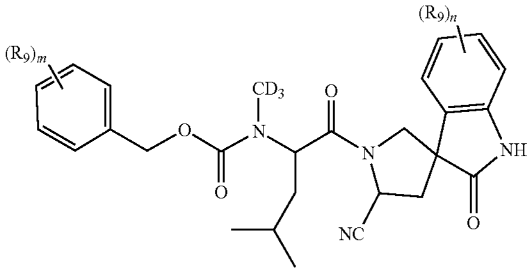

(XVII-3)

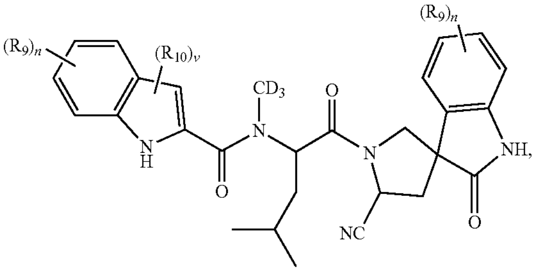

wherein $R_9$, $R_{10}$, m, n, and v are as previously defined.

In certain embodiments, the compound of Formula (Ia) is represented by Formula (XVIII-11 or Formula (XVIII-2):

(XVIII-1)

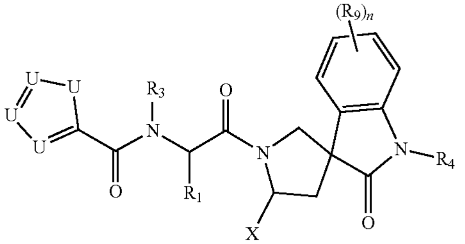

(XVIII-2)

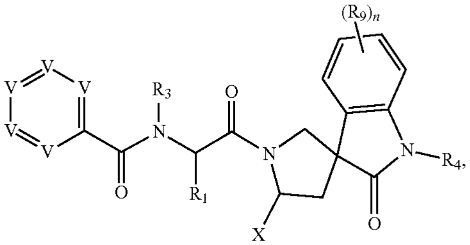

wherein one U is N or $NR_{13}$, another U is N, $NR_{13}$, or $CR_{13}$, another U is N, $NR_{13}$, or $CR_{13}$, and the fourth U is O, S, N, $NR_{13}$, or $CR_{13}$; each V is independently $CR_{13}$ or N; and $R_1$, $R_3$, $R_4$, $R_9$, n and X are as previously defined.

In certain embodiments, the compound of Formula (Ia) is represented by one of Formula (XIX-1) (XIX-9):

(XIX-1)

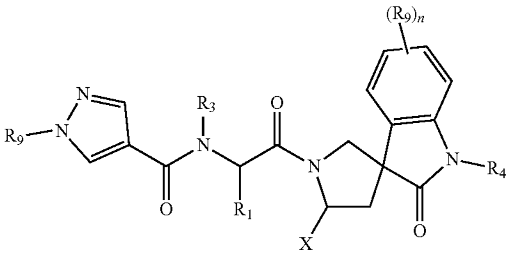

(XIX-2)

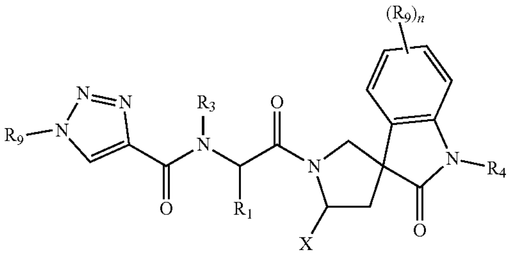

(XIX-3)

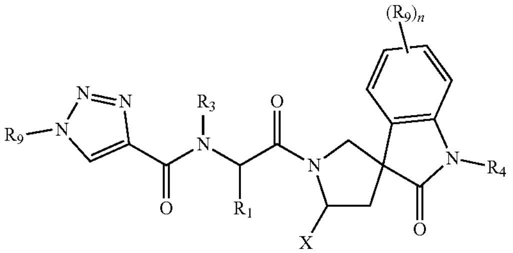

-continued
(XIX-4)
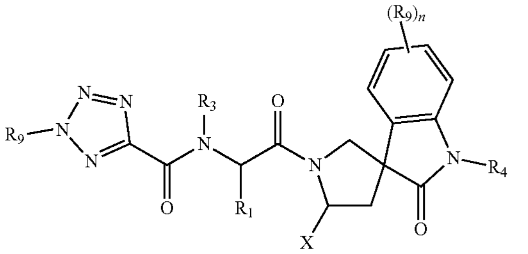
(XIX-5)
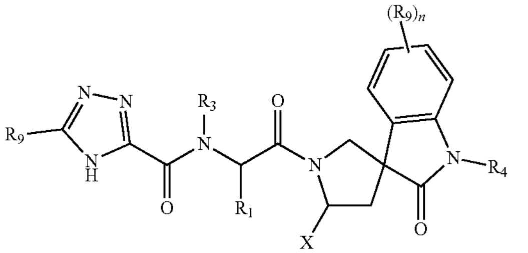
(XIX-6)
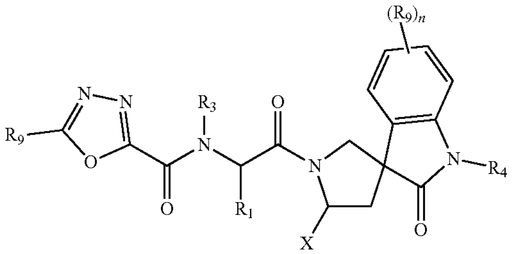
(XIX-7)
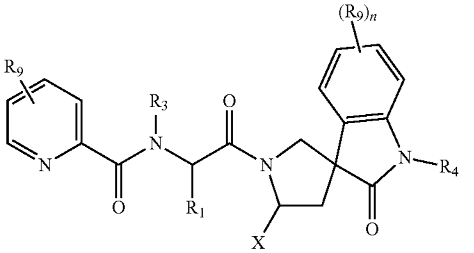
(XIX-8)
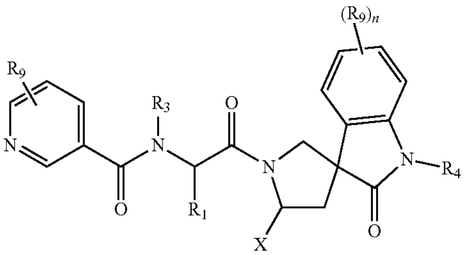
-continued
(XIX-9)
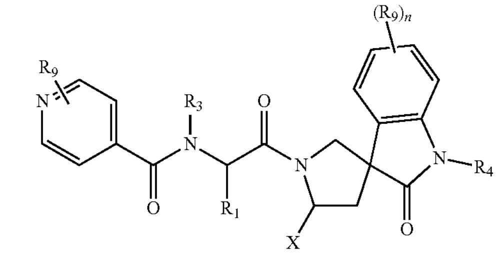
wherein $R_1$, $R_3$, $R_4$, $R_9$, n and X are as previously defined.
In certain embodiments, the compound of Formula (Ia) is represented by one of Formula (XX-1)~(XX-9):
(XX-1)
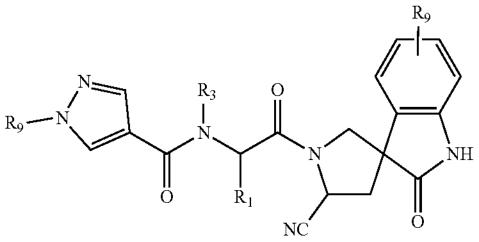
(XX-2)
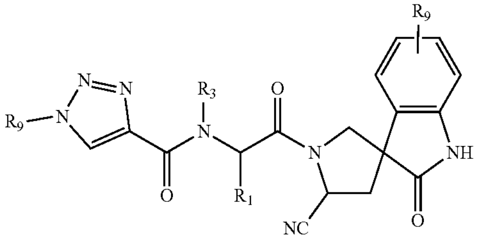
(XX-3)
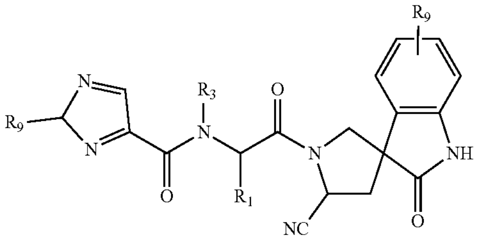
(XX-4)
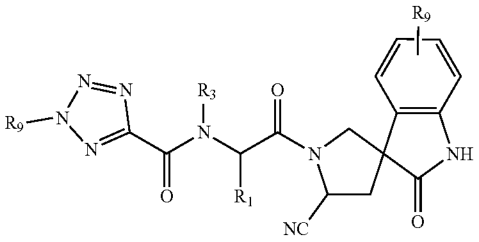

-continued (XX-5)

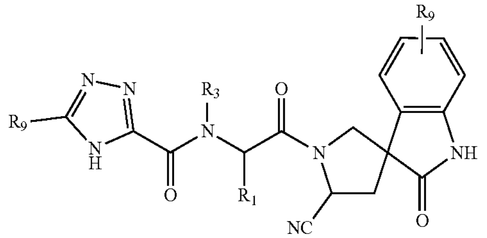

(XX-6)

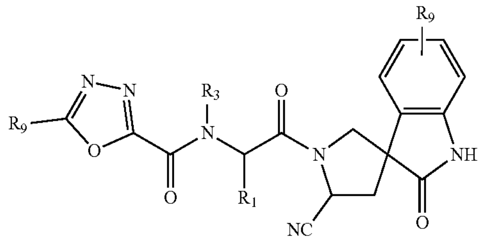

(XX-7)

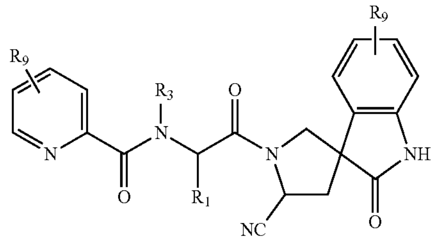

(XX-8)

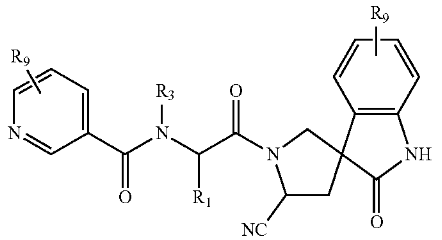

(XX-9)

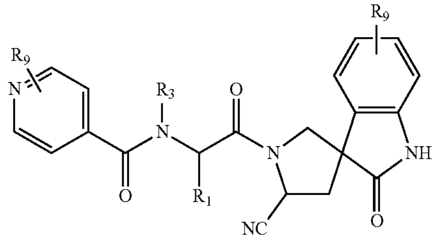

wherein $R_1$, $R_3$, and $R_9$ are as previously defined.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic; and the two rings can be fused or covalently attached.

The term "alkyl" as used herein, refers to saturated, straight- or branched-chain hydrocarbon radicals. "$C_1$-$C_4$ alkyl," "$C_1$-$C_6$ alkyl," "$C_1$-$C_8$ alkyl," "$C_1$-$C_{12}$ alkyl," "$C_2$-$C_4$ alkyl," or "$C_3$-$C_6$ alkyl," refer to alkyl groups containing from one to four, one to six, one to eight, one to twelve, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_8$ alkenyl," "$C_2$-$C_{12}$ alkenyl," "$C_2$-$C_4$ alkenyl," "$C_3$-$C_4$ alkenyl," or "$C_3$-$C_6$ alkenyl," refer to alkenyl groups containing from two to eight, two to twelve, two to four, three to four or three to six carbon atoms respectively. Alkenyl groups include, but are not limited to, for example, ethenyl, propenyl, butenyl, 2-methyl-2-buten-2-yl, heptenyl, octenyl, and the like.

The term "alkynyl" as used herein, refers to straight- or branched-chain hydrocarbon radicals having at least one carbon-carbon double bond by the removal of a single hydrogen atom. "$C_2$-$C_8$ alkynyl," "$C_2$-$C_{12}$ alkynyl," "$C_2$-$C_4$ alkynyl," "$C_3$-$C_4$ alkynyl," or "$C_3$-$C_6$ alkynyl," refer to alkynyl groups containing from two to eight, two to twelve, two to four, three to four or three to six carbon atoms respectively. Representative alkynyl groups include, but are not limited to, for example, ethynyl, 2-propynyl, 2-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-2-enyl, bicyclo[4.2.1]non-3-en-12-yl, and the like.

As used herein, the term "arylalkyl" means a functional group wherein an alkylene chain is attached to an aryl group, e.g., —$CH_2CH_2$-phenyl or benzyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted. Preferably, as used herein, arylalkyl is aryl-$C_1$-$C_6$ alkyl, and heteroarylalkyl is heteroaryl-$C_1$-$C_6$ alkyl.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 2-propoxy, 2-propoxy (isopropoxy) and the higher homologs and isomers. Preferred alkoxy are ($C_2$-$C_3$) alkoxy.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, $NH_2$, C(P), $S(O)_2$, C(O)O, C(O)NH, OC(O)O, OC(O)NH, $OC(O)NH_2$, $S(O)_2NH$, $S(O)_2NH_2$, $NHC(O)NH_2$, NHC(O)C(O)NH, $NHS(O)_2NH$, $NHS(O)_2NH_2$, $C(O)NHS(O)_2$, $C(O)NHS(O)_2NH$ or $C(O)NHS(O)_2NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 2-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "substituted" refers to substitution by independent replacement of one, two, or three or more of the hydrogen atoms with substituents including, but not limited to, —F, —$C_1$, —Br, —I, —OH, $C_1$-$C_{12}$-alkyl; $C_2$-$C_{12}$-alkenyl, $C_2$-$C_{12}$-alkynyl, —$C_3$-$C_{12}$-cycloalkyl, protected hydroxy, —$NO_2$, —$N_3$, —CN, —$NH_2$, protected amino, oxo, thioxo, —NH—$C_2$-$C_{12}$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)— heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH— heterocycloalkyl, —$OCO_2$—$C_1$-$C_{12}$-alkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$CO_2$—$C_1$-$C_{12}$ alkyl, —$CO_2$—$C_2$-$C_8$ alkenyl, —$CO_2$—$C_2$-$C_8$ alkynyl, $CO_2$—$C_3$-$C_{12}$-cycloalkyl, —$CO_2$-aryl, $CO_2$-heteroaryl, $CO_2$-heterocyloalkyl, —$OCONH_2$, —OCONH—$C_3$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocyclo-alkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocyclo-alkyl, —$NHCO_2$—$C_1$-$C_{12}$-alkyl, —$NHCO_2$—$C_2$-$C_8$-alkenyl, —$NHCO_2$—$C_2$-$C_8$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —$NHC(O)NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, $NHC(S)NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —$NHC(NH)NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$—S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —$SO_2NH_2$, —$SO_2NH$—$C_1$-$C_{12}$-alkyl, —$SO_2NH$—$C_2$-$C_8$-alkenyl, —$SO_2NH$—$C_2$-$C_8$-alkynyl, —$SO_2NH$—$C_3$-$C_{12}$-cycloalkyl, —$SO_2NH$-aryl, —$SO_2NH$-heteroaryl, —$SO_2NH$— heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthio-methyl. In certain embodiments, the substituents are independently selected from halo, preferably Cl and F; $C_1$-$C_4$-alkyl, preferably methyl and ethyl; halo-$C_1$-$C_4$-alkyl, such as fluoromethyl, difluoromethyl, and trifluoromethyl; $C_2$-$C_4$-alkenyl; halo-$C_2$-$C_4$-alkenyl; $C_3$-$C_6$-cycloalkyl, such as cyclopropyl; $C_1$-$C_4$-alkoxy, such as methoxy and ethoxy; halo-$C_1$-$C_4$-alkoxy, such as fluoromethoxy, difluoromethoxy, and trifluoromethoxy; acetyl; —CN; —OH; $NH_2$; $C_1$-$C_4$-alkylamino; di($C_1$-$C_4$-alkyl)amino; and $NO_2$. It is understood that the aryls, heteroaryls, alkyls, and the like can be further substituted. In some cases, each substituent in a substituted moiety is additionally optionally substituted with one or more groups, each group being independently selected from $C_1$-$C_4$-alkyl; —$CF_3$, —$OCH_3$, —$OCF_3$, —F, —$C_1$, —Br, —I, —OH, —$NO_2$, —CN, and —$NH_2$. Preferably, a substituted alkyl group is substituted with one or more halogen atoms, more preferably one or more fluorine or chlorine atoms.

The term "halo" or halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, methoxycarbonyl, t-butoxycarbonyl, 12-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* $2^{nd}$ Ed. Wiley-VCH (1999); T. W. Greene and P. G. M. Wuts, *Protective Groups in Organic Synthesis,* 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 2-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intra-arterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectable.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h)

absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to Van Devanter et al., U.S. Pat. No. 5,508,269 to Smith et al., and WO 98/43650 by Montgomery, all of which are incorporated herein by reference).

Antiviral Activity

In certain embodiments, the present invention provides a method of treating or preventing a viral infection in a subject in need thereof, comprising administering to the subject a therapeutically effective amount of a compound of Formula (I) or a pharmaceutically acceptable salt thereof. The viral infection is preferably a coronavirus infection. In certain embodiments, the coronavirus is SARS-CoV-1, SARS-CoV-2, or MERS-CoV. Preferably the coronavirus is SARS-CoV-2.

A viral inhibitory amount or dose of the compounds of the present invention may range from about 0.01 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). A therapeutically effective amount of the compound described above may range, for example, from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the present invention described herein can, for example, be administered by injection, intravenously, intra-arterial, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Combination and Alternation Therapy

The compounds of the present invention may be used in combination with one or more antiviral therapeutic agents or anti-inflammatory agents useful in the prevention or treatment of viral diseases or associated pathophysiology. Thus, the compounds of the present invention and their salts, solvates, or other pharmaceutically acceptable derivatives thereof, may be employed alone or in combination with other antiviral or anti-inflammatory therapeutic agents. The compounds herein and pharmaceutically acceptable salts thereof may be used in combination with one or more other agents which may be useful in the prevention or treatment of respiratory disease, inflammatory disease, autoimmune disease, for example; anti-histamines, corticosteroids, (e.g., fluticasone propionate, fluticasone furoate, beclomethasone dipropionate, budesonide, ciclesonide, mometasone furoate, triamcinolone, flunisolide), NSAIDs, leukotriene modulators (e.g., montelukast, zafirlukast.pranlukast), tryptase inhibitors, IKK2 inhibitors, p38 inhibitors, Syk inhibitors, protease inhibitors such as elastase inhibitors, integrin antagonists (e.g., beta-2 integrin antagonists), adenosine A2a agonists, mediator release inhibitors such as sodium chromoglycate, 5-lipoxygenase inhibitors (zyflo), DP1 antagonists, DP2 antagonists, PI3K delta inhibitors, ITK inhibitors, LP (lysophosphatidic) inhibitors or FLAP (5-lipoxygenase activating protein) inhibitors (e.g., sodium 3-(3-(tert-butylthio)-1-(4-(6-ethoxypyridin-3-yl)benzyl)-5-((5-ethylpyridin-2-yl)methoxy)-1H-indol-2-yl)-2,2-dimethylpropanoate), bronchodilators (e.g., muscarinic antagonists, beta-2 agonists), methotrexate, and similar agents; monoclonal antibody therapy such as anti-lgE, anti-TNF, anti-IL-5, anti-IL-6, anti-IL-12, anti-IL-1 and similar agents; cytokine receptor therapies e.g. etanercept and similar agents; antigen non-specific immunotherapies (e.g. interferon or other cytokines/chemokines, chemokine receptor modulators such as CCR3, CCR4 or CXCR2 antagonists, other cytokine/chemokine agonists or antagonists, TLR agonists and similar agents), suitable anti-infective agents including antibiotic agents, antifungal agents, antheimintic agents, antimalarial agents, antiprotozoal agents, antitubercuiosis agents, and antiviral agents, including those listed at https://www.drugs.com/drug-class/anti-infectives.html. In general, combination therapy is typically preferred over alternation therapy because it induces multiple simultaneous stresses on the virus.

When the compositions of this invention comprise a combination of a compound of the Formula described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, combined with a compound of this invention in a single composition.

The "additional therapeutic or prophylactic agents" include but are not limited to, immune therapies (e.g. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (e.g. N-acetylcysteine), cytokine agonists, cytokine antagonists, lung surfactants and/or antimicrobial and anti-viral agents (e.g. ribavirin and amantidine). The compositions according to the invention may also be used in combination with gene replacement therapy.

Abbreviations

Abbreviations which may be used in the descriptions of the scheme and the examples that follow are: Ac for acetyl; AcOH for acetic acid; $Boc_2O$ for di-tert-butyl-dicarbonate; Boc for t-butoxycarbonyl; Bz for benzoyl; Bn for benzyl; t-BuOK for potassium tert-butoxide; Brine for sodium chloride solution in water; CDI for carbonyldiimidazole; DCM or $CH_2Cl_2$ for dichloromethane; $CH_3$ for methyl; $CH_3CN$ for acetonitrile; $Cs_2CO_3$ for cesium carbonate; CuCl for copper (I) chloride; CuI for copper (I) iodide; dba for dibenzylidene acetone; DBU for 1,8-diazabicyclo[5.4.0]-undec-7-ene; DEAD for diethylazodicarboxylate; DIAD for diisopropyl azodicarboxylate; DIPEA or $(i\text{-}Pr)_2EtN$ for N,N,-diisopropylethyl amine; DMP or Dess-Martin periodinane for 1,1,2-tris(acetyloxy)-1,2-dihydro-1,2-benziodoxol-3-(1H)-one; DMAP for 4-dimethylamino-pyridine; DME for 1,2-dimethoxyethane; DMF for N,N-dimethylformamide; DMSO for dimethyl sulfoxide; EtOAc for ethyl acetate; EtOH for ethanol; $Et_2O$ for diethyl ether; HATU for O-(7-azabenzotriazol-2-yl)-N,N,N',N',-tetramethyluronium Hexafluorophosphate; HCl for hydrogen chloride; $K_2CO_3$ for potassium carbonate; n-BuLi for n-butyl lithium; DDQ for 2,3-dichloro-5,6-dicyano-1,4-benzoquinone; LDA for lithium diisopropylamide; LiTMP for lithium 2,2,6,6-tetramethylpiperidinate; MeOH for methanol; Mg for magnesium; MOM for methoxymethyl; Ms for mesyl or $—SO_2—CH_3$; NaHMDS for sodium bis(trimethylsilyl)amide; NaCl for sodium chloride; NaH for sodium hydride; $NaHCO_3$ for sodium bicarbonate or sodium hydrogen carbonate; $Na_2CO_3$ sodium carbonate; NaOH for sodium hydroxide; $Na_2SO_4$ for sodium sulfate; $NaHSO_3$ for sodium bisulfite or sodium hydrogen sulfite; $Na_2S_2O_3$ for sodium thiosulfate; $NH_2NH_2$ for hydrazine; $NH_4Cl$ for ammonium chloride; Ni for nickel; OH for hydroxyl; $OsO_4$ for osmium tetroxide; OTf for triflate; PPA for polyphosphoric acid; PTSA for p-toluenesulfonic acid; PPTS for pyridinium p-toluenesulfonate; TBAF for tetrabutylammonium fluoride; TEA or $Et_3N$ for triethylamine; TES for triethylsilyl; TESCl for triethylsilyl chloride; TESOTf for triethylsilyl trifluoromethanesulfonate; TFA for trifluoroacetic acid; THF for tetrahydrofuran; TMEDA for N,N,N',N'-tetramethylethylene-diamine; TPP or $PPh_3$ for triphenyl-phosphine; Tos or Ts for tosyl or $—SO_2—C_6H_4CH_3$; $Ts_2O$ for tolylsulfonic anhydride or tosyl-anhydride; TsOH for p-tolylsulfonic acid; Pd for palladium; Ph for phenyl; $Pd_2(dba)_3$ for tris(diben-zylideneacetone) dipalladium (0); $Pd(PPh_3)_4$ for tetrakis(triphenylphosphine)-palladium (0); $PdCl_2(PPh_3)_2$ for trans-dichlorobis-(triphenylphosphine)palladium (II); Pt for platinum; Rh for rhodium; rt for room temperature; Ru for ruthenium; TBS for tert-butyl dimethylsilyl; TMS for trimethylsilyl; and TMSCl for trimethylsilyl chloride.

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

Scheme 1

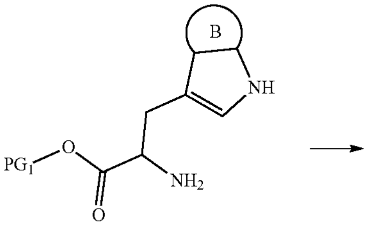

(X-1)

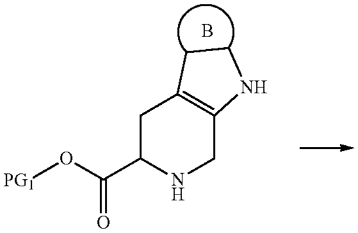

(X-2)

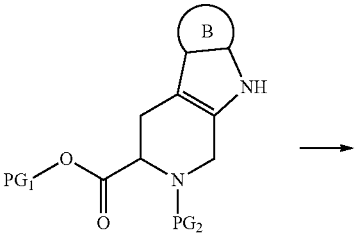

(X-3)

-continued

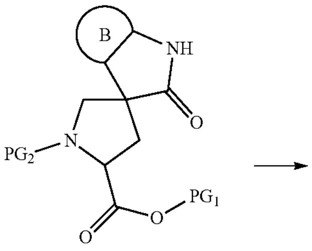

(X-4)

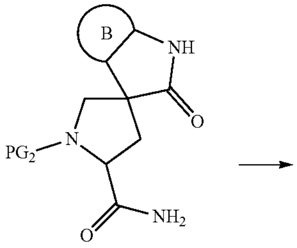

(X-5)

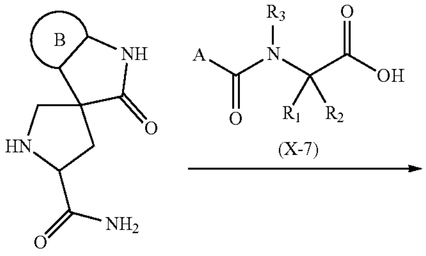

(X-6)

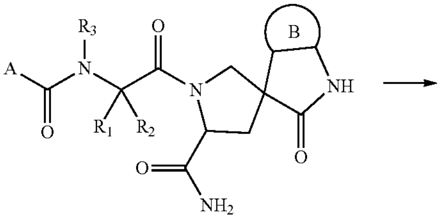

(X-8)

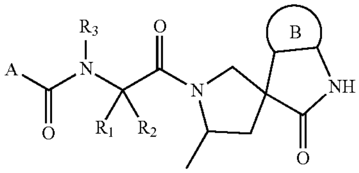

(IV-1)

(X-6)

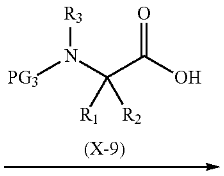

-continued

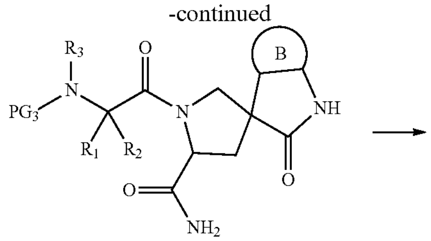

(X-10)

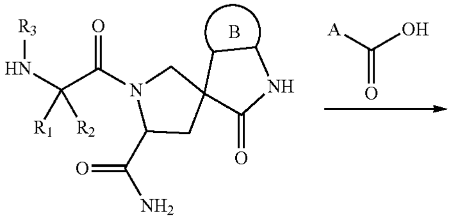

(X-8)

(X-11)

Scheme 1 illustrates a general method to prepare the compound of formular (IV-1) from the amino ester compound (X-1), wherein B is as previously defined and $PG_1$ is C1-C4 alkyl or Bn. Treatment of amine (X-1) with formaldehyde affords the cyclized amine (X-2), which is converted to (X-3) using appropriate protecting group $PG_2$ (e.g. Boc). Treatment of (X-3) with NBS in solvents containing AcOH at low temperature provides the rearranged spiral proline derivative (X-4). Examples of this sequence of transformation has been reported in literature (Pellegrini C. et al. "Synthesis of the Oxindole Alkaloid (−)-Horsfiline" Tetrahedron Asymmetry, 1994, vol. 5, No. 10, pp 1979-1992; Efremov, I. V. et al. "Discovery and Optimization of a Novel Spiropyrrolidine Inhibitor of β-Secretase (BACE1) through Fragment-Based Drug Design" Journal of Medicinal Chemistry, 2012, 55, 9069-9088). Treatment of ester (X-4) with $NH_3$ (e. g. ammonia in MeOH, $NH_3OH$, etc.) affords the amide compound (X-5), which is converted to amine compound (X-6) by removal of protecting group $PG_2$ (e.g. TFA, HCl, etc). Condensation of the amine (X-6) with acid (X-7) wherein A, $R_1$, $R_2$, and $R_3$ are previously defined, under amide coupling conditions (e.g. HATU, EDC, DCC, etc) provides amide compound (X-8). Amide (X-8) is converted to the nitrile compound (IV-1) under dehydration conditions, such as, but not limited to, $TFAA/Et_3N$, $Pd(OCOCF_3)_2/Cl_2CHCN$, Burgess reagent, or hT3P.

Alternatively, condensation of the amine (X-6) with acid (X-9) wherein $R_1$, $R_2$, and $R_3$ are previously defined and $PG_3$ is appropriate protecting group (e.g. Cbz), under amide coupling conditions (e.g. HATU, EDC, DCC, etc) provides amide compound (X-10). Removal of $PG_3$ (e.g. hydrogenation) affords amine compound (X-11). Condensation of amine (X-11) with acid (A-COOH) wherein A is previously defined, under amide coupling conditions (e.g. HATU, EDC, DCC, etc) or acylhalide generating conditions (e.g. Ghosez's reagent), provides amide compound (X-8).

Scheme 2

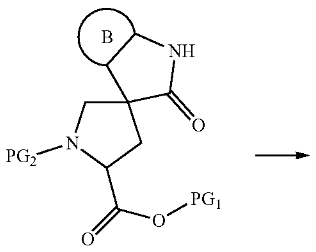

(X-4)

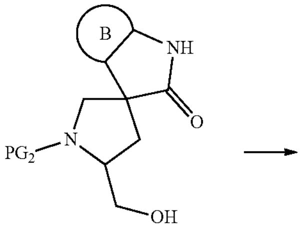

(XI-1)

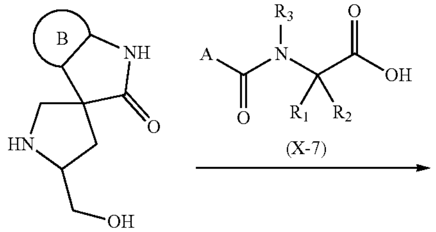

(X-7)

(XI-2)

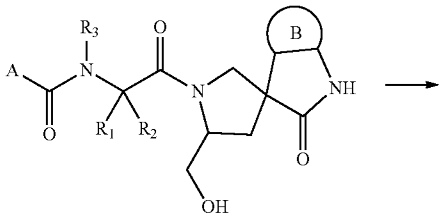

(XI-3)

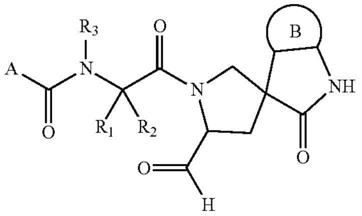

(IV-2)

Scheme 2 illustrates a general method to synthesize the aldehyde compound of formula (IV-2), wherein A, $R_1$, $R_2$, $R_3$, and B are previously defined. The ester compound of formula (X-4), wherein B, $PG_1$ and $PG_2$ are previously defined, is reduced to the alcohol compound (XI-1) employing reducing reagents such as, but not limited to, $LiBH_4$, $NaBH_4$, or DIBAL-H. The protecting group $PG_2$ (e.g. Boc) of (XI-1) is removed under acidic conditions using such as TFA, HCl, formic acid, TMSOTf/lutidine, etc. Coupling of the amine compound (XI-2) with the acid compound (X-7) wherein A, $R_1$, $R_2$, and $R_3$ are previously defined, using coupling reagents such as HATU, EDC, or DCC, provides compound (XI-3). Oxidation of the alcohol of (XI-3) with mild oxidation reagents such as DMSO/$Ac_2O$, Dess-Martin periodinane, IBX, $SO_3$-pyridine/DMSO/$Et_3N$, produces the aldehyde compound (IV-2).

Scheme 3

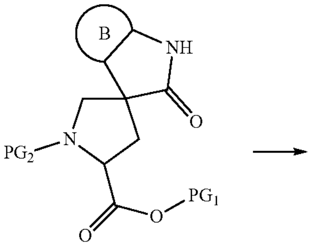

(X-4)

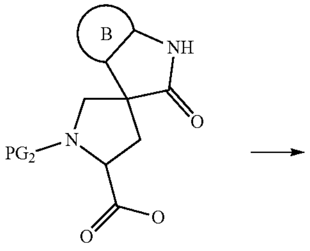

(XII-1)

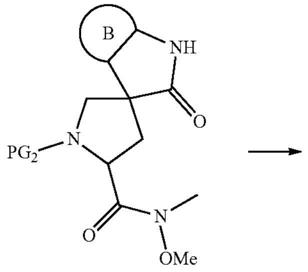

(XII-2)

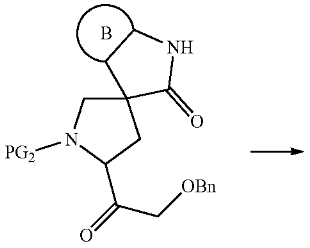

(XII-3)

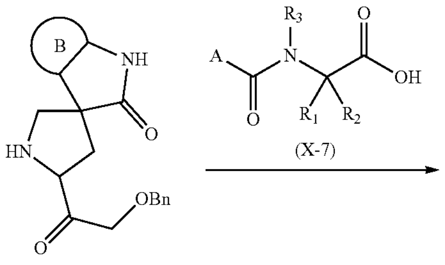

(XII-4)

(X-7)

-continued

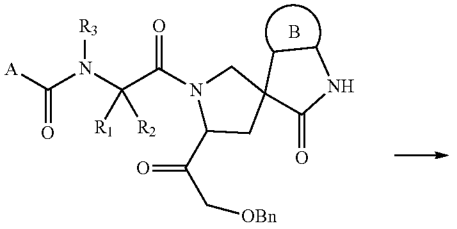

(XII-5)

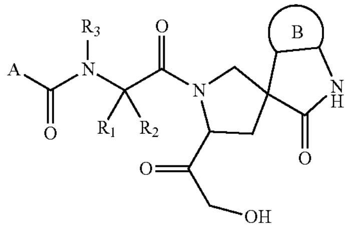

(IV-3)

Scheme 3 illustrates a general method to synthesize the hydroxymethylketone compound of formula (IV-3). Hydrolysis of the ester compound (X-4), wherein B, $PG_1$ and $PG_2$ are previously defined, provides the acid compound (XII-1). Amide (XII-2) can be obtained from the acid compound (XII-1) by coupling with N,O-dimethylhydroxyamine using reagents such as HATU, EDC, DCC, etc. Treatment of amide (XII-2) at low temperature (e.g. −60° C.) with an organometallic regeat generated by BOM-Cl, Mg, and $HgCl_2$ affords the ketone compound (XII-3). Removal of $PG_2$ (e.g. PTSA if $PG_2$ is BOC) provides amine compound (XII-4). Coupling of amine (XII-4) with acid (X-7), wherein A, $R_1$, $R_2$, and $R_3$ are previously defined, affords compound (XII-5) using amide coupling reagents such as HATU, EDC, DCC, etc. Removal of the benzyl group in (XII-5) under hydrogenation conditions (Pd/C, $H_2$) provides compound of formula (IV-3).

Scheme 4

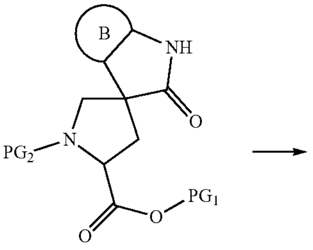

(X-4)

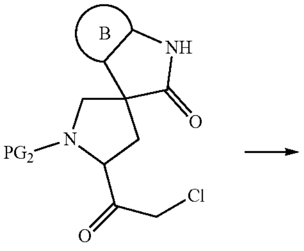

(XIII-1)

-continued

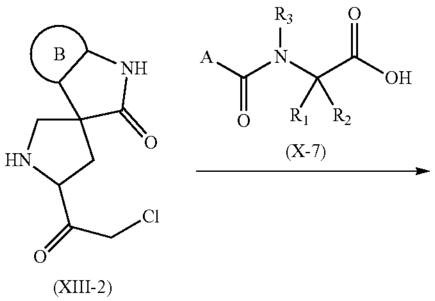

(XIII-2)

(X-7)

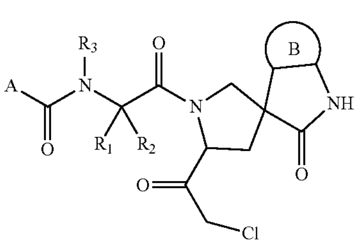

(IV-4)

Scheme 4 illustrates a general method to synthesize the chloromethylketone compound of formula (IV-4). Treatment of the ester compound (X-4) with an organometallic reagent generated by $ICH_2Cl$ and appropriate base, such as LDA, MeLi/LiBr, or BuLi, provides the chloroketone compound (XIII-1). Removal of $PG_2$ (e.g. PTSA if $PG_2$ is BOC) provides amine compound (XIII-2). Coupling of amine (XIII-2) with acid (X-7), wherein A, $R_1$, $R_2$, and $R_3$ are previously defined, affords compound (IV-4) using coupling reagents such as HATU, EDC, DCC, etc.

Scheme 5

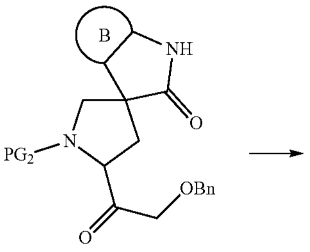

(XII-3)

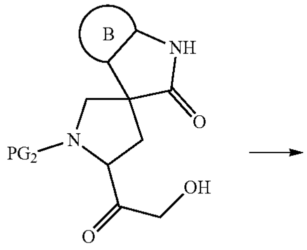

(XIV-1)

-continued

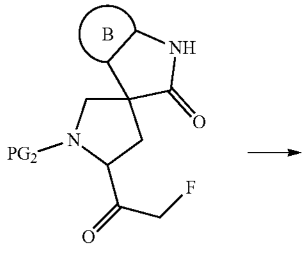

(XIV-2)

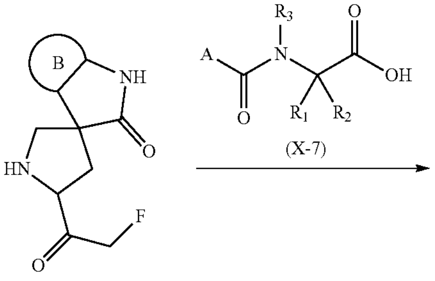

(XIV-3)

(X-7)

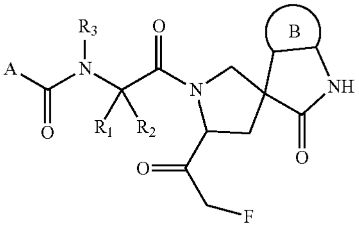

(IV-5)

Scheme 5 illustrates a general method to synthesize the fluoromethylketone compound of formula (IV-5). Removal of the Bn group of compound (XII-3) with Pd-catalyzed hydrogenation provides alcohol compound (XIV-1). Alcohol (XIV-1) is converted to fluoromethylketone compound (XIV-2) under conditions such as $SF_4$, $Tf_2O$/lutidine/TBAF, $C_4F_9SO_2F$/HF-$Et_3N$, etc. Removal of $PG_2$ (e.g. PTSA if $PG_2$ is BOC) provides amine compound (XIV-3). Coupling of amine (XIV-3) with acid (X-7), wherein A, $R_2$, and $R_3$ are previously defined, affords compound (IV-5) using amide coupling reagents such as HATU, EDC, DCC, etc.

Scheme 6

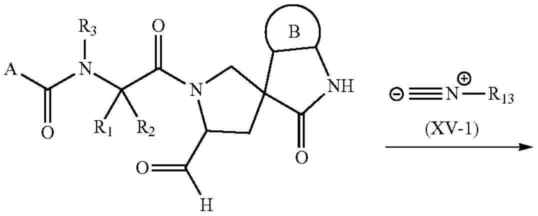

(IV-2)

(XV-1)

-continued

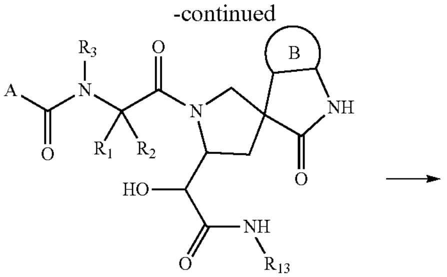

(XV-2)

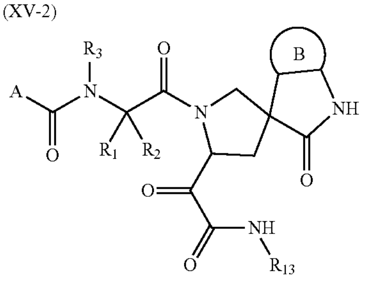

(IV-6')

Scheme 6 illustrates a general method to synthesize the α-ketoamide compound of formula (IV-6). Treatment of the aldehyde compound of formula (IV-2), wherein A, $R_1$, $R_2$, $R_3$, and B are previously defined, with isonitrile compound (XV-1), wherein $R_{13}$ is previously defined, affords α-hydroxylamide (XV-2). Oxidation of compound (XV-2) with appropriate oxidants such as Dess-Martin periodinane, $(COCl)_2$/DMSO/$Et_3N$, PCC, $SO_3$-pyridine/DMSO/$Et_3N$, affords α-ketoamide of formula (IV-6').

Scheme 7

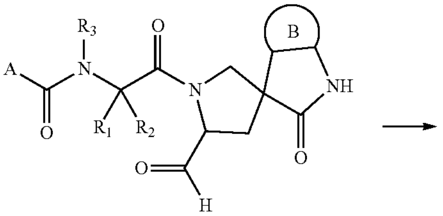

(IV-2)

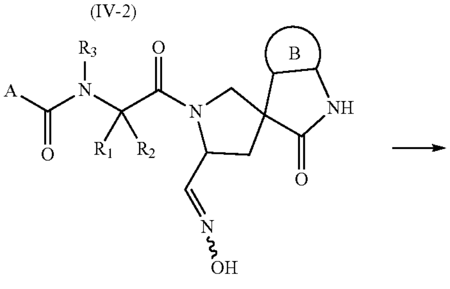

(XVI-1)

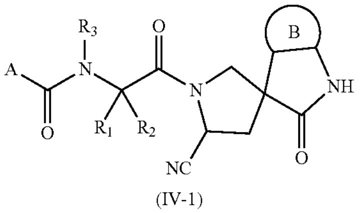

(IV-1)

Alternatively, nitrile compound (IV-1) can be synthesized from aldehyde compound (IV-2) using the method shown in Scheme 7. Condensation of aldehyde (IV-2) with hydroxyamine hydrochloride in appropriate solvents such as DMSO, i-PrOH, pyridine, etc. provides oxime compound (XVI-1). Treatment of the oxime compound (XVI-1) under acid-catalyzed dehydration conditions such as $(Cu(OAc)_2$/MeCN, HCl, etc.) affords the nitrile compound (IV-1).

Scheme 8

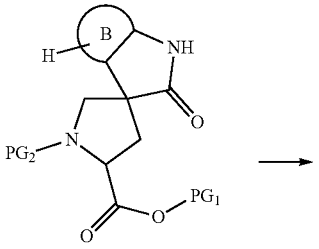

(XX-1)

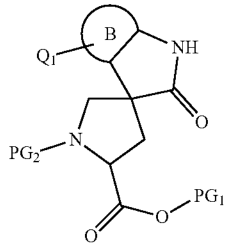

(XX-2)

Scheme 8 illustrates a general method to synthesize functionalized spirocycles of formula XX-2 (Qi defined as halogen or optionally substituted alkyl). Treatment of the spirocyclic compound of formula XX-1, wherein B, $PG_1$, and $PG_2$ are previously defined, with an electrophilic reagent, including, but not limited to: sulfuryl chloride, N-chlorosuccinimide, N-bromosuccinimide, SelectFluor, or NFSI, can provide functionalized spirocycle XX-2.

EXAMPLES

The compounds and processes of the present invention will be better understood in connection with the following examples, which are intended as an illustration only and not limiting of the scope of the invention. Starting materials were either available from a commercial vendor or produced by methods well known to those skilled in the art.

General Conditions:

Mass spectra were run on LC-MS systems using electrospray ionization. These were Agilent 1290 Infinity II systems with an Agilent 6120 Quadrupole detector. Spectra were obtained using a ZORBAX Eclipse XDB-C18 column (4.6x30 mm, 1.8 micron). Spectra were obtained at 298K using a mobile phase of 0.1% formic acid in water (A) and 0.1% formic acid in acetonitrile (B). Spectra were obtained with the following solvent gradient: 5% (B) from 0-1.5 min, 5-95% (B) from 1.5-4.5 min, and 95% (B) from 4.5-6 min. The solvent flowrate was 1.2 mL/min. Compounds were detected at 210 nm and 254 nm wavelengths. $[M+H]^+$ refers to mono-isotopic molecular weights.

NMR spectra were run on a Bruker 400 MHz spectrometer. Spectra were measured at 298K and referenced using the solvent peak. Chemical shifts for $^1H$ NMR are reported in parts per million (ppm).

Compounds were purified via reverse-phase high-performance liquid chromatography (RPHPLC) using a Gilson GX-281 automated liquid handling system. Compounds were purified on a Phenomenex Kinetex EVO C18 column (250x21.2 mm, 5 micron), unless otherwise specified. Compounds were purified at 298K using a mobile phase of water (A) and acetonitrile (B) using gradient elution between 0% and 100% (B), unless otherwise specified. The solvent flowrate was 20 mL/min and compounds were detected at 254 nm wavelength.

Alternatively, compounds were purified via normal-phase liquid chromatography (NPLC) using a Teledyne ISCO Combiflash purification system. Compounds were purified on a REDISEP silica gel cartridge. Compounds were purified at 298K and detected at 254 nm wavelength.

Example 1

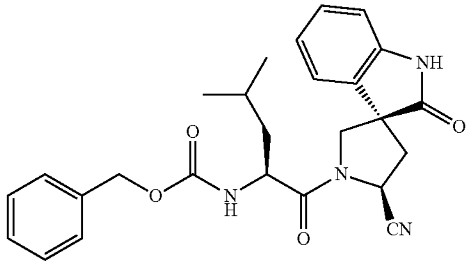

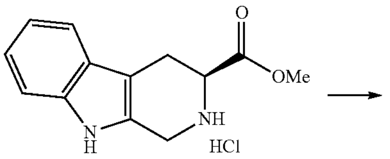

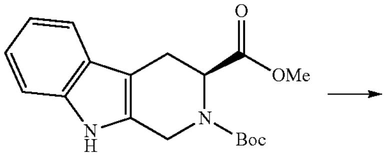

1-1

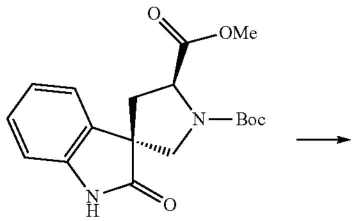

1-2

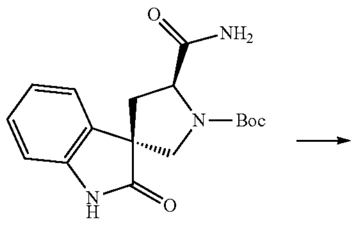

1-3

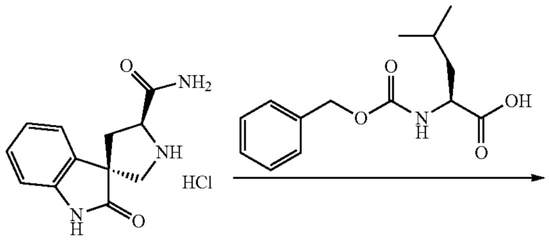

1-4

-continued

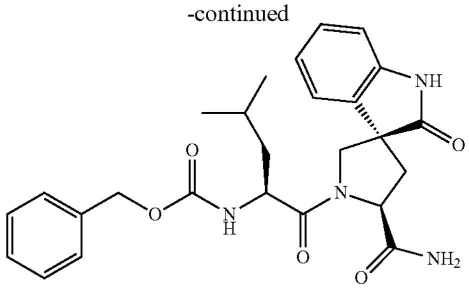

1-5

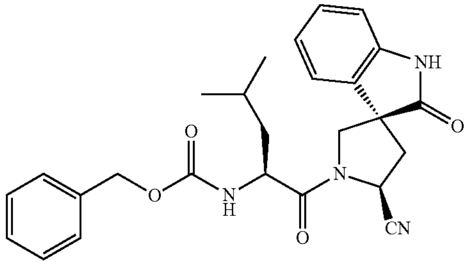

Example 1

Step 1-1 methyl (S)-2,3,4,9-tetrahydro-1H-pyrido[3,4-b]indole-3-carboxylate hydrochloride (500 mg, 1.875 mmol) was dissolved in $CH_2Cl_2$ (10 ml). Triethylamine (523 μl, 3.75 mmol) and a 2.0 M solution of di-tert-butyl dicarbonate in DCM (1031 μl, 2.062 mmol) was added. The mixture was stirred at rt for 3 h, quenched with sat. $NaHCO_3$, and extracted with DCM. The organic layer was washed with brine, dried over $MgSO_4$, and concentrated in vacuo. Purification of the residue on silica gel with 0-30% EtOAc/cyclohexane provided compound (1-1) (578 mg, 1.749 mmol, 93% yield).

Step 1-2

Compound (1-1) was dissolved in THF (15 ml), AcOH (10 ml), and water (10 ml). The solution was cooled to −15° C. A solution of NBS (328 mg, 1.843 mmol) in THF (5 mL) was added dropwise. The mixture was slowly warmed to 5° C. over 1 h. The reaction was quenched with $Na_2SO_3$ and sat. $NaHCO_3$, and extracted with DCM (2×). The organic layer was washed with brine, dried with $MgSO_4$, and concentrated in vacuo. Purification of the residue on silica gel with 0-50% EtOAc/cyclohexane provided compound (1-2) (328 mg, 0.947 mmol, 53.9% yield).

Step 1-3

Compound (1-2) (328 mg, 0.947 mmol) was dissolved in MeOH (3 ml). A solution of 7 N ammonia in MeOH (5 mL, 35.0 mmol) was added. The mixture was stirred at rt for 5 days. Solvent was removed in vacuo. Purification of the residue on silca gel with 0-10% MeOH/DCM, and on C18 column with 0-50% $MeCN/H_2O$ provided compound (1-3) (101 mg, 0.305 mmol, 32.2% yield).

Step 1-4

Compound (1-3) (100 mg, 0.302 mmol) was dissolved in DCM and trifluoroacetic acid (232 μl, 3.02 mmol) was added. The mixture was stirred at 0° C. for 1 h, and at rt for 2 h. DCM (10 mL) and toluene (10 mL) were added. Solvent was removed in vacuo. The residue was dissolved in MeOH and 1 M HCl (0.6 mL, 2 eq) was added. Solvent was removed. The obtained compound (1-4) (91 mg, 0.340 mmol, quantative yield) was used for next step.

Step 1-5

Compound (1-4) (15 mg, 0.056 mmol) and ((benzyloxy) carbonyl)-L-leucine (14.87 mg, 0.056 mmol) were dissolved in THF (0.5 ml) and DMF (0.1 ml). DIPEA (30.0 μl. 168 mmol) and HATU (21.30 mg, 0.056 mmol) were added. The mixture was stirred at rt for 20 min, quenched with water, and extracted with EtOAc (2×). The organic layer was loaded on silica gel and eluted with 0-70% acetone/cyclohexane to afford compound (1-5) (15 mg, 0.031 mmol, 55.9% yield).

Step 1-6

Compound (1-5) (60 mg, 0.125 mmol) was dissolved in DCM (1.254 ml) (not soluble). Triethylamine (140 μl, 1.003 mmol) and TFAA (70.8 μl, 0.502 mmol) was added. The mixture was stirred at rt for 30 min. The reaction was diluted with DCM and quenched with sat. $NaHCO_3$. The organic layer was loaded on silica gel and eluted with 0-50% acetone/cyclohexane, and on prep-HPLC with 20-85% $MeCN/H_2O$ with 0.1% formi acid to afford Example 1 (14 mg, 0.056 mmol) as a white powder. $^1H$ NMR (400 MHz, Acetone-$d_6$) δ 9.70 (s, 1H), 7.42-7.31 (m, 5H), 7.28 (td, J=7.7, 1.3 Hz, 1H), 7.12 (d, J=7.4 Hz, 1H), 7.04-6.96 (m, 2H), 6.65 (d, J=8.3 Hz, 1H), 5.17 (t, J=8.3 Hz, 1H), 5.06-4.94 (m, 2H), 4.48 (td, J=9.0, 5.0 Hz, 1H), 4.26 (d, J=10.4 Hz, 1H), 3.99 (d, J=10.3 Hz, 1H), 2.78-2.63 (m, 2H), 1.80 (dd, J=13.8, 6.9 Hz, 1H), 1.74-1.56 (m, 2H), 0.96 (dd, J=8.7, 6.6 Hz, 6H). [M+Na] m/e 483.18.

The following examples were prepared employing similar protocol as described above.

| Example # | Structure | MS | NMR |
|---|---|---|---|
| 2 | 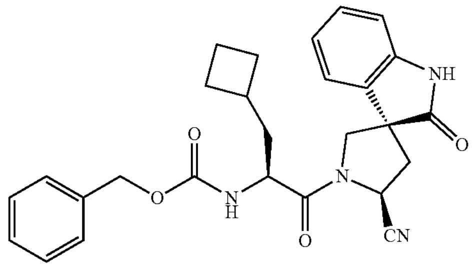 [SMILES: N#C[C@@H]1C[C@@]2(CN1C(=O)[C@H](CC1CCC1)NC(=O)OCc1ccccc1)C(=O)Nc1ccccc12] | $[M-H]^-$ 471.16 | $^1H$ NMR (400 MHz, Methanol-$d_4$) δ 7.39-7.28 (m, 5H), 7.28 (td, J = 7.7, 1.2 Hz, 1H), 7.11 (d, J = 7.4 Hz, 1H), 7.06-6.93 (m, 2H), 5.14 (t, J = 8.0 Hz, 1H), 5.00 (d, J = 2.4 Hz, 2H), 4.28 (dd, J = 8.2, 6.2 Hz, 1H),4.18 (d, J = 10.5 Hz, 1H), 3.95 (d, J = 10.5 Hz, 1H), 2.67 (dd, J = 7.9, 1.9 Hz, 2H), 2.44 (p, J = 7.9 Hz, 1H), 2.16-2.05 (m, 3H), 1.97-1.62 (m, 5H). |
| 3 | 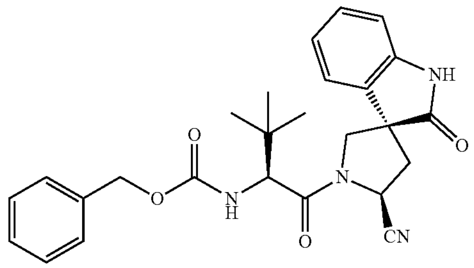 [SMILES: CC(C)(C)[C@H](NC(=O)OCc1ccccc1)C(=O)N1C[C@]2(C[C@H]1C#N)C(=O)Nc1ccccc12] | $[M-H]^-$ 459.17 | $^1H$ NMR (400 MHz, Acetone-$d_6$) δ 9.55 (s, 1H), 7.28-7.15 (m, 5H), 7.15-7.07 (M, 1H), 6.89 (d, J = 7.5 Hz, 1H), 6.84 (d, J = 7.8 Hz, 1H), 6.80 (t, J = 7.5 Hz, 1H), 6.40 (d, J = 9.0 Hz, 1H), 5.04 (t, J = 8.4 Hz, 1H), 4.84 (s, 2H), 4.16 (dd, J = 17.5, 9.8 Hz, 2H), 3.95-3.84 (m, 1H), 2.64-2.48 (m, 2H), 0.97 (s, 9H). |
| 4 | 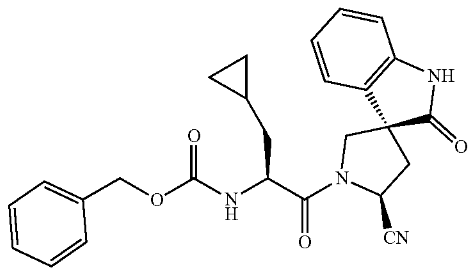 [SMILES: N#C[C@@H]1C[C@@]2(CN1C(=O)[C@H](CC1CC1)NC(=O)OCc1ccccc1)C(=O)Nc1ccccc12] | $[M+Na]^+$ 481.16 | $^1H$ NMR (500 MHz, Chloroform-d) δ 8.17 (s, 1H), 7.32-7.13 (m, 6H), 6.92-6.74 (m, 3H), 5.53 (d, J = 8.3 Hz, 1H), 4.96-4.78 (m, 3H), 4.36 (q, J = 7.2 Hz, 1H), 3.92 (dd, J = 49.8, 10.4 Hz, 2H), 2.71 (dd, J = 13.2, 8.7 Hz, 1H), 2.40 (dd, J = 13.2, 8.3 Hz, 1H), 1.55 (ddt, J = 36.2, 13.7, 6.8 Hz, 2H), 0.60 (ddt, J = 10.2, 7.6, 3.7 Hz, 1H), 0.41 (t, J = 7.9 Hz, 2H), 0.00 (d, J = 4.9 Hz, 2H). |
| 5 | 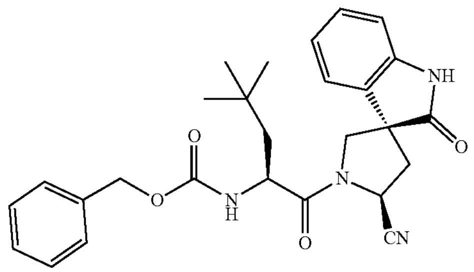 [SMILES: CC(C)(C)C[C@H](NC(=O)OCc1ccccc1)C(=O)N1C[C@]2(C[C@H]1C#N)C(=O)Nc1ccccc12] | $[M+Na]^+$ 497.19 | $^1H$ NMR (400 MHz, Chloroform-d) δ 8.26 (s, 1H), 7.32-7.16 (m, 6H), 6.95-6.82 (m, 3H), 5.35 (d, J = 9.0 Hz, 1H), 5.01-4.73 (m, 3H), 4.41 (td, J = 8.5, 4.7 Hz, 1H), 4.19 (d, J = 10.2 Hz, 1H), 3.90 (d, J = 10.2 Hz, 1H), 2.79 (dd, J = 13.1, 9.0 Hz, 1H), 2.45 (dd, J = 13.1, 8.2 Hz, 1H), 1.72 (dd, J = 14.5, 4.8 Hz, 1H), 1.51 (dd, J = 14.5, 8.2 Hz, 1H), 0.90 (s, 9H). |

-continued

| Example # | Structure | MS | NMR |
|---|---|---|---|
| 6 | 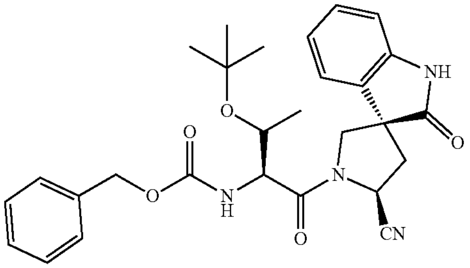 [SMILES: CC(OC(C)(C)C)[C@H](NC(=O)OCc1ccccc1)C(=O)N1C[C@]2(C[C@H]1C#N)C(=O)Nc1ccccc12] | [M + Na]+ 527.22 | $^1$H NMR (400 MHz, Chloroform-d) δ 8.44 (s, 1H), 7.47-7.28 (m, 6H), 7.05 (t, J = 7.6 Hz, 1H), 6.96 (dd, J = 19.5, 7.7 Hz, 2H), 5.87 (d, J = 7.9 Hz, 1H), 5.09 (s, 2H), 4.36 (dd, J = 8.0, 3.7 Hz, 1H), 4.21-4.07 (m, 1H), 4.07-3.92 (m, 2H), 2.87 (dd, J = 13.1, 9.0 Hz, 1H), 2.54 (dd, J = 13.1, 8.2 Hz, 1H), 1.23 (s, 9H), 1.21 (d, J = 6.3 Hz, 3H). |
| 7 | 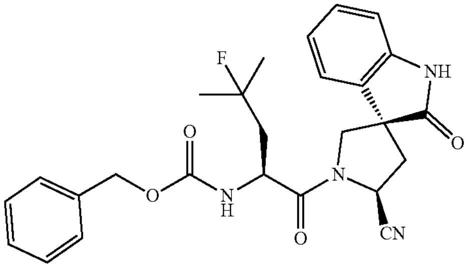 | [M + Na]+ 501.19 | $^1$H NMR (400 MHz, Chloroform-d) δ 8.66 (s, 1H), 7.46-7.20 (m, 6H), 7.07-6.86 (m, 3H), 5.71 (d, J = 8.3 Hz, 1H), 5.08-4.88 (m, 3H), 4.63 (td, J = 8.1, 4.7 Hz, 1H), 4.26-4.13 (m, 1H), 4.00 (d, J = 10.3 Hz, 1H), 2.83 (dd, J = 13.2, 8.4 Hz, 1H), 2.52 (dd, J = 13.2, 8.3 Hz, 1H), 2.08-1.86 (m, 1H), 1.41 (dd, J = 21.4, 4.6 Hz, 6H), 1.26 (s, 1H). |
| 8 | 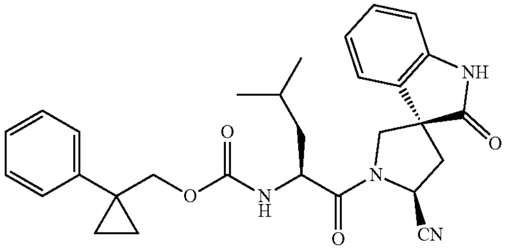 [SMILES: CC(C)C[C@H](NC(=O)OCC1(c2ccccc2)CC1)C(=O)N1C[C@]2(C[C@H]1C#N)C(=O)Nc1ccccc12] | [M + Na]+ 523.24 | $^1$H NMR (400 MHz, Acetone-$d_6$) δ 9.69 (s, 1H), 7.38-7.17 (m, 5H), 7.15-7.06 (m, 1H), 7.06-6.92 (m, 2H), 6.56 (d, J = 8.4 Hz, 1H), 5.15 (t J = 8.3 Hz, 1H), 4.42 (td, J = 9.2, 4.9 Hz, 1H), 4.23 (d, J = 10.3 Hz, 1H), 4.11 (d, J = 11.3 Hz, 1H), 4.10-3.93 (m, 2H), 2.83-2.56 (m, 2H), 1.84-1.53 (m, 3H), 0.94 (m, 8H), 0.92-0.81 (m, 2H). |
| 9 | 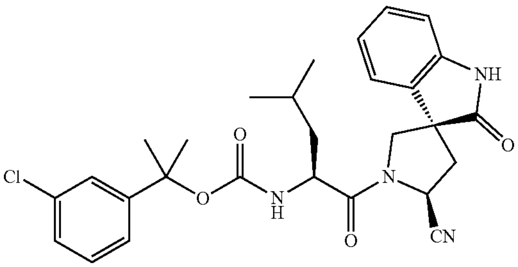 [SMILES: CC(C)C[C@H](NC(=O)OC(C)(C)c1cccc(Cl)c1)C(=O)N1C[C@]2(C[C@H]1C#N)C(=O)Nc1ccccc12] | [M − H]− 521, 523 | $^1$H NMR (400 MHz, Acetone-$d_6$) δ 9.66 (s, 1H), 7.40 (t, J = 1.9 Hz, 1H), 7.38-7.19 (m, 4H), 6.97 (dd, J = 7.5, 1.2 Hz, 2H), 6.93-6.84 (m, 1H), 6.66 (d, J = 8.7 Hz, 1H), 5.11 (t, J = 8.4 Hz, 1H), 4.35 (td, J = 9.5, 4.7 Hz, 1H), 4.14 (d, J = 10.4 Hz, 1H), 3.93 (d, J = 10.3 Hz, 1H), 2.68 (m, 2H), 1.80 (m, 1H), 1.66 (m, 7H), 1.58 (m, 1H), 0.98 (d, J = 6.6 Hz, 3H), 0.91 (d, J = 6.5 Hz, 3H). |
| 10 | 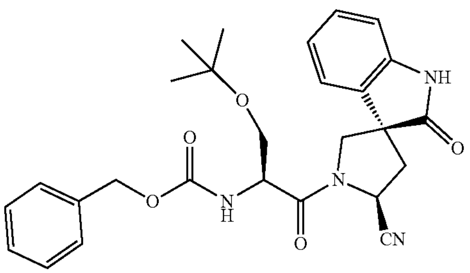 [SMILES: CC(C)(C)OC[C@H](NC(=O)OCc1ccccc1)C(=O)N1C[C@]2(C[C@H]1C#N)C(=O)Nc1ccccc12] | [M + Na]+ 513.20 | |

Example 11 & 12
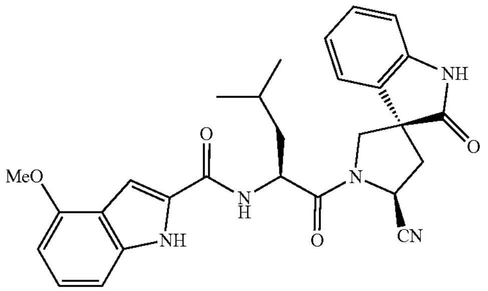
Example 11
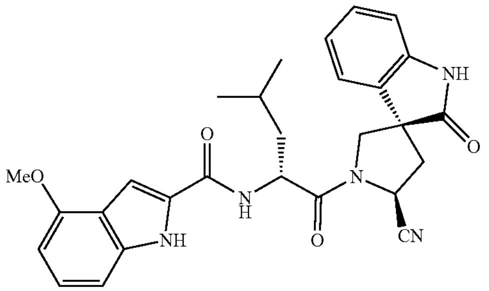
Example 12
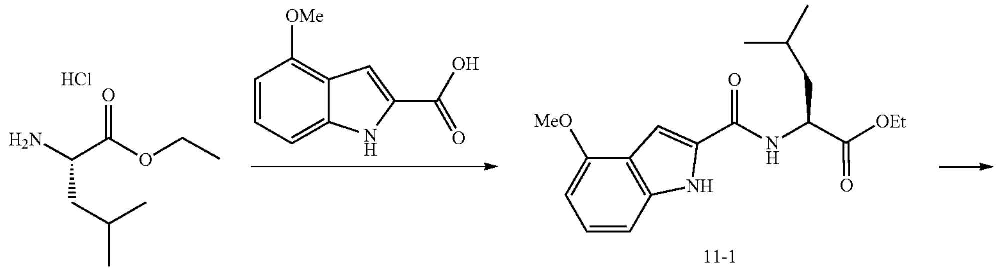
11-1
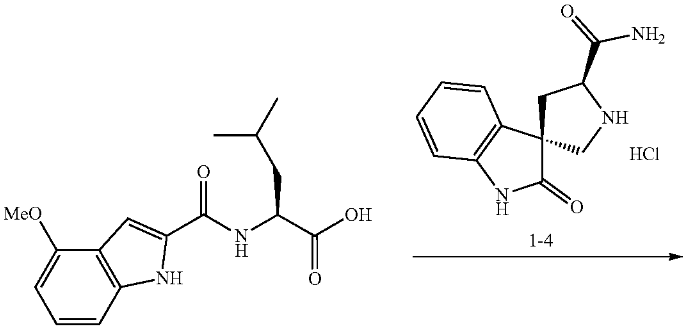
11-2
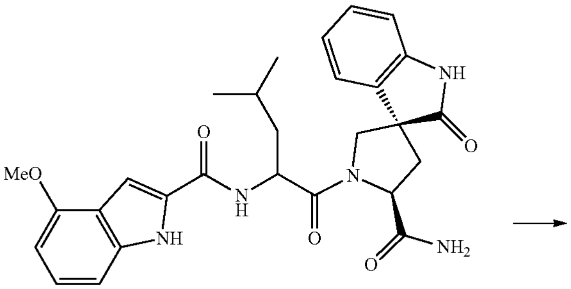
11-3
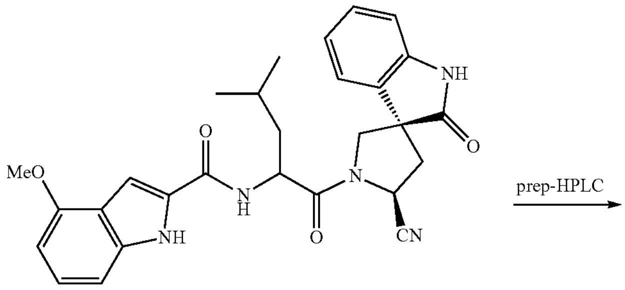
11-4

-continued

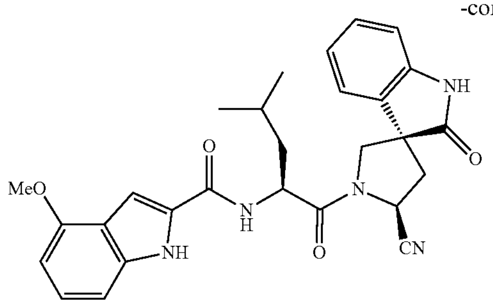

Example 11

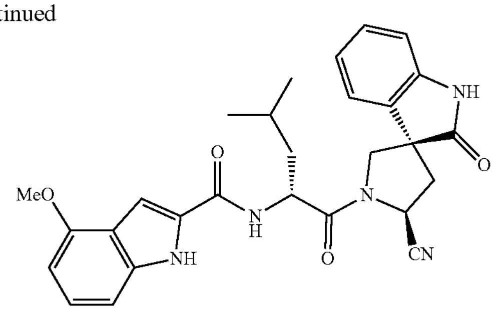

Example 12

Step 1

4-methoxy-1H-indole-2-carboxylic acid (1 g, 5.23 mmol) was dissolved in THF (25 mL). ethyl L-leucinate hydrochloride (1.024 g, 5.23 mmol), hunig'sbase (2.3 mL, 13.08 mmol), DMAP (0.032 g, 0.262 mmol), and HATU (2.0 g, 5.23 mmol) were added sequentially.

The mixture was stirred at rt for 1.5 h, quenched with water, and extracted with MTBE. The organic layer was washed with brine, dried with $MgSO_4$, and concentrated in vacuo. Purification of the residue on silica gel with 0-50% EtOAc/cyclohexane provided compound (11-1) (1.47 g, 4.42 mmol, 85% yield).

Step 2

Compound (11-1) (1.47 g, 4.42 mmol) was dissolved in THF (29.5 mL) and water (14.74 mL). At 0° C. LiOH—$H_2O$ (0.278 g, 6.63 mmol) was added. The mixture was stirred vigorously at 0° C. for 30 min, quenched with 1 M HCl (6.6 mL), and extracted with EtOAc. The organic layer was washed with brine, dried over $MgSO_4$, and concentrated in vacuo. Purification of the residue on silica gel with 0-15% MeOH/DCM provided compound (11-2) (1.32 g).

Step 3

Compound (1-4) (50 mg, 0.187 mmol) and compound (11-2) (56.8 mg, 0.187 mmol) was dissolved in THF (1.6 mL) and DMF (0.3 mL). hunig'sbase (98 μl, 0.560 mmol) and HATU (56.8 mg, 0.149 mmol) were added. The mixture was stirred at rt for 30 min, quenched with water, and extracted with EtOAc. The organic layer was loaded on silica gel and eluted with 0-50% acetone/cyclohexane to provide compound (11-3) (75 mg, 0.145 mmol, 78% yield) as a mixture of two diastereomers.

Step 4

To a suspension of compound (11-3) (67 mg, 0.129 mmol) in DCM (1.3 mL) was added at 0° C. triethylamine (144 μl, 1.036 mmol) and TFAA (73.1 μl, 0.518 mmol). The mixture was warmed to rt and stirred for 10 min. The reaction mixture was diluted with DCM and quenched with sat. $NaHCO_3$. The organic layer was loaded on silica gel and eluted with 0-50% EtOAc/cyclohexane to afford compound (11-4) (48 mg, 0.096 mmol, 74.2% yield) as a mixture of two diastereomers.

Step 5

Purification of compound (11-4) (5 mg) on prep-HPLC with 20-85% MeCN/$H_2O$ with 0.1% formic acid provided Example 11 (1.8 mg) and Example 12 (1.9 mg).

Example 11: $^1H$ NMR (400 MHz, Acetone-$d_6$) δ 10.47 (s, 1H), 9.56 (s, 1H), 7.74 (d, J=8.1 Hz, 1H), 7.21 (d, J=2.2 Hz, 1H), 7.10-6.89 (m, 5H), 6.85 (d, J=7.7 Hz, 1H), 6.76 (td, J=7.5, 1.0 Hz, 1H), 6.41 (dd, J=7.3, 1.1 Hz, 1H), 5.03 (t, J=8.2 Hz, 1H), 4.84-4.74 (m, 1H), 4.23 (d, J=10.2 Hz, 1H), 3.91 (d, J=10.3 Hz, 1H), 3.81 (s, 3H), 2.56 (td, J=13.5, 8.2 Hz, 2H), 1.71 (ddd, J=14.5, 9.9, 3.9 Hz, 2H), 1.58 (ddd, J=13.8, 9.7, 4.9 Hz, 1H), 0.86 (dd, J=11.9, 6.4 Hz, 6H). [M+Na] m/e 522.19.

Example 12: $^1H$ NMR (400 MHz, Acetone-$d_6$) δ 10.75 (s, 0.33H), 10.59 (s, 0.67H), 9.58 (s, 0.67H), 9.54 (s, 0.33H), 8.10 (d, J=7.8 Hz, 0.33H), 7.90 (d, J=8.7 Hz, 0.67H), 7.34-6.71 (m, 8H), 6.42 (m, 1H), 5.90 (t, J=8.0 Hz, 0.33H), 5.06 (t, J=8.3 Hz, 0.67H), 4.98 (ddd, J=11.3, 7.7, 4.0 Hz, 0.33H), 4.83 (td, J=9.1, 4.7 Hz, 0.67H), 4.00 (dd, J=11.7, 1.4 Hz, 0.39H), 3.97-3.87 (m, 1.41H), 3.81 (m, 3H), 3.51 (d, J=11.7 Hz, 0.39H), 2.65-2.49 (m, 1H), 1.91 (s, 2H), 1.71-1.51 (m, 2H), 0.96-0.90 (m, 2H), 0.75 (dd, J=6.3, 4.1 Hz, 4H). [M+Na] m/e 522.19.

The following examples were prepared employing similar protocol as described above.

| Example | Structure | MS | NMR |
|---|---|---|---|
| 13 | 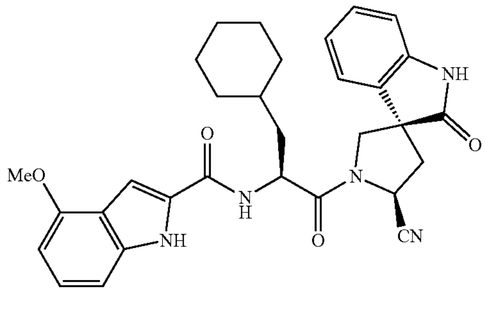 [SMILES: COc1cccc2[nH]c(C(=O)N[C@@H](CC3CCCCC3)C(=O)N3C[C@]4(C[C@H]3C#N)C(=O)Nc3ccccc34)cc12] | [M + H]+ 540.23 | $^1H$ NMR (400 MHz, Chloroform-d) δ 8.92 (s, 1H), 7.86 (s, 1H), 7.18-7.08 (m, 2H), 7.04 (dd, J = 2.2, 0.9 Hz, 1H), 6.95-6.76 (m, 4H), 6.44 (d, J = 7.7 Hz, 1H), 4.99 (t, J = 8.6 Hz, 1H), 4.89-4.79 (m, 1H), 4.17 (t, J = 9.4 Hz, 1H), 3.95 (d, J = 10.3 Hz, 1H), 3.89 (s, 3H), 2.82 (dd, J = 13.1, 8.9 Hz, 1H), 2.48 (dd, J = 13.1, 8.2 Hz, 1H), 1.77 (d, J = 12.8 Hz, 1H), 1.74-1.56 (m, 6H), 1.37 (s, 1H), 1.19 (d, J = 1.6 Hz, 4H), 1.14-1.01 (m, 1H), 0.89-0.76 (m, 1H). |

-continued
| Example | Structure | MS | NMR |
|---|---|---|---|
| 14 | 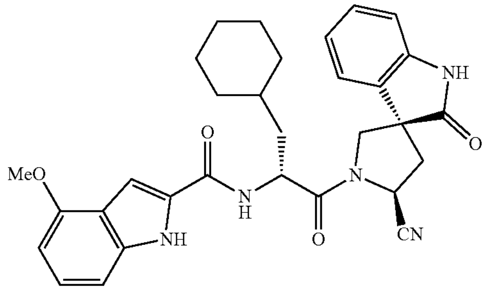 [SMILES: COc1cccc2[nH]c(C(=O)N[C@H](CC3CCCCC3)C(=O)N3C[C@]4(C[C@H]3C#N)C(=O)Nc3ccccc34)cc12] | $[M + H]^+$ 540.26 | |
| 15 | 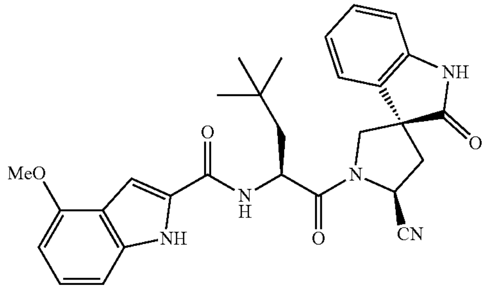 [SMILES: COc1cccc2[nH]c(C(=O)N[C@@H](CC(C)(C)C)C(=O)N3C[C@]4(C[C@H]3C#N)C(=O)Nc3ccccc34)cc12] | $[M + H]^+$ 514.21 | |
| 16 | 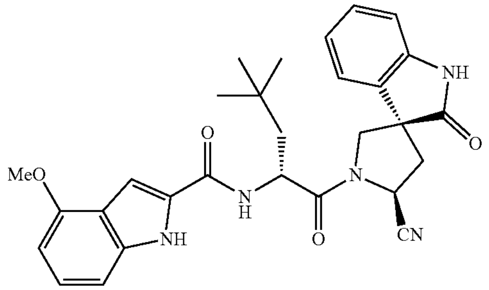 [SMILES: COc1cccc2[nH]c(C(=O)N[C@H](CC(C)(C)C)C(=O)N3C[C@]4(C[C@H]3C#N)C(=O)Nc3ccccc34)cc12] | $[M + Na]^+$ 536.22 | |
Example 17
Example 17
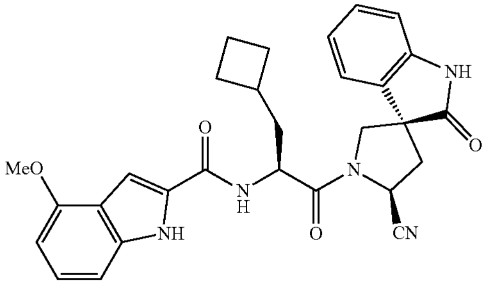
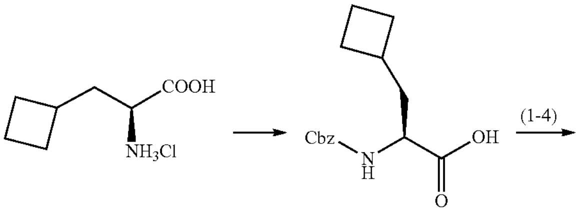
17-1
-continued
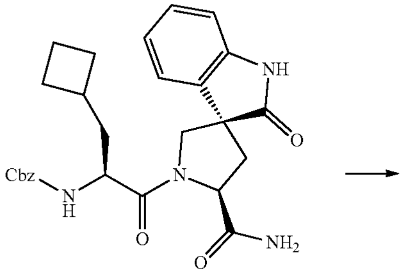
17-2
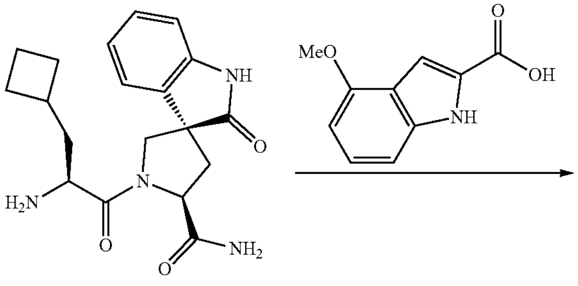
17-3

-continued

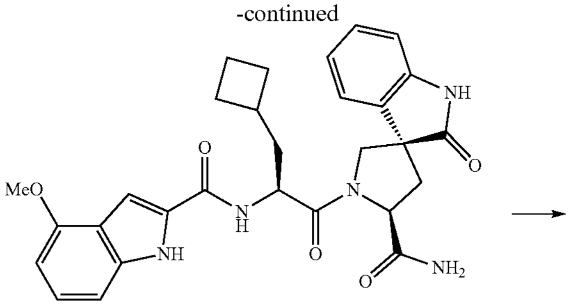

17-4

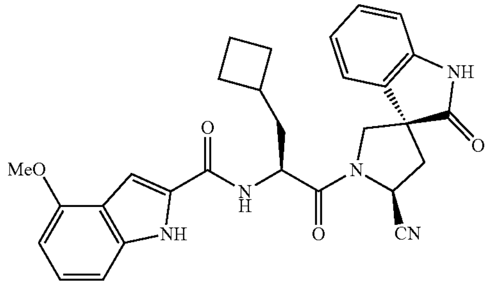

Example 17

Step 1

To a mixture of (2S)-2-amino-3-cyclobutylpropanoic acid hydrochloride (0.359 g, 2 mmol) and NaOH (240 mg, 6.00 mmol) in toluene/water (4 mL/4 mL) at 0° C. was added Cbz-Cl (0.314 ml, 2.200 mmol). After stirring at rt for 2 h, the two layers were separated and the aqueous layer was washed with MBTE. The aqueous layer was then treated with 1 M HCl solution to PH~2. The resulting mixture was extracted with EtOAc. The collected organic layer was washed with brine, dry over $Na_2SO_4$, filtered, and concentrated to give compound (17-1) (0.46 g, 1.659 mmol, 83% yield).

Step 2

To a mixture of compound (17-1) (104 mg, 0.374 mmol), compound (1-4) (80 mg, 0.299 mmol), and DIPEA (183 μl, 1.046 mmol) in DCM/DMF (1.0/0.5 mL) at rt was added HATU (136 mg, 0.359 mmol). The mixture was stirred at rt for 20 h, quenched with water, and extracted with EtOAc. The collected organic layer was washed with 1 N HCl, sat $NaHCO_3$, brine, and dried over $Na_2SO_4$ and filtered. The filtrate was concentrated in vacuo. Purification of the residue on silica gel column provided compound (17-2) (98 mg, 0.200 mmol, 66.9% yield). $[M-H]^-$, 489.16

Step 3

A suspension of (17-2) (25 mg, 0.051 mmol) and Pd—C (5.42 mg, 5.10 μmol) in MeOH (1 mL) was treated with 1 atm $H_2$ for 40 mins. The mixture was diluted with DCM, filtered through celite, washed with DCM, and concentrated in vacuo. The product (17-3) was used in next step directly. $[M-H]^-$, 355.15.

Step 4

To a suspension of 4-methoxy-1H-indole-2-carboxylic acid (15 mg, 0.077 mmol), compound (17-3) (18 mg, 0.051 mmol) and HATU (0.029 g, 0.077 mmol) in DCM (0.3 mL) was added DIPEA (0.031 ml, 0.179 mmol) in DMF (0.3 ML). The mixture was stirred at rt for 1 h, quenched with water, and extracted with EtOAc. The organic layer was washed with 1 N HCl, sat $NaHCO_3$, brine, dried over $Na_2SO_4$, and concentrated in vacuo. Purification of the residue with silica gel column conc afforded compound (17-4) (19 mg, 0.036 mmol, 70.3% yield). $[M-H]^-$, 528.18.

Step 5

To a mixture of compound (17-4) (19 mg, 0.036 mmol) and $Et_3N$ (60.0 μl. 431 mmol) in DCM (0.6 mL) at 0° C. was added TFAA (30.4 μl, 0.215 mmol). The mixture was warmed to rt and stirred for 1 h. The reaction was quenched with cold sat. $NaHCO_3$ and extracted with EtOAc. The organic layer was washed with 1 N HCl, sat $NaHCO_3$ and brine, dried over $Na_2SO_4$, and concentrated. Purification of the residue with silica gel column provided Example 17 (12 mg, 0.023 mmol, 65.4% yield). $[M-H]^-$ 510.17; $^1$H NMR (400 MHz, Methanol-$d_4$) δ 7.26 (d, J=0.9 Hz, 1H), 7.22-7.10 (m, 3H), 7.02 (d, J=8.3 Hz, 1H), 6.99-6.89 (m, 2H), 6.53 (d, J=7.7 Hz, 1H), 5.17 (t, J=7.9 Hz, 1H), 4.71 (dd, J=8.0, 6.4 Hz, 1H), 4.30 (d, J=10.5 Hz, 1H), 4.08 (d, J=10.5 Hz, 1H), 3.96 (s, 3H), 2.75-2.62 (m, 2H), 2.52 (hept, J=7.7 Hz, 1H), 2.20-2.12 (m, 3H), 2.15-2.02 (m, 1H), 2.05-1.88 (m, 2H), 1.90-1.80 (m, 1H), 1.83-1.70 (m, 1H).

The following examples were prepared employing similar protocol as described above.

| Example | Structure | MS | NMR |
|---|---|---|---|
| 18 | 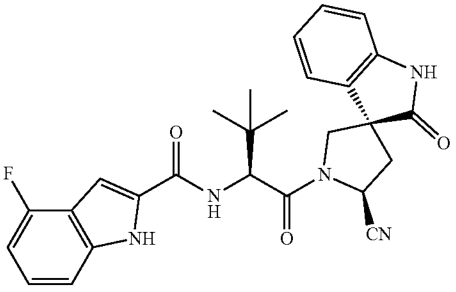 [SMILES: CC(C)(C)[C@H](NC(=O)c1cc2c(F)cccc2[nH]1)C(=O)N1C[C@]2(C[C@H]1C#N)C(=O)Nc1ccccc12] | $[M-H]^-$ 486.15 | $^1$H NMR (400 MHz, Acetone-$d_6$) δ 10.79 (s, 1H), 9.55 (s, 1H), 7.51 (d, J = 9.0 Hz, 1H), 7.34 (dd, J = 2.2, 0.9 Hz, 1H), 7.21 (dd, J = 8.3, 0.8 Hz, 1H), 7.13- 6.96 (m, 2H), 6.94-6.87 (m, 1H), 6.83 (dt, J = 7.8, 0.9 Hz, 1H), 6.72-6.62 (m, 2H), 5.06 (t, J = 8.2 Hz, 1H), 4.71 (d, J = 9.0 Hz, 1H), 4.20 (dd, J = 10.6, 1.0 Hz, 1H), 3.96 (d, J = 10.5 Hz, 1H), 2.69-2.50 (m, 2H), 1.04 (s, 9H). |

-continued

| Example | Structure | MS | NMR |
|---|---|---|---|
| 19 | 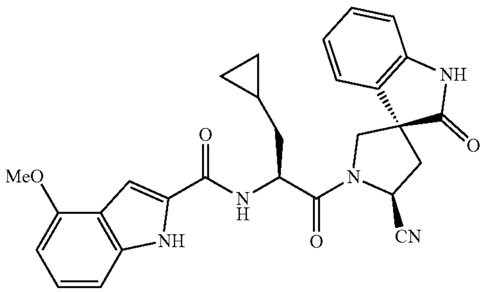 [SMILES: COc1cccc2[nH]c(C(=O)N[C@@H](CC3CC3)C(=O)N3C[C@]4(C[C@H]3C#N)C(=O)Nc3ccccc34)cc12] | [M + Na]+ 520.17 | $^1$H NMR (500 MHz, Chloroform-d) δ 9.28 (s, 1H), 8.51 (s, 1H), 7.44-7.25 (m, 1H), 7.05-6.92 (m, 3H), 6.82 (d, J = 8.3 Hz, 1H), 6.76-6.60 (m, 3H), 6.31 (d, J = 7.7 Hz, 1H), 4.93 (t, J = 8.4 Hz, 1H), 4.78 (q, J = 7.1 Hz, 1H), 4.05 (d, J = 10.4 Hz, 1H), 3.88 (d, J = 10.4 Hz, 1H), 3.76 (s, 3H), 2.69 (dd, J = 13.2, 8.7 Hz, 1H), 2.35 (dd, J = 13.2, 8.3 Hz, 1H), 1.66 (ddt, J = 46.7, 13.5, 6.9 Hz, 2H), 0.64 (dq, J = 12.7, 7.4, 6.3 Hz, 1H), 0.47-0.30 (m, 2H), 0.00 (d, J = 4.9 Hz, 2H). |
| 20 | 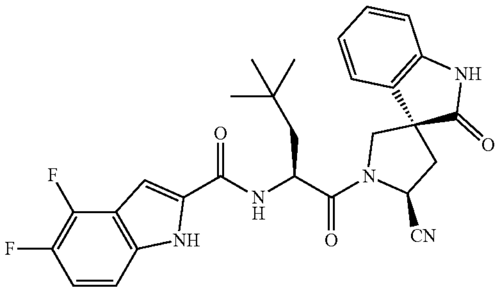 [SMILES: CC(C)(C)C[C@H](NC(=O)c1cc2c(F)c(F)ccc2[nH]1)C(=O)N1C[C@]2(C[C@H]1C#N)C(=O)Nc1ccccc12] | [M + Na]+ 542.18 | $^1$H NMR (400 MHz, Acetone-$d_6$) δ 7.39 (d, J = 0.9 Hz, 1H), 7.35-7.25 (m, 1H), 7.25-7.11 (m, 2H), 7.11-7.02 (m, 1H), 6.95 (d, J = 7.8 Hz, 1H), 6.82 (td, J = 7.6, 1.1 Hz, 1H), 5.16 (t, J = 8.3 Hz, 1H), 4.98 (dd, J = 8.6, 4.1 Hz, 1H), 4.38 (d, J = 10.3 Hz, 1H), 4.05 (d, J = 10.3 Hz, 1H), 3.27 (d, J = 2.2 Hz, 1H), 2.77-2.62 (m, 2H), 1.96-1.74 (m, 2H), 1.03 (s, 9H). |
| 21 | 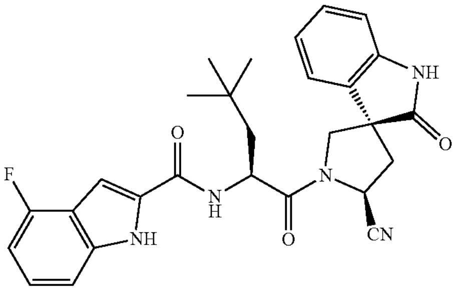 [SMILES: CC(C)(C)C[C@H](NC(=O)c1cc2c(F)cccc2[nH]1)C(=O)N1C[C@]2(C[C@H]1C#N)C(=O)Nc1ccccc12] | [M + H]+ 502.20 | |
| 22 | 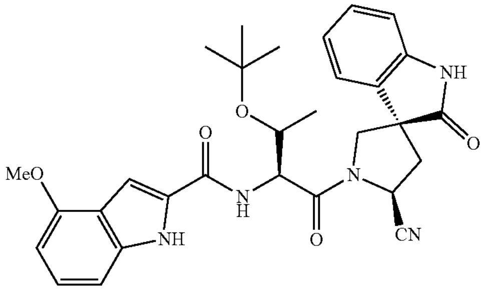 [SMILES: COc1cccc2[nH]c(C(=O)N[C@H](C(=O)N3C[C@]4(C[C@H]3C#N)C(=O)Nc3ccccc34)C(C)OC(C)(C)C)cc12] | [M + H]+ 544.25 | |
| 124 | 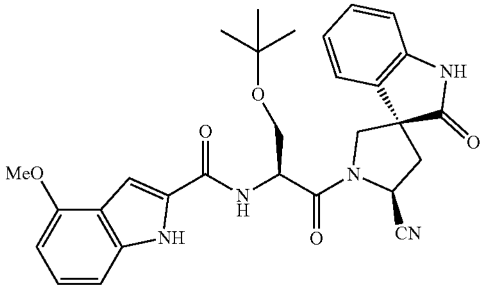 | [M + Na] 552.2 | $^1$H NMR (400 MHz, Chloroform-d) δ 9.73-9.65 (m, 1H), 8.96 (s, 1H), 7.47 (d, J = 7.9 Hz, 1H), 7.17-7.06 (m, 3H), 6.99 (d, J = 8.3 Hz, 1H), 6.92-6.76 (m, 3H), 6.43 (d, J = 7.8 Hz, 1H), 5.28 (s, 2H), 5.12-4.93 (m, 2H), 3.91 (s, 3H), 3.79-3.61 (m, 2H), 2.78 (dd, J = 13.2, 8.8 Hz, 1H), 2.43 (dd, J = 13.2, 8.2 Hz, 1H), 1.19 (s, 9H). |

-continued
| Example | Structure | MS | NMR |
|---|---|---|---|
| 125 | 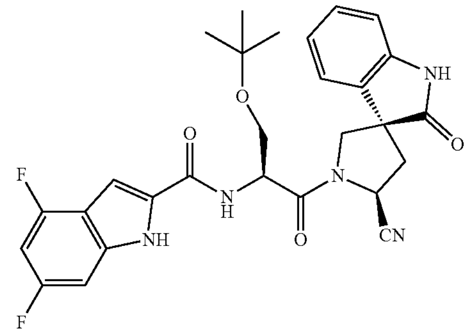 [SMILES: CC(C)(C)OC[C@H](NC(=O)c1cc2c(F)cc(F)cc2[nH]1)C(=O)N1C[C@]2(C[C@H]1C#N)C(=O)Nc1ccccc12] | [M + Na] 558.2 | |
| 126 | 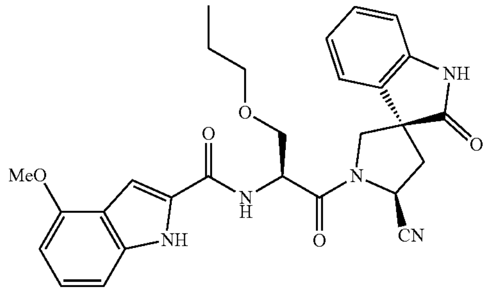 [SMILES: CCCOC[C@H](NC(=O)c1cc2c(OC)cccc2[nH]1)C(=O)N1C[C@]2(C[C@H]1C#N)C(=O)Nc1ccccc12] | [M + H] 516.2 | |
| 127 | 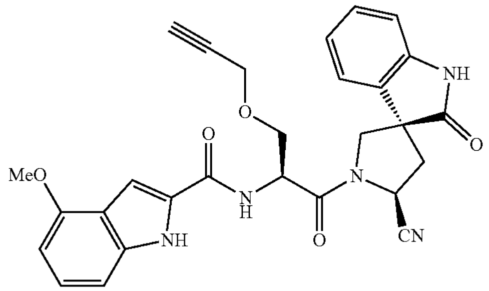 [SMILES: C#CCOC[C@H](NC(=O)c1cc2c(OC)cccc2[nH]1)C(=O)N1C[C@]2(C[C@H]1C#N)C(=O)Nc1ccccc12] | [M + H] 512.2 | |
| 128 | 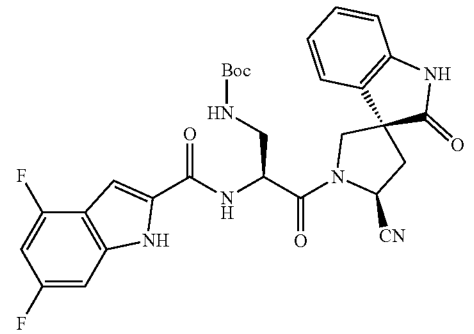 [SMILES: CC(C)(C)OC(=O)NC[C@H](NC(=O)c1cc2c(F)cc(F)cc2[nH]1)C(=O)N1C[C@]2(C[C@H]1C#N)C(=O)Nc1ccccc12] | [M + Na] 601.2 | $^1$H NMR (400 MHz, Methanol-$d_4$) δ 7.10 (d, J = 0.9 Hz, 1H), 7.07-6.99 (m, 2H), 6.88 (ddd, J = 9.3, 2.1, 0.8 Hz, 1H), 6.85-6.74 (m, 3H), 6.57 (td, J = 10.2, 2.0 Hz, 1H), 5.41 (s, 1H), 5.08 (t, J = 7.9 Hz, 1H), 4.88 (dd, J = 7.8, 5.6 Hz, 1H), 4.15 (d, J = 10.7 Hz, 1H), 4.09-3.95 (m, 1H), 3.45 (m, 1H), 2.60 (dd, J = 7.9, 2.3 Hz, 2H), 1.32 (s, 9H). |

-continued

| Example | Structure | MS | NMR |
|---|---|---|---|
| 129 | 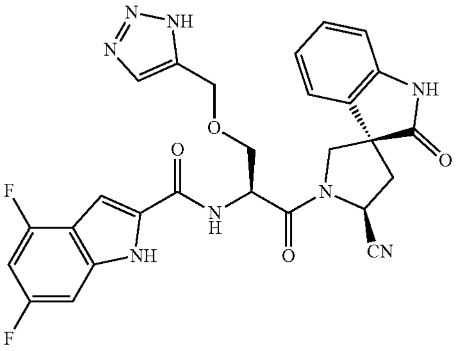 [SMILES: N#C[C@@H]1C[C@@]2(CN1C(=O)[C@H](COCc1cnn[nH]1)NC(=O)c1cc3c(F)cc(F)cc3[nH]1)C(=O)Nc1ccccc12] | [M + H] 561.2 | |
| 130 | 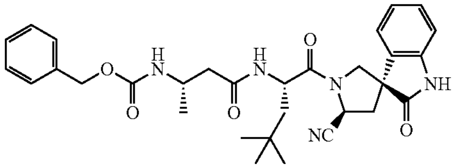 [SMILES: C[C@@H](CC(=O)N[C@@H](CC(C)(C)C)C(=O)N1C[C@]2(C[C@H]1C#N)C(=O)Nc1ccccc12)NC(=O)OCc1ccccc1] | [$M + H^+$] 560.3 | |
| 131 | 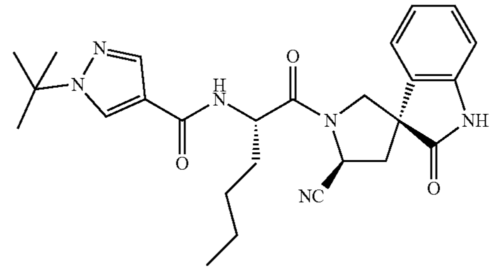 [SMILES: CCCC[C@H](NC(=O)c1cnn(C(C)(C)C)c1)C(=O)N1C[C@]2(C[C@H]1C#N)C(=O)Nc1ccccc12] | 475.24 $(M - H)^-$ | $^1$H NMR (400 MHz, Acetone-$d_6$) δ 9.74 (s, 1H), 8.20 (d, J = 0.7 Hz, 1H), 7.85 (d, J = 0.7 Hz, 1H), 7.54 (d, 8.0 Hz, 1H), 7.22 (td, J = 7.7, 1.2 Hz, 1H), 7.12 (dd, J = 7.5, 1.1 Hz, 1H), 7.02-6.89 (m, 2H), 5.16 (t, J = 8.3 Hz, 1H), 4.80 (td, J = 8.4, 5.7 Hz, 1H), 4.38-4.30 (m, 1H), 4.02 (d, J = 10.5 Hz, 1H), 2.79-2.63 (m, 2H), 1.89 (ddt, J = 13.6, 9.5, 5.9 Hz, 1H), 1.82-1.68 (m, 1H), 1.60 (s, 9H), 1.52-1.20 (m, 4H), 0.91 (t, J = 7.1 Hz, 3H). |
| 132 | 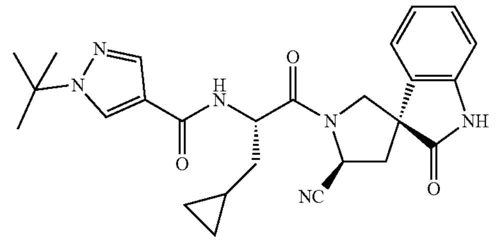 [SMILES: CC(C)(C)n1cc(C(=O)N[C@@H](CC2CC2)C(=O)N2C[C@]3(C[C@H]2C#N)C(=O)Nc2ccccc23)cn1] | 473.23 $(M - H)^-$ | $^1$H NMR (400 MHz, Acetone-$d_6$) δ 9.52 (s, 1H), 7.99 (d, J = 0.7 Hz, 1H), 7.65 (d, J = 0.7Hz, 1H), 7.36 (d, J = 7.7 Hz, 1H), 7.02 (td, J = 7.7, 1.2 Hz, 1H), 6.99-6.92 (m, 1H), 6.81-6.70 (m, 2H), 4.96 (t, J = 8.1 Hz, 1H), 4.66 (q, J = 7.3 Hz, 1H), 4.18 (dd, 10.5, 0.9 Hz, 1H), 3.85 (d, J = 10.5 Hz, 1H), 2.59-2.42 (m, 2H), 1.53 (td, J = 7.1, 2.9 Hz, 2H), 1.38 (s, 9H), 0.74-0.62 (m, 1H), 0.35-0.21 (m, 2H), 0.05-0.05 (m, 2H). |
| 133 | 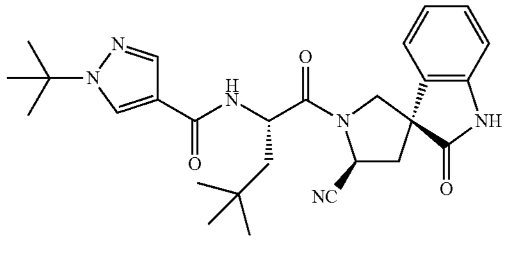 [SMILES: CC(C)(C)C[C@H](NC(=O)c1cnn(C(C)(C)C)c1)C(=O)N1C[C@]2(C[C@H]1C#N)C(=O)Nc1ccccc12] | 489.26 $(M - H)^-$ | $^1$H NMR (400 MHz, Acetone-$d_6$) δ 9.57 (s, 1H), 8.00 (d, J = 0.7 Hz, 1H), 7.69 (d, J = 0.7 Hz, 1H), 7.39 (d, J = 8.5 Hz, 1H), 7.06 (td, J = 7.7, 1.2 Hz, 1H), 6.92 (dd, J = 7.9, 1.0 Hz, 1H), 6.83 (dt, J = 7.8, 0.8 Hz, 1H), 6.74 (td, J = 7.6, 1.0 Hz, 1H), 4.99 (t, J = 8.3 Hz, 1H), 4.80 (td, J = 8.4, 4.4 Hz, 1H), 4.27 (dd, J = 10.4, 1.1 Hz, 1H), 3.95-3.87 (d, J = 10.3 Hz, 1H), 2.64-2.48 (m, 2H), 1.74 (dd, J = 14.4, 4.4 Hz, 1H), 1.56 (dd, J = 14.4, 8.4 Hz, 1H), 1.45 (s, 9H), 0.86 (s, 9H). |
| 134 | 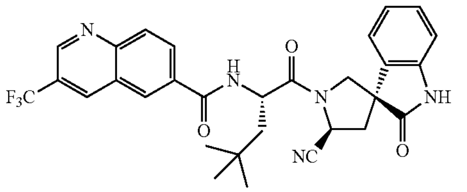 [SMILES: CC(C)(C)C[C@H](NC(=O)c1ccc2ncc(C(F)(F)F)cc2c1)C(=O)N1C[C@]2(C[C@H]1C#N)C(=O)Nc1ccccc12] | 564.53 | |

-continued
| Example | Structure | MS | NMR |
|---|---|---|---|
| 135 | 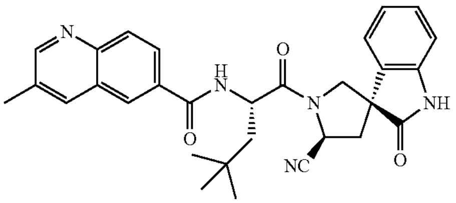 [SMILES: Cc1cnc2ccc(C(=O)N[C@@H](CC(C)(C)C)C(=O)N3C[C@]4(C[C@H]3C#N)C(=O)Nc3ccccc34)cc2c1] | 510.55 | |
| 136 | 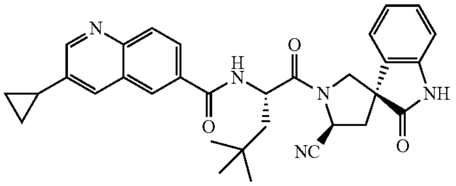 [SMILES: CC(C)(C)C[C@H](NC(=O)c1ccc2ncc(C3CC3)cc2c1)C(=O)N1C[C@]2(C[C@H]1C#N)C(=O)Nc1ccccc12] | 536.57 | |
| 137 | 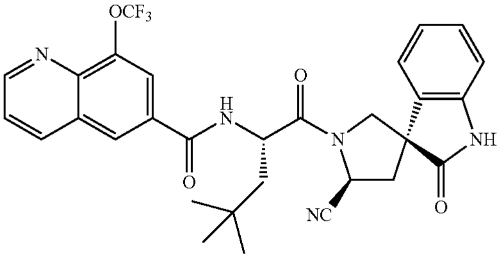 [SMILES: CC(C)(C)C[C@H](NC(=O)c1cc(OC(F)(F)F)c2ncccc2c1)C(=O)N1C[C@]2(C[C@H]1C#N)C(=O)Nc1ccccc12] | 580.53 | |
| 138 | 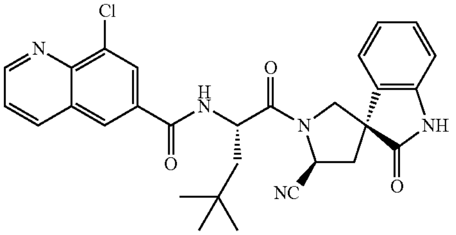 [SMILES: CC(C)(C)C[C@H](NC(=O)c1cc(Cl)c2ncccc2c1)C(=O)N1C[C@]2(C[C@H]1C#N)C(=O)Nc1ccccc12] | 530.47 | |
| 139 | 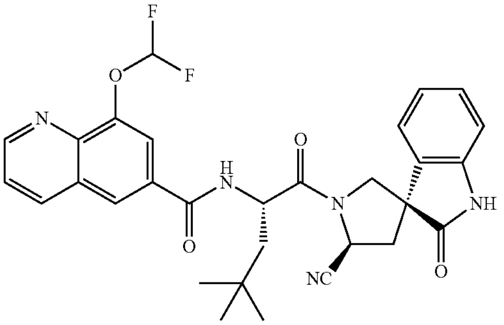 [SMILES: CC(C)(C)C[C@H](NC(=O)c1cc(OC(F)F)c2ncccc2c1)C(=O)N1C[C@]2(C[C@H]1C#N)C(=O)Nc1ccccc12] | 562.51 | |
| 140 | 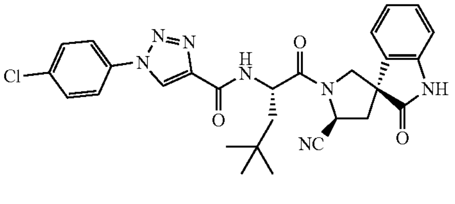 [SMILES: CC(C)(C)C[C@H](NC(=O)c1cn(-c2ccc(Cl)cc2)nn1)C(=O)N1C[C@]2(C[C@H]1C#N)C(=O)Nc1ccccc12] | 544.13 (M − H)⁻ | |

-continued
| Example | Structure | MS | NMR |
|---|---|---|---|
| 141 | 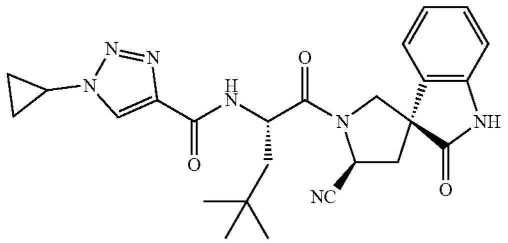 [SMILES: CC(C)(C)C[C@H](NC(=O)c1cn(C2CC2)nn1)C(=O)N1C[C@]2(C[C@H]1C#N)C(=O)Nc1ccccc12] | 474.37 (M − H)⁻ | |
| 142 | 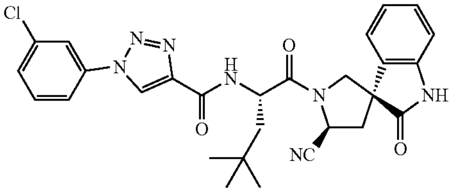 [SMILES: CC(C)(C)C[C@H](NC(=O)c1cn(-c2cccc(Cl)c2)nn1)C(=O)N1C[C@]2(C[C@H]1C#N)C(=O)Nc1ccccc12] | 546.46 | |
| 143 | 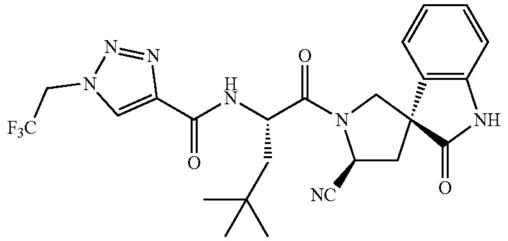 [SMILES: CC(C)(C)C[C@H](NC(=O)c1cn(CC(F)(F)F)nn1)C(=O)N1C[C@]2(C[C@H]1C#N)C(=O)Nc1ccccc12] | 518.44 | |
| 144 | 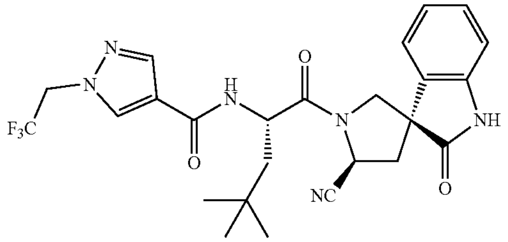 [SMILES: CC(C)(C)C[C@H](NC(=O)c1cnn(CC(F)(F)F)c1)C(=O)N1C[C@]2(C[C@H]1C#N)C(=O)Nc1ccccc12] | 517.42 | |
| 145 | 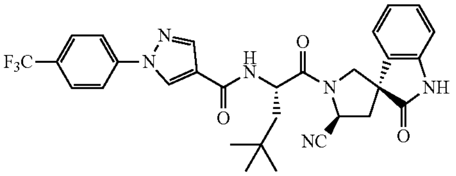 [SMILES: CC(C)(C)C[C@H](NC(=O)c1cnn(-c2ccc(C(F)(F)F)cc2)c1)C(=O)N1C[C@]2(C[C@H]1C#N)C(=O)Nc1ccccc12] | 579.60 | |
| 146 | 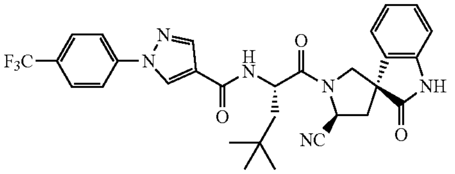 [SMILES: CC(C)(C)C[C@H](NC(=O)c1cnn(-c2ccc(C(F)(F)F)cc2)c1)C(=O)N1C[C@]2(C[C@H]1C#N)C(=O)Nc1ccccc12] | 529.44 | |
| 147 | 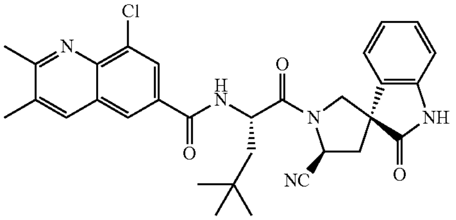 [SMILES: Cc1cc2cc(C(=O)N[C@@H](CC(C)(C)C)C(=O)N3C[C@]4(C[C@H]3C#N)C(=O)Nc3ccccc34)cc(Cl)c2nc1C] | 558.40 | |

-continued
| Example | Structure | MS | NMR |
|---|---|---|---|
| 148 | 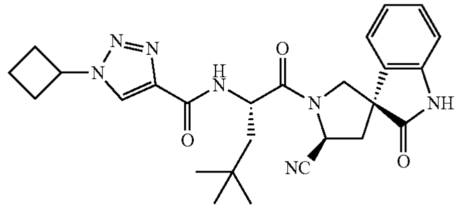 [SMILES: CC(C)(C)C[C@H](NC(=O)c1cn(C2CCC2)nn1)C(=O)N1C[C@]2(C[C@H]1C#N)C(=O)Nc1ccccc12] | 490.31 | |
Example 23
Example 23
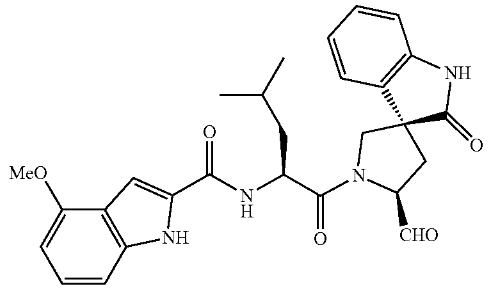
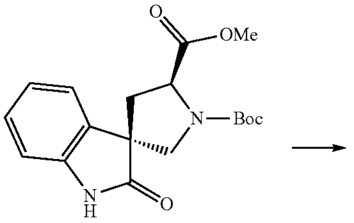
1-2
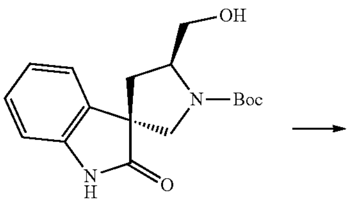
23-1
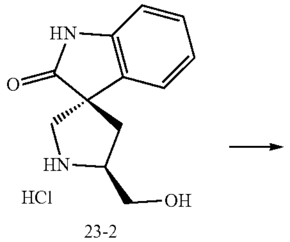
23-2
-continued
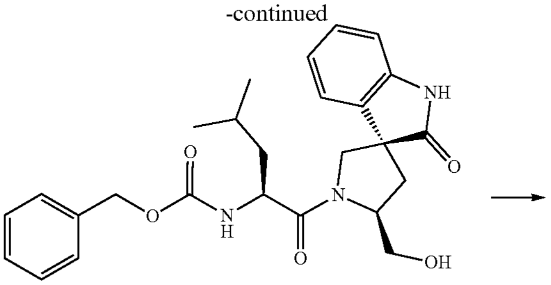
23-3
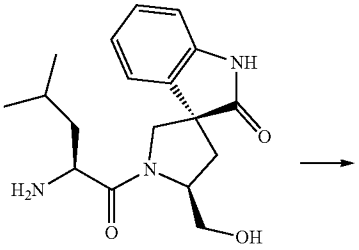
23-4
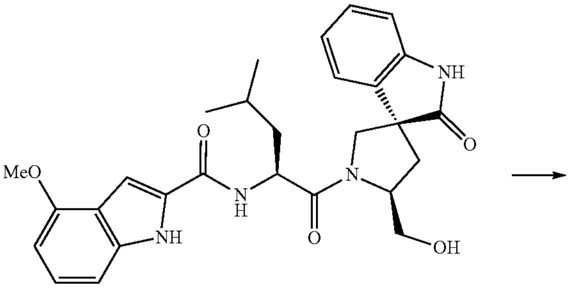
23-5
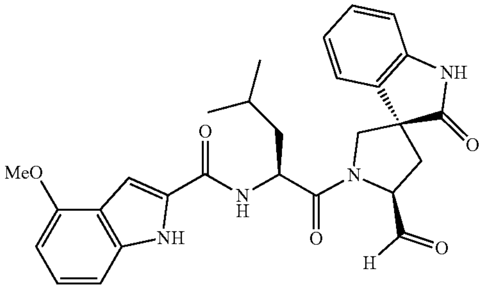
Example 23
Step 1
To a solution of compound (1-2) (2.5 g, 7.22 mmol) in THF (24.06 mL) was added drowpise a solution of 2M $LiBH_4$ in THF (10.83 mL, 21.65 mmol). The mixture was stirred at rt for 2 hrs and the majority of THF was removed in vacuo. The reaction was quenched carefully with 1N HCl to pH=5-6 (~22 mL) and extracted with EtOAc (3×40 mL). The combined organic layers were washed with sat $NaHCO_3$, brine, dried and concentrated. Purification of the residue on silica gel with 0-50% EtOAc/Cyclohexane provided the desired alcohol (23-1) (1.54 g, 67% yield).

Step 2

Compound (23-1) (0.5 g, 1.570 mmol) was dissolved in a solution of 4M HCl in dioxane (3.93 mL, 15.70 mmol. The mixture was stirred at rt for 1 hrs and concentrated to dryness. Compound (23-2) (492 mg, 80% yield) was obtained as a yellow solid. LC-MS, ES+: 218.85 [M+1].

Step 3

To a solution of compound (23-2) (960 mg, 3.13 mmol) and ((benzyloxy)carbonyl)-L-leucine (913 mg, 3.44 mmol) in dry DMF (15.64 mL) at 0° C. was added HATU (1546 mg, 4.07 mmol) and Hunig's base (1912 μl, 10.95 mmol). The resulting mixture was stirred at 0° C. for 1 h, diluted with EtOAc, and washed with 10% citric acid, water, and brine. The organic layer was dried and concentrated. Purification of the residue on silica gel with 0-40% EtOAc/Cyclohexane provided 1.2 g of compound (23-3). LC-MS, ES+: 466.19 [M+1].

Step 4

Compound (23-3) (800 mg, 1.718 mmol) was dissolved in MeOH (17 mL). 10% Pd on carbon (40 mg, 0.038 mmol) was added. The mixture was stirred under hydrogen for 2.5 h, and filtered through a pad of Celite. Solvent was removed and the crude product (23-4) (543 mg, 1.638 mmol, 95% yield), was used for next step. [M+1] 332.20.

Step 5

Compound (23-4) (195 mg, 0.588 mmol) and 4-methoxy-1H-indole-2-carboxylic acid (118 mg, 0.618 mmol) was dissolved in $CH_2Cl_2$ (5.9 mL). At 0° C., Hunig's base (308 μl, 1.765 mmol) and HATU (235 mg, 0.618 mmol) were added. The mixture was stirred at 0° C. for 30 min. The reaction was quenched with water and extracted with DCM. The organic layer was loaded on silica gel and eluted with 0-50% acetone/cyclohexane to afford compound (23-5) (213 mg, 0.422 mmol, 71.7% yield).

Step 6

In a flame dried flask, acetic anhydride (422 μl, 4.46 mmol) was added to anhydrous DMSO (3.10 mL) at rt. After stirring for 10 mins, compound (23-5) (150 mg, 0.297 mmol) was added in one portion. The mixture was stirred at rt for 6 h. The reaction was cooled to 0° C. and diluted with water (~8 mL). The white precipitate was collected by filtration, rinsed with water, and dried under vacuum. Purification of the solid on silica gel with 0-45% acetone/cyclohexane provided Example 23 as a colorless solid (112 mg, 75% yield). $[M+H]^+$503.16. $^1H$ NMR (500 MHz, DMSO-$d_6$) δ 11.52 (d, J=2.3 Hz, 1H), 10.66 (s, 1H), 9.52 (d, J=2.1 Hz, 1H), 8.61 (d, J=7.7 Hz, 1H), 7.40-7.32 (m, 1H), 7.26 (d, J=7.9 Hz, 1H), 7.26-7.18 (m, 1H), 7.17-7.02 (m, 1H), 7.04-6.97 (m, 2H), 6.89 (d, J=8.9 Hz, 1H), 6.52 (t, J=8.4 Hz, 1H), 4.75 (s, 1H), 4.62 (td, J=8.1, 7.1, 3.8 Hz, 1H), 4.11 (d, J=10.5 Hz, 1H), 3.97 (d, J=10.5 Hz, 1H), 3.89 (s, 3H), 3.88 (d, J=7.4 Hz, 1H), 2.41 (dd, J=13.0, 9.0 Hz, 1H), 2.21 (dd, J=13.2, 6.2 Hz, 1H), 1.77 (m, 1H), 1.60 (m, 1H), 0.96 (d, J=7.0 Hz, 3H), 0.89 (d, J=7.0 Hz, 3H).

The following examples were prepared employing similar protocol as described above.

| Example # | Structure | MS | NMR |
|---|---|---|---|
| 24 | 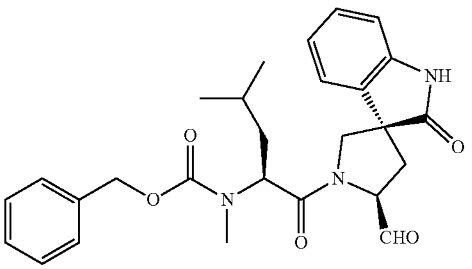 [SMILES: CC(C)C[C@@H](C(=O)N1C[C@]2(C[C@H]1C=O)C(=O)Nc1ccccc12)N(C)C(=O)OCc1ccccc1] | $[M - H]^-$ 476.2 | |
| 25 | 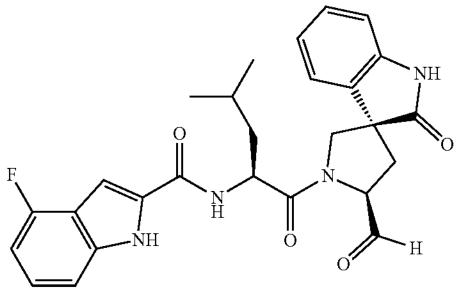 [SMILES: CC(C)C[C@H](NC(=O)c1cc2c(F)cccc2[nH]1)C(=O)N1C[C@]2(C[C@H]1C=O)C(=O)Nc1ccccc12] | $[M + H]^+$ 491.19 | $^1H$ NMR (400 MHz, Acetone-$d_6$) δ 10.99 (s, 1H), 9.65 (d, J = 1.9 Hz, 1H), 9.64 (s, 1H), 8.06-7.96 (m, 1H), 7.42-7.32 (m, 3H), 7.32-7.17 (m, 2H), 7.12-6.90 (m, 2H), 6.81 (dd, J = 10.6, 7.8 Hz, 1H), 5.15-4.98 (m, 1H), 4.80-4.65 (m, 1H), 4.28 (d, J = 10.4 Hz, 1H), 4.13 (d, J = 10.4 Hz, 1H), 2.51 (dd, J = 13.1, 9.1 Hz, 1H), 2.37 (dd, J = 13.1, 6.1 Hz, 1H), 1.92-1.70 (m, 2H), 1.44 (s, 1H), 1.00 (dd, J = 6.5, 4.8 Hz, 6H). |

-continued
| Example # | Structure | MS | NMR |
|---|---|---|---|
| 149 | 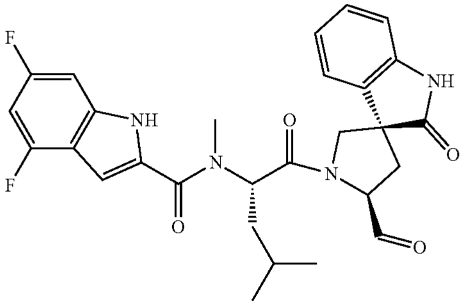 [SMILES: CC(C)C[C@@H](C(=O)N1C[C@]2(C[C@H]1C=O)C(=O)Nc1ccccc12)N(C)C(=O)c1cc2c(F)cc(F)cc2[nH]1] | [M − 1] 521.2 | $^1$H NMR (400 MHz, DMSO-$d_6$) δ 11.99 (d, J = 17.3 Hz, 1H), 10.64 (s, 1H), 9.56 (d, J = 2.1 Hz, 1H), 7.24 (d, J = 7.3 Hz, 1H), 7.16 (t, J = 7.7 Hz, 1H), 7.10-6.85 (m, 4H), 6.85 (d, J = 7.7 Hz, 1H), 5.42 (s, 1H), 4.64 (d, J = 7.8 Hz, 1H), 3.93 (d, J = 10.6 Hz, 1H), 3.83 (d, J = 11.2 Hz, 1H), 3.32 (s, 3H), 2.49-2.42 (m, 1H), 2.25-2.11 (m, 1H), 1.78-1.66 (m, 2H), 1.61-1.51 (m, 1H), 0.96 (td, J = 12.7, 12.1, 6.6 Hz, 6H). |
| 150 | 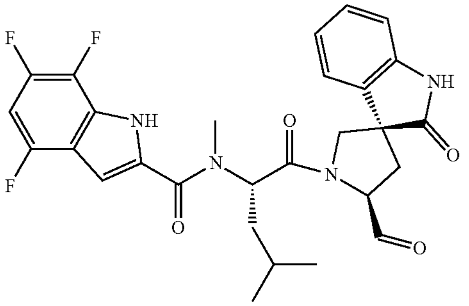 [SMILES: CC(C)C[C@@H](C(=O)N1C[C@]2(C[C@H]1C=O)C(=O)Nc1ccccc12)N(C)C(=O)c1cc2c(F)cc(F)c(F)c2[nH]1] | [M − 1] 539.0 | |
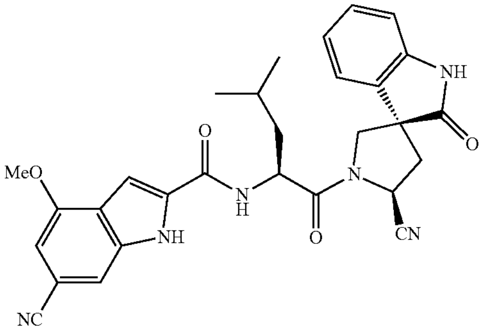 [SMILES: COc1cc(C#N)cc2[nH]c(C(=O)N[C@@H](CC(C)C)C(=O)N3C[C@]4(C[C@H]3C#N)C(=O)Nc3ccccc34)cc12]
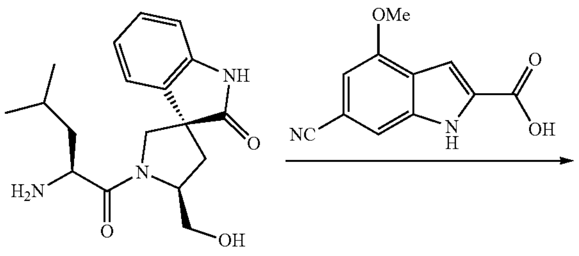
23-4
-continued
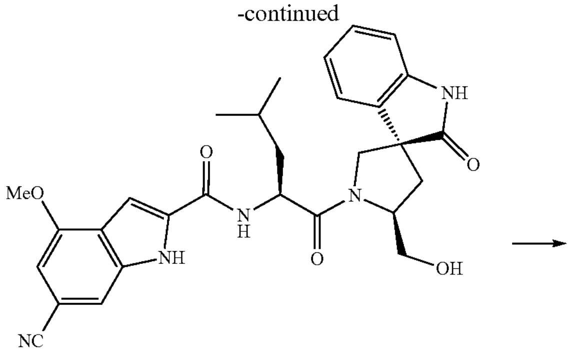
26-1
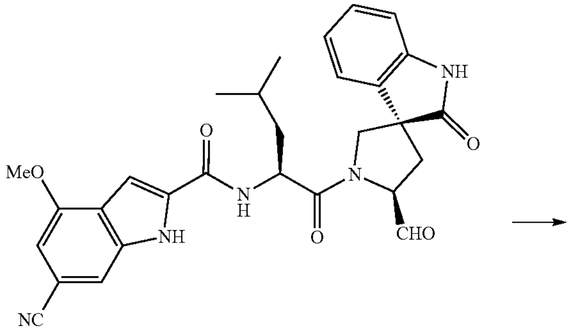
26-2

-continued

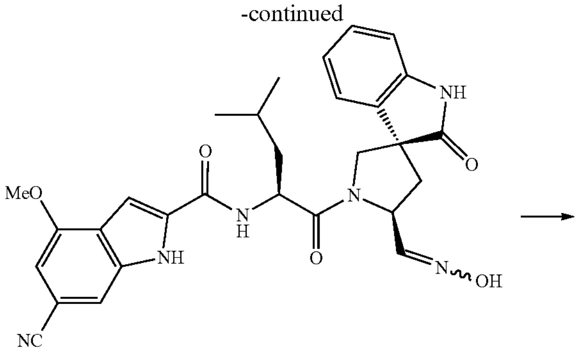

26-3

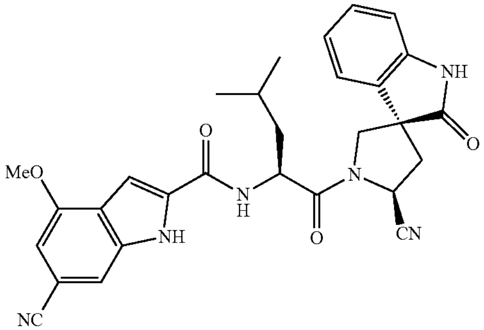

Example 26

Step 1

Compound 23-4 (45 mg, 0.136 mmol) was dissolved in DCM (1.358 mL). DIPEA (48.5 μl, 0.272 mmol), 6-cyano-4-methoxy-1H-indole-2-carboxylic acid (32.3 mg, 0.149 mmol), and HATU (51.6 mg, 0.136 mmol) were added. The mixture was stirred at rt for 1 h, quenched with water, and extracted with DCM. The organic layer was loaded on silica gel and eluted with 0-50% acetone/cyclohexane to afford Compound 26-1 (22 mg, 0.042 mmol, 30.6% yield). $[M-OH]^+$, 512.20.

Step 2

Acetic anhydride (78 μl, 0.831 mmol) was added to DMSO (0.415 mL) at rt. The mixture was stirred at rt for 5 min, and transferred to a vial containing compound 26-1 (22 mg, 0.042 mmol). The reaction mixture was stirred at rt for 6 h, quenched with water at 0° C., and extracted with EtOAc. The organic layer was washed with water, brine, and concentrated. Purification of the residue on silca gel with 0-50% acetone/cyclohexane provided compound 26-2 (15 mg, 0.028 mmol, 68.4% yield). $[M+H]^+$, 528.21.

Step 3

Compound 26-2 (15 mg, 0.028 mmol) was dissolved in 2-propanol. A 1 M solution of hydroxylamine hydrochloride (56.9 μl, 0.057 mmol) in t-BuOH/$H_2O$ (1:1) was added. The mixture was stirred at rt for 30 min, quenched with aq $NaHCO_3$, and extracted with EtOAc. The organic layer was dried over $Na_2SO_4$, and concentrated in vacuo. The crude product, compound 26-3 (14 mg, 0.026 mmol, 91% yield) was used in the next step. $[M+H]^+$, 543.22.

Step 4

To a vial containing compound 26-3 (14 mg, 0.026 mmol) was added MeCN (0.516 mL) and copper (II) acetate (1.406 mg, 7.74 μmol). The resulting mixture was stirred at 70° C. for 2 h, and concentrated in vacuo. Purification of the residue on silica gel with 0-50% EtOAc/cyclohexane, followed by prep-HPLC, provided Example 26 (2.8 mg, 5.34 μmol, 20.69% yield). $[M+H]^+$, 525.22; $^1H$ NMR (400 MHz, Acetone-$d_6$) δ 11.06 (s, 1H), 9.57 (s, 1H), 7.96 (d, J=8.3 Hz, 1H), 7.45 (s, 1H), 7.32 (d, J=1.9 Hz, 1H), 7.08-6.92 (m, 2H), 6.84 (d, J=7.8 Hz, 1H), 6.77-6.68 (m, 2H), 5.03 (t, J=8.3 Hz, 1H), 4.84-4.75 (m, 1H), 4.23 (d, J=10.4 Hz, 1H), 3.91 (m, 5H), 2.58 (qd, J=13.3, 8.4 Hz, 2H), 1.72 (m, 2H), 1.61 (m, 1H), 0.85 (m, 6H).

The following examples were prepared employing similar protocol as described above.

| Example | Structure | MS | NMR |
|---|---|---|---|
| 27 | 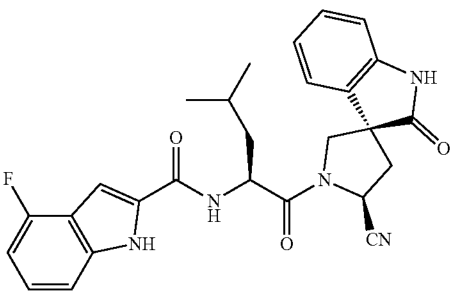 [SMILES: CC(C)C[C@H](NC(=O)c1cc2c(F)cccc2[nH]1)C(=O)N1C[C@]2(C[C@H]1C#N)C(=O)Nc1ccccc12] | $[M + H^+]$ 488.19 | $^1H$ NMR (400 MHz, Acetone-$d_6$) δ 10.78 (s, 1H), 9.56 (s, 1H), 7.90 (d, J = 8.2 Hz, 1H), 7.29-7.19 (m, 2H), 7.12-6.93 (m, 3H), 6.83 (dt, J = 7.8, 0.8 Hz, 1H), 6.73 (td, J = 7.6, 1.1 Hz, 1H), 6.70-6.62 (m, 1H), 5.03 (t, J = 8.3 Hz, 1H), 4.81 (ddd, J = 9.6, 8.2, 4.7 Hz, 1H), 4.21 (dd, J = 10.5, 1.0 Hz, 1H), 3.97-3.87 (m, 1H), 2.66-2.49 (m, 2H), 1.78-1.64 (m, 2H), 1.58 (ddd, J = 13.8, 9.6, 5.0 Hz, 1H), 0.85 (m, 6H). |
| 28 | 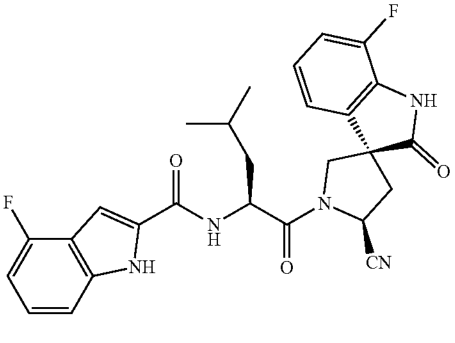 [SMILES: CC(C)C[C@H](NC(=O)c1cc2c(F)cccc2[nH]1)C(=O)N1C[C@]2(C[C@H]1C#N)C(=O)Nc1c(F)cccc12] | $[M + H]^+$ 505.93 | $^1H$ NMR (500 MHz, Acetone-$d_6$) δ 10.90 (s, 1H), 10.10 (s, 1H), 8.01 (d, J = 8.2 Hz, 1H), 7.37-7.34 (m, 1H), 7.21 (m, 1H), 7.03-6.97 (m, 1H), 6.95 (d, J = 7.4 Hz, 1H), 6.85 (ddd, J = 8.4, 7.5, 4.8 Hz, 1H), 6.82-6.77 (m, 1H), 5.17 (t, J = 8.3 Hz, 1H), 4.93 (ddd, J = 9.6, 8.3, 4.7 Hz, 1H), 4.42 (dd, J = 10.6, 1.2 Hz, 1H), 4.06 (d, J = 10.5 Hz, 1H), 2.80-2.76 (m, 1H), 2.70 (dd, J = 13.3, 8.1 Hz, 1H), 1.86-1.78 (m, 2H), 1.71 (m, 1H), 0.97 (m, 6H). |

-continued

| Example | Structure | MS | NMR |
|---|---|---|---|
| 151 | 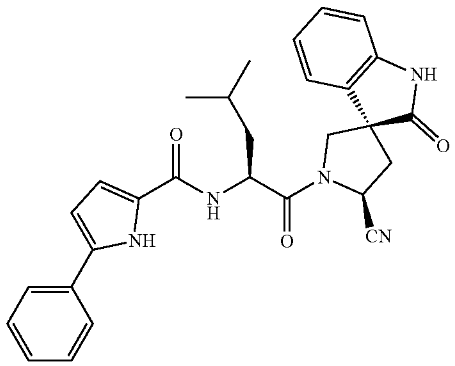 [SMILES: CC(C)C[C@H](NC(=O)c1ccc(-c2ccccc2)[nH]1)C(=O)N1C[C@]2(C[C@H]1C#N)C(=O)Nc1ccccc12] | [M + Na$^+$] 518.2 | |
| 152 | 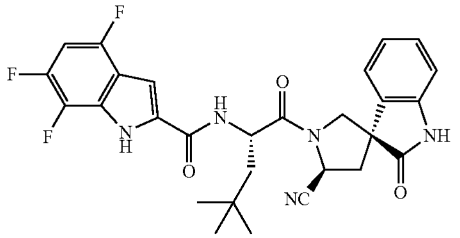 [SMILES: CC(C)(C)C[C@H](NC(=O)c1cc2c(F)cc(F)c(F)c2[nH]1)C(=O)N1C[C@]2(C[C@H]1C#N)C(=O)Nc1ccccc12] | [M + Na$^+$] 546.2 | $^1$H NMR (400 MHz, Acetone-$d_6$) δ 11.49 (s, 1H), 9.70 (s, 1H), 8.10 (d, J = 8.2 Hz, 1H), 7.41 (d, J = 2.7 Hz, 1H), 7.26-7.07 (m, 2H), 7.07-6.89 (m, 2H), 6.93-6.83 (m, 1H), 5.19 (t, J = 8.3 Hz, 1H), 4.97 (ddd, J = 9.6, 8.3, 4.7 Hz, 1H), 4.37-4.25 (m, 1H), 4.12-3.93 (m, 2H), 2.80-2.71 (m, 1H), 2.75-2.64 (m, 1H), 1.91-1.68 (m, 2H), 1.13-0.86 (m, 6H). |

Example 29

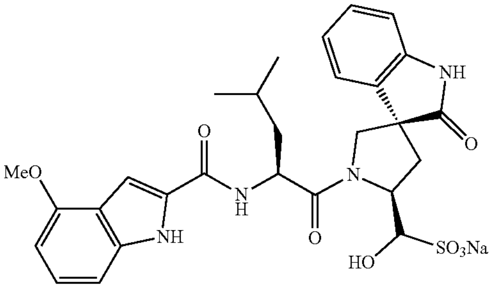

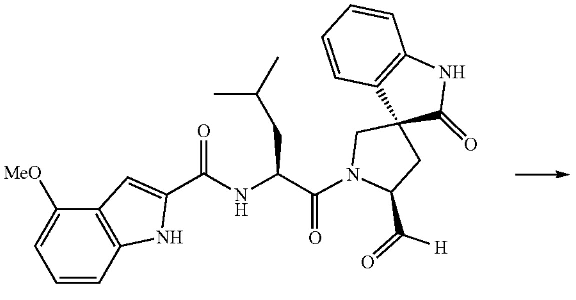

-continued

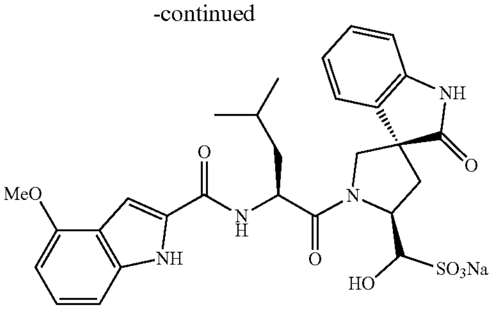

To a solution of Example 23 (45 mg, 0.090 mmol) in EtOH (2 mL) and water (0.2 mL) was added sodium bisulfate (9.32 mg, 0.090 mmol). The mixture was stirred at rt for 4 h and then concentrated. DCM was added to the residue and white solid precipitated. The collected solid was washed with acetone and dried to afford Example 29 as a white solid. [M−Na]$^-$ 583.0. $^1$H NMR (500 MHz, DMSO-$d_6$) δ 11.42 (s, 1H), 10.57 (d, J=7.9 Hz, 1H), 9.88 (s, 1H), 8.47 (d, J=8.2 Hz, 1H), 7.35-7.31 (m, 1H), 7.14-7.05 (m, 2H), 7.02-6.96 (m, 1H), 6.86 (ddt, J=24.0, 15.0, 8.1 Hz, 3H), 6.50 (d, J=7.7 Hz, 1H), 5.65 (d, J=5.5 Hz, 1H), 4.83-4.78 (m, 1H), 4.70 (t, J=9.3 Hz, 2H), 3.96 (d, J=9.3 Hz, 1H), 3.90 (s, 3H), 3.61 (d, J=9.8 Hz, 1H), 2.79 (dd, J=13.1, 9.8 Hz, 1H), 1.81-1.67 (m, 3H), 0.99 (td, J=15.4, 7.0 Hz, 1H), 0.90 (d, J=6.4 Hz, 3H), 0.85 (d, J=6.1 Hz, 3H).

The following example was prepared employing similar protocol as described above.

| Example | Structure | MS |
|---|---|---|
| 30 | 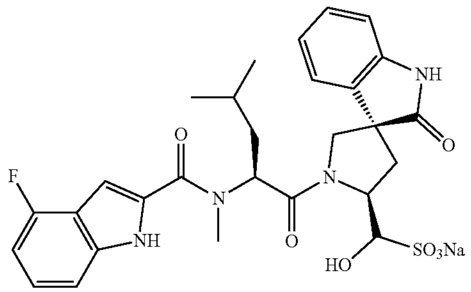 | [M − Na]⁻ 585.1 |
| 153 | 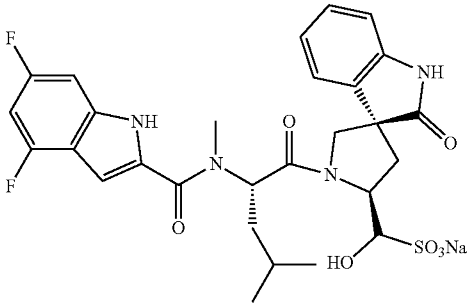 | [M − 23] 602.91 |
| 154 | 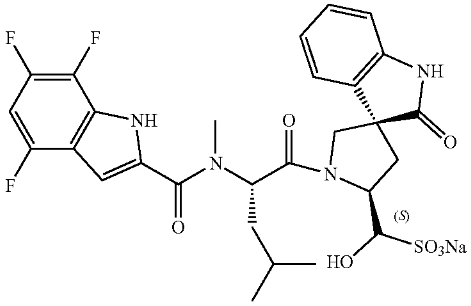 | [M − 23] 620.93 |

Example 31

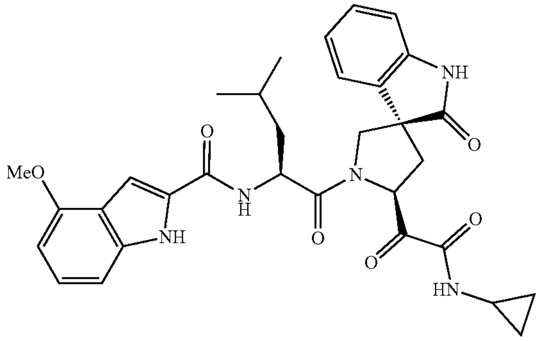

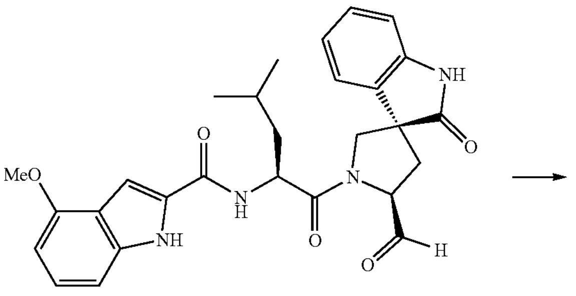

Example 23

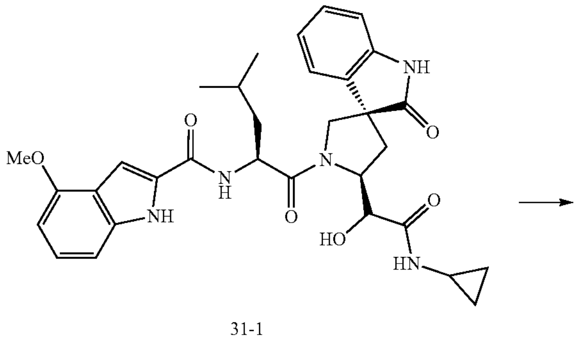

31-1

-continued

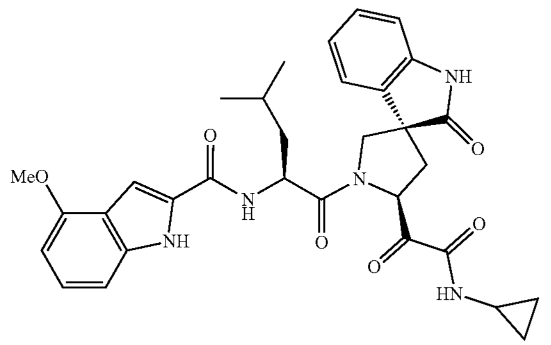

Example 31

Step 1

To Example 23 (18 mg, 0.036 mmol) at 0° C. was added acetic acid (2.4 μl, 0.041 mmol) and a solution of isocyanocyclopropane (2.64 mg, 0.039 mmol) in DCM (0.20 mL). The mixture was stirred at 0° C. to rt for 5 h. The reaction mixture was concentrated to dryness and redissolved in MeOH (0.35 mL). A 0.5 M solution of $K_2CO_3$ in water (179 μl, 0.090 mmol) was added. The mixture was stirred at rt for 2 h. MeOH was removed in vacuo and the aqueous layer was extracted with EtOAc (3×). The combined organic layer was washed with water and brine, dried, and concentrated. The crude product (31-1) was directly used in the next step. [M+1], 588.2.

Step 2

To a solution of compound (31-1) in DCM (0.360 mL) at 0° C. was added Dess-Martin Periodinane (0.023 g, 0.054 mmol). The mixture was stirred at 0° C. for 2.5 h. At 0° C., the reaction mixture was diluted with DCM, quenched with 10% $Na_2S_2O_3$, and washed with 5% $NaHCO_3$. The collected organic layer was washed with water and brine, dried, and concentrated. Purification of the residue on silica gel with 0-60% acetone/cyclohexane provided Example 31 (6.5 mg). $[M-1]^-$ 584.07. $^1H$ NMR (400 MHz, Acetone-$d_6$) δ 10.62 (s, 1H), 9.67 (s, 1H), 7.90 (d, J=4.9 Hz, 1H), 7.78 (d, J=8.2 Hz, 1H), 7.31 (dd, J=2.3, 0.8 Hz, 1H), 7.29-7.10 (m, 4H), 7.14-6.95 (m, 2H), 6.92 (td, J=7.6, 1.1 Hz, 1H), 6.53 (dd, J=7.2, 1.2 Hz, 1H), 5.69-5.54 (m, 1H), 4.93 (td, J=8.4, 6.0 Hz, 1H), 4.34 (d, J=9.9 Hz, 1H), 4.02 (d, J=9.9 Hz, 1H), 3.94 (s, 3H), 4.00-3.86 (m, 1H), 2.92-2.78 (m, 1H), 2.52-2.38 (m, 2H), 1.89 (dt, J=12.9, 6.5 Hz, 1H), 1.72 (ddd, J=8.1, 5.7, 2.3 Hz, 2H), 1.13-0.93 (m, 6H), 0.83-0.65 (m, 4H).

The following examples were prepared employing similar protocol as described above.

| Example | Structure | MS | NMR |
|---|---|---|---|
| 32 | 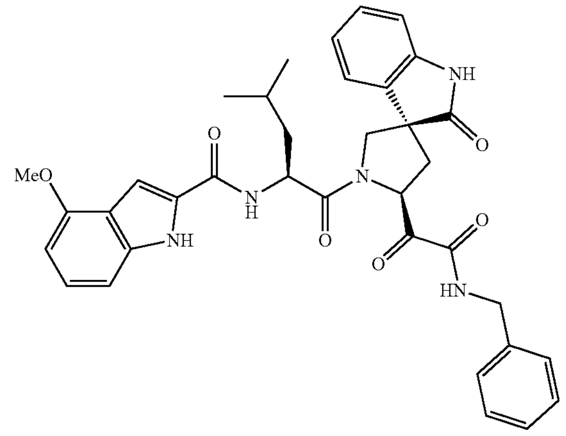 [SMILES: COc1cccc2[nH]c(C(=O)N[C@@H](CC(C)C)C(=O)N3C[C@]4(C[C@H]3C(=O)C(=O)NCc3ccccc3)C(=O)Nc3ccccc34)cc12] | [M − H]⁻ 634.0 | $^1$H NMR (500 MHz, DMSO-$d_6$) δ 11.49 (d, J = 2.4 Hz, 1H), 10.74 (s, 1H), 9.37 (t, J = 6.4 Hz, 1H), 8.53 (d, J = 7.5 Hz, 1H), 7.40-7.26 (m, 4H), 7.28-7.20 (m, 3H), 7.15 (d, J = 7.3 Hz, 1H), 7.10 (t, J = 8.0 Hz, 1H), 7.06-6.88 (m, 3H), 6.51 (d, J = 7.7 Hz, 1H), 5.44 (dd, J = 10.5, 7.7 Hz, 1H), 4.71-4.63 (m, 1H), 4.39-4.28 (m, 2H), 4.19 (d, J = 10.2 Hz, 1H), 3.89 (s, 3H), 3.88-3.80 (m, 1H), 2.35-2.27 (m, 1H), 2.25 (dd, J = 12.6, 10.4 Hz, 1H), 1.80-1.64 (m, 2H), 1.50 (ddd, J = 13.5, 8.8, 4.3 Hz, 1H), 0.94 (d, J = 6.5 Hz, 3H), 0.88 (d, J = 6.5 Hz, 3H). |
| 33 | 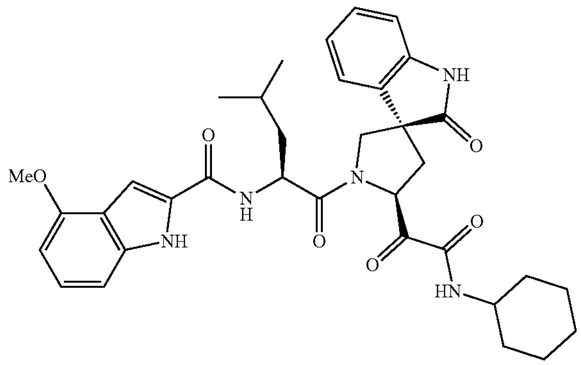 | [M − H]⁻ 626.1 | $^1$H NMR (500 MHz, DMSO-$d_6$) δ 11.48 (d, J = 2.3 Hz, 1H), 10.73 (s, 1H), 8.64 (d, J = 8.4 Hz, 1H), 8.52 (d, J = 7.4 Hz, 1H), 7.35 (dd, J = 2.4, 0.9 Hz, 1H), 7.22 (qd, J = 7.5, 1.2 Hz, 1H), 7.13 (d, J = 7.5 Hz, 1H), 7.09 (t, J = 7.9 Hz, 1H), 7.03-6.90 (m, 3H), 6.50 (d, J = 7.7 Hz, 1H), 5.37 (dd, J = 10.3, 7.8 Hz, 1H), 4.66 (ddd, J = 10.6, 7.3, 4.1 Hz, 1H), 4.17 (d, J = 10.1 Hz, 1H), 3.89 (s, 3H), 3.87-3.79 (m, 1H), 3.56 (s, 1H), 2.34-2.21 (m, 2H), 1.77 (s, 1H), 1.70 (d, J = 12.1 Hz, 6H), 1.61-1.46 (m, 2H), 1.33 (q, J = 11.3 Hz, 2H), 1.26 (s, 3H), 0.94 (d, J = 6.6 Hz, 3H), 0.88 (d, J = 6.5 Hz, 3H). |
| 34 | 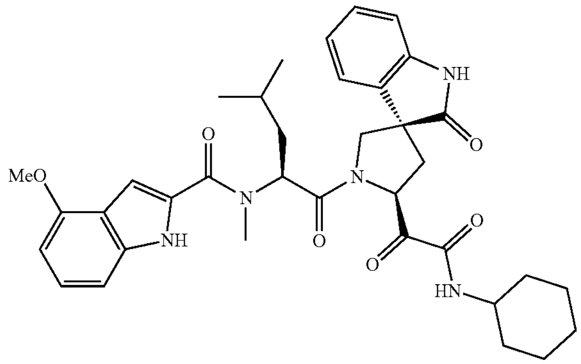 [SMILES: COc1cccc2[nH]c(C(=O)N(C)[C@@H](CC(C)C)C(=O)N3C[C@]4(C[C@H]3C(=O)C(=O)NC3CCCCC3)C(=O)Nc3ccccc34)cc12] | [M − H]⁻ 640.2 | $^1$H NMR (500 MHz, DMSO-$d_6$) δ 11.44 (s, 1H), 10.70 (s, 1H), 8.69 (d, J = 8.4 Hz, 1H), 7.12 (dt, J = 24.9, 8.1 Hz, 3H), 6.93 (q, J = 7.6, 6.8 Hz, 2H), 6.85 (d, J = 7.8 Hz, 1H), 6.70 (s, 1H), 6.50 (d, J = 7.6 Hz, 1H), 5.40 (dd, J = 10.2, 8.0 Hz, 1H), 5.33 (s, 1H), 3.93 (s, 1H), 3.89 (s, 3H), 3.84 (d, J = 10.0 Hz, 1H), 3.57 (d, J = 10.5 Hz, 2H), 3.25 (s, 3H), 2.34 (dd, J = 12.9, 8.2 Hz, 1H), 1.71 (s, 6H), 1.57 (s, 3H), 1.35-1.22 (m, 5H), 0.96 (d, J = 6.3 Hz, 3H), 0.90 (d, J = 6.1 Hz, 3H). |
| 35 | 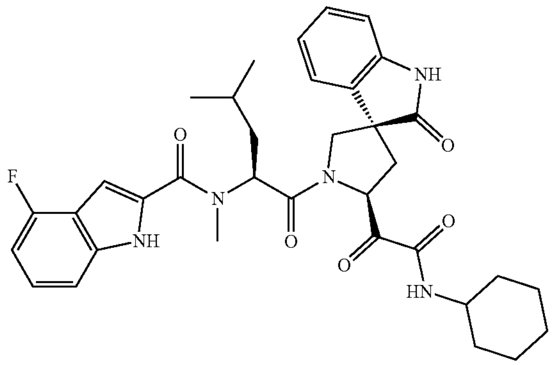 [SMILES: CC(C)C[C@@H](C(=O)N1C[C@]2(C[C@H]1C(=O)C(=O)NC1CCCCC1)C(=O)Nc1ccccc12)N(C)C(=O)c1cc2c(F)cccc2[nH]1] | [M − H]⁻ 628.02 | |

-continued
| Example | Structure | MS | NMR |
|---|---|---|---|
| 36 | 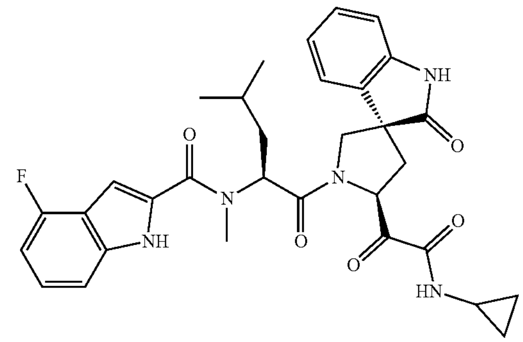 [SMILES: CC(C)C[C@@H](C(=O)N1C[C@]2(C[C@H]1C(=O)C(=O)NC1CC1)C(=O)Nc1ccccc12)N(C)C(=O)c1cc2c(F)cccc2[nH]1] | [M − H]⁻ 586.12 | 1H NMR (500 MHz, Acetone-d6) δ 10.72 (s, 1H), 9.64 (s, 1H), 7.95 (d, J = 4.9 Hz, 1H), 7.32 (d, J = 8.3 Hz, 1H), 7.23-7.15 (m, 2H), 7.11 (t, J = 7.7 Hz, 1H), 6.96-6.86 (m, 3H), 6.79 (dd, J = 10.5, 7.7 Hz, 1H), 5.60 (dd, J = 10.3, 8.1 Hz, 1H), 5.53 (t, J = 7.5 Hz, 1H), 4.21 (d, J = 9.5 Hz, 1H), 3.96 (d, J = 10.1 Hz, 1H), 3.44 (s, 3H), 2.93-2.87 (m, 1H), 2.44 (dd, J = 8.1, 1.4 Hz, 1H), 2.38 (dd, J = 12.7, 10.3 Hz, 1H), 1.82 (dt, J = 14.0, 7.2 Hz, 1H), 1.79-1.67 (m, 2H), 1.67-1.58 (m, 1H), 0.99 (dd, J = 27.9, 6.6 Hz, 6H), 0.84-0.69 (m, 4H). |
| 155 | 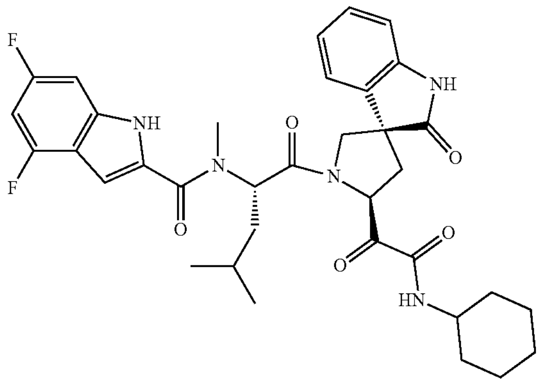 [SMILES: CC(C)C[C@@H](C(=O)N1C[C@]2(C[C@H]1C(=O)C(=O)NC1CCCCC1)C(=O)Nc1ccccc12)N(C)C(=O)c1cc2c(F)cc(F)cc2[nH]1] | [M − 1] 646.3 | |
| 156 | 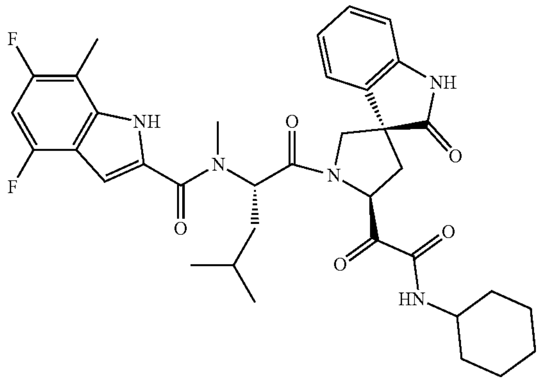 [SMILES: Cc1c(F)cc(F)c2cc(C(=O)N(C)[C@@H](CC(C)C)C(=O)N3C[C@]4(C[C@H]3C(=O)C(=O)NC3CCCCC3)C(=O)Nc3ccccc34)[nH]c12] | [M − 1] 664.0 | |

Example 37

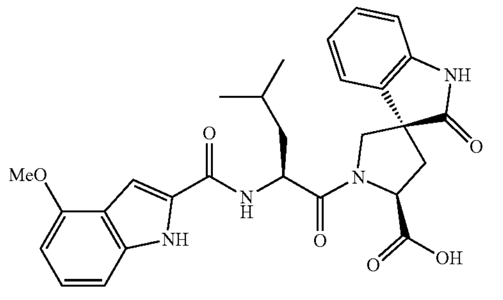

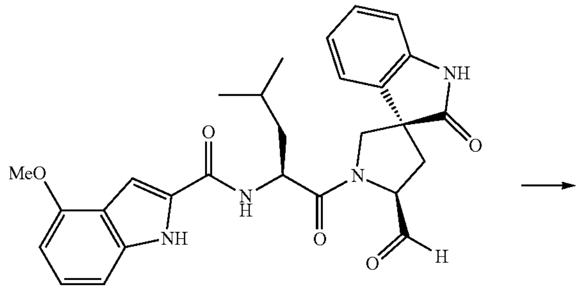

Example 23

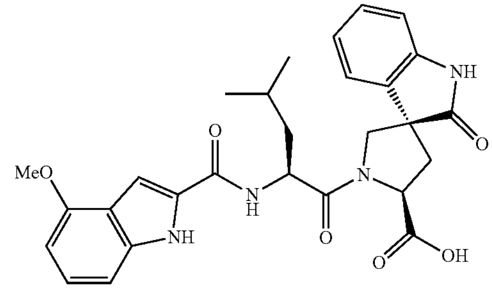

Example 37

To a mixture of Example 23 (105 mg, 0.209 mmol) in tert-butanol (2.79 mL) at rt was added 2-methyl-2-butene, 2M in THF (2.09 mL, 4.18 mmol) to achieve a clear solution. A solution of sodium chlorite (236 mg, 2.089 mmol) and sodium phosphate monobasic (251 mg, 2.089 mmol) in water (1.39 mL) was added dropwise over 10 minutes. After stirring at rt for 1 h, the reaction mixture was concentrated to remove most of the volatiles. The resulting mixture was diluted with EtOAc, washed with water, brine, dried and concentrated. Purification of the residue on silica gel chromatography with 0-10% MeOH/DCM provided Example 37 (40 mg, 36% yield). LC-MS, $ES^-$: 516.94 $[M-H]^-$.

Example 38

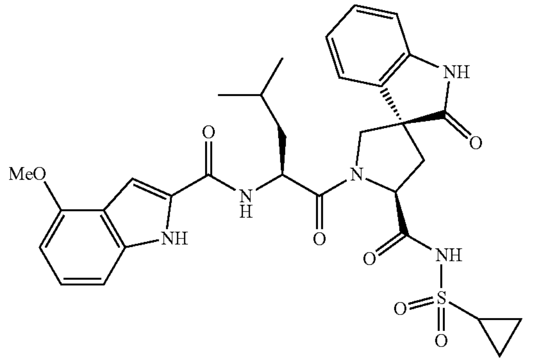

A solution of Example 37 (18 mg, 0.035 mmol), cyclopropanesulfonamide (8.41 mg, 0.069 mmol), EDCI (7.2 mg, 0.038 mmol) and DMAP (4.59 mg, 0.038 mmol) in dry DCM was stirred at rt for 4 hrs. The reaction mixture was diluted with DCM, washed with brine, dried, and concentrated. The residue was purified by chromatography on silica gel using 0 to 50% acetone/cyclohexane to give Example 38 (3.5 mg, 16% yield) as a white solid. LC-MS, ES−: 619.80 $[M-H]^-$.

Example 157

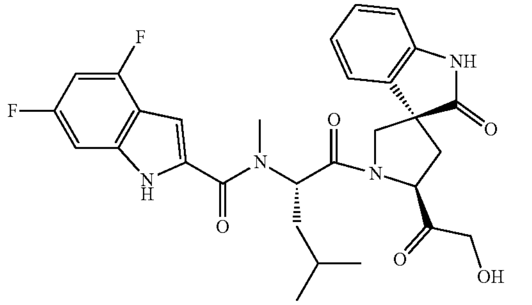

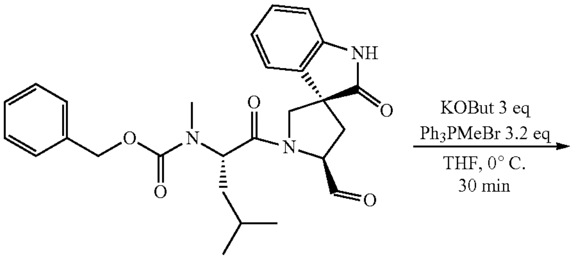

157-1

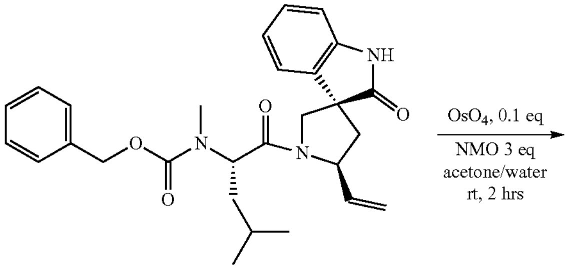

157-2

-continued

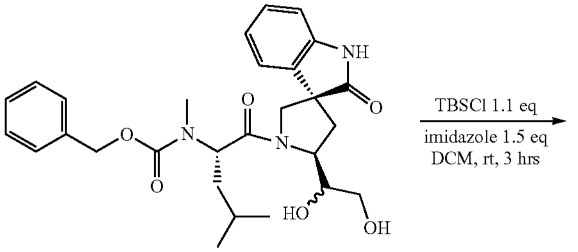

157-3

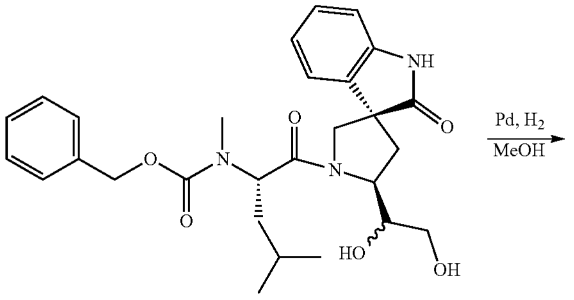

157-4

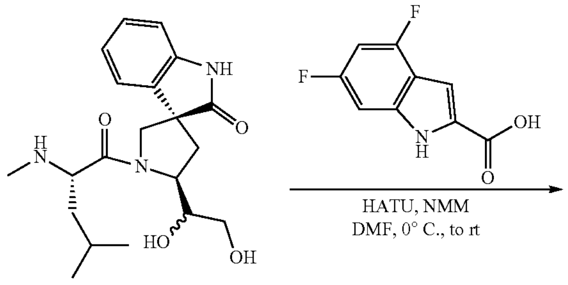

157-5

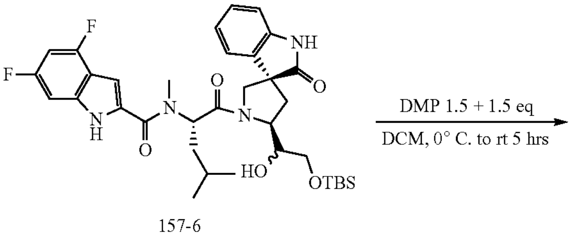

157-6

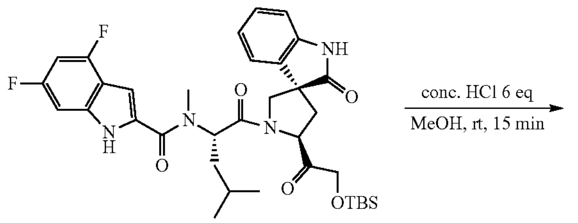

157-7

-continued

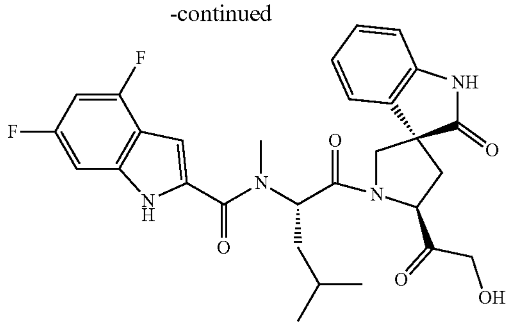

Example 157

Step 1:

To a suspension of methyltriphenylphosphonium bromide (479 mg, 1.34 mmol) (co-evaporated with dry toluente twice before use) in THF (4.2 mL) at 0° C. was added potassium tert-butoxide in THF (1M, 1.26 mL, 1.26 mmol). The mixture turned into a yellow slurry. It was stirred at 0° C. for 0.5 h. A solution of 157-(200 mg, 0.419 mmol) in THF (1.0 mL) was added dropwise at 0° C. The yellow slurry was stirred at 0° C. for 1 h. Excess amount of saturated $NH_4Cl$ solution was the added to quench the reaction. The mixture was diluted with EtOAc and water. The organic layer was separated, washed with brine, dried over $Na_2SO_4$, and concentrated. Purification of the residue on silica gel chromatography with 0-50% EtOAc in cyclohexane provided 157-2 (160 mg, 80% yield). LC-MS, $ES^+$: 476.10 [M+1].

Step 2:

To a mixture of 157-2 (112 mg, 0.235 mmol) and NMO (83 mg, 0.706 mmol) in acetone (2.10 mL)/water (0.24 mL) at rt was added osmium tetroxide, 2.5% in tBuOH (443 μL, 0.035 mmol). After stirring at rt for ~3 hrs, the reaction mixture was quenched with aqueous $Na_2SO_3$ solution, then extracted with EtOAc (2×). The combined organic layers were washed with brine, dried over $Na_2SO_4$, and concentrated. The crude 157-3 (118 mg, 98% yield) was directly used in the next step without further purification. LC-MS, $ES^-$: 508.1 [M−H].

Step 3:

To a solution of 157-3 (118 mg, 0.232 mmol) in $CH_2Cl_2$ (2.32 mL) and 1H-imidazole (23.65 mg, 0.347 mmol) at 0° C. was added tert-butylchlorodimethylsilane (36.6 mg, 0.243 mmol). After stirring at rt for ~2 hrs, the reaction mixture was quenched with sat. $Na_2SO_3$ and extracted with EtOAc (2×). The combined organic layers were washed with brine, dried over $Na_2SO_4$, and concentrated in vacuo. Purification of the residue on silica gel chromatography with 0-40% EtOAc in cyclohexane provided 157-4 (126 mg, 87% yield). LC-MS, $ES^+$: 624.28 [M+1].

Step 4:

A mixture of 157-4 (126 mg, 0.202 mmol) and 10% Pd—C (21.49 mg, 0.020 mmol) in MeOH (2.0 mL) was stirred at rt under a hydrogen balloon. After ~1 h, the reaction mixture was filtered through celite, washed with MeOH, and concentrated to give crude 157-5 (99 mg, 100% yield), which was used in next step directly. LC-MS, $ES^+$: 490.5 [M+1].

Step 5:

To a mixture of 157-5 (99 mg, 0.202 mmol) and 4,6-difluoro-1H-indole-2-carboxylic acid (39.9 mg, 0.202 mmol) in dry DMF (0.81 mL) at 0° C. was added 4-methylmorpholine (66.7 μL, 0.606 mmol), followed by addition of HATU (85 mg, 0.222 mmol). The resulting mixture was then stirred at rt for 3-4 hrs. Workup: the reaction mixture was diluted with EtOAc, washed with water (2×), brine, dried over $Na_2SO_4$, and concentrated. Purification of the residue on silica gel chromatography with 0-40% EtOAc in cyclohexane provided 157-6 (105 mg, 0.157 mmol, 78% yield). LC-MS, $ES^+$: 669.22 [M+1].

Step 6:

To a mixture of 157-6 (104 mg, 0.155 mmol) in DCM (1.56 mL) at 0° C. was added Dess-Martin Periodinane (198 mg, 0.46 mmol). The mixture was stirred at 0° C. for 4-5 hrs until TLC (acetone/cyclohexane 1/3) showed that all the sm was consumed. Work-up: the reaction mixture was diluted with DCM, quenched with 10% $Na_2S_2O_3$ and 5% $NaHCO_3$.

The organic layer was separated, washed with water, brine, dried over $Na_2SO_4$, and concentrated. Purification of the residue on silica gel chromatography with 0-40% acetone/cyclohexane provided 157-7 (50 mg, 0.075 mmol, 48.2% yield). LC-MS, $ES^-$: 665.0 [M-H].

Step 7:

To a suspension of 157-7 (42 mg, 0.063 mmol) in MeOH (0.63 mL) at rt was added conc. HCl in water (31.5 μL, 0.378 mmol). After stirring at rt for ~15 min, the reaction mixture was concentrated to dryness under vacuum. The residue was diluted with EtOAc, washed with sat $NaHCO_3$, brine, dried over $Na_2SO_4$, and concentrated. Purification of the residue on silica gel chromatography with 0-50% acetone in cyclohexane provided Example 157-(26 mg, 0.047 mmol, 74.7% yield). LC-MS, $ES^-$: 550.90 [M-H]. 1H NMR (400 MHz, Acetone-d6) δ 10.83 (s, 1H), 9.63 (s, 1H), 7.07 (dd, J=7.7, 4.5 Hz, 3H), 6.97-6.83 (m, 3H), 6.74 (td, J=10.3, 2.1 Hz, 1H), 5.55 (t, J=7.6 Hz, 1H), 5.12 (dd, J=9.6, 8.1 Hz, 1H), 4.56 (dd, J=18.6, 5.7 Hz, 1H), 4.42 (dd, J=18.6, 5.8 Hz, 1H), 4.26 (d, J=10.3 Hz, 1H), 4.09 (t, J=5.7 Hz, 1H), 3.93 (d, J=10.2 Hz, 1H), 3.46 (s, 3H), 2.44 (ddd, J=12.7, 8.1, 1.3 Hz, 1H), 2.36 (dd, J=12.7, 9.6 Hz, 1H), 1.81 (tq, J=14.0, 7.4, 6.7 Hz, 2H), 1.63 (ddd, J=14.3, 12.9, 6.7 Hz, 1H), 1.02 (d, J=6.6 Hz, 3H), 0.96 (d J=6.5 Hz 3H).

Example 158

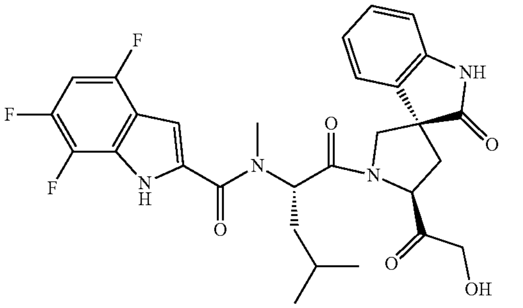

Example 158 was prepared employing similar protocol as described above. [M-1] 569.0; $^1H$ NMR (400 MHz, Acetone-d6) δ 11.25 (s, 1H), 9.63 (s, 1H), 7.13-7.02 (m, 2H), 6.96-6.81 (m, 4H), 5.54 (t, J=7.6 Hz, 1H), 5.14 (dd, J=9.7, 8.1 Hz, 1H), 4.57 (dd, J=18.7, 5.7 Hz, 1H), 4.42 (dd, J=18.7, 5.8 Hz, 1H), 4.23 (d, J=10.5 Hz, 1H), 4.11 (t, J=5.7 Hz, 1H), 3.95 (d, J=10.3 Hz, 1H), 3.45 (s, 3H), 2.45 (dd, J=12.7, 8.1 Hz, 1H), 2.36 (dd, J=12.7, 9.7 Hz, 1H), 1.90-1.74 (m, 2H), 1.67 (dp, J=13.6, 6.7 Hz, 1H), 1.03 (d, J=6.6 Hz, 3H), 0.97 (d, J=6.5 Hz, 3H).

Example 159

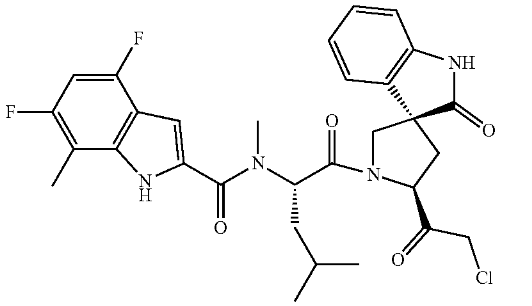

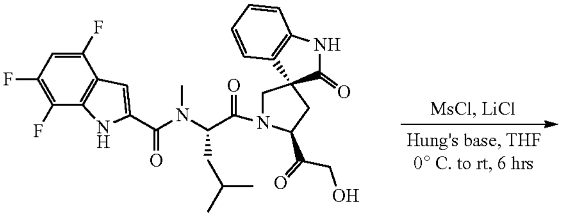

Example 158

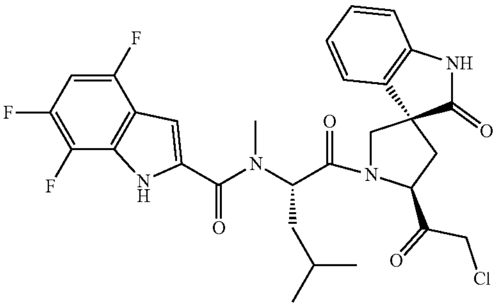

Example 159

To a solution of Example 158 (11.6 mg, 0.020 mmol) in THF (0.25 mL) at 0° C. were added lithium chloride (11.20 mg, 0.264 mmol) and Hunig's base (10.6 μL, 0.061 mmol). Then, methanesulfonyl chloride (3.78 μL, 0.048 mmol) was added. The reaction was stirred at 0° C. to rt for ~6 hrs. Work-up: the reaction mixture was quenched with sat. $NH_4Cl$, extracted with EtOAc. The organic layer was separated, washed with brine, dried over $Na_2SO_4$, and concentrated. Purification of the residue on silica gel chromatography with 0-30% acetone in cyclohexane provided Example 159 (4.5 mg, 37.6% yield). LC-MS, $ES^-$: 586.86 [M-H]; 1H NMR (400 MHz, Acetone-d6) δ 11.22 (s, 1H), 9.64 (s, 1H), 7.18-7.06 (m, 2H), 7.00-6.85 (m, 3H), 5.55 (t, J=7.7 Hz, 1H), 5.13 (t, J=8.5 Hz, 1H), 4.81 (d, J=16.5 Hz, 1H), 4.65 (d, J=16.5 Hz, 1H), 4.23 (d, J=10.6 Hz, 1H), 4.00 (d, J=10.3 Hz, 1H), 3.44 (s, 3H), 2.55-2.38 (m, 2H), 1.92-1.74 (m, 2H), 1.65 (dt, J=13.9, 6.7 Hz, 1H), 1.00 (dd, J=22.0, 6.6 Hz, 6H).

Example 39

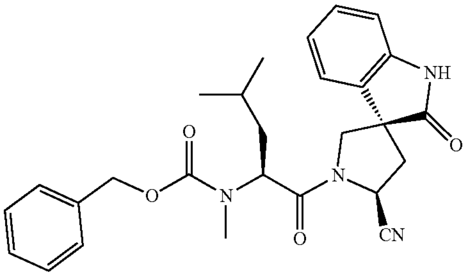

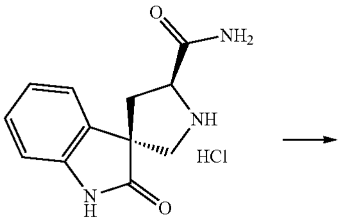

1-4

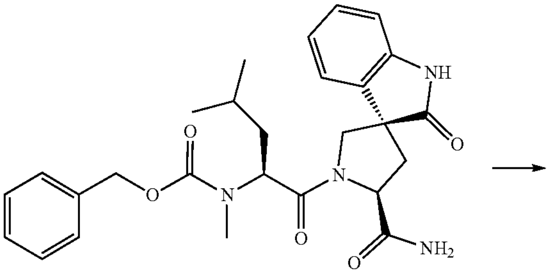

39-1

-continued

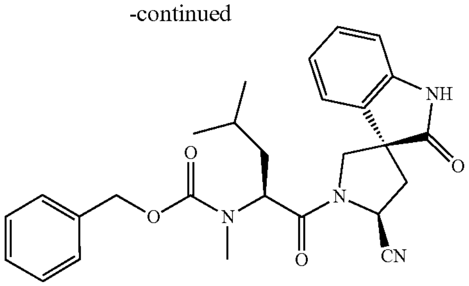

Example 39

Step 1

Compound (1-4) (300 mg, 1.121 mmol) and N-((benzyloxy)carbonyl)-N-methyl-L-leucine (344 mg, 1.233 mmol) was taken up in $CH_2Cl^2$ (5 ml) and DMF (1 ml). 4-methylmorpholine (246 μl, 2.241 mmol) and HATU (469 mg, 1.233 mmol) were added. The mixture was stirred at rt for 1 h, diluted with DCM (30 mL), and washed with sat. $NaHCO_3$. The collected organic layer was washed with 1 M HCl and brine, filtered through $Na_2SO_4$, and concentrated in vacuo. Purification of the residue on silica gel with 0-100% acetone/cyclohexane provided compound (39-1) (417 mg, 0.847 mmol, 76% yield). $[M-1]^-$, 491.02.

Step 2

To a suspension of (39-1) (28 mg, 0.057 mmol) in DCM (0.6 mL) at 0° C. was added $Et_3N$ (79 μl, 0.568 mmol) and TFAA (40.1 μl, 0.284 mmol). The mixture was warmed to rt and stirred for 1 h. The reaction was quenched with cold $NaHCO_3$ solution and extracted with EtOAc. The organic layer was washed with water, 1N HCl, sat $NaHCO_3$ and brine, dried over $Na_2SO_4$, filtered, and concentrated. Purification of the residue on silica gel column provided Example 39 (24 mg, 0.051 mmol, 89% yield). $[M-H]^-$ 473.17. $^1H$ NMR (400 MHz, Methanol-$d_4$) δ 7.35-7.15 (m, 5H), 7.07-6.88 (m, 4H), 5.21-4.88 (m, 2H), 4.77 (dd, J=12.1, 3.8 Hz, 1H), 4.19-4.07 (m, 1H), 3.92 (d, J=10.7 Hz, 1H), 3.71 (p, J=10.8 Hz, 1H), 2.93 (d, J=4.8 Hz, 3H), 2.75-2.57 (m, 2H), 1.79 (ddt, J=14.4, 9.2, 5.0 Hz, 1H), 1.67 (dq, J=14.8, 7.2, 6.6 Hz, 1H), 1.56-1.47 (m, 1H), 1.05-0.88 (m, 6H).

The following examples were prepared employing similar protocol as described above.

| Example | Structure | MS | NMR |
|---|---|---|---|
| 40 | 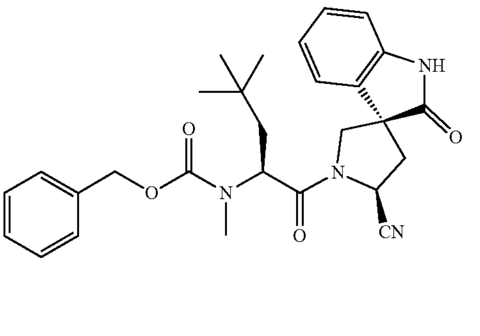 [SMILES: CN(C(=O)OCc1ccccc1)[C@@H](CC(C)(C)C)C(=O)N1C[C@]2(C[C@H]1C#N)C(=O)Nc1ccccc12] | $[M + Na]^+$ 511.21 | |

-continued
| Example | Structure | MS | NMR |
|---|---|---|---|
| 41 | 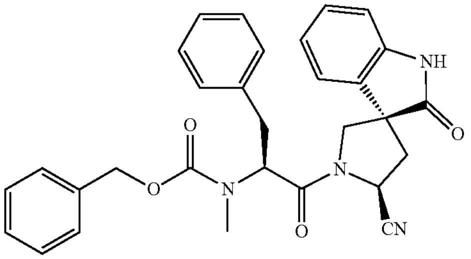 [SMILES: CN(C(=O)OCc1ccccc1)[C@@H](Cc1ccccc1)C(=O)N1C[C@]2(C[C@H]1C#N)C(=O)Nc1ccccc12] | [M − H]⁻ 507.20 | |
| 160 | 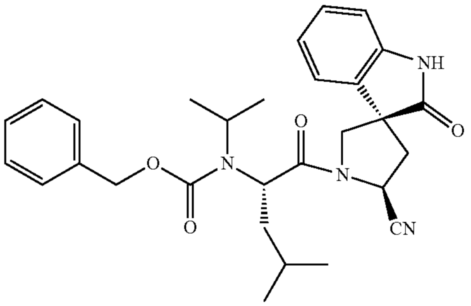 [SMILES: CC(C)C[C@@H](C(=O)N1C[C@]2(C[C@H]1C#N)C(=O)Nc1ccccc12)N(C(=O)OCc1ccccc1)C(C)C] | [M − 1] 501.1 | $^1$H NMR (400 MHz, DMSO-$d_6$) δ 10.71 (s, 1H), 7.35-7.12 (m, 6H), 7.00-6.90 (m, 3H), 5.18 (t, J = 7.7 Hz, 1H), 4.98-4.61(m, 3H), 3.87 (s, 1H), 3.76-3.68 (m, 2H), 2.63 (s, 2H), 1.61 (s, 2H), 1.44 (d, J = 26.5 Hz, 1H), 1.22 (m, 6H), 0.88 (m, 6H). |
| 161 | 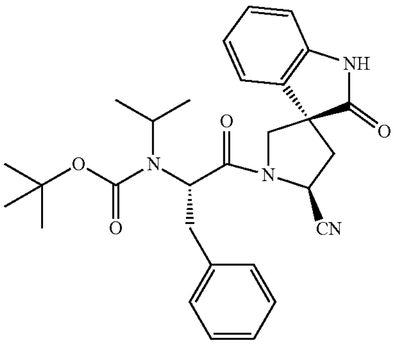 [SMILES: CC(C)N(C(=O)OC(C)(C)C)[C@@H](Cc1ccccc1)C(=O)N1C[C@]2(C[C@H]1C#N)C(=O)Nc1ccccc12] | [M − 1] 501.2 | |
Example 42
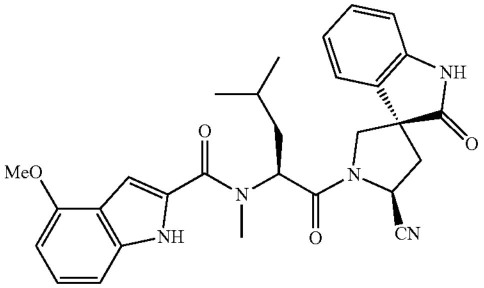
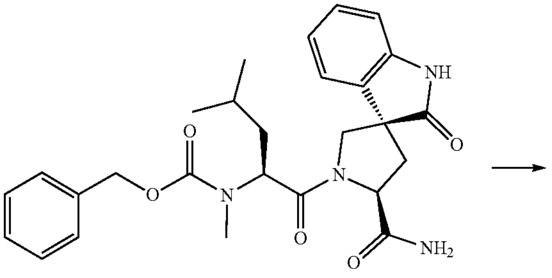
39-1
-continued
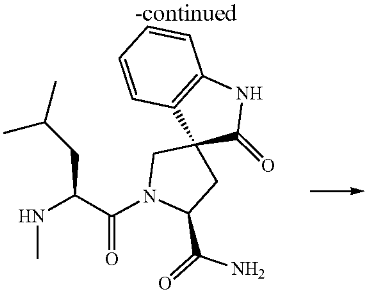
42-1
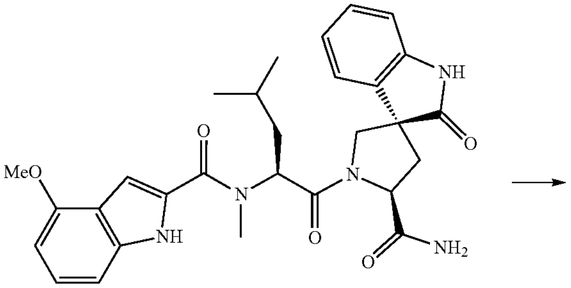
42-2

-continued

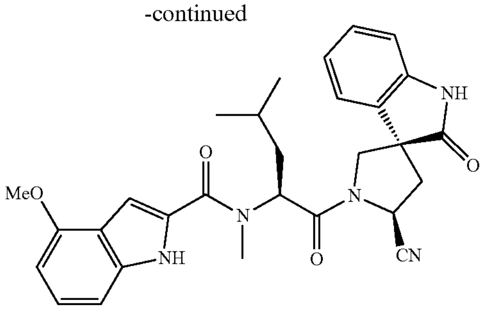

Example 42

Step 1

Compound (39-1) (1323 mg, 2.69 mmol) was dissolved in MeOH (30 ml). 10% Pd—C (143 mg, 0.134 mmol) was added. The mixture was stirred under $H_2$ (balloon) for 1 h and filtered through a pad of Celite. The filtrate was concentrated in vacuo to provide compound (42-1). $[M+H]^+$ 359.2

Step 2

To a suspension of 4-methoxy-1H-indole-2-carboxylic acid (0.111 g, 0.583 mmol), compound (42-1) (0.182 g, 0.507 mmol) and HATU (0.212 g, 0.558 mmol) in DCM (0.3 mL) was added DIPEA (0.266 ml, 1.521 mmol) in DMF (0.35 mL). The mixture was stirred at rt for 1 h, quenched with water, and extracted with EtOAc. The organic layer was washed with 1 N HCl, sat $NaHCO_3$ and brine, dried over $Na_2SO_4$, filtered, and concentrated. Purification of the residue on silica gel column afforded compound (42-2) (160 mg, 0.301 mmol, 59.4% yield). $[M-H]^+$ 530.18.

Step 3

Compound (42-2) (150 mg, 0.282 mmol) was dissolved in $CH_2Cl_2$ (1.9 ml). At 0° C., $Et_3N$ (0.32 mL, 2.26 mmol) and TFAA (0.16 mL, 1.13 mmol) was added. The mixture was stirred at 0° C. for 20 min, quenched with aq. $NaHCO_3$, and extracted with DCM (2×). The combined organic layer was dried over $Na_2SO_4$ and concentrated in vacuo. Purification of the residue on silica gel with 0-40% acetone/cyclohexane provided Example 42 (114 mg, 0.222 mmol, 79% yield). $[M-H]^-$ 512.18; $^1$H NMR (400 MHz, Methanol-$d_4$) δ 7.15 (t, J=8.0 Hz, 1H), 7.05 (t, J=7.8 Hz, 1H), 7.01-6.94 (m, 2H), 6.90 (s, 1H), 6.85 (dd, J=15.4, 7.7 Hz, 2H), 6.52 (d, J=7.7 Hz, 1H), 5.53 (brs, 1H), 5.19 (t, J=8.0 Hz, 1H), 4.21 (d, J=11.0 Hz, 1H), 3.99 (d, J=11.0 Hz, 1H), 3.96 (s, 3H), 3.40 (s, 3H), 2.75-2.60 (m, 2H), 1.96-1.76 (m, 2H), 1.63 (ddt, J=14.6, 13.0, 6.6 Hz, 1H), 1.47 (s, 1H), 1.26 (t, J=7.1 Hz, 1H), 1.01 (m, 6H).

The following examples were prepared employing similar protocol as described above.

| Example | Structure | MS | NMR |
|---|---|---|---|
| 43 | 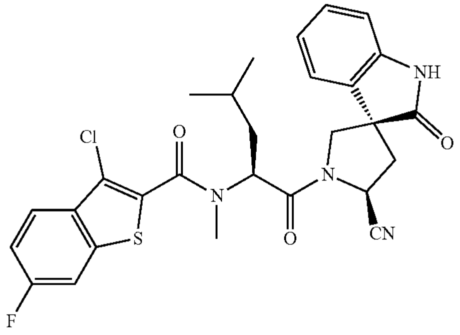 [SMILES: CC(C)C[C@@H](C(=O)N1C[C@]2(C[C@H]1C#N)C(=O)Nc1ccccc12)N(C)C(=O)c1sc2cc(F)ccc2c1Cl] | $[M + Na]^+$ 575.11 | $^1$H NMR (400 MHz, Acetone-$d_6$) δ 9.58 (s, 1H), 7.77-7.68 (m, 2H), 7.27 (td, J = 8.9, 2.3 Hz, 1H), 7.17 (t, J = 7.6 Hz, 1H), 7.03 (d, J = 7.3 Hz, 1H), 6.91 (t, J = 7.2 Hz, 2H), 5.36 (dd, J = 9.7, 5.2 Hz, 1H), 5.08 (t, J = 8.2 Hz, 1H), 4.10 (d, J = 10.5 Hz, 1H), 3.96 (d, J = 10.5 Hz, 1H), 3.00 (s, 3H), 2.71-2.56 (m 2H), 1.82 (m, 1H), 1.74-1.61 (m, 2H), 0.89 (m, 6H). |
| 44 | 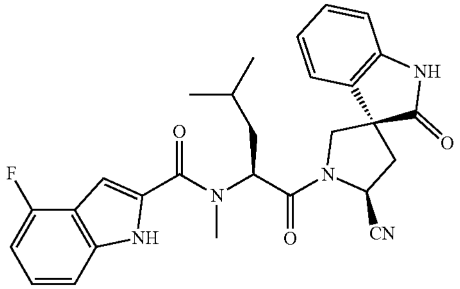 [SMILES: CC(C)C[C@@H](C(=O)N1C[C@]2(C[C@H]1C#N)C(=O)Nc1ccccc12)N(C)C(=O)c1cc2c(F)cccc2[nH]1] | $[M + Na]^+$ 524.19 | $^1$H NMR (400 MHz, Acetone-$d_6$) δ 10.70 (s, 1H), 9.67 (s, 1H), 7.33 (d, J = 8.2 Hz, 1H), 7.22 (td, J = 8.0, 5.2 Hz, 1H), 7.03 (d, J = 7.7 Hz, 2H), 6.96-6.88 (m, 2H), 6.87-6.76 (m, 2H), 5.59 (dd, J = 9.5, 5.6 Hz, 1H), 5.21 (t, J = 8.2 Hz, 1H), 4.28 (d, J = 10.7 Hz, 1H), 4.00 (d, J = 10.6 Hz, 1H), 3.46 (s, 3H), 2.83-2.64 (m, 2H), 1.94 (ddd, J = 14.5, 9.6, 5.2 Hz, 1H), 1.79 (ddd, J = 14.2, 8.7, 5.6 Hz, 1H), 1.64 (dtd, J = 8.7, 6.7, 5.1 Hz, 1H), 0.99 (m, 6H). |
| 45 | 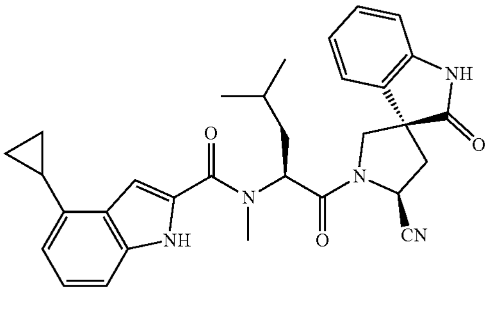 [SMILES: CC(C)C[C@@H](C(=O)N1C[C@]2(C[C@H]1C#N)C(=O)Nc1ccccc12)N(C)C(=O)c1cc2c(C3CC3)cccc2[nH]1] | $[M + Na]^+$ 546.23 | $^1$H NMR (400 MHz, Acetone-$d_6$) δ 10.39 (s, 1H), 9.67 (s, 1H), 7.29 (d, J = 8.3 Hz, 1H), 7.17-7.03 (m, 4H), 6.95-6.84 (m, 2H), 6.65 (d, J = 7.2 Hz, 1H), 5.61 (m, 1H), 5.20 (t, J = 8.2 Hz, 1H), 4.27 (d, J = 10.7 Hz, 1H), 4.01 (d, J = 10.6 Hz, 1H), 3.47 (s, 3H), 2.83-2.63 (m, 2H), 2.32 (br s, 1H), 1.92 (ddd, J = 14.3, 9.3, 5.2 Hz, 1H), 1.86-1.74 (m, 1H), 1.64 (dt, J = 13.7, 6.8 Hz, 1H), 1.01 (m, 8H), 0.84-0.78 (m, 2H). |

-continued

| Example | Structure | MS | NMR |
|---|---|---|---|
| 46 | 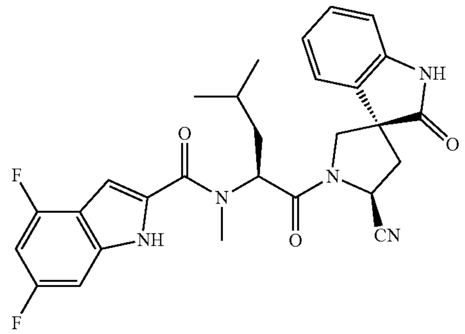 [SMILES: CC(C)C[C@@H](C(=O)N1C[C@]2(C[C@H]1C#N)C(=O)Nc1ccccc12)N(C)C(=O)c1cc2c(F)cc(F)cc2[nH]1] | [M + Na]+ 542.17 | $^1$H NMR (400 MHz, Acetone-$d_6$) δ 10.79 (s, 1H), 9.67 (s, 1H), 7.04 (m, 3H), 6.96 (s, 1H), 6.91 (d, J = 7.7 Hz, 1H), 6.85-6.70 (m, 2H), 5.59 (dd, J = 9.5, 5.6 Hz, 1H), 5.21 (t, J = 8.3 Hz, 1H), 4.30 (d, J = 10.8 Hz, 1H), 3.98 (d, J = 10.6 Hz, 1H), 3.45 (s, 3H), 2.78-2.66 (m, 2H), 1.95 (td, J = 9.4, 4.7 Hz, 1H), 1.78 (ddd, J = 14.2, 8.7, 5.5 Hz, 1H), 1.63 (dt, J = 13.8, 6.4 Hz, 1H), 0.98 (m, 6H). |
| 47 | 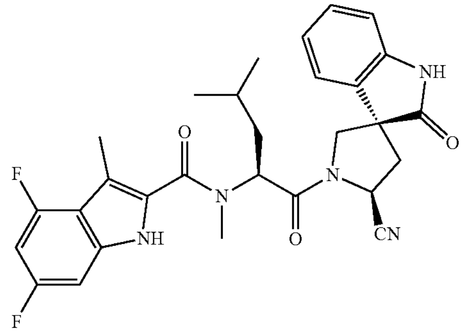 [SMILES: Cc1c(C(=O)N(C)[C@@H](CC(C)C)C(=O)N2C[C@]3(C[C@H]2C#N)C(=O)Nc2ccccc23)[nH]c2cc(F)cc(F)c12] | [M + Na]+ 556.18 | $^1$H NMR (500 MHz, Acetone-$d_6$) δ 10.47 (s, 1H), 9.71 (s, 1H), 7.28 (td, J = 7.7, 1.2 Hz, 1H), 7.16 (d, J = 7.4 Hz, 1H), 7.02 (t, J = 7.3 Hz, 2H), 6.96 (s, 1H), 6.66 (ddd, J = 11.3, 10.1, 2.1 Hz, 1H), 5.37 (s, 1H), 5.19 (t, J = 8.3 Hz, 1H), 4.32 (br s, 1H), 4.07 (br s, 1H), 3.20 (s, 3H), 2.82-2.66 (m, 2H), 2.27 (s, 3H), 2.00-1.91 (m, 1H), 1.81 (s, 1H), 1.72 (s, 1H), 1.05 (d, J = 6.5 Hz, 3H), 0.99 (br s, 3H). |
| 48 | 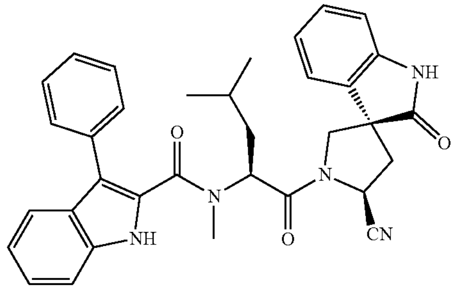 [SMILES: CC(C)C[C@@H](C(=O)N1C[C@]2(C[C@H]1C#N)C(=O)Nc1ccccc12)N(C)C(=O)c1[nH]c2ccccc2c1-c1ccccc1] | [M + Na]+ 582.22 | $^1$H NMR (500 MHz, Acetone-$d_6$) δ 10.37 (s, 1H), 9.72 (s, 1H), 7.73 (d, J = 8.0 Hz, 1H), 7.55-7.46 (m, 5H), 7.39 (tt, J = 5.8, 2.9 Hz, 1H), 7.31-7.23 (m, 2H), 7.15 (t, J = 7.6 Hz, 1H), 7.11 (d, J = 7.5 Hz, 1H), 7.04 (d, J = 7.8 Hz, 1H), 6.94 (t, J = 7.5 Hz, 1H), 5.31 (dd, J = 10.7, 4.9 Hz, 1H), 5.15 (t, J = 8.3 Hz, 1H), 4.34 (d, J = 10.5 Hz, 1H), 4.05 (d, J = 10.5 Hz, 1H), 2.77 (s, 3H), 2.70 (m, 2H), 1.82-1.72 (m, 1H), 1.62 (ddd, J = 14.4, 9.6, 4.9 Hz, 1H), 1.41 (m, 1H), 0.99 (d, J = 6.5 Hz, 3H), 0.93 (d, J = 6.7 Hz, 3H). |
| 49 | 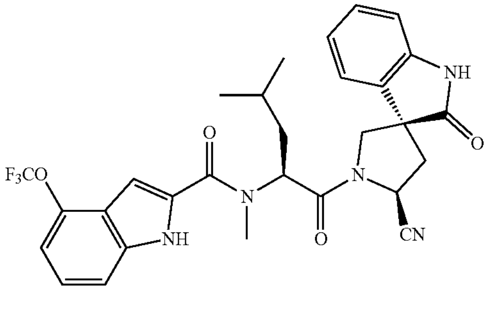 [SMILES: CC(C)C[C@@H](C(=O)N1C[C@]2(C[C@H]1C#N)C(=O)Nc1ccccc12)N(C)C(=O)c1cc2c(OC(F)(F)F)cccc2[nH]1] | [M + Na]+ 590.20 | $^1$H NMR (400 MHz, Acetone-$d_6$) δ 10.81 (s, 1H), 9.66 (s, 1H), 7.53 (d, J = 8.3 Hz, 1H), 7.31 (t, J = 8.0 Hz, 1H), 7.10-6.96 (m, 4H), 6.91 (d, J = 7.4 Hz, 1H), 6.81 (t, J = 7.5 Hz, 1H), 5.60 (dd, J = 9.4, 5.8 Hz, 1H), 5.21 (t, J = 8.2 Hz, 1H), 4.28 (d, J = 10.6 Hz, 1H), 4.00 (d, J = 10.6 Hz, 1H), 3.46 (s, 3H), 2.82-2.60 (m, 2H), 2.00-1.90 (m, 1H), 1.85-1.74 (m, 1H), 1.64 (dt, J = 13.8, 6.6 Hz, 1H), 0.99 (m, 6H). |
| 50 | 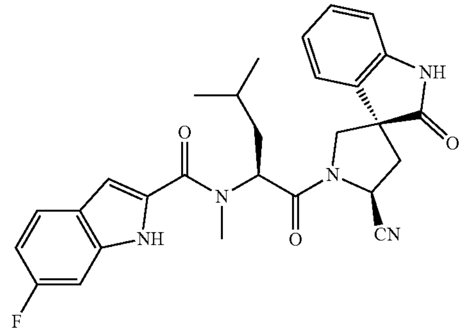 [SMILES: CC(C)C[C@@H](C(=O)N1C[C@]2(C[C@H]1C#N)C(=O)Nc1ccccc12)N(C)C(=O)c1cc2ccc(F)cc2[nH]1] | [M + Na]+ 524.22 | $^1$H NMR (400 MHz, Acetone-$d_6$) δ 10.51 (s, 1H), 9.67 (s, 1H), 7.66 (s, 1H), 7.24-7.16 (m, 1H), 7.08-6.98 (m, 2H), 6.92 (d, J = 8.3 Hz, 3H), 6.82 (s, 1H), 5.59 (dd, J = 9.5, 5.7 Hz, 1H), 5.21 (t, J = 8.3 Hz, 1H), 4.29 (d, J = 10.8 Hz, 1H), 3.99 (d, J = 10.6 Hz, 1H), 3.43 (s, 3H), 2.78-2.63 (m, 2H), 2.00-1.91 (m, 1H), 1.77 (m, 1H), 1.61 (m, 1H), 0.98 (m, 6H). |

-continued

| Example | Structure | MS | NMR |
|---|---|---|---|
| 51 | 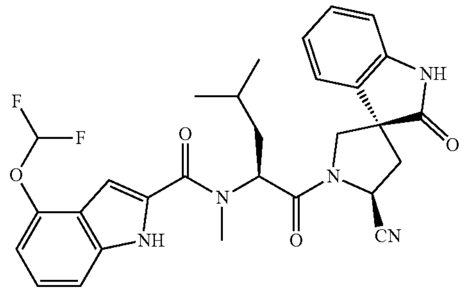 [SMILES: CC(C)C[C@@H](C(=O)N1C[C@]2(C[C@H]1C#N)C(=O)Nc1ccccc12)N(C)C(=O)c1cc2c(OC(F)F)cccc2[nH]1] | [M + Na]+ 572.22 | $^1$H NMR (400 MHz, Acetone-$d_6$) δ 10.69 (s, 1H), 9.66 (s, 1H), 7.39 (d, J = 8.3 Hz, 1H), 7.25 (t, J = 8.0 Hz, 1H), 7.15 (s, 1H), 7.03 (d, J = 7.6 Hz, 2H), 6.97-6.79 (m, 4H), 5.59 (dd, J = 9.4, 5.6 Hz, 1H), 5.21 (t, J = 8.2 Hz, 1H), 4.28 (d, J = 10.8 Hz, 1H), 4.00 (d, J = 10.6 Hz, 1H), 3.46 (s, 3H), 2.78-2.66 (m, 2H), 2.00-1.90 (m, 1H), 1.79 (ddd, J = 14.2, 8.8, 5.7 Hz, 1H), 1.64 (dt, J = 14.0, 6.8 Hz, 1H), 0.99 (m, 6H). |
| 52 | 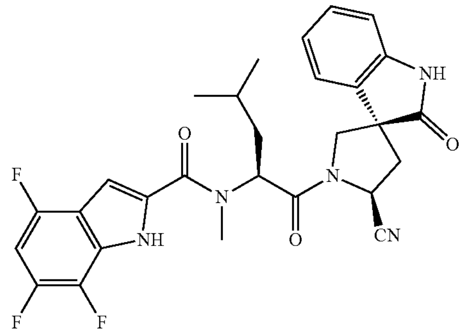 [SMILES: CC(C)C[C@@H](C(=O)N1C[C@]2(C[C@H]1C#N)C(=O)Nc1ccccc12)N(C)C(=O)c1cc2c(F)cc(F)c(F)c2[nH]1] | [M + Na]+ 560.20 | $^1$H NMR (400 MHz, Acetone-$d_6$) δ 9.67 (s, 1H), 7.04 (dd, J = 14.4, 7.4 Hz, 2H), 6.93 (ddd, J = 10.6, 8.9, 5.1 Hz, 3H), 6.84 (t, J = 7.5 Hz, 1H), 5.61-5.53 (m, 1H), 5.22 (t, J = 8.3 Hz, 1H), 4.25 (d, J = 10.6 Hz, 1H), 3.99 (d, J = 10.7 Hz, 1H), 3.43 (s, 3H), 2.82-2.73 (m, 5H), 2.76-2.64 (m, 1H), 1.80 (ddd, J = 14.2, 8.7, 5.6 Hz, 1H), 1.64 (dt, J = 13.7, 6.6 Hz, 1H), 1.44 (s, 3H), 0.99 (dd, J = 18.3, 6.6 Hz, 5H). |
| 53 | 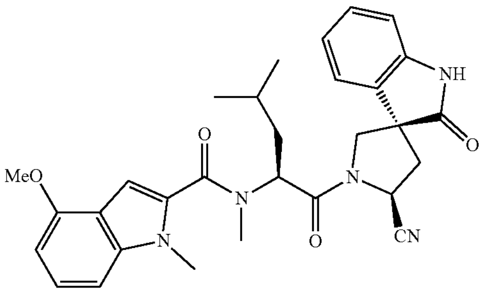 [SMILES: COc1cccc2c1cc(C(=O)N(C)[C@@H](CC(C)C)C(=O)N1C[C@]3(C[C@H]1C#N)C(=O)Nc1ccccc13)n2C] | [M + Na]+ 550.25 | $^1$H NMR (400 MHz, Acetone-$d_6$) δ 9.72 (s, 1H), 7.26 (td, J = 7.7, 1.3 Hz, 1H), 7.19 (t, J = 8.1 Hz, 1H), 7.13 (s, 1H), 7.05-6.95 (m, 3H), 6.63-6.55 (m, 2H), 5.56 (br s, 1H), 5.24 (t, J = 8.3 Hz, 1H), 4.40 (d, J = 10.9 Hz, 1H), 4.05 (d, J = 10.6 Hz, 1H), 3.95 (s, 3H), 3.47 (s, 3H), 2.83 (d, J = 0.5 Hz, 4H), 2.78-2.66 (m, 2H), 1.98 (ddd, J = 14.1, 9.6, 4.8 Hz, 1H), 1.79 (ddd, J = 13.8, 8.7, 5.6 Hz, 1H), 1.71 (br s, 1H), 1.05 (d, J = 6.5 Hz, 3H), 1.00 (d, J = 6.2 Hz, 3H). |
| 54 | 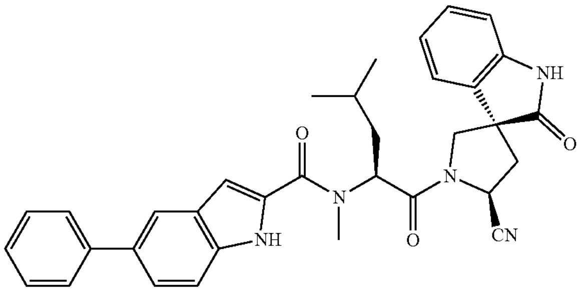 [SMILES: CC(C)C[C@@H](C(=O)N1C[C@]2(C[C@H]1C#N)C(=O)Nc1ccccc12)N(C)C(=O)c1cc2cc(-c3ccccc3)ccc2[nH]1] | [M + Na]+ 582.26 | $^1$H NMR (400 MHz, Acetone-$d_6$) δ 10.50 (s, 1H), 9.67 (s, 1H), 7.91 (s, 1H), 7.69 (d, J = 7.7 Hz, 2H), 7.58 (s, 2H), 7.47 (t, J = 7.7 Hz, 2H), 7.38-7.29 (m, 1H), 7.07 (s, 2H), 6.94 (d, J = 9.1 Hz, 2H), 6.88 (s, 1H), 5.59 (br s, 1H), 5.22 (t, J = 7.9 Hz, 1H), 4.29 (br s, 1H), 4.01 (d, J = 10.5 Hz, 1H), 2.77-2.66 (m, 2H), 1.94 (br s, 1H), 1.85-1.73 (m, 1H), 1.63 (br s, 1H), 1.02 (d, J = 6.6 Hz, 3H), 0.97 (br s, 3H). |

-continued

| Example | Structure | MS | NMR |
|---|---|---|---|
| 55 | 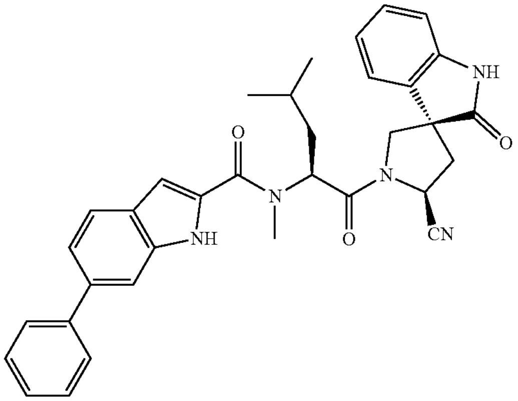 [SMILES: CC(C)C[C@@H](C(=O)N1C[C@]2(C[C@H]1C#N)C(=O)Nc1ccccc12)N(C)C(=O)c1cc2ccc(-c3ccccc3)cc2[nH]1] | [M + Na]+ 582.26 | $^1$H NMR (500 MHz, Acetone-$d_6$) δ 10.48 (s, 1H), 9.67 (s, 1H), 7.76 (s, 1H), 7.73-7.67 (m, 2H), 7.48 (dd, J = 8.4, 7.1 Hz, 2H), 7.41 (d, J = 8.4 Hz, 1H), 7.39-7.33 (m, 1H), 7.09 (s, 2H), 7.05 (s, 1H), 6.94 (d, J = 7.8 Hz, 2H), 6.87 (s, 1H), 5.61 (d, J = 9.5 Hz, 1H), 5.22 (t, J = 8.2 Hz, 1H), 4.29 (d, J = 10.1 Hz, 1H), 4.01 (d, J = 10.6 Hz, 1H), 3.46 (s, 3H), 2.78-2.65 (m, 2H), 1.94 (m, 1H), 1.79 (m, 1H), 1.64 (dt, J = 13.8, 6.7 Hz, 1H), 1.02 (d, J = 6.7 Hz, 3H), 0.97 (d, J = 6.3 Hz, 3H). |
| 56 | 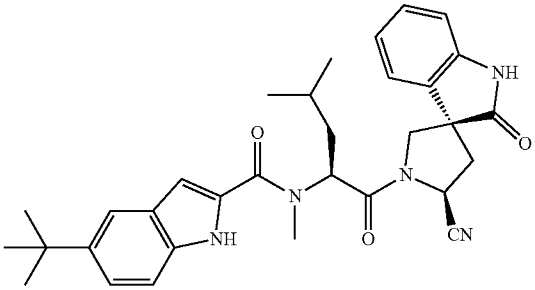 [SMILES: CC(C)C[C@@H](C(=O)N1C[C@]2(C[C@H]1C#N)C(=O)Nc1ccccc12)N(C)C(=O)c1cc2cc(C(C)(C)C)ccc2[nH]1] | [M − H]− 538.1 | $^1$H NMR (400 MHz, Acetone-$d_6$) δ 10.28 (s, 1H), 9.67 (s, 1H), 7.62 (s, 1H), 7.45-7.34 (m, 2H), 7.12 (s, 1H), 7.06 (s, 1H), 6.94 (d, J = 7.8 Hz, 1H), 6.87 (d, J = 15.3 Hz, 2H), 5.57 (dd, J = 9.6, 5.5 Hz, 1H), 5.21 (t, J = 8.1 Hz, 1H), 4.27 (br s, 1H), 4.01 (d, J = 10.5 Hz, 1H), 3.43 (s, 3H), 2.68 (m, 2H), 1.93 (m, 1H), 1.83-1.72 (m, 1H), 1.61 (dd, J = 13.8, 6.7 Hz, 1H), 1.38 (s, 9H), 1.01 (d, J = 6.6 Hz, 3H), 0.95 (br s, 3H). |
| 57 | 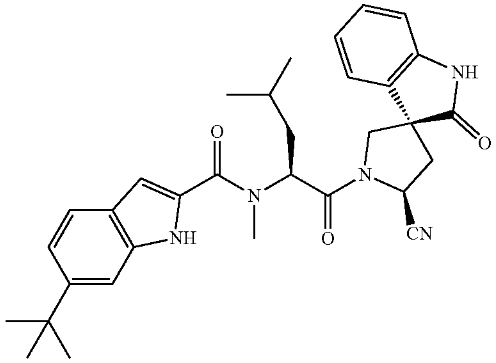 [SMILES: CC(C)C[C@@H](C(=O)N1C[C@]2(C[C@H]1C#N)C(=O)Nc1ccccc12)N(C)C(=O)c1cc2ccc(C(C)(C)C)cc2[nH]1] | [M − H]− 538.1 | $^1$H NMR (400 MHz, Acetone-$d_6$) δ 10.25 (s, 1H), 9.66 (s, 1H), 7.55 (s, 1H), 7.50 (d, J = 1.5 Hz, 1H), 7.21 (d, J = 8.5 Hz, 1H), 7.11 (s, 1H), 7.06 (s, 1H), 6.94 (d, J = 7.8 Hz, 1H), 6.89 (s, 1H), 6.82 (s, 1H), 5.58 (dd, J = 9.5, 5.6 Hz, 1H), 5.21 (t, J = 8.2 Hz, 1H), 4.24 (br s, 1H), 4.01 (d, J = 10.6 Hz, 1H), 3.42 (s, 3H), 2.83 (d, J = 0.8 Hz, 3H), 2.78-2.63 (m, 2H), 1.91 (m, 1H), 1.78 (ddd, J = 14.1, 8.7, 5.6 Hz, 1H), 1.62 (dt, J = 13.8, 6.7 Hz, 1H), 1.37 (s, 9H), 0.98 (d, J = 6.4 Hz, 3H), 0.95 (br s, 3H). |
| 58 | 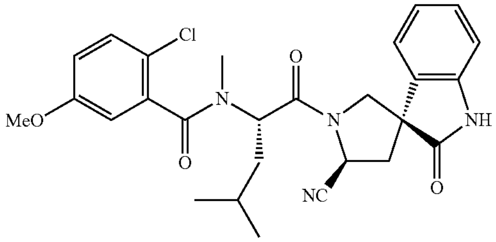 [SMILES: COc1ccc(Cl)c(C(=O)N(C)[C@@H](CC(C)C)C(=O)N2C[C@]3(C[C@H]2C#N)C(=O)Nc2ccccc23)c1] | [M + Na]+ 531.15, 533.10 | $^1$H NMR (500 MHz, Methanol-$d_4$) δ 7.38-7.29 (m, 2H), 7.07-6.94 (m, 5H), 5.52 (t, J = 7.5 Hz, 1H), 5.21 (q, J = 8.0 Hz, 1H), 4.17 (d, J = 11.8 Hz, 1H), 4.07 (dd, J = 19.0, 10.5 Hz, 1H), 3.82-3.73 (m, 3H), 3.23 (s 3 H), 2.72 (qd, J = 13.2, 8.4 Hz, 2H), 1.85 (m, 3H), 1.05 (m, 6H). |
| 59 | 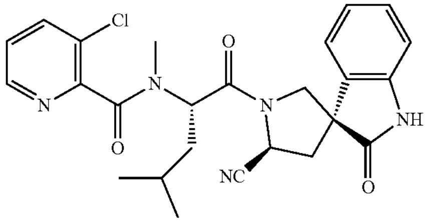 [SMILES: CC(C)C[C@@H](C(=O)N1C[C@]2(C[C@H]1C#N)C(=O)Nc1ccccc12)N(C)C(=O)c1ncccc1Cl] | [M + Na]+ 480.27, 450.10 | $^1$H NMR (500 MHz, Acetone-$d_6$) δ 9.70 (s, 1H), 8.49 (dd, J = 4.7, 1.4 Hz, 1H), 7.91 (dd, J = 8.2, 1.4 Hz, 1H), 7.47 (dd, J = 8.3, 4.7 Hz, 1H), 7.39-7.13 (m, 2H), 7.06-6.97 (m, 2H), 5.60 (dd, J = 9.7, 5.1 Hz, 1H), 5.23-5.16 (m, 1H), 4.26 (dd, J = 10.5, 1.0 Hz, 1H), 4.11 (d, J = 10.6 Hz, 1H), 2.82 (s, 3 H), 2.82-2.76 (m, 1H), 2.70 (dd, J = 13.2, 7.6 Hz, 1H), 2.00-1.87 (m, 1H), 1.83-1.70 (m, 3H), 1.03 (t, J = 6.5 Hz, 6H), |

-continued

| Example | Structure | MS | NMR |
|---|---|---|---|
| 60 | 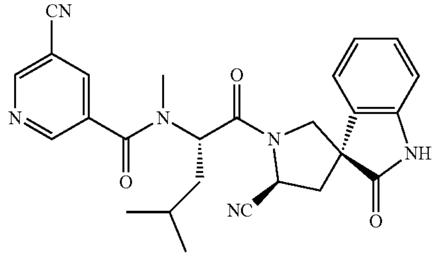 [SMILES: CC(C)C[C@@H](C(=O)N1C[C@]2(C[C@H]1C#N)C(=O)Nc1ccccc12)N(C)C(=O)c1cncc(C#N)c1] | $[M+H]^+$ 471.24 | $^1$H NMR (400 MHz, Acetone-$d_6$) δ 9.79 (s, 1H), 8.99 (d, J = 2.0 Hz, 1H), 8.50 (d, J = 2.1 Hz, 1H), 7.71 (t, J = 2.1 Hz, 1H), 7.33 (td, J = 7.7, 1.4 Hz, 1H), 7.13-7.05 (m, 2H), 7.01 (td, J = 7.5, 1.1 Hz, 1H), 5.54 (dd, J = 9.0, 6.0 Hz, 1H), 5.24 (t, J = 8.5 Hz, 1H), 4.38 (dd, J = 10.7, 1.3 Hz, 1H), 4.12-3.96 (m, 1H), 3.04 (s, 3H), 2.82-2.67 (m, 2H), 1.92 (ddd, J = 14.0, 8.9, 5.4 Hz, 1H), 1.82 (ddd, J = 14.0, 8.5, 6.1 Hz, 1H), 1.78-1.65 (m, 1H), 1.01 (dd, J = 14.7, 6.5 Hz, 6H). |
| 61 | 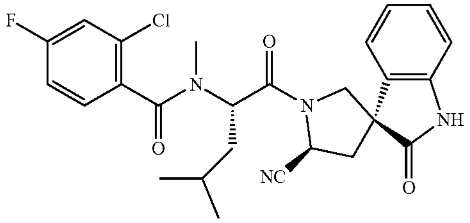 [SMILES: CC(C)C[C@@H](C(=O)N1C[C@]2(C[C@H]1C#N)C(=O)Nc1ccccc12)N(C)C(=O)c1ccc(F)cc1Cl] | $[M+Na]^+$ 519.04, 521.08 | $^1$H NMR (400 MHz, Acetone-$d_6$) δ 9.79 (s, 1H), 7.49-7.23 (m, 3H), 7.20-6.90 (m, 4H), 5.59 (dd, J = 8.6, 6.3 Hz, 1H), 5.23 (br, 1H), 4.21 (d, J = 10.8 Hz, 1H), 4.08 (br, 1H), 2.85 (s, 3 H) 2.74 (td, J = 14.0, 13.0, 8.5 Hz, 2H), 1.97-1.61 (m, 3H), 1.01 (t, J = 6.3 Hz, 6H). |
| 62 | 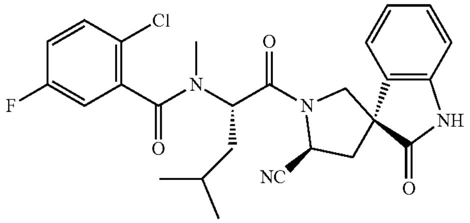 [SMILES: CC(C)C[C@@H](C(=O)N1C[C@]2(C[C@H]1C#N)C(=O)Nc1ccccc12)N(C)C(=O)c1cc(F)ccc1Cl] | $[M+Na]^+$ 519.19, 521.11 | $^1$H NMR (400 MHz, Acetone-$d_6$) δ 9.80 (s, 1H), 7.50 (s, 1H), 7.31 (d, J = 21.4 Hz, 1H), 7.22 (td, J = 8.6, 3.1 Hz, 1H), 7.07 (d, J = 26.1 Hz, 4H), 5.58 (t, J = 7.4 Hz, 1H), 5.22 (d, J = 9.0 Hz, 1H), 4.23 (d, J = 10.6 Hz, 1H), 4.16-3.97 (m, 1H), 2.82 (s, 3 H), 2.80-2.67 (m, 2H), 1.94-1.64 (m, 3H), 1.01 (t, J = 6.4 Hz, 6H). |
| 63 | 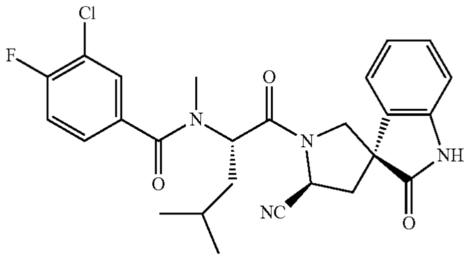 [SMILES: CC(C)C[C@@H](C(=O)N1C[C@]2(C[C@H]1C#N)C(=O)Nc1ccccc12)N(C)C(=O)c1ccc(F)c(Cl)c1] | $[M+Na]^+$ 519.13, 521.02 | $^1$H NMR (400 MHz, Acetone-$d_6$) δ 9.78 (s, 1H), 7.35 (td, J = 7.6, 1.5 Hz, 1H), 7.28 (t, J = 8.9 Hz, 1H), 7.18-7.03 (m, 4H), 7.04-6.94 (m, 2H), 5.51 (dd, J = 8.9, 6.0 Hz, 1H), 5.23 (t, J = 8.5 Hz, 1H), 4.42-4.26 (m, 1H), 4.00 (d, J = 10.7 Hz, 1H), 2.97 (s, 3H), 2.82-2.60 (m, 2H), 1.89 (ddd, J = 14.2, 10.9, 5.5 Hz, 1H), 1.79 (ddd, J = 14.0, 8.4, 6.1 Hz, 1H), 1.69 (dq, J = 13.9, 6.6 Hz, 1H), 1.00 (dd, J = 14.5, 6.5 Hz, 6H). |
| 64 | 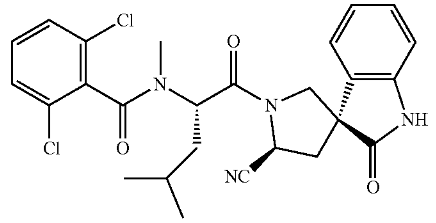 [SMILES: CC(C)C[C@@H](C(=O)N1C[C@]2(C[C@H]1C#N)C(=O)Nc1ccccc12)N(C)C(=O)c1c(Cl)cccc1Cl] | $[M+Na]^+$ 535.11, 537.00 | $^1$H NMR (400 MHz, Acetone-$d_6$) δ 9.73 (s, 1H), 7.49 (ddt, J = 7.3, 3.9, 1.9 Hz, 1H), 7.46-7.42 (m, 2H), 7.28 (tt, J = 7.7, 1.1 Hz, 1H), 7.15 (d, J = 7.5 Hz, 1H), 7.01 (dt, J = 7.5, 3.7 Hz, 2H), 5.62-5.54 (m, 1H), 5.20 (t, J = 8.4 Hz, 1H), 4.27 (d, J = 10.3 Hz, 1H), 4.15 (d, J = 10.3 Hz, 1H), 2.90 (s, 3H), 2.79-2.61 (m, 2H), 1.98-1.68 (m, 3H), 1.03 (dd, J = 8.9, 6.5 Hz, 6H). |
| 65 | 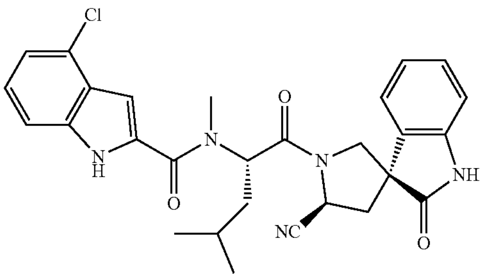 [SMILES: CC(C)C[C@@H](C(=O)N1C[C@]2(C[C@H]1C#N)C(=O)Nc1ccccc12)N(C)C(=O)c1cc2c(Cl)cccc2[nH]1] | $[M+Na]^+$ 540.13, 542.10 | $^1$H NMR (400 MHz, Acetone-$d_6$) δ 10.77 (s, 1H), 9.67 (s, 1H), 7.47 (d, J = 8.2 Hz, 1H), 7.23 (t, J = 7.9 Hz, 1H), 7.14 (dd, J = 7.5, 0.8 Hz, 1H), 7.04 (d, J = 7.4 Hz, 2H), 6.95-6.89 (m, 2H), 6.84 (t, J = 7.5 Hz, 1H), 5.60 (dd, J = 9.5, 5.7 Hz, 1H), 5.22 (t, J = 8.2 Hz, 1H), 4.27 (d, J = 10.7 Hz, 1H), 4.01 (d, J = 10.6 Hz, 1H), 3.47 (s, 3H), 2.81-2.63 (m, 2H), 1.94 (td, J = 9.3, 4.7 Hz, 1H), 1.80 (ddd, J = 14.2, 8.7, 5.7 Hz, 1H), 1.65 (dpd, J = 8.6, 6.6, 5.2 Hz, 1H), 0.99 (m, 6H). |

-continued

| Example | Structure | MS | NMR |
|---|---|---|---|
| 66 | 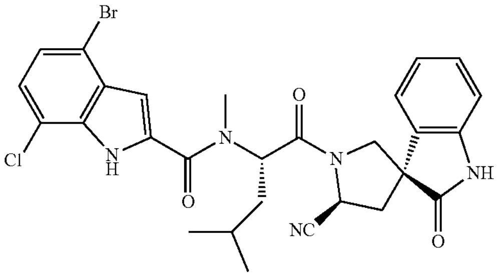 [SMILES: CC(C)C[C@@H](C(=O)N1C[C@]2(C[C@H]1C#N)C(=O)Nc1ccccc12)N(C)C(=O)c1cc2c(Br)ccc(Cl)c2[nH]1] | [M − H]⁻ 594.05, 596.03 | $^1$H NMR (400 MHz, Acetone-$d_6$) δ 9.69 (s, 1H), 7.61 (d, J = 8.2 Hz, 1H), 7.49 (d, J = 8.2 Hz, 1H), 7.39 (s, 1H), 7.19-7.08 (m, 2H), 7.08-6.97 (m, 1H), 6.93 (t, J = 8.7 Hz, 1H), 5.44 (dd, J = 9.7, 5.4 Hz, 1H), 5.22 (td, J = 8.3, 3.9 Hz, 1H), 4.13-3.97 (m, 2H), 3.62 (s, 3H), 2.84-2.61 (m, 2H), 1.86 (ddd, J = 14.5, 9.0, 5.5 Hz, 1H), 1.79-1.58 (m, 2H), 1.10-0.90 (m, 6H). |
| 67 | 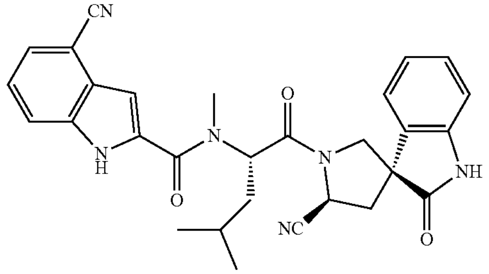 | [M + H]⁺ 509.22 | $^1$H NMR (400 MHz, Acetone-$d_6$) δ 11.02 (s, 1H), 9.67 (s, 1H), 7.84 (d, J = 8.3 Hz, 1H), 7.59 (dd, J = 7.3, 0.9 Hz, 1H), 7.41 (dd, J = 8.4, 7.3 Hz, 1H), 7.13-6.94 (m, 3H), 6.96-6.77 (m, 2H), 5.60 (dd, J = 9.4, 5.7 Hz, 1H), 5.23 (t, J = 8.2 Hz, 1H), 4.26 (d, J = 10.7 Hz, 1H), 4.00 (d, J = 10.7 Hz, 1H), 3.49 (s, 3H), 2.81-2.66 (m, 2H), 2.00-1.88 (m, 1H), 1.81 (ddd, J = 14.2, 8.6, 5.7 Hz, 1H), 1.66 (dtd, J = 8.4, 6.6, 5.1 Hz, 1H), 1.00 (dd, J = 16.8, 6.6 Hz, 6H). |
| 68 | 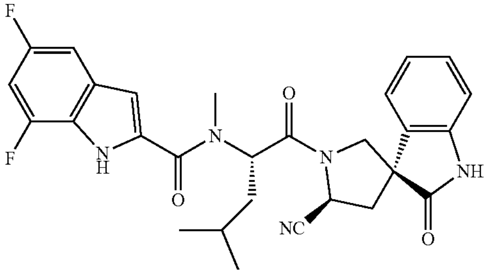 | [M + H]⁺ 509.22 | $^1$H NMR (400 MHz, Acetone-$d_6$) δ 10.75 (s, 1H), 9.68 (s, 1H), 7.21 (d, J = 9.2 Hz, 1H), 7.13-6.99 (m, 2H), 6.96 (d, J = 9.7 Hz, 2H), 6.88 (s, 2H), 5.56 (br, 1H), 5.22 (t, J = 8.3 Hz, 1H), 4.24 (d, J = 10.7 Hz, 1H), 3.99 (d, J = 10.6 Hz, 1H), 3.40 (s, 3H), 2.77-2.60 (m, 2H), 1.98 (s, 1H), 1.87-1.70 (m, 1H), 1.63 (s, 1H), 0.99 (dd, J = 17.8, 6.5 Hz, 6H). |
| 69 | 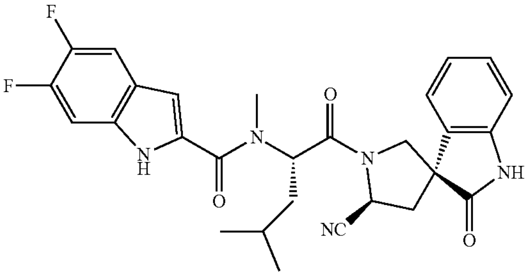 [SMILES: CC(C)C[C@@H](C(=O)N1C[C@]2(C[C@H]1C#N)C(=O)Nc1ccccc12)N(C)C(=O)c1cc2cc(F)c(F)cc2[nH]1] | [M + Na]⁺ 542.22 | $^1$H NMR (400 MHz, Acetone-$d_6$) δ 10.61 (s, 1H), 9.67 (s, 1H), 7.54 (s, 1H), 7.38 (dd, J = 11.0, 6.9 Hz, 1H), 7.16-6.96 (m, 2H), 6.93 (br, 2H), 6.81 (br, 1H), 5.57 (d, J = 9.3 Hz, 1H), 5.21 (t, J = 8.3 Hz, 1H), 4.29 (d, J = 10.8 Hz, 1H), 3.99 (d, J = 10.6 Hz, 1H), 3.42 (s, 3H), 2.72 (qd, J = 13.2, 8.3 Hz, 2H), 1.99-1.89 (m, 1H), 1.77 (ddd, J = 14.2, 8.8, 5.5 Hz, 1H), 1.62 (dq, J = 14.1, 6.7 Hz, 1H), 0.98 (dd, J = 20.8, 6.5 Hz, 6H). |
| 70 | 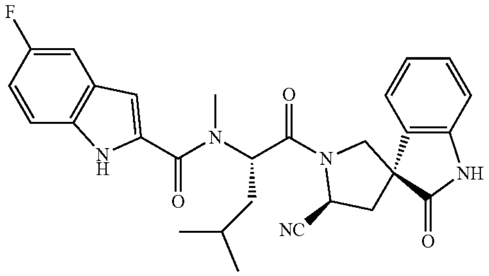 | [M + Na]⁺ 524.20 | $^1$H NMR (400 MHz, Acetone-$d_6$) δ 10.53 (s, 1H), 9.68 (s, 1H), 7.50 (dd, J = 9.0, 4.5 Hz, 1H), 7.33 (d, J = 9.6 Hz, 1H), 7.16-6.98 (m, 3H), 6.89 (dd, J = 26.7, 10.6 Hz, 3H), 5.64-5.46 (m, 1H), 5.21 (t, J = 8.2 Hz, 1H), 4.27 (d, J = 10.6 Hz, 1H), 4.00 (d, J = 10.6 Hz, 1H), 3.43 (s, 3H), 2.71 (tt, J = 13.3, 6.4 Hz, 2H), 1.97-1.88 (m, 1H), 1.78 (ddd, J = 14.2, 8.8, 5.6 Hz, 1H), 1.63 (dd, J = 13.7, 7.0 Hz, 1H), 0.98 (dd, J = 20.0, 6.5 Hz, 6H). |

-continued

| Example | Structure | MS | NMR |
|---|---|---|---|
| 71 | 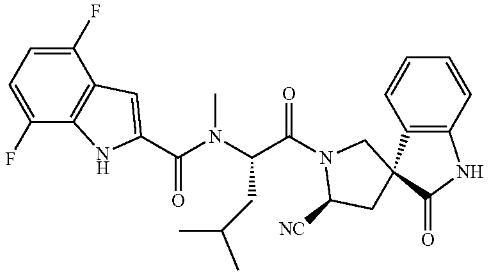 [SMILES: CC(C)C[C@@H](C(=O)N1C[C@]2(C[C@H]1C#N)C(=O)Nc1ccccc12)N(C)C(=O)c1cc2c(F)ccc(F)c2[nH]1] | [M + Na]$^+$ 542.21 | $^1$H NMR (400 MHz, Acetone-d$_6$) δ 10.96 (s, 1H), 9.67 (s, 1H), 7.04 (d, J = 7.6 Hz, 2H), 7.00-6.89 (m, 3H), 6.85 (t, J = 7.5 Hz, 1H), 6.77 (ddd, J = 9.8, 8.5, 3.0 Hz, 1H), 5.57 (dd, J = 9.5, 5.7 Hz, 1H), 5.22 (t, J = 8.3 Hz, 1H), 4.26 (d, J = 10.7 Hz, 1H), 4.00 (d, J = 10.7 Hz, 1H), 2.80-2.64 (m, 2H), 1.00 (dd, J = 18.1, 6.6 Hz, 6H). |
| 72 | 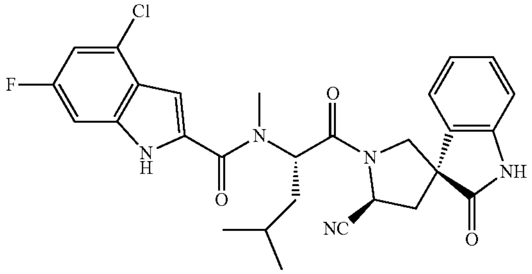 [SMILES: CC(C)C[C@@H](C(=O)N1C[C@]2(C[C@H]1C#N)C(=O)Nc1ccccc12)N(C)C(=O)c1cc2c(Cl)cc(F)cc2[nH]1] | [M + H]$^+$ 536.11 | $^1$H NMR (400 MHz, Acetone-d$_6$) δ 10.84 (s, 1H), 9.67 (s, 1H), 7.27-7.14 (m, 1H), 7.11-6.98 (m, 3H), 6.98-6.87 (m, 2H), 6.82 (t, J = 7.5 Hz, 1H), 5.59 (dd, J = 9.5, 5.6 Hz, 1H), 5.21 (t, J = 8.3 Hz, 1H), 4.29 (d, J = 10.7 Hz, 1H), 3.99 (d, J = 10.6 Hz, 1H), 3.47 (s, 3H), 2.79-2.62 (m, 2H), 1.99-1.87 (m, 1H), 1.79 (ddd, J = 14.2, 8.8, 5.7 Hz, 1H), 1.63 (dddd, J = 13.2, 11.7, 8.8, 6.5 Hz, 1H), 0.99 (dd, J = 19.1, 6.6 Hz, 6H). |
| 73 | 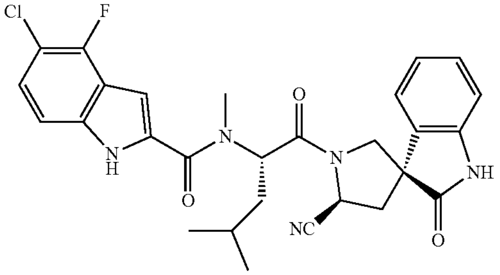 [SMILES: CC(C)C[C@@H](C(=O)N1C[C@]2(C[C@H]1C#N)C(=O)Nc1ccccc12)N(C)C(=O)c1cc2c(F)c(Cl)ccc2[nH]1] | [M − H]$^-$ 534.24, 535.68 | $^1$H NMR (400 MHz, Acetone-d$_6$) δ 10.87 (s, 1H), 9.68 (s, 1H), 7.36 (d, J = 8.7 Hz, 1H), 7.28 (dd, J = 8.8, 6.9 Hz, 1H), 7.03 (dd, J = 11.8, 7.4 Hz, 2H), 6.97 (s, 1H), 6.91 (d, J = 7.7 Hz, 1H), 6.82 (t, J = 7.5 Hz, 1H), 5.59 (dd, J = 9.4, 5.7 Hz, 1H), 5.22 (t, J = 8.3 Hz, 1H), 4.28 (d, J = 10.7 Hz, 1H), 3.99 (d, J = 10.6 Hz, 1H), 3.46 (s, 3H), 2.78-2.65 (m, 2H), 1.99-1.89 (m, 1H), 1.79 (ddd, J = 14.2, 8.7, 5.6 Hz, 1H), 1.72-1.44 (m, 1H), 0.99 (m, 6H). |
| 74 | 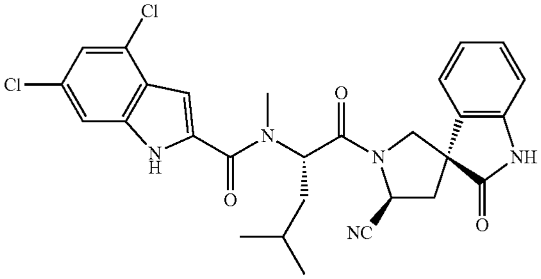 [SMILES: CC(C)C[C@@H](C(=O)N1C[C@]2(C[C@H]1C#N)C(=O)Nc1ccccc12)N(C)C(=O)c1cc2c(Cl)cc(Cl)cc2[nH]1] | [M − H]$^-$ 550.13, 552.14 | $^1$H NMR (400 MHz, Acetone-d$_6$) δ 10.89 (s, 1H), 9.67 (s, 1H), 7.52 (s, 1H), 7.19 (d, J = 1.7 Hz, 1H), 7.08-6.97 (m, 2H), 6.97-6.88 (m, 2H), 6.82 (t, J = 7.5 Hz, 1H), 5.59 (dd, J = 9.5, 5.6 Hz, 1H), 5.22 (t, J = 8.3 Hz, 1H), 4.29 (d, J = 10.7 Hz, 1H), 3.99 (d, J = 10.6 Hz, 1H), 3.47 (s, 3H), 2.79-2.63 (m, 2H), 2.02-1.87 (m, 1H), 1.79 (ddd, J = 14.2, 8.7, 5.6 Hz, 1H), 1.64 (dtd, J = 8.7, 6.7, 5.1 Hz, 1H), 0.99 (m, 6H). |
| 75 | 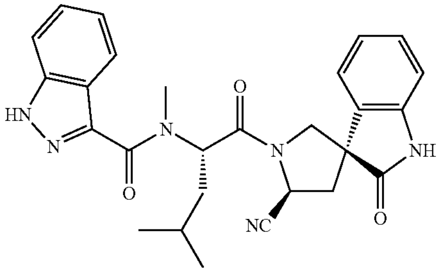 [SMILES: CC(C)C[C@@H](C(=O)N1C[C@]2(C[C@H]1C#N)C(=O)Nc1ccccc12)N(C)C(=O)c1n[nH]c2ccccc12] | [M − H]$^-$ 483.16 | |

-continued

| Example | Structure | MS | NMR |
|---|---|---|---|
| 76 | 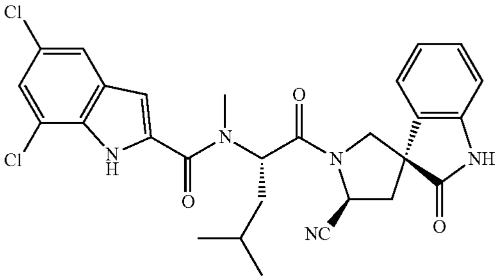 [SMILES: CC(C)C[C@@H](C(=O)N1C[C@]2(C[C@H]1C#N)C(=O)Nc1ccccc12)N(C)C(=O)c1cc2cc(Cl)cc(Cl)c2[nH]1] | [M − H]⁻ 550.07, 551.95 | $^{1}$H NMR (400 MHz, Acetone-$d_6$) δ 10.31 (s, 1H), 9.67 (s, 1H), 7.63 (s, 1H), 7.32 (s, 1H), 7.14-6.88 (m, 3H), 6.82 (d, J = 13.9 Hz, 2H), 5.53 (s, 1H), 5.20 (t, J = 8.4 Hz, 1H), 4.25 (d, J = 10.8 Hz, 1H), 3.95 (d, J = 10.6 Hz, 1H), 3.36 (s, 3H), 2.68 (td, J = 14.1, 13.3, 8.4 Hz, 2H), 1.85 (br, 1H), 1.79 (m, J1H), 1.61 (m, 1H), 0.96 (dd, J = 16.7, 6.6 Hz, 6H). |
| 77 | 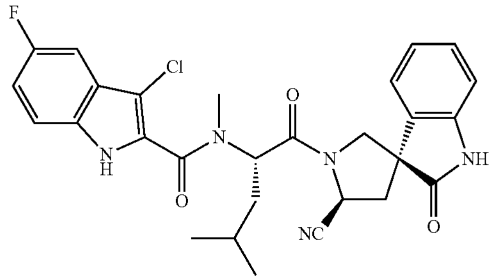 [SMILES: CC(C)C[C@@H](C(=O)N1C[C@]2(C[C@H]1C#N)C(=O)Nc1ccccc12)N(C)C(=O)c1[nH]c2ccc(F)cc2c1Cl] | [M + H]⁺ 536.15, 538.06 | $^{1}$H NMR (400 MHz, Acetone-$d_6$) δ 10.80 (s, 1H), 9.72 (s, 1H), 7.51 (dd, J = 9.1, 4.3 Hz, 1H), 7.25 (t, J = 7.9 Hz, 2H), 7.18 (d, J = 7.4 Hz, 1H), 7.16-7.08 (m, 1H), 6.99 (dd, J = 17.6, 7.9 Hz, 2H), 5.47-5.30 (m, 1H), 5.21 (t, J = 8.1 Hz, 1H), 4.26 (d, J = 10.5 Hz, 1H), 4.09 (d, J = 10.5 Hz, 1H), 3.24 (s, 3H), 2.86-2.63 (m, 2H), 2.03-1.93 (m, 1H), 1.82 (d, J = 15.3 Hz, 2H), 1.02 (dd, J = 23.0, 6.0 Hz, 6484.20 H). |
| 78 | 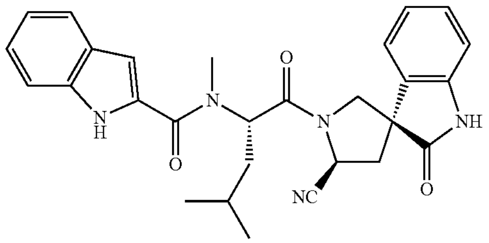 [SMILES: CC(C)C[C@@H](C(=O)N1C[C@]2(C[C@H]1C#N)C(=O)Nc1ccccc12)N(C)C(=O)c1cc2ccccc2[nH]1] | [M + H]⁺ 484.20 | $^{1}$H NMR (400 MHz, Acetone-$d_6$) δ 10.43 (s, 1H), 9.67 (s, 1H), 7.64 (s, 1H), 7.49 (d, J = 8.3 Hz, 1H), 7.23 (ddd, J = 8.2, 6.9, 1.1 Hz, 1H), 7.06 (q, J = 9.4, 8.4 Hz, 3H), 6.89 (dd, J = 20.9, 11.6 Hz, 3H), 5.59 (dd, J = 9.5, 5.6 Hz, 1H), 5.21 (t, J = 8.2 Hz, 1H), 4.27 (d, J = 10.6 Hz, 1H), 4.01 (d, J = 10.6 Hz, 1H), 3.44 (s, 3H), 2.79-2.63 (m, 2H), 1.94 (ddd, J = 19.1, 9.7, 4.9 Hz, 1H), 1.78 (ddd, J = 14.2, 8.7, 5.6 Hz, 1H), 1.71-1.55 (m, 1H), 0.98 (dd, J = 20.7, 6.5 Hz, 6H). |
| 79 | 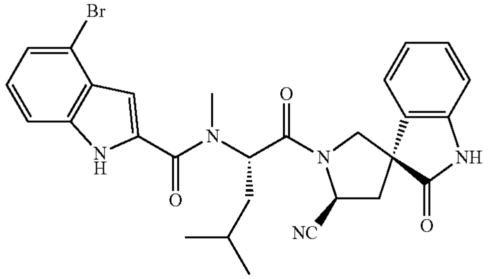 [SMILES: CC(C)C[C@@H](C(=O)N1C[C@]2(C[C@H]1C#N)C(=O)Nc1ccccc12)N(C)C(=O)c1cc2c(Br)cccc2[nH]1] | [M − H]⁻ 560.00, 562.00 | $^{1}$H NMR (400 MHz, Acetone-$d_6$) δ 10.79 (s, 1H), 9.67 (s, 1H), 7.52 (d, J = 8.2 Hz, 1H), 7.31 (d, J = 7.5 Hz, 1H), 7.17 (t, J = 7.9 Hz, 1H), 7.04 (d, J = 7.6 Hz, 2H), 6.97-6.78 (m, 3H), 5.60 (dd, J = 9.4, 5.7 Hz, 1H), 5.21 (t, J = 8.2 Hz, 1H), 4.33-4.02 (m, 1H), 4.00 (d, J = 10.6 Hz, 1H), 3.47 (s, 3H), 2.79-2.63 (m, 2H), 1.94 (ddd, J = 14.4, 9.5, 5.2 Hz, 1H), 1.80 (ddd, J = 14.2, 8.6, 5.6 Hz, 1H), 1.72-1.57 (m, 1H), 0.99 (dd, J = 18.4, 6.5 Hz, 6H). |
| 80 | 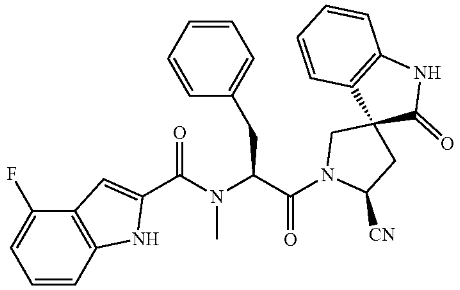 [SMILES: CN(C(=O)c1cc2c(F)cccc2[nH]1)[C@@H](Cc1ccccc1)C(=O)N1C[C@]2(C[C@H]1C#N)C(=O)Nc1ccccc12] | [M − H]⁻ 534.19 | $^{1}$H NMR (400 MHz, Acetone-$d_6$) δ 10.59 (s, 1H), 9.64 (s, 1H), 7.42-7.35 (m, 2H), 7.32-7.21 (m, 3H), 7.24-7.13 (m, 2H), 7.02 (dt, J = 7.4, 1.9 Hz, 2H), 6.92-6.85 (m, 1H), 6.85-6.74 (m, 3H), 5.76 (dd, J = 8.6, 6.7 Hz, 1H), 5.21 (t, J = 8.3 Hz, 1H), 4.24 (d, J = 10.6 Hz, 1H), 3.73 (d, J = 10.6 Hz, 1H), 3.53 (s, 3H), 3.40 (dd, J = 14.0, 6.7 Hz, 1H), 3.26 (dd, J = 14.1, 8.6 Hz, 1H), 2.72 (ddd, J = 13.3, 8.5, 1.1 Hz, 1H), 2.62 (dd, J = 13.2, 8.0 Hz, 1H). |

-continued

| Example | Structure | MS | NMR |
|---|---|---|---|
| 81 | 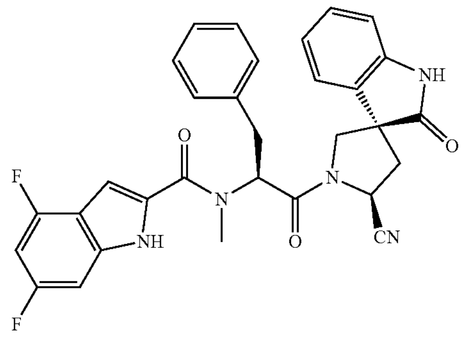 [SMILES: CN(C(=O)c1cc2c(F)cc(F)cc2[nH]1)[C@@H](Cc1ccccc1)C(=O)N1C[C@]2(C[C@H]1C#N)C(=O)Nc1ccccc12] | [M − H]⁻ 552.18 | $^{1}$H NMR (400 MHz, Acetone-$d_6$) δ 10.69 (s, 1H), 9.65 (s, 1H), 7.41-7.34 (m, 2H), 7.29-7.21 (m, 2H), 7.24-7.13 (m, 1H), 7.07-6.97 (m, 3H), 6.89 (d, J = 7.6 Hz, 1H), 6.85 (s, 1H), 6.79 (t, J = 7.5 Hz, 1H), 6.72 (td, J = 10.3, 2.1 Hz, 1H), 5.76 (dd, J = 8.8, 6.6 Hz, 1H), 5.21 (t, J = 8.3 Hz, 1H), 4.25 (d, J = 10.7 Hz, 1H), 3.73 (d, J = 10.6 Hz, 1H), 3.52 (s, 3H), 3.39 (dd, J = 14.1, 6.7 Hz, 1H), 3.26 (dd, J = 14.1, 8.8 Hz, 1H), 2.72 (ddd, J = 13.2, 8.5, 1.2 Hz, 1H), 2.63 (dd, J = 13.3, 8.1 Hz, 1H). |
| 82 | 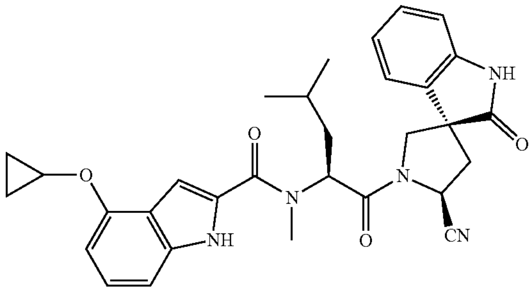 [SMILES: CC(C)C[C@@H](C(=O)N1C[C@]2(C[C@H]1C#N)C(=O)Nc1ccccc12)N(C)C(=O)c1cc2c(OC3CC3)cccc2[nH]1] | [M + Na]⁺ 562.24 | $^{1}$H NMR (400 MHz, Acetone-$d_6$) δ 10.39 (s, 1H), 9.67 (s, 1H), 7.17 (t, J = 7.9 Hz, 1H), 7.13-6.96 (m, 3H), 6.87 (td, J = 18.4, 16.6, 7.2 Hz, 5H), 5.58 (d, J = 9.4 Hz, 1H), 5.20 (t, J = 8.2 Hz, 1H), 4.27 (d, J = 10.8 Hz, 1H), 4.03-3.92 (m, 1H), 3.43 (s, 3H), 3.38 (d, J = 7.2 Hz, 1H), 2.78-2.62 (m, 2H), 1.99-1.85 (m, 1H), 1.77 (dt, J = 14.2, 7.2 Hz, 1H), 1.63 (dd, J = 14.3, 7.7 Hz, 1H), 1.45-1.35 (m, 2H), 1.34-1.28 (m, 1H), 1.19 (q, J = 8.0, 7.3 Hz, 1H), 1.01 (d, J = 6.7 Hz, 3H), 0.95 (d, J = 6.6 Hz, 3H). |
| 83 | 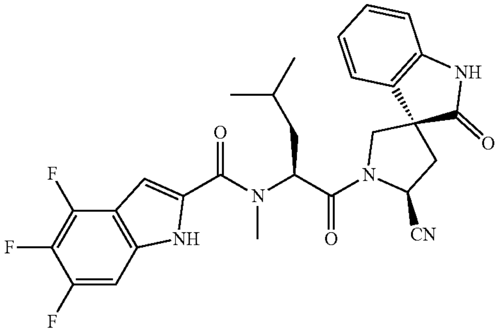 [SMILES: CC(C)C[C@@H](C(=O)N1C[C@]2(C[C@H]1C#N)C(=O)Nc1ccccc12)N(C)C(=O)c1cc2c(F)c(F)c(F)cc2[nH]1] | [M + Na]⁺ 560.19 | $^{1}$H NMR (400 MHz, Acetone-$d_6$) δ 10.87 (s, 1H), 9.69 (s, 1H), 7.31-7.20 (m, 1H), 7.09-6.95 (m, 3H), 6.91 (d, J = 7.7 Hz, 1H), 6.80 (t, J = 7.5 Hz, 1H), 5.58 (dd, J = 9.5, 5.6 Hz, 1H), 5.21 (t, J = 8.3 Hz, 1H), 4.29 (d, J = 10.7 Hz, 1H), 3.98 (d, J = 10.6 Hz, 1H), 3.46 (s, 3H), 2.81-2.58 (m, 2H), 1.94 (ddd, J = 14.4, 9.6, 5.0 Hz, 1H), 1.78 (ddd, J = 14.2, 8.8, 5.6 Hz, 1H), 1.70-1.55 (m, 1H), 1.01 (d, J = 6.6 Hz, 3H), 0.96 (d, J = 6.5 Hz, 3H). |
| 84 | 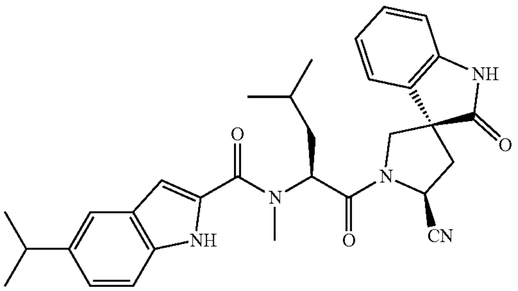 [SMILES: CC(C)C[C@@H](C(=O)N1C[C@]2(C[C@H]1C#N)C(=O)Nc1ccccc12)N(C)C(=O)c1cc2cc(C(C)C)ccc2[nH]1] | [M + Na]⁺ 548.26 | $^{1}$H NMR (400 MHz, Acetone-$d_6$) δ 10.28 (s, 1H), 9.68 (s, 1H), 7.54 (s, 1H), 7.20-6.97 (m, 3H), 6.97-6.72 (m, 3H), 5.58 (dd, J = 9.4, 5.6 Hz, 1H), 5.21 (t, J = 8.2 Hz, 1H), 4.25 (d, J = 10.6 Hz, 1H), 4.01 (d, J = 10.6 Hz, 1H), 3.43 (s, 3H), 3.01 (td, J = 13.5, 6.6 Hz, 1H), 2.81-2.60 (m, 2H), 2.01-1.85 (m, 1H), 1.78 (ddd, J = 14.2, 8.7, 5.6 Hz, 1H), 1.63 (dq, J = 13.6, 6.6 Hz, 1H), 1.29 (d, J = 6.9 Hz, 6H), 1.01 (d, J = 6.6 Hz, 3H), 0.99-0.89 (m, 3H). |
| 85 | 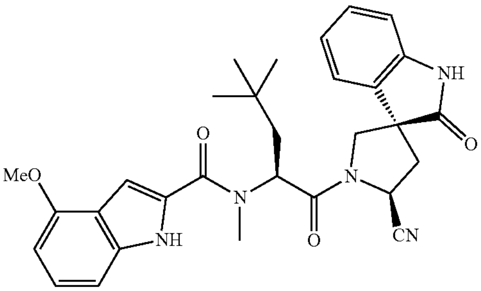 | [M + Na]⁺ 550.24 | $^{1}$H NMR (400 MHz, Chloroform-d) δ 8.81 (s, 1H), 8.14 (s, 1H), 7.20 (t, J = 8.0 Hz, 1H), 7.04-6.89 (m, 3H), 6.83 (d, J = 7.8 Hz, 1H), 6.73-6.58 (m, 2H), 6.50 (d, J = 7.8 Hz, 1H), 5.59 (t, J = 6.4 Hz, 1H), 5.00 (t, J = 8.6 Hz, 1H), 4.65 (d, J = 10.4 Hz, 1H), 4.01-3.91 (m, 1H), 3.99 (s, 3H), 3.49 (s, 3H), 2.94-2.78 (m, 1H), 2.51 (dd, J = 13.2, 8.5 Hz, 1H), 2.11 (q, J = 6.5, 5.3 Hz, 1H), 1.74 (dd, J = 14.3, 6.0 Hz, 1H), 0.99 (s, 9H). |

-continued
| Example | Structure | MS | NMR |
|---|---|---|---|
| 86 | 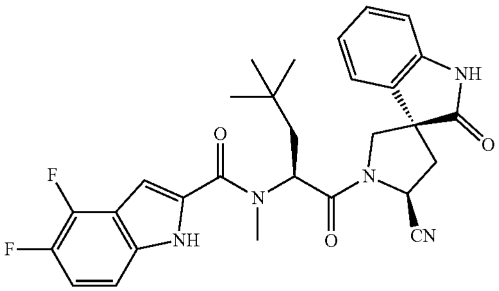 | [M + Na]+ 556.21 | $^1$H NMR (500 MHz, Chloroform-d) δ 9.21 (s, 1H), 8.67 (s, 1H), 7.10 (ddd, J = 10.6, 8.9, 7.3 Hz, 1H), 7.07-6.89 (m, 2H), 6.89-6.74 (m, 2H), 6.74-6.54 (m, 2H), 5.55 (t, J = 6.4 Hz, 1H), 5.03 (t, J = 8.5 Hz, 1H), 4.48 (d, J = 10.5 Hz, 1H), 3.98 (d, J = 10.5 Hz, 1H), 3.48 (s, 3H), 2.86 (dd, J = 13.3, 8.7 Hz, 1H), 2.52 (ddd, J = 13.3, 8.4, 1.3 Hz, 1H), 2.20-2.13 (m, 1H), 1.73 (dd, J = 14.3, 6.0 Hz, 1H), 0.99 (s, 9H). |
| 87 | 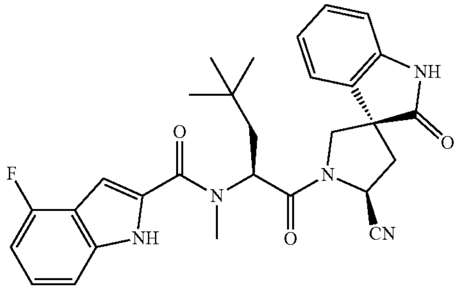 [SMILES: CN(C(=O)c1cc2c(F)cccc2[nH]1)[C@@H](CC(C)(C)C)C(=O)N1C[C@]2(C[C@H]1C#N)C(=O)Nc1ccccc12] | [M + Na]+ 538.22 | |
| 88 | 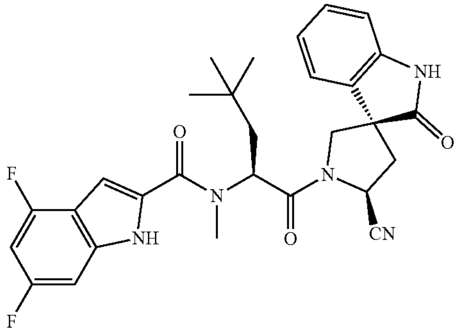 [SMILES: CN(C(=O)c1cc2c(F)cc(F)cc2[nH]1)[C@@H](CC(C)(C)C)C(=O)N1C[C@]2(C[C@H]1C#N)C(=O)Nc1ccccc12] | [M + Na]+ 556.21 | $^1$H NMR (400 MHz, Chloroform-d) δ 9.34 (s, 1H), 8.79 (s, 1H), 6.96 (t, J = 7.6 Hz, 1H), 6.89-6.79 (m, 3H), 6.73-6.54 (m, 3H), 5.57 (t, J = 6.4 Hz, 1H), 5.03 (t, J = 8.5 Hz, 1H), 4.51 (d, J = 10.5 Hz, 1H), 3.97 (d, J = 10.5 Hz, 1H), 3.47 (s, 3H), 2.85 (dd, J = 13.3, 8.5 Hz, 1H), 2.52 (dd, J = 13.3, 8.5 Hz, 1H), 2.21-2.11 (m, 1H), 1.76 (d, J = 6.2 Hz, 1H), 0.99 (s, 9H). |
| 162 | 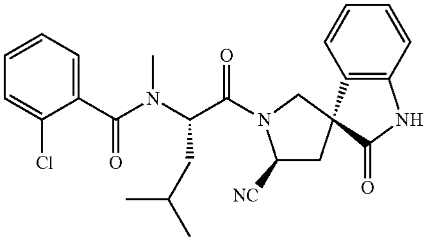 [SMILES: CC(C)C[C@@H](C(=O)N1C[C@]2(C[C@H]1C#N)C(=O)Nc1ccccc12)N(C)C(=O)c1ccccc1Cl] | 479.10 | |
| 163 | 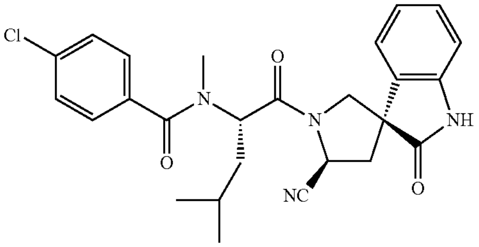 [SMILES: CC(C)C[C@@H](C(=O)N1C[C@]2(C[C@H]1C#N)C(=O)Nc1ccccc12)N(C)C(=O)c1ccc(Cl)cc1] | 479.10 | |

-continued
| Example | Structure | MS | NMR |
|---|---|---|---|
| 164 | 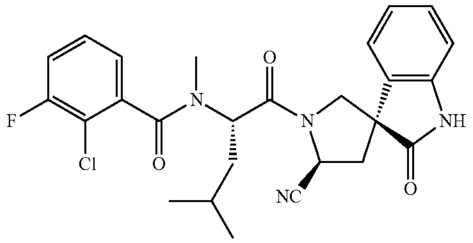 [SMILES: CC(C)C[C@@H](C(=O)N1C[C@]2(C[C@H]1C#N)C(=O)Nc1ccccc12)N(C)C(=O)c1cccc(F)c1Cl] | 497.10 | |
| 165 | 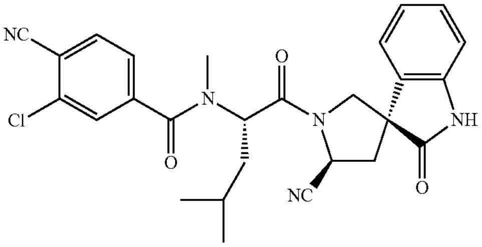 [SMILES: CC(C)C[C@@H](C(=O)N1C[C@]2(C[C@H]1C#N)C(=O)Nc1ccccc12)N(C)C(=O)c1ccc(C#N)c(Cl)c1] | 504.05 | |
| 166 | 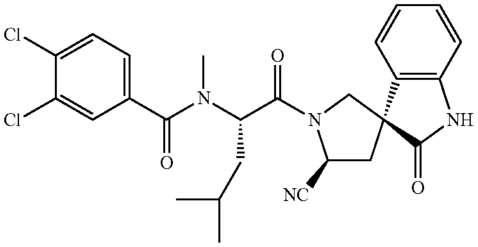 [SMILES: CC(C)C[C@@H](C(=O)N1C[C@]2(C[C@H]1C#N)C(=O)Nc1ccccc12)N(C)C(=O)c1ccc(Cl)c(Cl)c1] | 535.15 [M + Na]+ | |
| 167 | 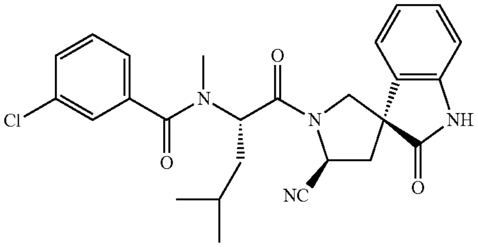 [SMILES: CC(C)C[C@@H](C(=O)N1C[C@]2(C[C@H]1C#N)C(=O)Nc1ccccc12)N(C)C(=O)c1cccc(Cl)c1] | 479.10 | |
| 168 | 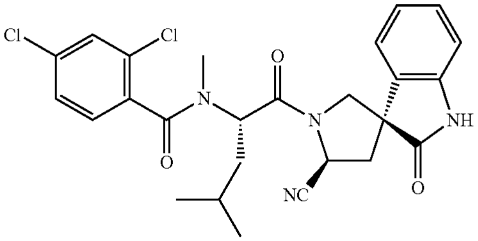 [SMILES: CC(C)C[C@@H](C(=O)N1C[C@]2(C[C@H]1C#N)C(=O)Nc1ccccc12)N(C)C(=O)c1ccc(Cl)cc1Cl] | 513.15 | |
| 169 | 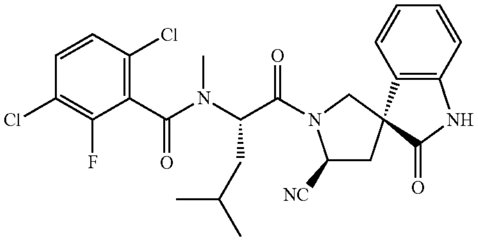 [SMILES: CC(C)C[C@@H](C(=O)N1C[C@]2(C[C@H]1C#N)C(=O)Nc1ccccc12)N(C)C(=O)c1c(Cl)ccc(Cl)c1F] | 531.05 | |

-continued
| Example | Structure | MS | NMR |
|---|---|---|---|
| 170 | 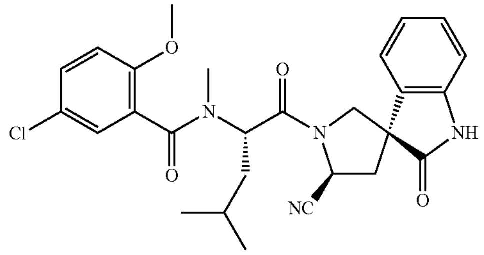 [SMILES: COc1ccc(Cl)cc1C(=O)N(C)[C@@H](CC(C)C)C(=O)N1C[C@]2(C[C@H]1C#N)C(=O)Nc1ccccc12] | 509.20 | |
| 171 | 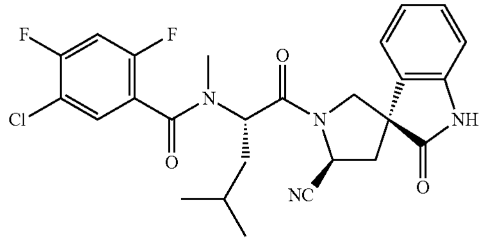 [SMILES: CC(C)C[C@@H](C(=O)N1C[C@]2(C[C@H]1C#N)C(=O)Nc1ccccc12)N(C)C(=O)c1cc(Cl)c(F)cc1F] | 537.05 [M + Na]+ | |
| 172 | 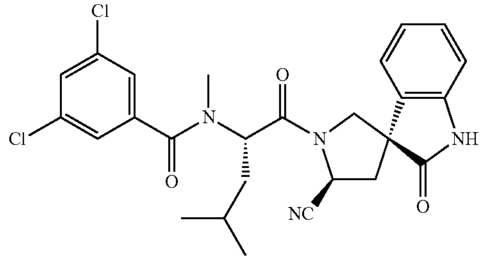 [SMILES: CC(C)C[C@@H](C(=O)N1C[C@]2(C[C@H]1C#N)C(=O)Nc1ccccc12)N(C)C(=O)c1cc(Cl)cc(Cl)c1] | 537.05 [M + Na]+ | |
| 173 | 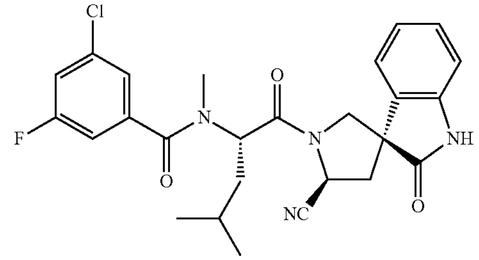 [SMILES: CC(C)C[C@@H](C(=O)N1C[C@]2(C[C@H]1C#N)C(=O)Nc1ccccc12)N(C)C(=O)c1cc(F)cc(Cl)c1] | 497.15 | |
| 174 | 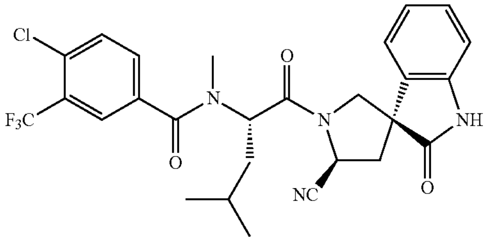 [SMILES: CC(C)C[C@@H](C(=O)N1C[C@]2(C[C@H]1C#N)C(=O)Nc1ccccc12)N(C)C(=O)c1ccc(Cl)c(C(F)(F)F)c1] | 569.05 [M + Na]+ | |
| 175 | 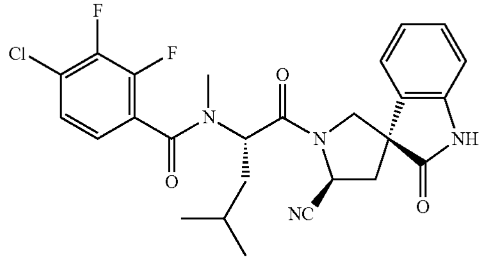 [SMILES: CC(C)C[C@@H](C(=O)N1C[C@]2(C[C@H]1C#N)C(=O)Nc1ccccc12)N(C)C(=O)c1ccc(Cl)c(F)c1F] | 537.05 [M + Na]+ | |

-continued
| Example | Structure | MS | NMR |
|---|---|---|---|
| 176 | 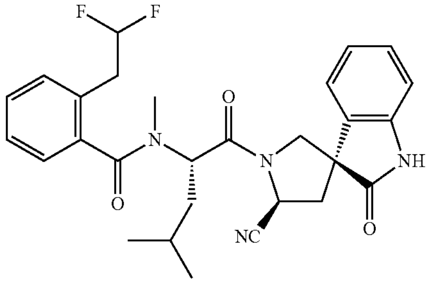 [SMILES: CC(C)C[C@@H](C(=O)N1C[C@]2(C[C@H]1C#N)C(=O)Nc1ccccc12)N(C)C(=O)c1ccccc1CC(F)F] | 511.10 | |
| 177 | 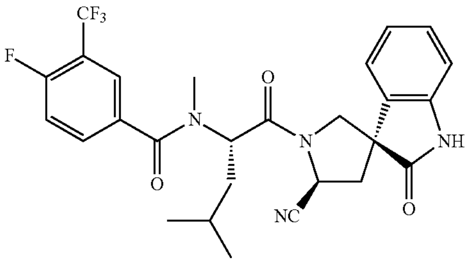 | 531.15 | |
| 178 | 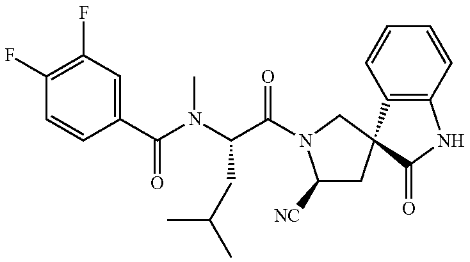 [SMILES: CC(C)C[C@@H](C(=O)N1C[C@]2(C[C@H]1C#N)C(=O)Nc1ccccc12)N(C)C(=O)c1ccc(F)c(F)c1] | 481.10 | |
| 179 | 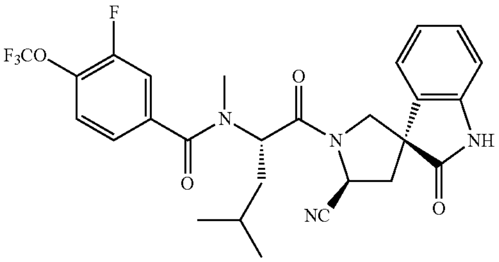 | 547.15 | |
| 180 | 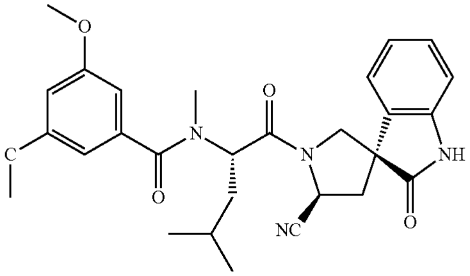 [SMILES: CCc1cc(OC)cc(C(=O)N(C)[C@@H](CC(C)C)C(=O)N2C[C@]3(C[C@H]2C#N)C(=O)Nc2ccccc23)c1] | 543.10 | |

-continued
| Example | Structure | MS | NMR |
|---|---|---|---|
| 181 | 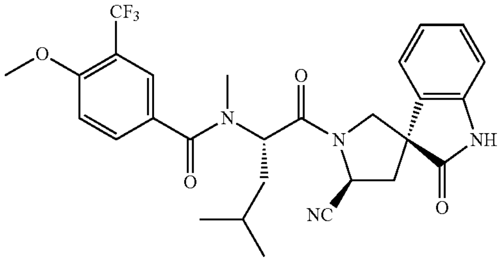 [SMILES: COc1ccc(C(=O)N(C)[C@@H](CC(C)C)C(=O)N2C[C@]3(C[C@H]2C#N)C(=O)Nc2ccccc23)cc1C(F)(F)F] | 543.10 | |
| 182 | 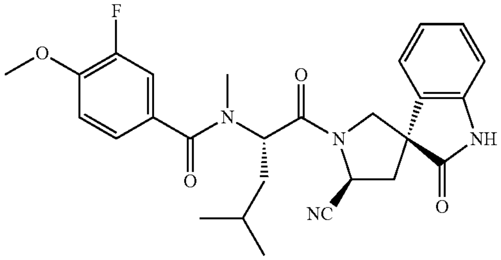 [SMILES: COc1ccc(C(=O)N(C)[C@@H](CC(C)C)C(=O)N2C[C@]3(C[C@H]2C#N)C(=O)Nc2ccccc23)cc1F] | 493.10 | |
| 183 | 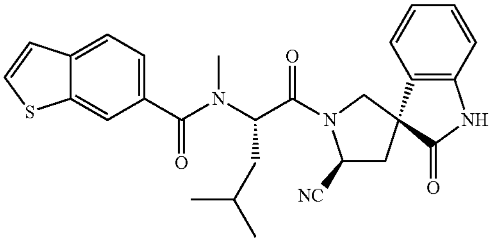 [SMILES: CC(C)C[C@@H](C(=O)N1C[C@]2(C[C@H]1C#N)C(=O)Nc1ccccc12)N(C)C(=O)c1ccc2ccsc2c1] | 523.15 | |
| 184 | 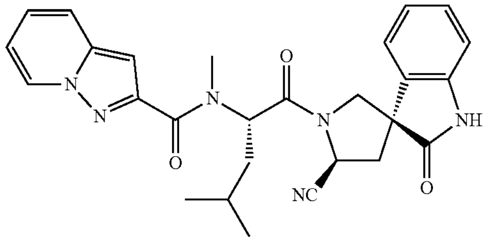 [SMILES: CC(C)C[C@@H](C(=O)N1C[C@]2(C[C@H]1C#N)C(=O)Nc1ccccc12)N(C)C(=O)c1cc2ccccn2n1] | 585.18 | |
| 185 | 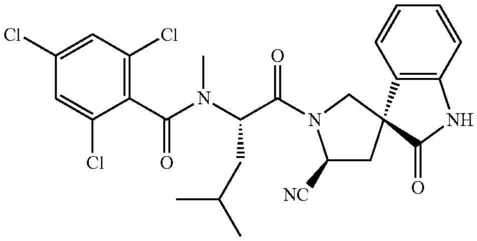 [SMILES: CC(C)C[C@@H](C(=O)N1C[C@]2(C[C@H]1C#N)C(=O)Nc1ccccc12)N(C)C(=O)c1c(Cl)cc(Cl)cc1Cl] | 569.05 [M + Na]+ | |
| 186 | 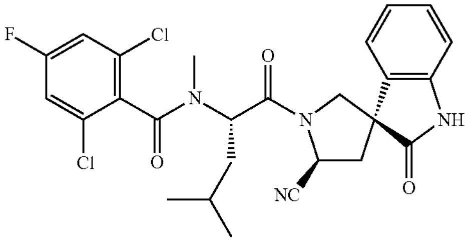 [SMILES: CC(C)C[C@@H](C(=O)N1C[C@]2(C[C@H]1C#N)C(=O)Nc1ccccc12)N(C)C(=O)c1c(Cl)cc(F)cc1Cl] | 531.15 | |

-continued
| Example | Structure | MS | NMR |
| --- | --- | --- | --- |
| 187 | 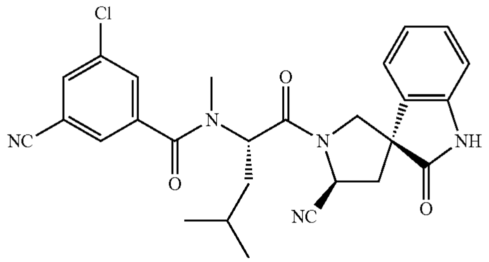 [SMILES: CC(C)C[C@@H](C(=O)N1C[C@]2(C[C@H]1C#N)C(=O)Nc1ccccc12)N(C)C(=O)c1cc(Cl)cc(C#N)c1] | 504.20 | |
| 188 | 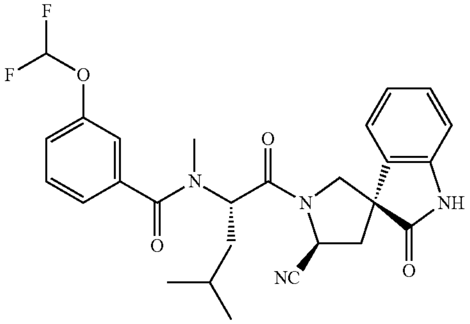 [SMILES: CC(C)C[C@@H](C(=O)N1C[C@]2(C[C@H]1C#N)C(=O)Nc1ccccc12)N(C)C(=O)c1cccc(OC(F)F)c1] | 511.10 | |
| 189 | 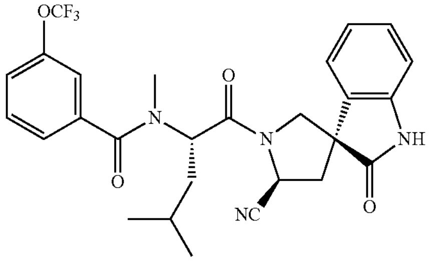 [SMILES: CC(C)C[C@@H](C(=O)N1C[C@]2(C[C@H]1C#N)C(=O)Nc1ccccc12)N(C)C(=O)c1cccc(OC(F)(F)F)c1] | 529.05 | |
| 190 | 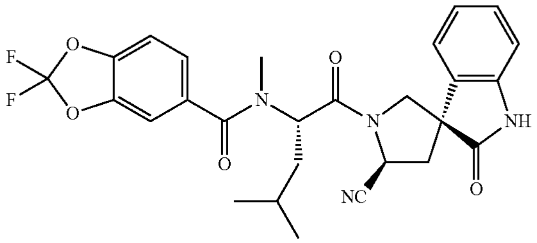 [SMILES: CC(C)C[C@@H](C(=O)N1C[C@]2(C[C@H]1C#N)C(=O)Nc1ccccc12)N(C)C(=O)c1ccc2c(c1)OC(F)(F)O2] | 525.10 | |
| 191 | 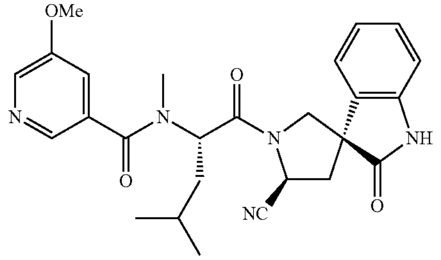 | 576.15 | |

-continued
| Example | Structure | MS | NMR |
|---|---|---|---|
| 192 | 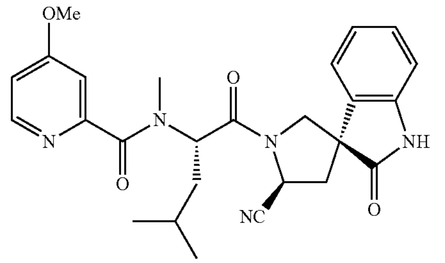 [SMILES: COc1ccnc(C(=O)N(C)[C@@H](CC(C)C)C(=O)N2C[C@]3(C[C@H]2C#N)C(=O)Nc2ccccc23)c1] | 476.20 | |
| 193 | 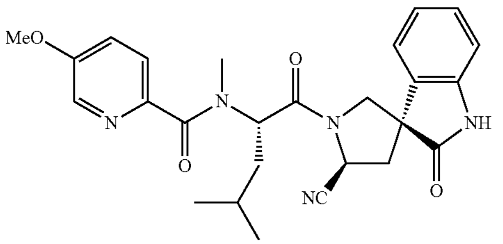 [SMILES: COc1ccc(C(=O)N(C)[C@@H](CC(C)C)C(=O)N2C[C@]3(C[C@H]2C#N)C(=O)Nc2ccccc23)nc1] | 476.20 | |
| 194 | 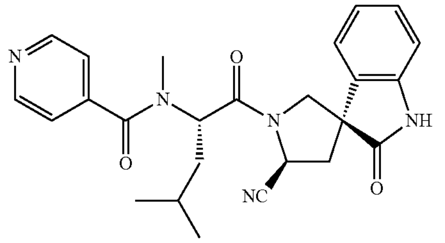 [SMILES: CC(C)C[C@@H](C(=O)N1C[C@]2(C[C@H]1C#N)C(=O)Nc1ccccc12)N(C)C(=O)c1ccncc1] | 446.20 | |
| 195 | 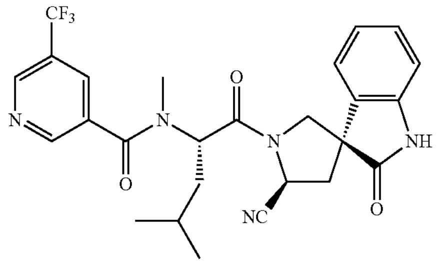 | 514.10 | |
| 196 | 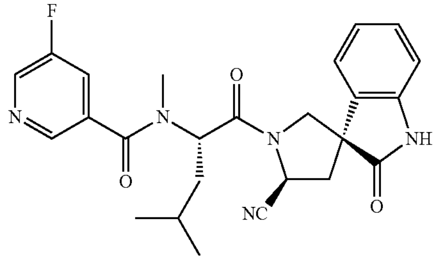 | 464.10 | |
| 197 | 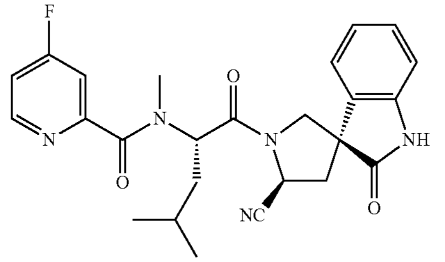 [SMILES: CC(C)C[C@@H](C(=O)N1C[C@]2(C[C@H]1C#N)C(=O)Nc1ccccc12)N(C)C(=O)c1cc(F)ccn1] | 464.15 | |

-continued
| Example | Structure | MS | NMR |
| --- | --- | --- | --- |
| 198 | 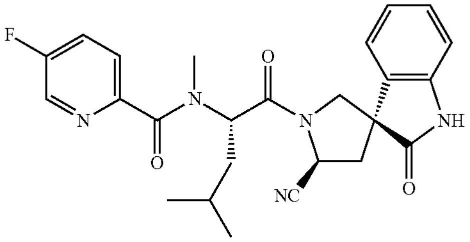 [SMILES: CC(C)C[C@@H](C(=O)N1C[C@]2(C[C@H]1C#N)C(=O)Nc1ccccc12)N(C)C(=O)c1ccc(F)cn1] | 464.15 | |
| 199 | 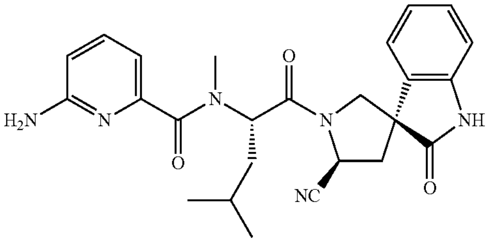 [SMILES: CC(C)C[C@@H](C(=O)N1C[C@]2(C[C@H]1C#N)C(=O)Nc1ccccc12)N(C)C(=O)c1cccc(N)n1] | 461.20 | |
| 200 | 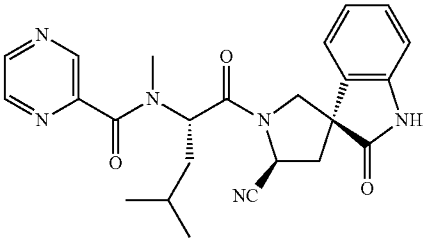 [SMILES: CC(C)C[C@@H](C(=O)N1C[C@]2(C[C@H]1C#N)C(=O)Nc1ccccc12)N(C)C(=O)c1cnccn1] | 447.15 | |
| 201 | 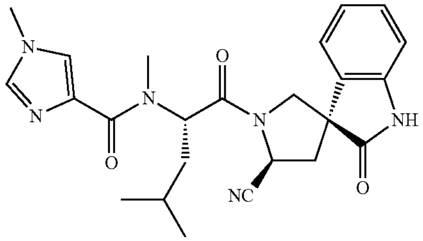 [SMILES: CC(C)C[C@@H](C(=O)N1C[C@]2(C[C@H]1C#N)C(=O)Nc1ccccc12)N(C)C(=O)c1cn(C)cn1] | 449.20 | |
| 202 | 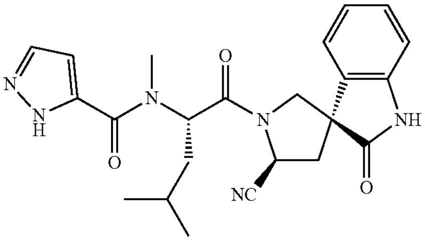 [SMILES: CC(C)C[C@@H](C(=O)N1C[C@]2(C[C@H]1C#N)C(=O)Nc1ccccc12)N(C)C(=O)c1ccn[nH]1] | 435.15 | |
| 203 | 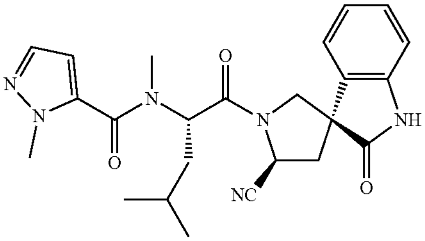 | 449.15 | |

-continued
| Example | Structure | MS | NMR |
|---|---|---|---|
| 204 | 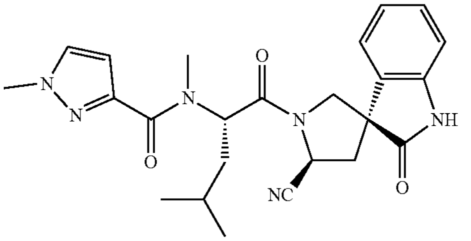 [SMILES: CC(C)C[C@@H](C(=O)N1C[C@]2(C[C@H]1C#N)C(=O)Nc1ccccc12)N(C)C(=O)c1ccn(C)n1] | 449.20 | |
| 205 | 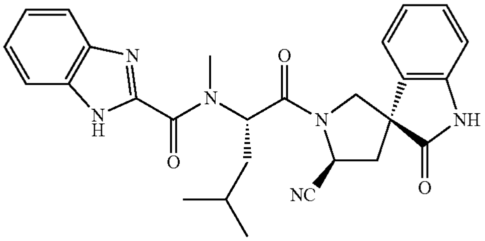 [SMILES: CC(C)C[C@@H](C(=O)N1C[C@]2(C[C@H]1C#N)C(=O)Nc1ccccc12)N(C)C(=O)c1nc2ccccc2[nH]1] | 485.15 | |
| 206 | 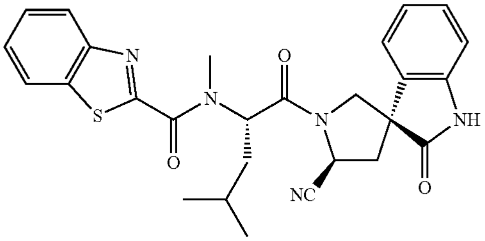 [SMILES: CC(C)C[C@@H](C(=O)N1C[C@]2(C[C@H]1C#N)C(=O)Nc1ccccc12)N(C)C(=O)c1nc2ccccc2s1] | 502.30 | |
| 207 | 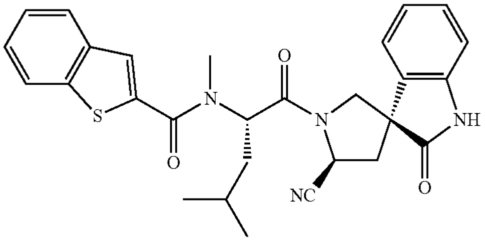 [SMILES: CC(C)C[C@@H](C(=O)N1C[C@]2(C[C@H]1C#N)C(=O)Nc1ccccc12)N(C)C(=O)c1cc2ccccc2s1] | 501.15 | |
| 208 | 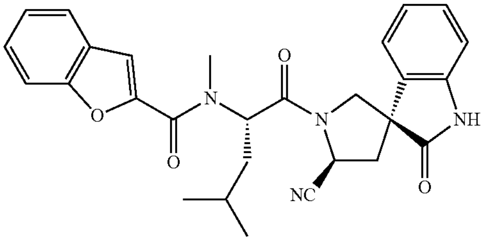 [SMILES: CC(C)C[C@@H](C(=O)N1C[C@]2(C[C@H]1C#N)C(=O)Nc1ccccc12)N(C)C(=O)c1cc2ccccc2o1] | 485.15 | |
| 209 | 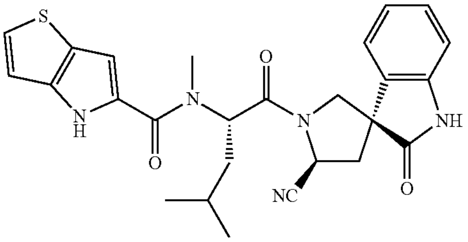 [SMILES: CC(C)C[C@@H](C(=O)N1C[C@]2(C[C@H]1C#N)C(=O)Nc1ccccc12)N(C)C(=O)c1cc2sccc2[nH]1] | 490.15 | |

-continued
| Example | Structure | MS | NMR |
|---|---|---|---|
| 210 | 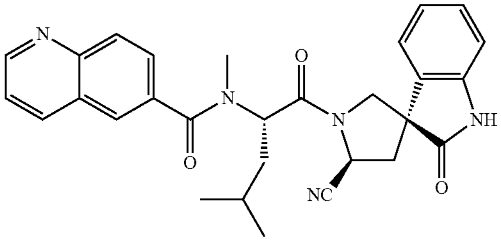 | 496.35 | |
| 211 | 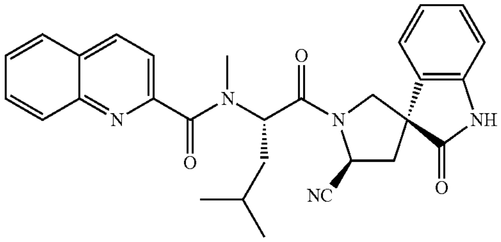 | 496.20 | |
| 212 | 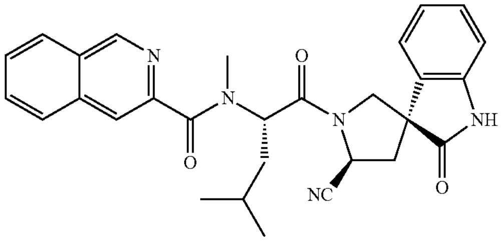 | 496.25 | |
| 213 | 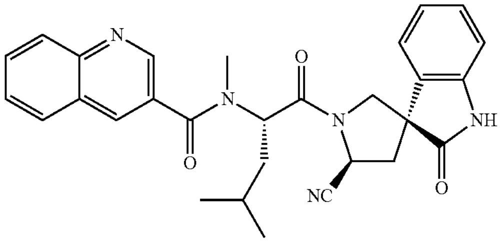 | 496.25 | |
| 214 | 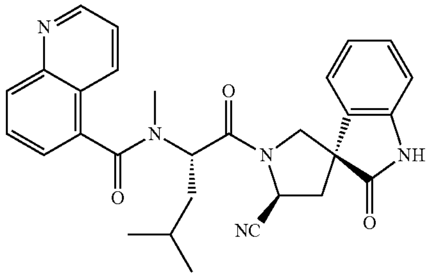 [SMILES: CC(C)C[C@@H](C(=O)N1C[C@]2(C[C@H]1C#N)C(=O)Nc1ccccc12)N(C)C(=O)c1cccc2ncccc12] | 496.25 | |
| 215 | 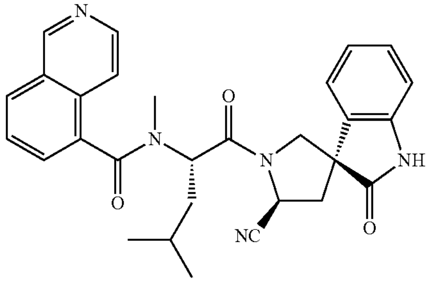 [SMILES: CC(C)C[C@@H](C(=O)N1C[C@]2(C[C@H]1C#N)C(=O)Nc1ccccc12)N(C)C(=O)c1cccc2cnccc12] | 496.35 | |

-continued
| Example | Structure | MS | NMR |
| --- | --- | --- | --- |
| 216 | 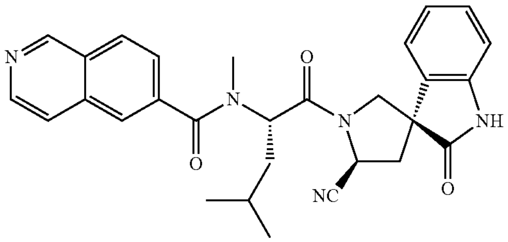 | 496.20 | |
| 217 | 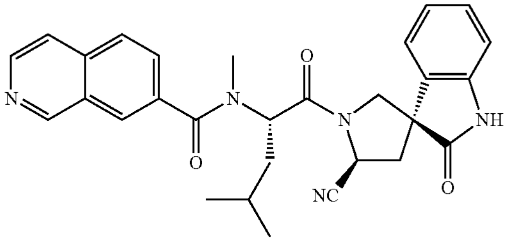 [SMILES: CC(C)C[C@@H](C(=O)N1C[C@]2(C[C@H]1C#N)C(=O)Nc1ccccc12)N(C)C(=O)c1ccc2ccncc2c1] | 496.25 | |
| 218 | 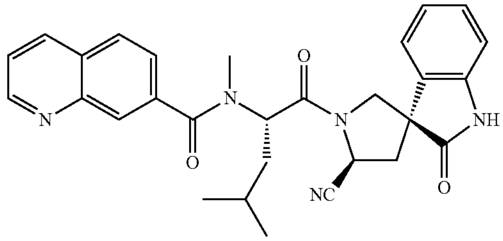 | 496.20 | |
| 219 | 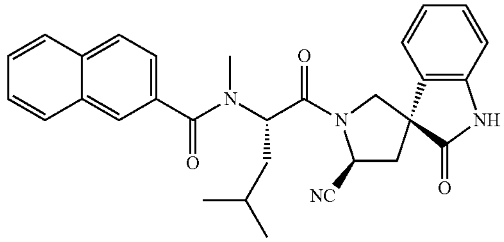 | 495.40 | |
| 220 | 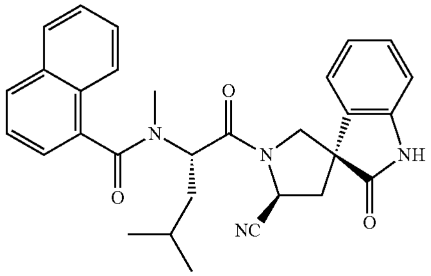 [SMILES: CC(C)C[C@@H](C(=O)N1C[C@]2(C[C@H]1C#N)C(=O)Nc1ccccc12)N(C)C(=O)c1cccc2ccccc12] | 496.25 | |
| 221 | 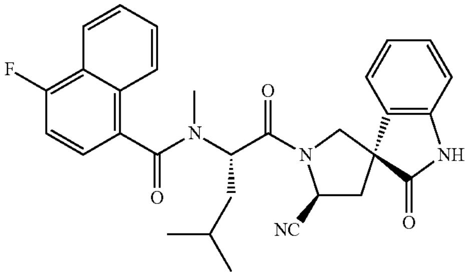 [SMILES: CC(C)C[C@@H](C(=O)N1C[C@]2(C[C@H]1C#N)C(=O)Nc1ccccc12)N(C)C(=O)c1ccc(F)c2ccccc12] | 535.20 [M + Na]+ | |

-continued
| Example | Structure | MS | NMR |
|---|---|---|---|
| 222 | 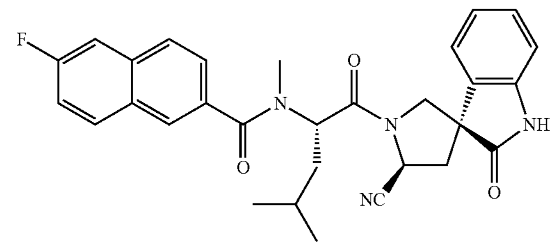 [SMILES: CC(C)C[C@@H](C(=O)N1C[C@]2(C[C@H]1C#N)C(=O)Nc1ccccc12)N(C)C(=O)c1ccc2cc(F)ccc2c1] | 513.15 | |
| 223 | 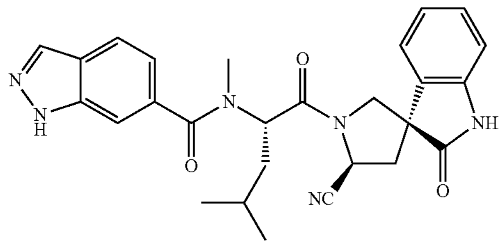 | 485.23 | |
| 224 | 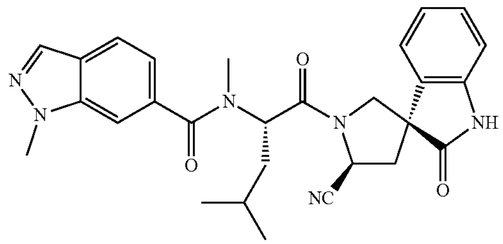 | 499.25 | |
| 225 | 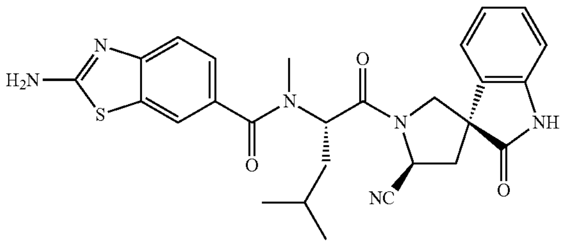 [SMILES: CC(C)C[C@@H](C(=O)N1C[C@]2(C[C@H]1C#N)C(=O)Nc1ccccc12)N(C)C(=O)c1ccc2nc(N)sc2c1] | 517.20 | |
| 226 | 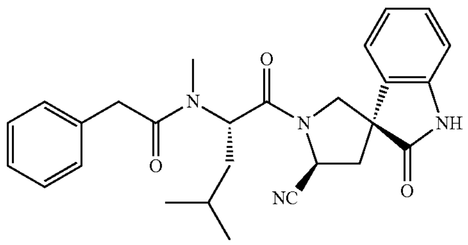 [SMILES: CC(C)C[C@@H](C(=O)N1C[C@]2(C[C@H]1C#N)C(=O)Nc1ccccc12)N(C)C(=O)Cc1ccccc1] | 459.20 | |
| 227 | 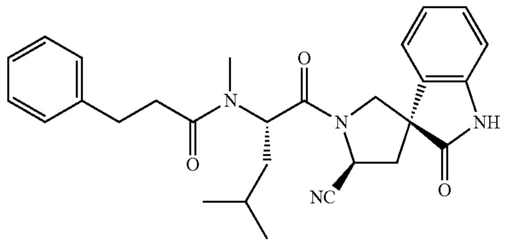 [SMILES: CC(C)C[C@@H](C(=O)N1C[C@]2(C[C@H]1C#N)C(=O)Nc1ccccc12)N(C)C(=O)CCc1ccccc1] | 495.20 [M + Na]+ | |

-continued
| Example | Structure | MS | NMR |
|---|---|---|---|
| 228 | 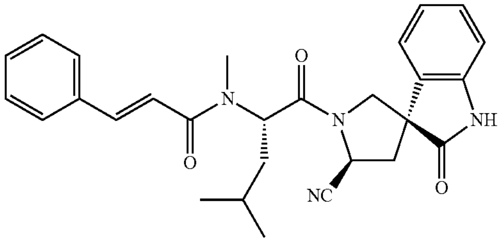 [SMILES: CC(C)C[C@@H](C(=O)N1C[C@]2(C[C@H]1C#N)C(=O)Nc1ccccc12)N(C)C(=O)/C=C/c1ccccc1] | 493.20 [M + Na]$^+$ | |
| 229 | 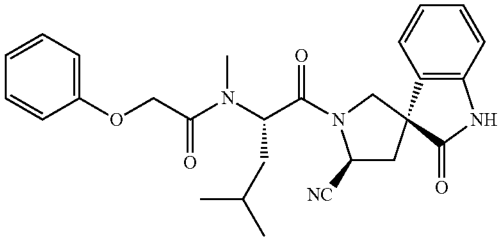 [SMILES: CC(C)C[C@@H](C(=O)N1C[C@]2(C[C@H]1C#N)C(=O)Nc1ccccc12)N(C)C(=O)COc1ccccc1] | 475.20 | |
| 230 | 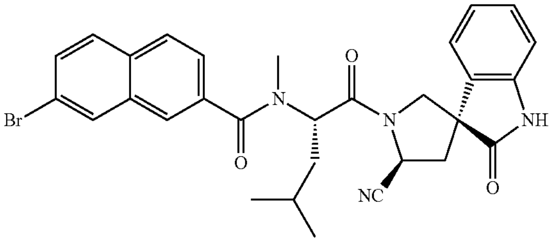 | 574.48 | |
| 231 | 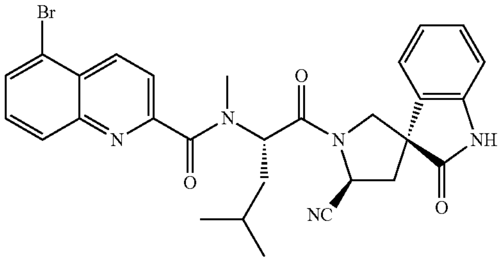 [SMILES: CC(C)C[C@@H](C(=O)N1C[C@]2(C[C@H]1C#N)C(=O)Nc1ccccc12)N(C)C(=O)c1ccc2c(Br)cccc2n1] | 575.15 | |
| 232 | 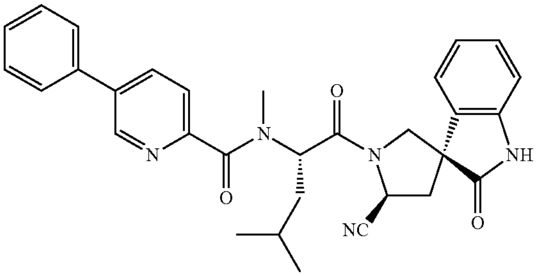 [SMILES: CC(C)C[C@@H](C(=O)N1C[C@]2(C[C@H]1C#N)C(=O)Nc1ccccc12)N(C)C(=O)c1ccc(-c2ccccc2)cn1] | 520.25 | |
| 233 | 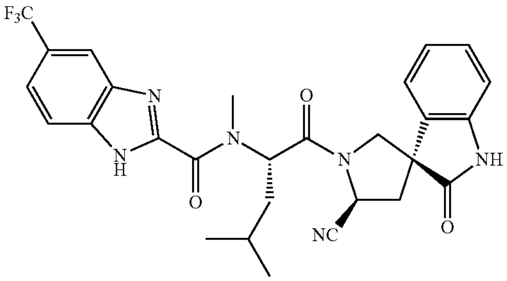 | 522.30 | |

-continued
| Example | Structure | MS | NMR |
|---|---|---|---|
| 234 | 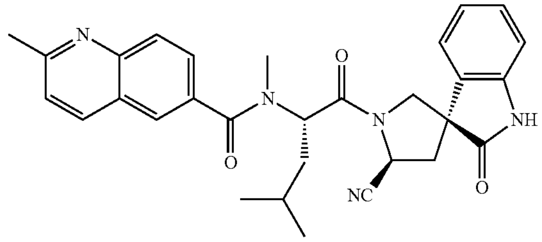 [SMILES: Cc1ccc2cc(C(=O)N(C)[C@@H](CC(C)C)C(=O)N3C[C@]4(C[C@H]3C#N)C(=O)Nc3ccccc34)ccc2n1] | 510.25 | |
| 235 | 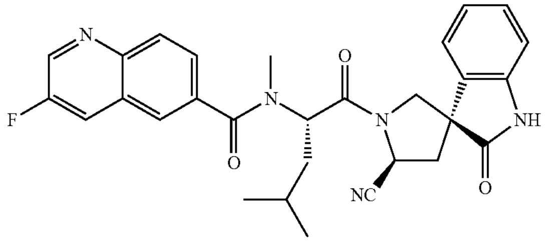 [SMILES: CC(C)C[C@@H](C(=O)N1C[C@]2(C[C@H]1C#N)C(=O)Nc1ccccc12)N(C)C(=O)c1ccc2ncc(F)cc2c1] | 514.20 | |
| 236 | 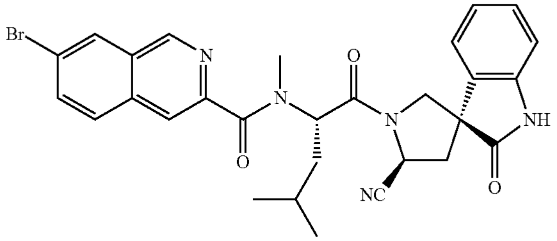 [SMILES: CC(C)C[C@@H](C(=O)N1C[C@]2(C[C@H]1C#N)C(=O)Nc1ccccc12)N(C)C(=O)c1cc2ccc(Br)cc2cn1] | 574.15 | |
| 237 | 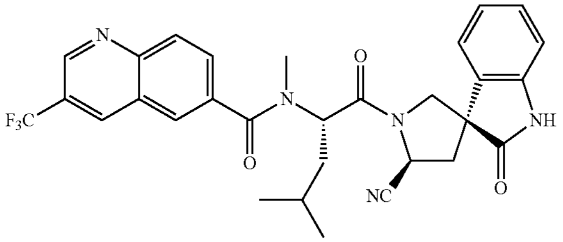 [SMILES: CC(C)C[C@@H](C(=O)N1C[C@]2(C[C@H]1C#N)C(=O)Nc1ccccc12)N(C)C(=O)c1ccc2ncc(C(F)(F)F)cc2c1] | 564.09 | |
| 238 | 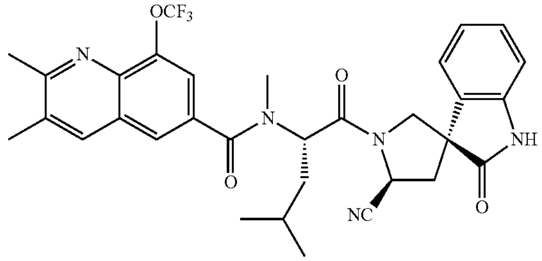 [SMILES: Cc1cc2cc(C(=O)N(C)[C@@H](CC(C)C)C(=O)N3C[C@]4(C[C@H]3C#N)C(=O)Nc3ccccc34)cc(OC(F)(F)F)c2nc1C] | 608.23 | |
| 239 | 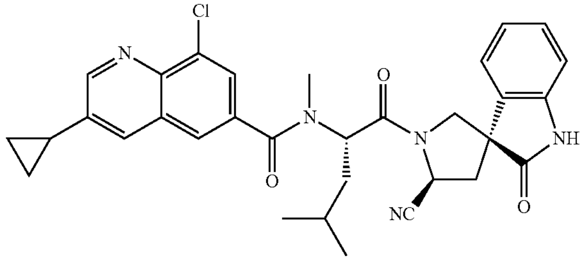 [SMILES: CC(C)C[C@@H](C(=O)N1C[C@]2(C[C@H]1C#N)C(=O)Nc1ccccc12)N(C)C(=O)c1cc(Cl)c2ncc(C3CC3)cc2c1] | 570.13 | |

-continued
| Example | Structure | MS | NMR |
|---|---|---|---|
| 240 | 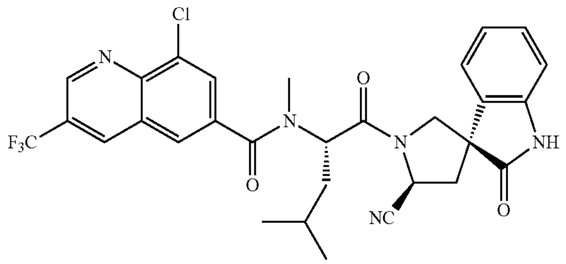 [SMILES: CC(C)C[C@@H](C(=O)N1C[C@]2(C[C@H]1C#N)C(=O)Nc1ccccc12)N(C)C(=O)c1cc(Cl)c2ncc(C(F)(F)F)cc2c1] | 597.97 | |
| 241 | 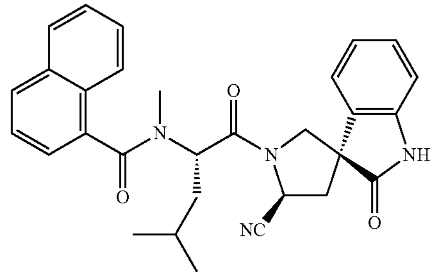 [SMILES: CC(C)C[C@@H](C(=O)N1C[C@]2(C[C@H]1C#N)C(=O)Nc1ccccc12)N(C)C(=O)c1cccc2ccccc12] | 495.25 | |
| 242 | 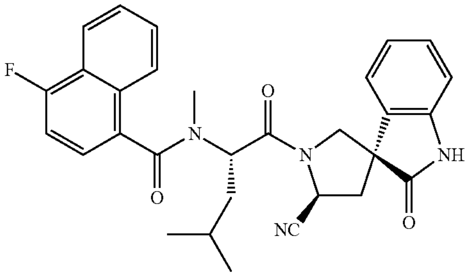 [SMILES: CC(C)C[C@@H](C(=O)N1C[C@]2(C[C@H]1C#N)C(=O)Nc1ccccc12)N(C)C(=O)c1ccc(F)c2ccccc12] | 535.20 [M + Na]+ | |
| 243 | 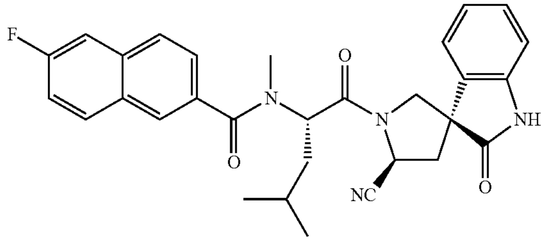 [SMILES: CC(C)C[C@@H](C(=O)N1C[C@]2(C[C@H]1C#N)C(=O)Nc1ccccc12)N(C)C(=O)c1ccc2cc(F)ccc2c1] | 513.15 | |
| 244 | 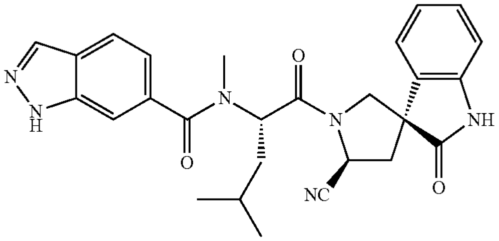 [SMILES: CC(C)C[C@@H](C(=O)N1C[C@]2(C[C@H]1C#N)C(=O)Nc1ccccc12)N(C)C(=O)c1ccc2cn[nH]c2c1] | 485.23 | |
| 245 | 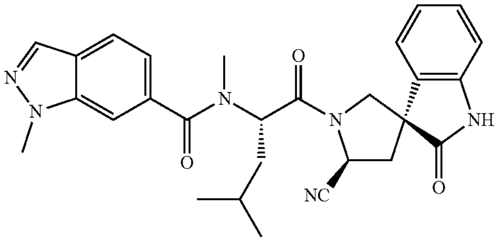 | 499.25 | |

-continued
| Example | Structure | MS | NMR |
|---|---|---|---|
| 246 | 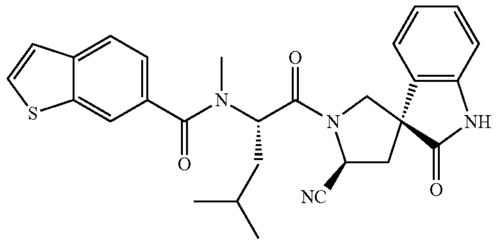 [SMILES: CC(C)C[C@@H](C(=O)N1C[C@]2(C[C@H]1C#N)C(=O)Nc1ccccc12)N(C)C(=O)c1ccc2ccsc2c1] | 523.15 | |
| 247 | 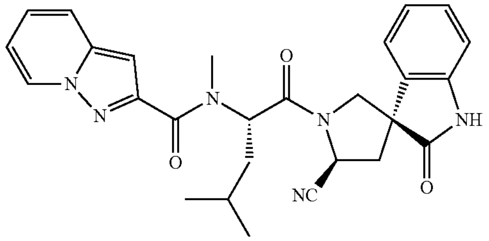 [SMILES: CC(C)C[C@@H](C(=O)N1C[C@]2(C[C@H]1C#N)C(=O)Nc1ccccc12)N(C)C(=O)c1cc2ccccn2n1] | 485.15 | |
| 248 | 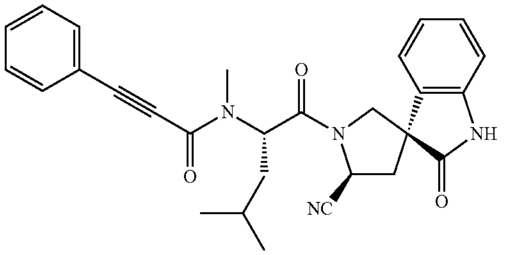 [SMILES: CC(C)C[C@@H](C(=O)N1C[C@]2(C[C@H]1C#N)C(=O)Nc1ccccc12)N(C)C(=O)C#Cc1ccccc1] | 469.75 | |
| 249 | 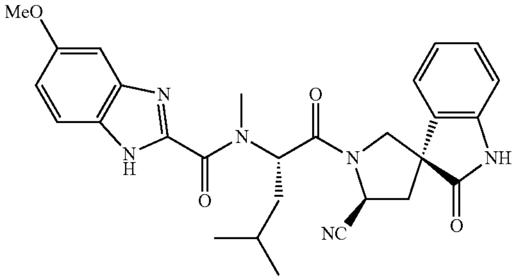 [SMILES: COc1ccc2[nH]c(C(=O)N(C)[C@@H](CC(C)C)C(=O)N3C[C@]4(C[C@H]3C#N)C(=O)Nc3ccccc34)nc2c1] | 515.20 | |
| 250 | 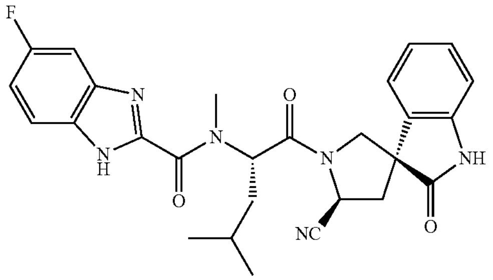 [SMILES: CC(C)C[C@@H](C(=O)N1C[C@]2(C[C@H]1C#N)C(=O)Nc1ccccc12)N(C)C(=O)c1nc2cc(F)ccc2[nH]1] | 503.25 | |

-continued
| Example | Structure | MS | NMR |
|---|---|---|---|
| 251 | 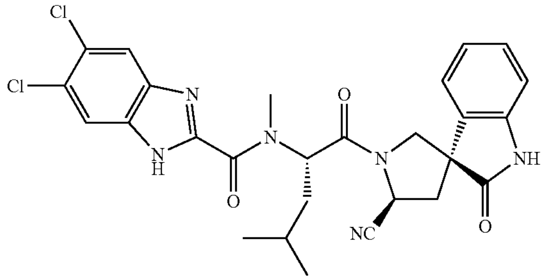 [SMILES: CC(C)C[C@@H](C(=O)N1C[C@]2(C[C@H]1C#N)C(=O)Nc1ccccc12)N(C)C(=O)c1nc2cc(Cl)c(Cl)cc2[nH]1] | 553.45 | |
| 252 | 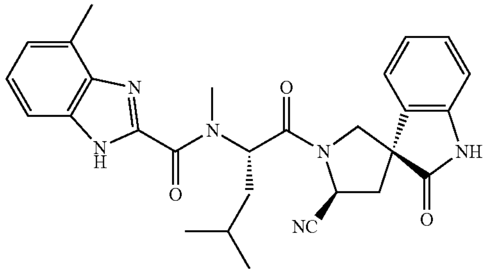 [SMILES: Cc1cccc2[nH]c(C(=O)N(C)[C@@H](CC(C)C)C(=O)N3C[C@]4(C[C@H]3C#N)C(=O)Nc3ccccc34)nc12] | 499.20 | |
| 253 | 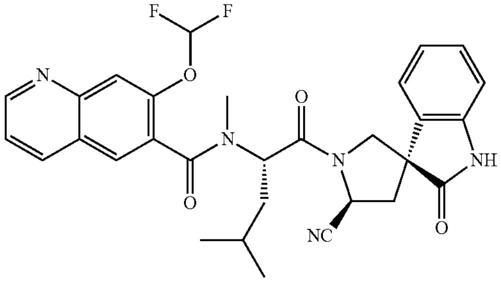 [SMILES: CC(C)C[C@@H](C(=O)N1C[C@]2(C[C@H]1C#N)C(=O)Nc1ccccc12)N(C)C(=O)c1cc2cccnc2cc1OC(F)F] | 562.23 | |
| 254 | 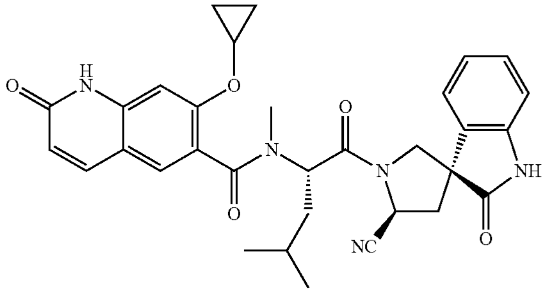 [SMILES: CC(C)C[C@@H](C(=O)N1C[C@]2(C[C@H]1C#N)C(=O)Nc1ccccc12)N(C)C(=O)c1cc2ccc(=O)[nH]c2cc1OC1CC1] | 566.00 | |
| 255 | 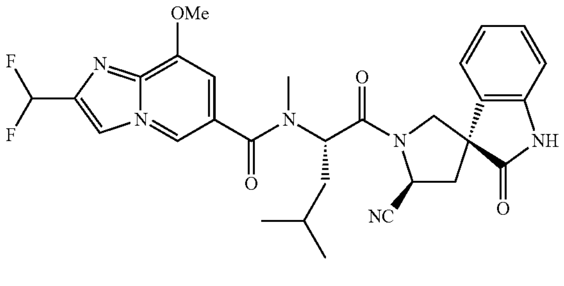 | 565.24 | |

-continued
| Example | Structure | MS | NMR |
| --- | --- | --- | --- |
| 256 | 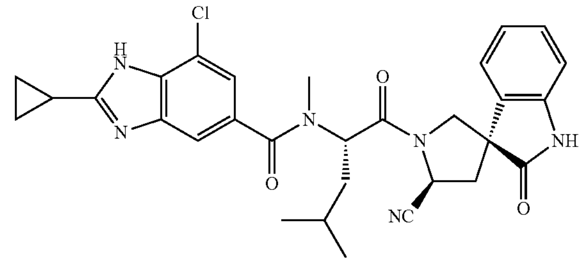 [SMILES: CC(C)C[C@@H](C(=O)N1C[C@]2(C[C@H]1C#N)C(=O)Nc1ccccc12)N(C)C(=O)c1cc(Cl)c2[nH]c(C3CC3)nc2c1] | 559.22 | |
| 257 | 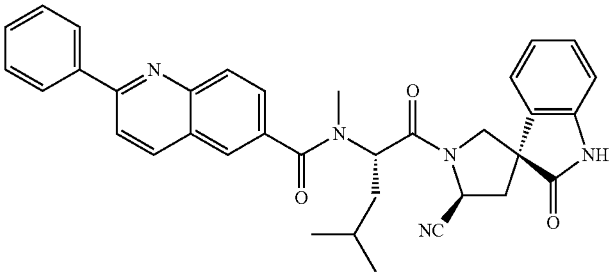 [SMILES: CC(C)C[C@@H](C(=O)N1C[C@]2(C[C@H]1C#N)C(=O)Nc1ccccc12)N(C)C(=O)c1ccc2nc(-c3ccccc3)ccc2c1] | 572.35 | |
| 258 | 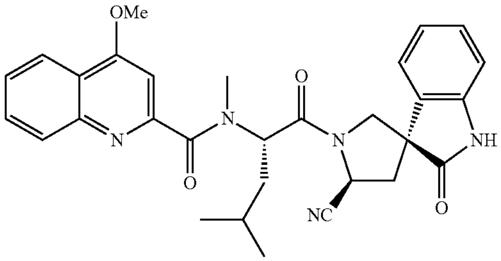 [SMILES: COc1cc(C(=O)N(C)[C@@H](CC(C)C)C(=O)N2C[C@]3(C[C@H]2C#N)C(=O)Nc2ccccc23)nc2ccccc12] | 526.30 | |
| 259 | 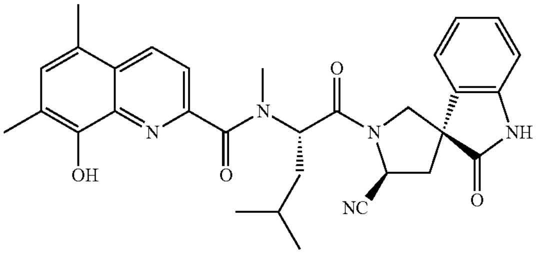 [SMILES: Cc1cc(C)c2ccc(C(=O)N(C)[C@@H](CC(C)C)C(=O)N3C[C@]4(C[C@H]3C#N)C(=O)Nc3ccccc34)nc2c1O] | 540.25 | |
| 260 | 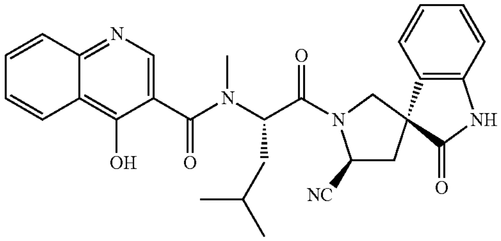 [SMILES: CC(C)C[C@@H](C(=O)N1C[C@]2(C[C@H]1C#N)C(=O)Nc1ccccc12)N(C)C(=O)c1cnc2ccccc2c1O] | 512.20 | |
| 261 | 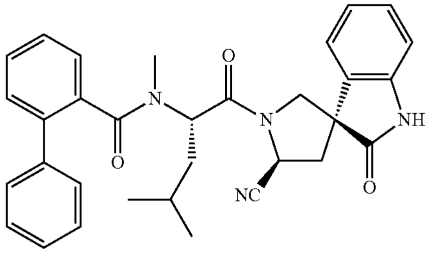 [SMILES: CC(C)C[C@@H](C(=O)N1C[C@]2(C[C@H]1C#N)C(=O)Nc1ccccc12)N(C)C(=O)c1ccccc1-c1ccccc1] | 521.20 | |

-continued
| Example | Structure | MS | NMR |
|---|---|---|---|
| 262 | 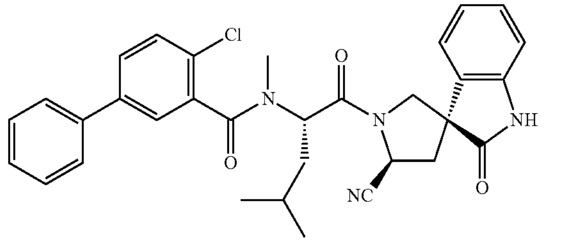 [SMILES: CC(C)C[C@@H](C(=O)N1C[C@]2(C[C@H]1C#N)C(=O)Nc1ccccc12)N(C)C(=O)c1cc(-c2ccccc2)ccc1Cl] | 577.25 | |
| 263 | 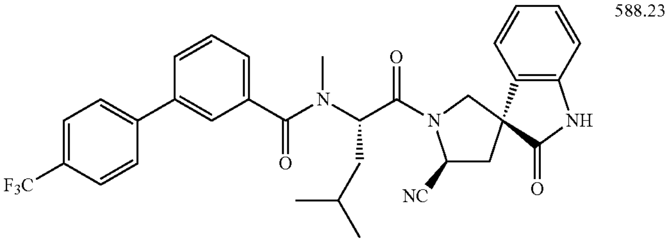 | 588.23 | |
| 264 | 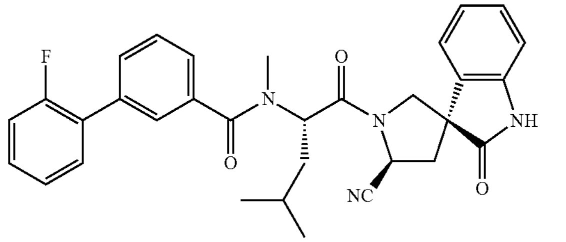 [SMILES: CC(C)C[C@@H](C(=O)N1C[C@]2(C[C@H]1C#N)C(=O)Nc1ccccc12)N(C)C(=O)c1cccc(-c2ccccc2F)c1] | 539.30 | |
| 265 | 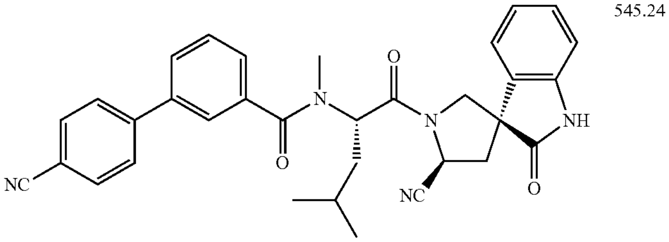 | 545.24 | |
| 266 | 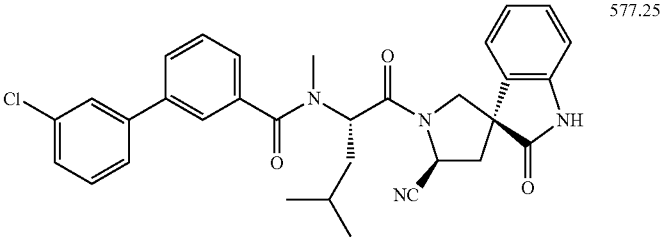 | 577.25 | |
| 267 | 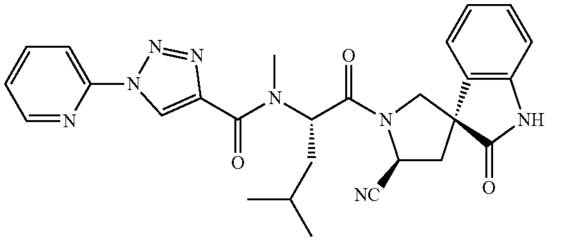 [SMILES: CC(C)C[C@@H](C(=O)N1C[C@]2(C[C@H]1C#N)C(=O)Nc1ccccc12)N(C)C(=O)c1cn(-c2ccccn2)nn1] | 511.22 | |

-continued
| Example | Structure | MS | NMR |
|---|---|---|---|
| 268 | 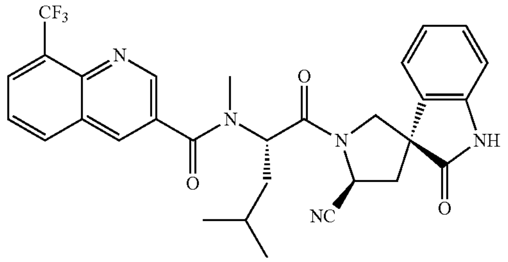 [SMILES: CC(C)C[C@@H](C(=O)N1C[C@]2(C[C@H]1C#N)C(=O)Nc1ccccc12)N(C)C(=O)c1cnc2c(C(F)(F)F)cccc2c1] | 562.20 | |
| 269 | 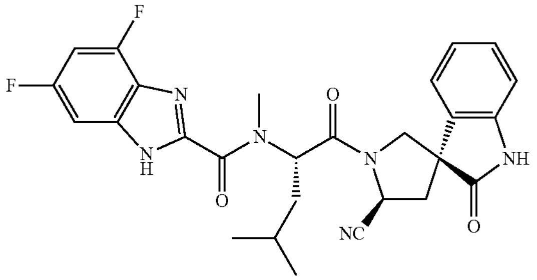 [SMILES: CC(C)C[C@@H](C(=O)N1C[C@]2(C[C@H]1C#N)C(=O)Nc1ccccc12)N(C)C(=O)c1nc2c(F)cc(F)cc2[nH]1] | 520.20 | |
| 270 | 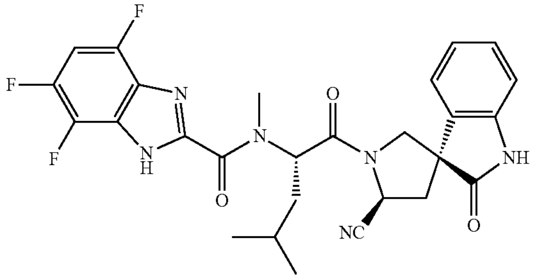 [SMILES: CC(C)C[C@@H](C(=O)N1C[C@]2(C[C@H]1C#N)C(=O)Nc1ccccc12)N(C)C(=O)c1nc2c(F)cc(F)c(F)c2[nH]1] | 539.25 | |
| 271 | 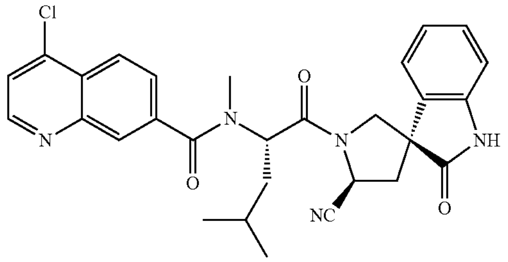 [SMILES: CC(C)C[C@@H](C(=O)N1C[C@]2(C[C@H]1C#N)C(=O)Nc1ccccc12)N(C)C(=O)c1ccc2c(Cl)ccnc2c1] | 530.15 | |
| 272 | 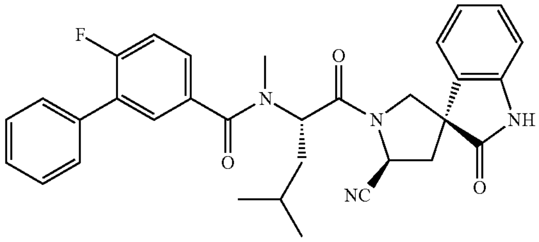 [SMILES: CC(C)C[C@@H](C(=O)N1C[C@]2(C[C@H]1C#N)C(=O)Nc1ccccc12)N(C)C(=O)c1ccc(F)c(-c2ccccc2)c1] | 539.25 | |

-continued
| Example | Structure | MS | NMR |
|---|---|---|---|
| 273 | 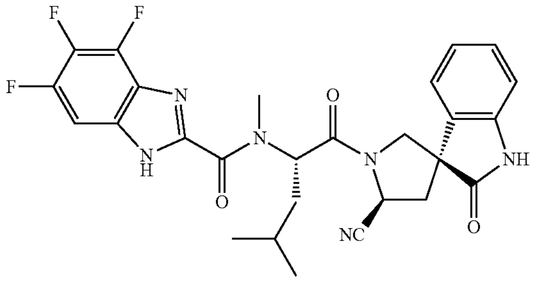 [SMILES: CC(C)C[C@@H](C(=O)N1C[C@]2(C[C@H]1C#N)C(=O)Nc1ccccc12)N(C)C(=O)c1nc2c(F)c(F)c(F)cc2[nH]1] | 538.55 | |
| 274 | 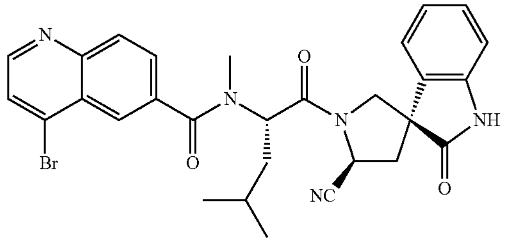 [SMILES: CC(C)C[C@@H](C(=O)N1C[C@]2(C[C@H]1C#N)C(=O)Nc1ccccc12)N(C)C(=O)c1ccc2nccc(Br)c2c1] | 574.15 | |
| 275 | 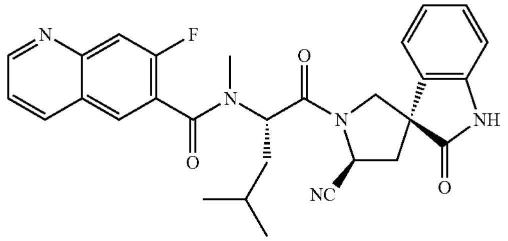 [SMILES: CC(C)C[C@@H](C(=O)N1C[C@]2(C[C@H]1C#N)C(=O)Nc1ccccc12)N(C)C(=O)c1cc2cccnc2cc1F] | 514.25 | |
| 276 | 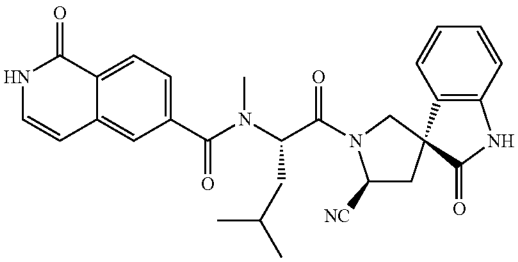 [SMILES: CC(C)C[C@@H](C(=O)N1C[C@]2(C[C@H]1C#N)C(=O)Nc1ccccc12)N(C)C(=O)c1ccc2c(=O)[nH]ccc2c1] | 512.20 | |
| 277 | 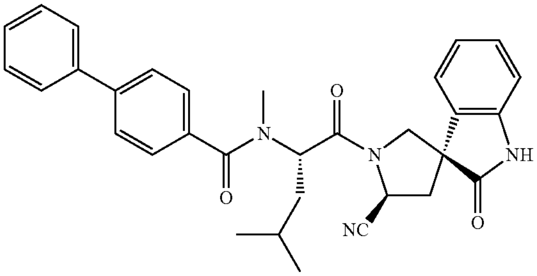 | 521.25 | |
| 278 | 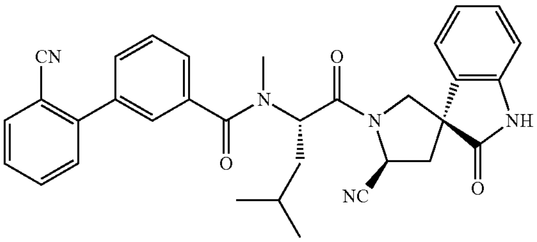 | 568.25 [M + Na]+ | |

-continued
| Example | Structure | MS | NMR |
|---|---|---|---|
| 279 | 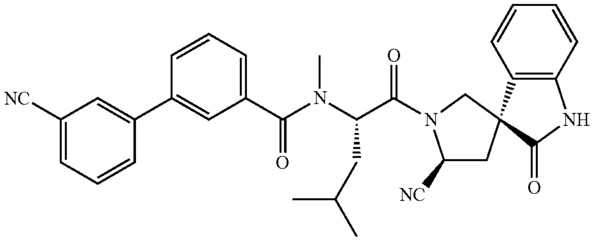 [SMILES: CC(C)C[C@@H](C(=O)N1C[C@]2(C[C@H]1C#N)C(=O)Nc1ccccc12)N(C)C(=O)c1cccc(-c2cccc(C#N)c2)c1] | 568.25 [M + Na]+ | |
| 280 | 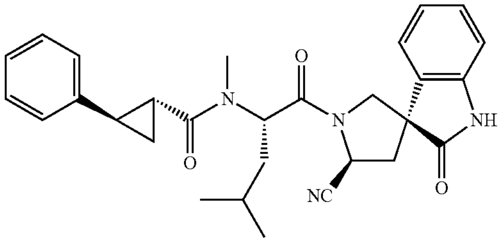 [SMILES: CC(C)C[C@@H](C(=O)N1C[C@]2(C[C@H]1C#N)C(=O)Nc1ccccc12)N(C)C(=O)[C@@H]1C[C@H]1c1ccccc1] | 485.25 | |
| 281 | 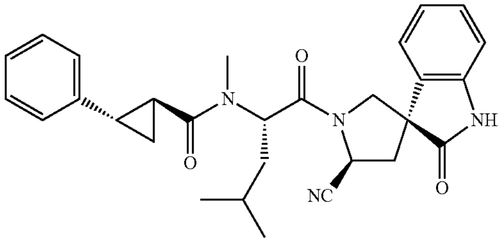 [SMILES: CC(C)C[C@@H](C(=O)N1C[C@]2(C[C@H]1C#N)C(=O)Nc1ccccc12)N(C)C(=O)[C@H]1C[C@@H]1c1ccccc1] | 485.20 | |
| 282 | 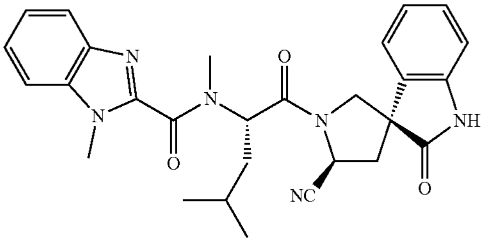 [SMILES: CC(C)C[C@@H](C(=O)N1C[C@]2(C[C@H]1C#N)C(=O)Nc1ccccc12)N(C)C(=O)c1nc2ccccc2n1C] | 499.20 | |
| 283 | 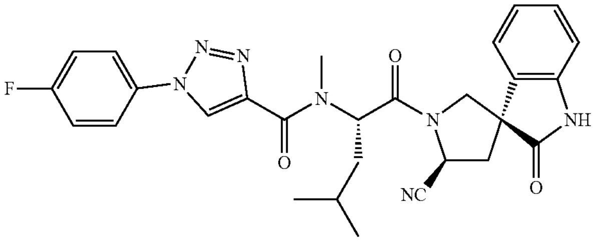 [SMILES: CC(C)C[C@@H](C(=O)N1C[C@]2(C[C@H]1C#N)C(=O)Nc1ccccc12)N(C)C(=O)c1cn(-c2ccc(F)cc2)nn1] | 552.22 [M + Na]+ | |
| 284 | 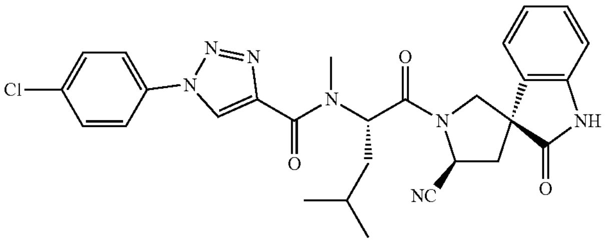 [SMILES: CC(C)C[C@@H](C(=O)N1C[C@]2(C[C@H]1C#N)C(=O)Nc1ccccc12)N(C)C(=O)c1cn(-c2ccc(Cl)cc2)nn1] | 568.19 [M + Na]+ | |

-continued
| Example | Structure | MS | NMR |
|---|---|---|---|
| 285 | 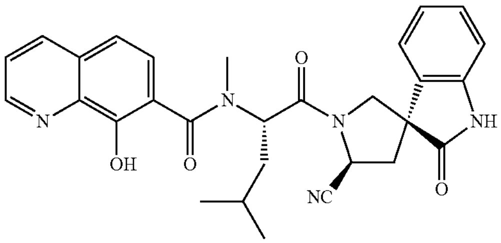 [SMILES: CC(C)C[C@@H](C(=O)N1C[C@]2(C[C@H]1C#N)C(=O)Nc1ccccc12)N(C)C(=O)c1ccc2cccnc2c1O] | 512.25 | |
| 286 | 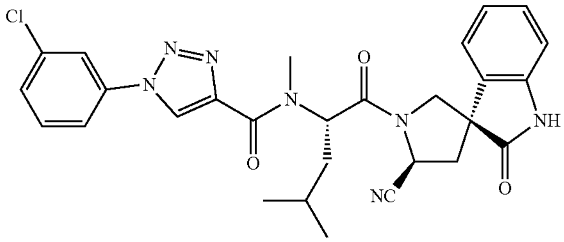 [SMILES: CC(C)C[C@@H](C(=O)N1C[C@]2(C[C@H]1C#N)C(=O)Nc1ccccc12)N(C)C(=O)c1cn(-c2cccc(Cl)c2)nn1] | 545.85 | |
| 287 | 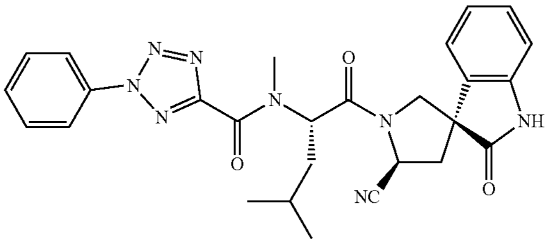 [SMILES: CC(C)C[C@@H](C(=O)N1C[C@]2(C[C@H]1C#N)C(=O)Nc1ccccc12)N(C)C(=O)c1nnn(-c2ccccc2)n1] | 537.05 [M − Na]⁻ | |
| 288 | 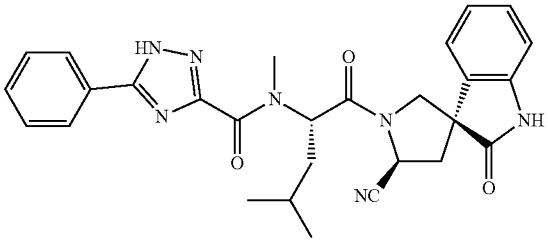 [SMILES: CC(C)C[C@@H](C(=O)N1C[C@]2(C[C@H]1C#N)C(=O)Nc1ccccc12)N(C)C(=O)c1n[nH]c(-c2ccccc2)n1] | 512.03 | |
| 289 | 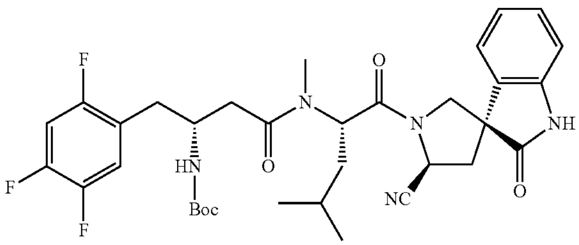 [SMILES: CC(C)C[C@@H](C(=O)N1C[C@]2(C[C@H]1C#N)C(=O)Nc1ccccc12)N(C)C(=O)C[C@@H](Cc1cc(F)c(F)cc1F)NC(=O)OC(C)(C)C] | [M + Na]+ 678.3 | |
| 290 | 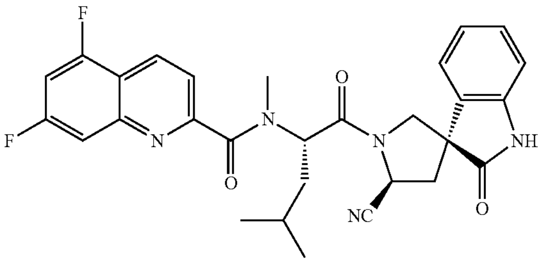 [SMILES: CC(C)C[C@@H](C(=O)N1C[C@]2(C[C@H]1C#N)C(=O)Nc1ccccc12)N(C)C(=O)c1ccc2c(F)cc(F)cc2n1] | [M + Na]+ 554.2 | |

-continued
| Example | Structure | MS | NMR |
|---|---|---|---|
| 291 | 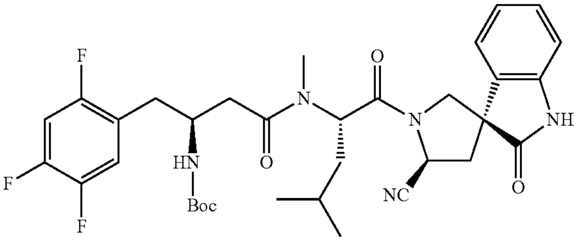 [SMILES: CC(C)C[C@@H](C(=O)N1C[C@]2(C[C@H]1C#N)C(=O)Nc1ccccc12)N(C)C(=O)C[C@H](Cc1cc(F)c(F)cc1F)NC(=O)OC(C)(C)C] | [M + Na]+ 678.3 | |
| 292 | 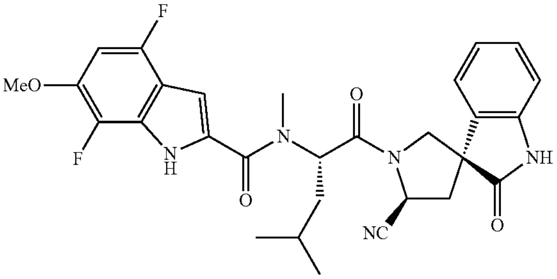 [SMILES: COc1cc(F)c2cc(C(=O)N(C)[C@@H](CC(C)C)C(=O)N3C[C@]4(C[C@H]3C#N)C(=O)Nc3ccccc34)[nH]c2c1F] | [M + Na]+ 572.2 | $^1$H NMR (400 MHz, Acetone-$d_6$) δ 10.64 (s, 1H), 9.67 (s, 1H), 7.10-7.00 (m, 2H), 6.92 (d, J = 7.6 Hz, 1H), 6.89-6.77 (m, 3H), 5.56 (s, 1H), 5.21 (t, J = 8.3 Hz, 1H), 4.26 (d, J = 10.7 Hz, 1H), 3.99 (d, J = 10.6 Hz, 1H), 3.95 (s, 3H), 3.42 (s, 3H), 2.78-2.71 (m, 1H), 2.69 (dd, J = 13.3, 8.0 Hz, 1H), 1.91 (m, 1H), 1.79 (ddd, J = 14.2, 8.7, 5.8 Hz, 1H), 1.64 (dt, J = 13.8, 6.5 Hz, 1H), 0.99 (m, 6H). |
| 293 | 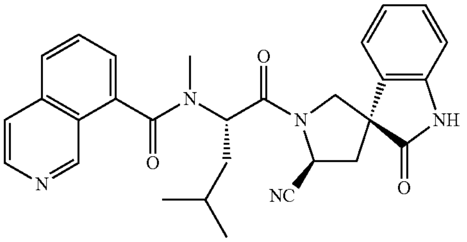 [SMILES: CC(C)C[C@@H](C(=O)N1C[C@]2(C[C@H]1C#N)C(=O)Nc1ccccc12)N(C)C(=O)c1cccc2ccncc12] | [M + Na]+ 496.2 | |
| 294 | 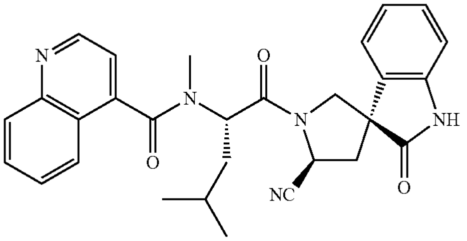 [SMILES: CC(C)C[C@@H](C(=O)N1C[C@]2(C[C@H]1C#N)C(=O)Nc1ccccc12)N(C)C(=O)c1ccnc2ccccc12] | [M + Na]+ 496.2 | |
| 295 | 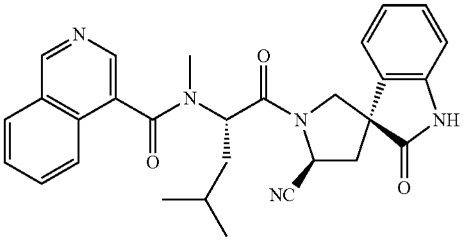 [SMILES: CC(C)C[C@@H](C(=O)N1C[C@]2(C[C@H]1C#N)C(=O)Nc1ccccc12)N(C)C(=O)c1cncc2ccccc12] | [M + Na]+ 496.2 | $^1$H NMR (400 MHz, Acetone-$d_6$) δ 9.77 (s, 1H), 9.32 (d, J = 1.0 Hz, 1H), 8.22-8.15 (m, 1H), 7.84-7.71 (m, 2H), 7.67 (d, J = 8.2 Hz, 1H), 7.31 (t, J = 7.6 Hz, 1H), 7.22 (dd, J = 7.3, 1.1 Hz, 1H), 7.05 (dd, J = 14.0, 7.6 Hz, 2H), 5.74-5.62 (m, 1H), 5.28 (t, J = 8.4 Hz, 1H), 4.41 (d, J = 10.5 Hz, 1H), 4.17 (d, J = 10.5 Hz, 1H), 2.92 (s, 3H), 2.88-2.70 (m, 2H), 2.04-1.73 (m, 2H), 1.10 (dd, J = 6.6, 1.5 Hz, 6H). |
| 296 | 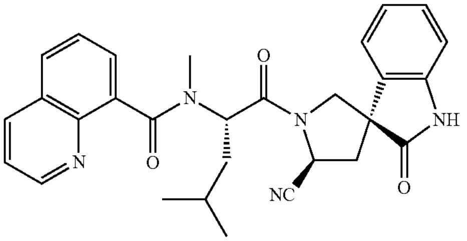 [SMILES: CC(C)C[C@@H](C(=O)N1C[C@]2(C[C@H]1C#N)C(=O)Nc1ccccc12)N(C)C(=O)c1cccc2cccnc12] | [M + Na]+ 518.2 | |

-continued
| Example | Structure | MS | NMR |
|---|---|---|---|
| 297 | 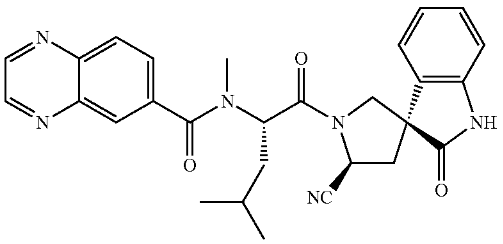 | [M + Na]+ 519.2 | |
| 298 | 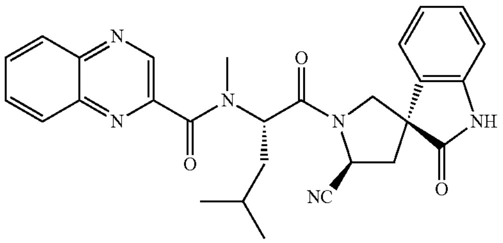 [SMILES: CC(C)C[C@@H](C(=O)N1C[C@]2(C[C@H]1C#N)C(=O)Nc1ccccc12)N(C)C(=O)c1cnc2ccccc2n1] | [M + Na]+ 519.2 | |
| 299 | 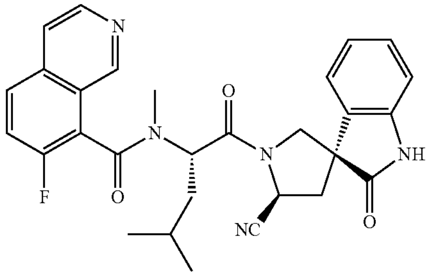 [SMILES: CC(C)C[C@@H](C(=O)N1C[C@]2(C[C@H]1C#N)C(=O)Nc1ccccc12)N(C)C(=O)c1c(F)ccc2ccncc12] | [M + Na]+ 514.2 | |
| 300 | 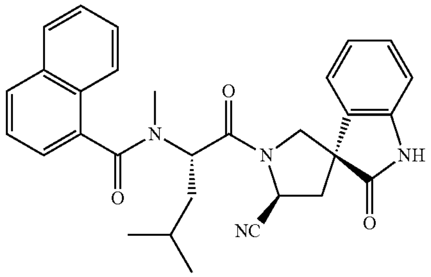 [SMILES: CC(C)C[C@@H](C(=O)N1C[C@]2(C[C@H]1C#N)C(=O)Nc1ccccc12)N(C)C(=O)c1cccc2ccccc12] | [M + Na]+ 518.2 | |
| 301 | 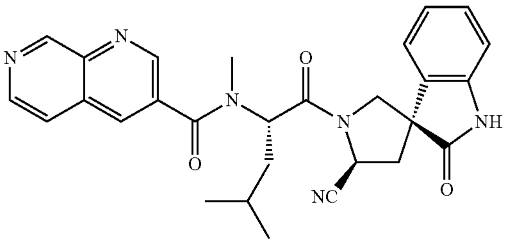 | [M + Na]+ 497.1 | |
| 302 | 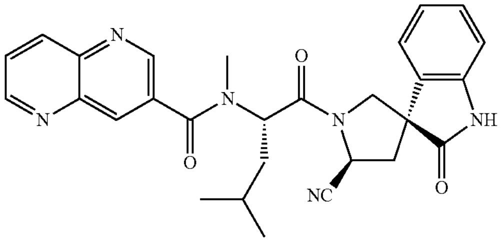 | [M + Na]+ 497.1 | |

-continued
| Example | Structure | MS | NMR |
|---|---|---|---|
| 303 | 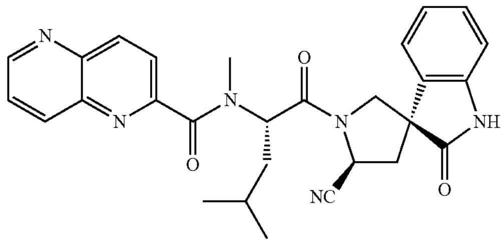 [SMILES: CC(C)C[C@@H](C(=O)N1C[C@]2(C[C@H]1C#N)C(=O)Nc1ccccc12)N(C)C(=O)c1ccc2ncccc2n1] | [M + Na]+ 497.1 | |
| 304 | 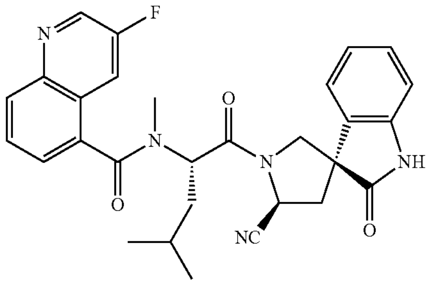 [SMILES: CC(C)C[C@@H](C(=O)N1C[C@]2(C[C@H]1C#N)C(=O)Nc1ccccc12)N(C)C(=O)c1cccc2ncc(F)cc12] | [M + Na]+ 514.1 | |
| 305 | 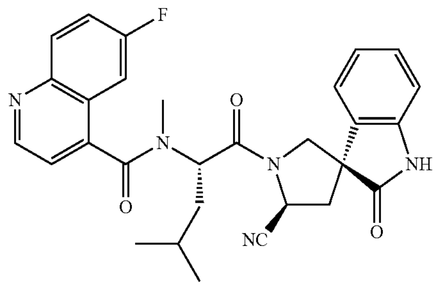 [SMILES: CC(C)C[C@@H](C(=O)N1C[C@]2(C[C@H]1C#N)C(=O)Nc1ccccc12)N(C)C(=O)c1ccnc2ccc(F)cc12] | [M + Na]+ 514.1 | |
| 306 | 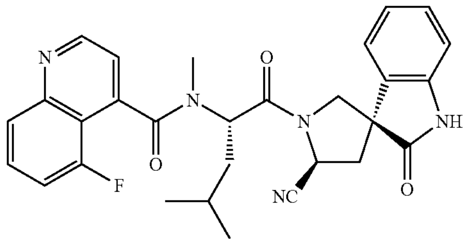 [SMILES: CC(C)C[C@@H](C(=O)N1C[C@]2(C[C@H]1C#N)C(=O)Nc1ccccc12)N(C)C(=O)c1ccnc2cccc(F)c12] | [M + Na]+ 514.2 | |
| 307 | 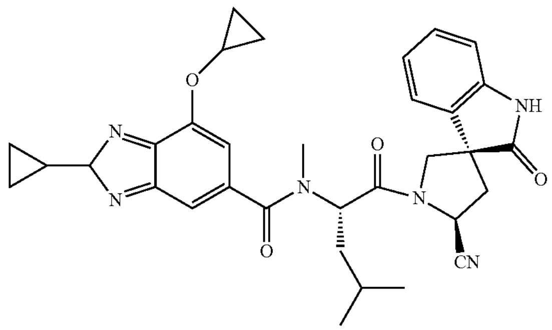 [SMILES: CC(C)C[C@@H](C(=O)N1C[C@]2(C[C@H]1C#N)C(=O)Nc1ccccc12)N(C)C(=O)c1cc(OC2CC2)c2c(c1)=NC(C1CC1)N=2] | [M − 1] 579.1 | 1H NMR (400 MHz, Acetone-$d_6$) δ 9.74 (s, 1H), 8.32 (s, 1H), 7.36 (t, J = 7.7 Hz, 1H), 7.10 (dd, J = 20.9, 7.5 Hz, 2H), 7.04 (s, 1H), 6.78 (s, 1H), 6.70 (s, 1H), 5.52 (s, 1H), 4.39 (d, J = 10.7 Hz, 1H), 4.10 (s, 1H), 4.03 (d, J = 10.4 Hz, 1H), 3.95 (s, 1H), 3.03 (s, 3H), 2.79-2.69 (m, 2H), 1.83 (m, 2H), 1.72 (m, 2H), 1.34 (m, 3H), 1.24-1.10 (m, 3H), 1.02 (m, 4H), 0.80 (m, 4H). |

-continued
| Example | Structure | MS | NMR |
|---|---|---|---|
| 308 | 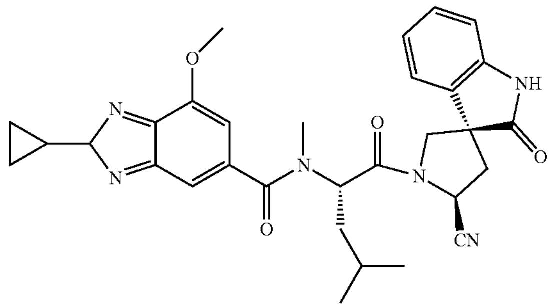 [SMILES: COc1cc(C(=O)N(C)[C@@H](CC(C)C)C(=O)N2C[C@]3(C[C@H]2C#N)C(=O)Nc2ccccc23)cc2c1=NC(C1CC1)N=2] | [M − 1] 553.1 | $^1$H NMR (400 MHz, Acetone-$d_6$) δ 9.75 (s, 1H), 8.32 (s, 1H), 7.37 (t, J = 7.8 Hz, 1H), 7.08 (q, J = 10.0, 8.8 Hz, 3H), 6.77 (s, 1H), 6.31 (s, 1H), 5.52 (s, 1H), 5.22 (t, J = 8.4 Hz, 1H), 4.39 (d, J = 10.5 Hz, 1H), 4.11 (s, 1H), 4.03 (d, J = 10.5 Hz, 1H), 3.90 (s, 3H), 3.02 (s, 3H), 2.79-2.69 (m, 2H), 1.84 (q, J = 8.2 Hz, 2H), 1.70 (s, 1H), 1.36 (s,2H), 1.24-1.11 (m, 2H), 1.02 (s, 6H). |
| 309 | 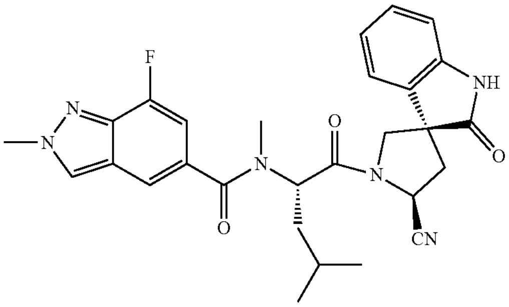 [SMILES: CC(C)C[C@@H](C(=O)N1C[C@]2(C[C@H]1C#N)C(=O)Nc1ccccc12)N(C)C(=O)c1cc(F)c2nn(C)cc2c1] | [M − 1] 515.1 | |
| 310 | 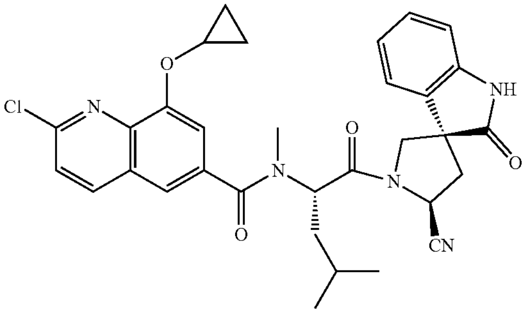 [SMILES: CC(C)C[C@@H](C(=O)N1C[C@]2(C[C@H]1C#N)C(=O)Nc1ccccc12)N(C)C(=O)c1cc(OC2CC2)c2nc(Cl)ccc2c1] | [M − 1] 584.2 | |
| 311 | 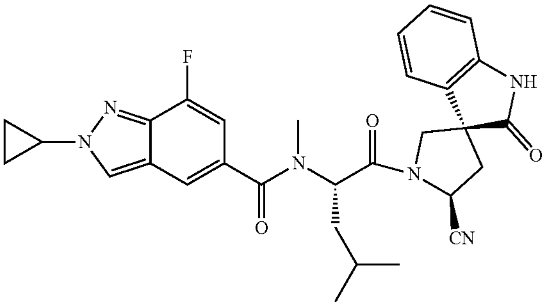 [SMILES: CC(C)C[C@@H](C(=O)N1C[C@]2(C[C@H]1C#N)C(=O)Nc1ccccc12)N(C)C(=O)c1cc(F)c2nn(C3CC3)cc2c1] | [M − 1] 541.2 | |
| 312 | 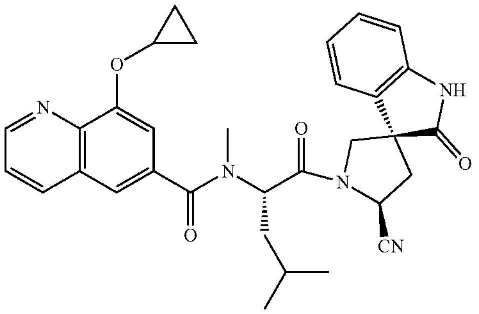 [SMILES: CC(C)C[C@@H](C(=O)N1C[C@]2(C[C@H]1C#N)C(=O)Nc1ccccc12)N(C)C(=O)c1cc(OC2CC2)c2ncccc2c1] | [M − 1] 550.0 | |

-continued
| Example | Structure | MS | NMR |
|---|---|---|---|
| 313 | 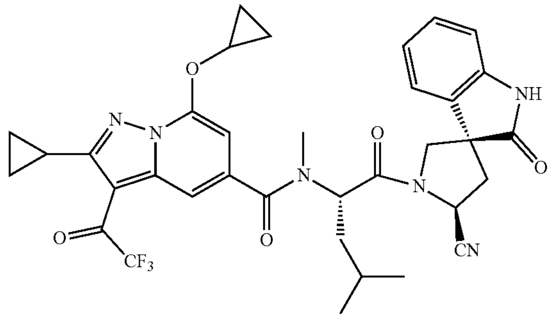 [SMILES: CC(C)C[C@@H](C(=O)N1C[C@]2(C[C@H]1C#N)C(=O)Nc1ccccc12)N(C)C(=O)c1cc(OC2CC2)n2nc(C3CC3)c(C(=O)C(F)(F)F)c2c1] | [M − 1] 675.0 | |
| 314 | 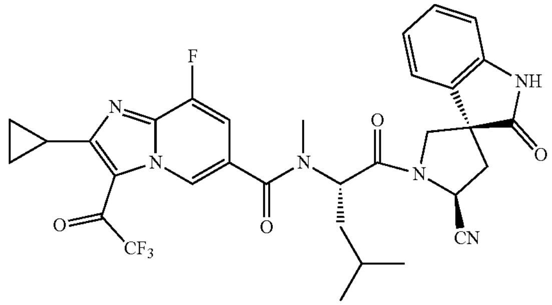 [SMILES: CC(C)C[C@@H](C(=O)N1C[C@]2(C[C@H]1C#N)C(=O)Nc1ccccc12)N(C)C(=O)c1cc(F)c2nc(C3CC3)c(C(=O)C(F)(F)F)n2c1] | [M − 1] 637.0 | |
| 315 | 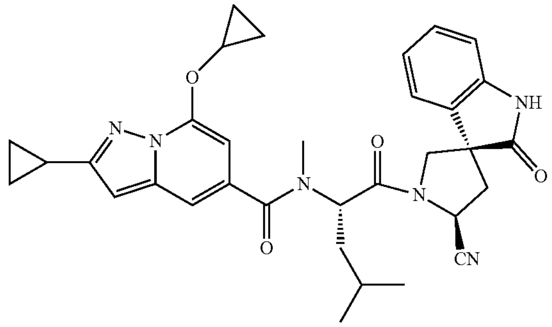 [SMILES: CC(C)C[C@@H](C(=O)N1C[C@]2(C[C@H]1C#N)C(=O)Nc1ccccc12)N(C)C(=O)c1cc(OC2CC2)n2nc(C3CC3)cc2c1] | [M − 1] 579.1 | |
| 316 | 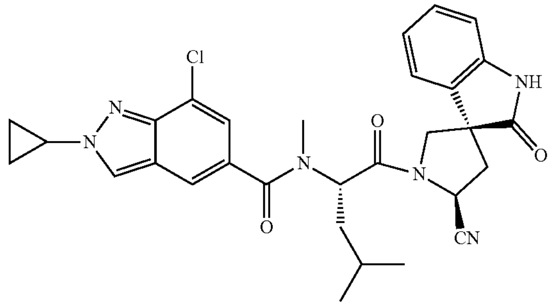 [SMILES: CC(C)C[C@@H](C(=O)N1C[C@]2(C[C@H]1C#N)C(=O)Nc1ccccc12)N(C)C(=O)c1cc(Cl)c2nn(C3CC3)cc2c1] | [M − 1] 557.0 | |
| 317 | 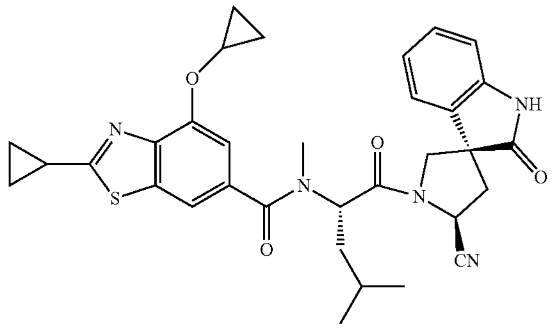 [SMILES: CC(C)C[C@@H](C(=O)N1C[C@]2(C[C@H]1C#N)C(=O)Nc1ccccc12)N(C)C(=O)c1cc(OC2CC2)c2nc(C3CC3)sc2c1] | [M − 1] 596.0 | |

-continued
| Example | Structure | MS | NMR |
|---|---|---|---|
| 318 | 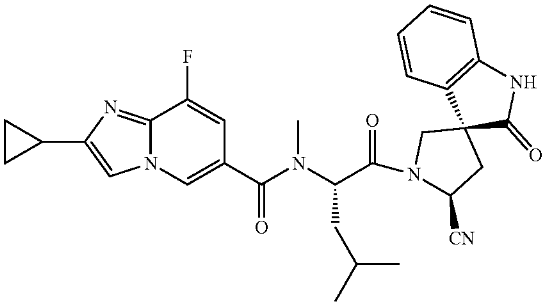 [SMILES: CC(C)C[C@@H](C(=O)N1C[C@]2(C[C@H]1C#N)C(=O)Nc1ccccc12)N(C)C(=O)c1cc(F)c2nc(C3CC3)cn2c1] | [M − 1] 541.1 | |
| 319 | 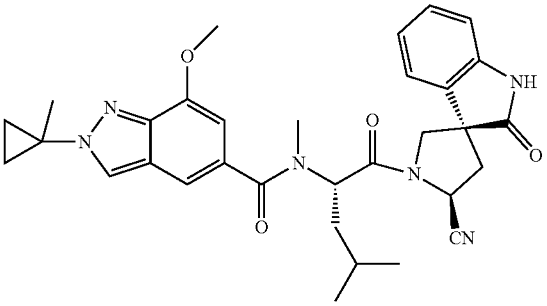 [SMILES: COc1cc(C(=O)N(C)[C@@H](CC(C)C)C(=O)N2C[C@]3(C[C@H]2C#N)C(=O)Nc2ccccc23)cc2cn(C3(C)CC3)nc12] | [M − 1] 567.2 | |
| 320 | 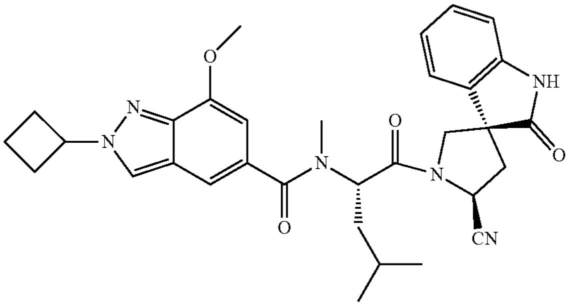 [SMILES: COc1cc(C(=O)N(C)[C@@H](CC(C)C)C(=O)N2C[C@]3(C[C@H]2C#N)C(=O)Nc2ccccc23)cc2cn(C3CCC3)nc12] | [M − 1] 567.1 | |
| 321 | 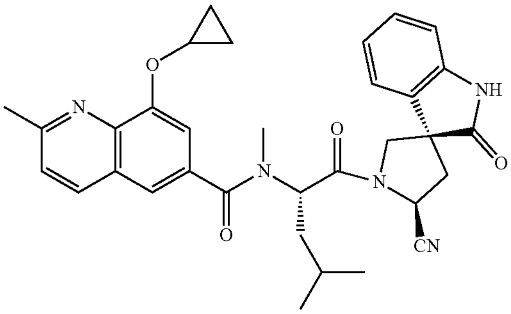 [SMILES: Cc1ccc2cc(C(=O)N(C)[C@@H](CC(C)C)C(=O)N3C[C@]4(C[C@H]3C#N)C(=O)Nc3ccccc34)cc(OC3CC3)c2n1] | [M − 1] 564.2 | |
| 322 | 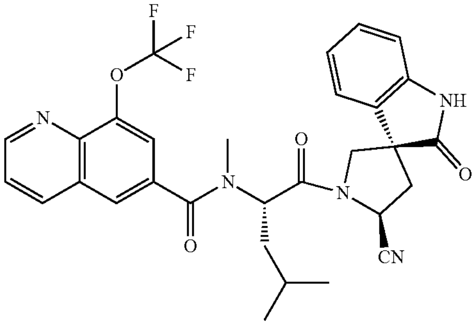 [SMILES: CC(C)C[C@@H](C(=O)N1C[C@]2(C[C@H]1C#N)C(=O)Nc1ccccc12)N(C)C(=O)c1cc(OC(F)(F)F)c2ncccc2c1] | [M − 1] 578.1 | |

-continued

| Example | Structure | MS | NMR |
|---|---|---|---|
| 323 | 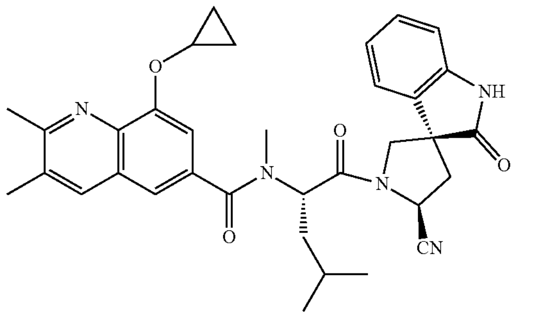 [SMILES: Cc1cc2cc(C(=O)N(C)[C@@H](CC(C)C)C(=O)N3C[C@]4(C[C@H]3C#N)C(=O)Nc3ccccc34)cc(OC3CC3)c2nc1C] | [M − 1] 578.2 | |
| 324 | 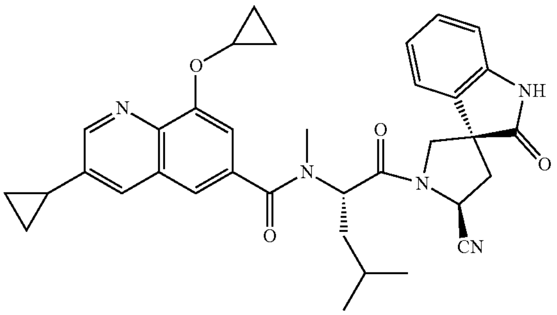 [SMILES: CC(C)C[C@@H](C(=O)N1C[C@]2(C[C@H]1C#N)C(=O)Nc1ccccc12)N(C)C(=O)c1cc(OC2CC2)c2ncc(C3CC3)cc2c1] | [M − 1] 590.1 | |
| 325 | 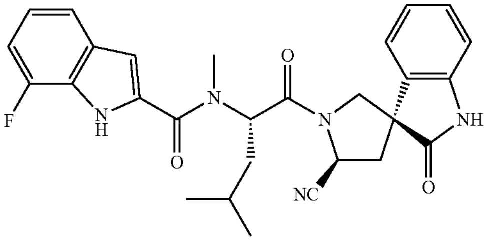 [SMILES: CC(C)C[C@@H](C(=O)N1C[C@]2(C[C@H]1C#N)C(=O)Nc1ccccc12)N(C)C(=O)c1cc2cccc(F)c2[nH]1] | [M − 1] 500.18 | $^1$H NMR (400 MHz, Acetone-$d_6$) δ 10.57 (s, 1H), 9.67 (s, 1H), 7.46 (s, 1H), 7.05-6.89 (m, 8H), 5.57 (s, 1H), 5.22 (t, J = 8.3 Hz, 1H), 4.27 (d, J = 10.3 Hz, 1H), 4.00 (d, J = 10.6 Hz, 1H), 3.41 (s, 3H), 2.78-2.71 (m, 1H), 2.69 (dd, J = 13.3, 8.1 Hz, 1H), 1.79 (dt, J = 14.1, 6.7 Hz, 1H), 1.68- 1.60 (m, 1H), 1.21 (d, J = 0.9 Hz, 1H), 0.99 (dd, J = 18.7, 6.5 Hz, 6H). |
| 326 | 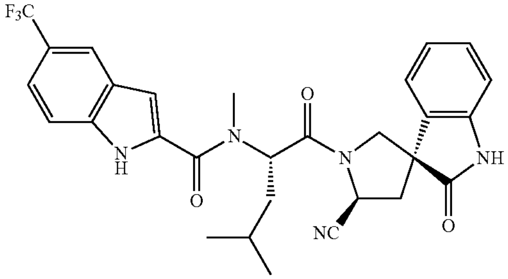 [SMILES: CC(C)C[C@@H](C(=O)N1C[C@]2(C[C@H]1C#N)C(=O)Nc1ccccc12)N(C)C(=O)c1cc2cc(C#N)ccc2[nH]1] | [M − 1] 550.17 | $^1$H NMR (400 MHz, Acetone-$d_6$) δ 10.85 (s, 1H), 9.69 (s, 1H), 8.05 (s, 1H), 7.69 (d, J = 8.7 Hz, 1H), 7.52 (d, J = 8.7 Hz, 1H), 7.08 (s, 1H), 7.02 (d, J = 8.3 Hz, 2H), 6.92 (d, J = 7.7 Hz, 1H), 6.83 (d, J = 8.5 Hz, 1H), 5.61 (s, 1H), 5.22 (t, J = 8.3 Hz, 1H), 4.30 (d, J = 10.8 Hz, 1H), 4.01 (d, J = 10.6 Hz, 1H), 3.44 (s, 3H), 2.87-2.60 (m, 2H), 1.92 (s, 1H), 1.79 (dt, J = 14.2, 7.3 Hz, 1H), 1.64 (dd, J = 13.9, 7.4 Hz, 1H), 0.99 (dd, J = 18.4, 6.6 Hz, 6H). |
| 327 | 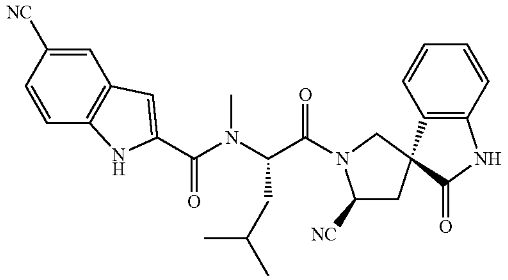 | [M − 1] 507.10 | $^1$H NMR (400 MHz, Acetone-$d_6$) δ 10.96 (s, 1H), 9.68 (s, 1H), 8.15 (s, 1H), 7.67 (d, J = 8.6 Hz, 1H), 7.53 (d, J = 8.0 Hz, 1H), 7.03 (d, J = 13.3 Hz, 3H), 6.91 (d, J = 7.7 Hz, 1H), 6.82 (d, J = 8.0 Hz, 1H), 5.59 (d, J = 8.2 Hz, 1H), 5.22 (t, J = 8.2 Hz, 1H), 4.28 (d, J = 10.7 Hz, 1H), 3.99 (d, J = 10.6 Hz, 1H), 3.45 (s, 3H), 2.75-2.66 (m, 2H), 1H), 1.95 (m, 1H), 1.79 (ddd, J = 14.2, 8.7, 5.6 Hz, 1H), 0.99 (dd, J = 18.2, 6.6 Hz, 6H). |

-continued

| Example | Structure | MS | NMR |
| --- | --- | --- | --- |
| 328 | 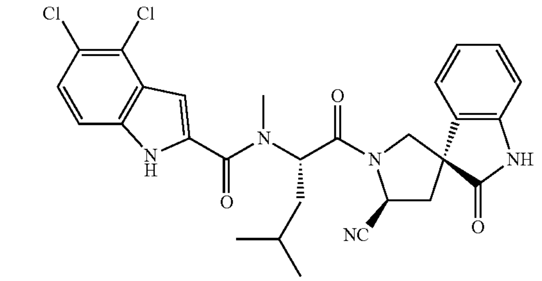 [SMILES: CC(C)C[C@@H](C(=O)N1C[C@]2(C[C@H]1C#N)C(=O)Nc1ccccc12)N(C)C(=O)c1cc2c(Cl)c(Cl)ccc2[nH]1] | [M + 1] 550.15, 552.14 | $^1$H NMR (400 MHz, Acetone-$d_6$) δ 10.90 (s, 1H), 9.67 (s, 1H), 7.50 (d, J = 8.7 Hz, 1H), 7.38 (d, J = 8.7 Hz, 1H), 7.03 (d, J = 7.8 Hz, 2H), 6.96-6.88 (m, 2H), 6.83 (t, J = 7.5 Hz, 1H), 5.60 (s, 1H), 5.22 (t, J = 8.2 Hz, 1H), 4.28 (d, J = 10.6 Hz, 1H), 3.99 (d, J = 10.6 Hz, 1H), 3.47 (s, 3H), 2.83-2.72 (m, 2H), 2.00-1.90 (m, 1H), 1.80 (ddd, J = 14.1, 8.8, 5.8 Hz, 1H), 1.64 (dt, J = 14.2, 6.7 Hz, 1H), 0.99 (dd, J = 18.5, 6.6 Hz, 6H). |
| 329 | 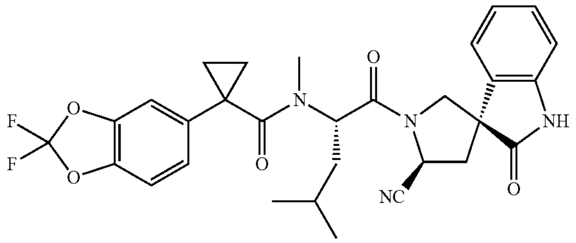 [SMILES: CC(C)C[C@@H](C(=O)N1C[C@]2(C[C@H]1C#N)C(=O)Nc1ccccc12)N(C)C(=O)C1(c2ccc3c(c2)OC(F)(F)O3)CC1] | [M − 1] 563.13 | $^1$H NMR (400 MHz, Acetone-$d_6$) δ 9.73 (s, 1H), 7.32 (td, J = 7.5, 1.9 Hz, 1H), 7.19 (d, J = 8.4 Hz, 1H), 7.11 (d, J = 1.8 Hz, 1H), 7.04 (td, J = 6.0, 5.6, 2.0 Hz, 4H), 5.36 (dd, J = 9.2, 6.1 Hz, 1H), 5.13 (t, J = 8.4 Hz, 1H), 4.15 (d, J = 10.4 Hz, 1H), 3.99 (d, J = 10.4 Hz, 1H), 2.93 (s, 3H), 2.78-2.60 (m, 2H), 1.78-1.60 (m, 2H), 1.39 (s, 1H), 1.48-1.17 (m, 3H), 0.97-0.82 (m, 6H). |
| 330 | 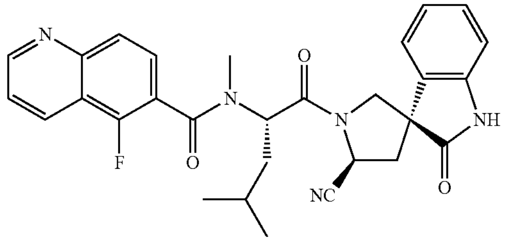 [SMILES: CC(C)C[C@@H](C(=O)N1C[C@]2(C[C@H]1C#N)C(=O)Nc1ccccc12)N(C)C(=O)c1ccc2ncccc2c1F] | [M + 1] 514.24 | $^1$H NMR (400 MHz, Acetone-$d_6$) δ 9.80 (s, 1H), 9.04 (dd, J = 4.2, 1.7 Hz, 1H), 8.49 (dt, J = 8.5, 1.3 Hz, 1H), 7.81 (d, J = 8.7 Hz, 1H), 7.68 (dd, J = 8.5, 4.2 Hz, 1H), 7.42-7.33 (m, 1H), 7.17-7.10 (m, 2H), 7.02 (td, J = 7.5, 1.0 Hz, 1H), 6.88 (s, 1H), 5.66 (dd, J = 9.7, 5.1 Hz, 1H), 5.26 (t, J = 8.4 Hz, 1H), 4.35 (d, J = 10.7 Hz, 1H), 4.08 (d, J 10.7 Hz, 1H), 2.93 (s, 3H), 2.86-2.67 (m, 3H), 2.10 (s, 2H), 2.04-1.92 (m, 1H), 1.84-1.69 (m, 2H), 1.05 (dd, J = 12.9, 6.2 Hz, 6H). |
| 331 | 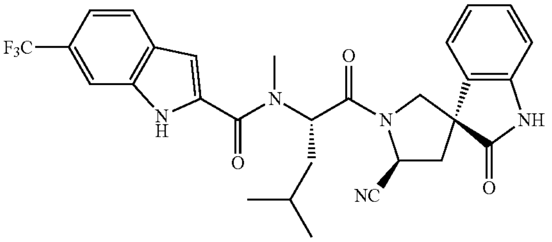 [SMILES: CC(C)C[C@@H](C(=O)N1C[C@]2(C[C@H]1C#N)C(=O)Nc1ccccc12)N(C)C(=O)c1cc2ccc(C(F)(F)F)cc2[nH]1] | [M − 1] 550.17 | |
| 332 | 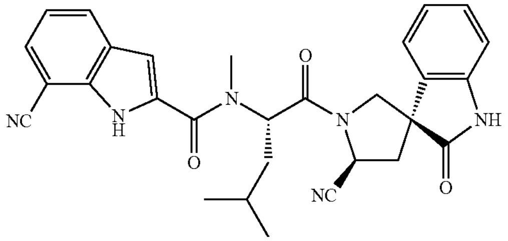 [SMILES: CC(C)C[C@@H](C(=O)N1C[C@]2(C[C@H]1C#N)C(=O)Nc1ccccc12)N(C)C(=O)c1cc2cccc(C#N)c2[nH]1] | [M − 1] 502.17 | $^1$H NMR (400 MHz, Acetone-$d_6$) δ 10.76 (s, 1H), 9.70 (s, 1H), 8.01 (d, J = 8.2 Hz, 1H), 7.70 (d, J = 7.4 Hz, 1H), 7.27 (t, J = 7.6 Hz, 1H), 7.07-6.92 (m, 4H), 6.81 (d, J = 7.6 Hz, 1H), 5.56 (d, J = 7.9 Hz, 1H), 5.23 (t, J = 8.3 Hz, 1H), 4.33 (d, J = 10.7 Hz, 1H), 3.99 (d, J = 10.6 Hz, 1H), 3.40 (s, 3H), 2.81-2.65 (m, 2H), 2.00-1.88 (m, 1H), 1.80 (ddd, J = 14.2, 8.6, 5.7 Hz, 1H), 1.65 (dt, J = 13.8, 6.7 Hz, 1H), 1.22 (s, 0H), 0.99 (dd, J = 18.2, 6.6 Hz, 6H). |

-continued
| Example | Structure | MS | NMR |
|---|---|---|---|
| 333 | 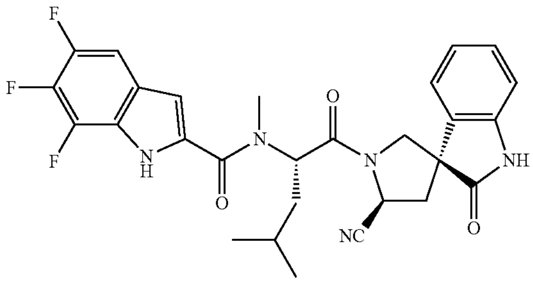 [SMILES: CC(C)C[C@@H](C(=O)N1C[C@]2(C[C@H]1C#N)C(=O)Nc1ccccc12)N(C)C(=O)c1cc2cc(F)c(F)c(F)c2[nH]1] | [M − 1] 536.15 | $^1$H NMR (400 MHz, Acetone-$d_6$) δ 10.99 (s, 1H), 9.68 (s, 1H), 7.41 (s, 1H), 7.07 (s, 1H), 7.02 (d, J = 7.3 Hz, 1H), 6.93 (d, J = 7.8 Hz, 2H), 6.84 (d, J = 7.7 Hz, 1H), 5.57 (s, 1H), 5.22 (t, J = 8.3 Hz, 1H), 4.25 (d, J = 10.7 Hz, 1H), 3.99 (d, J = 10.6 Hz, 1H), 3.41(s, 3H), 2.75 (dd, J = 13.3, 8.6 Hz, 1H), 2.74-2.60 (m, 1H), 2.00-1.87 (m, 1H), |
| 334 | 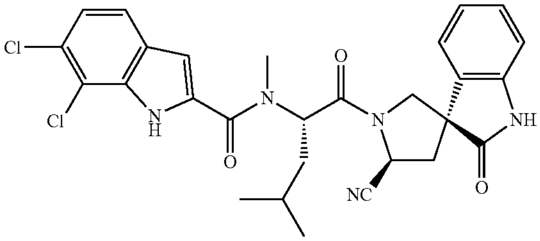 [SMILES: CC(C)C[C@@H](C(=O)N1C[C@]2(C[C@H]1C#N)C(=O)Nc1ccccc12)N(C)C(=O)c1cc2ccc(Cl)c(Cl)c2[nH]1] | | |
| 335 | 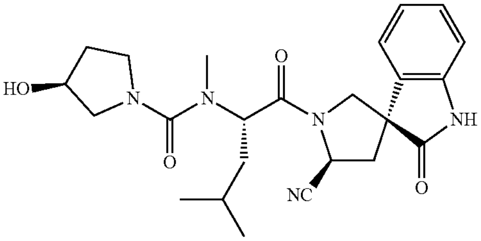 [SMILES: CC(C)C[C@@H](C(=O)N1C[C@]2(C[C@H]1C#N)C(=O)Nc1ccccc12)N(C)C(=O)N1CC[C@H](O)C1] | [M + 1] 454.27 | |
| 336 | 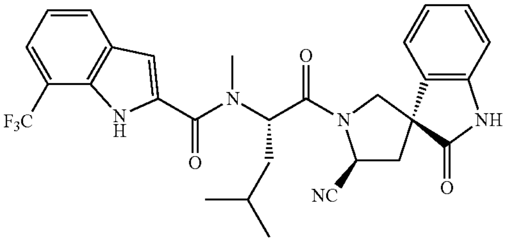 | [M − 1] 550.17, | 1H NMR (400 MHz, Acetone-$d_6$) δ 9.85 (s, 1H), 9.69 (s, 1H), 7.98 (d, J = 8.1 Hz, 1H), 7.63 (d, J = 7.5 Hz, 1H), 7.30 (t, J = 7.8 Hz, 1H), 7.08-6.98 (m, 1H), 7.02 (s, 2H), 6.94 (d, J = 7.8 Hz, 1H), 6.82 (d, J = 7.7 Hz, 1H), 5.56 (t, J = 7.7 Hz, 1H), 5.24 (t, J = 8.3 Hz, 1H), 4.36 (d, J = 10.6 Hz, 1H), 3.99 (d, J = 10.6 Hz, 1H), 3.44 (s, 3H), 2.82-2.65 (m, 2H), 1.93 (ddd, J = 14.4, 8.7, 5.4 Hz, 1H), 1.82 (dq, J = 14.3, 7.0, 6.5 Hz, 1H), 1.64 (dt, J = 13.6, 6.7 Hz, 1H), 0.99 (dd, J = 18.8, 6.6 Hz, 6H). |
| 337 | 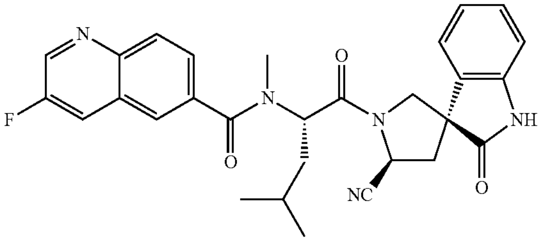 [SMILES: CC(C)C[C@@H](C(=O)N1C[C@]2(C[C@H]1C#N)C(=O)Nc1ccccc12)N(C)C(=O)c1ccc2ncc(F)cc2c1] | [M − 1] 512.12, | |

-continued
| Example | Structure | MS | NMR |
|---|---|---|---|
| 338 | 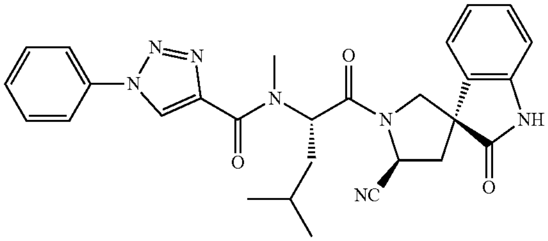 [SMILES: CC(C)C[C@@H](C(=O)N1C[C@]2(C[C@H]1C#N)C(=O)Nc1ccccc12)N(C)C(=O)c1cn(-c2ccccc2)nn1] | [M − 1] 510.19 | |
| 339 | 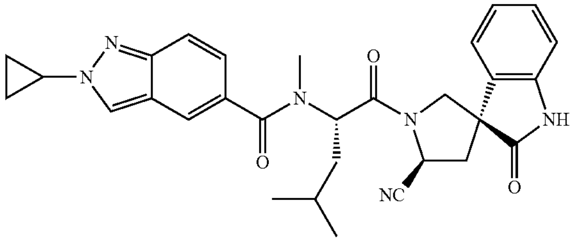 [SMILES: CC(C)C[C@@H](C(=O)N1C[C@]2(C[C@H]1C#N)C(=O)Nc1ccccc12)N(C)C(=O)c1ccc2nn(C3CC3)cc2c1] | [M − 1] 525.27 | $^1$H NMR (400 MHz, Acetone-$d_6$) δ 9.78 (s, 1H), 8.39 (s, 1H), 7.48 (d, J = 8.9 Hz, 1H), 7.39 (t, J = 7.9 Hz, 1H), 7.25 (s, 1H), 7.10 (ddd, J = 8.7, 7.7, 1.0 Hz, 2H), 7.03 (s, 1H), 6.80 (d, J = 9.0 Hz, 1H), 5.55 (s, 1H), 5.24 (t, J = 8.5 Hz, 1H), 4.38 (d, J = 10.7 Hz, 1H), 4.18-4.11 (m, 1H), 4.01 (d, J = 10.7 Hz, 1H), 2.96 (s, 3H), 2.75 (p, J = 12.8 Hz, 2H), 1.94-1.84 (m, 1H), 1.83-1.71 (m, 2H), 1.37 (p, J = 4.9 Hz, 2H), 1.25-1.12 (m, 3H), 1.03 (dd, J = 11.9, 6.2 Hz, 6H) |
| 340 | 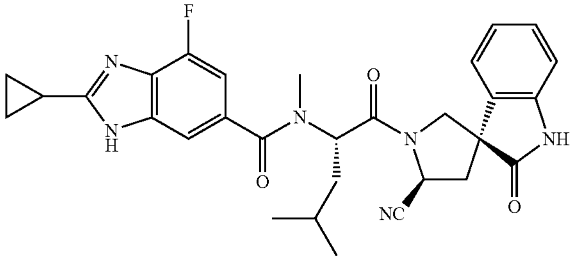 [SMILES: CC(C)C[C@@H](C(=O)N1C[C@]2(C[C@H]1C#N)C(=O)Nc1ccccc12)N(C)C(=O)c1cc(F)c2nc(C3CC3)[nH]c2c1] | [M + 1] 543.33 | |
| 341 | 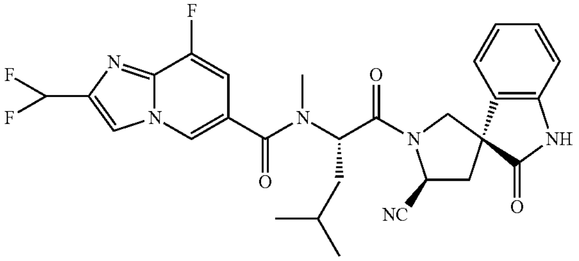 [SMILES: CC(C)C[C@@H](C(=O)N1C[C@]2(C[C@H]1C#N)C(=O)Nc1ccccc12)N(C)C(=O)c1cc(F)c2nc(C(F)F)cn2c1] | [M + 1] 553.25 | |
| 342 | 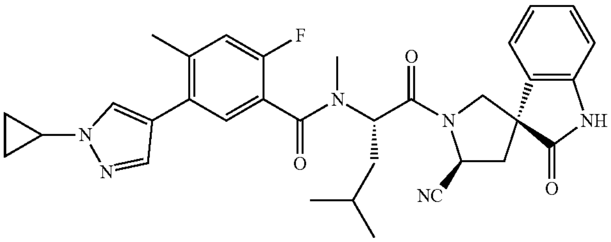 [SMILES: Cc1cc(F)c(C(=O)N(C)[C@@H](CC(C)C)C(=O)N2C[C@]3(C[C@H]2C#N)C(=O)Nc2ccccc23)cc1-c1cnn(C2CC2)c1] | [M − 1] 581.1 | $^1$H NMR (400 MHz, Acetone-$d_6$) δ 9.74 (s, 1H), 7.83 (d, J = 0.9 Hz, 1H), 7.51 (d, J = 0.9 Hz, 1H), 7.11-6.95 (m, 3H), 6.95-6.81 (m, 2H), 6.64 (s, 1H), 5.59 (dd, J = 9.5, 5.4 Hz, 1H), 5.18 (t, J = 8.4 Hz, 1H), 4.34 (d, J = 10.6 Hz, 1H), 4.03 (d, J = 10.7 Hz, 1H), 3.83 (tt, J = 7.4, 3.8 Hz, 1H), 2.92 (d, J = 1.4 Hz, 3H), 2.81-2.63 (m, 2H), 2.39 (s, 3H), 1.91 (ddt, J = 13.7, 9.5, 4.7 Hz, 1H), 1.80-1.63 (m, 2H), 1.25-1.15 (m, 2H), 1.10-1.04 (m, 2H), 1.03 (d, J = 6.4 Hz, 3H), 0.99 (d, J = 6.3 Hz, 3H). |

-continued

| Example | Structure | MS | NMR |
|---|---|---|---|
| 343 | 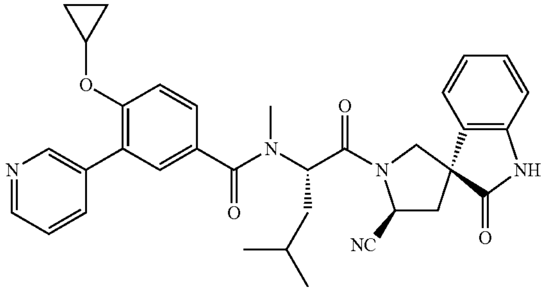 [SMILES: CC(C)C[C@@H](C(=O)N1C[C@]2(C[C@H]1C#N)C(=O)Nc1ccccc12)N(C)C(=O)c1ccc(OC2CC2)c(-c2cccnc2)c1] | [M − 1] 576.1 | 1H NMR (400 MHz, Acetone-d6) δ 9.73 (s, 1H), 8.60 (d, J = 13.8 Hz, 2H), 7.82 (d, J = 7.9 Hz, 1H), 7.42 (d, J = 9.2 Hz, 2H), 7.18-6.85 (m, 6H), 5.53 (t, J = 7.4 Hz, 1H), 5.21 (t, J = 8.5 Hz, 1H), 4.41 (d, J = 10.7 Hz, 1H), 4.00 (d, J = 10.7 Hz, 1H), 3.92 (br s, 1H), 3.05 (s, 3H), 2.81-2.63 (m, 2H), 1.92-1.85 (m, 1H), 1.83-1.76 (m, 1H), 1.73-1.66 (m, 1H), 1.03 (d, J = 6.5 Hz, 3H), 1.00 (d, J = 6.5 Hz, 3H), 0.87-0.82 (m, 2H), 0.73-0.68 (m, 2H). |
| 344 | 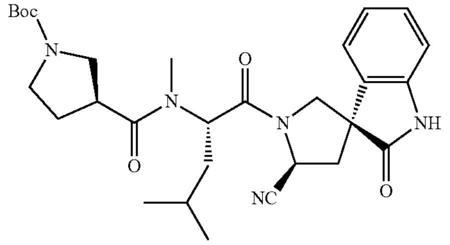 [SMILES: CC(C)C[C@@H](C(=O)N1C[C@]2(C[C@H]1C#N)C(=O)Nc1ccccc12)N(C)C(=O)[C@H]1CCN(C(=O)OC(C)(C)C)C1] | [M − 1] 536.34 | 1H NMR (400 MHz, Acetone-d6) δ 9.78 (d, J = 11.6 Hz, 1H), 7.28 (q, J = 9.4, 8.7 Hz, 1H), 7.12-6.86 (m, 3H), 5.48 (dd, J = 9.6, 5.7 Hz, 1H), 5.18 (t, J = 8.4 Hz, 1H), 4.28 (dd, J = 33.8, 10.9 Hz, 1H), 3.87 (d, J = 10.8 Hz, 1H), 3.36-3.15 (m, 2H), 3.11 (s, 3H), 3.08-2.96 (m, 2H), 2.76-2.62 (m, 2H), 2.10-2.05 (m, 1H), 1.86-1.75 (m, 2H), 1.66-1.59 (m, 1H), 1.48-1.44 (m, 2H), 1.44 (s, 9H), 0.96 (d, J = 6.6 Hz, 3H), 0.90 (d, J = 6.5 Hz, 3H). |
| 345 | 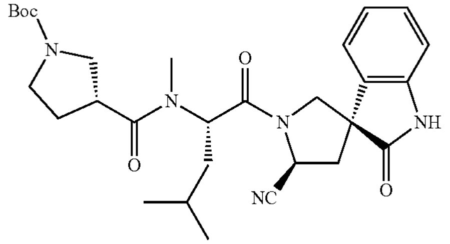 [SMILES: CC(C)C[C@@H](C(=O)N1C[C@]2(C[C@H]1C#N)C(=O)Nc1ccccc12)N(C)C(=O)[C@@H]1CCN(C(=O)OC(C)(C)C)C1] | [M − 1] 536.3 | 1H NMR (400 MHz, Acetone-d6) δ 9.74 (s, 1H), 7.31 (td,J = 7.7, 1.3 Hz, 1H), 7.09 (td, J = 7.6, 1.1 Hz, 1H), 7.02 (dd, J = 11.5, 7.6 Hz, 2H), 5.47 (t, J = 7.5 Hz, 1H), 5.18 (t, J = 8.5 Hz, 1H), 4.08 (dd, J = 26.7, 10.8 Hz, 1H), 3.90 (d, J = 10.7 Hz, 1H), 3.42 (t, J = 9.5 Hz, 1H), 3.38-3.20 (m, 2H), 3.18-3.08 (m, 2H), 3.06 (s, 3H), 2.78-2.63 (m, 2H), 1.69 (p, J = 8.3, 7.3 Hz, 1H), 1.57 (dq, J = 13.1, 6.7 Hz, 1H), 1.46-1.43 (m, 2H), 1.41 (s, 9H), 1.32-1.28 (m, 1H), 0.96 (d, J = 6.6 Hz, 3H), 0.91 (d, J = 6.6 Hz, 3H). |
| 346 | 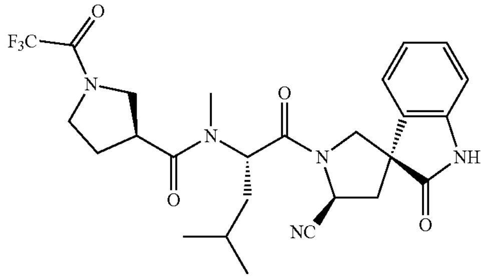 [SMILES: CC(C)C[C@@H](C(=O)N1C[C@]2(C[C@H]1C#N)C(=O)Nc1ccccc12)N(C)C(=O)[C@H]1CCN(C(=O)C(F)(F)F)C1] | [M − 1] 532.28 | |
| 347 | 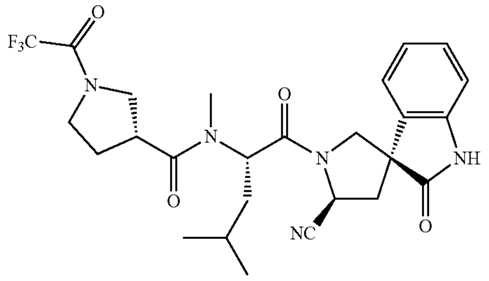 [SMILES: CC(C)C[C@@H](C(=O)N1C[C@]2(C[C@H]1C#N)C(=O)Nc1ccccc12)N(C)C(=O)[C@@H]1CCN(C(=O)C(F)(F)F)C1] | [M − 1] 532.28 | |

-continued

| Example | Structure | MS | NMR |
|---|---|---|---|
| 348 | 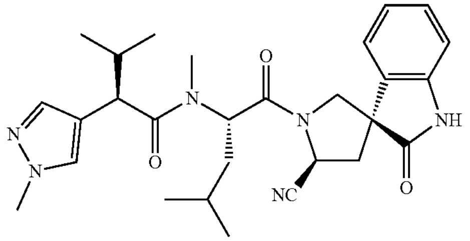 [SMILES: CC(C)C[C@@H](C(=O)N1C[C@]2(C[C@H]1C#N)C(=O)Nc1ccccc12)N(C)C(=O)[C@@H](c1cnn(C)c1)C(C)C] | [M − 1] 503.5 | |
| 349 | 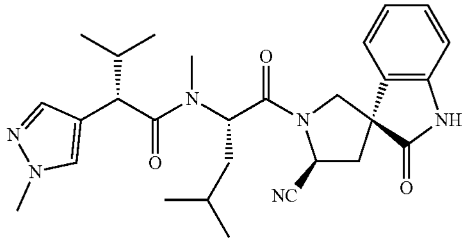 [SMILES: CC(C)C[C@@H](C(=O)N1C[C@]2(C[C@H]1C#N)C(=O)Nc1ccccc12)N(C)C(=O)[C@H](c1cnn(C)c1)C(C)C] | [M − 1] 503.5 | 1H NMR (400 MHz, Acetone-d6) δ 9.65 (s, 1H), 7.32-7.23 (m, 2H), 7.14 (s, 1H), 7.07-6.96 (m, 2H), 6.91 (d, J = 7.4 Hz, 1H), 5.47 (dd, J = 9.5, 5.8 Hz, 1H), 5.01 (t, J = 8.1 Hz, 1H), 3.94 (s, 2H), 3.78 (s, 3H), 3.47 (d, J = 9.4 Hz, 1H), 3.09 (s, 3H), 2.69-2.52 (m, 2H), 2.05-1.99 (m, 1H), 1.81-1.64 (m, 2H), 1.57 (dtd, J = 8.8, 6.6, 5.2 Hz, 1H), 1.00 (d, J = 6.6 Hz, 3H), 0.95 (d, J = 6.4 Hz, 3H), 0.89 (d, J = 6.5 Hz, 3H), 0.71 (d, J = 6.7 Hz, 3H). |
| 350 | 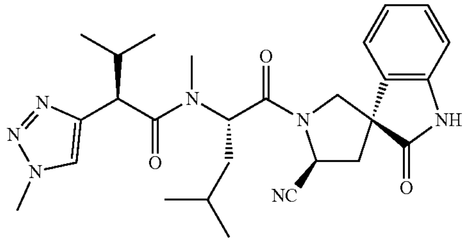 | [M − 1] 504.4 | — |
| 351 | 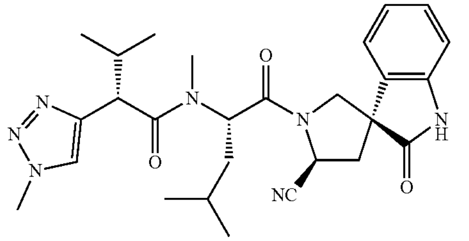 [SMILES: CC(C)C[C@@H](C(=O)N1C[C@]2(C[C@H]1C#N)C(=O)Nc1ccccc12)N(C)C(=O)[C@H](c1cn(C)nn1)C(C)C] | [M − 1] 504.4 | 1H NMR (400 MHz, Acetone-d6) δ 9.68 (s, 1H), 7.49 (s, 1H), 7.22 (td, J = 7.6, 1.6 Hz, 1H), 6.96 (dt, J = 7.8, 0.9 Hz, 1H), 6.94-6.84 (m, 2H), 5.48 (dd, J = 9.3, 6.0 Hz, 1H), 5.01 (dd, J = 8.6, 7.2 Hz, 1H), 3.97 (s, 3H), 3.90 (d, J = 2.3 Hz, 2H), 3.16 (s, 3H), 2.66 (dd, J = 13.3, 8.6 Hz, 1H), 2.58 (dd, J = 13.3, 7.2 Hz, 1H), 2.16 (dp, J = 9.0, 6.7 Hz, 1H), 1.83-1.64 (m, 2H), 1.64-1.52 (m, 1H), 1.00 (d, J = 6.6 Hz, 3H), 0.95 (t, J = 6.2 Hz, 6H), 0.87-0.77 (m, 1H), 0.72 (d, J = 6.8 Hz, 3H). |
| 352 | 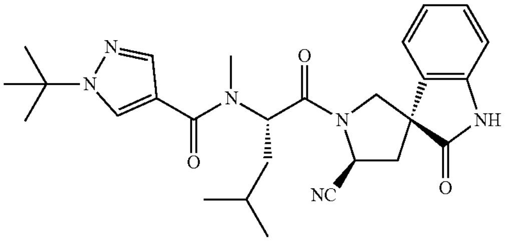 [SMILES: CC(C)C[C@@H](C(=O)N1C[C@]2(C[C@H]1C#N)C(=O)Nc1ccccc12)N(C)C(=O)c1cnn(C(C)(C)C)c1] | [M − 1] 489.4 | 1H NMR (400 MHz, Acetone-d6) δ 9.72 (s, 1H), 7.81 (s, 1H), 7.58 (s, 1H), 7.17 (t, J = 7.4 Hz, 1H), 6.99-6.89 (m, 3H), 5.53 (dd, J = 9.3, 5.9 Hz, 1H), 5.18 (t, J = 8.3 Hz, 1H), 4.37 (d, J = 10.6 Hz, 1H), 3.93 (d, J = 10.7 Hz, 1H), 3.24 (s, 3H), 2.75-2.63 (m, 2H), 1.84 (ddd, J = 14.3, 9.3, 5.3 Hz, 1H), 1.79-1.67 (m, 1H), 1.64-1.60 (m, 1H), 1.58 (s, 9H), 0.99 (d, J = 6.6 Hz, 3H), 0.95 (d, J = 6.5 Hz, 3H). |

-continued
| Example | Structure | MS | NMR |
| --- | --- | --- | --- |
| 353 | 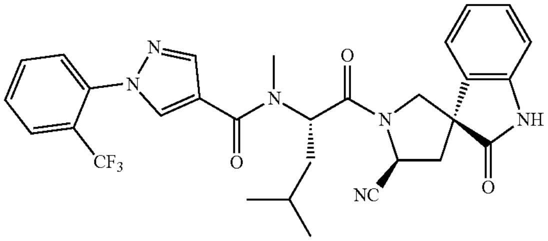 [SMILES: CC(C)C[C@@H](C(=O)N1C[C@]2(C[C@H]1C#N)C(=O)Nc1ccccc12)N(C)C(=O)c1cnn(-c2ccccc2C(F)(F)F)c1] | [M − 1] 577.3 | 1H NMR (400 MHz, Acetone-d6) δ 9.73 (s, 1H), 8.07 (s, 1H), 7.97 (d, J = 7.8 Hz, 1H), 7.94-7.85 (m, 1H), 7.85-7.72 (m, 2H), 7.66 (d, J = 7.9 Hz, 1H), 7.12 (td, J = 7.7, 1.3 Hz, 1H), 7.02 (d, J = 7.4 Hz, 1H), 6.97-6.83 (m, 2H), 5.55 (dd, J = 9.3, 5.8 Hz, 1H), 5.21 (t, J = 8.3 Hz, 1H), 4.39 (d, J = 10.7 Hz, 1H), 3.96 (d, J = 10.6 Hz, 1H), 3.29 (s, 3H), 2.75 - 2.65 (m, 2H), 1.88 (ddd, J = 14.3, 9.3, 5.3 Hz, 1H), 1.76 (ddd, J = 14.1, 8.4, 5.9 Hz, 1H), 1.69-1.53 (m, 1H), 1.00 (d, J = 6.7 Hz, 3H), 0.97 (d, J = 6.5 Hz, 3H). |
| 354 | 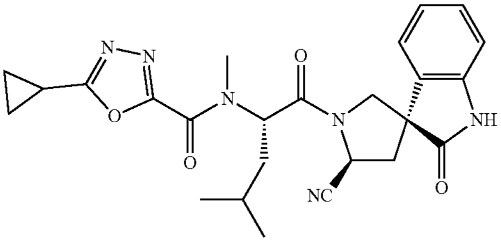 [SMILES: CC(C)C[C@@H](C(=O)N1C[C@]2(C[C@H]1C#N)C(=O)Nc1ccccc12)N(C)C(=O)c1nnc(C2CC2)o1] | [M − 1] 475.3 | — |
| 355 | 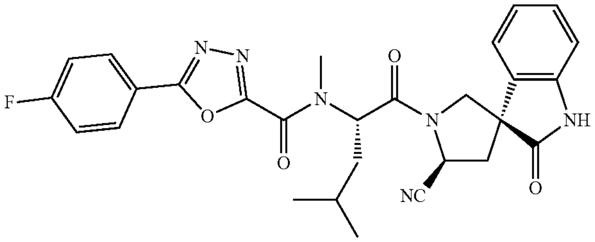 [SMILES: CC(C)C[C@@H](C(=O)N1C[C@]2(C[C@H]1C#N)C(=O)Nc1ccccc12)N(C)C(=O)c1nnc(-c2ccc(F)cc2)o1] | [M − 1] 529.4 | — |
| 356 | 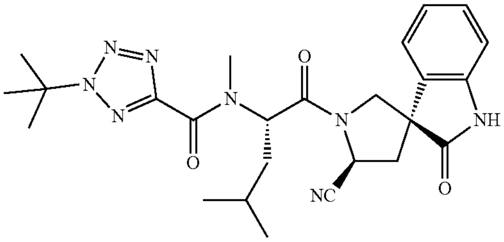 [SMILES: CC(C)C[C@@H](C(=O)N1C[C@]2(C[C@H]1C#N)C(=O)Nc1ccccc12)N(C)C(=O)c1nnn(C(C)(C)C)n1] | [M − 1] 491.4 | — |
| 357 | 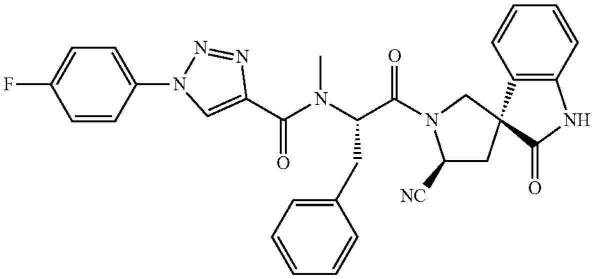 [SMILES: CN(C(=O)c1cn(-c2ccc(F)cc2)nn1)[C@@H](Cc1ccccc1)C(=O)N1C[C@]2(C[C@H]1C#N)C(=O)Nc1ccccc12] | 562.02 [M − 1]− | |

-continued
| Example | Structure | MS | NMR |
|---|---|---|---|
| 358 | 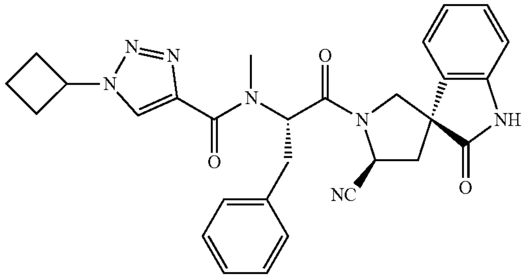 [SMILES: CN(C(=O)c1cn(C2CCC2)nn1)[C@@H](Cc1ccccc1)C(=O)N1C[C@]2(C[C@H]1C#N)C(=O)Nc1ccccc12] | 522.20 [M − 1]− | |
| 359 | 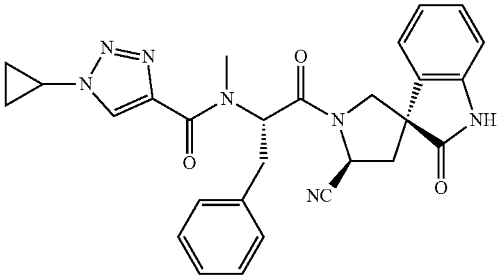 [SMILES: CN(C(=O)c1cn(C2CC2)nn1)[C@@H](Cc1ccccc1)C(=O)N1C[C@]2(C[C@H]1C#N)C(=O)Nc1ccccc12] | 508.21 [M − 1]− | |
| 360 | 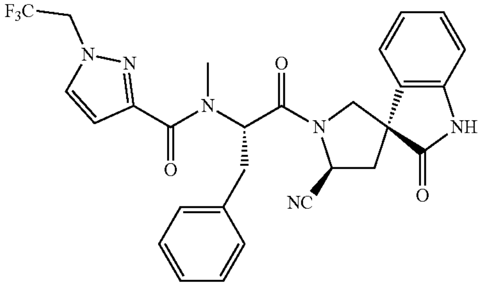 [SMILES: CN(C(=O)c1ccn(CC(F)(F)F)n1)[C@@H](Cc1ccccc1)C(=O)N1C[C@]2(C[C@H]1C#N)C(=O)Nc1ccccc12] | 549.13 [M − 1]− | |
| 361 | 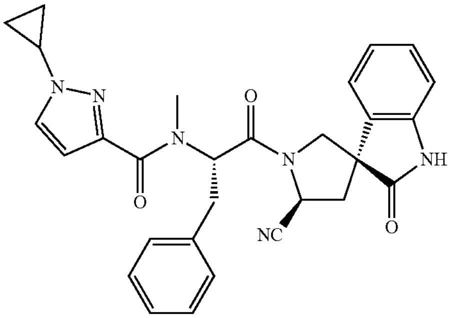 [SMILES: CN(C(=O)c1ccn(C2CC2)n1)[C@@H](Cc1ccccc1)C(=O)N1C[C@]2(C[C@H]1C#N)C(=O)Nc1ccccc12] | 507.20 [M − 1]− | |
| 362 | 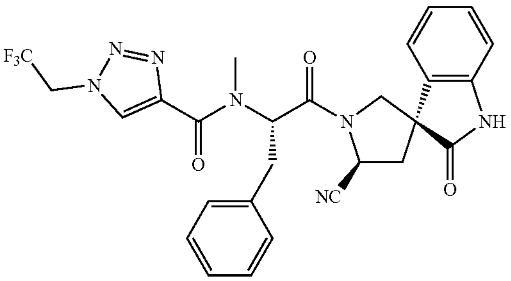 [SMILES: CN(C(=O)c1cn(CC(F)(F)F)nn1)[C@@H](Cc1ccccc1)C(=O)N1C[C@]2(C[C@H]1C#N)C(=O)Nc1ccccc12] | 550.17 [M − 1]− | |

-continued
| Example | Structure | MS | NMR |
|---|---|---|---|
| 363 | 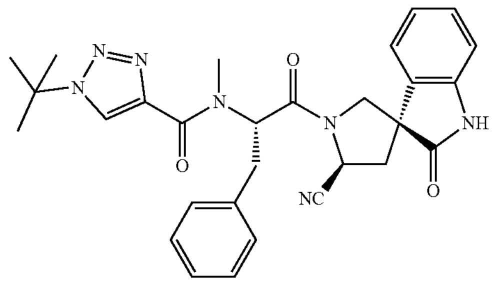 [SMILES: CN(C(=O)c1cn(C(C)(C)C)nn1)[C@@H](Cc1ccccc1)C(=O)N1C[C@]2(C[C@H]1C#N)C(=O)Nc1ccccc12] | 524.24 [M − 1]− | |
| 364 | 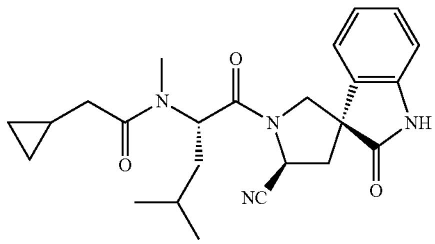 [SMILES: CC(C)C[C@@H](C(=O)N1C[C@]2(C[C@H]1C#N)C(=O)Nc1ccccc12)N(C)C(=O)CC1CC1] | 420.97 [M − 1]− | $^1$H NMR (400 MHz, Acetone-$d_6$) δ 9.51 (s, 1H), 7.04 (td, J = 7.7, 1.3 Hz, 1H), 6.82 (td, J = 7.6, 1.1 Hz, 1H), 6.77 (d, J = 7.8 Hz, 1H), 6.77-6.71 (m, 1H), 5.25 (dd, J = 8.8, 6.3 Hz, 1H), 4.93 (t, J = 8.5 Hz, 1H), 3.93 (dd, J = 10.8, 1.3 Hz, 1H), 3.65 (d, J = 10.7 Hz, 1H), 2.71 (s, 3H), 2.55-2.38 (m, 2H), 1.90 (dd, J = 15.9, 6.8 Hz, 1H), 1.6 (dd, J = 15.9, 6.8 Hz, 1H), 1.54-1.35 (m, 2H), 1.32- 1.17 (m, 1H), 0.70 (dd, J = 12.1, 6.6 Hz, 6H), 0.50-0.35 (m, 1H), 0.06-0.03 (m, 2H), 0.29 (tq, J = 7.9, 4.9 Hz, 1H), −0.48 (dtd, J = 11.1, 6.2, 5.3, 3.9 Hz, 1H). |
| 365 | 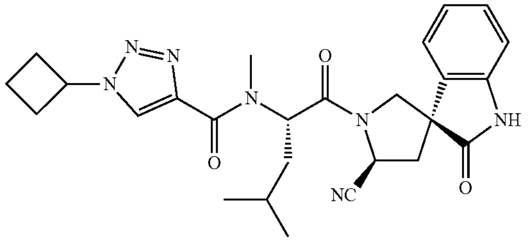 [SMILES: CC(C)C[C@@H](C(=O)N1C[C@]2(C[C@H]1C#N)C(=O)Nc1ccccc12)N(C)C(=O)c1cn(C2CCC2)nn1] | 488.00 [M − 1]− | |
| 366 | 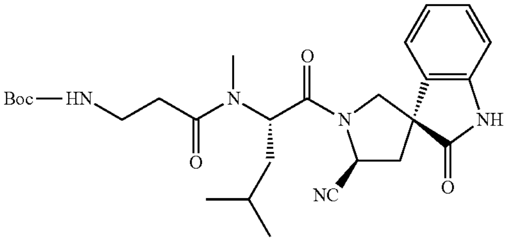 [SMILES: CC(C)C[C@@H](C(=O)N1C[C@]2(C[C@H]1C#N)C(=O)Nc1ccccc12)N(C)C(=O)CCNC(=O)OC(C)(C)C] | [M − 1] 510.40 | 1H NMR (400 MHz, Acetone-$d_6$) δ 9.75 (s, 1H), 7.28 (td, J = 7.7, 1.3 Hz, 1H), 7.08 (td, J = 7.5, 1.1 Hz, 1H), 7.01 (d, J = 7.7 Hz, 1H), 6.98-6.92 (m, 1H), 5.64 (s, 1H), 5.45 (dd, J = 9.3, 6.0 Hz, 1H), 5.18 (t, J = 8.4 Hz, 1H), 4.32-4.25 (m, 1H), 3.88 (d, J = 10.7 Hz, 1H), 3.05-2.94 (m, 2H), 3.00 (s, 3H), 2.79-2.63 (m, 2H), 2.48 (dt, J = 16.4, 7.0 Hz, 1H), 2.18 (dt, J = 16.4, 6.3 Hz, 1H), 1.76 (ddd, J = 14.3, 9.2, 5.3 Hz, 1H), 1.64 (ddd, J = 14.2, 8.6, 6.0 Hz, 1H), 1.54-1.35 (m, 1H), 1.40 (s, 9H), 0.93 (dd, J = 20.2, 6.6 Hz, 6H), |

Example 367

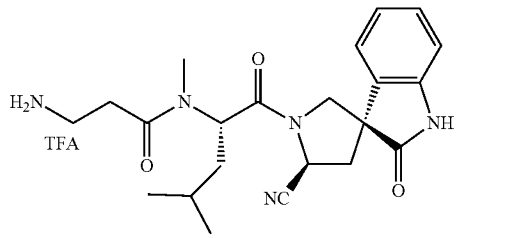

To a solution of Example 366 (17 mg, 0.033 mmol) in DCM (2 mL) was added TFA (0.03 mL), and the mixture was stirred for 4 hours at rt. Solvent was removed to afford the title Example 367 (17 mg, 100%). [M+1] 412.47.

Example 368

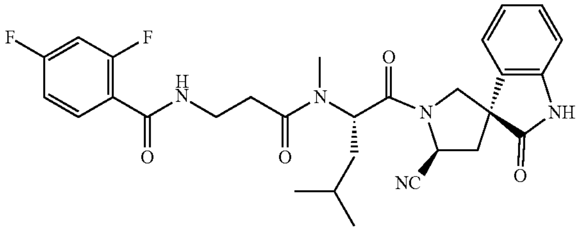

To a solution of Example 367 (61 mg, 0.12 mmol) and 2,4-difluorobenzoic acid (19 mg, 0.12 mmol) in DMF (2 mL) was added HATU (46 mg, 0.12 mmol) and DIPEA (0.04 mL, 0.36 mol). The mixture was stirred 4 hours at rt and was concentrated. The crude was chromatographied on silica to afford the Example 368 (17 mg, 21%). [M−1] 550.36

Example 89

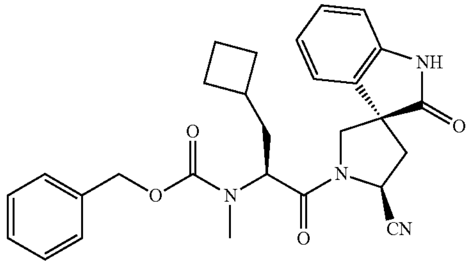

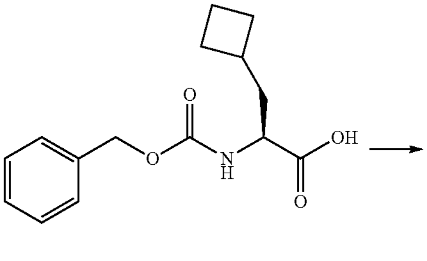

-continued

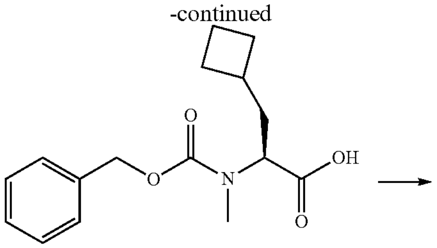

89-1

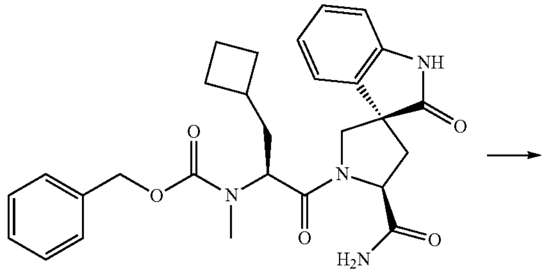

89-2

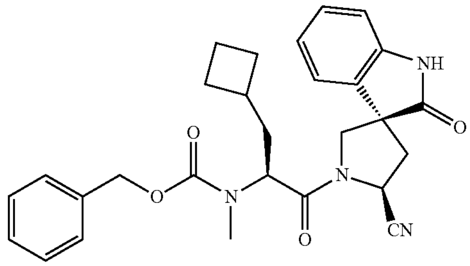

Example 89

Step 1

To a mixture of (S)-2-(((benzyloxy)carbonyl)amino)-3-cyclobutylpropanoic acid (2.68 g, 9.66 mmol) and MeI (4.83 mL, 77 mmol) in THF (30 mL) at 0° C. was added NaH (1.16 g, 29 mmol) portionwise. The resulting mixture was stirred at rt for 2 days, quenched with ice-water, and washed with MBTE (2×). The aqueous layer was acidified with 1 N HCl to PH ~2 and extracted with EtOAc. The collected organic layer was washed with brine, dried over $Na_2SO_4$, filtered, and concentrated give the desired compound (89-1) (2.54 g, 90% yield). ESI-MS m/z=290.12 $[M-H]^-$.

Step 2

To a solution of compound (1-4) (2.33 g, 6.96 mmol), compound (89-1) (2.54 g, 8.70 mmol) and 4-methylmorpholine (3.06 mL, 27.9 mmol) in DCM/DMF (5/5 mL) was added HATU (2.78 g, 7.31 mmol). The mixture was stirred at rt for 2 h, quenched with water, and extracted with EtOAc. The collected organic layer was washed with water, 1N HCl, sat $NaHCO_3$ and brine, dried over $Na_2SO_4$, filtered, and concentrated. Purification of the residue on silica gel column provided compound (89-2) (3.16 g, 90% yield). ESI-MS m/z=503.19 $[M-H]^-$.

Step 3

To a mixture of compound (89-2) (45 mg, 0.089 mmol) and $Et_3N$ (99 μl, 0.713 mmol) in DCM (1 mL) at 0° C. was added dropwise TFAA (50.4 μl, 0.357 mmol). The resulting mixture was stirred at rt for 30 min, quenched with cold sat. $NaHCO_3$ solution, and extracted with EtOAc. The collected organic layer was washed with water, 1N HCl, sat $NaHCO_3$, and brine, dried over $Na_2SO_4$, filtered, and concentrated. Purification of the residue on silica gel column provided Example 89 (23 mg, 53% yield). ESI-MS m/z=485.19 $[M-H]^-$.

The following example was prepared employing similar protocol as described above.

| Example | Structure | MS |
|---|---|---|
| 90 | 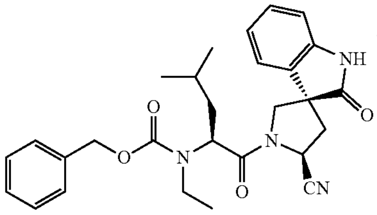 [SMILES: CCN(C(=O)OCc1ccccc1)[C@@H](CC(C)C)C(=O)N1C[C@]2(C[C@H]1C#N)C(=O)Nc1ccccc12] | [M - H] 487.19 |

Example 91

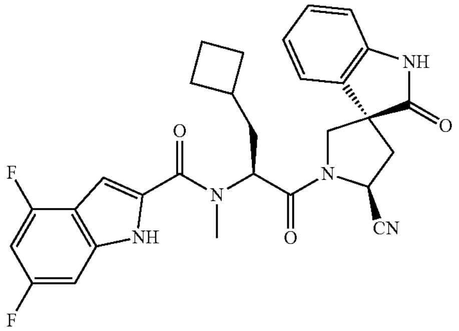

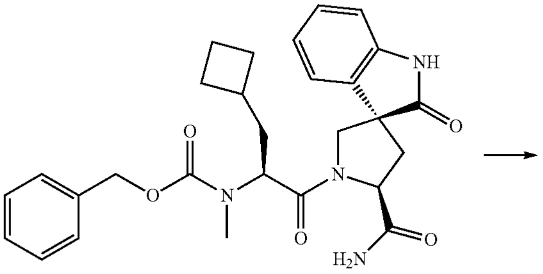

89-2

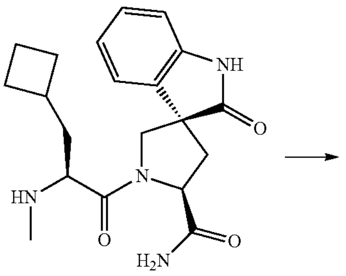

91-1

-continued

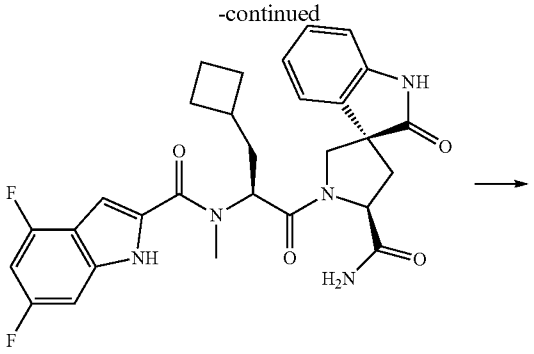

91-2

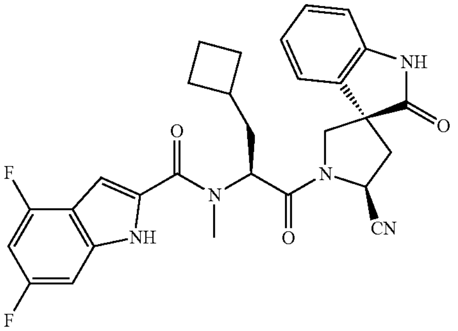

Example 91

Step 1

A mixture of compound (89-2) (65 mg, 0.13 mmol) and Pd—C (13.7 mg, 0.013 mmol) in MeOH (1 mL) was treated with $H_2$ using a hydrogen balloon. After 1 h, the mixture was diluted with DCM, filtered through celite, and concentrated to give compound (91-1) (48 mg, 100%). ESI-MS m/z=369.19 $[M-H]^-$.

Step 2

To a mixture of compound (91-1) (0.032 g, 0.086 mmol), 4,6-difluoro-1H-indole-2-carboxylic acid (0.021 g, 0.108 mmol), DIPEA (0.045 mL, 0.258 mmol) in DCM/DMF (0.5/0.5 mL) at rt was added HATU (39 mg, 0.103 mmol). The resulting mixture was stirred at rt for 20 h, quenched water, and extracted with EtOAc. The collected organic layer was washed with water and brine, dried over $Na_2SO_4$, filtered, and concentrated. Purification of the residue on silica gel column provided compound (91-2) (34 mg, 72% yield). ESI-MS m/z=548.21 $[M-H]^-$.

Step 3

To a mixture of compound (91-2) (34 mg, 0.062 mmol) and $Et_3N$ (86 μl, 0.619 mmol) in DCM (1 mL) at 0° C. was added TFAA (44 μl, 0.31 mmol). The mixture was stirred at rt for 30 min, quenched with cold sat. $NaHCO_3$, and extracted with EtOAc. The collected organic layer was washed with 1 N HCl, sat. $NaHCO_3$, brine, dried over $Na_2SO_4$, filtered, and concentrated. Purification of the residue on silica gel chromatography with 0-40% acetone/cyclohexane provided Example 91 (17 mg, 52% yield). ESI-MS m/z=530.20 $[M-H]^-$. $^1H$ NMR (400 MHz, Acetone-$d_6$) δ 10.65 (s, 1H), 9.51 (s, 1H), 6.97-6.83 (m, 3H), 6.81-6.72 (m, 2H), 6.67 (t, J=7.6 Hz, 1H), 6.60 (td, J=10.3, 2.1 Hz, 1H), 5.28 (t, J=7.4 Hz, 1H), 5.05 (t, J=8.2 Hz, 1H), 4.08 (d, J=10.7 Hz, 1H), 3.82 (d, J=10.6 Hz, 1H), 3.28 (s, 3H), 2.69 (s, 1H), 2.67-2.48 (m, 2H), 2.22 (hept, J=7.7 Hz, 1H), 1.89 (d, J=7.4 Hz, 3H), 1.74-1.53 (m, 4H).

The following examples were prepared employing similar protocol as described above.

| Example | Structure | MS | NMR |
|---|---|---|---|
| 92 | 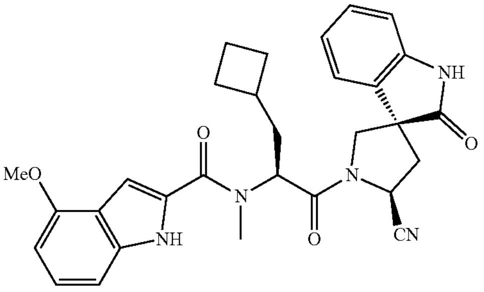 [SMILES: COc1cccc2[nH]c(C(=O)N(C)[C@@H](CC3CCC3)C(=O)N3C[C@]4(C[C@H]3C#N)C(=O)Nc3ccccc34)cc12] | $[M-H]^-$ 524.23 | $^1$H NMR (400 MHz, Acetone-$d_6$) δ 10.25 (s, 1H), 9.50 (s, 1H), 7.05-6.97 (m, 1H), 6.96-6.85 (m, 3H), 6.75 (dd, J = 4.9, 2.7 Hz, 2H), 6.68 (t, J = 7.5 Hz, 1H), 6.43-6.36 (m, 1H), 5.28 (t, J = 7.5 Hz, 1H), 5.04 (t, J = 8.1 Hz, 1H), 4.09 (d, J = 10.6 Hz, 1H), 3.83 (d, J = 9.9 Hz, 4H), 3.28 (s, 3H), 2.69 (s, 1H), 2.60 (ddd, J = 13.3, 8.6, 1.0 Hz, 1H), 2.53 (dd, J = 13.3, 7.6 Hz, 1H), 2.22 (dt, J = 15.0, 7.7 Hz, 1H), 1.89 (d, J = 7.6 Hz, 2H), 1.89 (s, 1H), 1.74-1.63 (m, 1H), 1.66-1.53 (m, 3H). |
| 93 | 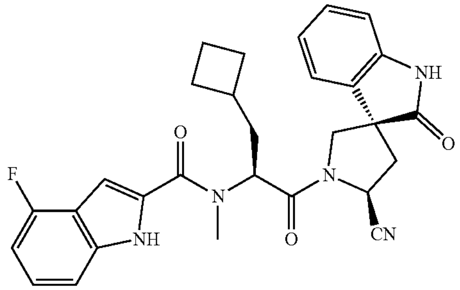 [SMILES: CN(C(=O)c1cc2c(F)cccc2[nH]1)[C@@H](CC1CCC1)C(=O)N1C[C@]2(C[C@H]1C#N)C(=O)Nc1ccccc12] | $[M-H]^-$ 512.18 | $^1$H NMR (400 MHz, Acetone-$d_6$) δ 10.72 (s, 1H), 9.66 (s, 1H), 7.33 (d, J = 8.3 Hz, 1H), 7.21 (td, J = 8.0, 5.2 Hz, 1H), 7.04 (d, J = 7.6 Hz, 2H), 6.94-6.87 (m, 2H), 6.87-6.76 (m, 2H), 5.44 (t, J = 7.5 Hz, 1H), 5.21 (t, J = 8.2 Hz, 1H), 4.22 (d, J = 10.6 Hz, 1H), 3.98 (d, J = 10.6 Hz, 1H), 3.44 (s, 3H), 2.76 (ddd, J = 13.3, 8.6, 1.0 Hz, 1H), 2.68 (dd, J = 13.3, 7.8 Hz, 1H), 2.38 (p, J = 7.7 Hz, 1H), 2.04 (m, 2H), 2.03 (s, 1H), 1.98 (s, 1H), 1.89-1.68 (m, 4H). |
| 94 | 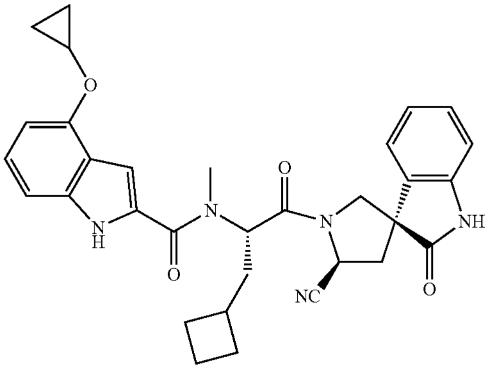 [SMILES: CN(C(=O)c1cc2c(OC3CC3)cccc2[nH]1)[C@@H](CC1CCC1)C(=O)N1C[C@]2(C[C@H]1C#N)C(=O)Nc1ccccc12] | $[M+Na]^+$ 574.25 | |
| 95 | 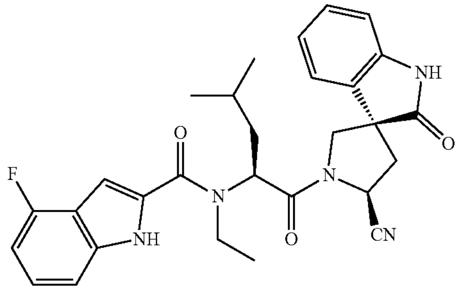 [SMILES: CCN(C(=O)c1cc2c(F)cccc2[nH]1)[C@@H](CC(C)C)C(=O)N1C[C@]2(C[C@H]1C#N)C(=O)Nc1ccccc12] | $[M-H]^-$ 514.22 | |
| 369 | 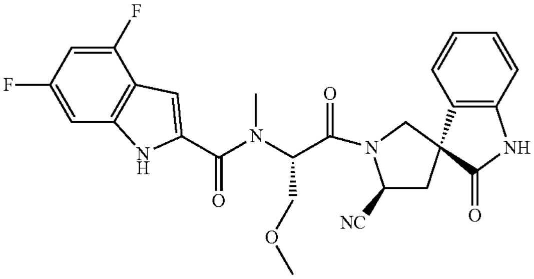 [SMILES: COC[C@@H](C(=O)N1C[C@]2(C[C@H]1C#N)C(=O)Nc1ccccc12)N(C)C(=O)c1cc2c(F)cc(F)cc2[nH]1] | 509.93 (M − H)− | |

-continued

| Example | Structure | MS | NMR |
|---|---|---|---|
| 370 | 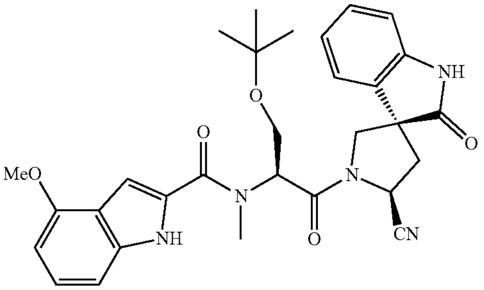 | [M + Na] 566.2 | |
| 371 | 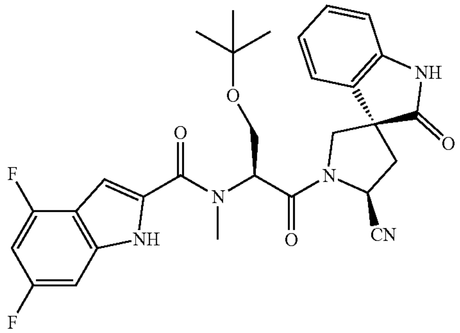 [SMILES: CN(C(=O)c1cc2c(F)cc(F)cc2[nH]1)[C@@H](COC(C)(C)C)C(=O)N1C[C@]2(C[C@H]1C#N)C(=O)Nc1ccccc12] | [M + H] 549.9 | $^1$H NMR (400 MHz, Methanol-$d_4$) δ 7.09-6.89 (m, 2H), 6.89-6.74 (m, 3H), 6.57 (td, J = 10.2, 2.1 Hz, 1H), 5.23 (s, 1H), 5.08 (t, J = 8.0 Hz, 1H), 4.10 (s, 1H), 4.00-3.72 (m, 3H), 3.38 (s, 3H), 2.72-2.52 (m, 2H), 1.17 (d, J = 1.9 Hz, 9H). |
| 372 | 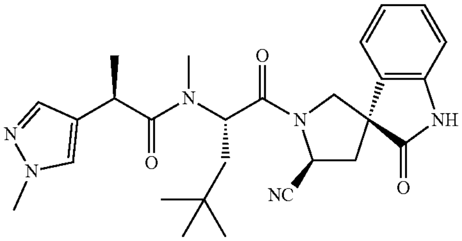 | [M − H] 489.3 | $^1$HNMR (400 MHz, Acetone-d6) δ 9.77 (s, 1H), 7.33 (d, J = 0.8 Hz, 1H), 7.30 (dd, J = 7.7, 1.3 Hz, 1H), 7.18 (d, J = 0.8 Hz, 1H), 7.11 (td, J = 7.6, 1.1 Hz, 1H), 7.03 (d, J = 7.8 Hz, 1H), 6.95 (d, J = 7.4 Hz, 1H), 5.55 (dd, J = 7.4, 5.0 Hz, 1H), 5.20 (t, J = 8.6 Hz, 1H), 4.28 (dd, J = 10.7, 1.4 Hz, 1H), 3.89 (d, J = 10.7 Hz, 1H), 3 .78 (s, 3H), 3 .64 (q, J = 6.8 Hz, 1H), 2.97 (s, 3H), 2.80-2.62 (m, 2H), 2.12-2.08 (m, 1H), 1.28 (dd, J = 14.0, 5.0 Hz, 1H), 0.86 (s, 9H), 0.74 (d, J = 6.8 Hz, 3H). |
| 373 | 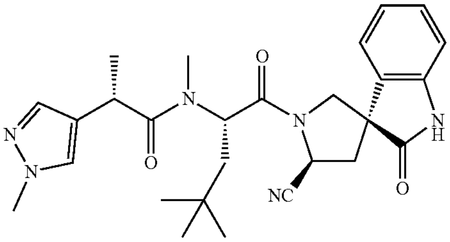 | [M + H] 549.9 | $^1$H NMR (400 MHz, Acetone-d6) δ 9.70 (s, 1H), 7.26 (td, J = 7.6, 1.3 Hz, 1H), 7.15 (s, 1H), 7.06 (s, 1H), 7.04-6.96 (m, 2H), 6.94 (dd, J = 7.8, 1.0 Hz, 1H), 5.53 (t, J = 6.3 Hz, 1H), 5.08 (t, J = 8.2 Hz, 1H), 4.08-4.00 (m, 1H), 3.97 (d, J = 10.5 Hz, 1H), 3.90 (q, J = 6.9 Hz, 1H), 3.77 (s, 3H), 3.12 (s, 3H), 2.73-2.58 (m, 2H), 2.09-2.07 (m, 1H), 1.58 (dd, J = 14.3, 6.2 Hz, 1H), 1.24 (d, J = 6.9 Hz, 3H), 0.97 (s, 9H). |
| 374 | 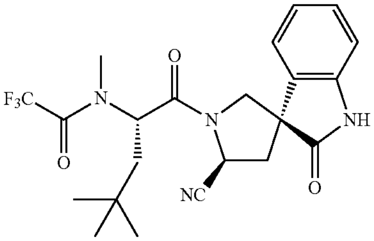 [SMILES: CN(C(=O)C(F)(F)F)[C@@H](CC(C)(C)C)C(=O)N1C[C@]2(C[C@H]1C#N)C(=O)Nc1ccccc12] | [M − H] 449.3 | 1H NMR (400 MHz, Acetone-d6) δ 9.72 (s, 1H), 7.28 (ddd, J = 7.8, 6.5, 2.6 Hz, 1H), 7.01 (ddd, J = 7.7, 3.9, 1.0 Hz, 3H), 5.38 (t, J = 6.3 Hz, 1H), 5.20 (t, J = 8.3 Hz, 1H), 4.06 (s, 2H), 2.78 (d, J = 4.7 Hz, 1H), 2.75 (s, 3H), 2.69 (dd, J = 13.3, 3807.9 Hz, 1H), 2.17 (dd, J = 14.4, 6.6 Hz, 1H), 1.73 (dd, J = 14.4, 6.1 Hz, 1H), 0.98 (s, 9H). |

-continued
| Example | Structure | MS | NMR |
|---|---|---|---|
| 375 | 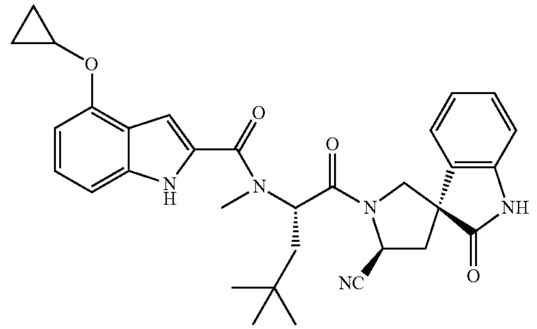 [SMILES: CN(C(=O)c1cc2c(OC3CC3)cccc2[nH]1)[C@@H](CC(C)(C)C)C(=O)N1C[C@]2(C[C@H]1C#N)C(=O)Nc1ccccc12] | 552.09 [M − H]⁻ | |
| 376 | 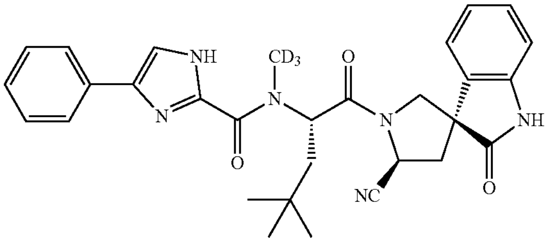 [SMILES: [2H]C([2H])([2H])N(C(=O)c1nc(-c2ccccc2)c[nH]1)[C@@H](CC(C)(C)C)C(=O)N1C[C@]2(C[C@H]1C#N)C(=O)Nc1ccccc12] | 528.23 | |
| 377 | 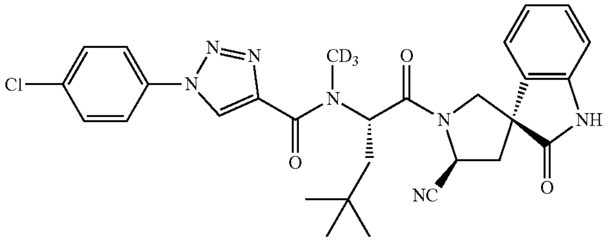 [SMILES: [2H]C([2H])([2H])N(C(=O)c1cn(-c2ccc(Cl)cc2)nn1)[C@@H](CC(C)(C)C)C(=O)N1C[C@]2(C[C@H]1C#N)C(=O)Nc1ccccc12] | 563.08 | |
| 378 | 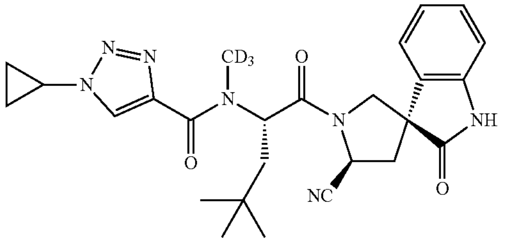 [SMILES: [2H]C([2H])([2H])N(C(=O)c1cn(C2CC2)nn1)[C@@H](CC(C)(C)C)C(=O)N1C[C@]2(C[C@H]1C#N)C(=O)Nc1ccccc12] | 491.36 [M − H]⁻ | |
| 379 | 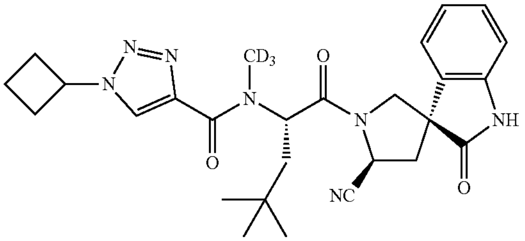 [SMILES: [2H]C([2H])([2H])N(C(=O)c1cn(C2CCC2)nn1)[C@@H](CC(C)(C)C)C(=O)N1C[C@]2(C[C@H]1C#N)C(=O)Nc1ccccc12] | 505.27 [M − H]⁻ | |
| 380 | 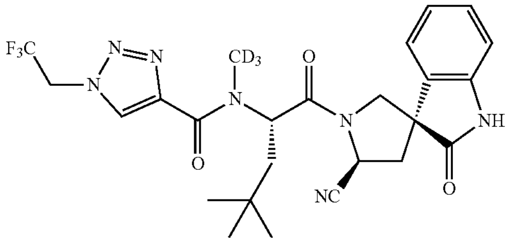 [SMILES: [2H]C([2H])([2H])N(C(=O)c1cn(CC(F)(F)F)nn1)[C@@H](CC(C)(C)C)C(=O)N1C[C@]2(C[C@H]1C#N)C(=O)Nc1ccccc12] | 533.22 [M − H]⁻ | |

-continued
| Example | Structure | MS | NMR |
|---|---|---|---|
| 381 | 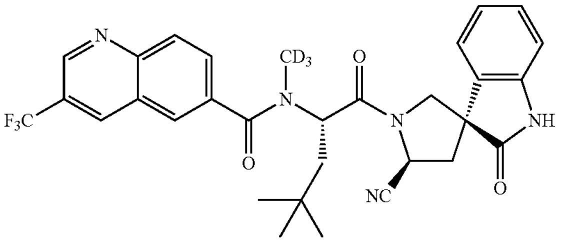 [SMILES: [2H]C([2H])([2H])N(C(=O)c1ccc2ncc(C(F)(F)F)cc2c1)[C@@H](CC(C)(C)C)C(=O)N1C[C@]2(C[C@H]1C#N)C(=O)Nc1ccccc12] | 581.47 | |
| 382 | 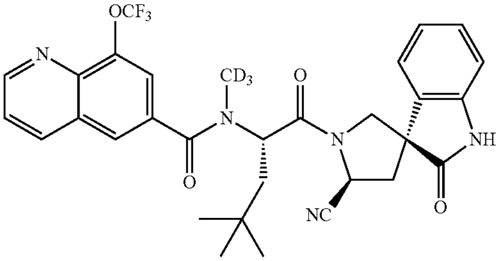 [SMILES: [2H]C([2H])([2H])N(C(=O)c1cc(OC(F)(F)F)c2ncccc2c1)[C@@H](CC(C)(C)C)C(=O)N1C[C@]2(C[C@H]1C#N)C(=O)Nc1ccccc12] | 597.45 | |
| 383 | 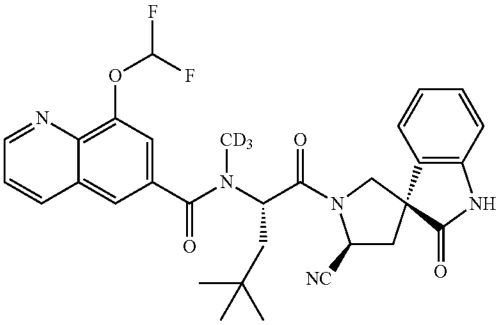 [SMILES: [2H]C([2H])([2H])N(C(=O)c1cc(OC(F)F)c2ncccc2c1)[C@@H](CC(C)(C)C)C(=O)N1C[C@]2(C[C@H]1C#N)C(=O)Nc1ccccc12] | 579.46 | |
| 384 | 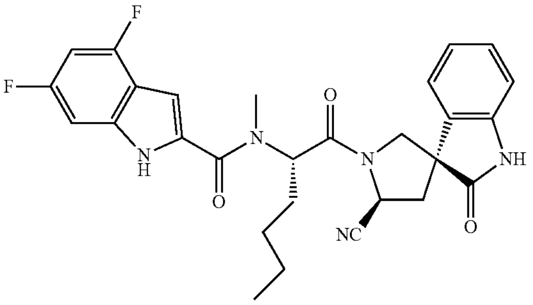 [SMILES: CCCC[C@@H](C(=O)N1C[C@]2(C[C@H]1C#N)C(=O)Nc1ccccc12)N(C)C(=O)c1cc2c(F)cc(F)cc2[nH]1] | 518.2 (M − H) | |
| 385 | 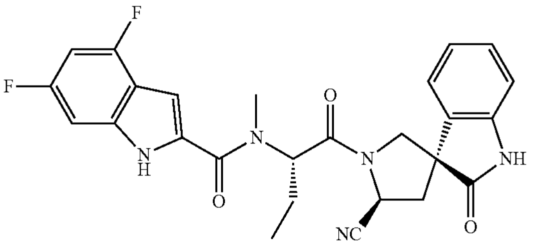 [SMILES: CC[C@@H](C(=O)N1C[C@]2(C[C@H]1C#N)C(=O)Nc1ccccc12)N(C)C(=O)c1cc2c(F)cc(F)cc2[nH]1] | 490.2 (M − H) | |

-continued
| Example | Structure | MS | NMR |
|---|---|---|---|
| 386 | 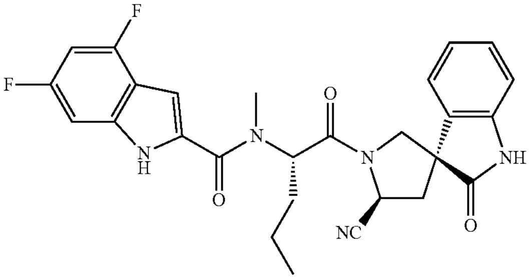 | 504.19 (M − H) | |
| 387 | 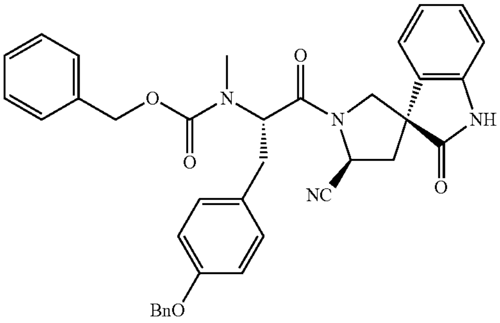 [SMILES: CN(C(=O)OCc1ccccc1)[C@@H](Cc1ccc(OCc2ccccc2)cc1)C(=O)N1C[C@]2(C[C@H]1C#N)C(=O)Nc1ccccc12] | 613.01 (M − H)− | |
| 388 | 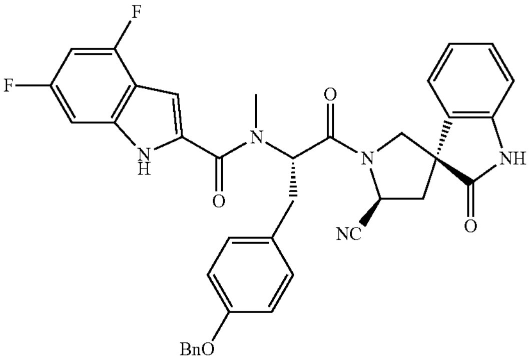 [SMILES: CN(C(=O)c1cc2c(F)cc(F)cc2[nH]1)[C@@H](Cc1ccc(OCc2ccccc2)cc1)C(=O)N1C[C@]2(C[C@H]1C#N)C(=O)Nc1ccccc12] | 567.97 (M − H)− | |
| 389 | 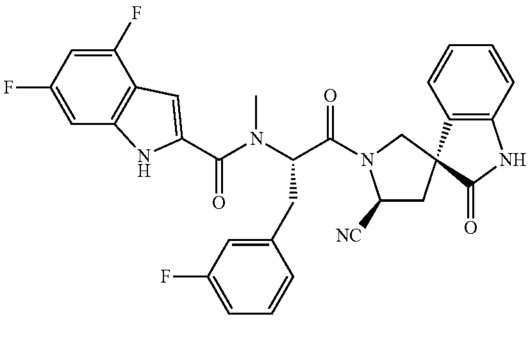 [SMILES: CN(C(=O)c1cc2c(F)cc(F)cc2[nH]1)[C@@H](Cc1cccc(F)c1)C(=O)N1C[C@]2(C[C@H]1C#N)C(=O)Nc1ccccc12] | 570.20 (M − H)− | |

-continued
| Example | Structure | MS | NMR |
|---|---|---|---|
| 390 | 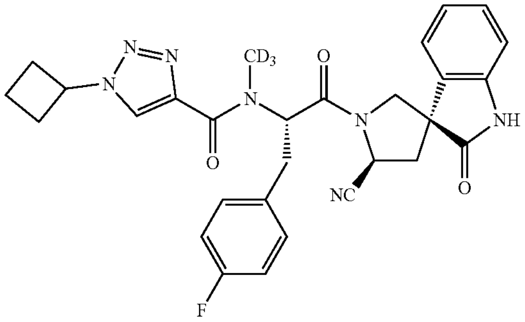 [SMILES: [2H]C([2H])([2H])N(C(=O)c1cn(C2CCC2)nn1)[C@@H](Cc1ccc(F)cc1)C(=O)N1C[C@]2(C[C@H]1C#N)C(=O)Nc1ccccc12] | 543.22 (M − H)− | |
| 391 | 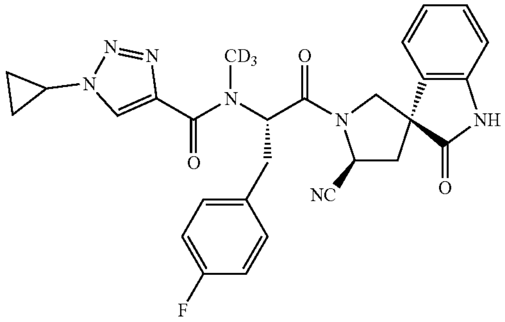 [SMILES: [2H]C([2H])([2H])N(C(=O)c1cn(C2CC2)nn1)[C@@H](Cc1ccc(F)cc1)C(=O)N1C[C@]2(C[C@H]1C#N)C(=O)Nc1ccccc12] | 529.00 (M − H)− | |
| 392 | 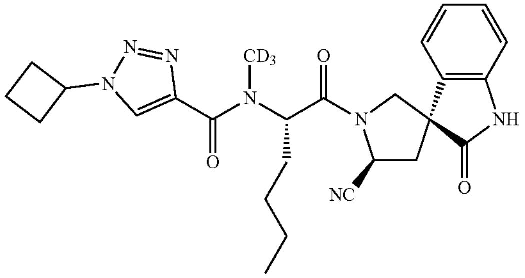 [SMILES: [2H]C([2H])([2H])N(C(=O)c1cn(C2CCC2)nn1)[C@@H](CCCC)C(=O)N1C[C@]2(C[C@H]1C#N)C(=O)Nc1ccccc12] | 491.27 (M − H)− | |
| 393 | 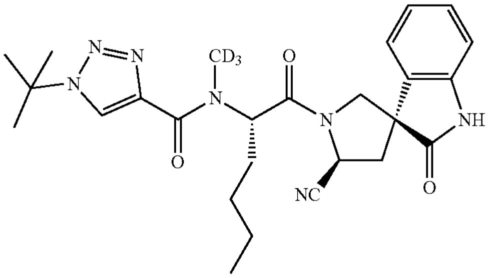 [SMILES: [2H]C([2H])([2H])N(C(=O)c1cn(C(C)(C)C)nn1)[C@@H](CCCC)C(=O)N1C[C@]2(C[C@H]1C#N)C(=O)Nc1ccccc12] | 493.28 (M − H)− | $^1$H NMR (500 MHz, Acetone-$d_6$) δ 9.67 (d, J = 8.8 Hz, 1H), 8.01 (s, 1H), 7.13 (td, J = 7.7, 1.2 Hz, 1H), 7.01-6.93 (m, 2H), 6.80 (td, J = 7.6, 1.0 Hz, 1H), 5.45 (t, J = 7.6 Hz, 1H), 5.23-5.16 (m, 1H), 4.35 (dd, J = 10.7, 1.2 Hz, 1H), 3.96 (dd, J = 26.7, 10.5 Hz, 1H), 2.79-2.62 (m, 2H), 2.03-1.89 (m, 2H), 1.70 (s, 6H), 1.62 (s, 3H), 1.43 (d, J = 14.8 Hz, 2H), 1.40-1.28 (m, 2H), 0.89 (dt, J = 22.7, 7.1 Hz, 3H). |
| 394 | 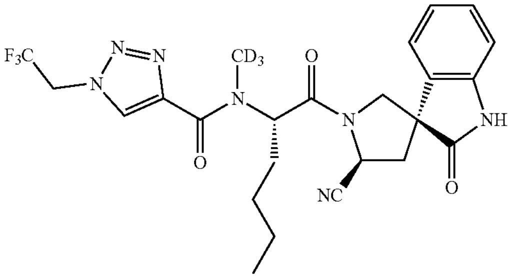 | 518.2 (M − H)− | |

-continued
| Example | Structure | MS | NMR |
|---|---|---|---|
| 395 | 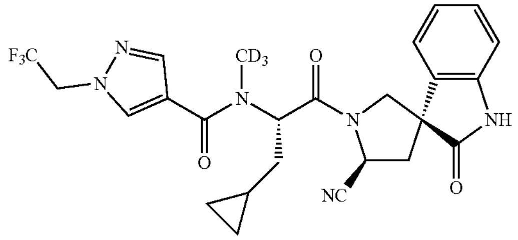 [SMILES: [2H]C([2H])([2H])N(C(=O)c1cnn(CC(F)(F)F)c1)[C@@H](CC1CC1)C(=O)N1C[C@]2(C[C@H]1C#N)C(=O)Nc1ccccc12] | 516.2 (M − H)− | |
| 396 | 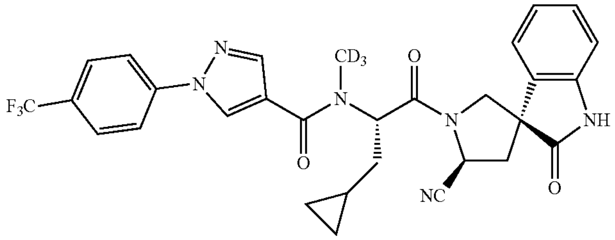 [SMILES: [2H]C([2H])([2H])N(C(=O)c1cnn(-c2ccc(C(F)(F)F)cc2)c1)[C@@H](CC1CC1)C(=O)N1C[C@]2(C[C@H]1C#N)C(=O)Nc1ccccc12] | 578.22 (M − H)− | |
| 397 | 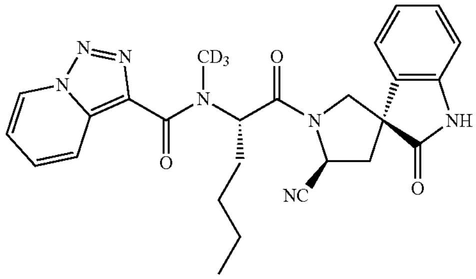 [SMILES: [2H]C([2H])([2H])N(C(=O)c1nnn2ccccc12)[C@@H](CCCC)C(=O)N1C[C@]2(C[C@H]1C#N)C(=O)Nc1ccccc12] | 487.2 (M − H)− | |
| 398 | 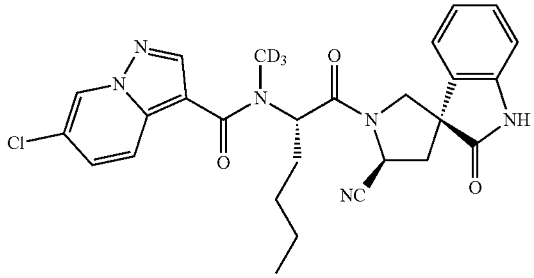 [SMILES: [2H]C([2H])([2H])N(C(=O)c1cnn2cc(Cl)ccc12)[C@@H](CCCC)C(=O)N1C[C@]2(C[C@H]1C#N)C(=O)Nc1ccccc12] | 520.2, 552.2 (M − H)− | |
| 399 | 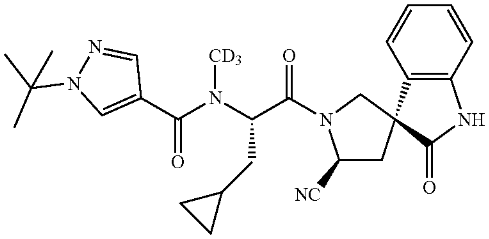 [SMILES: [2H]C([2H])([2H])N(C(=O)c1cnn(C(C)(C)C)c1)[C@@H](CC1CC1)C(=O)N1C[C@]2(C[C@H]1C#N)C(=O)Nc1ccccc12] | 490.27 (M − H)− | $^1$H NMR (400 MHz, Acetone-$d_6$) δ 9.51 (s, 1H), 7.63 (s, 1H), 7.40 (s, 1H), 7.02 (t, J = 7.7 Hz, 1H), 6.88-6.82 (m, 1H), 6.77 (dd, J = 14.0, 7.5 Hz, 2H), 5.27 (s, 1H), 4.99 (t, J = 8.3 Hz, 1H), 4.22 (d, J = 10.5 Hz, 1H), 3.77 (d, J = 10.7 Hz, 1H), 2.59-2.46 (m, 2H1.65-1.56 (m, 2H), 1.39 (s, 9H), 0.62-0.54 (m, 1H), 0.34-0.25 (m, 2H), 0.06-0.00 (m, 2H). |
| 400 | 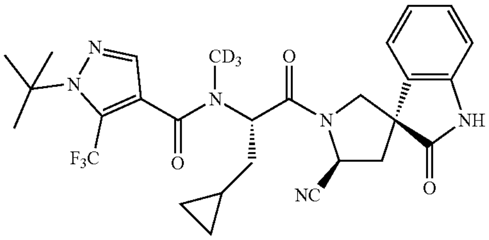 [SMILES: [2H]C([2H])([2H])N(C(=O)c1cnn(C(C)(C)C)c1C(F)(F)F)[C@@H](CC1CC1)C(=O)N1C[C@]2(C[C@H]1C#N)C(=O)Nc1ccccc12] | 558.25 (M − H)− | |

-continued
| Example | Structure | MS | NMR |
|---|---|---|---|
| 401 | 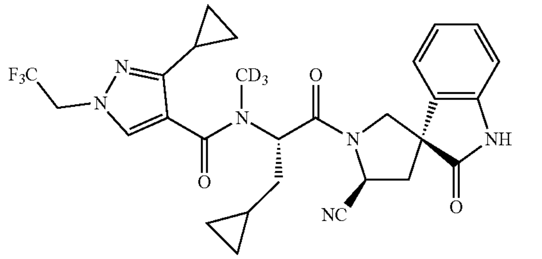 [SMILES: [2H]C([2H])([2H])N(C(=O)c1cn(CC(F)(F)F)nc1C1CC1)[C@@H](CC1CC1)C(=O)N1C[C@]2(C[C@H]1C#N)C(=O)Nc1ccccc12] | 556.24 (M − H)− | |
| 402 | 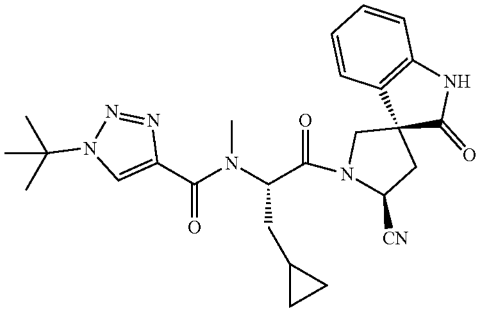 [SMILES: CN(C(=O)c1cn(C(C)(C)C)nn1)[C@@H](CC1CC1)C(=O)N1C[C@]2(C[C@H]1C#N)C(=O)Nc1ccccc12] | [M − 1] 488.40 | $^1$H NMR (400 MHz, Methanol-$d_4$) δ 8.20 (d, J = 39.5 Hz, 1H), 7.30-7.10 (m, 1H), 7.10-6.95 (m, 1H), 6.95-6.82 (m, 2H), 5.43 (t, J = 7.5 Hz, 1H), 5.18 (q, J = 7.5 Hz, 1H), 4.28 (d, J = 10.7 Hz, 1H), 4.10 (q, J = 7.1 Hz, 1H), 4.04-3.93 (m, 1H), 3.43 (s, 2H), 3.18 (s, 1H), 2.71-2.61 (m, 2H), 1.87 (t, J = 7.3 Hz, 1H), 1.72 (d, J = 5.4 Hz, 1H), 1.28-1.21 (m, 2H), 0.82-0.59 (m, 1H), 0.56-0.42 (m, 2H), 0.26-0.12 (m, 2H). |
| 403 | 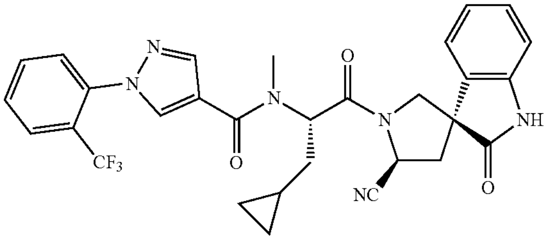 [SMILES: CN(C(=O)c1cnn(-c2ccccc2C(F)(F)F)c1)[C@@H](CC1CC1)C(=O)N1C[C@]2(C[C@H]1C#N)C(=O)Nc1ccccc12] | 575.28 (M − H)− | $^1$H NMR (400 MHz, Acetone-$d_6$) δ 9.50 (s, 1H), 7.86 (s, 1H), 7.80-7.74 (m, 1H), 7.70 (t, J = 7.6 Hz, 1H), 7.59 (dd, J = 14.9, 5.8 Hz, 2H), 7.45 (d, J = 8.0 Hz, 1H), 6.95 (td, J = 7.7, 1.3 Hz, 1H), 6.87 (ddd, J = 7.5, 1.4, 0.7 Hz, 1H), 6.74 (dd, J = 8.0, 7.0 Hz, 2H), 5.28 (t, J = 1.1 Hz, 1H), 5.00 (t, J = 8.3 Hz, 1H), 4.21 (d, J = 10.7 Hz, 1H), 3.78 (d, J = 10.6 Hz, 1H), 3.10 (s, 3H), 2.64-2.44 (m, 2H), 1.66 (dd, J = 15.1, 7.7 Hz, 2H), 0.64-0.54 (m, 1H), 0.33-0.23 (m, 2H), 0.05-0.00 (m, 2H). |
| 404 | 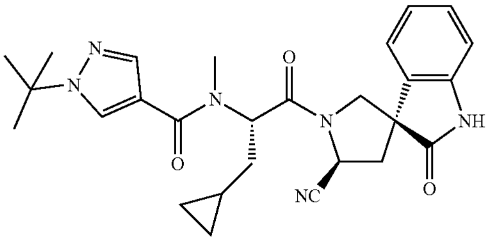 [SMILES: CN(C(=O)c1cnn(C(C)(C)C)c1)[C@@H](CC1CC1)C(=O)N1C[C@]2(C[C@H]1C#N)C(=O)Nc1ccccc12] | 487.25 (M − H)− | |
| 405 | 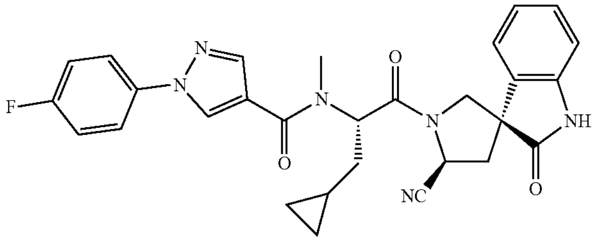 [SMILES: CN(C(=O)c1cnn(-c2ccc(F)cc2)c1)[C@@H](CC1CC1)C(=O)N1C[C@]2(C[C@H]1C#N)C(=O)Nc1ccccc12] | 525.21 (M − H)− | |

-continued
| Example | Structure | MS | NMR |
|---|---|---|---|
| 406 | 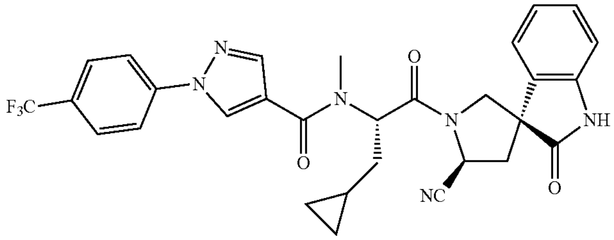 [SMILES: CN(C(=O)c1cnn(-c2ccc(C(F)(F)F)cc2)c1)[C@@H](CC1CC1)C(=O)N1C[C@]2(C[C@H]1C#N)C(=O)Nc1ccccc12] | 575.20 (M − H)− | |
| 407 | 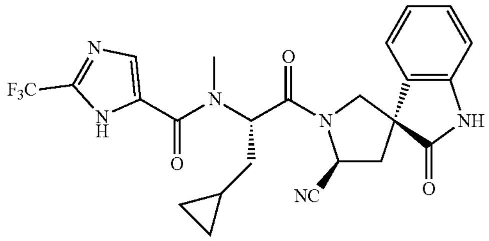 [SMILES: CN(C(=O)c1cnc(C(F)(F)F)[nH]1)[C@@H](CC1CC1)C(=O)N1C[C@]2(C[C@H]1C#N)C(=O)Nc1ccccc12] | 499.17 (M − H)− | |
| 408 | 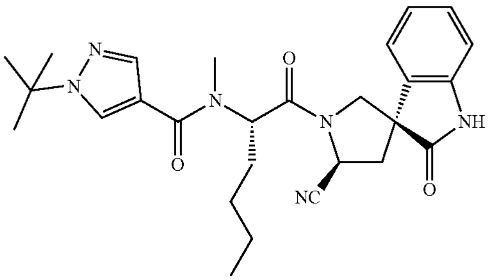 [SMILES: CCCC[C@@H](C(=O)N1C[C@]2(C[C@H]1C#N)C(=O)Nc1ccccc12)N(C)C(=O)c1cnn(C(C)(C)C)c1] | 489.26 (M − H)− | |
| 409 | 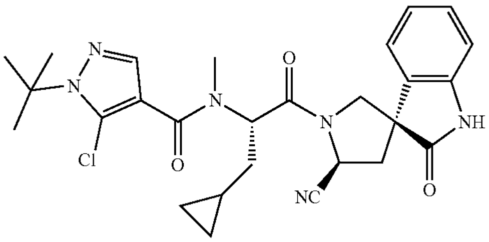 [SMILES: CN(C(=O)c1cnn(C(C)(C)C)c1Cl)[C@@H](CC1CC1)C(=O)N1C[C@]2(C[C@H]1C#N)C(=O)Nc1ccccc12] | 521.21 523.21 (M − H)− | |
| 410 | 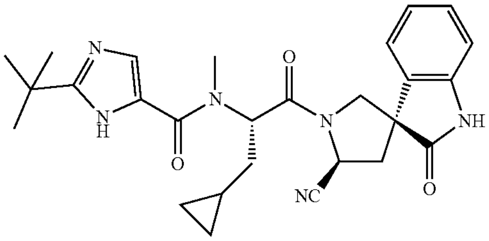 [SMILES: CN(C(=O)c1cnc(C(C)(C)C)[nH]1)[C@@H](CC1CC1)C(=O)N1C[C@]2(C[C@H]1C#N)C(=O)Nc1ccccc12] | 487.23 (M − H)− | |
| 411 | 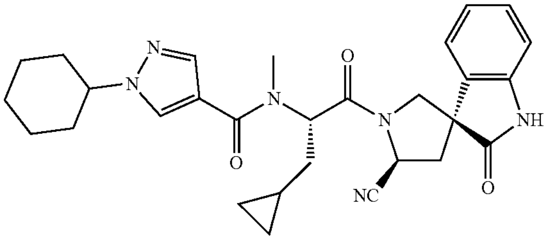 [SMILES: CN(C(=O)c1cnn(C2CCCCC2)c1)[C@@H](CC1CC1)C(=O)N1C[C@]2(C[C@H]1C#N)C(=O)Nc1ccccc12] | 513.26 (M − H)− | |

Example 96

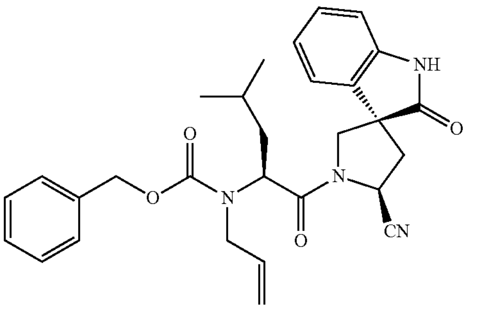

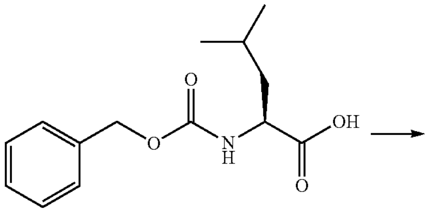

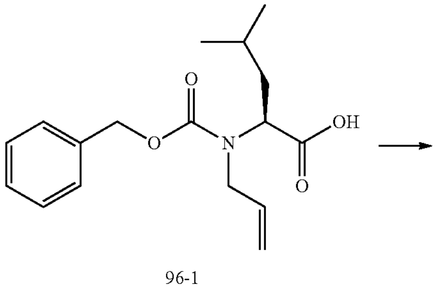

96-1

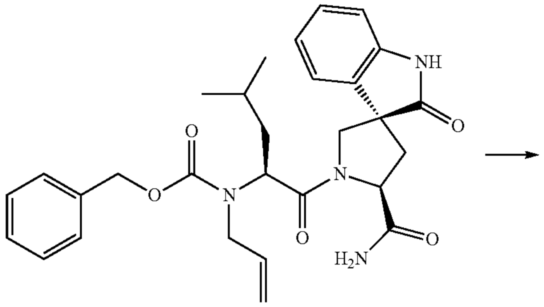

96-2

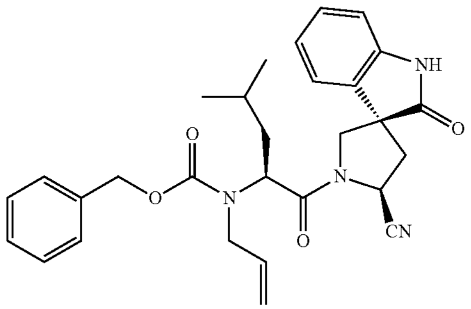

Example 96

Step 1

To a solution of ((benzyloxy)carbonyl)-L-leucine (1.56 g, 5.88 mmol) and 3-iodoprop-1-ene (0.807 mL, 8.82 mmol) in THF (30 mL) at 0° C. was added NaH (0.706 g, 17.64 mmol) in portions. The mixture was stirred at rt for 4 days, quenched with ice-water, and washed with MBTE twice. The aqueous layer was acidified with 1 N HCl to PH ~2, and extracted with EtOAc. The collected organic layer was washed with brine, dry over $Na_2SO_4$, filtered, and concentrated to afford compound (96-1) (1.15 g, 64.0% yield). ESI-MS m/z=304.12 $[M-H]^-$.

Step 2

To a mixture of compound (1-4) (221 mg, 0.826 mmol), compound (96-1) (265 mg, 0.868 mmol) and DIPEA (577 μl, 3.31 mmol) in DCM/DMF (0.8/0.8 mL) was added HATU (314 mg, 0.826 mmol). The resulting mixture was stirred at rt for 16 h, quenched with water, and extracted with EtOAc. The organic layer was washed with water, 1N HCl, sat $NaHCO_3$ and brine, dried over $Na_2SO_4$, filtered, and concentrated. Purification of the residue by silica gel chromatography with 0-10% MeOH/DCM provided compound (96-2) (262 mg, 61.1% yield). ESI-MS m/z=517.20 $[M-H]^-$.

Step 3

To a mixture of compound (96-2) (22 mg, 0.042 mmol) and $Et_3N$ (59.1 μl, 0.424 mmol) in DCM (1 mL) at 0° C. was added TFAA (30.0 μl. 212 mmol). The mixture was stirred at rt for 30 min, quenched with cold sat. $NaHCO_3$ solution, and extracted with EtOAc. The organic layer was washed with water, 1N HCl, sat $NaHCO_3$ and brine, dried over $Na_2SO_4$, filtered, and concentrated. Purification of the residue on silica gel chromatography with 0-50% acetone/cyclohexane provided Example 96 (20 mg, 94% yield). ESI-MS m/z=499.20 $[M-H]^-$.

Example 97

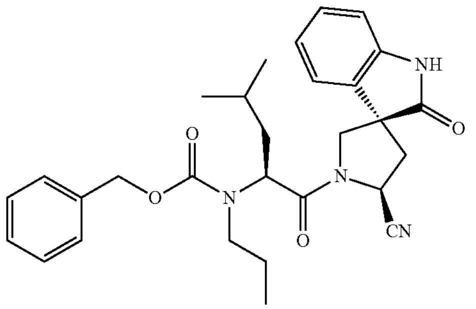

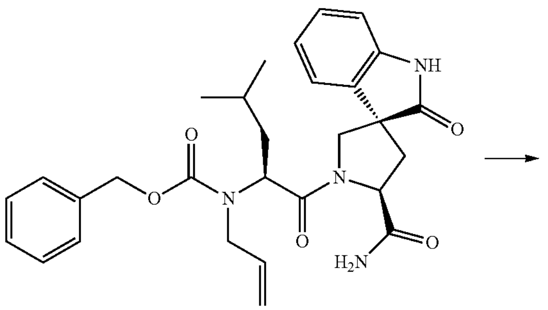

96-2

-continued

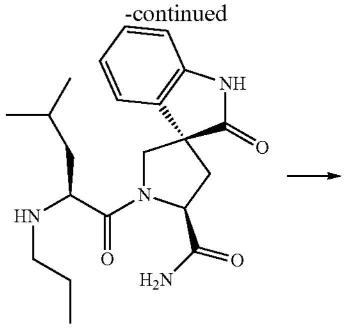

97-1

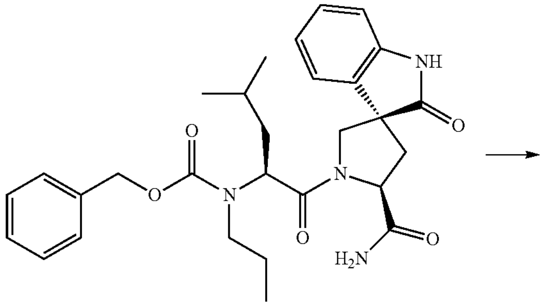

97-2

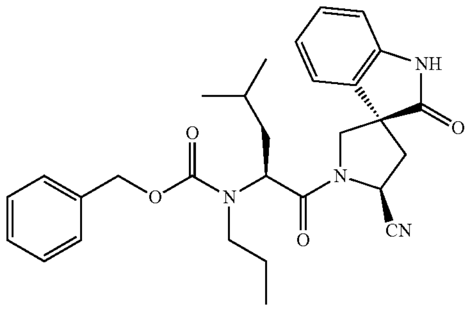

Example 97

Step 1

A mixture of compound (96-2) (105 mg, 0.202 mmol) and Pd—C (21.55 mg, 0.020 mmol) in MeOH (3 mL) was stirred under $H_2$ using a hydrogen balloon. After 1 h, the mixture was diluted with DCM, filtered through celite, and concentrated to give compound (97-1) (79 mg, 100%). ESI-MS m/z=385.19 $[M-H]^-$.

Step 2

To a mixture of compound (97-1) (0.039 g, 0.10 mmol) in DCM/DMF (0.5/0.5 mL) and $Et_3N$ (0.098 mL, 0.70 mmol) was added Cbz-Cl (0.042 mL, 0.30 mmol). The mixture was stirred at rt for 16 h, quenched with aqueous $NH_3$, and extracted with EtOAc. The organic layer was washed with water and brine, dried over $N_2SO_4$, filtered, and concentrated. Purification of the residue by silica gel chromatography with 0-10% MeOH/DCM provided (97-2) (10 mg, 19% yield). ESI-MS m/z=519.22 $[M-H]^-$.

Step 3

To a mixture compound (97-2) (10 mg, 0.019 mmol) and $Et_3N$ (53.5 μl, 0.384 mmol) in DCM (0.5 mL) was added TFAA (27.1 μl, 0.192 mmol) at 0° C. quenched with cold sat. $NaHCO_3$ solution, and extracted with EtOAc. The organic layer was washed with 1 N HCl, sat. $NaHCO_3$ solution and brine, dried over $Na_2SO_4$, filtered, and concentrated. Purification of the residue by silica gel chromatography with 0-50% acetone/cyclohexane provided Example 97 (7.0 mg, 72.5% yield) ESI-MS m/z=501.22 $[M-H]^-$.

Example 98

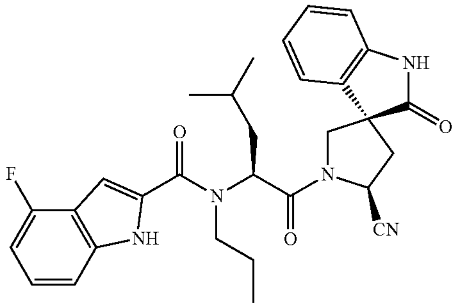

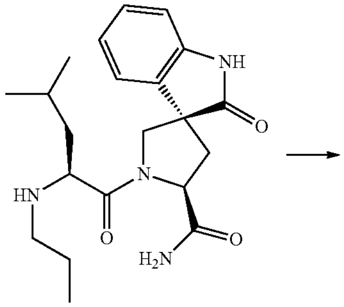

97-1

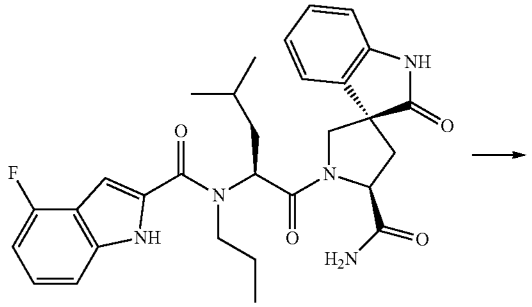

98-1

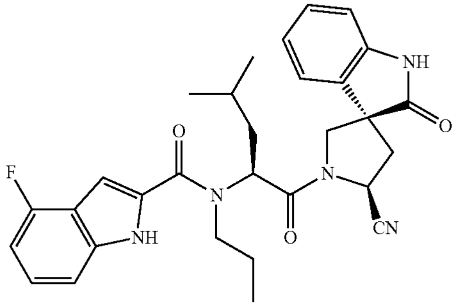

Example 98

Step 1

A mixture of 4-fluoro-1H-indole-2-carboxylic acid (0.054 g, 0.30 mmol) and 1-chloro-N,N,2-trimethylprop-1-en-1-amine (0.044 mL, 0.330 mmol) in DCM (1 mL) was stirred at rt for 1 h. The resulting mixture was added to a solution of compound (97-1) and $Et_3N$ (0.108 mL, 0.85 mmol) in DCM/DMF (0.5/0.5 mL). The resulting mixture was stirred rt for 20 h, quenched aqueous $NH_3$, and extracted with EtOAc. The organic layer was washed with water and brine, dried over $Na_2SO_4$, filtered, and concentrated. Purification of the residue by silica gel chromatography with 0-10% MeOH/DCM provided compound (98-1)(40 mg, 69% yield). ESI-MS m/z=546.23 [M−H]⁻.

Step 2

To a mixture of compound (98-1) (40 mg, 0.073 mmol) and $Et_3N$ (10.18 µl, 0.073 mmol) in DCM (1 mL) at 0° C. was added TFAA (10.32 µl, 0.073 mmol). The mixture was stirred at rt for 30 min, quenched with cold sat. $NaHCO_3$, and extracted with EtOAc. The organic layer was washed with 1 N HCl, sat. $NaHCO_3$ and brine, dried over $Na_2SO_4$, filtered, and concentrated. Purification of the residue by silica gel chromatography with 0-50% acetone/cyclohexane provided Example 98 (35 mg, 90% yield) ESI-MS m/z=528.20 [M−H]⁻.

The following example was prepared employing similar protocol as described above.

| Example | Structure | MS |
|---|---|---|
| 99 | 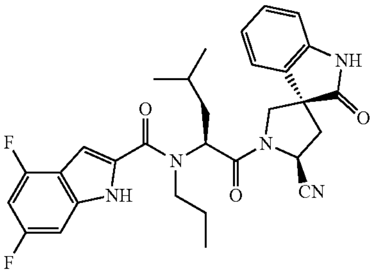 [SMILES: CCCN(C(=O)c1cc2c(F)cc(F)cc2[nH]1)[C@@H](CC(C)C)C(=O)N1C[C@]2(C[C@H]1C#N)C(=O)Nc1ccccc12] | [M - H] 546.23 |

Example 100

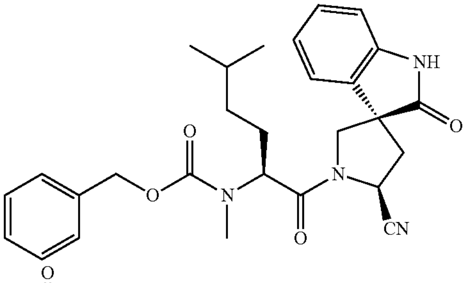

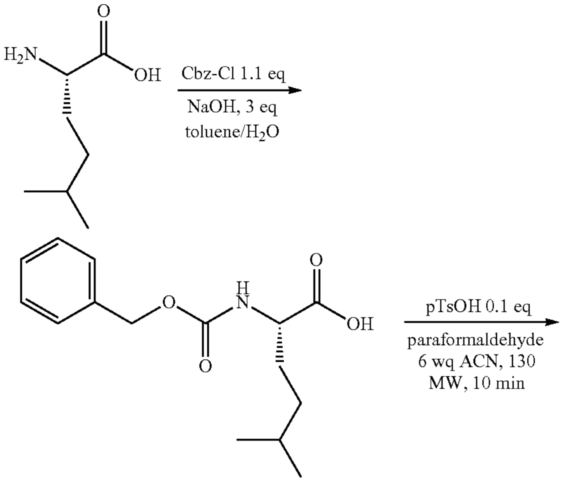

-continued

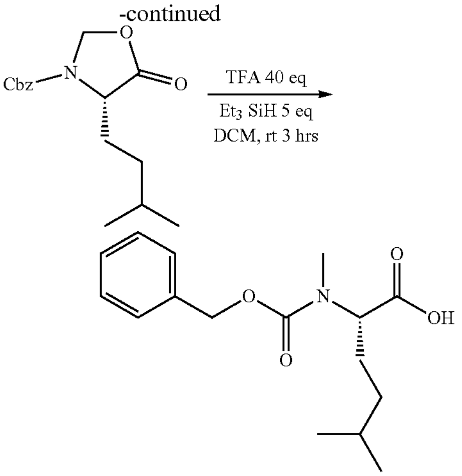

Synthesis of (S)-2-(((benzyloxy)carbonyl)(methyl) amino)-5-methylhexanoic Acid

Step 1:

To a mixture of (S)-2-amino-5-methylhexanoic acid (0.9 g, 6.20 mmol) in toluene/water (12.4 mL/3 mL) at 0° C. was added 2N NaOH (9.30 mL, 18.59 mmol), followed by addition of Cbz-Cl (0.973 mL, 6.82 mmol). After stirring at rt for 2 hrs, the two layers were separated, and the aqueous layer was washed with MBTE (2×), and then acidified to pH ~2 with 1 N HCl solution at 0° C. The mixture was extracted with EtOAc (3×). The combined organics were washed with brine, dried over $Na_2SO_4$, and concentrated to give (S)-2-(((benzyloxy)carbonyl)amino)-5-methylhexanoic acid (1.42 g, 5.08 mmol, 82% yield), which was used in the next step without further purification. LC-MS, ES−: 277.77 [M−1].

Step 2:

To a solution of (S)-2-(((benzyloxy)carbonyl)amino)-5-methylhexanoic acid (660 mg, 2.363 mmol) and paraformaldehyde (426 mg, 14.18 mmol)) in dry acetonitrile (11.8 mL) was added 4-methylbenzenesulfonic acid hydrate (44.9 mg, 0.236 mmol). The resulting mixture was heated under microwave at 130° C. for 10 min. After cooling to rt, the mixture was filtered through celite, concentrated, and chased with DCM to give the crude benzyl (S)-4-isopentyl-5-oxooxazolidine-3-carboxylate as a sticky oil, which was used in the next step without further purification.

Step 3:

To the crude benzyl (S)-4-isopentyl-5-oxooxazolidine-3-carboxylate from previous step was added DCM (24 mL), triethylsilane (1.89 mL, 11.81 mmol), and 2,2,2-trifluoroacetic acid (7.28 mL, 95 mmol). The mixture was stirred at rt for 2 hrs, concentrated, and chased with DCM (3×). The residue was basified with 1N NaOH at 0° C. to pH ~10, and washed with EtOAc (lx) and MBTE (lx). The aqueous layer was acidified to pH ~2 with 1N HCl, and extracted with EtOAc (2×). The combined organics were washed with brine, dried, and concentrated to give (S)-2-(((benzyloxy) carbonyl)(methyl)amino)-5-methylhexanoic acid (715 mg, 92% yield for 2 steps). 1H NMR (400 MHz, DMSO-d6) δ 12.56 (s, 1H), 7.41-7.27 (m, 5H), 5.17-5.00 (m, 2H), 4.48 (ddd, J=27.4, 11.1, 4.7 Hz, 1H), 2.81 (s, 2H, N-Me rotamer), 2.78 (s, 1H, N-Me rotamer), 1.84 (tq, J=9.6, 4.6, 4.1 Hz, 1H), 1.70 (ddd, J=14.4, 9.6, 4.5 Hz, 1H), 1.52 (dt, J=12.8, 6.5 Hz, 1H), 1.21-0.99 (m, 2H), 0.84 (dd, J=9.2, 6.6 Hz, 6H).

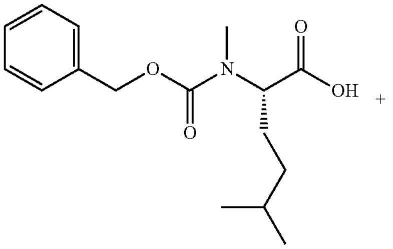

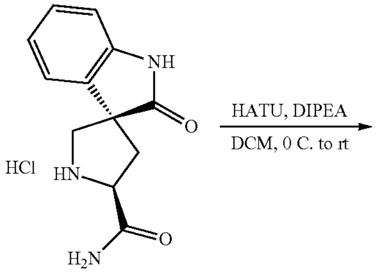

1-4

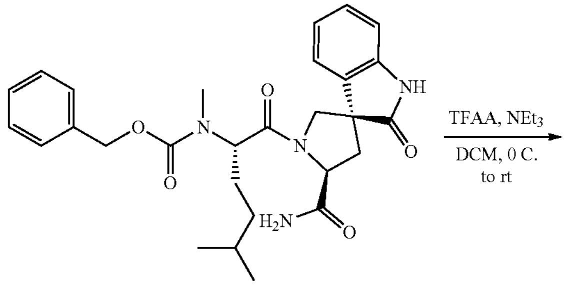

100-1

-continued

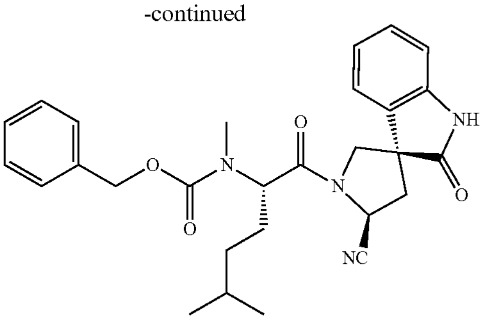

Synthesis of Example 100

Step 1:

To a mixture of (S)-2-(((benzyloxy)carbonyl)(methyl)amino)-5-methylhexanoic acid (300 mg, 1.023 mmol) and (1-4) (261 mg, 0.974 mmol) in dry $CH_2Cl_2$ (2.96 mL) at 0° C. was added DIPEA (510 µl, 2.92 mmol) and HATU (481 mg, 1.266 mmol). The resulting mixture was stirred at rt for 2 hrs. The mixture was diluted with DCM, washed with water (2×), brine, dried, and concentrated. Purification of the residue on silica gel chromatography with 0-10% MeOH/DCM provided benzyl ((S)-1-((3R,5'S)-5'-carbamoyl-2-oxospiro[indoline-3,3'-pyrrolidin]-1'-yl)-5-methyl-1-oxohexan-2-yl)(methyl)carbamate (100-1) (189 mg, 38% yield). LC-MS, ES−: 505.0 [M−1].

Step 2

To a mixture of compound (100-1) (31 mg, 0.061 mmol) and $Et_3N$ (85 µL, 0.612 mmol) in dry DCM (0.8 mL) at 0° C. was added TFAA (43.2 µl, 0.306 mmol). After stirring at rt for 1 h, the reaction mixture was diluted with DCM, washed with sat $NaHCO_3$, water, brine, dried and concentrated. Purification of the residue by silica gel chromatography with 0-40% acetone/cyclohexane provided Example 100 (25 mg, 84% yield). LC-MS, $ES^+$: 488.96 [M+1].

The following examples were prepared employing similar protocol as described above.

| Example | Structure | MS |
|---|---|---|
| 101 | 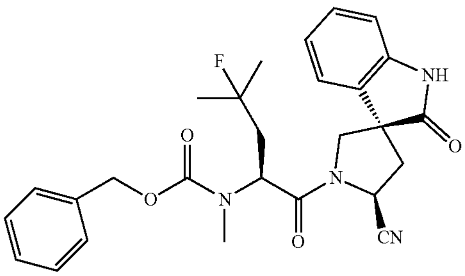 [SMILES: CN(C(=O)OCc1ccccc1)[C@@H](CC(C)(C)F)C(=O)N1C[C@]2(C[C@H]1C#N)C(=O)Nc1ccccc12] | $[M + Na]^+$ 515.20 |

-continued

| Example | Structure | MS |
|---|---|---|
| 102 | 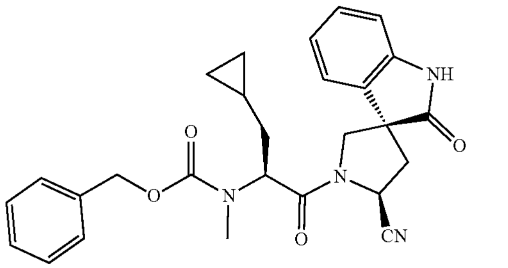 [SMILES: CN(C(=O)OCc1ccccc1)[C@@H](CC1CC1)C(=O)N1C[C@]2(C[C@H]1C#N)C(=O)Nc1ccccc12] | $[M + Na]^+$ 495.19 |
| 103 | 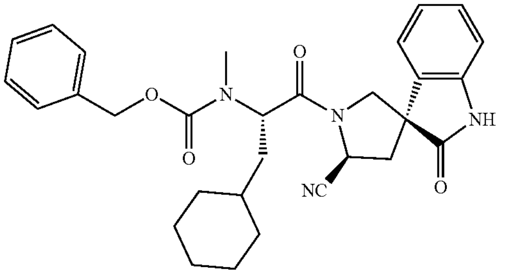 | $[M + H]^+$ 533.33 |

Example 104

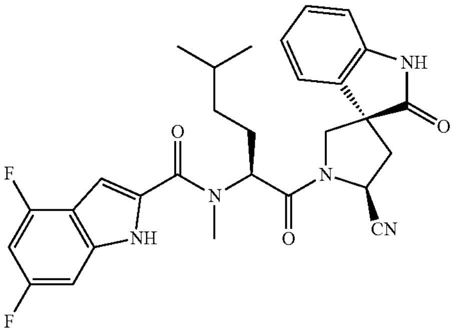

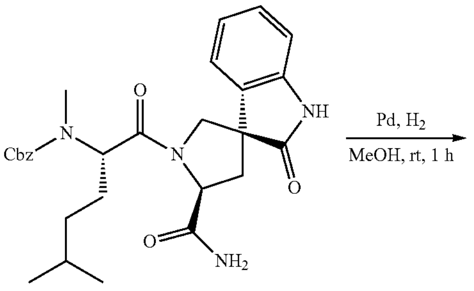

100-1

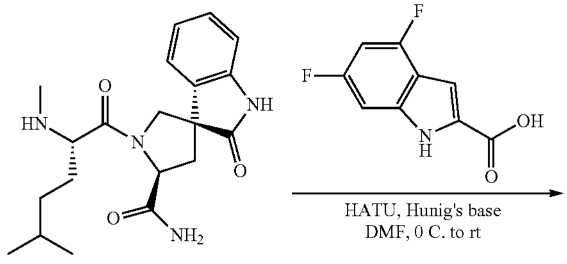

104-1

-continued

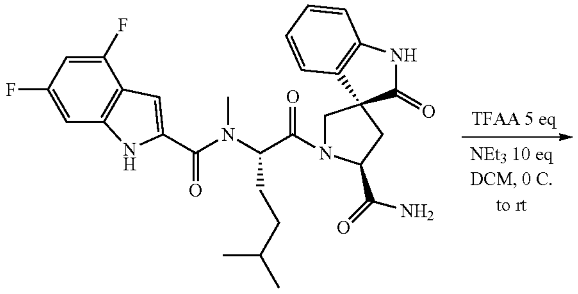

104-2

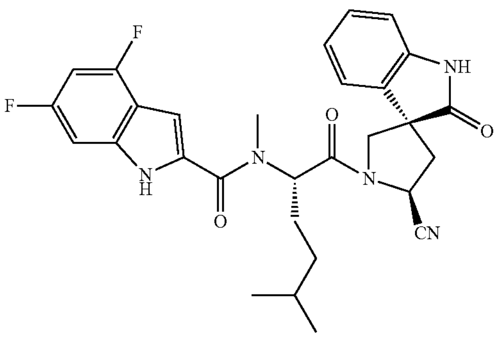

Example 104

Step 1:

A mixture of compound (100-1) (152 mg, 0.300 mmol) and 10% Pd—C (31.9 mg, 0.030 mmol) in MeOH (3.00 mL) was stirred at rt under a hydrogen balloon. After 1 h, the reaction mixture was filtered through celite, rinsed with MeOH, and concentrated to give the crude (3R,5'S)-1'-((S)-5-methyl-2-(methylamino)hexanoyl)-2-oxospiro[indoline-3,3'-pyrrolidine]-5'-carboxamide (104-1) (112 mg, 0.301 mmol, 100% yield), which was used in the next step directly. LC-MS, ES+: 372.99 $[M+H]^+$.

Step 2:

To a mixture of compound (104-1) (85 mg, 0.228 mmol) and 4,6-difluoro-1H-indole-2-carboxylic acid (47.2 mg, 0.240 mmol) in dry DMF (1.14 mL) at 0° C. were added Hunig's base (122 μL, 0.685 mmol) and HATU (113 mg, 0.297 mmol). The resulting mixture was then stirred at rt for 1 h, diluted with DCM, washed with water (2×) and brine. The organic layer was dried and concentrated. The crude product (104-2) was used in the next step without further purification. LC-MS, ES-: 550.2 $[M-H]^-$.

Step 3:

A mixture of crude (3R,5'S)-1'-((S)-2-(4,6-difluoro-N-methyl-1H-indole-2-carboxamido)-5-methylhexanoyl)-2-oxospiro[indoline-3,3'-pyrrolidine]-5'-carboxamide (104-2) (0.121 g, 0.22 mmol) and $Et_3N$ (0.307 mL, 2.20 mmol) in DCM (2.9 mL) at 0° C. was treated with TFAA (0.155 mL, 1.100 mmol). After stirring at rt for 30 min, the reaction mixture was diluted with DCM, washed with sat $NaHCO_3$, water and brine, dried, and concentrated. Purification of the residue by silica gel chromatography with 0-40% acetone/cyclohexane provided Example 104 (62 mg, 53% yield for 3 steps). LC-MS, ES-: 532.01 $[M-H]^-$. $^1H$ NMR (400 MHz, Acetone-d6) δ 10.84 (s, 1H), 9.69 (s, 1H), 7.12-6.99 (m, 3H), 6.97-6.93 (m, 1H), 6.90 (d, J=7.6 Hz, 1H), 6.86-6.78 (m, 1H), 6.74 (td, J=10.3, 2.1 Hz, 1H), 5.45 (dd, J=8.8, 6.4 Hz, 1H), 5.22 (t, J=8.2 Hz, 1H), 4.26 (d, J=10.7 Hz, 1H), 3.99 (d, J=10.7 Hz, 1H), 3.46 (s, 3H), 2.74-2.64 (m, 2H), 2.04-1.91.

The following examples were prepared employing similar protocol as described above.

| Example | Structure | MS | NMR |
|---|---|---|---|
| 105 | 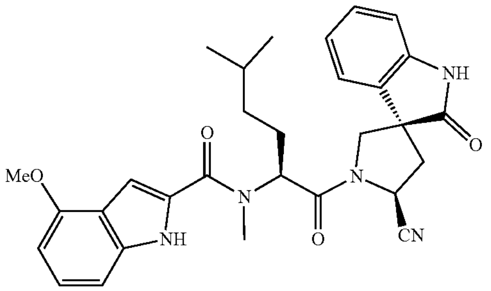 [SMILES: COc1cccc2[nH]c(C(=O)N(C)[C@@H](CCC(C)C)C(=O)N3C[C@]4(C[C@H]3C#N)C(=O)Nc3ccccc34)cc12] | $[M + H]^+$ 528.00 | |
| 106 | 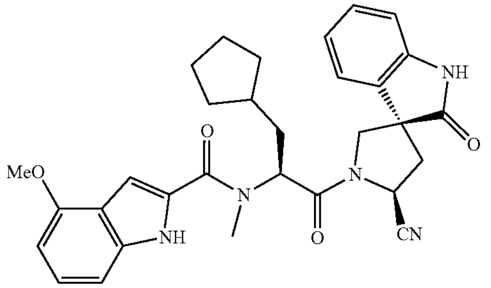 [SMILES: COc1cccc2[nH]c(C(=O)N(C)[C@@H](CC3CCCC3)C(=O)N3C[C@]4(C[C@H]3C#N)C(=O)Nc3ccccc34)cc12] | $[M + H]^+$ 539.97 | 1H NMR (400 MHz, Acetone-d6) δ 10.39 (s, 1H), 9.65 (s, 1H), 7.20-7.12 (m, 1H), 7.12-6.99 (m, 3H), 6.95-6.87 (m, 2H), 6.82 (t, J = 7.5 Hz, 1H), 6.54 (dd, J = 7.7, 0.7 Hz, 1H), 5.55 (dd, J = 9.1, 5.7 Hz, 1H), 5.20 (t, J = 8.2 Hz, 1H), 4.29 (d, J = 10.7 Hz, 1H), 3.99 (d, J = 10.6 Hz, 1H), 3.96 (s, 3H), 3.45 (s, 3H), 2.81-2.63 (m, 2H), 2.05-1.98 (m, 1H), 1.96-1.90 (m, 1H), 1.88-1.79 (m, 3H), 1.67-1.58 (m, 2H), 1.52-1.45 (m, 2H), 1.31-1.14 (m, 2H). |
| 107 | 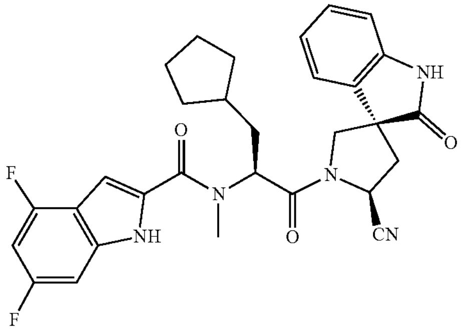 [SMILES: CN(C(=O)c1cc2c(F)cc(F)cc2[nH]1)[C@@H](CC1CCCC1)C(=O)N1C[C@]2(C[C@H]1C#N)C(=O)Nc1ccccc12] | $[M + H]^+$ 545.95 | 1H NMR (400 MHz, Acetone-d6) δ 10.80 (s, 1H), 9.67 (s, 1H), 7.08 (dd, J = 9.4, 2.0 Hz, 1H), 7.05-6.97 (m, 2H), 6.96 (s, 1H), 6.91 (d, J = 7.7 Hz, 1H), 6.80 (dd, J = 13.7, 6.1 Hz, 1H), 6.77-6.68 (m, 1H), 5.55 (dd, J = 9.1, 5.7 Hz, 1H), 5.21 (t, J = 8.3 Hz, 1H), 4.29 (d, J = 10.7 Hz, 1H), 3.98 (d, J = 10.6 Hz, 1H), 3.46 (s, 3H), 2.75-2.64 (m, 2H), 2.06-1.99 (m, 1H), 1.99-1.89 (m, 1H), 1.83 (p, J = 6.3 Hz, 3H), 1.63 (q, J = 6.9, 5.8 Hz, 2H), 1.51 (dt, J = 14.5, 5.3 Hz, 2H), 1.32-1.11 (m, 2H). |
| 108 | 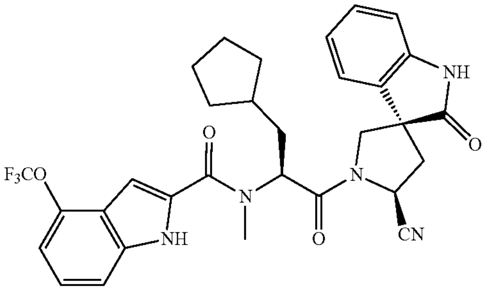 [SMILES: CN(C(=O)c1cc2c(OC(F)(F)F)cccc2[nH]1)[C@@H](CC1CCCC1)C(=O)N1C[C@]2(C[C@H]1C#N)C(=O)Nc1ccccc12] | $[M - H]^-$ 592.00 | 1H NMR (400 MHz, Acetone-d6) δ 10.82 (s, 1H), 9.65 (s, 1H), 7.50 (d, J = 8.3 Hz, 1H), 7.28 (t, J = 8.0 Hz, 1H), 7.07-6.93 (m, 4H), 6.87 (d, J = 7.7 Hz, 1H), 6.78 (t, J = 7.5 Hz, 1H), 5.54 (dd, J = 9.1, 5.9 Hz, 1H), 5.19 (t, J = 8.2 Hz, 1H), 4.25 (d, J = 10.7 Hz, 1H), 3.98 (d, J = 10.6 Hz, 1H), 2.72-2.62 (m, 2H), 1.99 (dd, J = 8.9, 5.1 Hz, 1H), 1.92 (dt, J = 13.6, 6.3 Hz, 1H), 1.86-1.76 (m, 3H), 1.64-1.56 (m, 2H), 1.53-1.43 (m, 2H), 1.27-1.16 (m, 2H). |

-continued

| Example | Structure | MS | NMR |
|---|---|---|---|
| 109 | 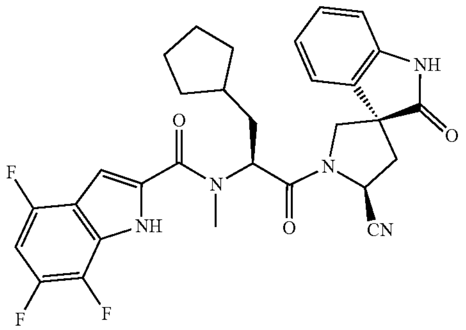 [SMILES: CN(C(=O)c1cc2c(F)cc(F)c(F)c2[nH]1)[C@@H](CC1CCCC1)C(=O)N1C[C@]2(C[C@H]1C#N)C(=O)Nc1ccccc12] | [M − H]⁻ 561.99 | 1H NMR (400 MHz, Acetone-d6) δ 11.10 (s, 1H), 9.60 (s, 1H), 6.98-6.91 (m, 2H), 6.84 (tt, J = 9.0, 4.0 Hz, 3H), 6.74 (t, J = 7.5 Hz, 1H), 5.45 (dd, J = 9.0, 5.8 Hz, 1H), 5.14 (t, J = 8.3 Hz, 1H), 4.17 (d, J = 10.7 Hz, 1H), 3.91 (d, J = 10.6 Hz, 1H), 3.36 (s, 3H), 2.65-2.55 (m, 2H), 1.97-1.91 (m, 1H), 1.91-1.83 (m, 1H), 1.80-1.72 (m, 3H), 1.59-1.51 (m, 2H), 1.49-1.38 (m, 2H), 1.24-1.09 (m, 2H). |
| 110 | 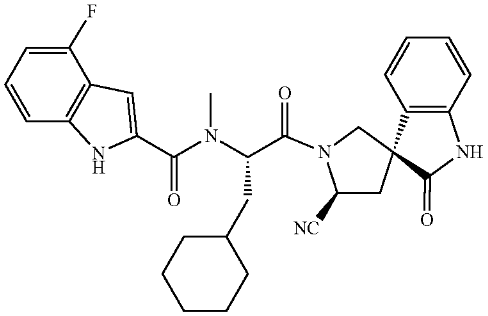 [SMILES: CN(C(=O)c1cc2c(F)cccc2[nH]1)[C@@H](CC1CCCCC1)C(=O)N1C[C@]2(C[C@H]1C#N)C(=O)Nc1ccccc12] | [M + Na]⁺ 564.20 | $^1$H NMR (400 MHz, Acetone-$d_6$) δ 10.73 (s, 1H), 9.67 (s, 1H), 7.33 (d, J = 8.2 Hz, 1H), 7.22 (td, J = 8.0, 5.2 Hz, 1H), 7.04 (d, J = 7.9 Hz, 2H), 6.99-6.89 (m, 2H), 6.91-6.75 (m, 2H), 5.62 (dt, J = 9.5, 4.6 Hz, 1H), 5.21 (t, J = 8.2 Hz, 1H), 4.27 (d, J = 10.6 Hz, 1H), 3.99 (d, J = 10.6 Hz, 1H), 3.47 (s, 3H), 2.79-2.62 (m, 2H), 1.87 (dddd, J = 38.4, 18.2, 9.6, 4.4 Hz, 4H), 1.76-1.56 (m, 3H), 1.42-0.82 (m, 6H). |
| 111 | 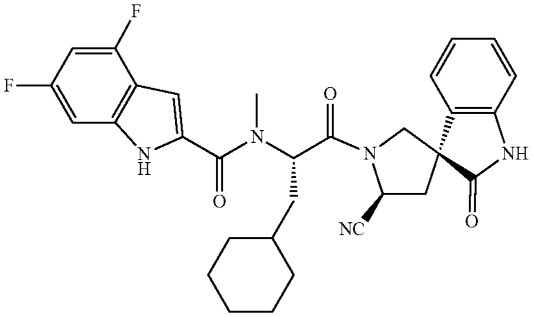 [SMILES: CN(C(=O)c1cc2c(F)cc(F)cc2[nH]1)[C@@H](CC1CCCCC1)C(=O)N1C[C@]2(C[C@H]1C#N)C(=O)Nc1ccccc12] | [M − H]⁻ 558.26 | $^1$H NMR (400 MHz, Acetone-$d_6$) δ 10.83 (s, 1H), 9.68 (s, 1H), 7.17-6.93 (m, 4H), 6.91 (d, J = 7.7 Hz, 1H), 6.82 (t, J = 7.5 Hz, 1H), 6.75 (td, J = 10.3, 2.1 Hz, 1H), 5.71-5.56 (m, 1H), 5.21 (t, J = 8.3 Hz, 1H), 4.28 (d, J = 10.7 Hz, 1H), 3.99 (d, J = 10.6 Hz, 1H), 3.47 (s, 3H), 2.81-2.63 (m, 2H), 1.98-1.78 (m, 4H), 1.75-1.54 (m, 3H), 1.37-0.84 (m, 6H). |
| 112 | 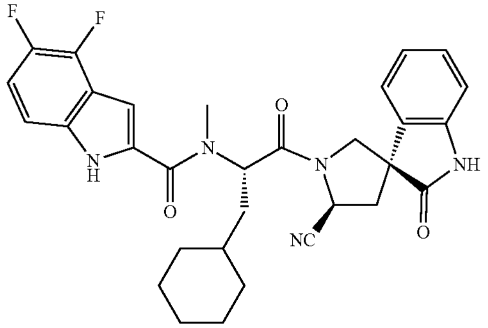 [SMILES: CN(C(=O)c1cc2c(F)c(F)ccc2[nH]1)[C@@H](CC1CCCCC1)C(=O)N1C[C@]2(C[C@H]1C#N)C(=O)Nc1ccccc12] | [M + H]⁺ 560.15 | $^1$H NMR (400 MHz, Acetone-$d_6$) δ 10.80 (s, 1H), 9.68 (s, 1H), 7.31 (dd, J = 9.0, 3.5 Hz, 1H), 7.20 (ddd, J = 11.2, 8.9, 7.5 Hz, 1H), 7.13-6.95 (m, 3H), 6.91 (d, J = 7.7 Hz, 1H), 6.84 (t, J = 7.6 Hz, 1H), 5.66-5.49 (m, 1H), 5.21 (t, J = 8.2 Hz, 1H), 4.26 (d, J = 10.7 Hz, 1H), 3.99 (d, J = 10.6 Hz, 1H), 3.47 (s, 3H), 2.79-2.64 (m, 2H), 1.94-1.76 (m, 4H), 1.76-1.55 (m, 3H), 1.38-0.89 (m, 6H). |

-continued

| Example | Structure | MS | NMR |
|---|---|---|---|
| 113 | 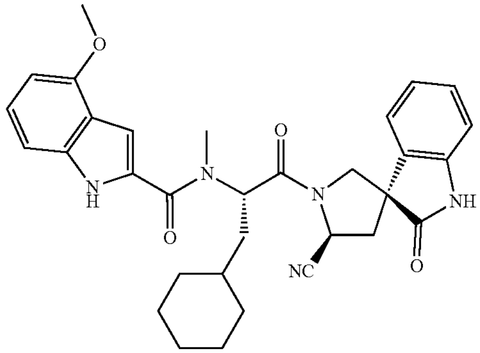 [SMILES: COc1cccc2[nH]c(C(=O)N(C)[C@@H](CC3CCCCC3)C(=O)N3C[C@]4(C[C@H]3C#N)C(=O)Nc3ccccc34)cc12] | [M − H]⁻ 552.08 | $^1$H NMR (400 MHz, Methanol-d$_4$) δ 7.16 (t, J = 8.0 Hz, 1H), 7.06 (t, J = 7.7 Hz, 1H), 7.02-6.94 (m, 2H), 6.93-6.80 (m, 3H), 6.53 (d, J = 7.7 Hz, 1H), 5.54 (m, 1H), 5.18 (t, J = 7.9 Hz, 1H), 4.61 (s, 0H), 4.20 (d, J = 10.7 Hz, 1H), 3.96 (s, 3H), 3.95 (d, J = 2.8 Hz, 1H), 3.40 (s, 3H), 2.70 (dd, J = 12.0, 6.0 Hz, 1H), 2.67 (m, 1H), 1.86-1.67 (m, 7H), 1.25-0.93 (m, 6H). |
| 114 | 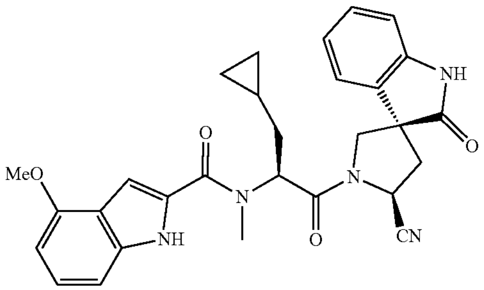 [SMILES: COc1cccc2[nH]c(C(=O)N(C)[C@@H](CC3CC3)C(=O)N3C[C@]4(C[C@H]3C#N)C(=O)Nc3ccccc34)cc12] | [M + Na]$^+$ 534.21 | $^1$H NMR (500 MHz, Chloroform-d) δ 8.98 (s, 1H), 8.27 (s, 1H), 7.20 (t, J = 8.0 Hz, 1H), 7.10-7.04 (m, 1H), 7.02-6.88 (m, 2H), 6.88-6.76 (m, 3H), 6.50 (d, J = 7.8 Hz, 1H), 5.42 (t, J = 7.5 Hz, 1H), 5.02 (t, J = 8.5 Hz, 1H), 4.56 (d, J = 10.5 Hz, 1H), 4.03 (d, J = 10.5 Hz, 1H), 3.96 (s, 3H), 3.51 (s, 3H), 2.85 (dd, J = 13.2, 8.6 Hz, 1H), 2.52 (ddd, J = 13.2, 8.3, 1.2 Hz, 1H), 1.92 (tq, J = 13.8, 7.4 Hz, 2H), 0.73 (qq, J = 7.6, 5.2, 3.8 Hz, 1H), 0.64-0.43 (m, 2H), 0.20 (ddt, J = 14.6, 9.0, 4.7 Hz, 2H). |
| 115 | 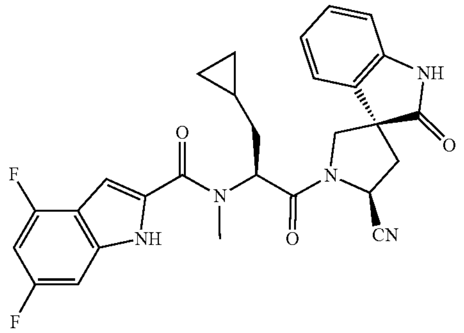 [SMILES: CN(C(=O)c1cc2c(F)cc(F)cc2[nH]1)[C@@H](CC1CC1)C(=O)N1C[C@]2(C[C@H]1C#N)C(=O)Nc1ccccc12] | [M + Na]$^+$ 540.18 | $^1$H NMR (400 MHz, Chloroform-d) δ 9.38 (s, 1H), 8.51 (s, 1H), 7.26 (s, 1H), 7.08 (td, J = 7.4, 6.5, 2.1 Hz, 1H), 6.91-6.74 (m, 5H), 6.62 (td, J = 10.0, 2.0 Hz, 1H), 5.39 (t, J = 7.6 Hz, 1H), 5.05 (t, J = 8.4 Hz, 1H), 4.46 (d, J = 10.4 Hz, 1H), 4.04 (d, J = 10.4 Hz, 1H), 3.50 (s, 3H), 2.85 (dd, J = 13.3, 8.3 Hz, 1H), 2.53 (dd, J = 13.3, 8.4 Hz, 1H), 1.92 (h, J = 6.6 Hz, 2H), 0.88-0.66 (m, 1H), 0.66-0.45 (m, 2H), 0.21 (p, J = 4.5 Hz, 2H). |
| 116 | 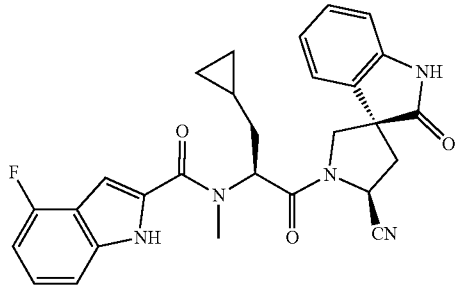 [SMILES: CN(C(=O)c1cc2c(F)cccc2[nH]1)[C@@H](CC1CC1)C(=O)N1C[C@]2(C[C@H]1C#N)C(=O)Nc1ccccc12] | [M + Na]$^+$ 522.19 | |

-continued
| Example | Structure | MS | NMR |
|---|---|---|---|
| 117 | 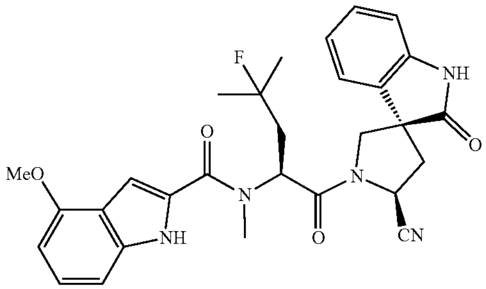 [SMILES: COc1cccc2[nH]c(C(=O)N(C)[C@@H](CC(C)(C)F)C(=O)N3C[C@]4(C[C@H]3C#N)C(=O)Nc3ccccc34)cc12] | [M + Na] 554.23 | $^1$H NMR (400 MHz, Chloroform-d) δ 9.32 (s, 1H), 9.03 (s, 1H), 7.18 (t, J = 8.0 Hz, 1H), 7.05-6.86 (m, 3H), 6.79 (d, J = 7.8 Hz, 1H), 6.68 (dd, J = 21.4, 7.4 Hz, 2H), 6.47 (d, J = 7.8 Hz, 1H), 5.75 (t, J = 6.5 Hz, 1H), 5.02 (t, J = 8.2 Hz, 1H), 4.48 (d, J = 10.7 Hz, 1H), 4.00 (d, J = 10.8 Hz, 1H), 3.95 (s, 3H), 3.47 (s, 3H), 2.82 (dd, J = 13.4, 8.1 Hz, 1H), 2.55-2.42 (m, 2H), 2.37-2.21 (m, 1H), 1.45 (s, 3H), 1.39 (s, 3H). |
| 118 | 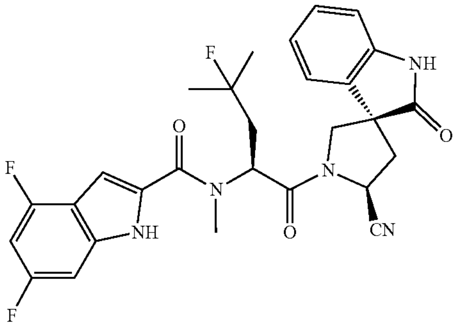 | [M + Na] 560.19 | |
| 412 | 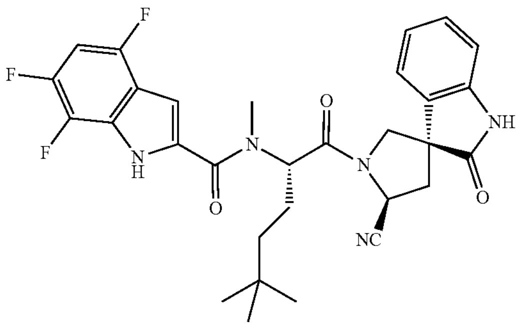 [SMILES: CN(C(=O)c1cc2c(F)cc(F)c(F)c2[nH]1)[C@@H](CCC(C)(C)C)C(=O)N1C[C@]2(C[C@H]1C#N)C(=O)Nc1ccccc12] | [M − 1] 564.1 | 1H NMR (400 MHz, Acetone-d6) δ 11.25 (s, 1H), 9.69 (s, 1H), 7.03 (d, J = 7.5 Hz, 2H), 6.99-6.86 (m, 3H), 6.86-6.76 (m, 1H), 5.42 (t, J = 7.6 Hz, 1H), 5.22 (t, J = 8.3 Hz, 1H), 4.23 (d, J = 10.7 Hz, 1H), 3.99 (d, J = 10.7 Hz, 1H), 3.46 (s, 3H), 2.75-2.66 (m,2H), 1.98 (ddq, J = 14.3, 9.8, 5.5, 5.0 Hz, 2H), 1.39-1.22 (m, 2H), 0.95 (s, 9H). |

Example 413

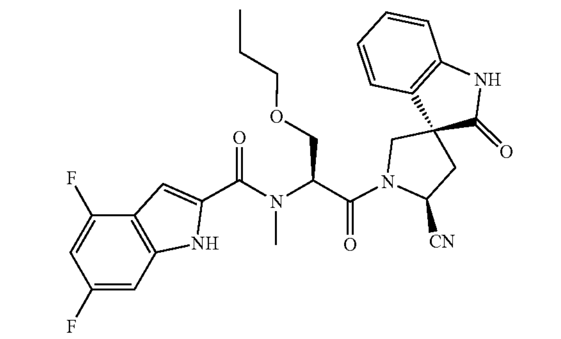

Step 1.

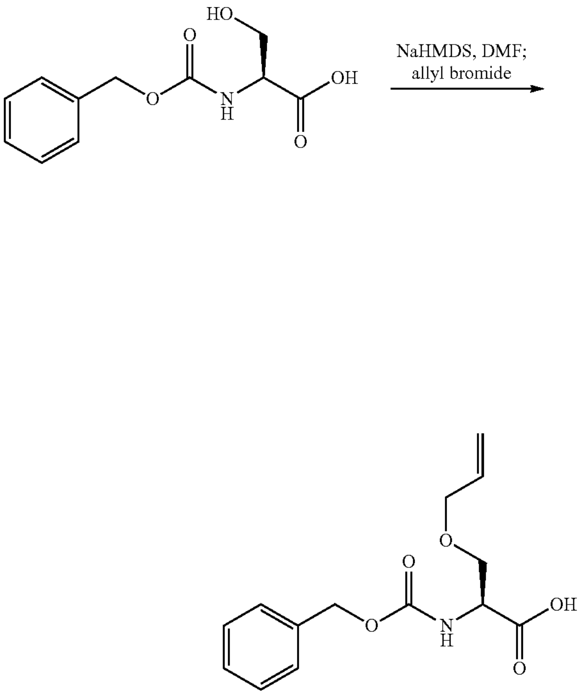

To a solution of ((benzyloxy)carbonyl)-L-serine (1.25 g, 5.23 mmol) in DMF (20 ml) at −45° C. was added NaHMDS (1 M in THF) (10.97 ml, 10.97 mmol) and the resulting mixture was stirred at −45° C. for 20 min, allyl bromide (0.543 ml, 6.27 mmol) (shaked over $K_2CO_3$) was added and the reaction mixture was slowly warmed up to RT and stirred for 18 h. The mixture was cooled down to −20° C., quenched with AcOH (0.359 ml, 6.27 mmol), diluted with EtOAc/1N HCl, and the organic layer was separated, washed with water, brine, dried, filtered and concentrated. The residue was purified by CombiFlash on silica gel eluting with 0-60% acetone/cyclohexane to give O-allyl-N-((benzyloxy)carbonyl)-L-serine (1.04 g, 3.72 mmol, 71.3% yield). $^1H$ NMR (400 MHz, Chloroform-d) δ 7.45-7.25 (m, 5H), 5.96-5.71 (m, 1H), 5.65 (d, J=8.5 Hz, 1H), 5.26-5.12 (m, 2H), 5.10 (d, J=3.3 Hz, 2H), 4.49 (dt, J=7.6, 3.4 Hz, 1H), 3.97 (d, J=5.8 Hz, 2H), 3.90 (dd, J=9.5, 3.2 Hz, 1H), 3.68 (dd, J=9.5, 3.6 Hz, 1H).

Step 2.

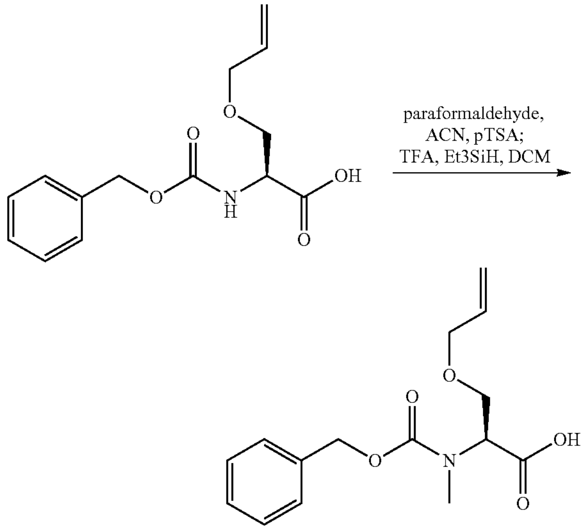

To a mixture of O-allyl-N-((benzyloxy)carbonyl)-L-serine (500 mg, 1.790 mmol), paraformaldehyde (323 mg, 10.74 mmol) in Acetonitrile (8 ml) was added pTSA (23.84 mg, 0.125 mmol) and the resulting mixture was stirred at 70° C. for 14 h, the mixture was cooled down to RT, filtered through celite and the filtrate was collected and concentrated. The residue was chased with DCM.

To the residue was added DCM (8 ml) and TFA (2759 μl, 35.8 mmol), triethylsilane (858 μl, 5.37 mmol) and the resulting mixture was stirred at RT for 6 h. The mixture was concentrated, and chased with DCM. The mixture was diluted with EtOAc, NaOH (1N) solution, then HCl (1N) to adjust pH to ~4. The organic layer was separated, and the aq. layer was extracted with EtOAc (2λ). The organic layer was combined, washed with brine, dried, filtered and concentrated and the residue was purified by CombiFlash on silica gel eluting with 0-5% MeOH/DCM to give O-allyl-N-((benzyloxy)carbonyl)-N-methyl-L-serine (287 mg, 0.978 mmol, 54.7% yield).

Step 3.

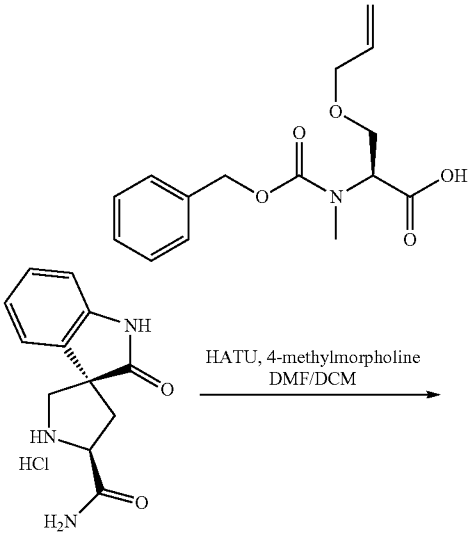

-continued

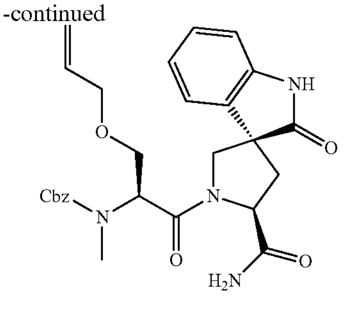

To a mixture of O-allyl-N-((benzyloxy)carbonyl)-N-methyl-L-serine (70 mg, 0.239 mmol), (3R,5'S)-2-oxospiro [indoline-3,3'-pyrrolidine]-5'-carboxamide hydrochloride (80 mg, 0.239 mmol) and HATU (109 mg, 0.286 mmol) in DCM (2 ml)/DMF (0.4 ml) was added 4-methylmorpholine (121 mg, 1.193 mmol). The resulting mixture was stirred at RT for 14 h, the mixture was concentrated, and the residue was diluted with EtOAc, washed with water, brine, dried, filtered and concentrated. The residue was purified by CombiFlash on silica gel eluting with 0 to 10% MeOH/DCM to give benzyl ((S)-3-(allyloxy)-1-((3R,5'S)-5'-carbamoyl-2-oxospiro[indoline-3,3'-pyrrolidin]-1'-yl)-1-oxopropan-2-yl) (methyl)carbamate (163 mg). LC-MS, $ES^+$: 507.22 [M+H].

Step 4.

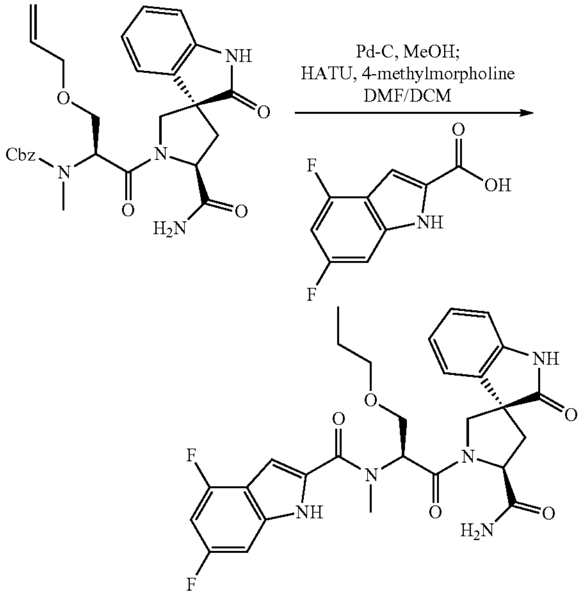

To benzyl ((S)-3-(allyloxy)-1-((3R,5'S)-5'-carbamoyl-2-oxospiro[indoline-3,3'-pyrrolidin]-1'-yl)-1-oxopropan-2-yl) (methyl)carbamate (30 mg, 0.06 mmol), Pd—C (6.39 mg, 6.00 μmol) was added MeOH (1.5 ml) and the resulting mixture was stirred under $H_2$ balloon for 1.5 h. The mixture was filtered through celite, and the filtrate was concentrated.

To the residue was added 4,6-difluoro-1H-indole-2-carboxylic acid (15 mg, 0.078 mmol), HATU (32 mg, 0.084 mmol), DCM (1 ml) and DMF (0.25 ml) and 4-methylmorpholine (24 mg, 0.240 mmol) and the resulting mixture was stirred at RT for 18 h. The mixture was concentrated, and the residue was purified on silical gel eluting with 0-10% MeOH/DCM to give (3R,5'S)-1'-(N-(4,6-difluoro-1H-indole-2-carbonyl)-N-methyl-O-propyl-L-seryl)-2-oxospiro [indoline-3,3'-pyrrolidine]-5'-carboxamide (36 mg). LC-MS, $ES^+$: 576.2 [M+Na].

Step 5.

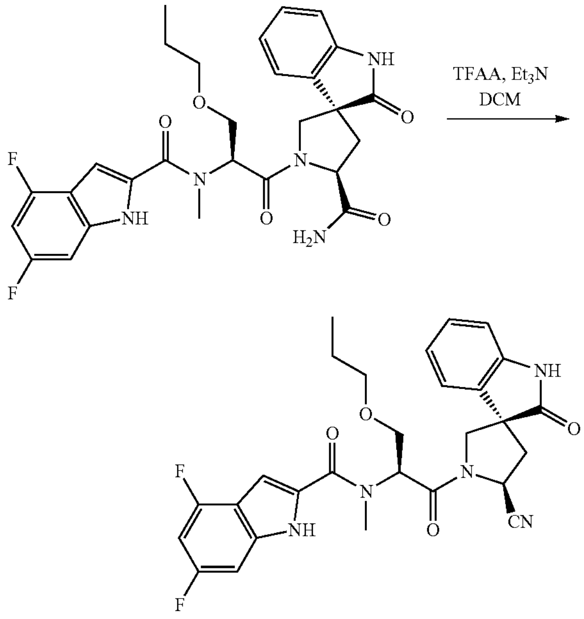

To (3R,5'S)-1'-(N-(4,6-difluoro-1H-indole-2-carbonyl)-N-methyl-O-propyl-L-seryl)-2-oxospiro[indoline-3,3'-pyrrolidine]-5'-carboxamide (36 mg, 0.065 mmol) in DCM (2 ml) at RT was added TEA (72.5 μl, 0.52 mmol) and TFAA (45.9 μl, 0.325 mmol), the resulting mixture was stirred at RT for 30 min. The mixture was concentrated, diluted with MeOH (1.2 ml), and then added $NH_3$ (Conc. 0.8 ml) and stirred at RT for 30 min. The mixture was concentrated. The residue was purified by CombiFlash on silica gel eluting with 0-60% acetone/cyclohexane to give N—((S)-1-((3R, 5'S)-5'-cyano-2-oxospiro[indoline-3,3'-pyrrolidin]-1'-yl)-1-oxo-3-propoxypropan-2-yl)-4,6-difluoro-N-methyl-1H-indole-2-carboxamide (12 mg). LC-MS, $ES^+$: 558.2 [M+Na].

Example 414

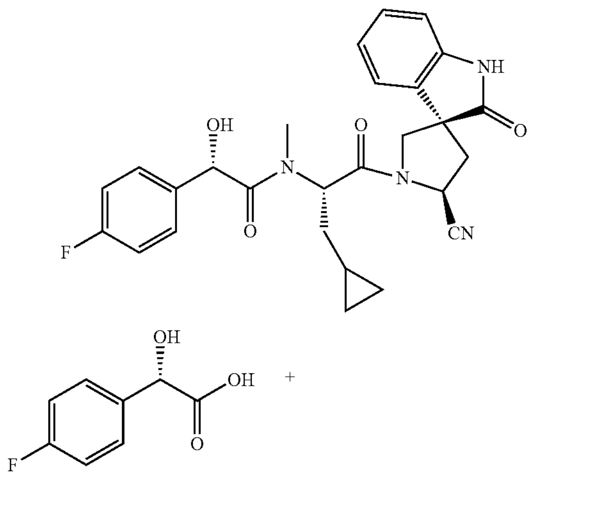

-continued

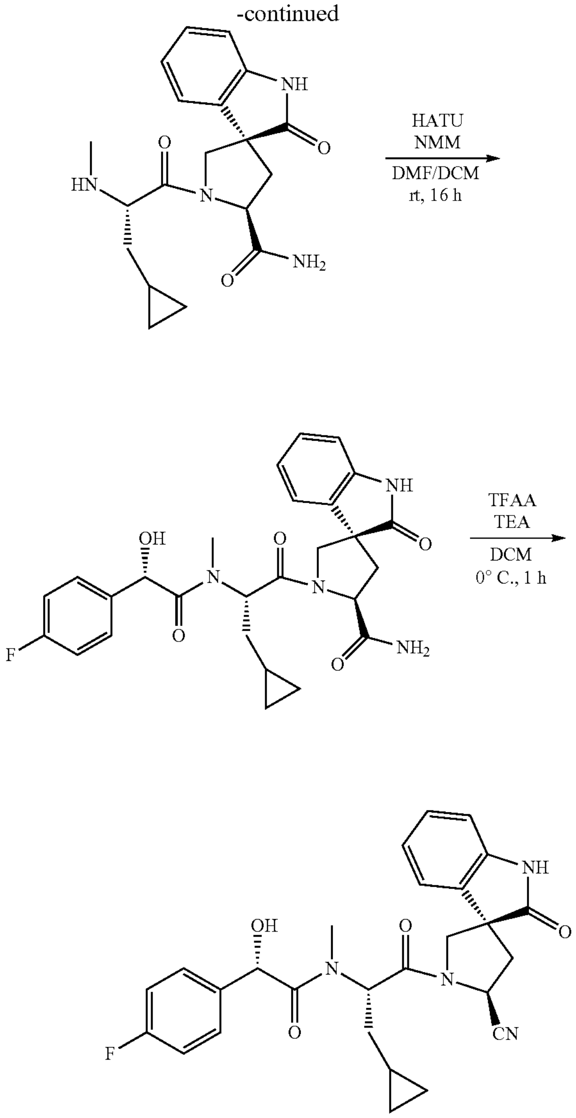

Step 1:

A solution of (3R,5'S)-1'-((S)-3-cyclopropyl-2-(methylamino)propanoyl)-2-oxospiro[indoline-3,3'-pyrrolidine]-5'-carboxamide (44 mg, 0.123 mmol) and (S)-2-(4-fluorophenyl)-2-hydroxyacetic acid (22.00 mg, 0.129 mmol) in DMF (0.1 ml) and $CH_2Cl_2$ (0.4 ml) was treated with N-methylmorpholine (50 μl, 0.455 mmol) and HATU (52 mg, 0.137 mmol). The reaction was stirred at room temperature overnight. The mixture was diluted with dichloromethane and quenched with a saturated solution of sodium bicarbonate. The aqueous layer was extracted with dichloromethane over 3 times. The combined organic layer was dried over sodium sulfate, filtered and concentrated in vacuo. The crude was added to a 4 g silica gel column and eluted by acetone/cyclohexane from 0% to 100% to give (3R,5'S)-1'-((S)-3-cyclopropyl-2-((S)-2-(4-fluorophenyl)-2-hydroxy-N-methylacetamido)propanoyl)-2-oxospiro[indoline-3,3'-pyrrolidine]-5'-carboxamide (16 mg, 0.031 mmol, 25.5% yield) as a white solid. LC-MS, $ES^-$: 507.36 [M-H].

Step 2:

A solution of (3R,5'S)-1'-((S)-3-cyclopropyl-2-((S)-2-(4-fluorophenyl)-2-hydroxy-N-methylacetamido)propanoyl)-2-oxospiro[indoline-3,3'-pyrrolidine]-5'-carboxamide (14 mg, 0.028 mmol) in $CH_2Cl_2$ (0.4 ml) was treated with TEA (40 μl, 0.287 mmol) and TFAA (16 μl, 0.113 mmol) at 0° C. The reaction was stirred at 0° C. for 1 h, then quenched with ammonium hydroxide and stirred for additional 30 min. The aqueous layer was extracted with dichloromethane over 3 times. The combined organic layer was dried over sodium sulfate, filtered and concentrated in vacuo. The crude was added to a 4 g silica gel column and eluted by ethyl acetate/cyclohexane from 0% to 100% to give (S)—N—((S)-1-((3R,5'S)-5'-cyano-2-oxospiro[indoline-3,3'-pyrrolidin]-1'-yl)-3-cyclopropyl-1-oxopropan-2-yl)-2-(4-fluorophenyl)-2-hydroxy-N-methyl acetamide (12 mg, 0.024 mmol, 89% yield) as a white solid. LC-MS, $ES^-$: 489.34 [M-H]; $^1H$ NMR (500 MHz, Methanol-$d_4$) δ 7.35-7.18 (m, 3H), 7.03-6.86 (m, 5H), 5.37-5.27 (m, 2H), 5.05 (t, J=7.9 Hz, 2H), 3.98 (d, J=10.6 Hz, 1H), 3.79 (d, J=10.5 Hz, 1H), 2.93 (s, 3H), 2.67-2.52 (m, 2H), 1.88 (dt, J=14.5, 7.5 Hz, 1H), 1.64 (dt, J=14.0, 7.0 Hz, 1H), 0.73 (ddt, J=10.3, 7.4, 3.7 Hz, 1H), 0.57-0.44 (m, 2H), 0.22-0.10 (m, 2H).

The following examples were prepared employing similar protocol as described above.

| Example | Structure | MS | NMR |
| --- | --- | --- | --- |
| 415 | 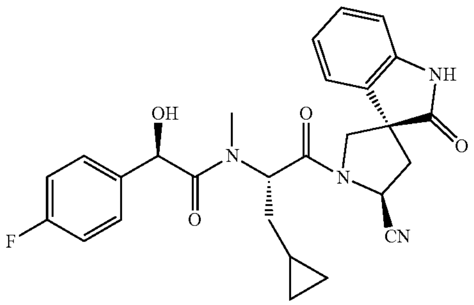 [SMILES: CN(C(=O)[C@H](O)c1ccc(F)cc1)[C@@H](CC1CC1)C(=O)N1C[C@]2(C[C@H]1C#N)C(=O)Nc1ccccc12] | [M - 1] 489.30 | $^1H$ NMR (500 MHz, Methanol-$d_4$) δ 7.41-7.33 (m, 1H), 7.30 (ddd, J = 8.1, 6.7, 2.2 Hz, 1H), 7.13-7.01 (m, 3H), 6.97 (d, J = 7.8 Hz, 1H), 5.33 (t, J = 7.7 Hz, 1H), 5.25 (s, 1H), 5.14 (t, J = 7.8 Hz, 1H), 4.18 (d, J = 10.8 Hz, 1H), 4.10 (q, J = 7.1 Hz, 1H), 4.00 (d, J = 10.8 Hz, 1H), 2.89 (s, 3H), 2.67 (d, J = 7.8 Hz, 1H), 1.73-1.57 (m, 2H), 1.27-1.21 (m, 1H), 0.53-0.37 (m, 2H), 0.37-0.26 (m, 1H), 0.10 (dt, J = 7.1, 5.0 Hz, 1H), 0.00 (dq, J = 9.5, 4.9 Hz, 1H). |

-continued

| Example | Structure | MS | NMR |
|---|---|---|---|
| 416 | 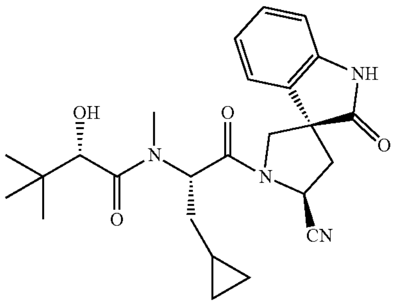 [SMILES: CN(C(=O)[C@@H](O)C(C)(C)C)[C@@H](CC1CC1)C(=O)N1C[C@]2(C[C@H]1C#N)C(=O)Nc1ccccc12] | [M − 1] 454.40 | $^1$H NMR (500 MHz, Methanol-$d_4$) δ 7.26 (td, J = 7.6, 1.5 Hz, 1H), 7.02 (dtd, J = 15.0, 7.5, 1.3 Hz, 2H), 6.95 (d, J = 7.8 Hz, 1H), 5.30 (dd, J = 8.7, 6.4 Hz, 1H), 5.13 (t, J = 8.2 Hz, 1H), 4.16 (d, J = 10.5 Hz, 1H), 4.10 (d, J = 8.8 Hz, 1H), 4.02 (d, J = 10.5 Hz, 1H), 3.14 (s, 3H), 2.72-2.60 (m, 2H), 2.17 (d, J = 12.1 Hz, 1H), 1.84 (ddd, J = 13.3, 8.8, 7.3 Hz, 1H), 1.70 (dt, J = 13.4, 6.4 Hz, 1H), 1.28-1.22 (m, 1H), 0.95-0.88 (m, 1H), 0.73 (ddd, 13.8, 6.6, 3.6 Hz, 1H), 0.53 (d, J = 7.9 Hz, 2H), 0.25-0.12 (m, 2H). |
| 417 | 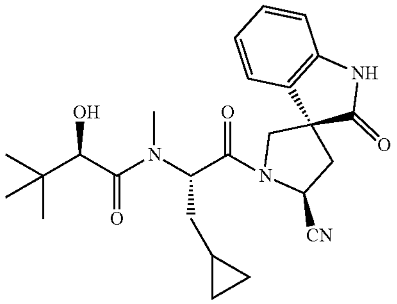 [SMILES: CN(C(=O)[C@H](O)C(C)(C)C)[C@@H](CC1CC1)C(=O)N1C[C@]2(C[C@H]1C#N)C(=O)Nc1ccccc12] | [M − 1] 4541.39 | $^1$H NMR (500 MHz, Methanol-$d_4$) δ 7.26 (td, J = 7.7, 1.3 Hz, 1H), 7.13 (d, J = 7.4 Hz, 1H), 7.04 (t, J = 7.7 Hz, 1H), 6.94 (d, J = 7.8 Hz, 1H), 5.23 (t, J = 7.7 Hz, 1H), 5.11 (t, J = 7.7 Hz, 1H), 4.27 (d, J = 10.7 Hz, 1H), 4.23 (s, 1H), 4.10 (q, J = 7.1 Hz, 1H), 4.04 (d, J = 10.6 Hz, 1H), 3.20 (s, 3H), 2.65 (td, J = 8.5, 2.6 Hz, 2H), 2.16 (d, J = 1.2 Hz, 2H), 1.91-1.70 (m, 2H), 1.28-1.20 (m, 1H), 1.04 (d, J = 12.5 Hz, 1H), 0.85 (d, J = 22.5 Hz, 1H), 0.82-0.69 (m, 1H), 0.59-0.47 (m, 2H), 0.26-0.12 (m, 2H). |
| 418 | 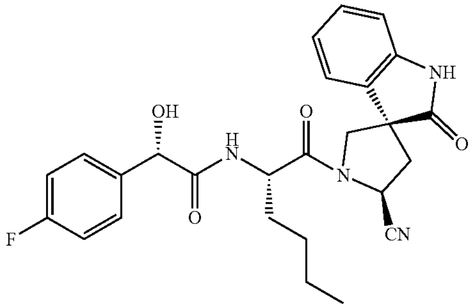 [SMILES: CCCC[C@H](NC(=O)[C@@H](O)c1ccc(F)cc1)C(=O)N1C[C@]2(C[C@H]1C#N)C(=O)Nc1ccccc12] | [M − 1] 477.36 | $^1$H NMR (400 MHz, Methanol-$d_4$) δ 7.44 (ddd, J = 8.8, 5.4, 2.7 Hz, 2H), 7.26 (td, J = 7.6, 1.5 Hz, 1H), 7.11-6.99 (m, 4H), 6.94 (d, J = 7.7 Hz, 1H), 5.15 (t, J = 7.9 Hz, 1H), 4.97 (s, 1H), 4.58 (dd, J = 8.1, 5.7 Hz, 1H), 4.10 (d, J = 10.6 Hz, 1H), 3.95 (d, J = 10.6 Hz, 1H), 2.70-2.60 (m, 2H), 1.90-1.67 (m, 2H), 1.39-1.26 (m, 4H), 0.94-0.83 (m, 3H). |
| 419 | 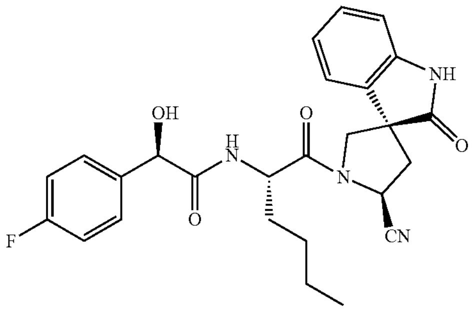 [SMILES: CCCC[C@H](NC(=O)[C@H](O)c1ccc(F)cc1)C(=O)N1C[C@]2(C[C@H]1C#N)C(=O)Nc1ccccc12] | [M − 1] 477.32 | $^1$H NMR (400 MHz, Methanol-$d_4$) δ 7.47-7.39 (m, 2H), 7.23 (td, J = 7.7, 1.3 Hz, 1H), 7.09-6.97 (m, 3H), 6.95-6.89 (m, 2H), 5.11 (t, J = 7.8 Hz, 1H), 5.02 (s, 1H), 4.57 (dd, J = 8.1, 5.8 Hz, 1H), 4.04 (d, J = 10.5 Hz, 1H), 3.94 (d, J = 10.5 Hz, 1H), 2.68-2.57 (m, 2H), 1.94-1.82 (m, 1H), 1.77 (dd, J = 7.9, 5.9 Hz, 1H), 1.45-1.27 (m, 4H), 0.98-0.84 (m, 3H). |
| 420 | 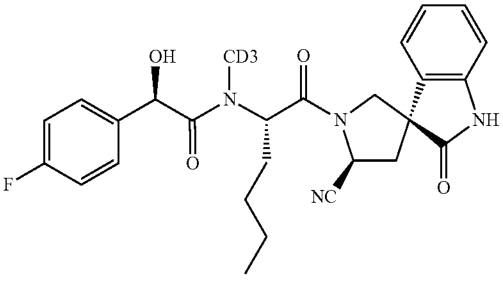 [SMILES: [2H]C([2H])([2H])N(C(=O)[C@H](O)c1ccc(F)cc1)[C@@H](CCCC)C(=O)N1C[C@]2(C[C@H]1C#N)C(=O)Nc1ccccc12] | 494.23 (M − H)− | |

-continued

| Example | Structure | MS | NMR |
|---|---|---|---|
| 421 | 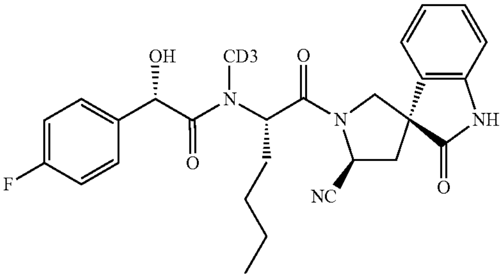 [SMILES: [2H]C([2H])([2H])N(C(=O)[C@@H](O)c1ccc(F)cc1)[C@@H](CCCC)C(=O)N1C[C@]2(C[C@H]1C#N)C(=O)Nc1ccccc12] | 494.23 (M − H)− | |
| 422 | 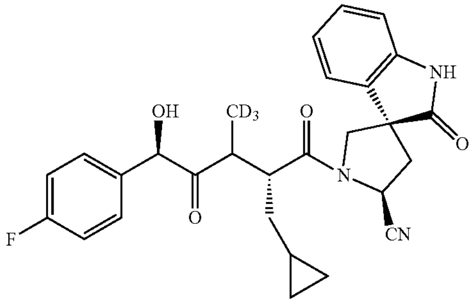 [SMILES: [2H]C([2H])([2H])C(C(=O)[C@H](O)c1ccc(F)cc1)[C@@H](CC1CC1)C(=O)N1C[C@]2(C[C@H]1C#N)C(=O)Nc1ccccc12] | [M − 1] 492.29 | $^1$H NMR (400 MHz, Methanol-$d_4$) δ 7.42-7.20 (m, 4H), 7.20-7.01 (m, 4H), 7.01-6.88 (m, 1H), 5.32 (t, J = 7.6 Hz, 1H), 5.24 (s, 1H), 5.14 (t, J = 7.9 Hz, 1H), 4.19(d, J = 10.8 Hz, 1H), 4.00 (d, J = 10.7 Hz, 1H), 2.67 (d, J = 7.8 Hz, 2H), 1.63 (ddd, J = 27.8, 14.1, 7.1 Hz, 2H), 0.52-0.38 (m, 2H), 0.32 (ddd, J = 13.3, 9.1, 4.9 Hz, 1H), 0.10 (dd, J = 9.1, 5.4 Hz, 1H), 0.00 (dq, J = 9.4, 4.8 Hz, 1H). |
| 423 | 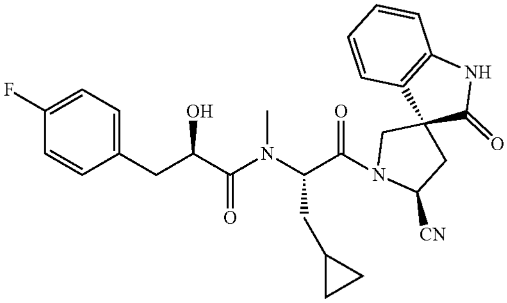 [SMILES: CN(C(=O)[C@H](O)Cc1ccc(F)cc1)[C@@H](CC1CC1)C(=O)N1C[C@]2(C[C@H]1C#N)C(=O)Nc1ccccc12] | [M − 1] 503.33 | $^1$H NMR (500 MHz, Methanol-$d_4$) δ 7.32-7.17 (m, 2H), 7.10-7.05 (m, 1H), 7.02 (td, J = 7.5, 1.0 Hz, 1H), 6.99-6.89 (m, 2H), 5.20 (t, J = 7.6 Hz, 1H), 5.10 (t, J = 7.7 Hz, 1H), 4.61-4.48 (m, 2H), 4.14 (d, J = 10.7 Hz, 1H), 3.99 (d, J = 10.8 Hz, 1H), 3.04 (s, 3H), 2.88 (dd, J = 13.8, 5.6 Hz, 1H), 2.75 (dd, J = 13.8, 7.6 Hz, 1H), 2.70-2.60 (m, 2H), 1.79-1.57 (m, 3H), 1.28 (s, 2H), 0.93-0.83 (m, 1H), 0.64-0.38 (m, 3H), 0.23-0.07 (m, 2H). |
| 424 | 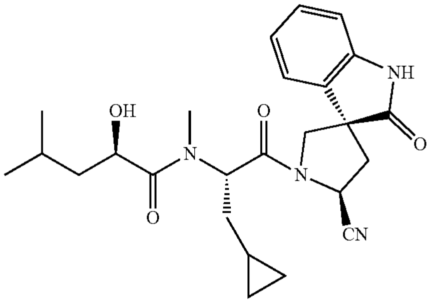 [SMILES: CC(C)C[C@@H](O)C(=O)N(C)[C@@H](CC1CC1)C(=O)N1C[C@]2(C[C@H]1C#N)C(=O)Nc1ccccc12] | [M − 1] 451.35 | $^1$H NMR (500 MHz, Methanol-$d_4$) δ 7.26 (td, J = 7.6, 1.4 Hz, 1H), 7.08 (dd, J = 7.6, 1.4 Hz, 1H), 7.03 (td, J = 7.5, 1.0 Hz, 1H), 6.93 (d, J = 7.8 Hz, 1H), 5.25 (t, J = 7.6 Hz, 1H), 5.11 (t, J = 7.7 Hz, 1H), 4.34 (dd, J = 9.8, 3.3 Hz, 1H), 4.13 (d, J = 10.8 Hz, 1H), 3.99 (d, J = 10.8 Hz, 1H), 3.07 (s, 3H), 2.69-2.61 (m, 2H), 1.86-1.70 (m, 3H), 1.37 (ddd, J = 14.3, 9.8, 4.6 Hz, 1H), 1.29 (ddd, J = 14.0, 9.3, 3.3 Hz, 1H), 0.92 (dd, J = 11.8, 6.7 Hz, 5H), 0.71-0.63 (m, 1H), 0.52-0.44 (m, 2H), 0.15 (ddd, J = 6.8, 4.9, 3.4 Hz, 2H). |
| 425 | 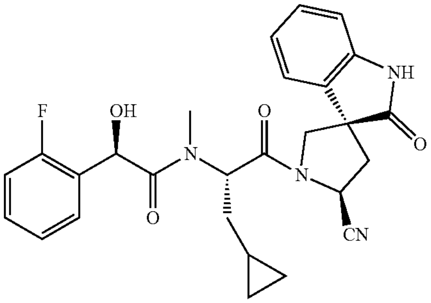 [SMILES: CN(C(=O)[C@H](O)c1ccccc1F)[C@@H](CC1CC1)C(=O)N1C[C@]2(C[C@H]1C#N)C(=O)Nc1ccccc12] | [M − 1] 489.28 | $^1$H NMR (400 MHz, Chloroform-d) δ 8.09 (s, 1H), 7.38-7.27 (m, 2H), 7.17-7.02 (m, 4H), 6.97 (dd, J = 7.8, 0.9 Hz, 1H), 6.91-6.85 (m, 1H), 5.37 (s, 1H), 5.23 (t, J = 7.7 Hz, 1H), 5.02 (t, J = 8.5 Hz, 1H), 4.47 (dd, J = 10.5, 1.3 Hz, 1H), 4.28 (d, J = 14.6 Hz, 1H), 4.02 (d, J = 10.4 Hz, 1H), 2.86 (s, 3H), 2.56 (ddd, J = 13.2, 8.3, 1.2 Hz, 1H), 1.80-1.68 (m, 1H), 1.62 (dt, J = 14.2, 7.5 Hz, 2H), 0.54-0.33 (m, 3H), 0.18-0.09 (m, 1H), 0.03 (dt, J = 9.3, 4.6 Hz, 1H). |

-continued
| Example | Structure | MS | NMR |
|---|---|---|---|
| 426 | 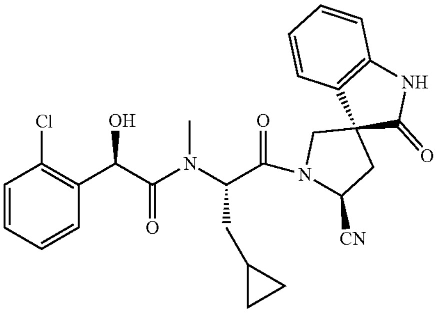 [SMILES: CN(C(=O)[C@H](O)c1ccccc1Cl)[C@@H](CC1CC1)C(=O)N1C[C@]2(C[C@H]1C#N)C(=O)Nc1ccccc12] | [M − 1] 505.25; 507.21 | $^1$H NMR (400 MHz, Chloroform-d) δ 7.90 (s, 1H), 7.39 (dd, J = 8.0, 1.4 Hz, 1H), 7.34 (td, J = 7.8, 1.2 Hz, 1H), 7.29-7.23 (m, 3H), 7.19 (td, J = 7.5, 1.4Hz, 1H), 7.14-7.04 (m, 2H), 6.97 (dt, J = 7.8, 0.9 Hz, 1H), 6.92-6.86 (m, 1H), 5.48 (s, 1H), 5.26 (t, J = 7.7 Hz, 1H), 5.02 (t, J = 8.6 Hz, 1H), 4.46 (dd, J = 10.5, 1.3 Hz, 1H), 4.24 (dt, J = 19.6, 10.2 Hz, 1H), 4.02 (d, J = 10.4 Hz, 1H), 2.88 (dd, J = 13.2, 8.8 Hz, 1H), 2.80 (s, 3H), 2.57 (ddd, J = 13.2, 8.3, 1.3 Hz, 1H), 1.83-1.68 (m, 1H), 1.61 (dt, J = 13.9, 7.3 Hz, 3H), 0.46 (dddd, J = 25.5, 13.3, 10.2, 6.5 Hz, 3H), 0.21-0.11 (m, 1H), 0.11-0.00 (m, 1H). |
| 427 | 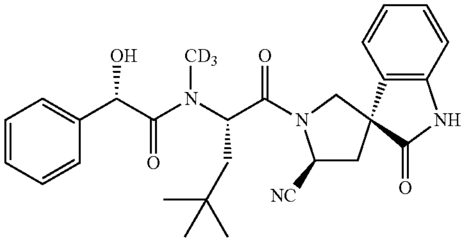 [SMILES: [2H]C([2H])([2H])N(C(=O)[C@@H](O)c1ccccc1)[C@@H](CC(C)(C)C)C(=O)N1C[C@]2(C[C@H]1C#N)C(=O)Nc1ccccc12] | 492.30 | |
| 428 | 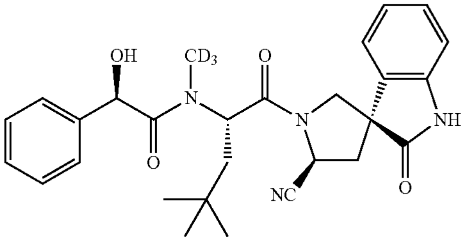 [SMILES: [2H]C([2H])([2H])N(C(=O)[C@H](O)c1ccccc1)[C@@H](CC(C)(C)C)C(=O)N1C[C@]2(C[C@H]1C#N)C(=O)Nc1ccccc12] | 492.30 | |
Example 429
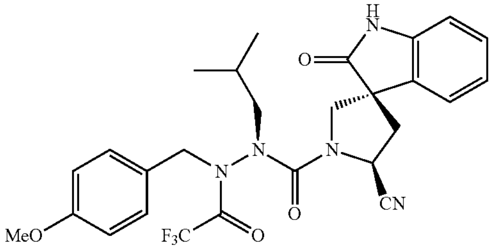
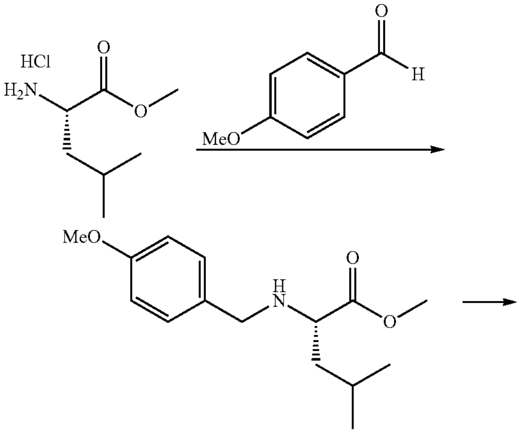
-continued
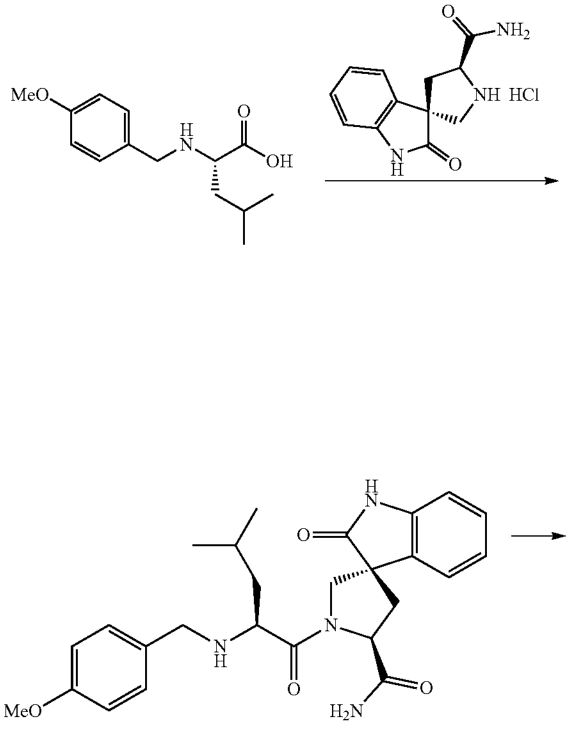

-continued

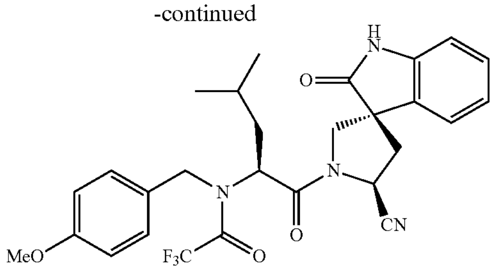

Step 1:

To a solution of methyl L-leucine hydrochloride (200 mg, 1.10 mmol) in THF (3.3 mL) was added 4-methoxybenzaldehyde (300 mg, 2.2 mmol), DIPEA (192 µL, 1.1 mmol) and $MgSO_4$ (225 mg, 1/87 mmol). The reaction mixture was stirred at room temperature overnight. The crude material was filtered through celite and evaporated to dryness. The crude material was taken up in methanol (3.3 mL) and sodium borohydride (83 mg, 2.2 mmol) was added. The reaction mixture was quenched with sat. $NH_4Cl$, extracted with EtOAc. The organic layer was separated, washed with brine, dried over $Na_2SO_4$, and concentrated. Purification of the residue on silica gel chromatography with 0-70% EtOAc in cyclohexane provided desired product (249 mg, 85%).

Step 2:

To material from step 1 (249 mg, 0.94 mmol) in THF (3 mL) and methanol (2 mL) was added LiOH (1 mL, 2M, 2 mmol). Upon completion the reaction mixture was acidified to pH 3 with 1M HCl, extracted with EtOAc, washed with brine and dried over $Na_2SO_4$ to give desired product that was used without purification.

Step 3:

To a solution of material from step 3 (35 mg, 0.139 mmol) and spirocycle intermediate (37 mg, 0.139 mmol) was added HATU (53 mg, 0.139 mmol) and DIPEA (73 µL, 0.418 mmol). The reaction mixture was stirred overnight at room temperature. The reaction mixture was quenched with water, extracted with EtOAc. The organic layer was separated, washed with brine, dried over $Na_2SO_4$, and concentrated. Purification of the residue on silica gel chromatography with 0-80% acetone in cyclohexane provided desired product (41 mg, 63%).

Step 4:

To a solution of material from step 3 (41 mg, 0.088 mmol) in DCM (1 mL) at 0° C. was added TFAA (37 µL, 0.265 mmol) and $Et_3N$ (74 µL, 0.530 mmol). The crude product was loaded directly onto a silica gel column and subjected to chromatography with 0-80% acetone in cyclohexane provided EP-037611 (30 mg, 63%). LC-MS, ES+543.056 [M+H]. 1H NMR (400 MHz, Acetone-d6 1H NMR (400 MHz, Acetone-$d_6$) δ 9.65 (s, 1H), 7.38-7.26 (m, 3H), 7.19 (d, J=7.4 Hz, 1H), 7.11-7.05 (m, 1H), 7.07-6.95 (m, 3H), 6.97 (s, 1H), 5.04 (s, 1H), 4.81 (s, 2H), 4.06 (s, 1H), 4.00 (d, J=10.7 Hz, 1H), 3.88 (d, J=10.2 Hz, 1H), 3.82 (s, 3H), 2.63 (t, J=5.9 Hz, 2H), 2.56 (s, 1H), 1.94 (s, 1H), 1.37 (s, 1H), 0.85 (d, J=7.1 Hz, 4H), 0.75 (d, J=5.9 Hz, 2H), 0.62 (s, 1H). 19F NMR (400 MHz, Acetone-$d_6$) δ 69.4.

The following examples were prepared employing similar protocol as described above.

| Example | Structure | MS | NMR |
|---|---|---|---|
| 430 | 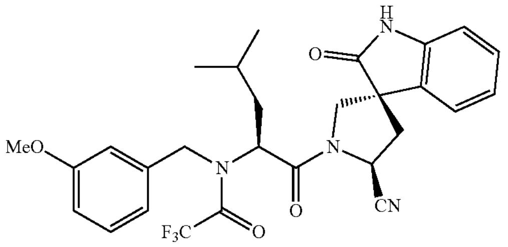 [SMILES: COc1cccc(CN(C(=O)C(F)(F)F)[C@@H](CC(C)C)C(=O)N2C[C@]3(C[C@H]2C#N)C(=O)Nc2ccccc23)c1] | 543.016 [M + H]. | 1H NMR (400 MHz, Acetone-d6) δ 9.66 (s, 2H), 7.39-7.26 (m, 6H), 7.23 (d, J = 7.5 Hz, 2H), 7.08 (t, J = 7.4 Hz, 4H), 7.01 (d, J = 7.5 Hz, 4H), 6.97-6.89 (m, 8H), 5.19 (t, J = 7.2 Hz, 2H), 5.09 (d, J = 15.9 Hz, 1H), 5.00 (s, 1H), 4.94 (d, J = 17.5 Hz, 2H), 4.89-4.80 (m, 6H), 4.13-4.02 (m, 3H), 3.98 (d, J = 10.4 Hz, 2H), 3.78 (d, J = 10.4 Hz, 1H), 2.84 (s, 1H), 2.64 (d, J = 6.6 Hz, 4H), 2.64-2.55 (m, 1H), 1.74 (dh, J = 27.3, 7.0 Hz, 2H), 1.56-1.48 (m, 1H), 0.86 (d, J = 7.3 Hz, 9H), 0.78 (d, J = 6.6 Hz, 5H), 0.60 (d, J = 6.2 Hz, 3H). 19F NMR (400 MHz, Acetone-d6) δ −66.6 |
| 431 | 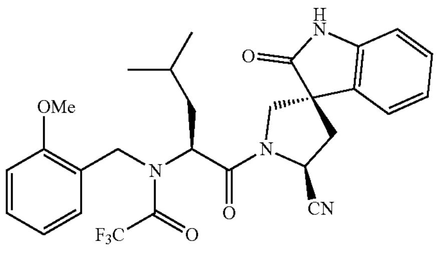 [SMILES: COc1ccccc1CN(C(=O)C(F)(F)F)[C@@H](CC(C)C)C(=O)N1C[C@]2(C[C@H]1C#N)C(=O)Nc1ccccc12] | 543.037 [M + H]. | 1H NMR (400 MHz, Acetone-d6) δ 9.68 (s, 1H), 7.37 - 7.29 (m, 1H), 7.33-7.18 (m, 2H), 7.16 - 6.97 (m, 4H), 5.13 (d, J = 7.6 Hz, 1H), 5.02 (s, 1H), 4.97 (s, 2H), 4.82 (s, 1H), 4.10 (d, J = 10.1 Hz, 1H), 4.04 (d, J = 10.2 Hz, 1H), 3.93 - 3.88 (m, 4H), 2.73 (dd, J = 13.3, 8.5 Hz, 1H), 2.65 (dd, J = 19.3, 6.1 Hz, 1H), 1.84-1.75 (m, 1H), 1.61-1.52 (m, 0H), 1.44 (s, 12H), 0.86 (d, J = 6.5 Hz, 4H), 0.80 (d, J = 6.5 Hz, 3H), 0.50 (s, 1H). 19F NMR (400 MHz, Acetone-d6) δ −69.1 |

-continued

| Example | Structure | MS | NMR |
|---|---|---|---|
| 432 | 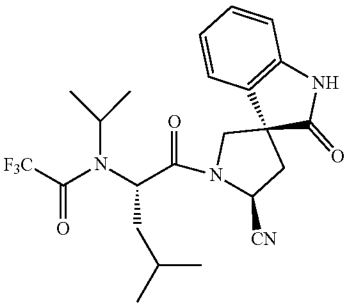 [SMILES: CC(C)C[C@@H](C(=O)N1C[C@]2(C[C@H]1C#N)C(=O)Nc1ccccc12)N(C(=O)C(F)(F)F)C(C)C] | [M - 1] 463.0 | |

Example 119

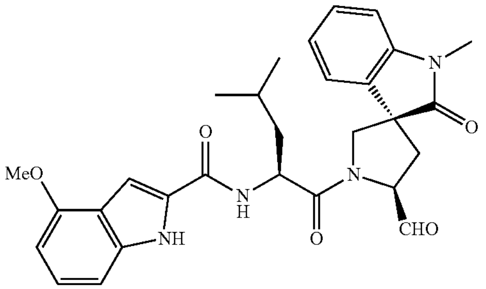

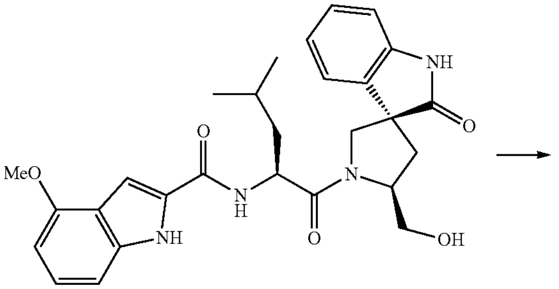

23-5

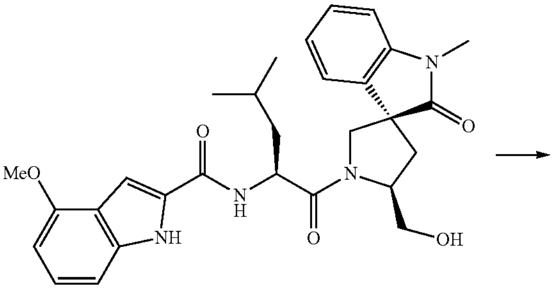

119-1

-continued

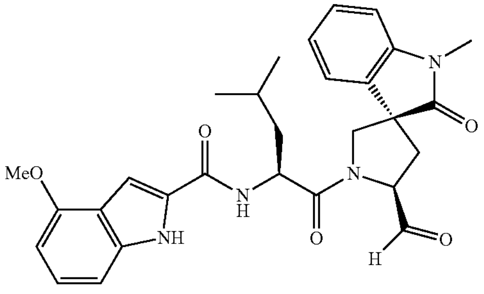

Example 119

Step 1

To a solution of compound (23-5) (64 mg, 0.127 mmol) in dry acetone (0.634 mL) was added $K_2CO_3$ (26.3 mg, 0.190 mmol) and dimethyl sulfate (18.04 μL, 0.190 mmol) at rt. The reaction mixture was then heated and refluxed for 2 hrs. After 2 hrs, another portion of dimethyl sulfate (6.0 μl. 06 mmol) was added and the mixture was heated for another 3 hrs. The reaction mixture was concentrated to dryness. The residue was diluted with EtOAc, washed with water, brine, dried, and concentrated. Purification of the residue by silica gel chromatography with 0-50% acetone/cyclohexane provided compound (119-1) (53 mg, 81% yield). LC-MS, ES+: 519.14 $[M+H]^+$.

Step 2

To a solution of compound (119-1) (51 mg, 0.098 mmol) in dry DCM (0.98 mL) at 0° C. was added Dess-Martin periodinane (62.6 mg, 0.148 mmol). The mixture was stirred at 0° C. for 3 hrs. Purification of the crude reaction mixture on silica gel chromatography with 0-55% EtOAc/cyclohexane provided Example 119 (28 mg, 55% yield). LC-MS, ES+: 517.06 $[M+H]^+$. $^1H$ NMR (400 MHz, Acetone-d6) δ 10.52 (s, 1H), 9.52 (d, J=1.9 Hz, 1H), 7.75-7.69 (m, 1H), 7.23-7.16 (m, 3H), 7.03-6.95 (m, 2H), 6.92-6.85 (m, 2H), 6.40 (dd, J=7.2, 1.2 Hz, 1H), 4.84 (ddd, J=9.7, 8.3, 4.8 Hz, 1H), 4.54 (ddd, J=9.2, 6.1, 2.0 Hz, 1H), 4.12 (d, J=10.4 Hz, 1H), 3.96 (d, J=10.4 Hz, 1H), 3.79 (s, 3H), 3.07 (s, 3H), 2.37-2.29 (m, 1H), 2.20 (dd, J=13.1, 6.1 Hz, 1H), 1.71 (ddd, J=14.5, 9.8, 4.2 Hz, 2H), 1.66-1.58 (m, 1H), 0.84 (dd, J=10.7, 6.4 Hz, 6H)

Example 120

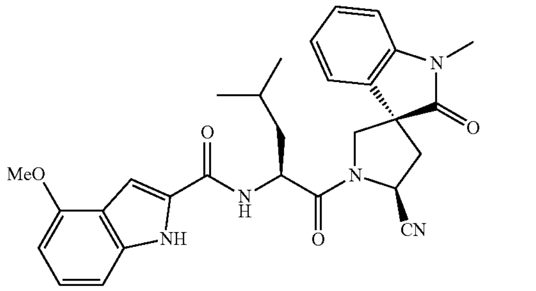

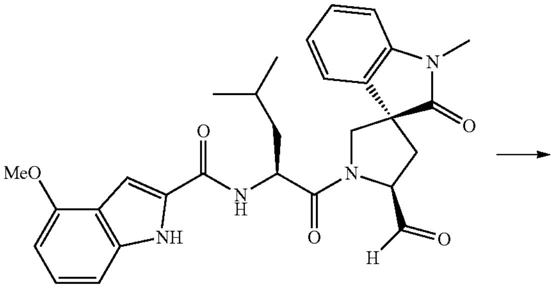

Example 119

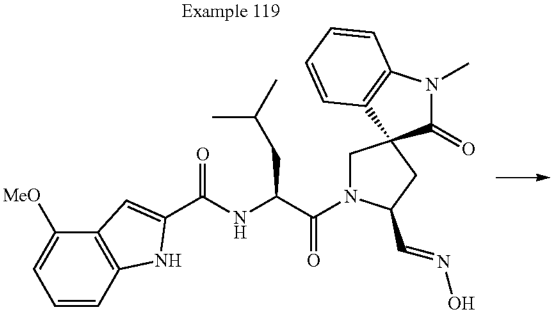

120-1

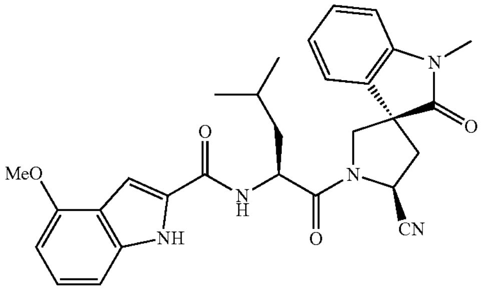

Example 120

Step 1

To a solution of Example 119 (24 mg, 0.046 mmol) in dry DMSO (0.186 mL) was added hydroxylamine hydrochloride (4.36 mg, 0.063 mmol). After stirring at rt for 1 h, the reaction mixture was diluted with EtOAc, washed with water (2×), brine, dried, and concentrated to provide the crude oxime intermediate (118-1) (21 mg), which was directly used in the next step. LC-MS, ES+: 532.13 $[M+H]^+$.

Step 2

To a solution of the crude oxime intermediate (120-1) (21 mg, 0.046 mmol) in dry acetonitrile (0.79 mL) was added $Cu(OAc)_2$ (1.4 mg, 7.9 μmol). The reaction mixture was heated at 70° C. for 1 h and concentrated. Purification of the residue by silica gel chromatography using 0 to 50% acetone/cyclohexane afforded Example 120 (8 mg, 40% yield). LC-MS, ES+: 514.09 $[M+H]^+$. $^1H$ NMR (400 MHz, Acetone-$d_6$) δ 10.60 (s, 1H), 7.88 (d, J=8.2 Hz, 1H), 7.35 (dd, J=2.3, 0.8 Hz, 1H), 7.29 (td, J=7.7, 1.2 Hz, 1H), 7.20-7.08 (m, 3H), 7.02 (d, J=7.8 Hz, 1H), 6.95 (td, J=7.6, 1.0 Hz, 1H), 6.55 (dd, J=7.4, 1.0 Hz, 1H), 5.17 (t, J=8.3 Hz, 1H), 4.91 (ddd, J=9.8, 8.2, 4.6 Hz, 1H), 4.34 (d, J=10.3 Hz, 1H), 4.05 (d, J=10.4 Hz, 1H), 3.95 (s, 3H), 3.24 (s, 3H), 2.70 (dd, J=8.3, 3.9 Hz, 2H), 1.85 (ddd, J=12.7, 9.4, 4.7 Hz, 2H), 1.73 (dt, J=9.4, 5.3 Hz, 1H) 0.99 (dd, J=15.9, 6.4 Hz, 6H).

Example 121

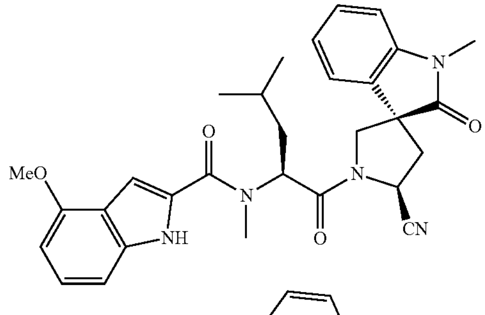

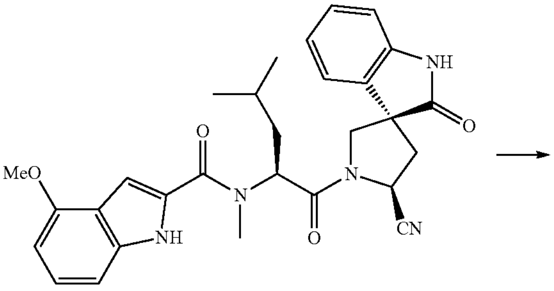

Example 42

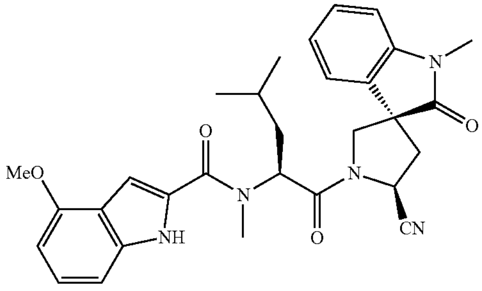

Example 121

Step 1

To a solution of Example 42 (30 mg, 0.058 mmol) in dry acetone (0.29 mL) was added $K_2CO_3$ (12.11 mg, 0.088 mmol) and dimethyl sulfate (8.31 μL, 0.088 mmol) at rt. The reaction mixture was then heated to reflux for 3 hrs. The mixture was then concentrated to remove acetone, diluted with EtOAc, washed with water and brine, dried and concentrated. Purification of the residue on silica gel with 0-50% acetone/cyclohexane provided Example 121 (16 mg, 81% yield). LC-MS, ES−: 526.03 [M−1]. $^1H$ NMR (400 MHz, Acetone-d6) δ 10.36 (s, 1H), 7.20-7.10 (m, 2H), 7.10-7.03 (m, 2H), 7.00-6.91 (m, 2H), 6.87 (t, J=7.5 Hz, 1H), 6.55 (d, J=7.7 Hz, 1H), 5.57 (dd, J=9.6, 5.6 Hz, 1H), 5.20 (t, J=8.1 Hz, 1H), 4.25 (d, J=10.7 Hz, 1H), 4.00 (d, J=10.6 Hz, 1H), 3.97 (s, 3H), 3.45 (s, 3H), 3.22 (s, 3H), 2.77-2.63 (m, 2H), 1.93 (ddd, J=14.4, 9.6, 5.1 Hz, 1H), 1.77 (ddd, J=14.2, 8.7, 5.6 Hz, 1H), 1.62 (dtd, J=8.6, 6.6, 5.0 Hz, 1H), 0.98 (dd, J=23.1, 6.6 Hz, 6H).

Example 122

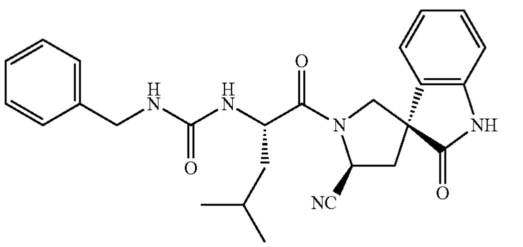

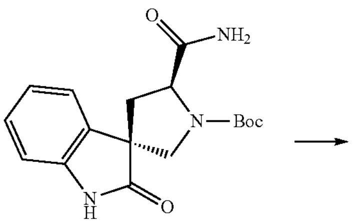

1-3

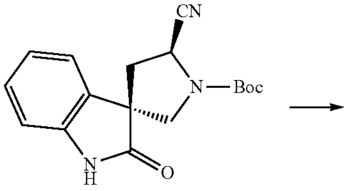

122-1

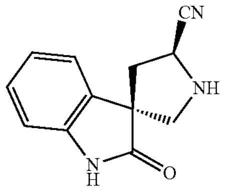

122-2

Step 1

Compound (1-3) (425 mg, 1.38 mmol) was suspended in DCM (5 mL). $Et_3N$ (0.54 mL, 3.9 mmol) and TFAA (0.36 mL, 2.57 mmol) were added dropwise. The mixture was stirred at rt for 30 mins. The 2nd portion of $Et_3N$ (0.2 mL) was added, followed by TFAA (0.12 mL). The mixture was stirred at rt for 20 min and concentrated. Purification of the residue on silica gel afforded compound (122-1) (320 mg, 80%). ESI-MS m/z=314.05 $[M+H]^+$ Step 2:

Lutidine (0.18 mL, 1.05 mmol) in DCM (1 mL) was cooled to 0° C. TMSOTf (0.2 mL, 0.95 mmol) was added and the mixture was stirred at 0° C. for 5 mins. In another tube, compound (122-1) (100 mg, 0.32 mmol) in DCM (1 mL) was cooled to 0° C. The TMSOTf/lutidine solution (1.9 mL) was added dropwise and the resulting mixture was stirred at 0° C. for 20 mins. Aq. $NaHCO_3$ (4 mL) was added and the mixture was stirred for 10 min and extracted with DCM (2×). The combined organic layer was washed with aq. CsF (0.5 M) and brine, dried with $Na_2SO_4$, and concentrated to afford compound (122-2) (68 mg, 100%) as a yellow solid. ESI-MS m/z=213.88 $[M-41]^+$.

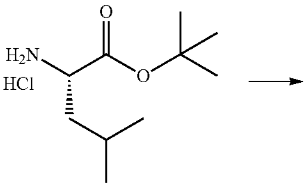

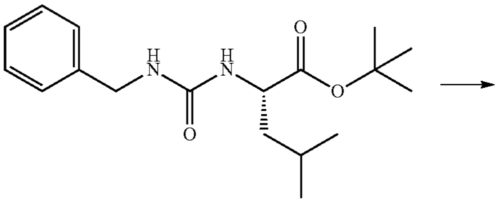

122-3

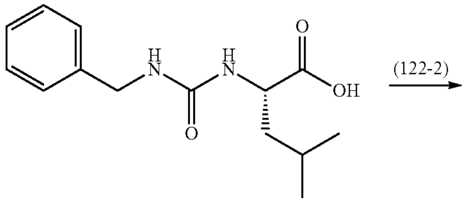

122-4

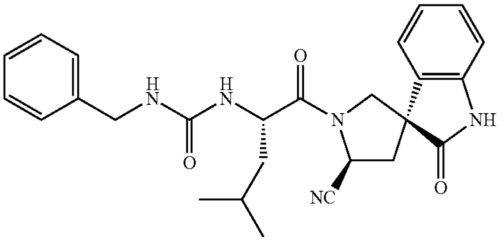

Example 122

Step 3

Leucine t-butyl ester hydrochloride salt (1.0 g, 4.47 mmol) and benzyl isocyanate (595 mg, 4.47 mmol) was mixed in DCM (6 mL). At 0° C. TEA (1.25 mL, 8.95 mmol) was added. The mixture was stirred at rt for 3 h and concentrated. Purification of the residue on silica provided the compound (122-3) (1.5 g) as a colorless syrup. ESI-MS m/z=321.07 $[M+H]^+$.

Step 4

To a solution of compound (122-3) (1.5 g) in DCM (12 mL) was added TFA (1.27 mL, 23 mmol). The mixture was stirred at rt overnight and concentrated. Purification of the residue on silica provided compound (122-4) (301 mg, 25% for two steps) as light yellow oil. ESI-MS m/z=265.02 $[M+H]^+$.

Step 5

To a solution of compound (122-2) (20 mg, 0.094 mmol) and compound (122-4) (32 mg, 1.122 mol) in DMF (1 mL) was added TCFH (39 mg, 0.14 mmol) and methyl imidazole (23 mg, 0.38 mmol). The reaction was stirred at rt for 15 mins, diluted with EtOAc, and washed with water and brine. The organic layer was dried over $Na_2SO_4$ and concentrated. Purification of the residue on silica provided Example 122 (30 mg, 70%) as a yellow solid. ESI-MS m/z=460.31 $[M+H]^+$; $^1H$ NMR (400 MHz, Chloroform-d) δ 9.06 (br, 1H), 7.21 (d, J=4.3 Hz, 4H), 7.18-7.11 (m, 1H), 7.06 (t, J=7.8 Hz, 1H), 6.85 (d, J=7.6 Hz, 1H), 6.83-6.73 (m, 1H), 6.65 (d, J=7.9 Hz, 1H), 6.03 (br, 1H), 5.61 (br, 1H), 4.63 (d, J=7.8 Hz, 1H), 4.45 (t, J=8.3 Hz, 1H), 4.33 (d, J=14.6 Hz, 1H), 4.20 (dd, J=20.2, 12.6 Hz, 2H), 3.85 (d, J=10.3 Hz, 1H), 2.72-2.58 (m, 1H), 2.24 (dd, J=13.0, 8.0 Hz, 1H), 1.80-1.46 (m, 3H), 0.98-0.81 (m, 6H).

Example 433

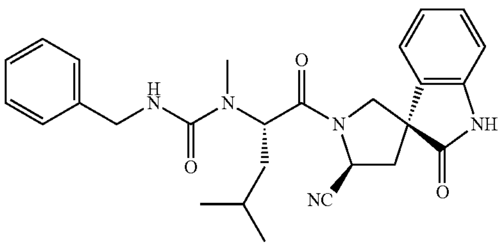

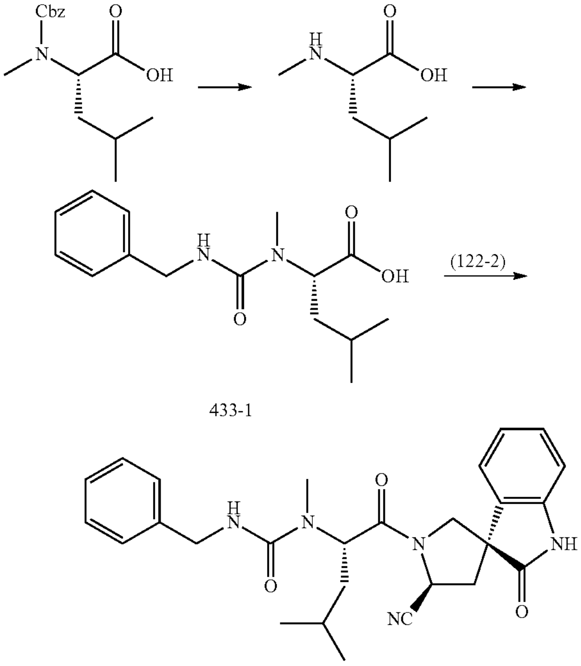

433-1

Example 433

Step 1:

To a solution of N-((benzyloxy)carbonyl)-N-methyl-L-leucine (300 mg, 1.07 mmol) in MeOH (10 mL) was added Pd/C (w/w 10%, 23 mg, 0.02 eq). After degassing, hydrogen balloon was introduced. The mixture was stirred for 1 h at rt, LCMS showed the reaction was completed. The mixture was filtered and the filtrate was concentrated. The crude product was used directly in next step.

Step 2:

The crude product from Step 1 (N-Me-Leucine) and (isocyanatomethyl)benzene (0.15 g, 1.12 mmol, 1.05 eq) was mixed in pyridine (5 mL), and stirred three hours at rt. It was filtered and concentrated. The crude was used directly in next step. ESI-MS m/z=279.07 $[M+H]^+$.

Step 3,

To the solution of crude product of step 2 (037625-1) (125 mg, calc. 0.45 mmol) and intermediate 122-2 (48 mg, 0.225 mmol) in DMF (2 mL) was added N-(chloro(dimethylamino)methylene)-N-methylmethanaminium hexafluorophosphate (126 mg, 0.45 mmol) and 1-methyl-1H-imidazole (92 mg, 1.13 mmol). The mixture was stirred o/n at rt and concentrated. The crude was chromatographied on silica to afford the title compound (40 mg, 38%). ESI-MS m/z=472.19, [M−1]. $^1$H NMR (500 MHz, Acetone-$d_6$) δ 9.71 (s, 1H), 7.27 (td, J=7.5, 1.7 Hz, 1H), 7.25-7.18 (m, 2H), 7.20-7.14 (m, 1H), 7.12-7.06 (m, 2H), 7.05-6.96 (m, 3H), 6.19 (t, J=5.9 Hz, 1H), 5.31 (dd, J=9.3, 5.8 Hz, 1H), 5.15 (t, J=8.4 Hz, 1H), 4.37 (dd, J=10.7, 1.3 Hz, 1H), 4.22-4.10 (m, 2H), 3.91 (d, J=10.7 Hz, 1H), 2.92 (s, 3H), 2.82-2.78 (m, 1H), 2.72 (ddd, J=13.1, 8.5, 1.2 Hz, 1H), 2.66 (dd, J=13.2, 8.2 Hz, 1H), 1.73 (ddd, J=14.3, 9.4, 5.2 Hz, 1H), 1.62 (ddd, J=14.0, 8.5, 5.9 Hz, 1H), 1.52 (dddd, J=15.1, 11.8, 7.6, 5.9 Hz, 1H), 1.31 (s, 1H), 0.95 (dd, J=12.2, 6.6 Hz, 6H).

Example 434

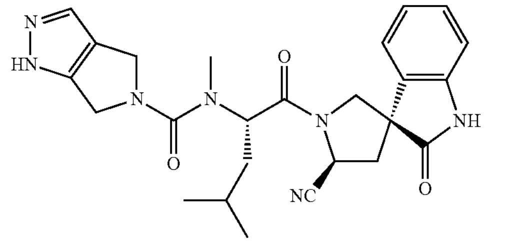

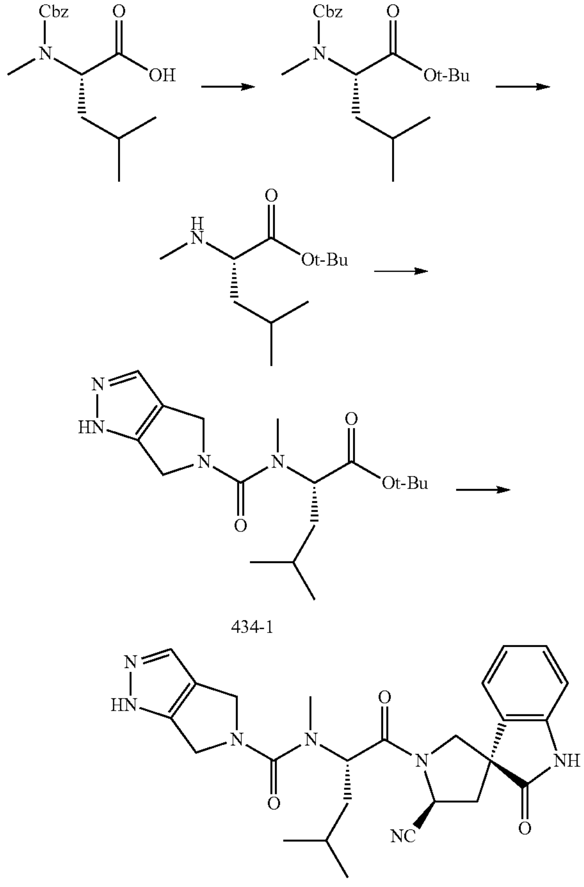

434-1

Example 434

Step 1,

To the solution of N-((benzyloxy)carbonyl)-N-methyl-L-leucine (3.0 g, 10.74 mmol) in DCM (30 mL), was added t-butyl alcohol (2.05 mL, 21.48 mmol) and DCC (2.66 g, 12.89 mmol). The resulting mixture was stirred at rt o/n and filtered. The filtrate was concentrated. The crude was chromatographied on silica to afford Cbz-N-Me-L-Leu-OtBu (3.2 g, 89%). ESI-MS m/z=336.03 $[M+H]^+$.

Step 2:

To a solution of Cbz-N-Me-L-Leu-OtBu (3.2 g, 9.54 mmol) in MeOH (30 mL) was added Pd/C (w/w 10%, 355 mg, 0.035 eq). After degassing, the mixture was stirred under hydrogen (balloon) at rt for 1 h. LCMS showed the reaction was completed. Solvent was removed to give the desired product N-Me-L-Leu-OtBu (1.68, 87%). ESI-MS m/z=202.02 $[M+H]^+$.

Step 3,

Bis(trichloromethyl) carbonate (103 mg, 0.35 mmol) was dissolved in DCM (3 mL). At 0° C. a solution of N-Me-L-Leu-OtBu (200 mg, 0.99 mmol) and TEA (0.54 mL, 3.97 mmol) in DCM (2 mL) was added and the mixture was stirred at 0° C. for 30 mins. 1,4,5,6-tetrahydropyrrolo[3,4-c]pyrazole dihydrochloride (I81 mg, 0.99 mmol) and TEA (0.45 mL) in THF (3 mL) were added. The mixture was stirred ar rt o/n. After concentration, the crude was chromatographied on silica to afford (037826-1) (225 mg, 67%). ESI-MS m/z=337.12 $[M+H]^+$. Example 434 was synthesized from (434-1) following the procedures described in Example 122. [M−1]. 473.97.

Example 435

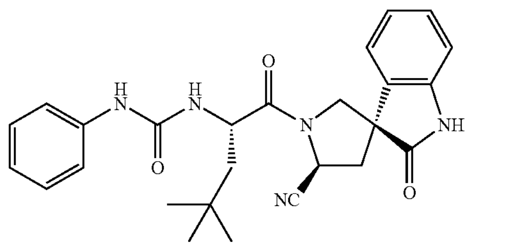

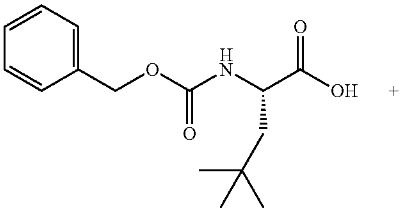

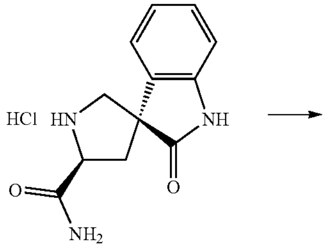

1-4

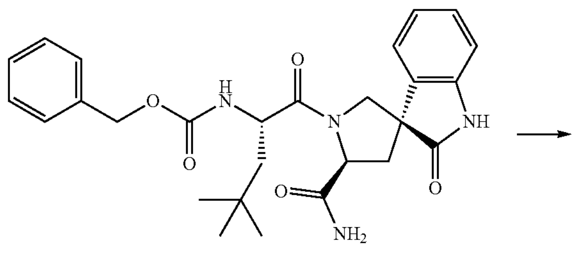

435-1

-continued

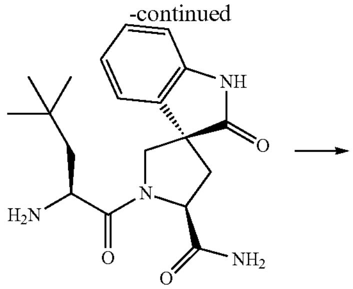

435-2

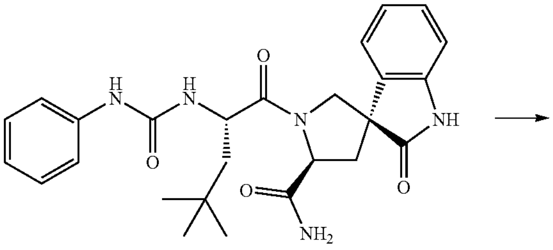

435-3

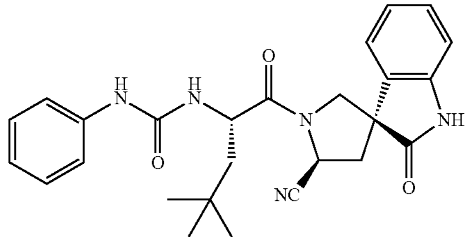

Example 435

Step 1

To a stirred solution of Compound 1-4 (4.65 g, 17.37 mmol, 1.0 equiv) and (S)-2-(((benzyloxy)carbonyl)amino)-4,4-dimethylpentanoic acid (1.1 equiv) in $CH_2Cl_2$ (80 mL) and DMF (8 mL) was added DIEA (3 equiv) and HATU (1.1 equiv). The resulting mixture was stirred at rt for 1 h. The reaction was quenched with 10% citric acid at rt. The resulting mixture was extracted with $CH_2Cl_2$. The combined organic layers were washed with brine, dried over anhydrous $Na_2SO_4$. After filtration, the filtrate was concentrated under reduced pressure. The residue was purified by silica gel column chromatography, eluted with cyclohexane/acetone (0-50%) to afford the desired product as an off-white solid. (ES, m/z): [M+H]+=493.35.

Step 2

To a solution of 435-1 (500.00 mg, 1.015 mmol, 1.00 equiv) in 10 mL MeOH was added Pd/C (10%, 50 mg) under nitrogen atmosphere in a 50 mL round-bottom flask. The mixture was hydrogenated at r.t. for 1 h under hydrogen atmosphere using a hydrogen balloon, filtered through a Celite pad, and concentrated under reduced pressure to give the desired product. (ES, m/z): $[M+H]^+$=359.25.

Step 3

To a stirred solution of 435-2 (79.74 mg, 0.222 mmol, 1 equiv) and DIEA (57.50 mg, 0.444 mmol, 2 equiv) in $CH_2Cl_2$ (2 mL) was added isocyanatobenzene (26.5 mg, 0.222 mmol, 1 equiv) in $CH_2Cl_2$ (3 mL) dropwise at 0° C. The reaction was monitored by LC-MS until complete conversion. The mixture was quenched with saturated $NaHCO_3$ solution, extracted with $CH_2Cl_2$ and concentrated under vacuum to afford the desired product (95.5 mg, 89.89%) as a yellow solid, which was used in the next step directly without further purification.

Step 4

A mixture of 435-3 (95.5 mg, 0.200 mmol, 1 equiv), DIEA (206.77 mg, 1.600 mmol, 8 equiv) and $T_3P$ (763.53 mg, 1.200 mmol, 6 equiv, 50%) in ethyl acetate (1 mL) was stirred for 1 h at 80° C. The mixture was extracted with ethyl acetate (30 mL) and the organic layer was concentrated under vacuum. The residue was purified by reverse flash chromatography to give the title compound (21.5 mg, 23.40%) as a white solid. $[M+H]^+$=460.30, 1H NMR (400 MHz, Methanol-$d_4$) δ 1.03 (s, 9H), 1.56-1.71 (m, 1H), 1.82 (dd, J=14.5, 4.3 Hz, 1H), 2.69 (d, J=8.0 Hz, 2H), 3.98 (d, J=10.3 Hz, 1H), 4.35 (d, J=10.3 Hz, 1H), 4.61 (dd, J=8.5, 4.2 Hz, 1H), 5.17 (t, J=8.0 Hz, 1H), 6.77-7.09 (m, 3H), 7.13-7.76 (m, 6H).

The following examples were prepared employing similar protocol as described above.

| Example | Structure | MS |
|---|---|---|
| 436 | 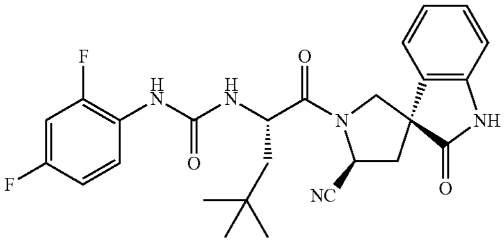 [SMILES: CC(C)(C)C[C@H](NC(=O)Nc1ccc(F)cc1F)C(=O)N1C[C@]2(C[C@H]1C#N)C(=O)Nc1ccccc12] | 496.25 |
| 437 | 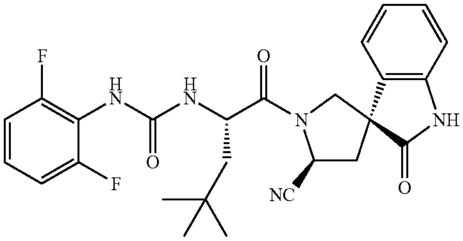 [SMILES: CC(C)(C)C[C@H](NC(=O)Nc1c(F)cccc1F)C(=O)N1C[C@]2(C[C@H]1C#N)C(=O)Nc1ccccc12] | 496.25 |
| 438 | 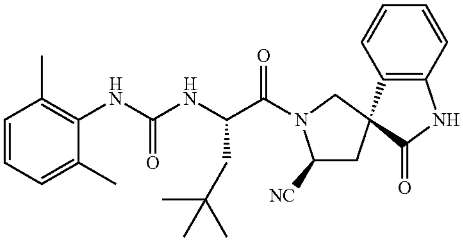 [SMILES: Cc1cccc(C)c1NC(=O)N[C@@H](CC(C)(C)C)C(=O)N1C[C@]2(C[C@H]1C#N)C(=O)Nc1ccccc12] | 488.30 |
| 439 | 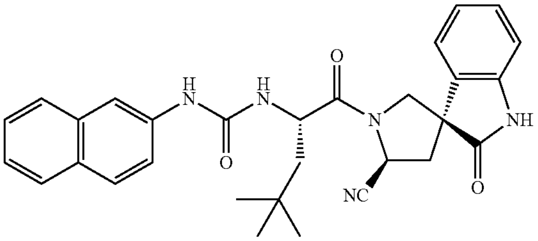 [SMILES: CC(C)(C)C[C@H](NC(=O)Nc1ccc2ccccc2c1)C(=O)N1C[C@]2(C[C@H]1C#N)C(=O)Nc1ccccc12] | 510.25 |
| 440 | 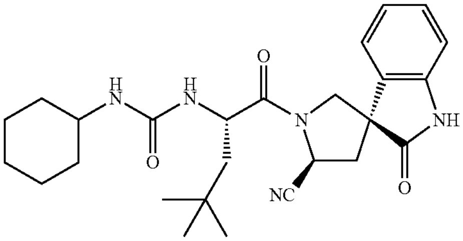 [SMILES: CC(C)(C)C[C@H](NC(=O)NC1CCCCC1)C(=O)N1C[C@]2(C[C@H]1C#N)C(=O)Nc1ccccc12] | 466.20 |

-continued

| Example | Structure | MS |
|---|---|---|
| 441 | 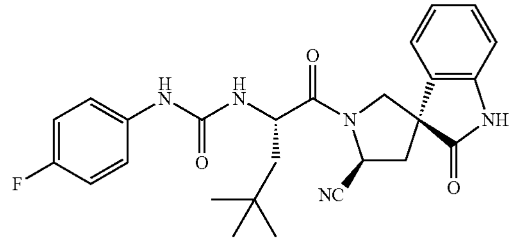 [SMILES: CC(C)(C)C[C@H](NC(=O)Nc1ccc(F)cc1)C(=O)N1C[C@]2(C[C@H]1C#N)C(=O)Nc1ccccc12] | 500.15 [M + Na]$^+$ |

Example 442

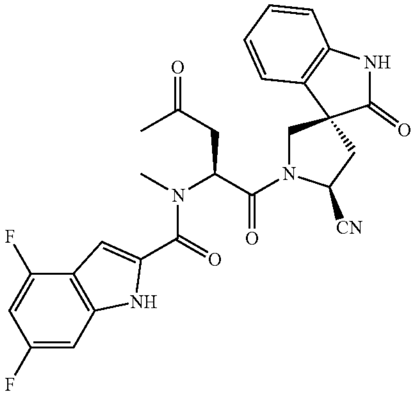

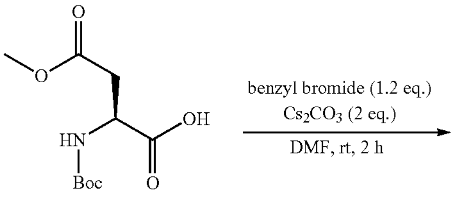

1

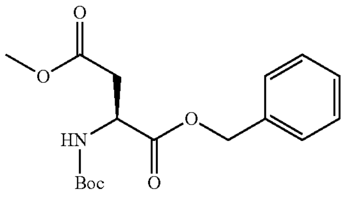

2

Step 1:

Into a round-bottom flask purged and maintained with a nitrogen atmosphere was added Boc-Asp-Ome 1 (20 g, 81 mmol), DMF (300 ml), cesium carbonate (52.7 g, 162 mmol) and benzyl bromide (11.55 ml, 97 mmol). The resulting solution was stirred at room temperature for 2 h, then diluted with EtOAc. The mixture was washed 3× with water and 3× with brine, then dried over anhydrous sodium sulfate, filtered and concentrated to yield crude 2. Carried forward crude.

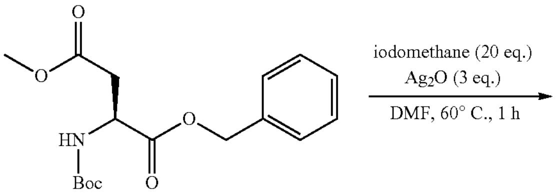

2

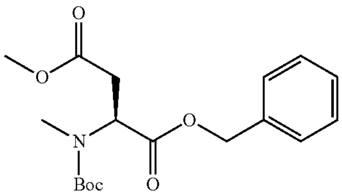

3

Step 2:

To a round-bottom flask purged and maintained with a nitrogen atmosphere containing crude 2 (27.3 g, 81 mmol) was added DMF (162 ml), silver oxide (56.3 g, 243 mmol) and iodomethane (101 ml, 1618 mmol). The resulting solution was heated at 60° C. for 1 h then diluted with ethyl acetate. The mixture was washed 3× with water and 3× with brine, then dried over anhydrous sodium sulfate, filtered and concentrated. Crude material was purified by flash chromatography (ethyl acetate/cyclohexane 0-20%) to yield 3 (17 g, 60% over two steps.) $^1H$ NMR (400 MHz, Chloroform-d) δ 7.44-7.27 (m, 5H), 5.27-5.10 (m, 2H), 4.86-4.56 (m, 1H), 3.73-3.65 (m, 3H), 3.13 (dd, J=16.5, 6.4 Hz, 1H), 3.01-2.85 (m, 3H), 2.78 (dq, J=15.7, 8.0 Hz, 1H), 1.41 (d, J=12.7 Hz, 9H).

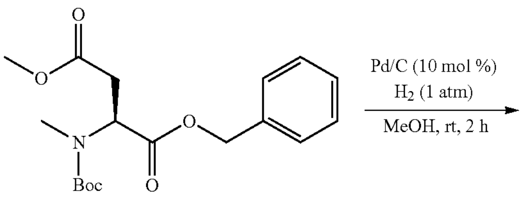

3

-continued

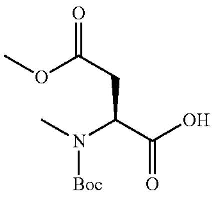

4

Step 3:

Palladium on carbon (2.120 g, 10 wt %, 1.992 mmol) was added to a round-bottom flask under nitrogen. 3 (7.0 g, 19.92 mmol) was added as a solution in methanol (100 ml). The reaction vessel was evacuated and backfilled 3× with a hydrogen balloon then stirred at room temperature for 2 h. Evacuated and backfilled with nitrogen then filtered through Celite and concentrated to yield crude 4 (5.2 g, 100% yield.) Carried forward crude. $^1$H NMR (400 MHz, Chloroform-d) δ 10.24 (br s, 1H), 4.64 (dt, J=26.4, 6.9 Hz, 1H), 3.67 (dd, J=13.9, 6.9 Hz, 3H), 3.07 (dd, J=15.6, 6.7 Hz, 1H), 2.97-2.80 (m, 3H), 2.80-2.52 (m, 1H), 1.43 (s, 9H).

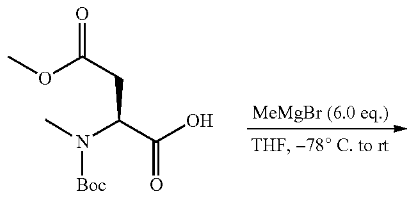

4

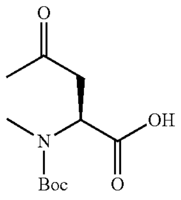

5

Step 4:

To a solution of 4 (967 mg, 3.70 mmol) in THF (35 mL) in a roundbottom flask under nitrogen at −78° C. was added methylmagnesium bromide solution (7.4 mL, 22.2 mmol, 3.0 M in $Et_2O$) dropwise. The mixture was stirred for 1 h at the same temperature, then warmed to room temperature, and stirred for an additional 1 h. The reaction was quenched with sat. ammonium chloride solution, and extracted 3× with DCM. The organic layer was dried over sodium sulfate, filtered, and concentrated. The crude was purified by flash chromatography (MeOH:DCM 0-10%) to yield 6 (85 mg, 9%.) $^1$H NMR (400 MHz, Chloroform-d) δ 11.10 (s, 1H), 4.65 (q, J=6.3 Hz, 1H), 3.31 (ddd, J=17.6, 10.9, 6.5 Hz, 1H), 2.95 (d, J=6.3 Hz, 3H), 2.80 (dd, J=17.6, 6.1 Hz, 1H), 2.22 (d, J=2.3 Hz, 3H), 1.45 (d, J=7.7 Hz, 9H).

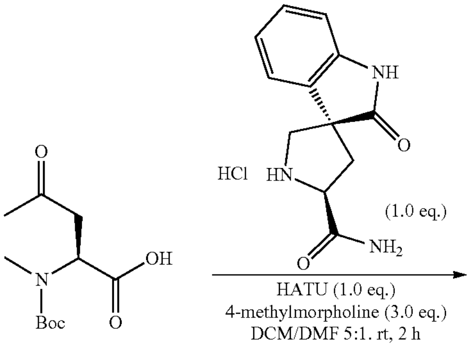

5

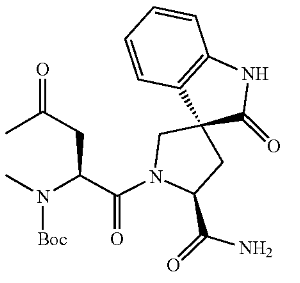

6

Step 5:

5 (85 mg, 0.347 mmol) and (3R,5'S)-2-oxospiro[indoline-3,3'-pyrrolidine]-5'-carboxamide hydrochloride (93 mg, 0.347 mmol) were taken up in DCM (1.16 mL) and DMF (0.23 mL). At 0° C., 4-methylmorpholine (114 μl, 1.04 mmol) was added, stirred for 5 min. HATU (132 mg, 0.347 mmol) was added at the same temperature. The mixture was stirred at at 0° C. for 5 min, then warmed to room temperature and stirred for 2 h. The mixture was diluted with DCM, washed with sat. sodium bicarbonate solution, 1 M HCl, and brine. The HCl aqueous layer was extracted an additional 3× with DCM. The collected organic layers were dried over sodium sulfate, filtered and concentrated. The crude residue was used in the next step. Observed M+H=458.92.

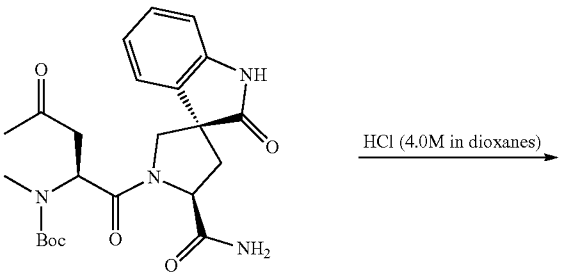

6

-continued

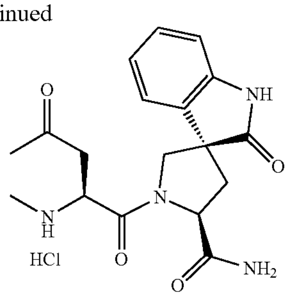

7

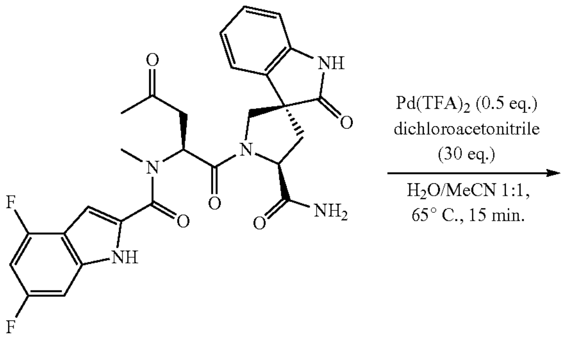

8

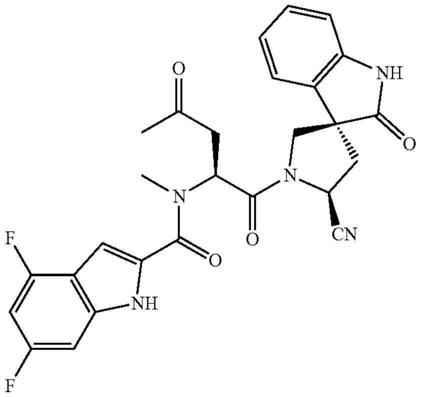

9
Example 442

Step 6:

Compound 6 (159 mg, 0.347 mmol) was treated with HCl (1.73 mL, 6.94 mmol, 4.0 M solution in dioxanes). The mixture was stirred at room temp for 30 min then volatiles was removed under a stream of nitrogen. The crude salt was used in next step. Observed M+H=340.87.

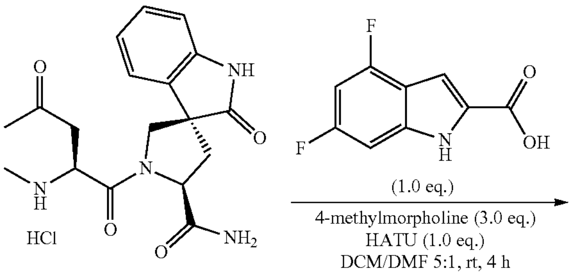

7

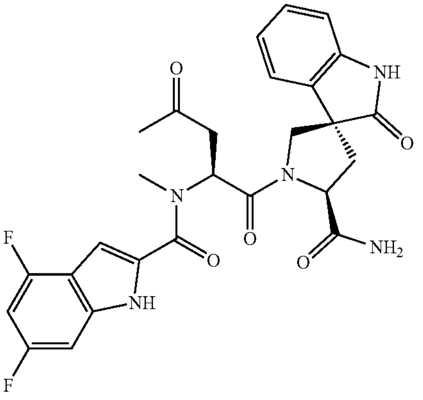

8

Step 7:

7 (137 mg, 0.347 mmol) and 4,6,-difluoro-1H-indole-2-carboxylic acid (68 mg, 0.347 mmol) were taken up in DCM (1.5 mL) and DMF (0.3 mL). 4-methylmorpholine (114 µl, 1.04 mmol) was added, stirred for 5 min at rt. HATU (132 mg, 0.347 mmol) was added. The mixture was stirred for 2 h, diluted with DCM, washed with sat. sodium bicarbonate solution, 1 M HCl and brine. The aqueous layer was extracted an additional 3× with DCM. The collected organic layers were passed through a phase separator and concentrated. The crude material was used in the next step. Observed M+H=537.84.

Step 8:

Crude 8 (187 mg, 0.347 mmol) was dissolved in water (1.74 mL)/acetonitrile (1.74 mL) Under nitrogen, 2,2-dichloroacetonitrile (0.56 mL, 6.94 mmol) was added, followed by palladium(II) trifluoroacetate (115 mg, 0.347 mmol). The mixture was heated to 65° C. and stirred for 15 min. The reaction was diluted with DCM and brine, extracted 3× with DCM. The collected organic layer was passed through a phase separator and concentrated. Purification of the residue by RPHPLC (0.1% TFA/MeCN/0.1% TFA/water 20-95%) yielded 30 mg 9, Example 442 (17%.) Observed M+Na=541.7. $^1$H NMR (400 MHz, Acetone-d$_6$) δ 10.79 (s, 1H), 9.66 (s, 1H), 7.12-6.96 (m, 3H), 6.96-6.65 (m, 4H), 5.80 (dd, J=8.9, 5.2 Hz, 1H), 5.21 (t, J=8.2 Hz, 1H), 4.20 (s, 1H), 3.97 (d, J=10.6 Hz, 1H), 3.52 (dd, J=17.2, 9.0 Hz, 1H), 3.40 (s, 3H), 2.96-2.68 (m, 3H), 2.23 (s, 3H).

Example 443

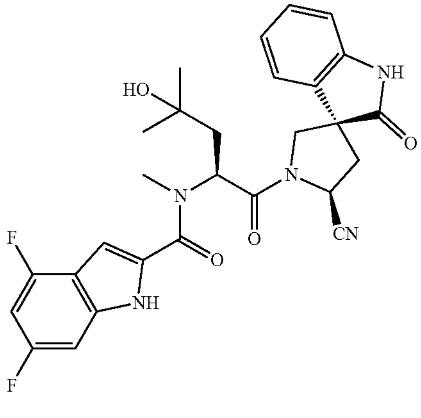

-continued

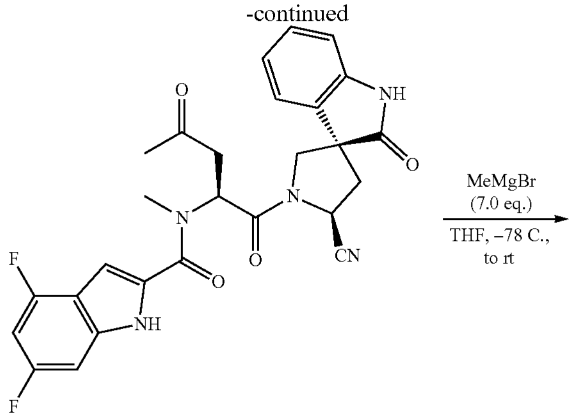

Example 442

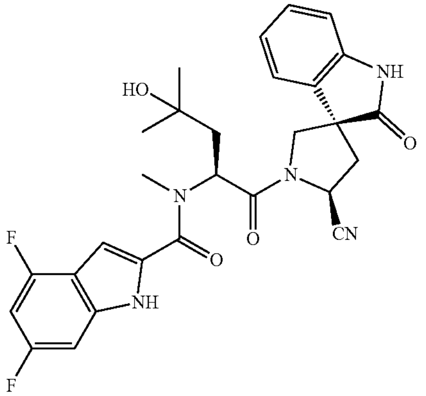

Example 443

Example 442 (30 mg, 0.058 mmol) was dissolved in THF (0.58 mL) in a vial under nitrogen. The solution was cooled to −78° C. and methylmangesium bromide solution (58 μl, 0.173 mmol, 3.0M in $Et_2O$) was added dropwise. The mixture was stirred for 1 h at the same temperature, then warmed to room temperature and stirred for an additional 1 h. The reaction was quenched with sat. ammonium chloride solution, extracted 3× with DCM and dried over sodium sulfate. The organic layers was filtered, concentrated, and purified by Shimadzu preparative HPLC (0-95% 0.1% FA/$H_2O$ and 0.1% FA/acetonitrile) to yield Example 443 (2 mg, 6%.) Observed M+H=535.9. $^1$H NMR (400 MHz, Acetone-$d_6$) δ 11.16 (s, 1H), 9.69 (s, 1H), 7.36-7.22 (m, 1H), 7.18-7.06 (m, 3H), 7.06-6.84 (m, 2H), 6.84-6.49 (m, 1H), 5.23 (t, J=8.2 Hz, 1H), 4.10-3.81 (m, 2H), 3.45 (s, 3H), 2.72 (dd, J=18.5, 8.4 Hz, 2H), 2.56-2.38 (m, 1H), 2.25 (s, 1H), 1.95-1.81 (m, 1H), 1.21 (s, 6H).

Example 444

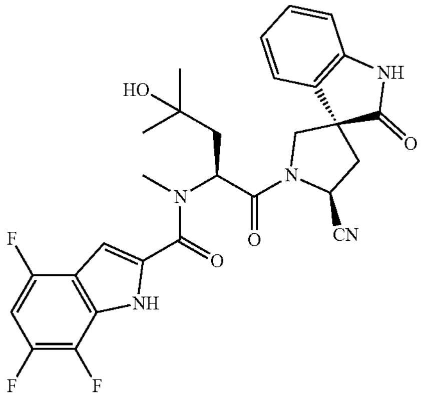

Example 444 was synthesized employing a similar protocol as described in Example 443. [M+H] 553.9.

Example 123

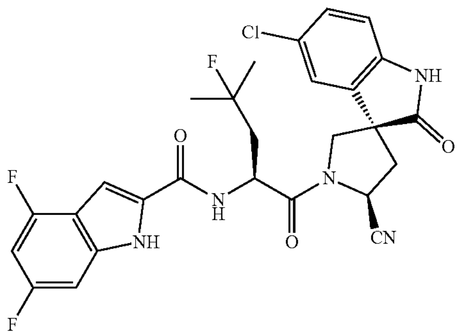

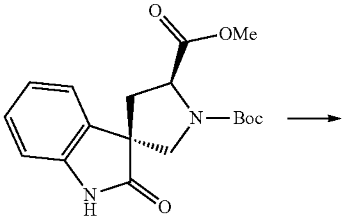

1-2

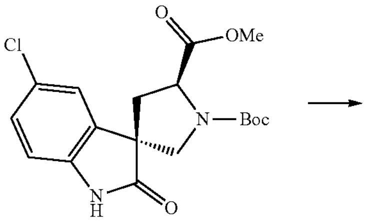

123-1

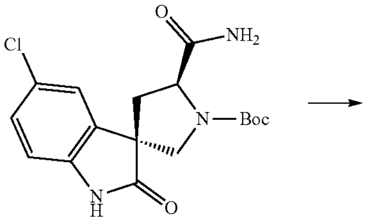

123-2

-continued

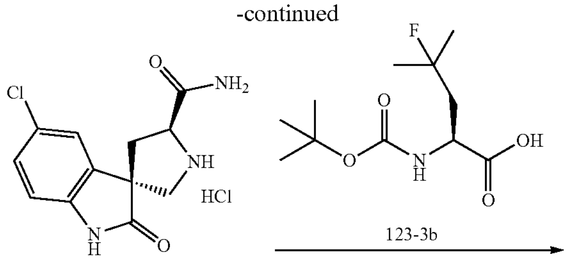

123-3

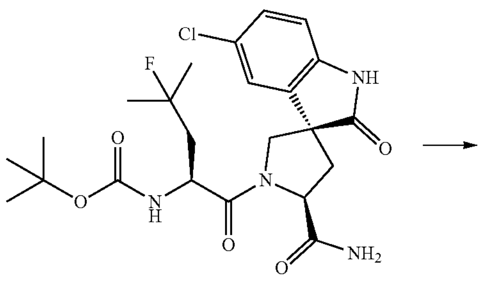

123-4

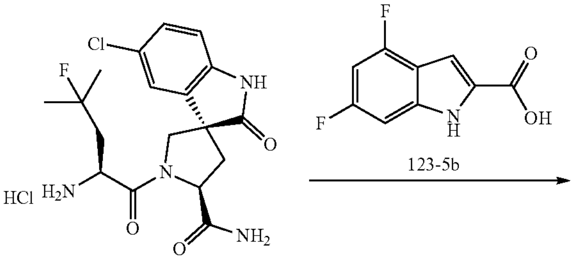

123-5

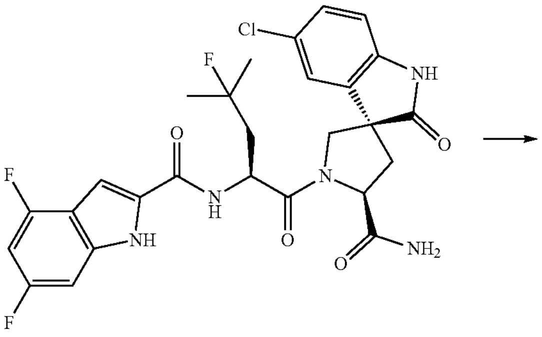

123-6

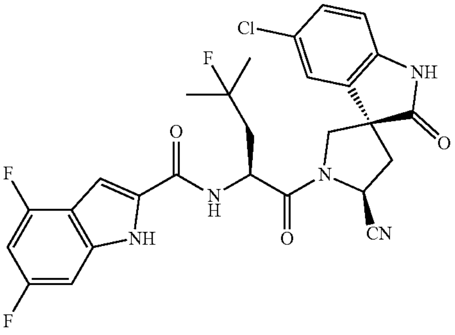

Example 123

Step 1

Compound (1-2) (5.00 g) was dissolved in acetic acid (115 mL). Sulfuryl chloride (2.09 g) was slowly added to the resulting solution at room temperature. The mixture was stirred overnight at room temperature. Then, the reaction mixture was concentrated. The crude residue was dissolved in methylene chloride (100 mL) and triethylamine (5.84 g, 8.05 mL, 4.0 equiv) was added, followed by tert-butyl dicarbonate (4.73 g, 1.5 equiv). Then, the organic layer was washed with 1M HCl (2×50 mL), then brine (100 mL), then dried over magnesium sulfate. Upon concentration, the crude residue was purified by RPHPLC, affording compound (123-1) (2.81 g, 51% yield). $[M+H]^+$, 381.1.

Step 2

Compound (123-1) (2.81 g) was dissolved in 7M methanolic ammonia (36.1 mL) in a 100 mL pressure vessel. The mixture was heated at 60° C. for 36 h. Upon concentration, the crude residue was triturated with acetonitrile to afford compound (123-2) as a colorless solid (1.92 g, 71% yield). $[M+H]^P$, 366.1.

Step 3

Compound (123-2) (1.61 g) was dissolved in 4M HCl/1,4-dioxane (22.0 mL). The resulting mixture was stirred at room temperature for 2 h. Concentration afforded compound (123-4) (1.33 g) as a white solid which was used without further purification. $[M+H]^+$, 266.1.

Step 4

Compound (123-3) (103.0 mg), compound (123-3b) (98.0 mg), and HATU (149.0 mg) were combined in a 40 mL vial equipped with a stir bar. DMF (2.27 mL) was added, followed by DIPEA (179 The resulting mixture was stirred at room temperature overnight. Upon completion, the reaction mixture was diluted with ethyl acetate (50 mL), washed with 1M HCl (2×20 mL) and brine (20 mL), then dried over magnesium sulfate. Upon concentration, the crude residue was purified by silica gel column chromatography (0 to 10% MeOH/DCM) affording compound (123-4) (58.1 mg, 34% yield). $[M+H]^+$, 497.2.

Step 5

Compound (123-4) (58.1 mg) was dissolved in 4M HCl/1,4-dioxane (585 μL). The resulting mixture was stirred for 1.5 h. The reaction mixture was concentrated to afford compound (123-5) (51.0 mg) which was used in the next step without purification. $[M+H]^+$, 397.2.

Step 6

Compound (123-5) (51.0 mg), compound (123-5b) (26.7 mg), and HATU (51.5 mg) were combined in 40 mL vial equipped with a stir bar. DMF (785 μL) was added, followed by DIPEA (62 The resulting mixture was stirred 2.5 h at room temperature. The reaction mixture was diluted with ethyl acetate (100 mL) and washed with 1M HCl (3×20 mL) and brine (20 mL). The organic layer was dried over magnesium sulfate then concentrated. Purification of the crude residue by silica gel column chromatography (0 to 10% MeOH/DCM) afforded compound (123-6) (26.9 mg, 40% yield). $[M+H]^+$, 576.1.

Step 7

Compound (123-6) (26.9 mg) was dissolved in a mixture of MeCN (500 μL) and water (500 μL) in a 20 mL vial. Next, 2,2-dichloroacetonitrile (56 μL) was added, followed by palladium(II) trifluoroacetate (1.5 mg). The vial was sealed and the mixture was heated at 65° C. for 2 h. Additional 2,2-dichloroacetonitrile (56 μL) and palladium(II) trifluoroacetate (1.5 mg) were added, and the mixture was heated at 70° C. for 20 min. Upon cooling to room temperature, the mixture was purified by RPHPLC to afford Example 123 as a white solid (10.0 mg, 38% yield). ESI MS m/z=558.1 $[M+H]^+$. $^1$H NMR (400 MHz, acetone-$d_6$, δ ppm): δ10.96 (s, 1H), 9.80 (s, 1H), 8.18-8.16 (m, 1H), 7.35-7.34 (m, 1H), 7.15-7.09 (m, 3H), 6.97-6.95 (m, 1H). 6.77-6.72 (m, 1H), 5.23 (app t, J=8.2, 8.2 Hz, 1H), 5.15-5.09 (m, 1H), 4.46 (d, J=10.5 Hz, 1H), 4.06 (10.5 Hz), 2.85-2.67 (m, 2H), 2.42-2.18 (m, 2H), 1.47 (d, $J_{19F\text{-}1H}$=3.2 Hz, 3H), 1.41 (d, $J_{19F\text{-}1H}$=3.2 Hz, 3H).

The following examples were prepared employing similar protocol as described above.

| Example | Structure | MS | NMR |
|---|---|---|---|
| 445 | 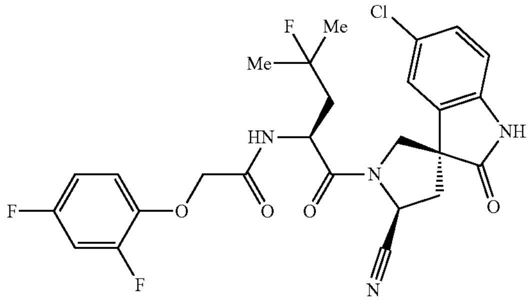 [SMILES: CC(C)(F)C[C@H](NC(=O)COc1ccc(F)cc1F)C(=O)N1C[C@]2(C[C@H]1C#N)C(=O)Nc1ccc(Cl)cc12] | [M + 1] 549.0 | $^1$H NMR (400 MHz, Acetone-d$_6$) δ 9.81 (s, 1H), 7.75 (d, J = 7.7 Hz, 1H), 7.30 (dd, J = 8.3, 2.1 Hz, 1H), 7.22-7.09 (m, 3H), 7.02 (d, J = 8.3 Hz, 1H), 6.98-6.93 (m, 1H), 5.22 (t, J = 8.2 Hz, 1H), 4.94-4.88 (m, 1H), 4.56 (s, 2H), 4.35 (d, J = 10.6 Hz, 1H), 4.04 (s, J = 10.6 Hz, 1H), 2.86-2.67 (m, 2H), 2.36-2.11 (m, 2H), 1.44 (s, 3H), 1.39 (s, 3H). |
| 446 | 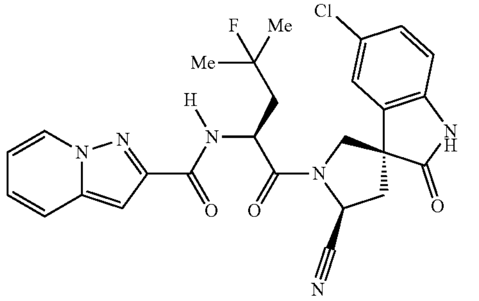 [SMILES: CC(C)(F)C[C@H](NC(=O)c1cc2ccccn2n1)C(=O)N1C[C@]2(C[C@H]1C#N)C(=O)Nc1ccc(Cl)cc12] | [M + 1] 523.2 | $^1$H NMR (400 MHz, Acetone-d$_6$) δ 8.62 (dd, J = 7.1, 1.1 Hz, 1H), 7.94 (d, J = 7.8 Hz, 1H), 7.76 (d, J = 8.9 Hz, 1H), 7.32-7.28 (m, 1H), 7.24 (d, J = 2.1 Hz, 1H), 7.21 (dd, J = 8.2, 2.1 Hz, 1H), 7.05 (td, J = 6.9, 1.4 Hz, 1H), 6.99 (d, J = 8.3 Hz, 1H), 6.94 (s, 1H), 5.25 (t, J = 8.1 Hz, 1H), 5.10-5.05 (m, 1H), 4.47 (d, J = 10.5 Hz, 1H), 4.09 (d, J = 10.5 Hz, 1H), 2.88-2.80 (m, 1H), 2.72 (dd, J = 13.4, 7.7 Hz, 1H), 2.45-2.25 (m, 2H), 1.51 (d, J = 3.4 Hz, 3H), 1.46 (d, J = 3.5 Hz, 3H). |

Example 447

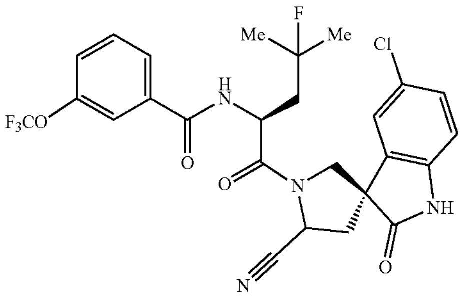

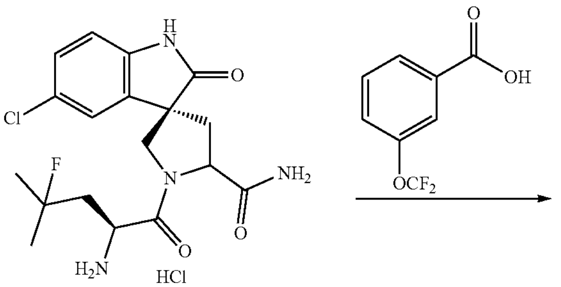

-continued

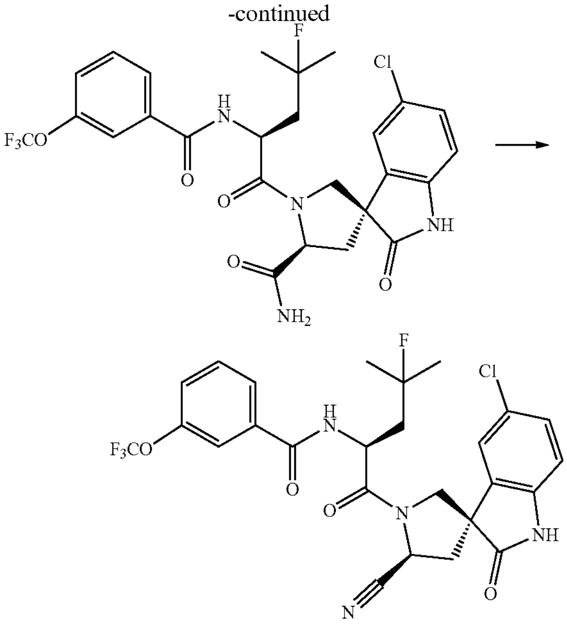

Step 1

In a 40 mL screw cap vial equipped with a stir bar and pressure release septum, (S)-1-((3R,5'S)-5'-carbamoyl-5-chloro-2-oxospiro[indoline-3,3'-pyrrolidin]-1'-yl)-4-fluoro-4-methyl-1-oxopentan-2-aminium chloride (1.0 equiv) was combined with 3-(trifluoromethoxy)benzoic acid (26.9 mg, 1.15 equiv) and HATU (49.5 mg, 1.15 equiv). Next, DMF (0.76 mL, 0.15M) was added, followed immediately by DIPEA (60 μL, 3.0 equiv). The resulting mixture was stirred at rt until complete consumption of the starting materials, which was determined by LCMS. The mixture was diluted with DCM (20 mL) and washed with 1.2M HCl and brine. The organic layer was passed through a phase separator and concentrated to afford crude (3R,5'S)-5-chloro-1'-((S)-4-fluoro-4-methyl-2-(3-(trifluoromethoxy)benzamido)pentanoyl)-2-oxospiro[indoline-3,3'-pyrrolidine]-5'-carboxamide. $[M+H]^+$, 585.3.

Step 2

In a 40 mL screw cap vial equipped with a stir bar and pressure release septum, the crude (3R,5'S)-5-chloro-1'-((S)-4-fluoro-4-methyl-2-(3-(trifluoromethoxy)benzamido)pentanoyl)-2-oxospiro[indoline-3,3'-pyrrolidine]-5'-carboxamide generated in Step 1 was dissolved in DCM (1.5 mL, 0.075M). The resulting solution was cooled in an ice bath and triethylamine (126 μL, 8.0 equiv) was added, followed by trifluoroacetic anhydride (64 μL, 4.0 equiv). The resulting mixture was stirred at rt for 1 h. At this time, the mixture was diluted with DCM (10 mL) and 2.0 mL of 30% ammonium hydroxide was added. The mixture was shaken briefly, and diluted with saturated aqueous sodium bicarbonate (7.5 mL). The organic phase was passed through a phase separator and concentrated. The crude residue was purified by RPHPLC (MeCN/water, 0.1% TFA) to afford the title compound $^1$H NMR (400 MHz, Acetone-$d_6$) δ 9.83 (s, 1H), 8.27 (d, J=7.7 Hz, 1H), 7.91 (dt, J=7.8, 1.3 Hz, 1H), 7.82-7.80 (m, 1H), 7.64-7.60 (m, 1H), 7.54-7.51 (m, 1H), 7.25 (dd, J=8.3, 2.1 Hz, 1H), 7.20 (d, J=2.1 Hz, 1H), 7.01 (d, J=8.3 Hz, 1H), 5.24 (t, J=8.3 Hz, 1H), 5.08-5.03 (m, 1H), 4.54 (d, J=10.5, 1H), 4.06 (d, J=10.5 Hz, 1H), 2.86-2.81 (m, 1H), 2.72 (dd, J=13.3, 8.2 Hz, 1H), 2.41-2.22 (m, 2H), 1.50 (d, J=6.7 Hz, 3H), 1.44 (d, J=6.7 Hz, 3H). [M−1], 564.7.

The following examples were prepared employing similar protocol as described above.

| Example | Structure | MS | NMR |
|---|---|---|---|
| 448 | 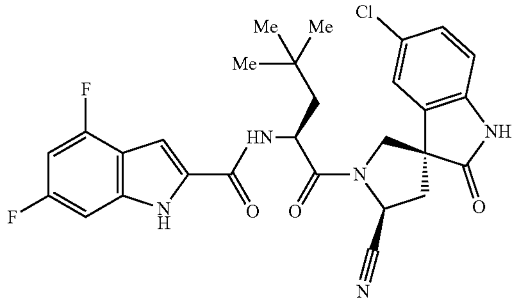 [SMILES: CC(C)(C)C[C@H](NC(=O)c1cc2c(F)cc(F)cc2[nH]1)C(=O)N1C[C@]2(C[C@H]1C#N)C(=O)Nc1ccc(Cl)cc12] | [M + 1] 554.1 | $^1$H NMR (400 MHz, Acetone-$d_6$) δ 11.08 (s, 1H), 9.86 (s, 1H), 8.28 (d, J = 8.5 Hz, 1H), 7.40-7.39 (m, 1H), 7.12-7.07 (m, 3H), 6.91 (d, J = 8.1 Hz, 1H), 6.72 (td, J = 10.3, 2.1 Hz, 1H), 5.28 (t, J = 8.2 Hz, 1H), 5.10-5.05 (m, 1H), 4.61-4.46 (m, 1H), 4.12 (d, J = 10.4 Hz, 1H), 2.88-2.69 (m, 2H), 2.02-1.85 (m, 2H), 1.05 (s, 9H). |
| 449 | 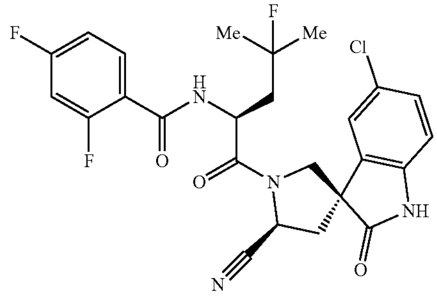 [SMILES: CC(C)(F)C[C@H](NC(=O)c1ccc(F)cc1F)C(=O)N1C[C@]2(C[C@H]1C#N)C(=O)Nc1ccc(Cl)cc12] | [M − 1] 517.1 | 1H NMR (400 MHz, Acetone-d6) δ 9.83 (s, 1H), 7.94-7.88 (m, 1H), 7.84-7.80 (m, 1H), 7.29-7.27 (m, 2H), 7.21-7.09 (m, 2H), 7.02-7.00 (m, 1H), 5.24 (t, J = 8.3 Hz, 1H), 5.06-4.97 (m, 1H), 4.45 (dd, J = 10.5, 1.1 Hz, 1H), 4.07 (d, J = 10.5 Hz, 1H), 2.89-2.67 (m, 2H), 2.41-2.20 (m, 2H), 1.51 (d, J = 4.3 Hz, 3H), 1.46 (d, J = 4.2 Hz, 3H). |
| 450 | 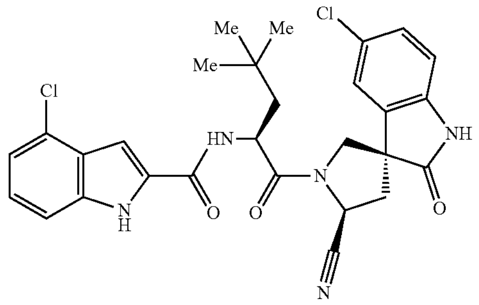 [SMILES: CC(C)(C)C[C@H](NC(=O)c1cc2c(Cl)cccc2[nH]1)C(=O)N1C[C@]2(C[C@H]1C#N)C(=O)Nc1ccc(Cl)cc12] | [M − 1] 550.1 | 1H NMR (400 MHz, Acetone-d6) δ 10.88 (s, 1H), 9.81 (s, 1H), 8.20 (d, J = 8.6 Hz, 1H), 7.51 (d, J = 8.2 Hz, 1H), 7.40-7.41 (m, 1H), 7.25-7.21 (m, 1H), 7.17-7.11 (m, 3H), 6.97 (d, J = 8.3 Hz, 1H), 5.24 (t, J = 8.2 Hz, 1H), 5.05-5.00 (m, 1H), 4.52 (d, J = 10.5, 1H), 4.08 (d, J = 10.4 Hz, 1H), 2.85-2.68 (m, 2H), 1.98-1.85 (m, 2H), 1.04 (s, 9H). |

-continued

| Example | Structure | MS | NMR |
|---|---|---|---|
| 451 | 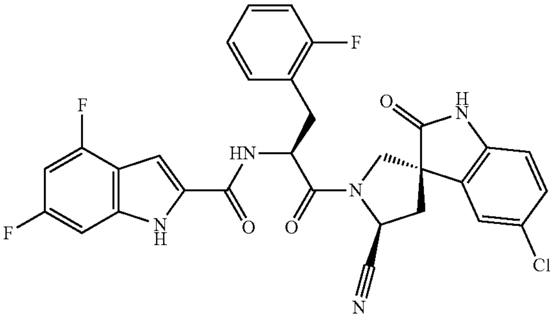 | [M + 1] 592.2 | 1H NMR (400 MHz, Acetone-d6) δ 10.94 (s, 1H), 9.80 (s, 1H), 8.28 (d, J = 8.4 Hz, 1H), 7.47 (td, J = 7.6, 1.8 Hz, 1H), 7.36-7.35 (m, 1H), 7.30-7.25 (m, 1H), 7.14-7.04 (m, 5H), 6.94-6.92 (m, 1H), 6.74 (td, J = 10.3, 2.1Hz, 1H), 5.27-5.18 (m, 2H), 4.39 (d, J = 10.6 Hz, 1H), 3.81 (d, J = 10.6 Hz, 1H), 3.37-3.21 (m, 2H), 2.83-2.63 (m, 2H). |
| 452 | 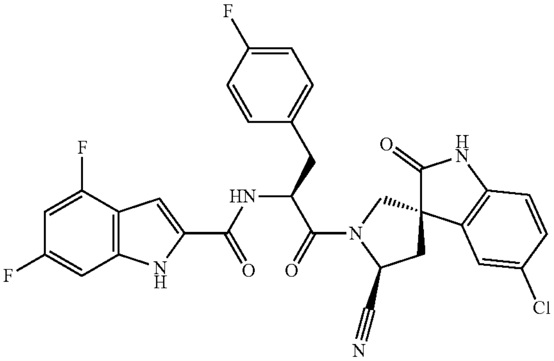 [SMILES: N#C[C@@H]1C[C@@]2(CN1C(=O)[C@H](Cc1ccc(F)cc1)NC(=O)c1cc3c(F)cc(F)cc3[nH]1)C(=O)Nc1ccc(Cl)cc12] | [M + 1] 592.2 | $^1$H NMR (400 MHz, Acetone-$d_6$) δ 10.91 (s, 1H), 9.78 (s, 1H), 8.21 (d, J = 8.2 Hz, 1H), 7.47-7.42 (m, 2H), 7.35 (m, 1H), 7.16-7.09 (m, 3H), 7.06-7.02 (m, 2H), 6.95 (d, J = 8.3 Hz, 1H) 6.75 (td, J = 10.3, 2.1 Hz, 1H), 5.24 (t, J = 8.3 Hz, 1H), 5.13-5.05 (m, 1H), 4.40 (d, J = 10.6 Hz, 1H), 3.73 (d, J = 10.6 Hz, 1H), 3.29 (dd, J = 13.7, 6.7 Hz, 1H), 3.17 (dd, J = 13.6, 8.0 Hz, 1H), 2.81-2.60 (m, 2H). |
| 453 | 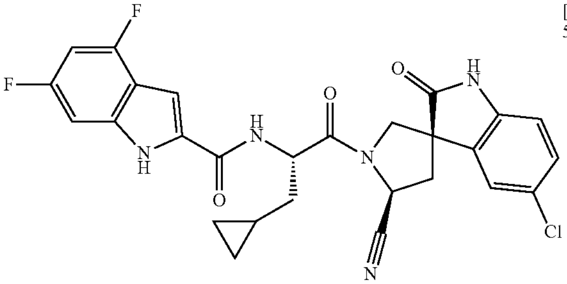 | $[M - 1]^-$ 535.528 | 1HNMR (500 MHz, Acetone-d6) δ 10.98 (s, 1H), 9.79 (s, 1H), 8.14-7.98 (m, 1H), 7.37 (dd, J = 2.1, 0.9 Hz, 1H), 7.20 (dd, J = 8.2, 2.1 Hz, 1H), 7.17 (d, J = 2.1 Hz, 1H), 7.13-7.09 (m, 1H), 6.98 (d, J = 8.2 Hz, 1H), 6.74 (td, J = 10.3, 2.1 Hz, 1H), 5.23 (dd, J = 8.6, 7.6 Hz, 1H), 4.93 (q, J = 7.3 Hz, 1H), 4.51-4.43 (m, 1H), 4.10 (d, J = 10.5 Hz, 1H), 2.85-2.75 (m, 5H), 2.69 (dd, J = 13.3, 7.6 Hz, 1H), 1.81 (td, J = 7.1, 4.0 Hz, 2H), 0.90 (dtd, J = 15.3, 7.4, 2.6 Hz, 1H), 0.50 (dq, J = 7.9, 2.0 Hz, 2H), 0.28-0.14 (m, 2H). |

Example 454

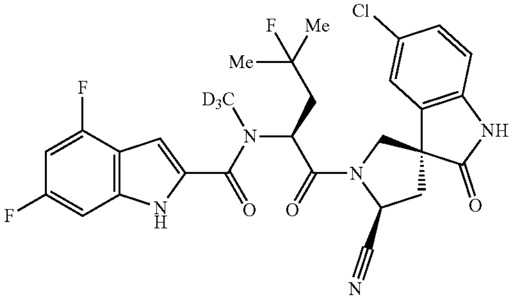

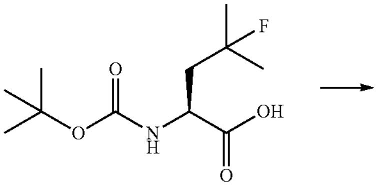

-continued

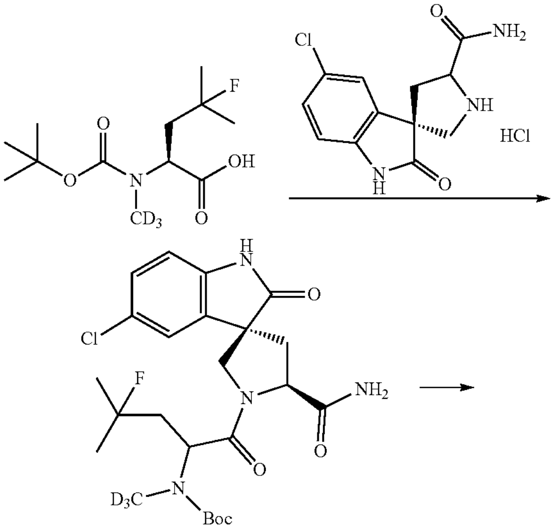

-continued

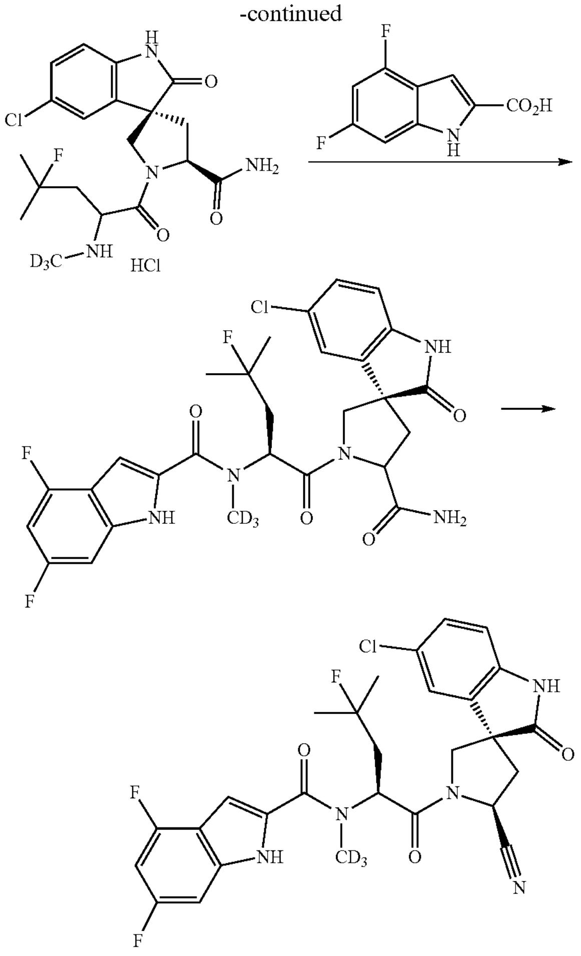

Step 1

In a 250 mL flame-dried round-bottomed flask, (S)-2-((tert-butoxycarbonyl)amino)-4-fluoro-4-methylpentanoic acid (3.00 g, 1.0 equiv) was combined in THF (35 mL, 0.34M) with iodomethane-d3 (6.00 mL, 8.0 equiv). The resulting solution was cooled in an ice bath, and sodium hydride (963.0 mg, 90 wt %, 3.0 equiv) was added. The mixture was allowed to warm to rt and was stirred for 72 h. Upon completion, the mixture was quenched with HCl (12 mL, 6M aq., 6.0 equiv) and diluted further with water (35 mL). The aqueous phase was extracted with ethyl acetate and the combined organic layers were dried over magnesium sulfate. Upon concentration, the crude residue was purified by silica gel column chromatography (gradient elution, 0 to 50% ethyl acetate/cyclohexane) to afford (S)-2-((tert-butoxycarbonyl)(methyl-d3)amino)-4-fluoro-4-methylpentanoic acid as a white solid (2.74 g, 86%). [M−1], 265.2.

Step 2

In a 250 mL round-bottomed flask equipped with a stir bar, (3R,5'S)-5-chloro-2-oxospiro[indoline-3,3'-pyrrolidine]-5'-carboxamide hydrochloride (2.73 g, 1.0 equiv) was combined with (S)-2-((tert-butoxycarbonyl)amino)-4-fluoro-4-methylpentanoic acid (2.40 g, 1.0 equiv) in DCM/DMF (4:1, 0.25M, 28.9 mL DCM, 7.2 mL DMF). The resulting mixture was cooled in an ice bath and N-methylmorpholine (3.2 mL, 3.2 equiv) was added. Next, HATU (3.43 g, 1.0 equiv) was added. Full consumption of the starting materials was observed by LCMS after 25 minutes. The reaction mixture was diluted with DCM (150 mL) and washed with saturated aqueous sodium bicarbonate (35 mL), 1.2M HCl (45 mL), and brine. The combined organic layer was dried over magnesium sulfate. Upon concentration, the crude residue was purified by silica gel column chromatography (gradient elution, 0 to 10% MeOH/DCM) to afford tert-butyl ((S)-1-((3R,5'S)-5'-carbamoyl-5-chloro-2-oxospiro[indoline-3,3'-pyrrolidin]-1'-yl)-4-fluoro-4-methyl-1-oxopentan-2-yl)(methyl-d3)carbamate as a white solid (4.02 g, 87%). [M+1], 514.2.

Step 3

In a 250 mL round-bottomed flask equipped with a stir bar, ((S)-1-((3R,5'S)-5'-carbamoyl-5-chloro-2-oxospiro[indoline-3,3'-pyrrolidin]-1'-yl)-4-fluoro-4-methyl-1-oxopentan-2-yl)(methyl-d3)carbamate (4.02 g, 1.0 equiv) was treated with 4M HCl in dioxane (39.1 mL, 20 equiv). The resulting mixture was stirred for 1 h at which time LCMS indicated full conversion. The reaction was concentrated to afford (3R,5'S)-5-chloro-1'-((S)-4-fluoro-4-methyl-2-((methyl-d3)amino)pentanoyl)-2-oxospiro[indoline-3,3'-pyrrolidine]-5'-carboxamide hydrochloride as a white solid that was used directly without purification. [M+H], 414.2.

Step 4

In a 250 mL round-bottomed flask equipped with a stir bar, the crude (3R,5'S)-5-chloro-1'-((S)-4-fluoro-4-methyl-2-((methyl-d3)amino)pentanoyl)-2-oxospiro[indoline-3,3'-pyrrolidine]-5'-carboxamide hydrochloride (1.0 equiv) produced in Step 3 was combined with 4,6-difluoro-1H-indole-2-carboxylic acid (1.54 g, 1.0 equiv) in DCM/DMF (5:1, 0.2M, 32.6 mL DCM, 6.5 mL DMF). The resulting mixture was cooled in an ice bath and N-methylmorpholine (2.58 mL, 3.0 equiv) was added, followed by HATU (2.97 g, 1.0 equiv). The reaction was stirred for 14 h, at which time full consumption of the starting materials was observed by LCMS. The mixture was quenched with 45 mL of saturated aqueous sodium bicarbonate and the layers were separated. The aqueous phase was extracted with DCM, and the combined organic layers were dried over magnesium sulfate. Upon concentration, the crude residue was purified by silica gel column chromatography (0 to 80% acetone/cyclohexane) to provide (3R,5'S)-5-chloro-1'-((S)-2-(4,6-difluoro-N-(methyl-d3)-1H-indole-2-carboxamido)-4-fluoro-4-methylpentanoyl)-2-oxospiro[indoline-3,3'-pyrrolidine]-5'-carboxamide as a white solid (3.59 g, 77%). [M−H], 591.0.

Step 5

In a 250 mL round-bottomed flask equipped with a stir bar, (3R,5'S)-5-chloro-1'-((S)-2-(4,6-difluoro-N-(methyl-d3)-1H-indole-2-carboxamido)-4-fluoro-4-methylpentanoyl)-2-oxospiro[indoline-3,3'-pyrrolidine]-5'-carboxamide (3.59 g, 1.0 equiv) was dissolved in DCM (40.4 mL, 0.15M). The resulting solution was cooled in an ice bath and triethylamine (5.06 mL, 6.0 equiv) was added, followed by trifluoroacetic anhydride (2.57 mL, 3.0 equiv). The mixture was warmed to rt and stirred for 45 minutes, at which time LCMS indicated full consumption of the starting material. The mixture was diluted with 150 mL of DCM and washed with saturated aqueous sodium bicarbonate (60 mL). The aqueous phase was extracted with methylene chloride. The combined organic layer was washed with brine and dried over magnesium sulfate. Upon concentration, the crude residue was purified by C18 column chromatography (gradient elution, water/MeCN) to afford N—((S)-1(3R,5'S)-5-chloro-5'-cyano-2-oxospiro[indoline-3,3'-pyrrolidin]-1'-yl)-4-fluoro-4-methyl-1-oxopentan-2-yl)-4,6-difluoro-N-(methyl-d3)-1H-indole-2-carboxamide as a white solid (3.08 g, 88% yield). $^1$H NMR (400 MHz, Acetone-$d_6$) δ 10.68 (s, 1H), 9.80 (s, 1H), 7.09-7.06 (m, 1H), 6.97-6.88 (m, 4H), 6.75 (td, J=10.3, 2.1 Hz, 1H), 5.84 (dd, J=7.6, 5.6 Hz, 1H), 5.33 (dd, J=8.8, 7.7 Hz, 1H), 4.50 (d, J=10.9 Hz, 1H), 3.95 (d, J=11.0 Hz, 1H), 2.84-2.65 (m, 2H), 2.52-2.25 (m, 2H), 1.45 (d, J=6.8 Hz, 3H), 1.40 (d, J=7.0 Hz, 3H). [M−1], 573.2.

The following examples were prepared employing similar protocol as described above.

| Example | Structure | MS | NMR |
|---|---|---|---|
| 455 | 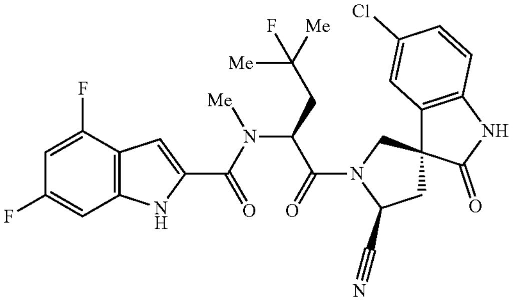 [SMILES: CN(C(=O)c1cc2c(F)cc(F)cc2[nH]1)[C@@H](CC(C)(C)F)C(=O)N1C[C@]2(C[C@H]1C#N)C(=O)Nc1ccc(Cl)cc12] | [M − 1] 570.0 | δ 10.68 (s, 1H), 9.80 (s, 1H), 7.12-7.05 (m, 1H), 7.01-6.85 (m, 4H), 6.75 (td, J = 10.3, 2.1 Hz, 1H), 5.85 (dd, J = 7.5, 5.6 Hz, 1H), 5.34 (dd, J = 8.8, 7.6 Hz, 1H), 4.50 (d, J = 10.9 Hz, 1H), 3.95 (d, J = 10.9 Hz, 1H), 3.47 (s, 3H), 2.85-2.68 (m, 2H), 2.48-2.29 (m, 2H), 1.45 (d, J = 6.9 Hz, 3H), 1.40 (d, J = 7.1 Hz, 3H). |
| 456 | 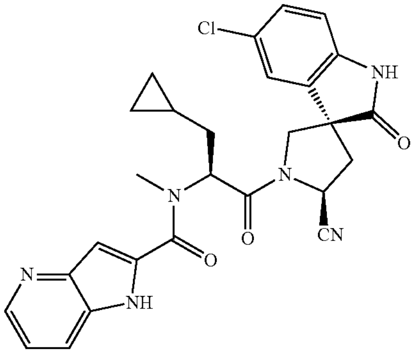 [SMILES: CN(C(=O)c1cc2ncccc2[nH]1)[C@@H](CC1CC1)C(=O)N1C[C@]2(C[C@H]1C#N)C(=O)Nc1ccc(Cl)cc12] | $[M + H]^+$ 516.805 | 1H NMR (400 MHz, Acetone-d6) δ 10.52 (s, 1H), 9.80 (s, 1H), 8.44 (ddd, J = 4.7, 3.3, 1.5 Hz, 1H), 7.84 (d, J = 8.3 Hz, 1H), 7.20 (ddd, J = 8.3, 4.5, 2.4 Hz, 1H), 7.12-6.97 (m, 3H), 6.91 (d, J = 8.2 Hz, 1H), 5.56 (t, J = 7.5 Hz, 1H), 5.29 (dd, J = 8.8, 7.4 Hz, 1H), 4.45 (d, J = 10.8 Hz, 1H), 4.00 (d, J = 10.8 Hz, 1H), 3.45 (s, 3H), 2.90-2.75 (m, 3H), 2.69 (dd, J = 13.4, 7.5 Hz, 1H), 1.97-1.81 (m, 2H), 0.82-0.72 (m, 1H), 0.53-0.39 (m, 2H), 0.29-0.10 (m, 2H). |
| 457 | 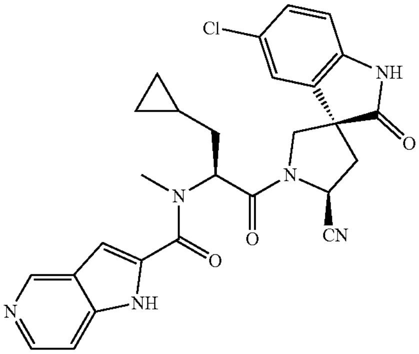 [SMILES: CN(C(=O)c1cc2cnccc2[nH]1)[C@@H](CC1CC1)C(=O)N1C[C@]2(C[C@H]1C#N)C(=O)Nc1ccc(Cl)cc12] | $[M + H]^+$ 516.997 | 1H NMR (400 MHz, Acetone-d6) δ 10.62 (s, 1H), 9.37 (s, 1H), 8.55 (d, J = 6.6 Hz, 1H), 8.10 (d, J = 6.5 Hz, 1H), 7.35 (s, 1H), 7.11-6.96 (m, 3H), 5.57 (t, J = 7.5 Hz, 1H), 5.35-5.24 (m, 1H), 4.42 (d, J = 10.8 Hz, 1H), 3.97 (d, J = 10.8 Hz, 1H), 3.80-3.69 (m, 1H), 3.46 (s, 3H), 2.85 (dd, J = 13.5, 9.0 Hz, 1H), 2.67 (dd, J = 13.4, 7.1Hz, 1H), 1.99-1.80 (m, 2H), 0.81z-0.72 (m, 1H), 1.95-1.85 (m, 2H), 0.46 (dd, J = 8.0, 5.6 Hz, 2H). |
| 458 | 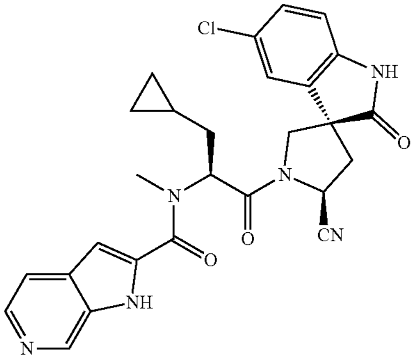 [SMILES: CN(C(=O)c1cc2ccncc2[nH]1)[C@@H](CC1CC1)C(=O)N1C[C@]2(C[C@H]1C#N)C(=O)Nc1ccc(Cl)cc12] | $[M + H]^+$ 516.901 | 1H NMR (400 MHz, Acetone-d6) δ 10.78 (s, 1H), 9.81 (s, 1H), 8.86 (s, 1H), 8.18 (d, J = 5.5 Hz, 1H), 7.57 (d, J = 5.3 Hz, 1H), 7.03 (d, J = 11.8 Hz, 2H), 6.92 (d, J = 7.4 Hz, 2H), 5.56 (t, J = 7.5 Hz, 1H), 5.30 (t, J = 8.2 Hz, 1H), 4.41 (d, J = 11.0 Hz, 1H), 3.99 (d, J = 10.9 Hz, 1H), 3.46 (s, 3H), 2.86-2.78 (m, 4H), 2.69 (dd, J = 13.5, 7.6 Hz, 1H), 1.88 (s, 2H), 0.81-0.71 (m, 1H), 0.46 (d, J = 7.7 Hz, 2H), 0.19 (d, J = 4.6 Hz, 2H). |

-continued

| Example | Structure | MS | NMR |
|---|---|---|---|
| 459 | 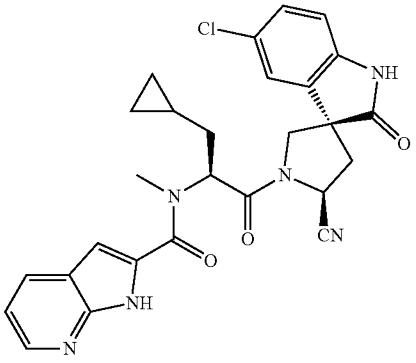 [SMILES: CN(C(=O)c1cc2cccnc2[nH]1)[C@@H](CC1CC1)C(=O)N1C[C@]2(C[C@H]1C#N)C(=O)Nc1ccc(Cl)cc12] | $[M + H]^+$ 517.200 | 1H NMR (400 MHz, Acetone-d6) δ 11.43 (s, 1H), 9.70 (s, 1H), 8.42 (dt, J = 4.8, 1.4 Hz, 1H), 8.06 (dd, J = 7.9, 1.7 Hz, 1H), 7.13 (dd, J = 7.9, 4.7 Hz, 1H), 7.03 (s, 1H), 6.90 (d, J = 5.4 Hz, 1H), 6.73 (d, J = 8.3 Hz, 1H), 5.58 (t, J = 7.5 Hz, 1H), 5.28 (t, J = 8.2 Hz, 1H), 4.56 (d, J = 10.9 Hz, 1H), 4.04-3.98 (m, 1H), 3.53-3.44 (m, 3H), 3.16 (dd, J = 9.1, 3.8 Hz, 2H), 2.81-2.74 (m, 1H), 2.68 (dd, J = 13.4, 7.8 Hz, 1H), 1.90 (t, J = 6.9 Hz, 2H), 0.87-0.74 (m, 1H), 0.52-0.44 (m, 2H), 0.24-0.18 (m, 2H). |
| 460 | 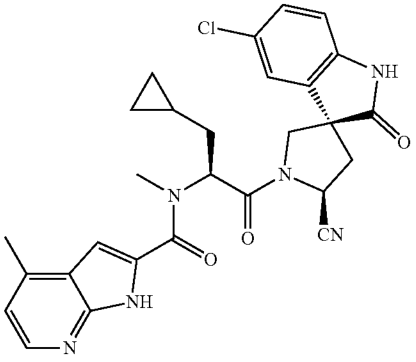 [SMILES: Cc1ccnc2[nH]c(C(=O)N(C)[C@@H](CC3CC3)C(=O)N3C[C@]4(C[C@H]3C#N)C(=O)Nc3ccc(Cl)cc34)cc12] | $[M + H]^+$ 531.212 | 1H NMR (400 MHz, Acetone-d6) δ 9.77 (s, 1H), 8.48 (d, J = 5.7 Hz, 1H), 7.40 (d, J = 5.8 Hz, 1H), 7.22 (s, 1H), 7.04 (d, J = 2.0 Hz, 1H), 6.98 (dd, J = 8.7, 5.8 Hz, 1H), 6.88 (d, J = 8.3 Hz, 1H), 5.55 (t, J = 7.5 Hz, 1H), 5.29 (dd, J = 8.8, 7.5 Hz, 1H), 4.40 (d, J = 11.0 Hz, 1H), 3.99 (d, J = 10.9 Hz, 1H), 3.47 (s, 3H), 2.86 - 2.77 (m, 4H), 2.70 (dd, J = 13.5, 7.6 Hz, 1H), 1.89 (td, J = 7.3, 3.3 Hz, 2H), 0.88 - 0.73 (m, 1H), 0.47 (m, 2H), 0.21 (m, 2H). |
| 461 | 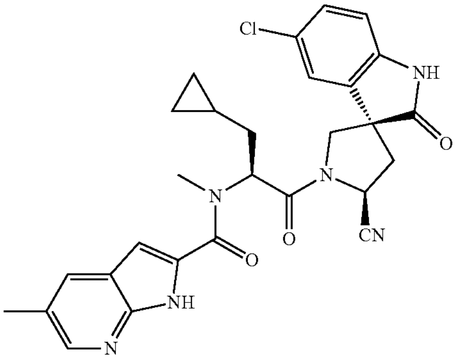 [SMILES: Cc1cnc2[nH]c(C(=O)N(C)[C@@H](CC3CC3)C(=O)N3C[C@]4(C[C@H]3C#N)C(=O)Nc3ccc(Cl)cc34)cc2c1] | $[M + H]^+$ 531.103 | 1H NMR (400 MHz, Acetone-d6) δ 8.41 (s, 1H), 8.29 (s, 1H), 7.02 (d, J = 22.6 Hz, 3H), 6.87 (d, J = 8.3 Hz, 1H), 5.53 (t, J = 7.5 Hz, 1H), 5.29 (t, J = 8.1 Hz, 1H), 4.45 (d, J = 11.0 Hz, 1H), 3.99 (d, J = 10.9 Hz, 1H), 2.81 (dd, J = 13.5, 8.7 Hz, 1H), 2.69 (dd, J = 13.5, 7.6 Hz, 1H), 2.53 (s, 3H), 1.89 (q, J = 8.4, 7.4 Hz, 2H), 0.87-0.74 (m, 1H), 0.47 (dd, J = 9.6, 4.7 Hz, 2H). |
| 462 | 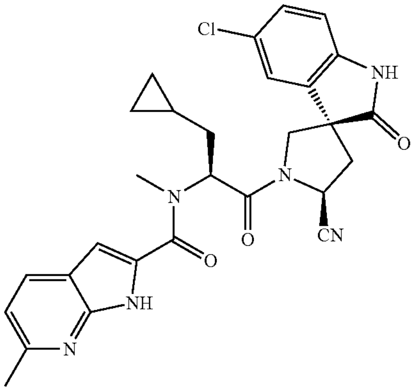 [SMILES: Cc1ccc2cc(C(=O)N(C)[C@@H](CC3CC3)C(=O)N3C[C@]4(C[C@H]3C#N)C(=O)Nc3ccc(Cl)cc34)[nH]c2n1] | $[M + H]^+$ 531.054 | 1H NMR (400 MHz, Acetone-d6) δ 8.51 (d, J = 8.0 Hz, 1H), 7.40 (d, J = 8.1 Hz, 1H), 7.17-6.93 (m, 3H), 6.89 (d, J = 8.3 Hz, 1H), 5.52 (t, J = 7.5 Hz, 1H), 5.29 (dd, J = 8.8, 7.4 Hz, 1H), 4.42 (d, J = 11.0 Hz, 1H), 4.00 (d, J = 10.9 Hz, 1H), 3.46 (s, 3H), 2.89-2.75 (m, 4H), 2.69 (dd, J = 13.5, 7.5 Hz, 1H), 1.95-1.76 (m, 2H), 0.87-0.72 (m, 1H), 0.54-0.39 (m, 2H), 0.29-0.13 (m, 2H). |

-continued

| Example | Structure | MS | NMR |
|---|---|---|---|
| 463 | 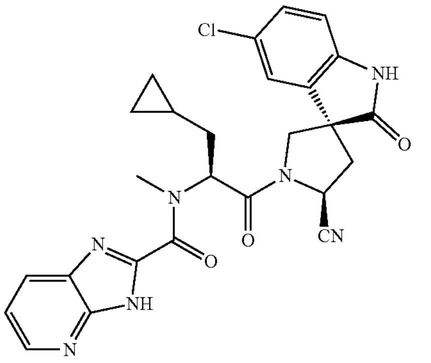 [SMILES: CN(C(=O)c1nc2cccnc2[nH]1)[C@@H](CC1CC1)C(=O)N1C[C@]2(C[C@H]1C#N)C(=O)Nc1ccc(Cl)cc12] | [M + H]+ 517.905 | 1H NMR (400 MHz, DMSO-d6) δ 10.76 (d, J = 25.7 Hz, 2H), 8.51-8.39 (m, 2H), 8.04 (s, 1H), 7.34 (dd, J = 8.1, 4.7 Hz, 1H), 7.12-7.03 (m, 2H), 6.97 (dd, J = 8.3, 2.1 Hz, 1H), 6.80 (d, J = 8.3 Hz, 2H), 6.60 (dd, J = 9.6, 5.3 Hz, 1H), 5.43 (t, J = 7.5 Hz, 1H), 5.25 (dt, J = 8.9, 6.1 Hz, 2H), 4.04 (dd, J = 24.2, 10.7 Hz, 5H), 3.91 (d, J = 10.9 Hz, 2H), 3.53 (s, 3H), 3.19 (s, 3H), 2.75-2.61 (m, 2H), 2.07-1.96 (m, 1H), 1.85 (q, J = 7.5 Hz, 1H), 1.80-1.72 (m, 1H), 1.62 (s, 1H), 0.70 (s, 1H), 0.58 (s, 1H), 0.39 (q, J = 8.3, 7.7 Hz, 2H), 0.19 (d, J = 14.9 Hz, 4H). |
| 464 | 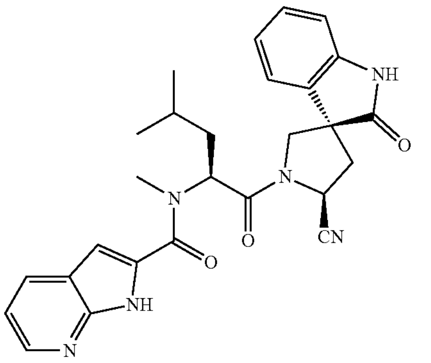 | [M + H]+ 485.220 | 1H NMR (400 MHz, Acetone-d6) δ 8.35 (d, J = 4.4 Hz, 1H), 8.02 (s, 1H), 7.08 (dd, J = 24.5, 7.8 Hz, 2H), 6.93-6.73 (m, 2H), 5.56 (s, 1H), 5.20 (t, J = 8.3 Hz, 1H), 4.30 (d, J = 10.3 Hz, 1H), 3.99 (d, J = 10.6 Hz, 1H), 3.42 (s, 3H), 2.77-2.64 (m, 2H), 1.98-1.86 (m, 1H), 1.79 (m, 1H), 1.66 (mz, 1H), 0.98 (m, 6H). |
| 465 | 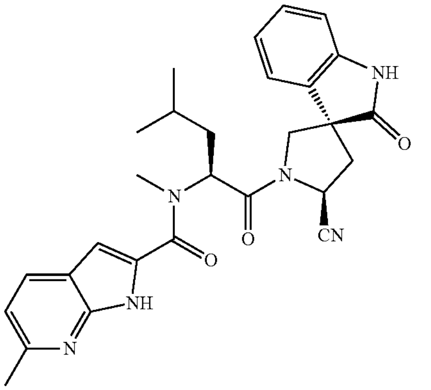 [SMILES: Cc1ccc2cc(C(=O)N(C)[C@@H](CC(C)C)C(=O)N3C[C@]4(C[C@H]3C#N)C(=O)Nc3ccccc34)[nH]c2n1] | [M + H]+ 499.188 | 1H NMR (400 MHz, Acetone-d6) δ 10.53 (s, 1H), 9.54 (s, 1H), 7.87 (s, 1H), 7.17-6.72 (m, 5H), 5.57 (s, 1H), 5.21 (t, J = 8.4 Hz, 1H), 4.46 (s, 1H), 4.01 (d, J = 10.6 Hz, 1H), 3.46 (s, 3H), 2.73-2.63 (m, 2H), 2.52 (s, 3H), 1.95 (ddd, J = 14.4, 10.3, 4.9 Hz, 1H), 1.85-1.71 (m, 1H), 1.66 (s, 1H), 1.00 (dd, J = 19.7, 6.4 Hz, 5H). |
| 466 | 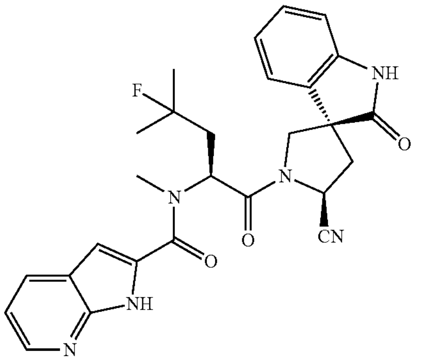 [SMILES: CN(C(=O)c1cc2cccnc2[nH]1)[C@@H](CC(C)(C)F)C(=O)N1C[C@]2(C[C@H]1C#N)C(=O)Nc1ccccc12] | [M+H]+ 503.144 | 1H NMR (400 MHz, Acetone-d6) δ 10.84 (s, 1H), 9.64 (s, 1H), 8.38 (dd, J = 4.6, 1.6 Hz, 1H), 8.09 (d, J = 35.7 Hz, 1H), 7.12 (dd, J = 7.9, 4.6 Hz, 1H), 7.03 (d, J = 7.7 Hz, 2H), 6.93-6.77 (m, 3H), 5.81 (t, J = 6.6 Hz, 1H), 5.23 (t, J = 8.3 Hz, 1H), 4.34 (s, 1H), 4.01 (d, J = 10.7 Hz, 1H), 3.44 (s, 3H), 2.77-2.62 (m, 2H), 2.55-2.25 (m, 2H), 1.45 (m, 6H). |

-continued

| Example | Structure | MS | NMR |
|---|---|---|---|
| 467 | 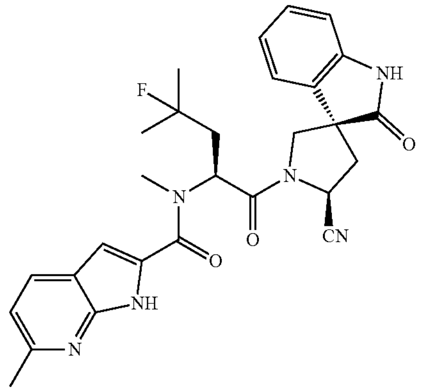 [SMILES: Cc1ccc2cc(C(=O)N(C)[C@@H](CC(C)(C)F)C(=O)N3C[C@]4(C[C@H]3C#N)C(=O)Nc3ccccc34)[nH]c2n1] | [M+H]+ 517.093 | 1H NMR (400 MHz, Acetone-d6) δ 10.42 (s, 1H), 9.61 (s, 1H), 7.89 (d, J = 8.0 Hz, 1H), 7.02 (dd, J = 16.4, 7.8 Hz, 3H), 6.86 (d, J = 8.0 Hz, 2H), 6.76 (s, 1H), 5.80 (t, J = 6.6 Hz, 1H), 5.22 (t, J = 8.3 Hz, 1H), 4.40 (s, 1H), 4.02 (d, J = 10.7 Hz, 1H), 3.45 (s, 3H), 2.78-2.64 (m, 2H), 2.55 (s, 3H), 2.51-2.21 (m, 2H), 1.45 (m, 6H). |
| 468 | 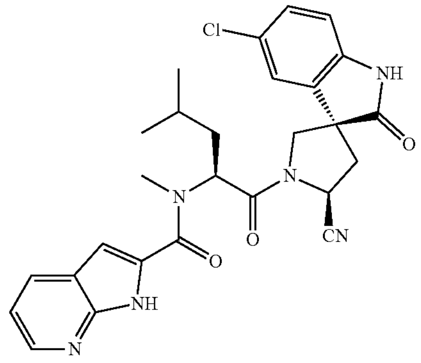 [SMILES: CC(C)C[C@@H](C(=O)N1C[C@]2(C[C@H]1C#N)C(=O)Nc1ccc(Cl)cc12)N(C)C(=O)c1cc2cccnc2[nH]1] | [M+H]+ 519.200 | 1H NMR (400 MHz, Acetone-d6) δ 8.37 (m, 1H), 8.04 (m, 1H), 7.12 (m, 1H), 7.04-6.90 (m, 2H), 6.90-6.77 (m, 2H), 5.30 (t, J = 8.3 Hz, 1H), 4.45 (d, J = 11.0 Hz, 1H), 3.98 (d, J = 10.8 Hz, 1H), 3.45 (s, 3H), 2.84-2.75 (m, 4H), 2.69 (dd, J = 13.4, 7.9 Hz, 1H), 1.98-1.86 (m, 1H), 1.79 (dt, J = 14.1, 7.0 Hz, 1H), 1.65 (dq, J = 13.6, 6.6 Hz, 1H), 0.99 (m, 6H). |
| 469 | 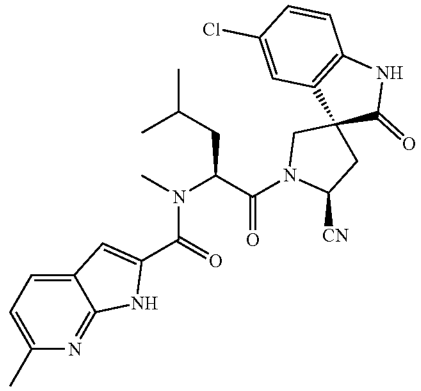 [SMILES: Cc1ccc2cc(C(=O)N(C)[C@@H](CC(C)C)C(=O)N3C[C@]4(C[C@H]3C#N)C(=O)Nc3ccc(Cl)cc34)[nH]c2n1] | | 1H NMR (400 MHz, Acetone-d6) δ 10.60 (s, 1H), 9.65 (s, 1H), 7.89 (t, J = 8.1 Hz, 1H), 6.99 (dd, J = 10.3, 8.0 Hz, 4H), 6.88-6.69 (m, 3H), 5.27 (t, J = 8.3 Hz, 1H), 4.58 (d, J = 10.9 Hz, 1H), 4.01 (d, J = 10.8 Hz, 1H), 3.50 (s, 4H), 2.76 (d, J = 8.9 Hz, 2H), 2.68 (dd, J = 13.4, 8.0 Hz, 1H), 2.52 (s, 3H), 1.96 (ddd, J = 14.1, 9.7, 4.9 Hz, 2H), 1.79 (ddd, J = 14.2, 8.8, 5.5 Hz, 1H), 1.66 (dd, J = 13.7, 6.9 Hz, 1H), 1.02 (d, J = 6.6 Hz, 3H), 0.98 (d, J = 6.5 Hz, 3H). |
| 470 | 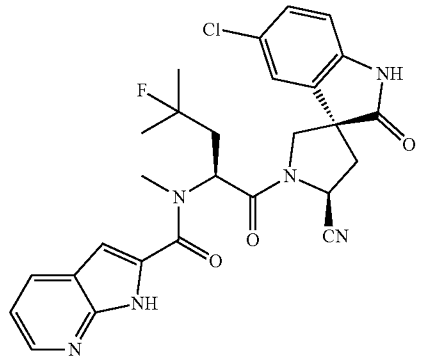 [SMILES: CN(C(=O)c1cc2cccnc2[nH]1)[C@@H](CC(C)(C)F)C(=O)N1C[C@]2(C[C@H]1C#N)C(=O)Nc1ccc(Cl)cc12] | | 1H NMR (400 MHz, Acetone-d6) δ 10.63 (s, 1H), 9.75 (s, 1H), 8.37 (dd, J = 4.6, 1.6 Hz, 1H), 8.04 (d, J = 8.0 Hz, 1H), 7.12 (dd, J = 7.9, 4.6 Hz, 1H), 6.99 (s, 1H), 6.92 (d, J = 8.6 Hz, 1H), 6.88-6.80 (m, 2H), 5.81 (t, J = 6.6 Hz, 1H), 5.34-5.27 (m, 1H), 4.45 (d, J = 11.3 Hz, 1H), 3.96 (d, J = 11.0 Hz, 1H), 3.44 (s, 3H), 2.69 (dd, J = 13.4, 7.7 Hz, 1H), 2.52-2.26 (m, 3H), 1.43 (m, 6H). |

-continued
| Example | Structure | MS | NMR |
|---|---|---|---|
| 471 | 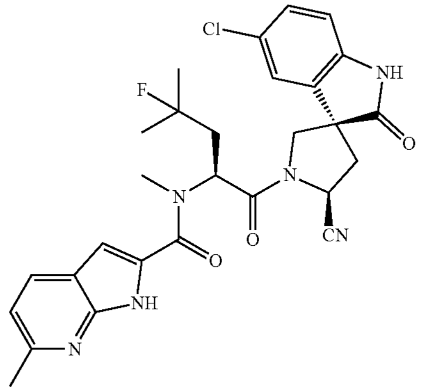 [SMILES: Cc1ccc2cc(C(=O)N(C)[C@@H](CC(C)(C)F)C(=O)N3C[C@]4(C[C@H]3C#N)C(=O)Nc3ccc(Cl)cc34)[nH]c2n1] | | 1H NMR (400 MHz, Acetone-d6) δ 10.28 (s, 1H), 9.76 (s, 1H), 7.91 (d, J = 8.1 Hz, 1H), 7.07-6.93 (m, 2H), 6.87 (d, J = 8.2 Hz, 1H), 6.81 (s, 1H), 5.81 (t, J = 6.6 Hz, 1H), 5.32 (t, J = 8.2 Hz, 1H), 4.46 (s, 1H), 3.99 (d, J = 10.9 Hz, 1H), 3.45 (s, 3H), 2.71 (dd, J = 13.5, 7.8 Hz, 1H), 2.56 (s, 3H), 2.51-2.25 (m, 2H), 1.44 (m, 6H). |
Example 472
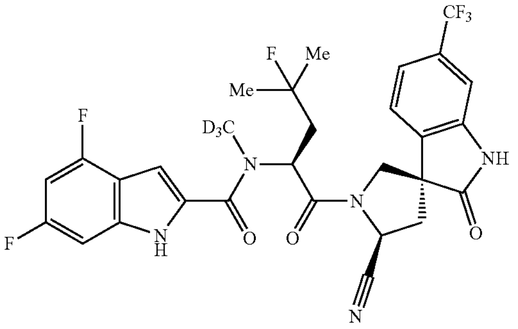
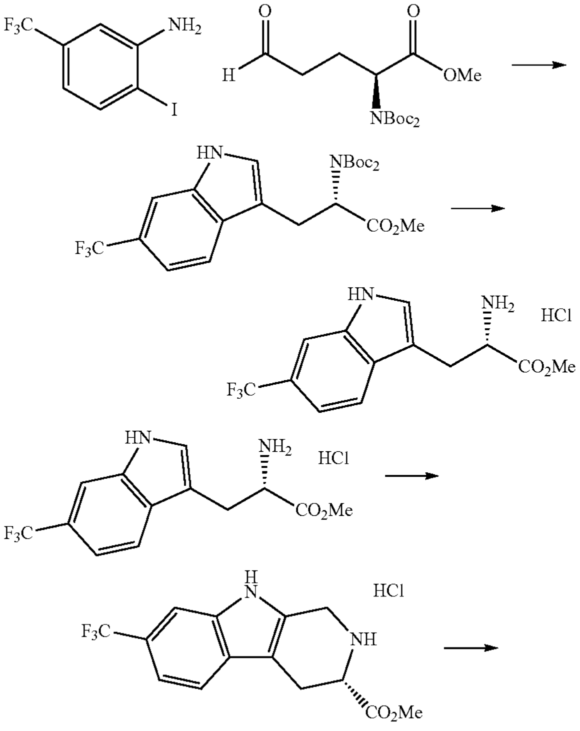
-continued
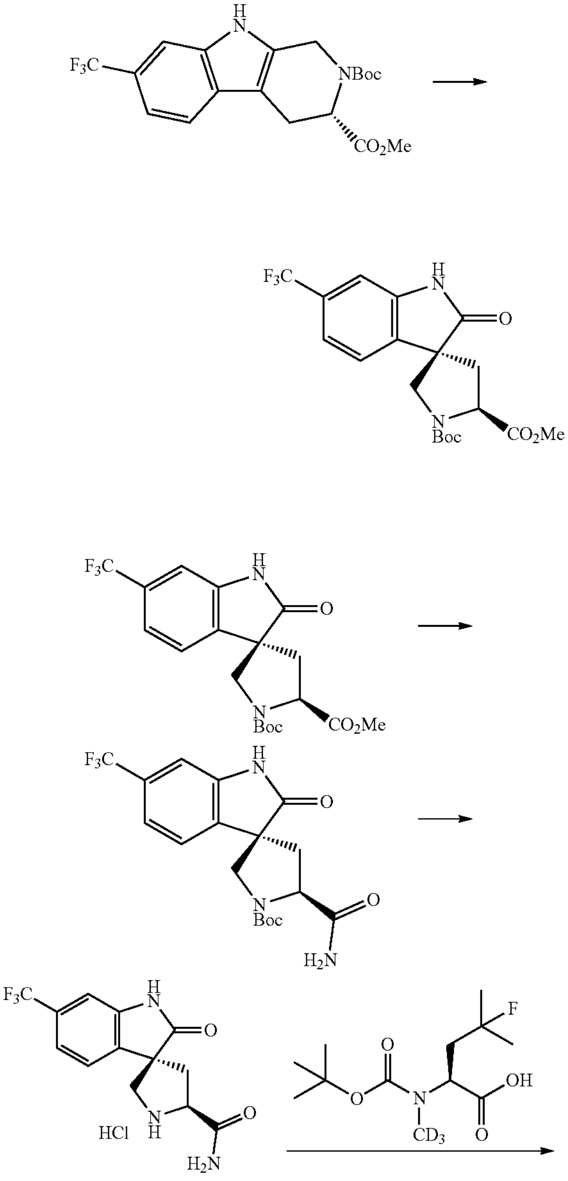

-continued

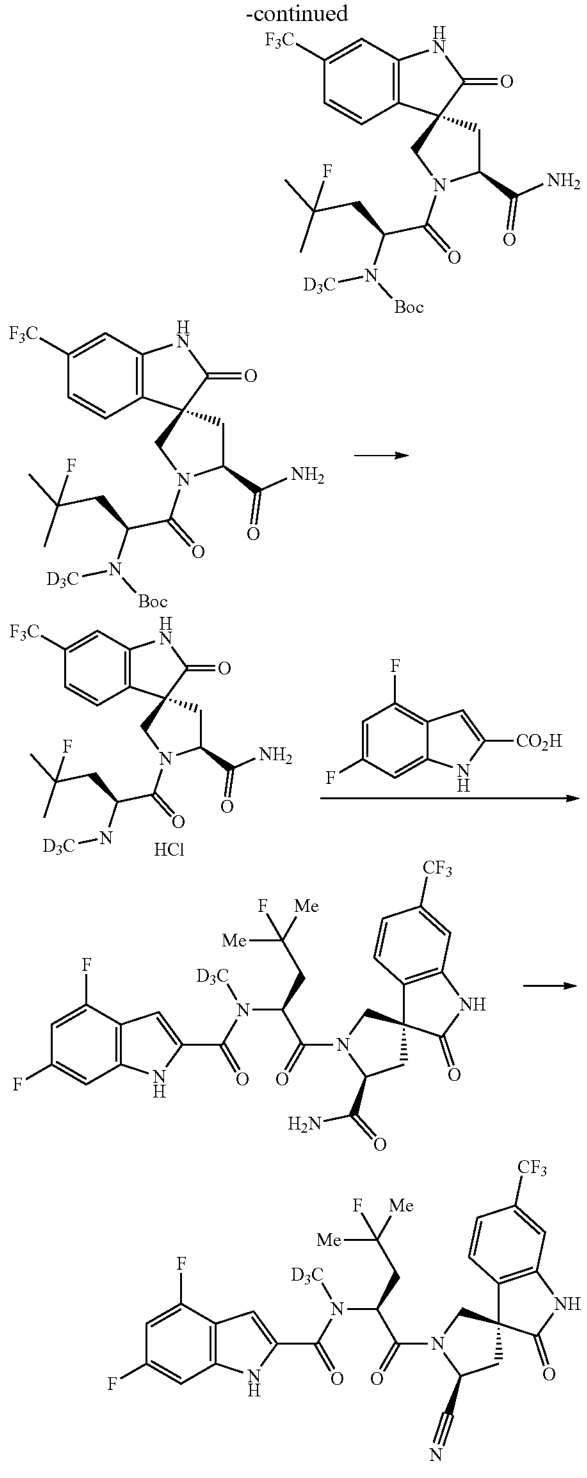

Step 1

A solution of methyl (S)-2-(bis(tert-butoxycarbonyl) amino)-5-oxopentanoate (1.10 g, 1.0 equiv), DABCO (1.07 g, 3.0 equiv), and 2-iodo-5-(trifluoromethyl)aniline (1.01 g, 1.1 equiv) in DMF (16 ml, 0.2M) was sparged for 20 min with nitrogen in a 100 mL Schlenk tube. Palladium(II) acetate (72.0 mg, 0.10 equiv) was then added added, and the mixture was heated at 90° C. under a nitrogen atmosphere for 30 h. Upon completion, the mixture was diluted with water and the aqueous phase was extracted with ethyl acetate. The combined organic layers were dried over magnesium sulfate. Upon concentration, the crude residue was purified by silica gel column chromatography (gradient elution, 0 to 40% ethyl acetate/cyclohexane) to afford methyl (S)-2-(bis(tert-butoxycarbonyl)amino)-3-(6-(trifluoromethyl)-1H-indol-3-yl)propanoate (1.09 g, 70%). [M+1], 487.2.

Step 2

In a 40 mL screw cap vial equipped with a pressure release septum and a stir bar, methyl (S)-2-(bis(tert-butoxycarbonyl)amino)-3-(6-(trifluoromethyl)-1H-indol-3-yl)propanoate (1.09 g, 1.0 equiv) was treated with 4M HCl in dioxane (11.2 mL, 20 equiv HCl). The resulting mixture was stirred for 12 h at rt. Upon completion, the mixture was concentrated to afford methyl (S)-2-amino-3-(6-(trifluoromethyl)-1H-indol-3-yl)propanoate hydrochloride which was used without purification in the next step. [M+1], 287.1.

Step 3

In a 40 mL screw cap vial equipped with a pressure release septum and a stir bar, methyl (S)-2-amino-3-(6-(trifluoromethyl)-1H-indol-3-yl)propanoate hydrochloride (722 mg, 1.0 equiv) was combined with aqueous formaldehyde (183 μL, 37 wt %, 1.1 equiv) in MeOH (4.5 mL, 0.5M). The resulting mixture was heated at 65° C. for 3 h. Upon completion, as judged by LCMS, the mixture was concentrated to afford crude methyl (S)-7-(trifluoromethyl)-2,3,4,9-tetrahydro-1H-pyrido[3,4-b]indole-3-carboxylate hydrochloride which was used directly in the next step without purification. [M+1], 299.1.

Step 4

In a 40 mL screw cap vial equipped with a pressure release septum and a stir bar, (S)-7-(trifluoromethyl)-2,3,4,9-tetrahydro-1H-pyrido[3,4-b]indole-3-carboxylate hydrochloride (1.0 equiv) was suspended in DCM (5.6 mL, 0.4M). Triethylamine (2.0 equiv, 623 μL) was then added, followed by Boc-anhydride (1.23 mL, 1.1 equiv, 2M DCM). The resulting mixture was stirred at rt for 20 h. The reaction was then concentrated and purified silica gel column chromatography to afford 2-(tert-butyl) 3-methyl (S)-7-(trifluoromethyl)-1,3,4,9-tetrahydro-2H-pyrido[3,4-b]indole-2,3-dicarboxylate (681 mg, 76%). [M−1], 397.0.

Step 5

In a 40 mL screw cap vial equipped with a pressure release septum and a stir bar, 2-(tert-butyl) 3-methyl (S)-7-(trifluoromethyl)-1,3,4,9-tetrahydro-2H-pyrido[3,4-b]indole-2,3-dicarboxylate (681.0 mg, 1.0 equiv) was suspended in a mixture of THF, water, and acetic acid (10 mL THF, 1 mL DI water, 685 μL acetic acid) at −40° C. To the solution was added N-bromosuccinimide (304 mg, 1.0 equiv) portionwise. After 2.5 h, the mixture was warmed to 0° C. using an ice bath, and additional acetic acid (685 μL) was added. After 20 minutes, full consumption of starting material was observed by LCMS and the mixture was slowly added to 75 mL of saturated aqueous sodium bicarbonate. The aqueous phase was extracted with ethyl acetate and the combined organic layers were dried over magnesium sulfate. Upon concentration, the crude residue was purified by silica gel column chromatography (gradient elution, 0 to 100% MTBE/cyclohexane) to afford 1'-(tert-butyl) 5'-methyl (3R,5'S)-2-oxo-6-(trifluoromethyl)spiro[indoline-3,3'-pyrrolidine]-1',5'-dicarboxylate (591.7 mg, 84%, 6:1 diastereomeric mixture) as a colorless oil [M−1], 413.0.

Step 6

In a 25 mL pressure tube equipped with a stir bar, 1'-(tert-butyl) 5'-methyl (3R,5'S)-2-oxo-6-(trifluoromethyl)spiro[indoline-3,3'-pyrrolidine]-1',5'-dicarboxylate (591.7 mg, 1.0 equiv) generated in Step 5 was dissolved in 7M $NH_3$ in MeOH (6.1 mL, 30 equiv $NH_3$). The resulting mixture was heated at 60° C. for 48 h. At this time, the reaction mixture was concentrated and the crude residue was purified by RPHPLC (MeCN/water, 0.1% TFA) to afford tert-butyl (3R,5'S)-5'-carbamoyl-2-oxo-6-(trifluoromethyl)spiro[indoline-3,3'-pyrrolidine]-1'-carboxylate (311.0 mg, 55%) as a single diastereomer. [M+Na], 422.1.

Step 7

In a 40 mL screw cap vial equipped with a pressure release septum and a stir bar, tert-butyl (3R,5'S)-5'-carbamoyl-2-oxo-6-(trifluoromethyl)spiro[indoline-3,3'-pyrrolidine]-1'-carboxylate (311.0 mg, 1.0 equiv) was treated with 4M HCl in dioxane (3.9 mL, 20 equiv HCl). The resulting mixture was stirred for 1 h at rt and then concentrated to afford (3R,5'S)-2-oxo-6-(trifluoromethyl)spiro[indoline-3,3'-pyrrolidine]-5'-carboxamide hydrochloride as a white solid (261.0 mg). [M+1], 300.1.

Step 8

In a 40 mL screw cap vial equipped with a pressure release septum and a stir bar, (3R,5'S)-2-oxo-6-(trifluoromethyl)spiro[indoline-3,3'-pyrrolidine]-5'-carboxamide hydrochloride (261.0 mg, 1.0 equiv) was combined with (S)-2-((tert-butoxycarbonyl)(methyl-d3)amino)-4-fluoro-4-methylpentanoic acid (91.0 mg, 1.15 equiv) and HATU (130.0 mg, 1.15 equiv) in DMF (2.0 mL, 0.15M). Next, DIPEA (156 μL, 3.0 equiv) was added and the resulting mixture was stirred for 14 h. The crude reaction mixture was then filtered and purified by RPHPLC (MeCN/water, 0.1% TFA) to afford tert-butyl ((S)-1-((3R,5'S)-5'-carbamoyl-2-oxo-6-(trifluoromethyl)spiro[indoline-3,3'-pyrrolidin]-1'-yl)-4-fluoro-4-methyl-1-oxopentan-2-yl)(methyl-d3)carbamate as a white solid (106.6 mg, 65%). [M−1], 546.3.

Step 9

In a 40 mL screw cap vial equipped with a pressure release septum and a stir bar, tert-butyl ((S)-1-((3R,5'S)-5'-carbamoyl-2-oxo-6-(trifluoromethyl)spiro[indoline-3,3'-pyrrolidin]-1'-yl)-4-fluoro-4-methyl-1-oxopentan-2-yl)(methyl-d3)carbamate (107 mg, 1.0 equiv) was treated with 4M HCl in dioxane (973 μL, 20 equiv HCl) at rt. After 1 h, the mixture was concentrated to afford (3R,5'S)-1'-((S)-4-fluoro-4-methyl-2-((methyl-d3)amino)pentanoyl)-2-oxo-6-(trifluoromethyl)spiro[indoline-3,3'-pyrrolidine]-5'-carboxamide hydrochloride which was used in the next step without purification. [M+1], 448.2.

Step 10

In a 40 mL screw cap vial equipped with a pressure release septum and a stir bar, (3R,5'S)-1'-((S)-4-fluoro-4-methyl-2-((methyl-d3)amino)pentanoyl)-2-oxo-6-(trifluoromethyl)spiro[indoline-3,3'-pyrrolidine]-5'-carboxamide hydrochloride (1.0 equiv) generated in Step 9 was combined with 4,6-difluoro-1H-indole-2-carboxylic acid (44.1 mg, 1.15 equiv) and HATU (85.0 mg, 1.15 equiv) in DMF (1.3 mL, 0.15M). Next, DIPEA (102 μL, 3.0 equiv) was added, and the resulting mixture was stirred for 14 h at rt. The crude reaction mixture was filtered and purified by RPHPLC (MeCN, water, 0.1% TFA) to afford (3R,5'S)-1'-((S)-2-(4,6-difluoro-N-(methyl-d3)-1H-indole-2-carboxamido)-4-fluoro-4-methylpentanoyl)-2-oxo-6-(trifluoromethyl)spiro[indoline-3,3'-pyrrolidine]-5'-carboxamide (88.3 mg, 72%) as a white solid. [M−1], 625.1.

Step 11

In a 40 mL screw cap vial equipped with a pressure release septum and a stir bar, (3R,5'S)-1'-((S)-2-(4,6-difluoro-N-(methyl-d3)-1H-indole-2-carboxamido)-4-fluoro-4-methylpentanoyl)-2-oxo-6-(trifluoromethyl)spiro[indoline-3,3'-pyrrolidine]-5'-carboxamide (88.3 mg, 1.0 equiv) was dissolved in DCM (2.8 mL, 0.05M) at 0° C. To the solution was added triethylamine (1.27 mL, 9.0 equiv), followed by trifluoroacetic anhydride (634 μL, 4.5 equiv). The resulting mixture was stirred 1.5 h at rt. Upon completion, ammonium hydroxide (250 μL, 30 wt %) was added and the mixture was briefly shaken. The mixture was then diluted with saturated aqueous sodium bicarbonate (5 mL) and DCM (5.0 mL) and passed through a phase separator. Upon concentration, the crude residue was purified by RPHPLC (MeCN, water, 0.1% TFA) to afford N—((S)-1-((3R,5'S)-5'-cyano-2-oxo-6-(trifluoromethyl)spiro[indoline-3,3'-pyrrolidin]-1'-yl)-4-fluoro-4-methyl-1-oxopentan-2-yl)-4,6-difluoro-N-(methyl-d3)-1H-indole-2-carboxamide (1.7 mg, 2%). $^1$H NMR (400 MHz, Acetone-$d_6$) δ 10.76 (s, 1H), 9.96 (s, 1H), 7.19-6.99 (m, 5H), 6.74 (td, J=10.3, 2.1 Hz, 1H), 5.83 (dd, J=7.6, 5.5 Hz, 1H), 5.28 (t, J=8.2 Hz, 1H), 4.52 (d, J=11.0 Hz, 1H), 4.01 (d, J=10.9 Hz, 1H), 2.88-2.71 (m, 2H), 2.48-2.29 (m, 2H), 1.45 (d, J=6.3 Hz, 3H), 1.40 (d, J=6.5 Hz, 3H). [M−1], 607.4.

Example 473

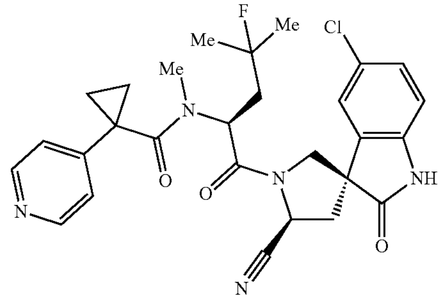

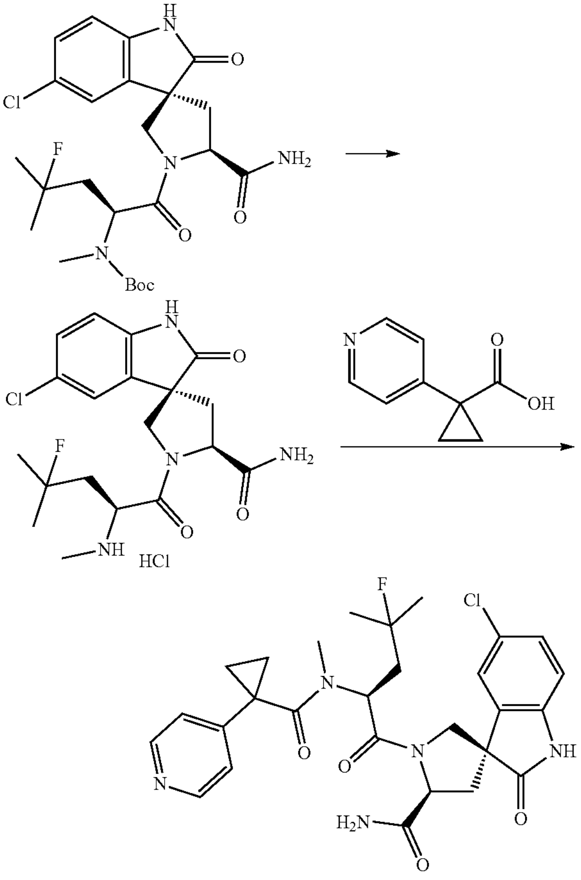

-continued

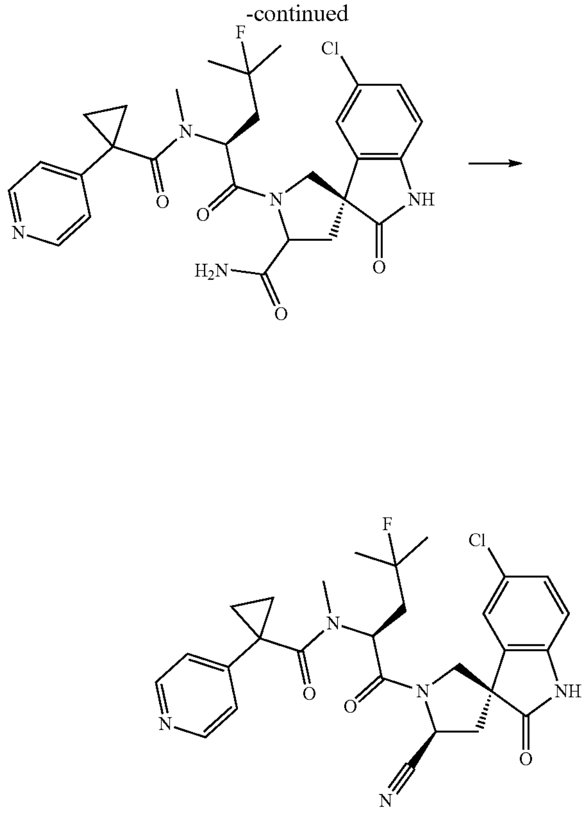

Step 1

In a 40 mL screw cap vial equipped with a pressure release septum and a stir bar, tert-butyl ((S)-1-((3R,5'S)-5'-carbamoyl-5-chloro-2-oxospiro[indoline-3,3'-pyrrolidin]-1'-yl)-4-fluoro-4-methyl-1-oxopentan-2-yl)(methyl)carbamate (318.0 mg, 1.0 equiv) was treated with 4M HCl in dioxane (3.1 mL, 20 equiv HCl). The resulting mixture was stirred 1.5 h at rt. Upon full consumption of starting material, as judged by LCMS, the reaction mixture was concentrated to afford (3R,5'S)-5-chloro-1'-((S)-4-fluoro-4-methyl-2-(methylamino)pentanoyl)-2-oxospiro[indoline-3,3'-pyrrolidine]-5'-carboxamide hydrochloride (278 mg) as a white solid that was used in Step 2 without purification. [M+1], 411.2.

Step 2

In a 40 mL screw cap vial equipped with a pressure release septum and a stir bar, (3R,5'S)-5-chloro-1'-((S)-4-fluoro-4-methyl-2-(methylamino)pentanoyl)-2-oxospiro[indoline-3,3'-pyrrolidine]-5'-carboxamide hydrochloride (50.0 mg, 1.0 equiv) was combined with 1-(pyridin-4-yl)cyclopropane-1-carboxylic acid (18.2 mg, 1.0 equiv) and N-methylmorpholine (40 μL, 3.2 equiv) in a mixture of DCM/DMF (5:1 DCM/DMF, 0.15M, 620 μL DCM/120 μL DMF) at 0° C. Next, HATU (42.5 mg, 1.0 equiv) was added and the reaction was stirred for 14 h. Upon completion, 100 uL of formic acid was added and the mixture was concentrated. The crude residue was purified by RPHPLC (MeCN/water/0.1% TFA) to afford (3R,5'S)-5-chloro-1'-((S)-4-fluoro-4-methyl-2-(N-methyl-1-(pyridin-4-yl)cyclopropane-1-carboxamido)pentanoyl)-2-oxospiro[indoline-3,3'-pyrrolidine]-5'-carboxamide (36.2 mg, 58%). [M+1], 556.4.

Step 3

In a 40 mL screw cap vial equipped with a pressure release septum and a stir bar, (3R,5'S)-5-chloro-1'-((S)-4-fluoro-4-methyl-2-(N-methyl-1-(pyridin-4-yl)cyclopropane-1-carboxamido)pentanoyl)-2-oxospiro[indoline-3,3'-pyrrolidine]-5'-carboxamide (36.2 mg, 1.0 equiv) was dissolved in DCM (870 μL, 0.075M) and the Burgess reagent (46.5 mg, 3.0 equiv) was added. The mixture was stirred 14 h at rt. The mixture was then diluted with saturated aqueous bicarbonate (3 mL) and DCM (5 mL) and passed through a phase separator. Upon concentration, the residue was purified by RHPLC to afford N—((S)-1-((3R,5'S)-5-chloro-5'-cyano-2-oxospiro[indoline-3,3'-pyrrolidin]-1'-yl)-4-fluoro-4-methyl-1-oxopentan-2-yl)-N-methyl-1-(pyridin-4-yl)cyclopropane-1-carboxamide (11.1 mg, 32%) as a white solid. $^{1}$H NMR (400 MHz, Acetone-$d_6$) δ 8.70 (d, J=6.7 Hz, 2H), 7.54 (d, J=6.7 Hz, 2H), 7.35 (dd, J=8.3, 2.1 Hz, 1H), 7.12 (d, J=2.1 Hz, 1H), 7.07 (d, J=8.3 Hz, 1H), 5.61 (dd, J=7.4, 5.6 Hz, 1H), 5.26 (t, J=8.4 Hz, 1H), 4.24 (d, J=10.6 Hz, 1H), 4.08 (d, J=10.6 Hz, 1H), 3.00 (s, 2H), 2.85-2.67 (m, 1H), 2.44-2.19 (m, 2H), 1.68-1.58 (m, 2H), 1.46 (d, J=7.8 Hz, 3H), 1.41 (d, J=7.7 Hz, 3H), 1.39-1.24 (m, 2H). [M+1], 538.2.

The following examples were prepared employing a similar protocol as described above.

| Example | Structure | MS | NMR |
|---|---|---|---|
| 474 | 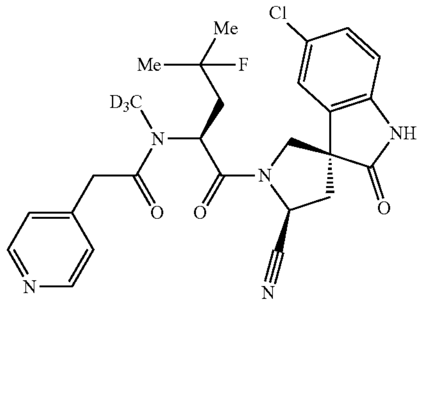 [SMILES: [2H]C([2H])([2H])N(C(=O)Cc1ccncc1)[C@@H](CC(C)(C)F)C(=O)N1C[C@]2(C[C@H]1C#N)C(=O)Nc1ccc(Cl)cc12] | [M + 1] 515.2 | $^{1}$H (400 MHz, Acetone-$d_6$) δ 8.82 (d, J = 6.2 Hz, 2H), 7.63 (d, J = 3.9 Hz, 2H), 7.37 (dd, J = 8.3, 2.1 Hz, 1H), 7.10 (d, J = 8.4 Hz, 1H), 7.05 (s, 1H), 5.69 (dd, 7 = 7.4, 5.8 Hz, 1H), 5.31 (t, J = 8.3 Hz, 1H), 4.32-4.28 (m, 1H), 4.13 (d, J = 17.1 Hz, 1H), 3.91 (d, J = 10.9 Hz, 1H), 3.84 (d, J = 16.9 Hz, 1H), 2.86-2.68 (m, 2H), 2.39-2.17 (m, 2H), 1.41 (d, J = 11.0 Hz, 3H), 1.36 (d, J = 11.1 Hz, 3H). |

-continued

| Example | Structure | MS | NMR |
|---|---|---|---|
| 475 | 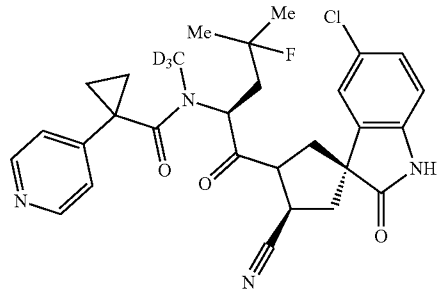 | [M + 1] 541.4 | $^1$H NMR (400 MHz, Acetone-$d_6$) δ 8.84 (d, J = 6.9 Hz, 2H), 7.79 (d, J = 6.9 Hz, 2H), 7.34 (dd, J = 8.3, 2.2 Hz, 1H), 7.11 (d, J = 2.1 Hz, 1H), 7.06 (d, J = 8.3 Hz, 1H), 5.61 (dd, J = 7.7, 5.5 Hz, 1H), 5.26 (t, J = 8.4 Hz, 1H), 4.24 (d, J = 10.6 Hz, 1H), 4.08 (d, J = 10.6 Hz, 1H), 2.86-2.67 (m, 2H), 2.43-2.21 (m,2H), 1.83-1.68 (m, 2H), 1.55-1.39 (m, 2H), 1.47 (d, J = 9.0 Hz, 3H), 1.42 (d, J= 8.8 Hz, 3H). |
| 476 | 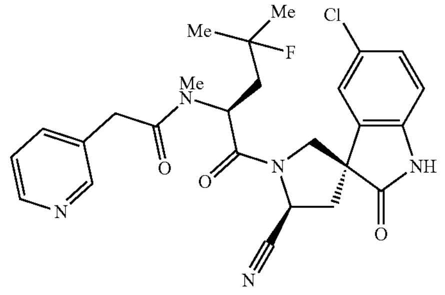 [SMILES: CN(C(=O)Cc1cccnc1)[C@@H](CC(C)(C)F)C(=O)N1C[C@]2(C[C@H]1C#N)C(=O)Nc1ccc(Cl)cc12] | [M + 1] 512.4 | $^1$H NMR (400 MHz, Acetone-$d_6$) δ 9.90 (s, 1H), 8.39 (dd, 4.7, 1.8 Hz, 1H), 8.12-8.11 (m, 1H), 7.37 (dd, J = 8.4, 2.1 Hz, 1H), 7.23 (dt, J = 7.8, 2.1 Hz, 1H), 7.18 (ddd, J = 7.8, 4.7, 0.9 Hz, 1H), 7.07-7.05 (m, 2H), 5.71 (dd, J = 7.4, 5.8 Hz, 1H), 5.32 (t, J = 8.4 Hz, 1H), 4.32 (dd, J = 10.9, 1.4 Hz, 1H), 3.88 (d, J = 10.9 Hz, 1H), 3.73-3.69 (m, 1H), 3.37 (d, J = 16.7 Hz, 1H), 3.16 (s, 3H), 2.87-2.68 (m, 2H), 2.37-2.13 (m, 2H), 1.39 (d, J = 10.7 Hz, 3H), 1.34 (d, J = 11.0 Hz, 3H). |
| 477 | 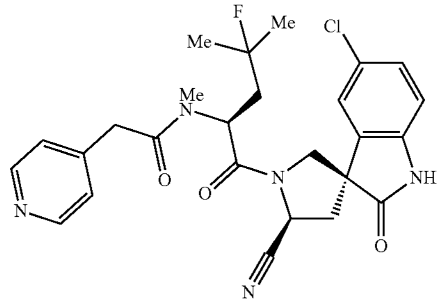 [SMILES: CN(C(=O)Cc1ccncc1)[C@@H](CC(C)(C)F)C(=O)N1C[C@]2(C[C@H]1C#N)C(=O)Nc1ccc(Cl)cc12] | [M + 1] 512.2 | $^1$H NMR (400 MHz, Acetone-$d_6$) δ 8.40 - 8.37 (m, 2H), 7.39 (dd, J = 8.3, 2.2 Hz, 1H), 7.10 (d, J = 8.3 Hz, 1H), 7.07 (d, J = 2.1 Hz, 1H), 6.89-6.86 (m, 2H), 5.70 (dd, J = 7.4, 5.8 Hz, 1H), 5.31 (t, J = 8.4 Hz, 1H), 4.33-4.28 (m, 1H), 3.89 (d, J = 10.9 Hz, 1H), 3.69 (d, J = 16.3 Hz, 1H), 3.42 (d, J = 16.5 Hz, 1H), 3.13 (s, 3H), 2.87-2.68 (m, 2H), 2.37-2.21 (m, 2H), 1.40 (d, J = 9.5 Hz, 3H), 1.34 (d, J = 9.7 Hz, 3H). |
| 478 | 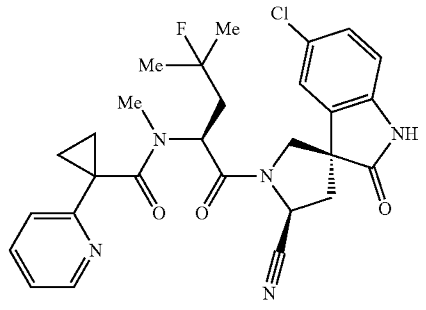 [SMILES: CN(C(=O)C1(c2ccccn2)CC1)[C@@H](CC(C)(C)F)C(=O)N1C[C@]2(C[C@H]1C#N)C(=O)Nc1ccc(Cl)cc12] | [M + 1] 538.2 | $^1$H NMR (400 MHz, Acetone-$d_6$) δ 9.86 (s, 1H), 8.43-8.41 (m, 1H), 7.67 (td, J = 7.8, 1.9 Hz, 1H), 7.33 (dd, J = 8.3, 2.1 Hz, 1H), 7.20-7.13 (m, 3H), 7.05 (d, J = 8.3 Hz, 1H), 5.66-5.62 (m, 1H), 5.25 (t, J = 8.3 Hz, 1H), 4.28 (d, J = 10.6 Hz, 1H), 4.06 (d, J = 10.6 Hz, 1H), 2.89 (s, 3H), 2.86-2.67 (m, 2H), 2.50-2.39 (m, 1H), 2.19-2.09 (m, 1H), 1.61-1.56 (m, 1H), 1.46 (s, 3H), 1.41 (s, 3H), 1.34-1.28 (m, 1H), 1.22-1.16 (m, 1H), 0.97-0.92 (m, 1H). |
| 479 | 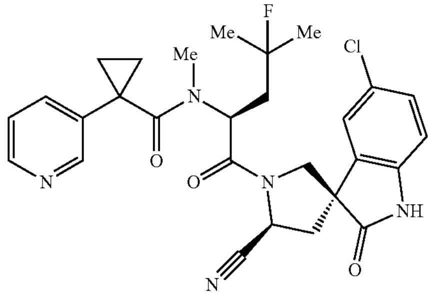 [SMILES: CN(C(=O)C1(c2cccnc2)CC1)[C@@H](CC(C)(C)F)C(=O)N1C[C@]2(C[C@H]1C#N)C(=O)Nc1ccc(Cl)cc12] | [M + 1] 538.4 | $^1$H NMR (400 MHz, Acetone-$d_6$) δ 9.85 (s, 1H), 8.44-8.43 (m, 2H), 7.57-7.54 (m, 1H), 7.36 (dd, J = 8.3, 2.1 Hz, 1H), 7.27 (dd, J = 8.0, 4.8 Hz, 1H), 7.11-7.05 (m, 2H), 5.58 (t, J = 6.5 Hz, 1H), 5.22 (t, J = 8.3 Hz, 1H), 4.20 (d, J = 10.6 Hz, 1H), 4.04 (d, J= 10.6 Hz, 1H), 2.95 (s, 3H), 2.84-2.66 (m, 2H), 2.39-2.28 (m, 1H), 1.16-2.04 (m, 1H), 1.48-1.31 (m, 2H), 1.41 (d, J = 11.3 Hz, 3H), 1.36 (d, J = 11.2 Hz, 3H), 1.00-0.94 (m, 2H). |

-continued

| Example | Structure | MS | NMR |
|---|---|---|---|
| 480 | 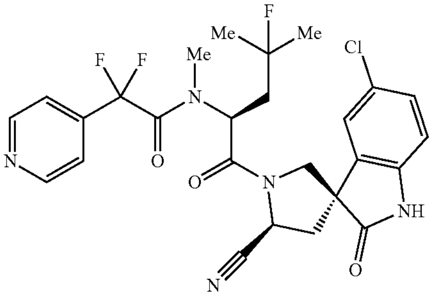 [SMILES: CN(C(=O)C(F)(F)c1ccncc1)[C@@H](CC(C)(C)F)C(=O)N1C[C@]2(C[C@H]1C#N)C(=O)Nc1ccc(Cl)cc12] | [M + 1] 548.3 | $^1$HNMR (400 MHz, Acetone-$d_6$) δ 9.84 (s, 1H), 8.72 (d, J = 6.1 Hz, 2H), 7.38-7.34 (m, 3H), 7.16 (d, J = 2.1 Hz, 1H), 7.07 (d, J = 8.3 Hz, 1H), 5.57 (dd, J = 7.4, 5.8 Hz, 1H), 5.28 (dd, J = 8.6, 7.7 Hz, 1H), 4.09-4.02 (m, 2H), 3.17 (t, J = 2.3 Hz, 4H), 2.88-2.80 (m, 1H), 2.72-2.67 (m, 1H), 2.37-2.30 (m, 2H), 1.43 (s, 3H), 1.38 (s, 3H). |
| 481 | 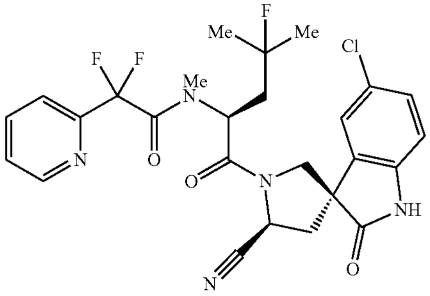 [SMILES: CN(C(=O)C(F)(F)c1ccccn1)[C@@H](CC(C)(C)F)C(=O)N1C[C@]2(C[C@H]1C#N)C(=O)Nc1ccc(Cl)cc12] | [M + 1] 548.4 | $^1$H NMR (400 MHz, Acetone-$d_6$) δ 9.81 (s, 1H), 8.50 (d, J = 4.8 Hz, 1H), 8.04 (td, J = 7.8, 1.7 Hz, 1H), 7.75 (d, J = 7.9 Hz, 1H), 7.58-7.55 (m, 1H), 7.33 (dd, J = 8.3, 2.2 Hz, 1H), 7.20 (d, J = 2.2 Hz, 1H), 7.05 (d, J = 8.3 Hz, 1H), 5.64-5.60 (m, 1H), 5.22 (dd, J = 8.7, 7.0 Hz, 1H), 4.13-4.07 (m, 2H), 2.96 (t, J = 1.8 Hz, 3H), 2.89-2.81 (m, 1H), 2.72-2.67 (m, 1H), 2.53-2.42 (m, 1H), 2.20-2.10 (m, 1H), 1.44 (d, J = 2.1 Hz, 3H), 1.39 (d, J = 2.4 Hz, 3H). |
| 482 | 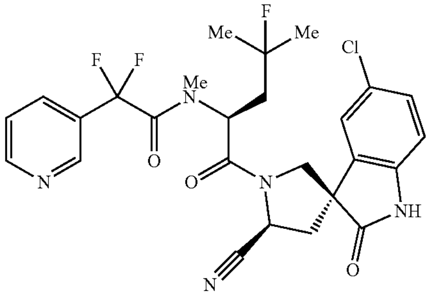 [SMILES: CN(C(=O)C(F)(F)c1cccnc1)[C@@H](CC(C)(C)F)C(=O)N1C[C@]2(C[C@H]1C#N)C(=O)Nc1ccc(Cl)cc12] | [M + 1] 548.2 | $^1$H NMR (400 MHz, Acetone-$d_6$) δ 9.84 (s, 1H), 8.74-8.73 (m, 1H), 8.61-8.59 (m, 1H), 7.79-7.75 (m, 1H), 7.50-7.47 (m, 1H), 7.35 (dd, J = 8.3, 2.2 Hz, 1H), 7.15 (d, J = 2.1 Hz, 1H), 7.06 (d, J = 8.3 Hz, 1H), 5.58 (dd, J = 7.2, 6.0 Hz, 1H), 5.29 (dd, J = 8.7, 7.6 Hz, 1H), 4.10-4.02 (m, 2H), 3.20 (t, J = 2.3 Hz, 3H), 2.90-2.80 (m, 1H), 2.70 (dd, J = 13.4, 7.6 Hz, 1H), 2.41-2.28 (m, 2H), 1.44 (s, 3H), 1.38 (s, 3H) |
| 483 | 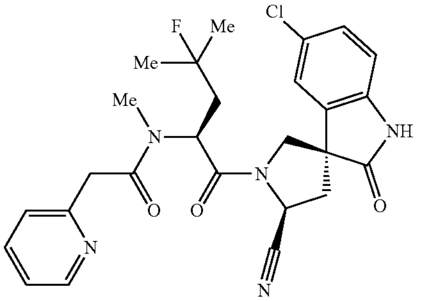 [SMILES: CN(C(=O)Cc1ccccn1)[C@@H](CC(C)(C)F)C(=O)N1C[C@]2(C[C@H]1C#N)C(=O)Nc1ccc(Cl)cc12] | [M + 1] 512.4 | $^1$H NMR (400 MHz, Acetone-$d_6$) δ 8.58 (d, J = 5.3 Hz, 1H), 7.96 (td, J = 7.8, 1.8 Hz, 1H), 7.52-7.49 (m, 1H), 7.34 (dd, J = 8.3, 2.1 Hz, 1H), 7.25 (d, J = 7.9 Hz, 1H), 7.13 (d, J = 2.2 Hz, 1H), 7.05 (d, J = 8.3 Hz, 1H), 5.66 (t, J = 6.5 Hz, 1H), 5.26 (dd, J = 8.8, 7.1 Hz, 1H), 4.27-4.24 (m, 1H), 3.92 (d, J = 10.9 Hz, 1H), 3.16 (s, 3H), 2.87-2.66 (m, 2H), 2.44-2.12 (m, 2H), 1.39 (d, J = 6.3 Hz, 3H), 1.33 (d, J = 6.6 Hz, 3H). |
| 484 | 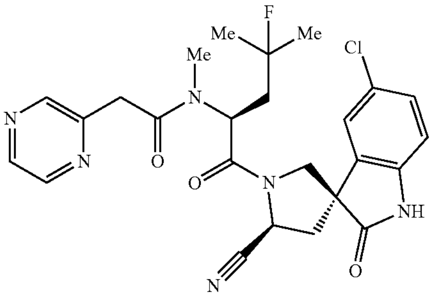 [SMILES: CN(C(=O)Cc1cnccn1)[C@@H](CC(C)(C)F)C(=O)N1C[C@]2(C[C@H]1C#N)C(=O)Nc1ccc(Cl)cc12] | [M + 1] 513.2 | $^1$H NMR (400 MHz, Acetone-$d_6$) δ 8.42-8.40 (m, 2H), 8.12 (dd, J = 2.6, 1.2 Hz, 1H), 7.37 (dd, J = 8.4, 2.1 Hz, 1H), 7.10-7.08 (m, 2H), 5.68 (dd, J = 7.3, 5.9 Hz, 1H), 5.31 (t, J = 8.3 Hz, 1H), 4.32-4.27 (m, 1H), 3.89 (d, J = 10.9 Hz, 1H), 3.18 (s, 2H), 2.90-2.66 (m, 2H), 2.41-2.13 (m, 2H), 1.39 (d, J = 9.4 Hz, 3H), 1.34 (d, J = 9.6 Hz, 3H). |

-continued
| Example | Structure | MS | NMR |
|---|---|---|---|
| 485 | 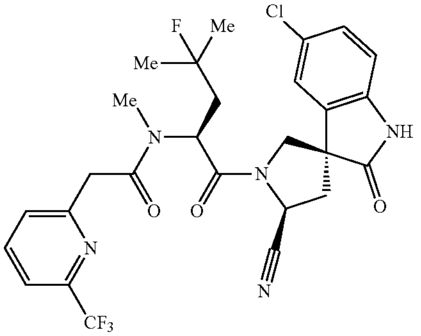 [SMILES: CN(C(=O)Cc1cccc(C(F)(F)F)n1)[C@@H](CC(C)(C)F)C(=O)N1C[C@]2(C[C@H]1C#N)C(=O)Nc1ccc(Cl)cc12] | [M + 1] 580.2 | |
| 486 | 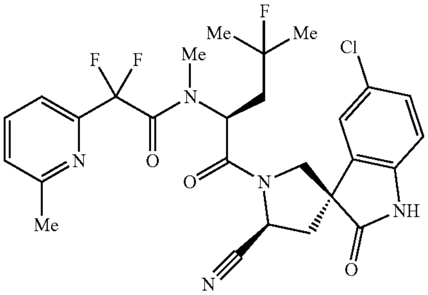 [SMILES: Cc1cccc(C(F)(F)C(=O)N(C)[C@@H](CC(C)(C)F)C(=O)N2C[C@]3(C[C@H]2C#N)C(=O)Nc2ccc(Cl)cc23)n1] | [M + 1] 562.3 | |
| 487 | 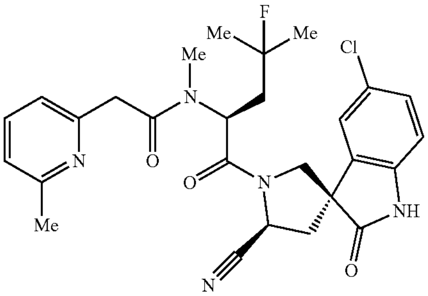 [SMILES: Cc1cccc(CC(=O)N(C)[C@@H](CC(C)(C)F)C(=O)N2C[C@]3(C[C@H]2C#N)C(=O)Nc2ccc(Cl)cc23)n1] | [M + 1] 526.2 | $^1$H NMR (400 MHz, Acetone-$d_6$) δ 9.79 (s, 1H), 7.84 (t, J = 7.8 Hz, 1H), 7.38-7.33 (m, 2H), 7.16 (d, J = 2.1 Hz, 1H), 7.07-7.03 (m, 2H), 5.66 (t, J = 6.5 Hz, 1H), 5.25 (dd, J = 8.9, 6.9 Hz, 1H), 4.28 (d, J = 10.8 Hz, 1H), 4.07 (d, J = 16.0 Hz, 1H), 3.93 (d, J = 10.9 Hz, 1H), 3.79 (d, J = 16.2 Hz, 1H), 3.14 (s, 3H), 2.85 (dd, J = 13.5, 8.9 Hz, 1H), 2.69 (dd, J = 13.5, 6.8 Hz, 1H), 2.59 (s, 3H), 2.46-2.35 (m, 1H), 2.17-2.08 (m, 1H), 1.39 (d, J = 8.3 Hz, 3H), 1.34 (d, J = 8.6 Hz, 3H). |
| 488 | 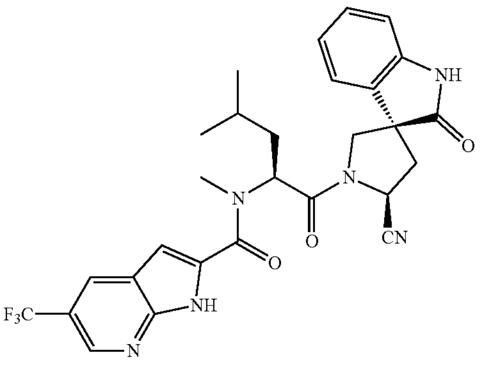 [SMILES: CC(C)C[C@@H](C(=O)N1C[C@]2(C[C@H]1C#N)C(=O)Nc1ccccc12)N(C)C(=O)c1cc2cc(C(F)(F)F)cnc2[nH]1] | 10.3 | $^1$H NMR (400 MHz, Acetone-$d_6$) δ 11.83 (s, 1H), 9.41 (s, 1H), 8.65 (d, J = 2.2 Hz, 1H), 8.42 (s, 1H), 7.09 (d, J = 2.2 Hz, 1H), 7.02-6.85 (m, 2H), 6.74 (t, J = 7.6 Hz, 1H), 6.61 (d, J = 7.8 Hz, 1H), 5.74 (dd, J = 9.6, 5.4 Hz, 1H), 5.23 (t, J = 8.5 Hz, 1H), 4.64 (d, J = 10.7 Hz, 1H), 4.03 (d, J = 10.7 Hz, 1H), 2.85 (s, 1H), 2.67 (d, J = 8.5 Hz, 2H), 2.01 (dt, J = 9.7, 4.8 Hz, 1H), 1.85 (ddd, J = 14.3, 9.0, 5.6 Hz, 1H), 1.78-1.65 (m, 1H), 1.03 (dd, J = 14.6, 6.5 Hz, 7H). |

-continued
| Example | Structure | MS | NMR |
| --- | --- | --- | --- |
| 489 | 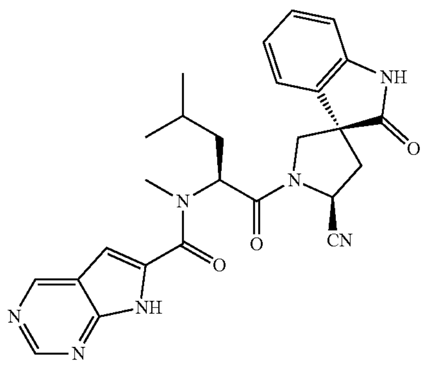 [SMILES: CC(C)C[C@@H](C(=O)N1C[C@]2(C[C@H]1C#N)C(=O)Nc1ccccc12)N(C)C(=O)c1cc2cncnc2[nH]1] | 4.5 | $^{1}$H NMR (400 MHz, DMSO-d6) δ 10.67 (s, 1H), 9.07 (s, 1H), 8.82 (s, 1H), 7.20-7.04 (m, 2H), 6.95-6.80 (m, 2H), 6.76 (s, 1H), 5.32 (m, 1H), 5.19 (t, J = 7.7 Hz, 1H), 3.87 (s, 3H), 3.19 (s, 3H), 2.66 (dd, J = 13.3, 8.8 Hz, 1H), 1.85-1.49 (m, 3H), 0.94 (dd, J = 17.5, 6.6 Hz, 6H). |
| 490 | 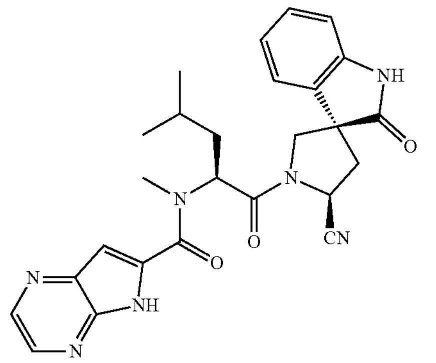 [SMILES: CC(C)C[C@@H](C(=O)N1C[C@]2(C[C@H]1C#N)C(=O)Nc1ccccc12)N(C)C(=O)c1cc2nccnc2[nH]1] | 4.1 | 1H NMR (400 MHz, Acetone-d6) δ 9.57 (s, 1H), 8.47 (d, J = 2.4 Hz, 1H), 8.32 (d, J = 2.4 Hz, 1H), 7.10-6.88 (m, 3H), 6.81 (t, J = 7.5 Hz, 2H), 5.62 (dd, J = 9.6, 5.5 Hz, 1H), 5.22 (t, J = 8.3 Hz, 1H), 4.41 (d, J = 10.6 Hz, 1H), 4.02 (d, J = 10.7 Hz, 1H), 3.49 (s, 3H), 2.70 (qd, J = 13.2, 8.3 Hz, 2H), 1.98 (ddd, J = 14.5, 9.6, 5.0 Hz, 1H), 1.82 (ddd, J = 14.2, 8.8, 5.5 Hz, 1H), 1.69 (tt, J = 14.0, 6.7 Hz, 1H), 1.00 (dd, J = 19.1, 6.6 Hz, 6H). |
| 491 | 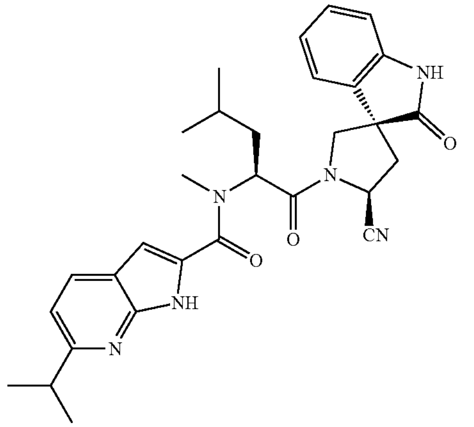 [SMILES: CC(C)C[C@@H](C(=O)N1C[C@]2(C[C@H]1C#N)C(=O)Nc1ccccc12)N(C)C(=O)c1cc2ccc(C(C)C)nc2[nH]1] | $[M-H]^-$ 527.171 | $^{1}$H NMR (400 MHz, Acetone-d6) δ 9.65 (s, 1H), 7.96 (d, J = 11.6 Hz, 1H), 7.06 (d, J = 8.6 Hz, 3H), 6.93 (d, J = 8.0 Hz, 2H), 6.75 (s, 1H), 5.53 (d, J = 8.2 Hz, 1H), 5.22 (t, J = 8.3 Hz, 1H), 4.28 (s, 1H), 4.01 (d, J = 10.6 Hz, 1H), 3.42 (s, 3H), 3.12 (p, J = 6.9 Hz, 1H), 2.77-2.64 (m, 2H), 1.93 (s, 1H), 1.80 (dt, J = 14.1, 7.0 Hz, 1H), 1.73-1.62 (m, 1H), 1.31 (d, J = 6.8 Hz, 6H), 1.06-0.92 (m, 6H). |

Example 492

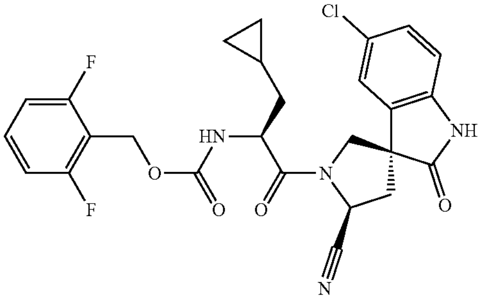

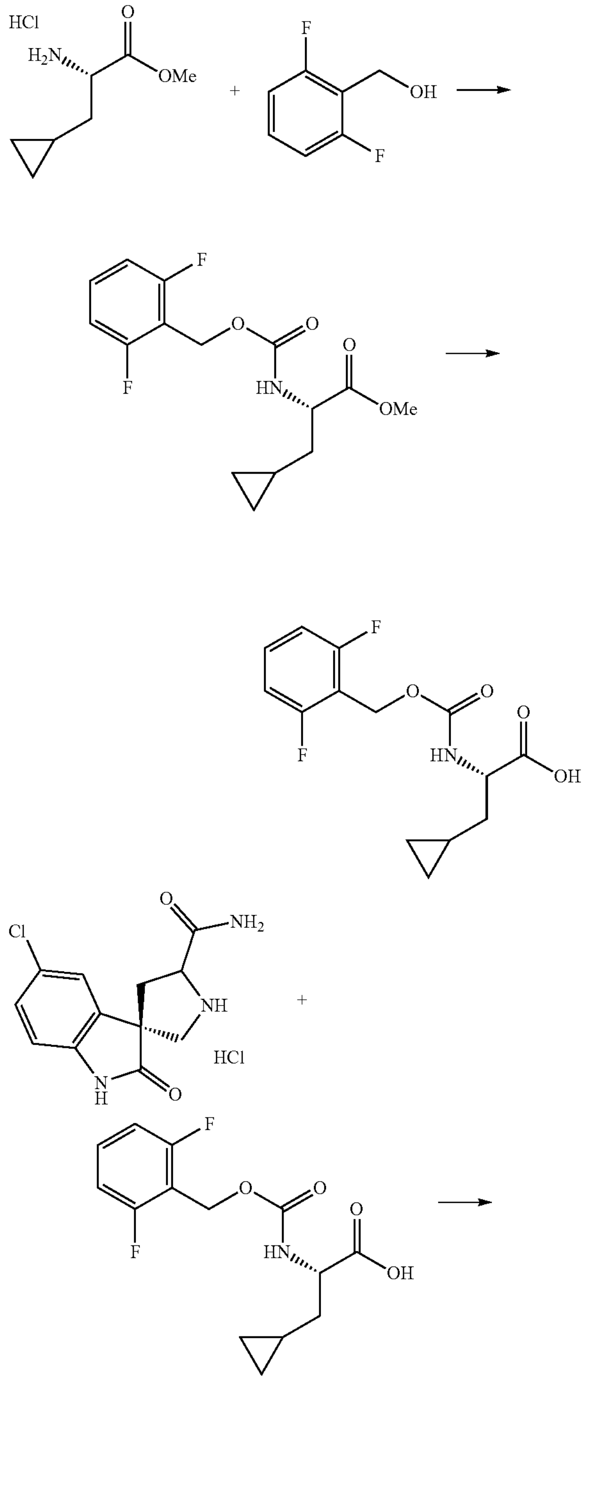

-continued

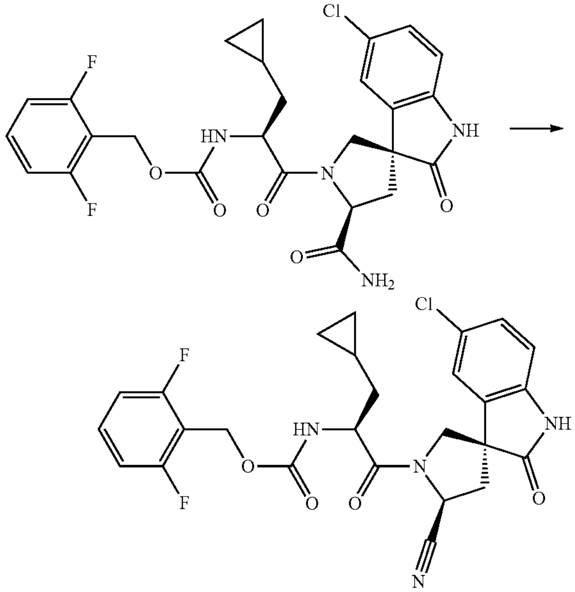

Step 1:

In a 40 mL vial equipped with a pressure release cap and a stir bar, (2,6-difluorophenyl)methanol (802.0 mg, 1.0 equiv) was dissolved in DMF (7.4 mL, 0.75M). Next, the solution was cooled in an ice bath and CDI (903.0 mg, 1.0 equiv) was added. The resulting mixture was then warmed to rt. After stirring for 20 minutes, methyl (S)-2-amino-3-cyclopropylpropanoate hydrochloride (1.00 g, 1.0 equiv) was added and the reaction was heated at 55° C. for 14 h. Upon cooling to rt, the reaction was diluted with brine and the aqueous phase was extracted with ethyl acetate. The combined organic layers were dried over magnesium sulfate. Upon concentration, the crude residue was purified by silica gel column chromatography (gradient elution, 0 to 40% ethyl acetate/cyclohexane) to afford methyl (S)-3-cyclopropyl-2-((((2,6-difluorobenzyl)oxy)carbonyl)amino)propanoate (1.23 g, 71%). [M+1], 314.2.

Step 2

In a 50 mL round-bottomed flask equipped with a stir bar, (S)-3-cyclopropyl-2-((((2,6-difluorobenzyl)oxy)carbonyl)amino)propanoate (1.23 g, 1.0 equiv) was dissolved in a mixture of MeOH and water (1:1, 0.26M, 7.6 mL MeOH, 7.6 mL water) at 0° C. Next, LiOH (235.0 mg, 2.5 equiv) was added. The reaction was then allowed to reach rt slowly and was stirred for 14 h. The mixture was concentrated to remove MeOH and acidified with 6M HCl. The aqueous phase was extracted with DCM, and the combined organic layers were dried over magnesium sulfate. Upon concentration, the crude residue was purified by silica gel column chromatography (gradient elution, 0 to 70% ethyl acetate/cyclohexane) to afford (S)-3-cyclopropyl-2-((((2,6-difluorobenzyl)oxy)carbonyl)amino)propanoic acid (431.0 mg, 37%). [M+1], 300.2.

Step 3

In a 40 mL vial equipped with a pressure release cap and a stir bar, (3R,5'S)-5-chloro-2-oxospiro[indoline-3,3'-pyrrolidine]-5'-carboxamide hydrochloride (100.0 mg, 1.0 equiv) and (S)-3-cyclopropyl-2-((((2,6-difluorobenzyl)oxy)carbonyl)amino)propanoic acid (114.0 mg, 1.15 equiv) were combined in DMF (2.2 mL, 0.15M). Next, HATU (145.0 mg, 1.15 equiv) was added, followed immediately by DIPEA (173 μL, 3.0 equiv). The reaction was stirred at rt for 14 h. Upon completion, the reaction was diluted with DCM, washed with 1.2M HCl and brine, and passed through a phase separator. Concentration afforded crude 2,6-difluorobenzyl ((S)-1-((3R,5'S)-5'-carbamoyl-5-chloro-2-oxospiro[indoline-3,3'-pyrrolidin]-1'-yl)-3-cyclopropyl-1-oxopropan-2-yl)carbamate that was used in the next step without purification. [M+1], 547.2.

Step 4:

In a 40 mL vial equipped with a pressure release cap and a stir bar, the crude 2,6-difluorobenzyl ((S)-1-((3R,5'S)-5'-carbamoyl-5-chloro-2-oxospiro[indoline-3,3'-pyrrolidin]-1'-yl)-3-cyclopropyl-1-oxopropan-2-yl)carbamate generated in Step 3 was dissolved in DCM (4.7 mL, 0.075M) at 0° C. To the resulting solution was added triethylamine (346 μL, 7.0 equiv), followed by trifluoroacetic anhydride (200 μL, 4.0 equiv). The reaction was allowed to stir for 1 h at rt and was then quenched with saturated aqueous sodium bicarbonate (5 mL) and 2.0 mL of ammonium hydroxide (30 wt %). The mixture was further diluted with DCM (5 mL) and passed through a phase separator. Upon concentration, the crude residue was purified by RPHPLC (MeCN/water/0.1% TFA) to afford 2,6-difluorobenzyl ((S)-1-((3R,5'S)-5-chloro-5'-cyano-2-oxospiro[indoline-3,3'-pyrrolidin]-1'-yl)-3-cyclopropyl-1-oxopropan-2-yl)carbamate (7.9 mg, 4.2%). $^{1}$H NMR (400 MHz, Acetone-$d_6$) δ 9.83 (s, 1H), 7.54-7.46 (m, 1H), 7.33-7.27 (m, 2H), 7.10-7.01 (m, 3H), 6.73 (d, J=7.6 Hz, 1H), 7.10-7.02 (m, 3H), 6.73 (d, J=7.6 Hz, 1H), 5.26 (t, J=8.1 Hz, 1H), 5.20 (d, J=11.8 Hz, 1H), 5.11 (d, J=11.8 Hz, 1H), 4.51 (q, J=7.3 Hz, 1H), 4.38 (d, J=10.5 Hz, 1H), 4.07 (d, J=10.5 Hz, 1H), 2.88-2.81 (m, 1H), 2.71 (dd, J=13.3, 7.8 Hz, 1H), 1.76-1.65 (m, 2H), 0.92-0.82 (m, 1H), 0.54-0.46 (m, 2H), 0.27-0.14 (m, 2H). [M−1], 527.0.

The following examples were prepared employing similar protocol as described above.

| Example | Structure | MS | NMR |
|---|---|---|---|
| 493 | 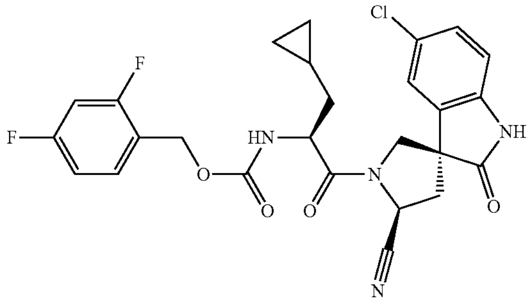 [SMILES: N#C[C@@H]1C[C@@]2(CN1C(=O)[C@H](CC1CC1)NC(=O)OCc1ccc(F)cc1F)C(=O)Nc1ccc(Cl)cc12] | [M - 1] 527.0 | |
| 494 | 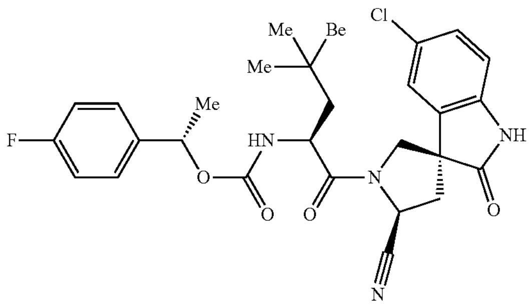 | [M - 1] 539.0 | $^{1}$H NMR (400 MHz, Acetone-d6) δ 9.84 (s, 1H), 7.39-7.35 (m, 2H), 7.31 (dd, J = 8.3, 2.1 Hz, 1H), 7.17 (d, J = 2.1 Hz, 1H), 7.10-7.06 (m, 2H), 7.02 (d, J = 8.3 Hz, 1H), 6.76 (d, J = 8.3 Hz, 1H), 5.67 (q, J = 6.6 Hz, 1H), 5.24 (t, J = 8.4 Hz, 1H), 4.46-4.38 (m, 2H), 4.00 (d, J = 10.4 Hz, 1H), 2.83-2.62 (m, 2H), 1.79 (dd, 14.5, 4.3 Hz, 1H), 1.67 (dd, J = 14.5, 8.4 Hz, 1H), 1.43 (d, J = 6.6 Hz, 3H), 0.96 (s, 9H). |
| 495 | 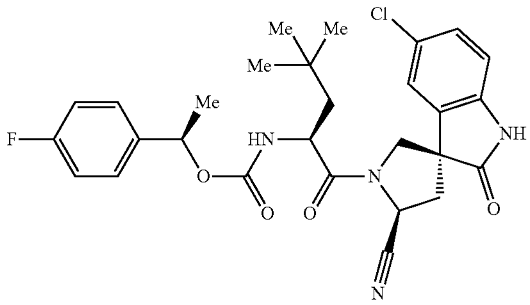 [SMILES: C[C@@H](OC(=O)N[C@@H](CC(C)(C)C)C(=O)N1C[C@]2(C[C@H]1C#N)C(=O)Nc1ccc(Cl)cc12)c1ccc(F)cc1] | [M - 1] 539.0 | $^{1}$H NMR (400 MHz, Acetone-$d_6$) δ 9.81 (s, 1H), 7.41-7.38 (m, 2H), 7.27 (dd, J = 8.3, 2.1 Hz, 1H), 7.15-7.09 (m, 3H), 7.00 (d, J = 8.3 Hz, 1H), 6.72 (d, J = 8.3 Hz, 1H), 5.74 (q, J = 6.5 Hz, 1H), 5.16 (t, J = 8.2 Hz, 1H), 4.48 (td, J = 8.5, 4.0 Hz, 1H), 4.29 (d, J = 10.3 Hz, 1H), 4.01 (d, J = 10.4 Hz, 1H), 2.80-2.64 (m, 2H), 1.82-1.65 (m, 2H), 1.45 (d, J = 6.6 Hz, 3H), 1.03 (s, 9H). |

-continued
| Example | Structure | MS | NMR |
|---|---|---|---|
| 496 | 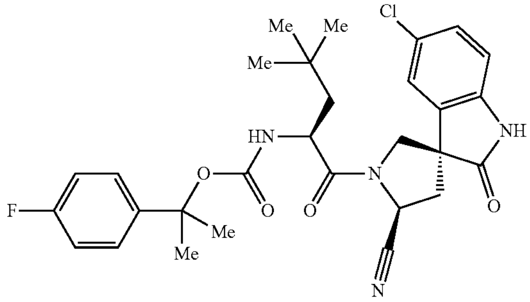 [SMILES: CC(C)(C)C[C@H](NC(=O)OC(C)(C)c1ccc(F)cc1)C(=O)N1C[C@]2(C[C@H]1C#N)C(=O)Nc1ccc(Cl)cc12] | [M − 1] 553.0 | $^1$H NMR (400 MHz, Acetone-$d_6$) δ 9.79 (s, 1H), 7.41-7.35 (m, 2H), 7.29 (dd, J = 8.3, 2.1 Hz, 1H), 7.10 (d, J = 2.1 Hz, 1H), 7.05-7.00 (m, 3H), 6.64 (d, J = 8.7 Hz, 1H), 5.17 (t, J = 8.3 Hz, 2H), 4.40-4.34 (m, 1H), 4.24 (d, J = 10.4 Hz, 1H), 3.96 (d, J = 10.4 Hz, 1H), 2.77-2.64 (m, 2H), 1.80-1.63 (m, 2H), 1.71 (s, 3H), 1.64 (s, 3H), 0.99 (s, 9H). |
Example 497
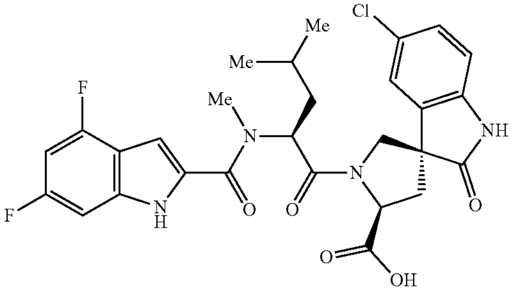
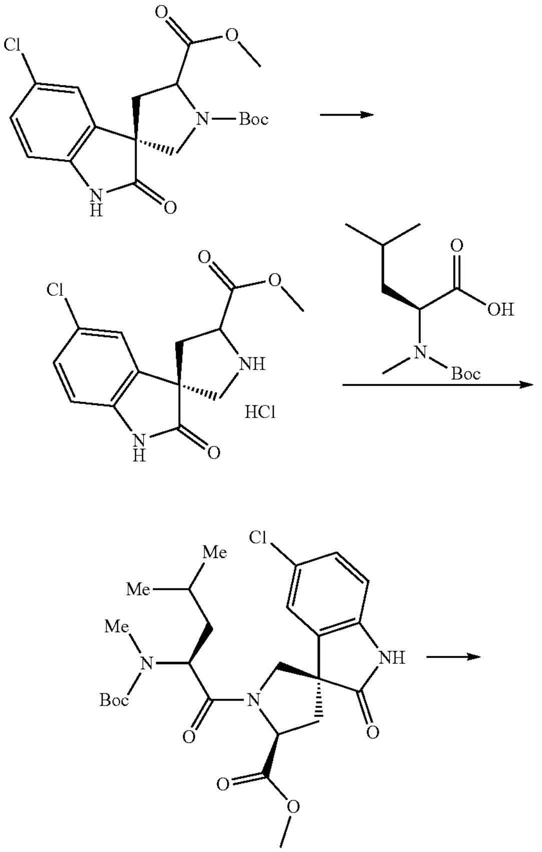
-continued
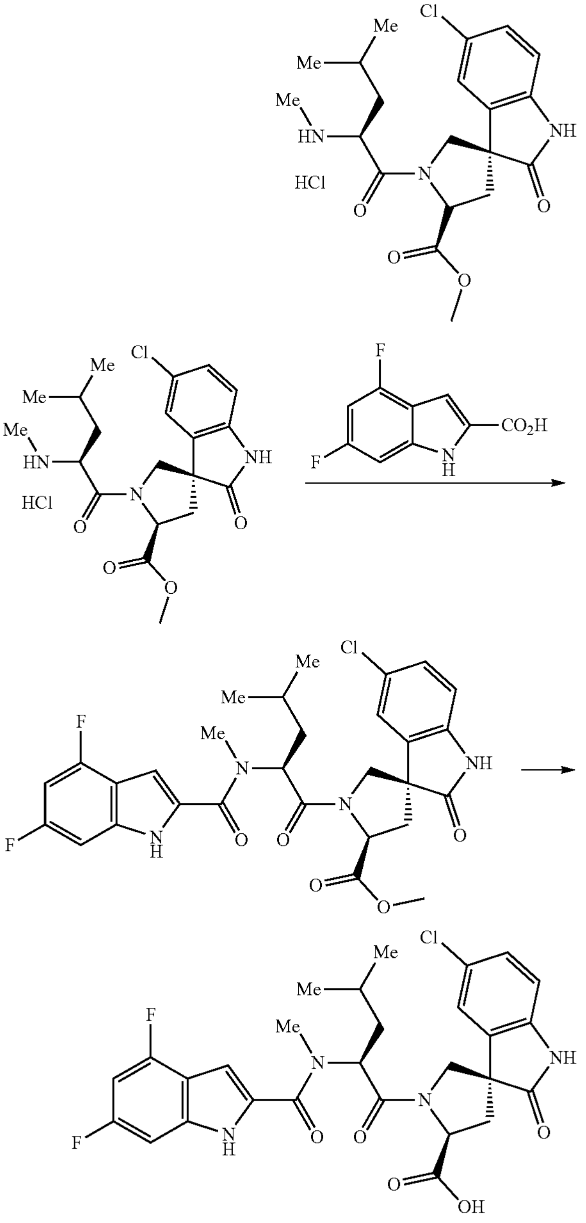

Step 1

In a 40 mL screw cap vial equipped with a pressure release septum and stir bar, 1'-(tert-butyl) 5'-methyl (3R, 5'S)-5-chloro-2-oxospiro[indoline-3,3'-pyrrolidine]-1',5'-dicarboxylate (209.0 mg, 1.0 equiv) was treated with 4M HCl in dioxane (2.7 mL, 20 equiv HCl). The mixture was stirred for 2 h and concentrated to afford methyl (3R,5'S)-5-chloro-2-oxospiro[indoline-3,3'-pyrrolidine]-5'-carboxylate hydrochloride (174.0 mg) which was used in the next step without purification. [M+1], 281.1.

Step 2

In a 40 mL screw cap vial equipped with a pressure release vial and a stir bar, methyl (3R,5'S)-5-chloro-2-oxospiro[indoline-3,3'-pyrrolidine]-5'-carboxylate hydrochloride (174.0 mg, 1.0 equiv) was combined with N-(tert-butoxycarbonyl)-N-methyl-L-leucine (135.0 mg, 1.0 equiv) in a mixture of DCM and DMF (5:1 DCM/DMF, 0.25M, 1.8 mL DCM, 370 μL DMF). The mixture was cooled in an ice bath, and N-methylmorpholine (181 μL, 3.0 equiv) was added, followed by HATU (209.0 mg, 1.0 equiv). The resulting mixture was allowed to slowly warm to room temperature and was stirred for 14 h. The reaction mixture was diluted with brine (5 mL) and DCM (5 mL) and the organic phase was passed through a phase separator. Upon concentration, the crude residue was purified by silica gel column chromatography (gradient elution, 0 to 55% ethyl acetate/cyclohexane) to afford methyl (3R,5'S)-1'-(N-(tert-butoxycarbonyl)-N-methyl-L-leucyl)-5-chloro-2-oxospiro[indoline-3,3'-pyrrolidine]-5'-carboxylate (246.6 mg, 88%). [M+1], 508.4.

Step 3

In a 40 mL screw cap vial equipped with a pressure release vial and a stir bar, (3R,5'S)-1'-(N-(tert-butoxycarbonyl)-N-methyl-L-leucyl)-5-chloro-2-oxospiro[indoline-3,3'-pyrrolidine]-5'-carboxylate (246.6 mg, 1.0 equiv) was treated with 4M HCl in dioxane (2.43 mL, 20 equiv HCl). The mixture was stirred for 2 h at rt and concentrated to afford methyl (3R,5'S)-5-chloro-1'-(methyl-L-leucyl)-2-oxospiro[indoline-3,3'-pyrrolidine]-5'-carboxylate hydrochloride as a white solid that was used without purification in the next step. [M+1], 408.2.

Step 4

In a 40 mL screw cap vial equipped with a pressure release vial and a stir bar, methyl (3R,5'S)-5-chloro-1'-(methyl-L-leucyl)-2-oxospiro[indoline-3,3'-pyrrolidine]-5'-carboxylate hydrochloride (1.0 equiv) generated in Step 3 was combined with 4,6-difluoro-1H-indole-2-carboxylic acid (96.0 mg, 1.0 equiv) in a mixture of DCM and DMF (5:1 DCM/DMF, 0.2M, 2.02 mL DCM, 410 μL DMF). The mixture was cooled in an ice bath and N-methylmorpholine was added (160 μL, 3.0 equiv), followed by HATU (185.0 mg, 1.0 equiv). The reaction was allowed to slowly warm to rt and was stirred for 14 h. Upon completion, the mixture was diluted with DCM (5 mL) and brine (5 mL) and passed through a phase separator. Upon concentration, the crude residue was purified by silica gel column chromatography to afford methyl (3R,5'S)-5-chloro-1'-(N-(4,6-difluoro-1H-indole-2-carbonyl)-N-methyl-L-leucyl)-2-oxospiro[indoline-3,3'-pyrrolidine]-5'-carboxylate (224.4 mg, 79%). [M−1], 585.1.

Step 5

In a 40 mL screw cap vial equipped with a pressure release vial and a stir bar, methyl (3R,5'S)-5-chloro-1'-(N-(4,6-difluoro-1H-indole-2-carbonyl)-N-methyl-L-leucyl)-2-oxospiro[indoline-3,3'-pyrrolidine]-5'-carboxylate (224.4 mg, 1.0 equiv) was dissolved in 1,2-DCE (3.82 mL, 0.1M). Next, trimethyltin hydroxide (207.0 mg, 3.0 equiv) was added and the mixture was heated at 75° C. for 16 h. Upon cooling to rt, the reaction mixture was diluted with DCM (20 mL), washed twice with 1.2M HCl (5 mL), and once with brine. The organic layer was passed through a phase separator. Upon concentration, the crude residue was purified by RPHPLC to afford (3R,5'S)-5-chloro-1'-(N-(4,6-difluoro-1H-indole-2-carbonyl)-N-methyl-L-leucyl)-2-oxospiro[indoline-3,3'-pyrrolidine]-5'-carboxylic acid as a white solid (1.44 mg, 0.7%). $^1$H NMR (400 MHz, Acetone-$d_6$) δ 10.71 (s, 1H), 9.78 (s, 1H), 7.12-7.05 (m, 1H), 7.02-6.95 (m, 3H), 6.89 (d, J=8.3 Hz, 1H), 6.74 (td, J=10.3, 2.1 Hz, 1H), 5.59 (t, J=7.5 Hz, 1H), 4.94 (t, J=8.8 Hz, 1H), 4.38 (d, J=10.4 Hz, 1H), 3.97 (d, J=10.5 Hz, 1H), 3.47 (s, 3H), 2.63-2.46 (m, 2H), 1.81 (t, J=7.2 Hz, 2H), 1.70-1.58 (m, 1H), 1.00 (d, J=6.6 Hz, 3H), 0.95 (d, J=6.6 Hz, 3H). [M−1], 570.9.

Example 498

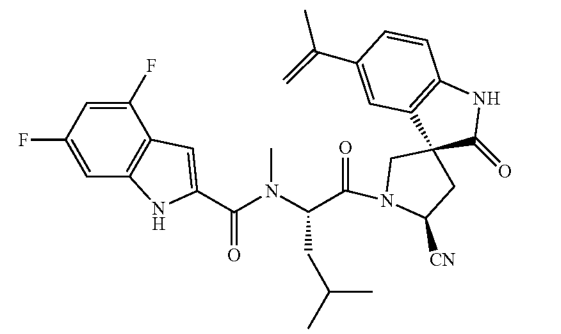

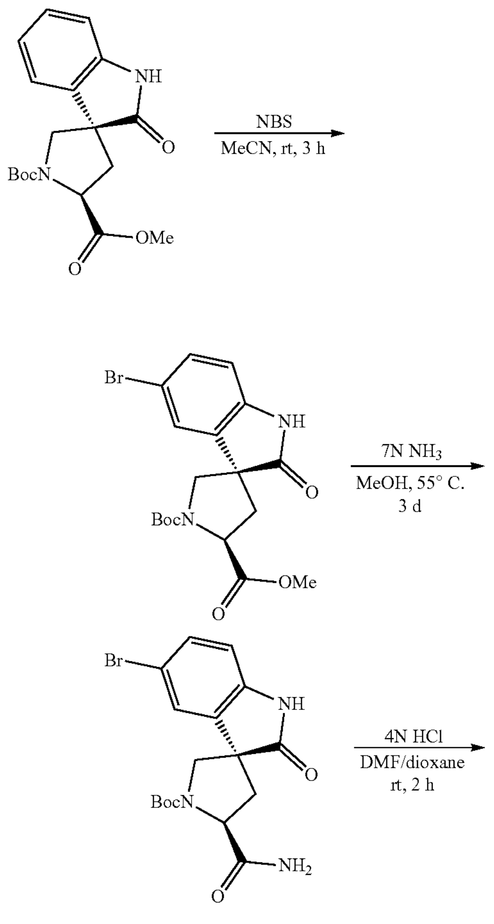

-continued

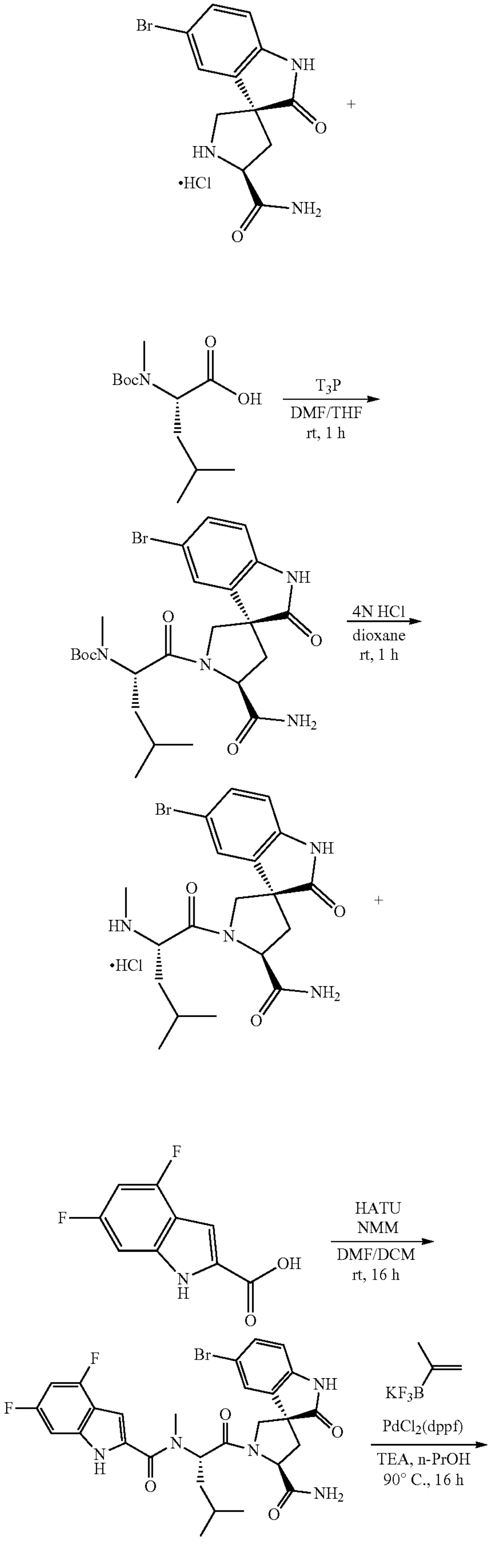

-continued

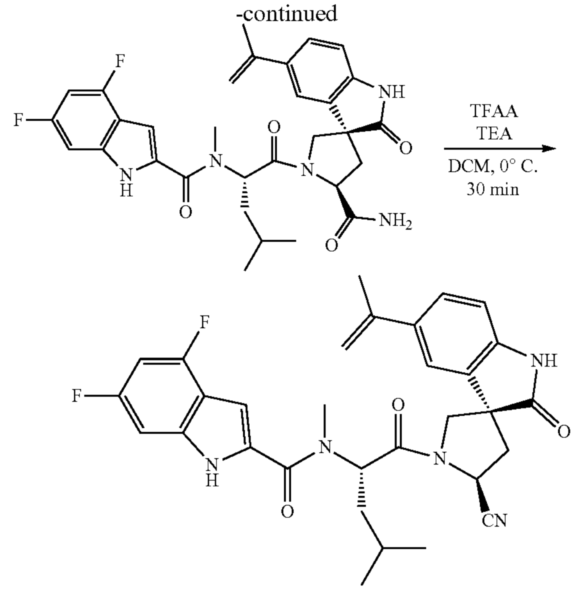

Step 1:

A clear colorless solution of 1'-(tert-butyl) 5'-methyl (3R, 5'S)-2-oxospiro[indoline-3,3'-pyrrolidine]-1',5'-dicarboxylate (3.94 g, 11.4 mmol, dr 10/1) in acetonitrile (40 mL) was treated with NB S (2.23 g, 12.5 mmol) in three portions at room temperature. The reaction was stirred at room temperature for 3 h. It became a light-yellow solution. LCMS showed no SM. The reaction was quenched with aqueous $Na_2S_2O_3$. The mixture was allowed to stir at room temperature for additional 30 min. The cloudy mixture was further diluted with EtOAc (80 mL). The aqueous layer was extracted with EtOAc twice. The combined organic layers were washed with brine, dried over $Na_2SO_4$, filtered and concentrated to afford crude product as an off-white solid. The crude was dissolved in DCM (10 mL) and filtered through an 80 g silica gel pad (MTBE) to afford the desired product (dr 10/1) as a white solid. The product was treated with MTBE/hexane (2:1) (30 mL). The mixture was sonicated over 10 min to form a milky suspension, which was filtered and washed with MTBE/hexane (2:1) to give 1'-(tert-butyl) 5'-methyl (3R,5'S)-5-bromo-2-oxospiro[indoline-3,3'-pyrrolidine]-1',5'-dicarboxylate as a white solid (4.23 g, 10.0 mmol, dr >100/1, 87% yield). LC-MS, $ES^-$: 422.74, 424.64 $[M-H]^-$.

Step 2:

1'-(tert-butyl) 5'-methyl (3R,5'S)-5-bromo-2-oxospiro[indoline-3,3'-pyrrolidine]-1',5'-dicarboxylate (5.3 g, 12.46 mmol) was treated with 7N ammonia in MeOH (40 ml, 280 mmol). The reaction was warmed to 50° C. and stirred over weekend. The mixture was concentrated in vacuo to give tert-butyl (3R,5'S)-5-bromo-5'-carbamoyl-2-oxospiro[indoline-3,3'-pyrrolidine]-1'-carboxylate (5.11 g, 12.5 mmol, 100% yield) as an off-white solid. LC-MS, $ES^-$: 408.10, 410.07 $[M-H]^-$.

Step 3:

A solution of tert-butyl (3R,5'S)-5-bromo-5'-carbamoyl-2-oxospiro[indoline-3,3'-pyrrolidine]-1'-carboxylate (2.39 g, 5.83 mmol) in DMF (4.8 ml) was treated with HCl, 4M in dioxane (20 ml, 80 mmol) at 0° C. dropwise. The reaction was warmed to room temperature and stirred for 3 h. The resulting solution was added to DCM (100 mL) to precipitate out product. The suspension was filtered and the solid was dried under high vacuum to give (3R,5'S)-5-bromo-2-oxospiro[indoline-3,3'-pyrrolidine]-5'-carboxamide hydrochloride (1.895 g, 5.47 mmol, 94% yield) as an off-white solid. LC-MS, $ES^+$: 265.14, 267.16 $[M+H]^+$.

Step 4:

A suspension of (3R,5'S)-5-bromo-2-oxospiro[indoline-3,3'-pyrrolidine]-5'-carboxamide hydrochloride (2.06 g, 5.94 mmol) and N-(tert-butoxycarbonyl)-N-methyl-L-leucine (1.531 g, 6.24 mmol) in THF (20.00 ml) and DMF (2.0 ml) was treated with N-methylmorpholine (1.960 ml, 17.83 mmol) and $T_3P$, 50% in DMF (3.82 ml, 6.54 mmol) at 0° C. The reaction was warmed to room temperature and stirred for 1 h, and then quenched with a saturated solution of sodium bicarbonate. The reaction mixture was extracted with ethyl acetate twice. The combined organic layers were washed with 1M HCl, water and brine, dried over sodium sulfate, filtered and concentrated in vacuo to give tert-butyl ((S)-1-(3R,5'S)-5-bromo-5'-carbamoyl-2-oxospiro[indoline-3,3'-pyrrolidin]-1'-yl)-4-methyl-1-oxopentan-2-yl)(methyl) carbamate (2.867 g, 5.33 mmol, 90% yield) as an off-white solid. LC-MS, $ES^-$: 535.23, 537.27 $[M-H]^-$.

Step 5:

Tert-butyl ((S)-1-((3R,5'S)-5-bromo-5'-carbamoyl-2-oxospiro[indoline-3,3'-pyrrolidin]-1'-yl)-4-methyl-1-oxopentan-2-yl)(methyl)carbamate (2.867 g, 5.33 mmol) was treated with HCl, 4M in dioxane (13.34 ml, 53.3 mmol) at room temperature. The reaction was stirred at room temperature for 1 h. The mixture was evaporated and dried under high vacuum to give (3R,5'S)-5-bromo-1'-(methyl-L-leucyl)-2-oxospiro[indoline-3,3'-pyrrolidine]-5'-carboxamide hydrochloride (2.44 g, 5.15 mmol, 97% yield) as a white solid. LC-MS, $ES^+$: 437.31, 439.27 $[M+H]^+$.

Step 6:

A solution of (3R,5'S)-5-bromo-1'-(methyl-L-leucyl)-2-oxospiro[indoline-3,3'-pyrrolidine]-5'-carboxamide hydrochloride (2.44 g, 5.15 mmol) and 4,6-difluoro-1H-indole-2-carboxylic acid (1.117 g, 5.66 mmol) in DMF (25.7 ml) was treated with HATU (2.350 g, 6.18 mmol) and DIPEA (2.70 ml, 15.45 mmol) at room temperature. The reaction was stirred at room temperature overnight. The reaction mixture was diluted with ethyl acetate and then washed with water and a saturated solution of sodium chloride. The organic layer was dried with sodium sulfate, filtered and concentrated in vacuo. The crude was added to a silica gel column (40 g) and was eluted with acetone/hexane from 0% to 75%. to give (3R,5'S)-5-bromo-1'-(N-(4,6-difluoro-1H-indole-2-carbonyl)-N-methyl-L-leucyl)-2-oxospiro[indoline-3,3'-pyrrolidine]-5'-carboxamide (2.7 g, 4.38 mmol, 85% yield) as an off-white solid. LC-MS, $ES^-$: 614.39, 616.31 $[M-H]^-$.

Step 7:

A solution of (3R,5'S)-5-bromo-1'-(N-(4,6-difluoro-1H-indole-2-carbonyl)-N-methyl-L-leucyl)-2-oxospiro[indoline-3,3'-pyrrolidine]-5'-carboxamide (41 mg, 0.067 mmol) in n-PrOH (0.5 ml) was treated with trifluoro(prop-1-en-2-yl)-14-borane, potassium salt (16 mg, 0.108 mmol), TEA (30 μl, 0.215 mmol) and $PdCl_2$(dppf) (6 mg, 8.20 μmol) under $N_2$. The mixture was bubbled with $N_2$ over 5 min. The reaction was warmed to 90° C. and stirred overnight. The mixture was filtered through celite and concentrated in vacuo. The crude was added to a 4 g silica gel column and eluted by acetone/cyclohexane from 0% to 100% to give (3R,5'S)-1'-(N-(4,6-difluoro-1H-indole-2-carbonyl)-N-methyl-L-leucyl)-2-oxo-5-(prop-1-en-2-yl)spiro[indoline-3,3'-pyrrolidine]-5'-carboxamide (19 mg, 0.033 mmol, 49.5% yield) as an orange solid. LC-MS, $ES^-$: 576.57 $[M-H]^-$.

Step 8:

A solution of (3R,5'S)-1'-(N-(4,6-difluoro-1H-indole-2-carbonyl)-N-methyl-L-leucyl)-2-oxo-5-(prop-1-en-2-yl)spiro[indoline-3,3'-pyrrolidine]-5'-carboxamide (19 mg, 0.033 mmol) in DCM (0.4 ml) was treated with TEA (30 μl, 0.215 mmol) and TFAA (15 μl, 0.106 mmol) dropwise at 0° C. The reaction was stirred at 0° C. for 30 min, then quenched with a saturated solution of sodium bicarbonate. The aqueous layer was extracted with dichloromethane over 3 times. The combined organic layer was dried over sodium sulfate, filtered and concentrated in vacuo. The crude was added to a 4 g silica gel column and eluted by ethyl acetate/cyclohexane from 0% to 100% to give N—((S)-1-((3R,5'S)-5'-cyano-2-oxo-5-(prop-1-en-2-yl)spiro[indoline-3,3'-pyrrolidin]-1'-yl)-4-methyl-1-oxopentan-2-yl)-4,6-difluoro-N-methyl-1H-indole-2-carboxamide (13 mg, 0.023 mmol, 70.6% yield) as a white solid. LC-MS, $ES^-$: 558.36 $[M-H]^-$; $^1H$ NMR (400 MHz, Chloroform-d) δ 9.07 (s, 1H), 8.25 (s, 1H), 7.19 (dd, J=8.2, 1.8 Hz, 1H), 6.96 (d, J=1.8 Hz, 1H), 6.91-6.73 (m, 3H), 6.63 (td, J=10.0, 1.9 Hz, 1H), 5.38 (dd, J=9.0, 6.2 Hz, 1H), 5.09 (dd, J=17.1, 8.6 Hz, 2H), 4.91 (t, J=1.5 Hz, 1H), 4.51 (d, J=10.5 Hz, 1H), 3.98 (d, J=10.5 Hz, 1H), 3.46 (s, 3H), 2.89 (dd, J=13.2, 8.9 Hz, 1H), 2.66-2.50 (m, 1H), 1.98-1.75 (m, 5H), 1.01 (d, J=6.6 Hz, 3H), 0.96 (d, J=6.5 Hz, 3H).

Example 499

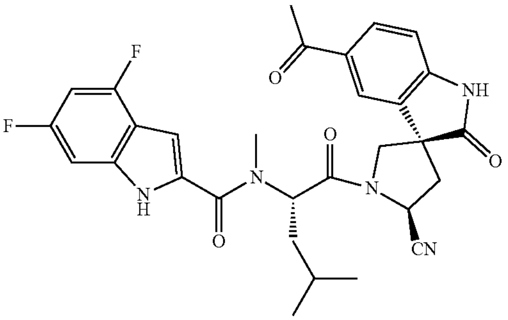

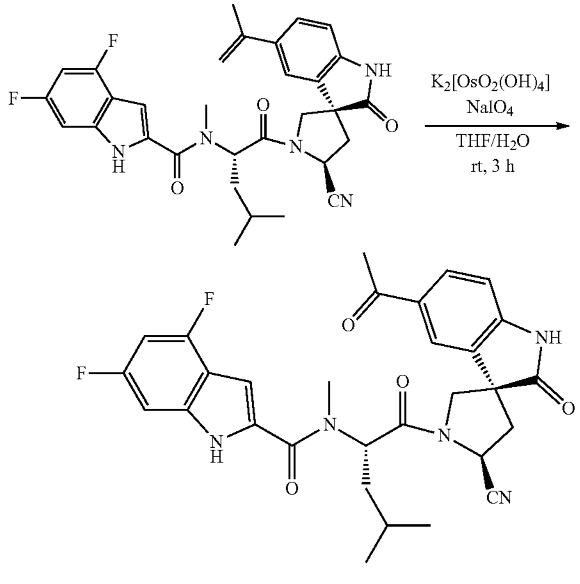

Step 1:

A solution of N—((S)-1-((3R,5'S)-5'-cyano-2-oxo-5-(prop-1-en-2-yl)spiro[indoline-3,3'-pyrrolidin]-1'-yl)-4-methyl-1-oxopentan-2-yl)-4,6-difluoro-N-methyl-1H-indole-2-carboxamide (8 mg, 0.014 mmol) in THF (0.2 ml) and Water (0.1 ml) was treated with potassium osmate dihydrate (3.4 mg, 9.23 μmol) and potassium osmate dihydrate (3.4 mg, 9.23 μmol). The reaction was stirred at room temperature for 3 h, then quenched with a saturated solution of sodium thiosulfate. The mixture was stirred for additional 30 min. The aqueous layer was extracted with dichloromethane over 3 times. The combined organic layer was dried over sodium sulfate, filtered and concentrated in vacuo. The crude was added to a 4 g silica gel column and eluted by ethyl acetate/cyclohexane from 0% to 100% to give N—((S)-14(3R,5'S)-5-acetyl-5'-cyano-2-oxospiro[indoline-3,3'-pyrrolidin]-1'-yl)-4-methyl-1-oxopentan-2-yl)-4,6-difluoro-N-methyl-1H-indole-2-carboxamide (6 mg, 10.68 μmol, 74.7% yield) as a white solid. LC-MS, $ES^-$: 560.37 $[M-H]^-$; $^1H$ NMR (400 MHz, Chloroform-d) δ 9.73 (s, 1H), 8.23 (s, 1H), 7.77 (d, J=1.7 Hz, 1H), 7.68 (dd, J=8.2, 1.7 Hz, 1H), 6.92 (dd, J=8.4, 2.2 Hz, 2H), 6.84-6.76 (m, 1H), 6.62 (td, J=10.0, 2.0 Hz, 1H), 5.24 (dd, J=8.4, 6.8 Hz, 1H), 5.12 (t, J=8.3 Hz, 1H), 4.75 (d, J=10.6 Hz, 1H), 3.99 (d, J=10.5 Hz, 1H), 3.51 (s, 3H), 2.89 (dd, J=13.4, 8.3 Hz, 1H), 2.54 (dd, J=13.5, 8.3 Hz, 1H), 2.38 (s, 3H), 1.98-1.79 (m, 2H), 1.70-1.62 (m, 1H), 1.02 (d, J=6.6 Hz, 3H), 0.97 (d, J=6.5 Hz, 3H), 0.86 (d, J=14.2 Hz, 1H).

Example 500

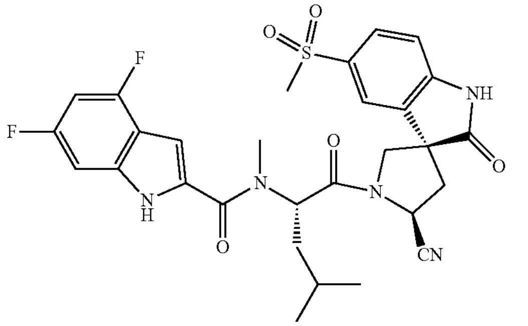

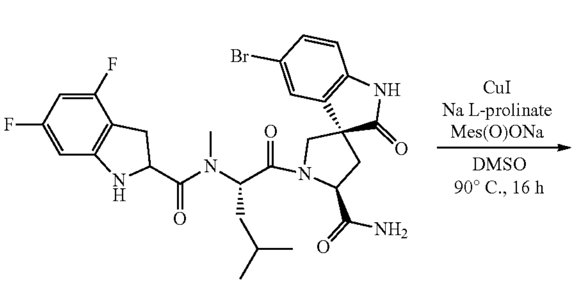

-continued

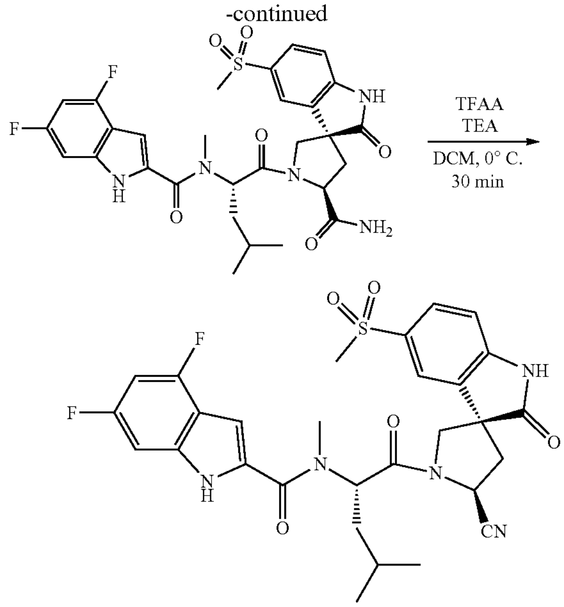

Step 1:

A solution of (3R,5'S)-5-bromo-1'-(N-(4,6-difluoro-1H-indole-2-carbonyl)-N-methyl-L-leucyl)-2-oxospiro[indoline-3,3'-pyrrolidine]-5'-carboxamide (43 mg, 0.070 mmol) in DMSO (0.5 ml) was treated with copper(I) iodide (3 mg, 0.016 mmol), sodium L-prolinate (6 mg, 0.044 mmol) and sodium methanesulfinate (13 mg, 0.127 mmol) under $N_2$. The mixture was bubbled with N2 over 5 min. The reaction was warmed to 90° C. and stirred overnight. The mixture was concentrated by V10 evaporator. The crude was added to a 4 g silica gel column and eluted by acetone/cyclohexane from 0% to 100% to give (3R,5'S)-1'-(N-(4,6-difluoro-1H-indole-2-carbonyl)-N-methyl-L-leucyl)-5-(methylsulfonyl)-2-oxospiro[indoline-3,3'-pyrrolidine]-5'-carboxamide (16 mg, 0.026 mmol, 37.3% yield) as a white solid. LC-MS, $ES^-$: 614.24 $[M-H]^-$.

Step 2:

A solution of (3R,5'S)-1'-(N-(4,6-difluoro-1H-indole-2-carbonyl)-N-methyl-L-leucyl)-5-(methylsulfonyl)-2-oxospiro[indoline-3,3'-pyrrolidine]-5'-carboxamide (15 mg, 0.024 mmol) in DCM (0.04 ml) was treated with TEA (30 μl, 0.215 mmol) and TFAA (11 μl, 0.078 mmol) dropwise at 0° C. The reaction was stirred at 0° C. for 30 min, and then quenched with a saturated solution of sodium bicarbonate. The aqueous layer was extracted with dichloromethane over 3 times. The combined organic layer was dried over sodium sulfate, filtered and concentrated in vacuo. The crude was added to a 4 g silica gel column and eluted by ethyl acetate/cyclohexane from 0% to 100% to give N—((S)-1-((3R,5'S)-5'-cyano-5-(methylsulfonyl)-2-oxospiro[indoline-3,3'-pyrrolidin]-1'-yl)-4-methyl-1-oxopentan-2-yl)-4,6-difluoro-N-methyl-1H-indole-2-carboxamide (12 mg, 0.020 mmol, 82% yield) as a white solid. LC-MS, $ES^-$: 596.31 $[M-H]^-$; $^1H$ NMR (500 MHz, Methanol-$d_4$) δ 7.80 (dd, J=8.3, 1.8 Hz, 1H), 7.64 (d, J=1.9 Hz, 1H), 7.10 (d, J=8.2 Hz, 1H), 6.98-6.89 (m, 2H), 6.65 (td, J=10.2, 2.0 Hz, 1H), 5.38 (dd, J=8.9, 6.3 Hz, 1H), 5.26 (t, J=8.0 Hz, 1H), 4.36 (d, J=10.9 Hz, 1H), 4.02 (d, J=10.8 Hz, 1H), 3.44 (s, 3H), 2.95 (s, 3H), 2.74 (d, J=8.1 Hz, 1H), 1.92 (ddd, J=14.4, 8.9, 5.6 Hz, 1H), 1.82 (ddd, J=14.2, 8.1, 6.2 Hz, 1H), 1.65 (ddd, J=12.2, 7.9, 6.1 Hz, 1H), 1.34-1.22 (m, 2H), 1.04 (d, J=6.7 Hz, 3H), 0.99 (d, J=6.6 Hz, 3H), 0.93-0.85 (m, 1H).

Example 501

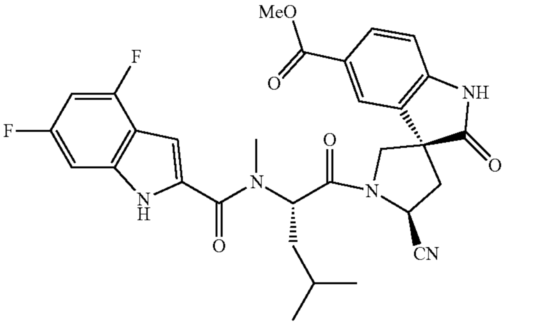

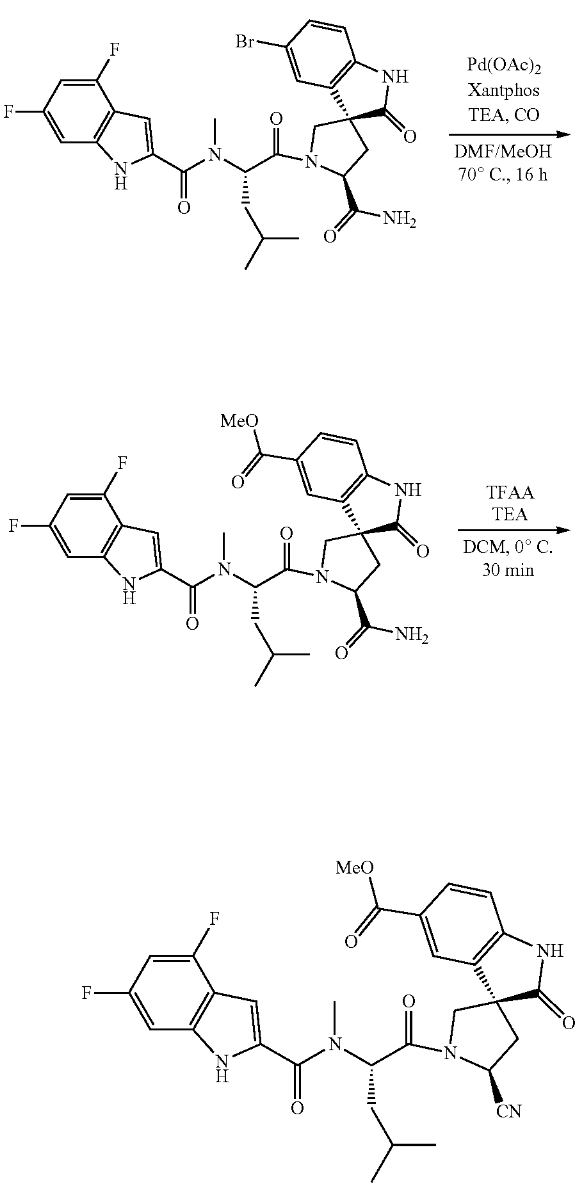

Step 1:

A solution of (3R,5'S)-5-bromo-1'-(N-(4,6-difluoro-1H-indole-2-carbonyl)-N-methyl-L-leucyl)-2-oxospiro[indoline-3,3'-pyrrolidine]-5'-carboxamide (137 mg, 0.222 mmol) in DMF (0.5 ml) and MeOH (0.5 ml) was treated with TEA (100 μl, 0.717 mmol), xantphos (20 mg, 0.035 mmol) and palladium(II) acetate (6.8 mg, 0.030 mmol) under Carbon monoxide (6.22 mg, 0.222 mmol) (1 atm). The mixture was bubbled with Carbon monoxide (6.22 mg, 0.222 mmol) over 5 min. The reaction was warmed to 70° C. and stirred overnight. The mixture was concentrated in vacuo. The crude was added to a 4 g silica gel column and eluted by acetone/cyclohexane from 0% to 100% to give methyl (3R,5'S)-5'-carbamoyl-1'-(N-(4,6-difluoro-1H-indole-2-carbonyl)-N-methyl-L-leucyl)-2-oxospiro[indoline-3,3'-pyrrolidine]-5-carboxylate (85 mg, 0.143 mmol, 64.2% yield) as an off-white solid. LC-MS, $ES^-$: 594.26 $[M-H]^-$ Step 2:

A solution of methyl (3R,5'S)-5'-carbamoyl-1'-(N-(4,6-difluoro-1H-indole-2-carbonyl)-N-methyl-L-leucyl)-2-oxospiro[indoline-3,3'-pyrrolidine]-5-carboxylate (8 mg, 0.013 mmol) in DCM (0.3 ml) was treated with TEA (20 μl, 0.143 mmol) and TFAA (7 μl, 0.050 mmol) dropwise at 0° C. The reaction was stirred at 0° C. for 30 min, then quenched with a saturated solution of sodium bicarbonate. The aqueous layer was extracted with dichloromethane over 3 times. The combined organic layer was dried over sodium sulfate, filtered and concentrated in vacuo. The crude was added to a 4 g silica gel column and eluted by ethyl acetate/cyclohexane from 0% to 100% to give methyl (3R,5'S)-5'-cyano-1'-(N-(4,6-difluoro-1H-indole-2-carbonyl)-N-methyl-L-leucyl)-2-oxospiro[indoline-3,3'-pyrrolidine]-5-carboxylate (7 mg, 0.012 mmol, 90% yield) as a white solid. LC-MS, $ES^-$: 576.34 $[M-H]^-$; $^1H$ NMR (500 MHz, Chloroform-d) δ 9.61 (s, 1H), 8.03 (s, 1H), 7.80 (dd, J=8.1, 1.7 Hz, 1H), 7.76 (d, J=1.7 Hz, 1H), 6.91 (d, J=8.1 Hz, 1H), 6.89-6.82 (m, 2H), 6.63 (td, J=10.0, 2.0 Hz, 1H), 5.25 (dd, J=8.4, 6.9 Hz, 1H), 5.10 (t, J=8.4 Hz, 1H), 4.78 (d, J=10.5 Hz, 1H), 3.99 (d, J=10.5 Hz, 1H), 3.80 (s, 3H), 3.54 (s, 3H), 2.90 (dd, J=13.4, 8.5 Hz, 1H), 2.55 (ddd, J=13.5, 8.4, 1.2 Hz, 1H), 1.93 (ddd, J=14.3, 8.4, 6.1 Hz, 1H), 1.84 (dt, J=14.2, 7.3 Hz, 1H), 1.64 (dt, J=13.7, 6.8 Hz, 2H), 1.03 (d, J=6.6 Hz, 3H), 0.97 (d, J=6.6 Hz, 3H), 0.90-0.79 (m, 1H).

Example 102

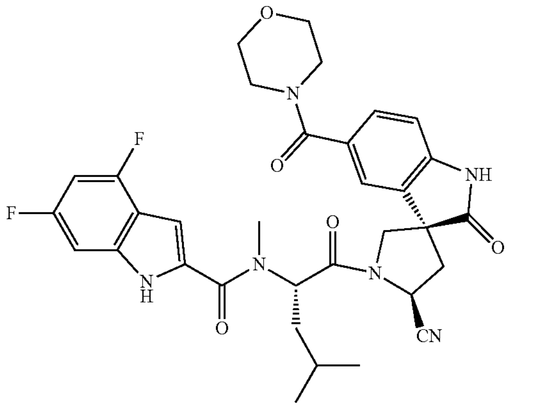

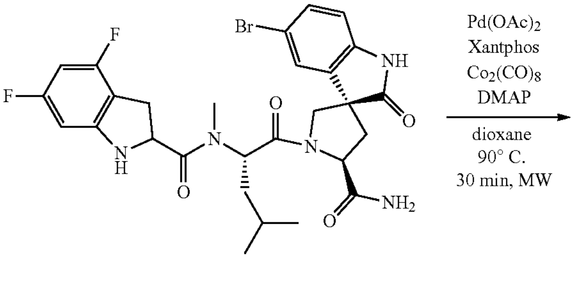

-continued

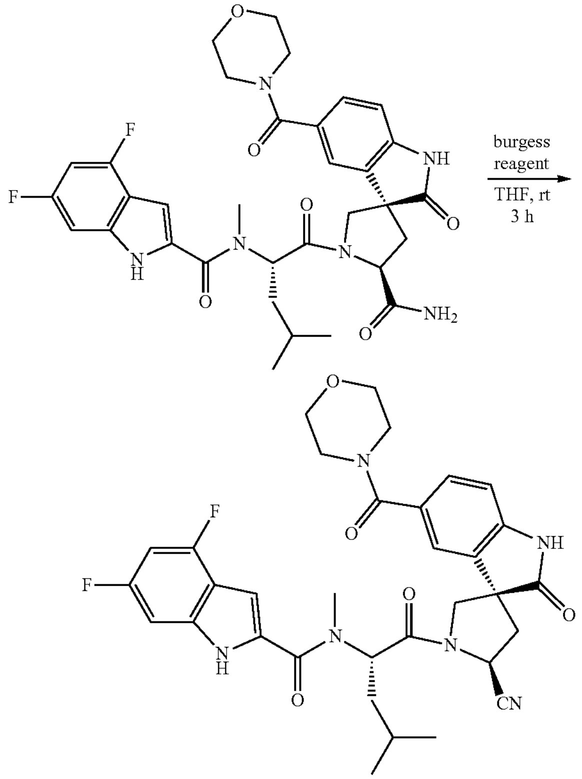

Step 1:

A solution of (3R,5'S)-5-bromo-1'-(N-(4,6-difluoro-1H-indole-2-carbonyl)-N-methyl-L-leucyl)-2-oxospiro[indoline-3,3'-pyrrolidine]-5'-carboxamide (21 mg, 0.034 mmol) in 1,4-Dioxane (0.4 ml) was treated with $Pd(OAc)_2$ (3 mg, 0.013 mmol), xantphos (8 mg, 0.014 mmol), $Co_2(CO)_8$ (8 mg, 0.023 mmol), DMAP (9 mg, 0.074 mmol) and morpholine (10 μl, 0.115 mmol) under $N_2$. The mixture was bubbled with $N_2$ for 3 min. The reaction was warmed to 90° C. and stirred for 30 min under microwave irradiation. After reaction, the mixture turned to a black suspension. The mixture was filtered through celite and rinsed with acetone over 3 times. The filtrate was concentrated in vacuo. The crude was added to a 4 g silica gel column and eluted by acetone/cyclohexane from 0% to 100% to give (3R,5'S)-1'-(N-(4,6-difluoro-1H-indole-2-carbonyl)-N-methyl-L-leucyl)-5-(morpholine-4-carbonyl)-2-oxospiro[indoline-3,3'-pyrrolidine]-5'-carboxamide (15 mg, 0.023 mmol, 67.7% yield) as a light-yellow solid. LC-MS, $ES^-$: 649.43 $[M-H]^-$.

Step 2:

A solution of (3R,5'S)-1'-(N-(4,6-difluoro-1H-indole-2-carbonyl)-N-methyl-L-leucyl)-5-(morpholine-4-carbonyl)-2-oxospiro[indoline-3,3'-pyrrolidine]-5'-carboxamide (5 mg, 7.68 μmol) in THF (0.3 ml) was treated with burgess reagent (11 mg, 0.046 mmol). The reaction was stirred at room temperature for 3 h. The mixture was added to a 4 g silica gel column and eluted ethyl acetate/cyclohexane from 0% to 100% to give N—((S)-1-((3R,5'S)-5'-cyano-5-(morpholine-4-carbonyl)-2-oxospiro[indoline-3,3'-pyrrolidin]-1'-yl)-4-methyl-1-oxopentan-2-yl)-4,6-difluoro-N-methyl-1H-indole-2-carboxamide (4 mg, 6.32 μmol, 82% yield) as a white solid. LC-MS, $ES^-$: 631.26 $[M-H]^-$; $^1H$ NMR (400 MHz, Chloroform-d) δ 11.35 (s, 1H), 8.26 (s, 1H), 7.25 (d, J=1.7 Hz, 1H), 7.13 (dd, J=8.0, 1.6 Hz, 1H), 6.98 (dd, J=9.8, 2.3 Hz, 1H), 6.89-6.83 (m, 1H), 6.71 (d, J=8.0 Hz, 1H), 6.60 (td, J=10.0, 2.0 Hz, 1H), 5.05-4.88 (m, 2H), 4.82 (d, J=10.2 Hz, 1H), 3.98 (d, J=10.1 Hz, 2H), 3.89-3.64 (m, 5H), 3.58 (s, 3H), 3.54-3.32 (m, 3H), 2.89 (dd, J=13.1, 10.4 Hz, 1H), 2.55-2.41 (m, 1H), 2.18 (d, J=2.3 Hz, 1H), 1.92 (dq, J=17.2, 6.7 Hz, 2H), 1.71 (p, J=6.7 Hz, 2H), 1.09 (d, J=6.6 Hz, 3H), 1.03 (d, J=6.5 Hz, 3H), 0.84 (s, 1H).

Example 503

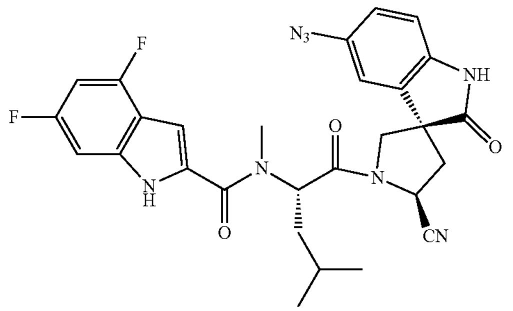

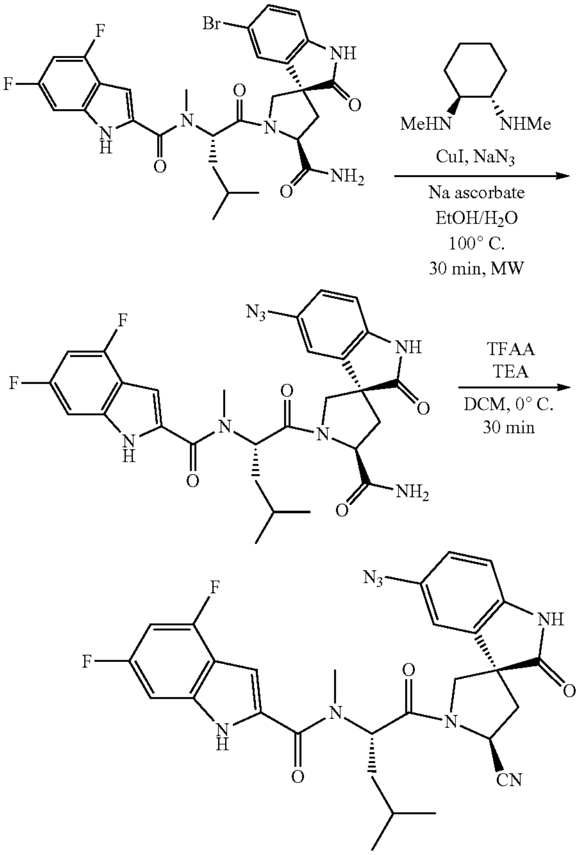

Step 1:

A solution of (3R,5'S)-5-bromo-1'-(N-(4,6-difluoro-1H-indole-2-carbonyl)-N-methyl-L-leucyl)-2-oxospiro[indoline-3,3'-pyrrolidine]-5'-carboxamide (65 mg, 0.105 mmol) in Ethanol (0.3 ml) and Water (0.15 ml) was treated with sodium azide (18 mg, 0.277 mmol), copper(I) iodide (4.6 mg, 0.024 mmol), (1S,2S)—N1,N2-dimethylcyclohexane-1,2-diamine (7 μl, 0.044 mmol) and sodium ascorbate (5.4 mg, 0.027 mmol) under $N_2$. The mixture was bubbled with $N_2$ over 5 min. The reaction was warmed to 100° C. and stirred for 30 min under microwave irradiation. The mixture was concentrated in vacuo. The crude was added to a 4 g silica gel column and eluted by acetone/cyclohexane from 0% to 100% to give (3R,5'S)-5-azido-1'-(N-(4,6-difluoro-1H-indole-2-carbonyl)-N-methyl-L-leucyl)-2-oxospiro[indoline-3,3'-pyrrolidine]-5'-carboxamide (33 mg, 0.057 mmol, 54.1% yield) as a yellow solid. LC-MS, ES$^-$: 577.36 [M-H]$^-$.

Step 2:

A solution of (3R,5'S)-5-azido-1'-(N-(4,6-difluoro-1H-indole-2-carbonyl)-N-methyl-L-leucyl)-2-oxospiro[indoline-3,3'-pyrrolidine]-5'-carboxamide (33 mg, 0.057 mmol) in DCM (0.5 ml) was treated with TEA (50 μl, 0.359 mmol) and TFAA (25 μl, 0.177 mmol) dropwise at 0° C. The reaction was stirred at 0° C. for 30 min, then quenched with a saturated solution of sodium bicarbonate. The aqueous layer was extracted with dichloromethane over 3 times. The combined organic layer was dried over sodium sulfate, filtered and concentrated in vacuo. The crude was added to a 4 g silica gel column and eluted by ethyl acetate/cyclohexane from 0% to 100% to give N—((S)-1-((3R,5'S)-5-azido-5'-cyano-2-oxospiro[indoline-3,3'-pyrrolidin]-1'-yl)-4-methyl-1-oxopentan-2-yl)-4,6-difluoro-N-methyl-1H-indole-2-carboxamide (14 mg, 0.025 mmol, 43.8% yield) as a white solid. LC-MS, ES$^-$: 559.34 [M-H]$^-$; $^1$H NMR (400 MHz, Chloroform-d) δ 9.17 (s, 1H), 8.27 (s, 1H), 6.93 (s, 1H), 6.83 (dd, J=8.9, 3.0 Hz, 2H), 6.71-6.55 (m, 2H), 6.42 (d, J=2.2 Hz, 1H), 5.39 (dd, J=9.2, 6.0 Hz, 1H), 5.03 (t, J=8.4 Hz, 1H), 4.55 (d, J=10.6 Hz, 1H), 3.95 (d, J=10.6 Hz, 1H), 3.50 (s, 3H), 2.88 (dd, J=13.4, 8.5 Hz, 1H), 2.53 (dd, J=13.4, 8.5 Hz, 1H), 2.18 (d, J=2.5 Hz, 1H), 1.95 (ddd, J=14.4, 9.1, 5.4 Hz, 1H), 1.79 (ddd, J=14.2, 8.4, 6.0 Hz, 1H), 1.02 (d, J=6.6 Hz, 3H), 0.96 (d, J=6.5 Hz, 3H), 0.87 (d, J=11.0 Hz, 1H).

Example 504

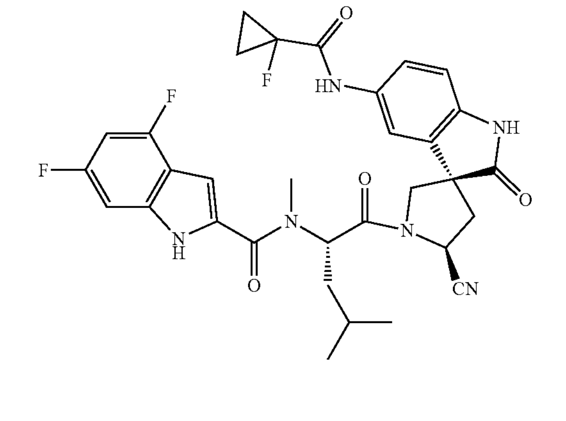

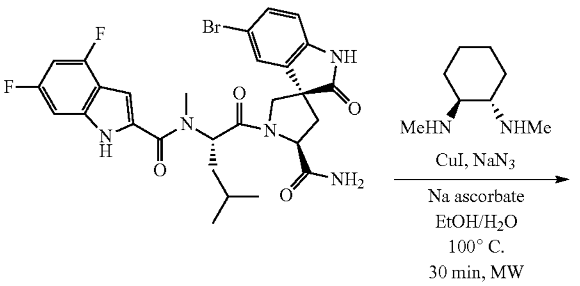

-continued

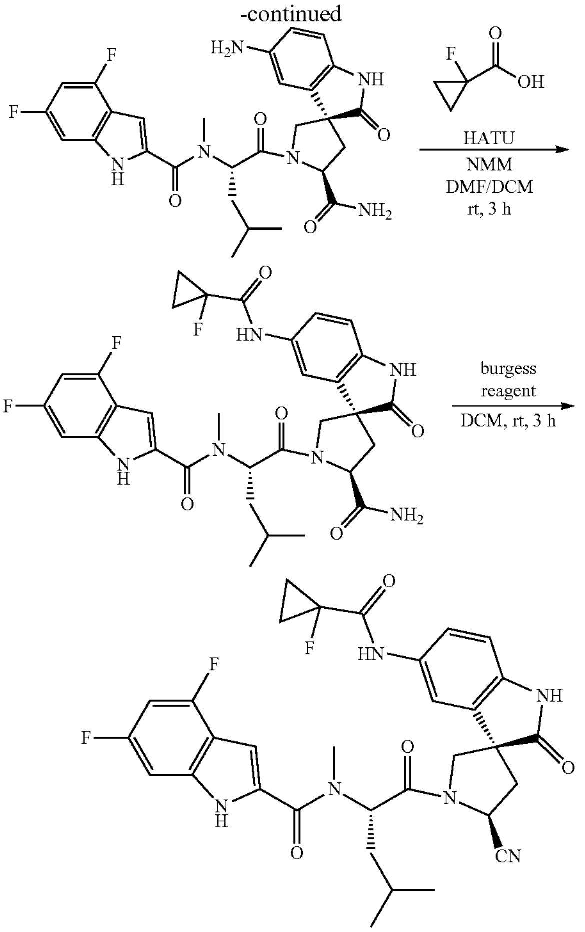

Step 1:

A solution of (3R,5'S)-5-bromo-1'-(N-(4,6-difluoro-1H-indole-2-carbonyl)-N-methyl-L-leucyl)-2-oxospiro[indoline-3,3'-pyrrolidine]-5'-carboxamide (65 mg, 0.105 mmol) in Ethanol (0.3 ml) and Water (0.15 ml) was treated with sodium azide (18 mg, 0.277 mmol), copper(I) iodide (4.6 mg, 0.024 mmol), (1S,2S)—N1,N2-dimethylcyclohexane-1,2-diamine (7 μl, 0.044 mmol) and sodium ascorbate (5.4 mg, 0.027 mmol) under $N_2$. The mixture was bubbled with $N_2$ over 5 min. The reaction was warmed to 100° C. and stirred for 30 min under microwave irradiation. The mixture was concentrated in vacuo. The crude was added to a 4 g silica gel column and eluted by acetone/cyclohexane from 0% to 100% to give (3R,5'S)-5-amino-1'-(N-(4,6-difluoro-1H-indole-2-carbonyl)-N-methyl-L-leucyl)-2-oxospiro[indoline-3,3'-pyrrolidine]-5'-carboxamide (19 mg, 0.034 mmol, 32.6% yield) as a yellow solid. LC-MS, ES$^-$: 551.27 [M-H]$^-$.

Step 2:

A solution of (3R,5'S)-5-amino-1'-(N-(4,6-difluoro-1H-indole-2-carbonyl)-N-methyl-L-leucyl)-2-oxospiro[indoline-3,3'-pyrrolidine]-5'-carboxamide (15 mg, 0.027 mmol) and 1-fluorocyclopropane-1-carboxylic acid (4.7 mg, 0.045 mmol) in DMF (0.1 ml) and DCM (0.3 ml) was treated with HATU (15 mg, 0.039 mmol) and N-methylmorpholine (20 μl, 0.182 mmol). The reaction was stirred at room temperature for 3 h and then quenched with a saturated solution of sodium bicarbonate. The aqueous layer was extracted with ethyl acetate over 3 times. The combined organic layer was dried over sodium sulfate, filtered and concentrated in vacuo. The crude was added to a 4 g silica gel column and eluted by acetone/cyclohexane from 0% to 100% to give (3R,5'S)-1'-(N-(4,6-difluoro-1H-indole-2-carbonyl)-N-methyl-L-leucyl)-5-(1-fluorocyclopropane-1-carboxamido)-2-oxospiro[indoline-3,3'-pyrrolidine]-5'-carboxamide (15 mg, 0.023 mmol, 87% yield) as a light-yellow solid. LC-MS, $ES^-$: 637.69 $[M-H]^-$.

Step 3:

A solution of (3R,5'S)-1'-(N-(4,6-difluoro-1H-indole-2-carbonyl)-N-methyl-L-leucyl)-5-(1-fluorocyclopropane-1-carboxamido)-2-oxospiro[indoline-3,3'-pyrrolidine]-5'-carboxamide (15 mg, 0.023 mmol) in DCM (0.3 ml) was treated with burgess reagent (17 mg, 0.071 mmol). The reaction was stirred at room temperature for 3 h. The mixture was added to a 4 g silica gel column and eluted by ethyl acetate/cyclohexane from 0% to 100% to give N—((S)-1-((3R,5'S)-5'-cyano-5-(1-fluorocyclopropane-1-carboxamido)-2-oxospiro[indoline-3,3'-pyrrolidin]-1'-yl)-4-methyl-1-oxopentan-2-yl)-4,6-difluoro-N-methyl-1H-indole-2-carboxamide (12 mg, 0.019 mmol, 82% yield) as a white solid. LC-MS, $ES^-$: 619.25 $[M-H]^-$; $^1H$ NMR (500 MHz, Chloroform-d) δ 9.43 (s, 1H), 8.28 (s, 1H), 8.20 (d, J=5.1 Hz, 1H), 7.35 (dd, J=8.4, 2.1 Hz, 1H), 7.25 (d, J=2.2 Hz, 1H), 6.92 (d, J=2.3 Hz, 1H), 6.79 (dd, J=24.3, 8.5 Hz, 2H), 6.63 (td, J=10.0, 2.0 Hz, 1H), 5.20 (dd, J=10.0, 5.2 Hz, 1H), 5.04 (t, J=8.6 Hz, 1H), 4.42 (d, J=10.6 Hz, 1H), 3.98 (d, J=10.5 Hz, 1H), 3.52 (s, 3H), 2.88 (dd, J=13.2, 9.0 Hz, 1H), 2.61-2.49 (m, 1H), 1.99 (ddd, J=14.4, 10.1, 4.8 Hz, 1H), 1.81-1.56 (m, 4H), 1.52-1.34 (m, 4H), 1.03 (d, J=6.4 Hz, 3H), 0.94 (d, J=6.3 Hz, 3H), 0.78-0.90 (m, 1H).

Example 505

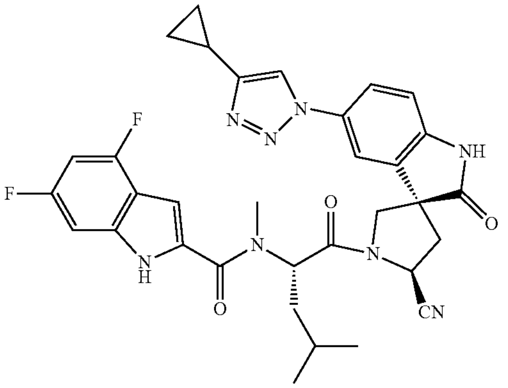

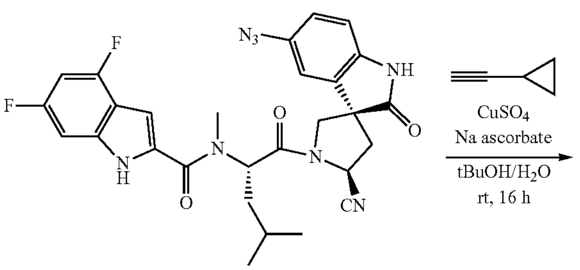

-continued

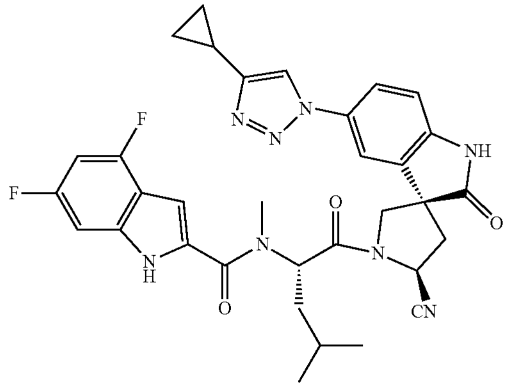

Step 1:

A solution of N—((S)-1-((3R,5'S)-5-azido-5'-cyano-2-oxospiro[indoline-3,3'-pyrrolidin]-1'-yl)-4-methyl-1-oxopentan-2-yl)-4,6-difluoro-N-methyl-1H-indole-2-carboxamide (8 mg, 0.014 mmol) and ethynylcyclopropane (3 μl, 0.035 mmol) in tBuOH (0.2 ml) and Water (0.2 ml) was treated with copper(II) sulfate pentahydrate (1.7 mg, 6.81 μmol) and sodium ascorbate (3.3 mg, 0.017 mmol). The reaction was stirred at room temperature overnight. The reaction was quenched with a saturated solution of sodium bicarbonate. The aqueous layer was extracted with dichloromethane over 3 times. The combined organic layer was dried over sodium sulfate, filtered and concentrated in vacuo. The crude was added to a 4 g silica gel column and eluted by ethyl acetate/cyclohexane from 0% to 100% to give N—((S)-1-((3R,5'S)-5'-cyano-5-(4-cyclopropyl-1H-1,2,3-triazol-1-yl)-2-oxospiro[indoline-3,3'-pyrrolidin]-1'-yl)-4-methyl-1-oxopentan-2-yl)-4,6-difluoro-N-methyl-1H-indole-2-carboxamide (2.4 mg, 3.83 μmol, 26.8% yield) as a white solid. LC-MS, $ES^+$: 627.53 $[M+H]^+$; $^1H$ NMR (500 MHz, Chloroform-d) δ 10.34 (s, 1H), 7.86 (s, 1H), 7.69 (d, J=2.0 Hz, 1H), 7.54 (s, 1H), 7.32 (dt, J=9.2, 2.6 Hz, 2H), 7.00 (d, J=8.3 Hz, 1H), 6.83 (d, J=2.2 Hz, 1H), 6.62 (td, J=10.0, 2.1 Hz, 1H), 5.00 (ddd, J=20.4, 8.9, 7.3 Hz, 2H), 4.85 (d, J=10.3 Hz, 1H), 4.04 (d, J=10.3 Hz, 1H), 3.56 (s, 3H), 2.94 (dd, J=13.3, 9.4 Hz, 1H), 2.57 (dd, J=13.2, 8.0 Hz, 1H), 2.18 (d, J=2.9 Hz, 2H), 2.08-1.94 (m, 2H), 1.80 (dt, J=14.1, 7.1 Hz, 1H), 1.70 (dt, J=13.5, 6.7 Hz, 1H), 1.26 (s, 2H), 1.05 (dd, J=7.6, 4.5 Hz, 4H), 1.02-0.95 (m, 3H), 0.95-0.87 (m, 3H), 0.85 (d, J=12.7 Hz, 1H).

Example 506

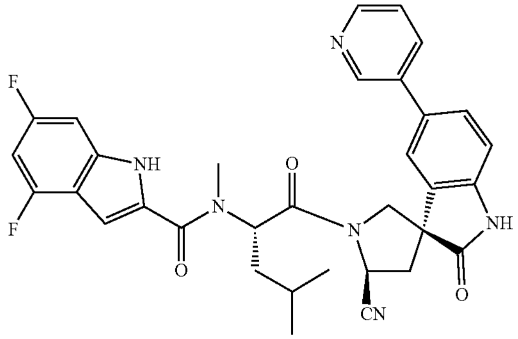

-continued

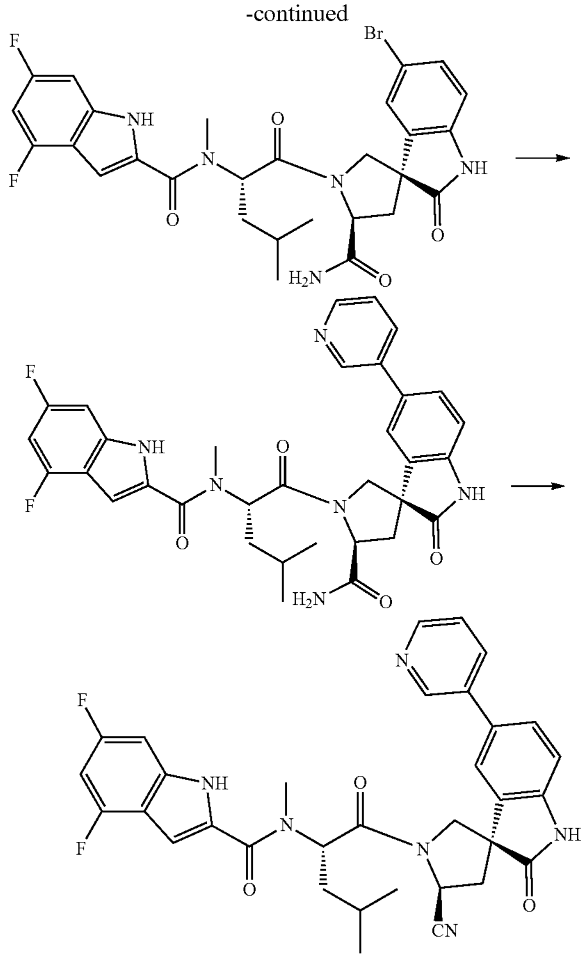

Step 1.

To a solution of bromide (85 mg, 0.138 mmol) and pyridine-3-ylboronic acid (25 mg, 0.207 mmol) in THF (0.7 mL) was added XPhosPd G3 (12 mg, 0.014 mmol) and $K_3PO_4$ (0.55 mL, 0.5 M aq). The reaction mixture was heated to 85° C. for 18 h. The reaction mixture was quenched with water, extracted with EtOAc. The organic layer was separated, washed with brine, dried over $Na_2SO_4$, and concentrated. Purification of the residue on silica gel chromatography with 0-80% acetone in cyclohexane provided desired product (25 mg, 30%).

Step 2:

To a solution of material from step 1 (25 mg, 0.041 mmol) in DCM (1 mL) at 0° C. was added TFAA (17 µl, 0.122 mmol) and $Et_3N$ (34 µL, 0.244 mmol). The crude product was loaded directly onto a silica gel column and subjected to chromatography with 0-80% acetone in cyclohexane provided EP-040278 (15 mg, 62%). 595.343 [M-H]. $^1H$ NMR (400 MHz, Acetone-$d_6$) δ 11.07 (s, 1H), 9.89 (s, 1H), 9.02 (d, J=2.5 Hz, 1H), 8.57 (dd, J=4.8, 1.6 Hz, 1H), 7.72 (dt, J=8.1, 1.9 Hz, 1H), 7.48 (dd, J=8.1, 1.9 Hz, 1H), 7.37 (d, J=1.9 Hz, 1H), 7.26 (dd, J=8.0, 4.8 Hz, 1H), 7.21-7.15 (m, 1H), 7.15-7.07 (m, 1H), 6.86 (dd, J=2.5, 0.9 Hz, 1H), 6.77 (td, J=10.3, 2.1 Hz, 1H), 5.56 (dd, J=10.7, 4.6 Hz, 1H), 5.37 (t, J=8.5 Hz, 1H), 4.53 (d, J=10.8 Hz, 1H), 4.06 (d, J=10.7 Hz, 1H), 3.39 (s, 3H), 2.83 (td, J=6.4, 3.0 Hz, 5H), 2.75 (dd, J=13.2, 8.6 Hz, 1H), 2.12-1.92 (m, 5H), 1.83-1.57 (m, 2H), 1.00 (dd, J=26.6, 6.3 Hz, 6H).

Example 507

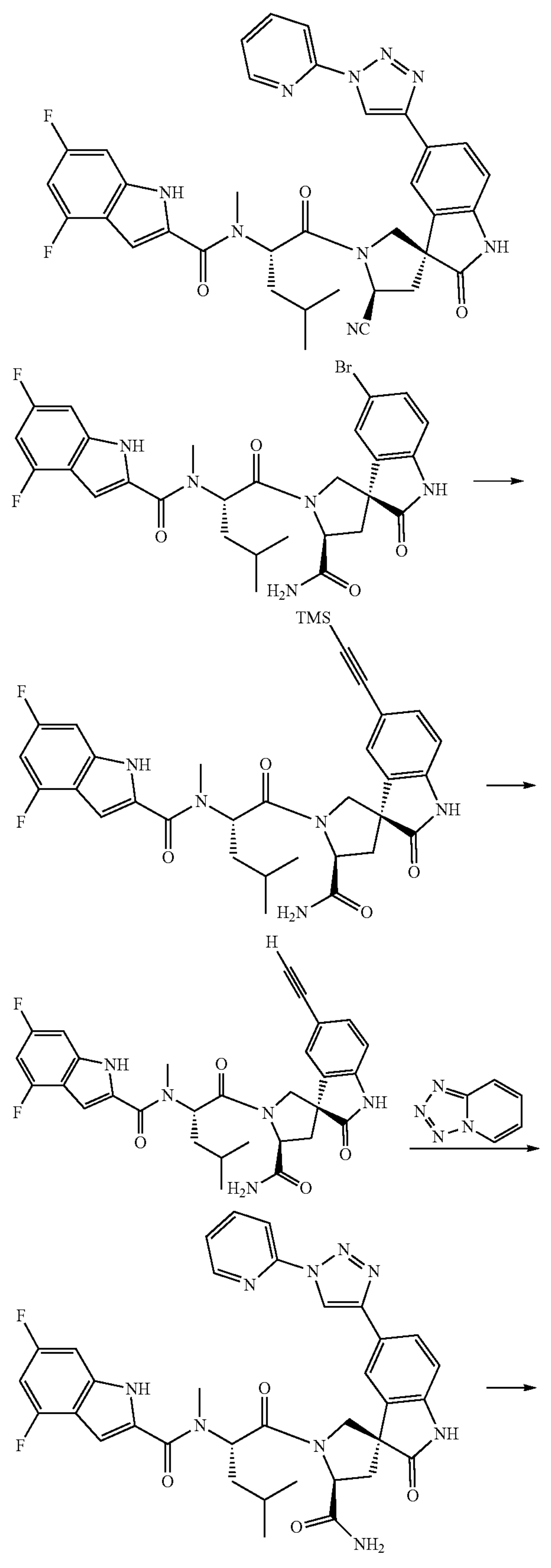

-continued

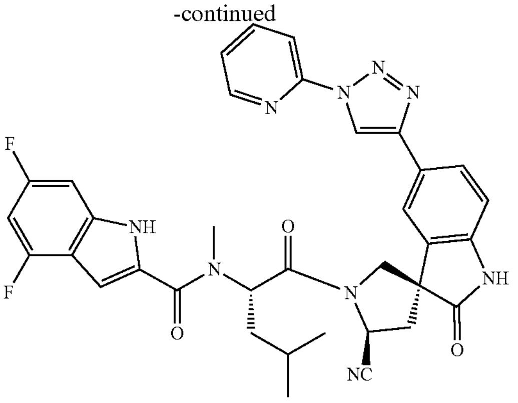

Step 1.

To a solution of bromide (252 mg, 0.409 mmol) in dioxane (2 mL) was added ethynyltrimethylsilane (87 μL, 0.613 mmol), $Pd(PPh_3)Cl_2$ (28.7 mg, 0.041 mmol), CuI (15.6 mg, 0.082 mmol), and $Et_3N$ (171 μL, 1.23 mmol). The reaction mixture was heated to 85° C. for 18 h. The reaction mixture was quenched with water, extracted with EtOAc. The organic layer was separated, washed with brine, dried over $Na_2SO_4$, and concentrated. Purification of the residue on silica gel chromatography with 0-80% acetone in cyclohexane provided desired product (165 mg, 64%).

Step 2.

To a solution of material from step 1 (139 mg, 0.219 mmol) in methanol (2 mL) was added $K_2CO_3$ (61 mg, 0.439 mmol). The reaction mixture was stirred at room temperature for 18 h. The reaction mixture was quenched with water, extracted with EtOAc. The organic layer was separated, washed with brine, dried over $Na_2SO_4$, and concentrated. Purification of the residue on silica gel chromatography with 0-80% acetone in cyclohexane provided desired product (77 mg, 63%).

Step 3.

To a solution of material from step 2 (77 mg, 0.137 mmol) and tetrazolo[1,5-a]pyridine (25 mg, 0.206 mmol) in DMF (2 mL) was added $CuSO_4$-pentahydrate (9 mg, 0.036 mmol), sodium ascorbate (7 mg, 0.035 mmol), and water (1 mL). The reaction mixture was heated to 80° C. for 18 h. The reaction mixture was quenched with water, extracted with EtOAc. The organic layer was separated, washed with brine, dried over $Na_2SO_4$, and concentrated. Purification of the residue on silica gel chromatography with 0-80% acetone in cyclohexane provided desired product (50 mg, 54%).

Step 4:

To a solution of material from step 3 (50 mg, 0.041 mmol) in DCM (1 mL) at 0° C. was added TFAA (31 μL, 0.220 mmol) and $Et_3N$ (62 μL, 0.440 mmol). The crude product was loaded directly onto a silica gel column and subjected to chromatography with 0-80% acetone in cyclohexane provided EP-040469. 662.405 [M−H]. $^1H$ NMR (400 MHz, Acetone-$d_6$) δ 10.49 (s, 1H), 9.87 (s, 1H), 8.58-8.49 (m, 2H), 8.18-8.08 (m, 2H), 7.71 (d, J=8.2 Hz, 1H), 7.67 (d, J=1.7 Hz, 1H), 7.52 (ddd, J=6.3, 4.8, 2.2 Hz, 1H), 7.05 (d, J=8.0 Hz, 1H), 7.03-6.94 (m, 1H), 6.70 (dd, J=2.3, 1.0 Hz, 1H), 6.44 (td, J=10.3, 2.1 Hz, 1H), 5.67-5.59 (m, 1H), 5.40 (t, J=8.4 Hz, 1H), 4.71 (d, J=10.7 Hz, 1H), 4.00 (d, J=10.8 Hz, 1H), 3.53 (s, 3H), 3.25 (s, 1H), 2.77 (dd, J=13.3, 8.1 Hz, 1H), 2.09-2.04 (m, 2H), 1.98 (ddd, J=14.3, 9.4, 5.2 Hz, 1H), 1.79 (ddd, J=14.1, 8.6, 5.7 Hz, 1H), 1.62 (dt, J=14.4, 6.9 Hz, 1H), 1.44 (d, J=0.9 Hz, 2H), 1.31 (s, 2H), 0.98 (dd, J=22.7, 6.5 Hz, 7H).

The following examples were prepared employing similar protocol as described above.

| Example | Structure | MS | NMR |
|---|---|---|---|
| 508 | 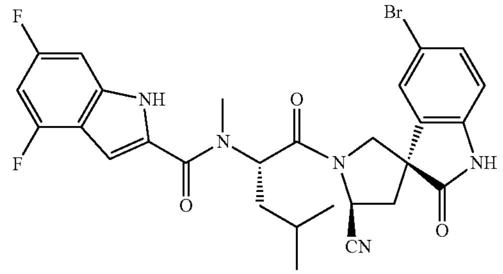 [SMILES: CC(C)C[C@@H](C(=O)N1C[C@]2(C[C@H]1C#N)C(=O)Nc1ccc(Br)cc12)N(C)C(=O)c1cc2c(F)cc(F)cc2[nH]1] | 596.334, 598.254 [M − H] | 1H NMR (400 MHz, Acetone-d6) δ 10.69 (s, 1H), 9.81 (s, 1H), 7.15-7.06 (m, 3H), 7.00 (s, 1H), 6.88-6.84 (m, 1H), 6.75 (td, J = 10.3, 2.1 Hz, 1H), 5.62 (dd, J = 9.4, 5.7 Hz, 1H), 5.33 (dd, J = 8.8, 7.7 Hz, 1H), 4.45 (d, J = 10.9 Hz, 1H), 3.95 (d, J = 10.9 Hz, 1H), 3.47 (s, 3H), 2.91-2.78 (m, 8H), 2.78-2.64 (m, 3H), 1.95 (ddd, J = 14.3, 9.4, 5.1 Hz, 2H), 1.77 (ddd, J = 14.2, 8.7, 5.7 Hz, 1H), 1.70-1.52 (m, 2H), 0.98 (dd, J = 18.3, 6.6 Hz, 8H). |
| 509 | 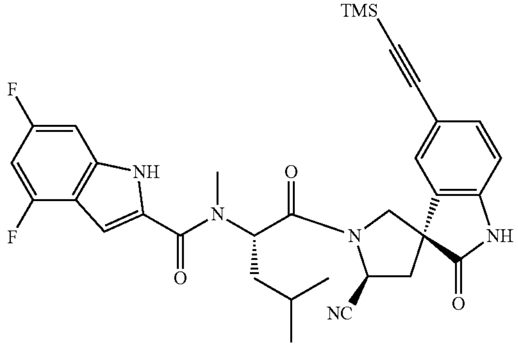 [SMILES: CC(C)C[C@@H](C(=O)N1C[C@]2(C[C@H]1C#N)C(=O)Nc1ccc(C#C[Si](C)(C)C)cc12)N(C)C(=O)c1cc2c(F)cc(F)cc2[nH]1] | 614.482 [M − H] | 1H NMR (400 MHz, Acetone-d6) δ 10.38 (s, 1H), 9.71 (s, 1H), 7.03-6.90 (m, 1H), 6.90 (ddd, J = 9.3, 4.2, 2.1 Hz, 1H), 6.85-6.65 (m, 3H), 6.58 (td, J = 10.3, 2.1 Hz, 1H), 5.47 (ddd, J = 14.9, 9.3, 5.6 Hz, 1H), 5.16 (td, J = 8.5, 6.5 Hz, 1H), 4.36 (d, J = 11.0 Hz, 1H), 3.75 (dd, J = 23.2, 11.0 Hz, 1H), 2.68 (s, 3H), 2.69-2.59 (m, 1H), 2.63-2.48 (m, 1H), 1.79 (ddd, J = 14.3, 9.5, 5.0 Hz, 1H), 1.64-1.51 (m, 1H), 1.42 (d, J = 8.8 Hz, 1H), 1.27 (s, 1H), 0.80 (ddd, J = 19.0, 6.5, 3.3 Hz, 6H), 0.00 (s, 9H). |

-continued

| Example | Structure | MS | NMR |
|---|---|---|---|
| 510 | 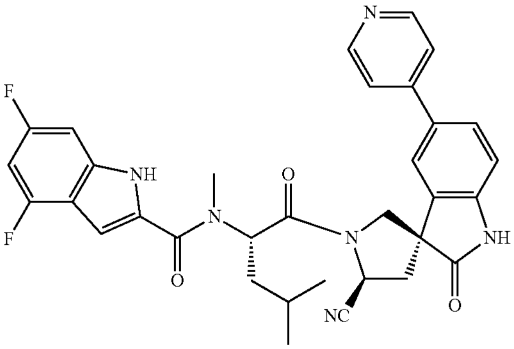 [SMILES: CC(C)C[C@@H](C(=O)N1C[C@]2(C[C@H]1C#N)C(=O)Nc1ccc(-c3ccncc3)cc12)N(C)C(=O)c1cc2c(F)cc(F)cc2[nH]1] | 597.540 [M + H] | 1H NMR (400 MHz, Acetone-d6) δ 10.59 (s, 1H), 9.92 (s, 1H), 8.35 (d, J = 5.3 Hz, 2H), 7.48 (dd, J = 8.1, 1.9 Hz, 1H), 7.36 (d, J = 1.8 Hz, 1H), 7.23 (d, J = 5.2 Hz, 2H), 7.09 (dd, J = 8.5, 2.5 Hz, 2H), 6.78 (td, J = 10.3, 2.1 Hz, 1H), 6.70 (s, 1H), 5.64 (s, 5H), 5.42 (t, J = 8.3 Hz, 1H), 4.60 (d, J = 10.8 Hz, 1H), 4.00 (d, J = 10.8 Hz, 1H), 3.26 (s, 3H), 2.92-2.70 (m, 3H), 1.94 (ddd, J = 14.4, 9.6, 4.9 Hz, 1H), 1.74 (ddd, J = 14.2, 8.9, 5.6 Hz, 1H), 1.59 (s, 1H), 1.11 (t, J = 7.2 Hz, 1H), 0.96 (dd, J = 20.7, 6.6 Hz, 6H). |
| 511 | 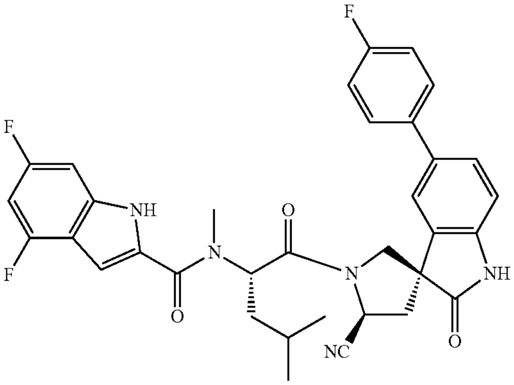 [SMILES: CC(C)C[C@@H](C(=O)N1C[C@]2(C[C@H]1C#N)C(=O)Nc1ccc(-c3ccc(F)cc3)cc12)N(C)C(=O)c1cc2c(F)cc(F)cc2[nH]1] | 612.423 [M − H] | 1H NMR (400 MHz, Acetone-d6) δ 10.65 (s, 1H), 9.82 (s, 1H), 7.34-7.22 (m, 3H), 7.20 (d, J = 1.9 Hz, 1H), 7.13-7.05 (m, 1H), 7.02 (d, J = 8.1 Hz, 1H), 6.94 (t, J = 8.8 Hz, 2H), 6.79 (td, J = 10.3, 2.1 Hz, 1H), 6.71 (dd, J = 2.3, 0.9 Hz, 1H), 5.63 (dd, J = 9.7, 5.5 Hz, 1H), 5.38 (t, J = 8.3 Hz, 1H), 4.57 (d, J = 10.8 Hz, 1H), 4.00 (d, J = 10.8 Hz, 1H), 3.23 (s, 3H), 2.89-2.79 (m, 1H), 2.74 (dd, J = 13.3, 8.0 Hz, 1H), 1.93 (ddd, J = 14.4, 9.6, 5.0 Hz, 1H), 1.74 (ddd, J = 14.2, 8.8, 5.5 Hz, 1H), 1.58 (dtd, J = 8.8, 6.7, 5.0 Hz, 1H), 0.96 (dd, J = 19.4, 6.6 Hz, 6H). |
| 512 | 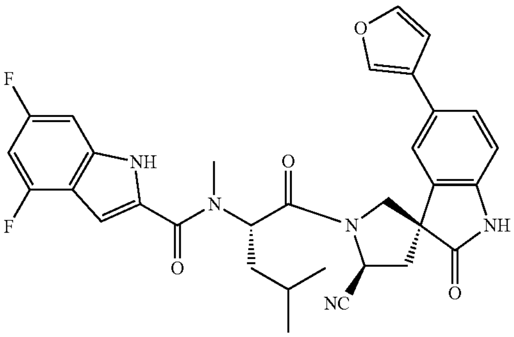 [SMILES: CC(C)C[C@@H](C(=O)N1C[C@]2(C[C@H]1C#N)C(=O)Nc1ccc(-c3ccoc3)cc12)N(C)C(=O)c1cc2c(F)cc(F)cc2[nH]1] | 584.457 [M − H] | 1H NMR (400 MHz, Acetone-d6) δ 10.61 (s, 1H), 9.73 (s, 1H), 7.64 (s, 1H), 7.48 (d, J = 1.8 Hz, 1H), 7.27-7.18 (m, 2H), 7.07 (dd, J = 9.4, 2.1 Hz, 1H), 6.93 (d, J = 8.0 Hz, 1H), 6.79-6.69 (m, 2H), 6.54 (s, 1H), 5.60 (dd, J = 9.5, 5.6 Hz, 1H), 5.36 (t, J = 8.3 Hz, 1H), 4.44 (d, J = 10.8 Hz, 1H), 3.97 (d, J = 10.8 Hz, 1H), 3.34 (s, 3H), 2.89-2.76 (m, 1H), 2.72 (dd, J = 13.3, 8.0 Hz, 1H), 1.92 (ddd, J = 14.4, 9.4, 5.1Hz, 1H), 1.76 (ddd, J = 14.2, 8.7, 5.7 Hz, 1H), 1.67-1.53 (m, 1H), , 0.97 (dd, J = 17.5, 6.5 Hz, 6H). |
| 513 | 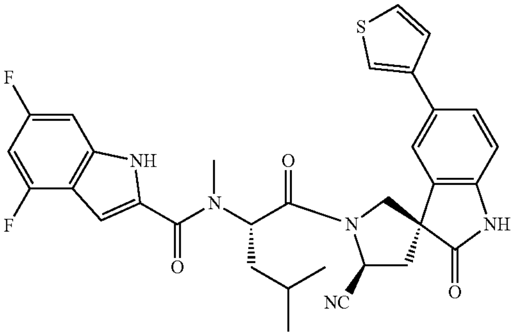 [SMILES: CC(C)C[C@@H](C(=O)N1C[C@]2(C[C@H]1C#N)C(=O)Nc1ccc(-c3ccsc3)cc12)N(C)C(=O)c1cc2c(F)cc(F)cc2[nH]1] | 600.367 [M − H] | 1H NMR (400 MHz, Acetone-d6) δ 10.58 (s, 1H), 9.76 (s, 1H), 7.36 (dq, J = 5.0, 2.4, 1.9 Hz, 2H), 7.28 (d, J = 4.1 Hz, 1H), 7.28 (s, 2H), 7.13 (d, J = 5.0 Hz, 1H), 7.08 (dd, J = 9.3, 2.0 Hz, 1H), 7.02 (s, 1H), 6.96 (d, J = 8.1 Hz, 1H), 6.75 (td, J = 10.3, 2.1 Hz, 1H), 6.68 (dd, J = 2.4, 0.9 Hz, 1H), 5.61 (dd, J = 9.5, 5.6 Hz, 1H), 5.39 (t, J = 8.3 Hz, 1H), 4.51 (d, J = 10.8 Hz, 1H), 3.98 (d, J = 10.7 Hz, 1H), 3.28 (s, 3H), 2.86-2.78 (m, 2H), 2.74 (s, 1H), 2.73 (dd, J = 13.3, 8.0 Hz, 1H), 2.07 (p, J = 2.2 Hz, 1H), 1.93 (ddd, J = 14.4, 9.5, 5.0 Hz, 1H), 1.75 (ddd, J = 14.3, 8.8, 5.6 Hz, 1H), 1.59 (dtd, J = 8.7, 6.7, 5.1 Hz, 1H), 0.97 (dd, J = 18.7, 6.5 Hz, 6H). |

-continued

| Example | Structure | MS | NMR |
|---|---|---|---|
| 514 | 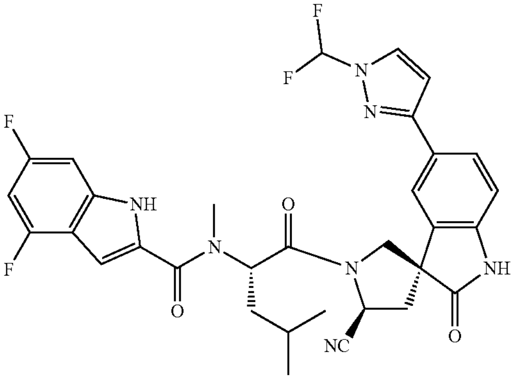 [SMILES: CC(C)C[C@@H](C(=O)N1C[C@]2(C[C@H]1C#N)C(=O)Nc1ccc(-c3ccn(C(F)F)n3)cc12)N(C)C(=O)c1cc2c(F)cc(F)cc2[nH]1] | 634.381 [M − H] | 1H NMR (400 MHz, Acetone-d6) δ 10.47 (s, 1H), 9.84 (s, 1H), 7.95 (d, J = 2.8 Hz, 1H), 7.58 (s, 0H), 7.52-7.41 (m, 2H), 7.08-6.93 (m, 2H), 6.66 (td, J = 10.3, 2.1 Hz, 1H), 6.62 (d, J = 2.3Hz, 1H), 6.46 (d, J = 2.8 Hz, 1H), 5.68 (dd, J = 9.2, 5.8 Hz, 1H), 5.31 (t, J = 8.3 Hz, 1H), 4.55 (d, J = 10.9 Hz, 1H), 3.97 (d, J = 10.8 Hz, 1H), 3.43 (s, 3H), 3.41 (s, 1H), 2.85 (ddd, J = 13.4, 8.8, 1.2 Hz, 1H), 2.74 (dd, J = 13.4, 8.0 Hz, 1H), 1.93 (ddd, J = 14.3, 9.2, 5.2 Hz, 1H), 1.76 (ddd, J = 14.2, 8.6, 5.8 Hz, 1H), 1.65-1.51 (m, 1H), 0.97 (dd, J = 15.9, 6.6 Hz, 7H). |
| 515 | 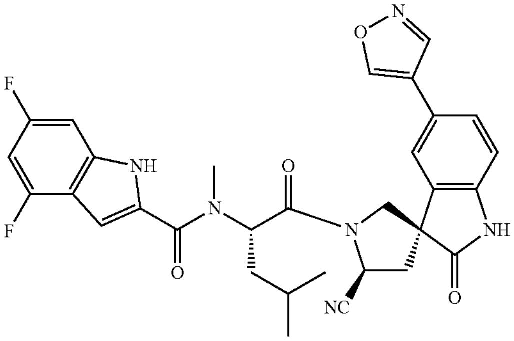 [SMILES: CC(C)C[C@@H](C(=O)N1C[C@]2(C[C@H]1C#N)C(=O)Nc1ccc(-c3cnoc3)cc12)N(C)C(=O)c1cc2c(F)cc(F)cc2[nH]1] | 585.346 [M − H] | 1H NMR (400 MHz, Acetone-d6) δ 10.61 (s, 1H), 9.80 (d, J = 16.1 Hz, 1H), 8.78 (s, 1H), 8.55 (s, 1H), 7.38-7.30 (m, 2H), 7.19-7.03 (m, 2H), 6.99 (dd, J = 8.0, 6.3 Hz, 1H), 6.81-6.70 (m, 2H), 5.55 (ddd, J = 24.5, 9.7, 5.3 Hz, 1H), 5.34 (t, J = 8.4 Hz, 1H), 4.49 (d, J = 10.8 Hz, 1H), 4.00 (dd, J = 14.7, 10.7 Hz, 1H), 3.50 (s, 1H), 3.36 (s, 3H), 3.32 (d, J = 10.5 Hz, 1H), 2.85-2.76 (m, 3H), 2.79-2.68 (m, 1H), 1.94 (ddd, J = 14.5, 9.7, 5.0 Hz, 1H), 1.76 (ddd, J = 14.1, 8.8, 5.6 Hz, 1H), 1.69-1.54 (m, 1H), 1.05-0.89 (m, 7H), 0.95 (s, 5H). |
| 516 | 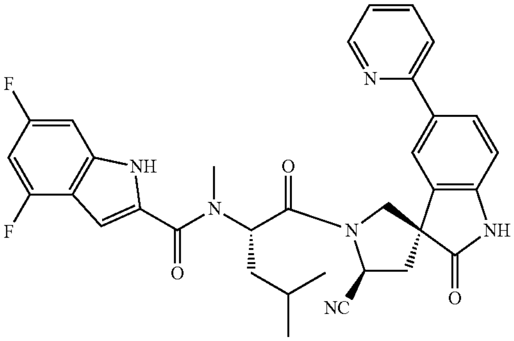 [SMILES: CC(C)C[C@@H](C(=O)N1C[C@]2(C[C@H]1C#N)C(=O)Nc1ccc(-c3ccccn3)cc12)N(C)C(=O)c1cc2c(F)cc(F)cc2[nH]1] | 597.517 [M + H] | 1H NMR (400 MHz, Acetone-d6) δ 10.50 (s, 1H), 9.86 (s, 1H), 8.54-8.48 (m, 1H), 7.79 (d, J = 1.8 Hz, 1H), 7.74 (d, J = 8.5 Hz, 1H), 7.61-7.53 (m, 1H), 7.42 (d, J = 8.0 Hz, 1H), 7.17 (dd, J = 7.5, 4.8 Hz, 1H), 6.99 (dd, J = 12.8, 9.2 Hz, 2H), 6.66 (td, J = 10.3, 2.0 Hz, 1H), 6.57 (d, J = 2.1 Hz, 1H), 5.65 (dd, J = 9.0, 5.9 Hz, 1H), 5.33 (t, J = 8.4 Hz, 1H), 4.56 (d, J = 10.8 Hz, 1H), 3.99 (d, J = 10.8 Hz, 1H), 3.39 (s, 3H), 2.85-2.70 (m, 3H), 2.06 (p, J = 2.2 Hz, 3H), 2.04 (s, 1H), 1.92 (ddd, J = 14.3, 9.0, 5.3 Hz, 1H), 1.78 (dt, J = 14.2, 7.4 Hz, 1H), 1.59 (dq, J = 13.9, 6.7 Hz, 1H), 1.44 (d, J = 0.9 Hz, 1H), 0.97 (dd, J = 15.7, 6.5 Hz, 6H). |

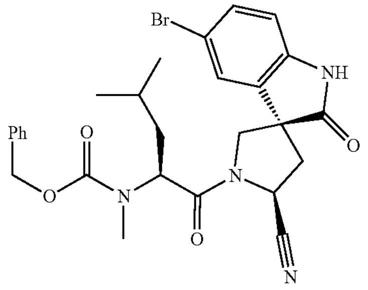

Example 517

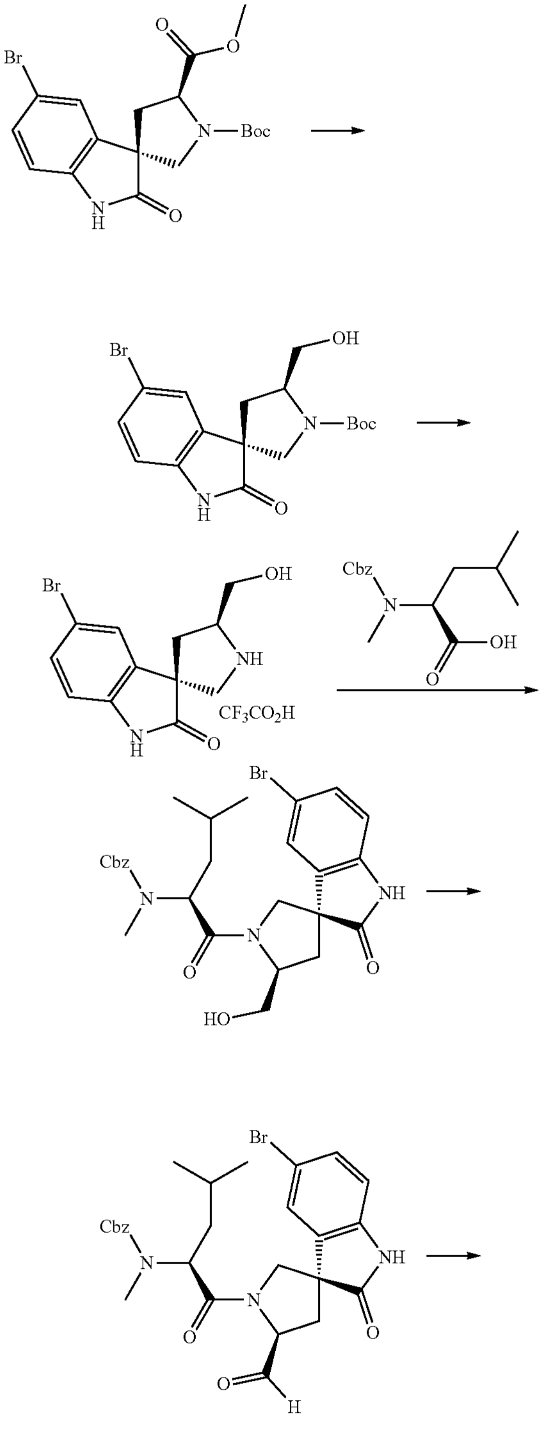

-continued

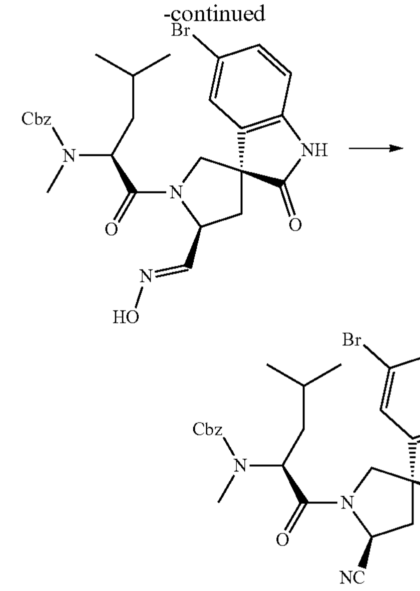

Step 1

1'-(tert-butyl) 5'-methyl (3R,5'S)-5-bromo-2-oxospiro[indoline-3,3'-pyrrolidine]-1',5'-dicarboxylate (897 mg, 2.11 mmol) was dissolved in MTBE (14 mL) and cooled to 0° C. Lithium borohydride (2.0 M in THF, 5.3 mL, 5 eq.) was added slowly, and the resulting mixture was stirred at 0° C. 2.5 mL additional lithium borohydride solution was added after 40 min and again after 60 min. The reaction was then quenched with saturated ammonium chloride. The mixture was extracted with EtOAc and diethyl ether, then the pooled organic fractions were washed with brine, dried over magnesium sulfate, filtered, and concentrated. The crude residue was subjected to preparative HPLC to afford tert-butyl (3R,5'S)-5-bromo-5'-(hydroxymethyl)-2-oxospiro[indoline-3,3'-pyrrolidine]-1'-carboxylate (202 mg, 0.508 mmol, 24% yield).

Step 2 tert-butyl (3R,5'S)-5-bromo-5'-(hydroxymethyl)-2-oxospiro[indoline-3,3'-pyrrolidine]-1'-carboxylate (60 mg, 0.151 mmol) was dissolved in DCM/TFA (1 mL, 1:1 ratio) and stirred at rt. After 45 min, the mixture was concentrated directly. The residue was redissolved in MeOH and reconcentrated. Then the residue was redissolved in EtOAc and reconcentrated. The resulting residue was used without further purification.

Step 3

Crude (3R,5'S)-5-bromo-5'-(hydroxymethyl)spiro[indoline-3,3'-pyrrolidin]-2-one 2,2,2-trifluoroacetate (crude, assumed 0.161 mmol) was dissolved in DMF (0.644 mL, 0.25 M), then $iPr_2NEt$ (87 mg, 0.676 mmol, 4.2 eq.) and N-((benzyloxy)carbonyl)-N-methyl-L-leucine (54 mg, 0.193 mmol, 1.2 eq.) were added. Once a homogenous solution was obtained, HATU (73 mg, 0.193 mmol, 1.2 eq.) was added. After 16 h, the reaction mixture was diluted with water and the mixture was subjected to solid phase extraction on an Oasis HLB (200 mg) extraction cartridge, eluting with water and methanol, to afford benzyl ((S)-1-((3R,5'S)-5-bromo-5'-(hydroxymethyl)-2-oxospiro[indoline-3,3'-pyrrolidin]-1'-yl)-4-methyl-1-oxopentan-2-yl)(methyl)carbamate (94 mg).

Step 4 benzyl ((S)-1-((3R,5'S)-5-bromo-5'-(hydroxymethyl)-2-oxospiro[indoline-3,3'-pyrrolidin]-1'-yl)-4-methyl-1-oxopentan-2-yl)carbamate (crude, assumed 0.173 mmol) was dissolved in $CH_2Cl_2$ (1.5 ml) and cooled to 0° C. Dess-Martin periodinane (110 mg, 0.259 mmol) was then added. The mixture was stirred at 0° C. for 2 h, then TLC indicated consumption of the SM (1:1 hexanes/ethyl acetate). The reaction mixture was then partitioned between DCM and sat $Na_2S_2O_3$, then the organic phase was washed with sat $NaHCO_3$ and brine, dried over magnesium sulfate, filtered, and concentrated. The crude residue was used without further purification.

Step 5 benzyl ((S)-1-((3R,5'S)-5-bromo-5'-formyl-2-oxospiro[indoline-3,3'-pyrrolidin]-1'-yl)-4-methyl-1-oxopentan-2-yl)(methyl)carbamate (crude, assumed 0.173 mmol) was dissolved in $CH_2Cl_2$ (6 mL), then iPr2NEt (67 mg, 0.519 mmol, 3 eq.) and hydroxylamine hydrochloride (240 mg, 3.46 mmol) were added. After 4 d, EtOAc and water were added. The organic phase was washed with brine, then dried over magnesium sulfate, filtered, and concentrated. The crude residue was used without further purification.

Step 6 benzyl ((S)-1-(3R,5'S)-5-bromo-5'-((hydroxyimino)methyl)-2-oxospiro[indoline-3,3'-pyrrolidin]-1'-yl)-4-methyl-1-oxopentan-2-yl)(methyl)carbamate (assumed 0.161 mmol) was dissolved in MeCN (3.22 mL) and copper (II) acetate (9 mg, 0.05 mmol) was added. The mixture was heated to 70° C. for 80 min. The mixture was then purified via preparative HPLC to afford benzyl ((S)-1-((3R,5'S)-5-bromo-5'-cyano-2-oxospiro[indoline-3,3'-pyrrolidin]-1'-yl)-4-methyl-1-oxopentan-2-yl)(methyl)carbamate (1.1 mg, 0.002 mmol, 1% yield over 5 steps). 1H NMR (400 MHz, Methanol-d4) δ 7.40 (dd, J=8.3, 2.0 Hz, 1H), 7.35-7.15 (m, 4H), 7.13-7.05 (m, 2H), 6.89 (dd, J=8.4, 3.3 Hz, 1H), 5.18 (t, J=8.2 Hz, 1H), 4.99 (dd, J=9.1, 6.1 Hz, 1H), 4.95-4.89 (m, 1H), 4.76 (d, J=12.3 Hz, 1H), 4.22 (d, J=10.9 Hz, 1H), 3.87 (d, J=10.8 Hz, 1H), 1.77 (ddd, J=14.3, 9.0, 5.4 Hz, 1H), 1.65 (ddd, J=13.9, 8.2, 5.9 Hz, 1H), 1.48 (dt, J=13.9, 6.8 Hz, 1H), 0.94 (dd, J=15.3, 6.5 Hz, 6H). [M+Na] m/z 574.82.

Example 518

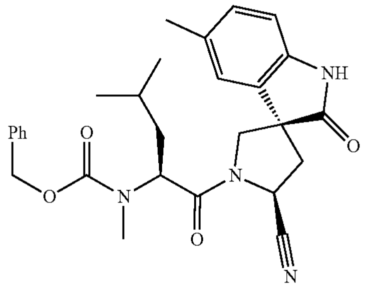

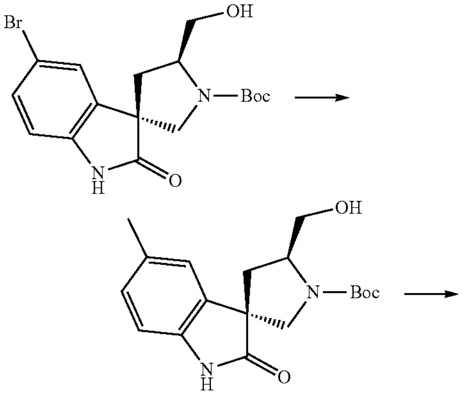

-continued

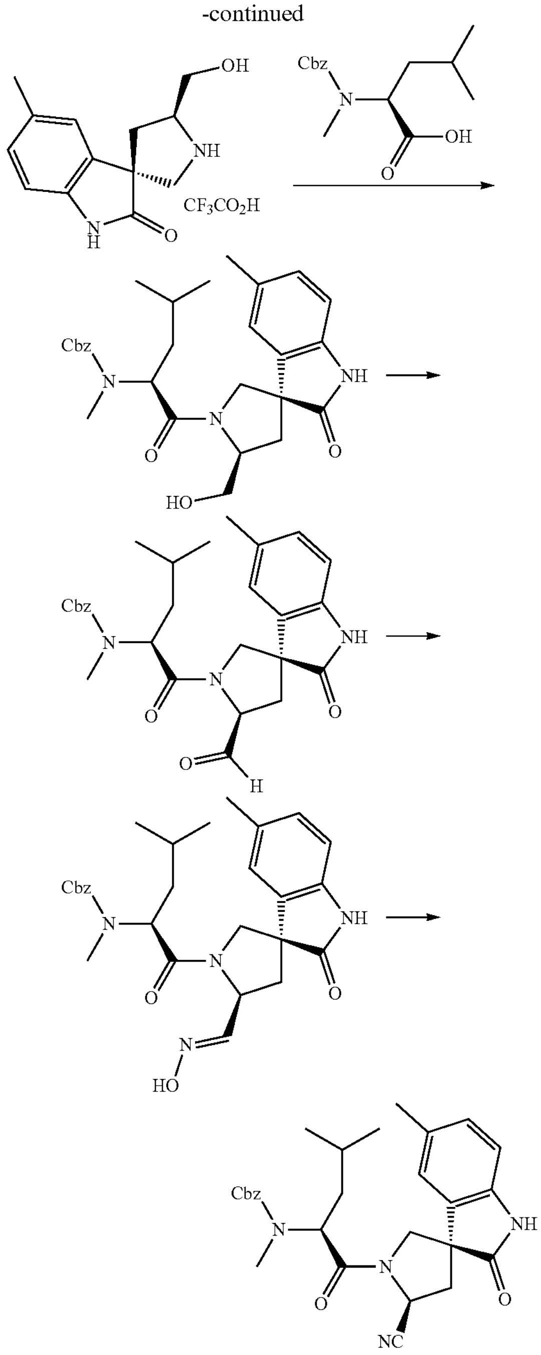

Step 1 tert-butyl (3R,5'S)-5-bromo-5'-(hydroxymethyl)-2-oxospiro[indoline-3,3'-pyrrolidine]-1'-carboxylate (60 mg, 0.151 mmol), cesium carbonate (148 mg, 0.453 mmol), potassium trifluoro(methyl)borate (36.8 mg, 0.302 mmol), and Pd(dppf)$Cl_2$ (27.6 mg, 0.038 mmol) were heated overnight at 80 deg in an N2-purged, sealed vial. The mixture was subjected to preparative HPLC to afford tert-butyl (3R,5'S)-5'-(hydroxymethyl)-5-methyl-2-oxospiro[indoline-3,3'-pyrrolidine]-1'-carboxylate (9 mg, 0.27 mmol, 18%).

Step 2 tert-butyl (3R,5'S)-5'-(hydroxymethyl)-5-methyl-2-oxospiro[indoline-3,3'-pyrrolidine]-1'-(60 mg, 0.151 mmol) was dissolved in DCM/TFA (1 mL, 1:1 ratio) and stirred at rt. After 45 min, the mixture was concentrated directly. The residue was redissolved in MeOH and reconcentrated. Then the residue was redissolved in EtOAc and reconcentrated. The resulting residue was used without further purification.

Step 3

Crude (3R,5'S)-5'-(hydroxymethyl)-5-methylspiro[indoline-3,3'-pyrrolidin]-2-one (crude, assumed 0.045 mmol) was dissolved in DMF (0.563 mL, 0.08 M), then $iPr_2NEt$ (38 mg, 0.293 mmol, 6.5 eq.) and N-((benzyloxy)carbonyl)-N-methyl-L-leucine (38 mg, 0.135 mmol, 3 eq.) were added. Once a homogenous solution was obtained, HATU (51 mg, 0.135 mmol, 3 eq.) was added. After 16 h, the reaction mixture was diluted with water and the mixture was subjected to solid phase extraction on an Oasis HLB (200 mg) extraction cartridge, eluting with water and methanol, to afford benzyl ((S)-14(3R,5'S)-5'-(hydroxymethyl)-5-methyl-2-oxospiro[indoline-3,3'-pyrrolidin]-1'-yl)-4-methyl-1-oxopentan-2-yl)(methyl)carbamate (42 mg). [M+H] m/z 494.387.

Step 4 benzyl ((S)-1-((3R,5'S)-5'-(hydroxymethyl)-5-methyl-2-oxospiro[indoline-3,3'-pyrrolidin]-1'-yl)-4-methyl-1-oxopentan-2-yl)carbamate (42 mg, assumed 0.088 mmol) was dissolved in $CH_2Cl_2$ (1.5 ml) and cooled to 0° C. Dess-Martin periodinane (110 mg, 0.259 mmol) was then added. The mixture was stirred at 0° C. for 2 h, then TLC indicated consumption of the SM (1:1 hexanes/ethyl acetate). The reaction mixture was then partitioned between DCM and sat $Na_2S_2O_3$, then the organic phase was washed with sat $NaHCO_3$ and brine, dried over magnesium sulfate, filtered, and concentrated. The crude residue was used without further purification.

Step 5 benzyl ((S)-1-((3R,5'S)-5'-formyl-5-methyl-2-oxospiro[indoline-3,3'-pyrrolidin]-1'-yl)-4-methyl-1-oxopentan-2-yl)(methyl)carbamate (crude, assumed 0.088 mmol) was dissolved in $CH_2Cl_2$ (4 mL), then iPr2NEt (34 mg, 0.264 mmol) and hydroxylamine hydrochloride (153 mg, 2.20 mmol) were added. After 4 d, EtOAc and water were added. The organic phase was washed with brine, then dried over magnesium sulfate, filtered, and concentrated. The crude residue was used without further purification.

Step 6 benzyl ((S)-14(3R,5'S)-5'-((hydroxyimino)methyl)-5-methyl-2-oxospiro[indoline-3,3'-pyrrolidin]-1'-yl)-4-methyl-1-oxopentan-2-yl)(methyl)carbamate (crude, assumed 0.045 mmol) was dissolved in MeCN (3 mL) and copper (II) acetate (9 mg, 0.05 mmol) was added. The mixture was heated to 70° C. for 80 min. The mixture was then subjected to preparative HPLC to afford benzyl ((S)-1-((3R,5'S)-5'-cyano-5-methyl-2-oxospiro[indoline-3,3'-pyrrolidin]-1'-yl)-4-methyl-1-oxopentan-2-yl)(methyl)carbamate (1.04 mg, 0.002 mmol, 5% yield over 5 steps). 1H NMR (400 MHz, Acetone-$d_6$) δ 9.60 (s, 1H), 7.43-7.17 (m, 5H), 7.15-7.04 (m, 1H), 6.92 (d, J=7.8 Hz, 1H), 6.81 (t, J=1.3 Hz, 1H), 5.22-5.14 (m, 1H), 5.08 (dd, J=9.6, 5.6 Hz, 1H), 4.94 (d, J=12.6 Hz, 1H), 4.67 (d, J=12.6 Hz, 1H), 4.35-4.25 (m, 1H), 3.91 (dd, J=10.4, 4.1 Hz, 1H), 2.94 (s, 3H), 2.22 (s, 3H), 1.81 (ddd, J=14.3, 9.6, 5.0 Hz, 1H), 1.64 (ddd, J=14.1, 8.7, 5.7 Hz, 1H), 1.52 (p, J=6.4 Hz, 1H), 1.04-0.91 (m, 6H). [M+Na] m/z 511.119.

Example 519

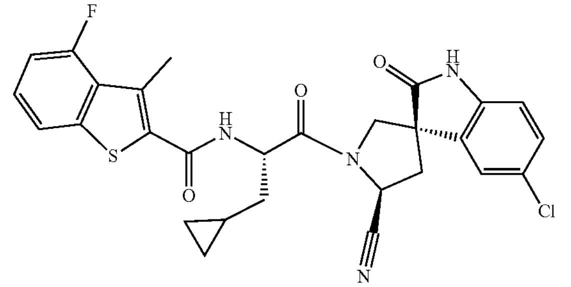

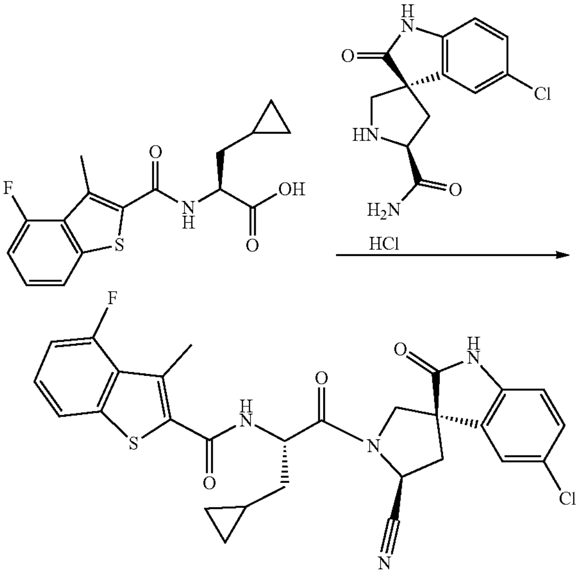

(S)-3-cyclopropyl-2-(4-fluoro-3-methylbenzo[b]thiophene-2-carboxamido)propanoic acid (33 mg, 0.103 mmol) and (3R,5'S)-5-chloro-2-oxospiro[indoline-3,3'-pyrrolidine]-5'-carboxamide hydrochloride (27 mg, 0.089 mmol) were dissolved in DMF (0.40 mL). HATU (39 mg, 0.103 mmol) and iPr2NEt (0.041 mL, 0.232 mmol) were then sequentially added, and the resulting solution was stirred at rt for 20 min. Additional HATU (~10 mg) and iPr2NEt (2-3 drops) were added as necessary (in this case, after 20 min). After 1 h at rt, palladium (II) trifluoroacetate (30 mg, 0.089 mmol), dichloroacetonitrile (0.4 mL), and water (0.4 mL) were added in sequence. The resulting suspension was then heated to 65° C. for 1 h before cooling to rt. The mixture was filtered and subjected to preparative HPLC to afford N—((S)-1-((3R,5'S)-5-chloro-5'-cyano-2-oxospiro[indoline-3,3'-pyrrolidin]-1'-yl)-3-cyclopropyl-1-oxopropan-2-yl)-4-fluoro-3-methylbenzo[b]thiophene-2-carboxamide (1.20 mg, 0.0022 mmol, 2% yield). 1H NMR (500 MHz, Acetone-$d_6$) δ 9.82 (s, 1H), 7.80-7.70 (m, 2H), 7.48 (td, J=8.0, 4.8 Hz, 1H), 7.36-7.25 (m, 2H), 7.16 (ddd, J=12.2, 8.0, 0.8 Hz, 1H), 7.02 (d, J=8.2 Hz, 1H), 5.29 (t, J=8.2 Hz, 1H), 4.88 (q, J=7.0 Hz, 1H), 4.50-4.44 (m, 1H), 4.13 (d, J=10.5 Hz, 1H), 2.86 (ddd, J=13.3, 8.5, 1.1 Hz, 1H), 2.80 (s, 3H), 2.73 (dd, J=13.3, 7.9 Hz, 1H), 1.85 (t, J=7.0 Hz, 2H), 0.95 (dddd, J=15.1, 10.2, 5.2, 2.4 Hz, 1H), 0.58-0.52 (m, 2H), 0.30 (dddd, J=9.4, 4.7, 2.7, 1.4 Hz, 1H), 0.24 (dddd, J=9.0, 6.3, 2.8, 1.2 Hz, 1H). $[M+H]^+$ 550.741

The following example was prepared employing a similar protocol as described above.

| Example | Structure | MS | NMR |
|---|---|---|---|
| 520 | 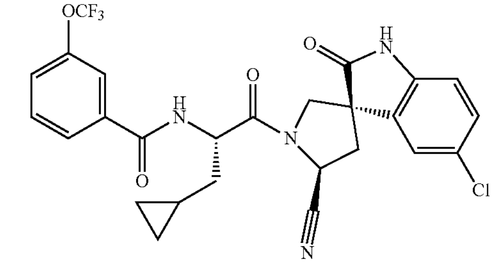 [SMILES: N#C[C@@H]1C[C@@]2(CN1C(=O)[C@H](CC1CC1)NC(=O)c1cccc(OC(F)(F)F)c1)C(=O)Nc1ccc(Cl)cc12] | [M − H]$^-$ 544.965 | $^1$H NMR (500 MHz, Acetone-d6) δ 9.81 (s, 1H), 8.21 (d, J = 7.1 Hz, 1H), 7.96 (dt, J = 7.8, 1.3 Hz, 1H), 7.86 (dt, J = 2.3, 1.2 Hz, 1H), 7.61 (t, J = 8.0 Hz, 1H), 7.51 (ddt, J = 8.2, 2.3, 1.1 Hz, 1H), 7.29-7.22 (m, 2H), 7.00 (d, J = 8.1 Hz, 1H), 5.23 (t, J = 8.3 Hz, 1H), 4.85 (q, J = 7.3 Hz, 1H), 4.55 (dd, J = 10.6, 1.2 Hz, 1H), 4.08 (d, J = 10.5 Hz, 1H), 2.82 (ddd, J = 13.4, 8.5, 1.2 Hz, 3H), 2.70 (dd, J = 13.3, 8.3 Hz, 1H), 1.89-1.75 (m, 2H), 0.97-0.86 (m, 1H), 0.58-0.45 (m, 2H), 0.31-0.16 (m, 2H). |
| 521 | 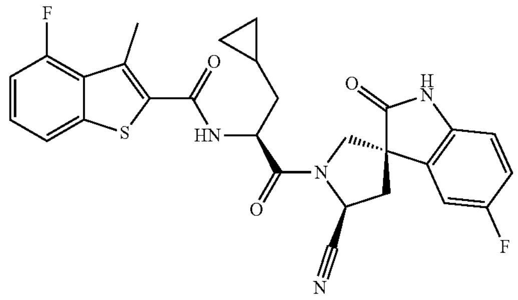 [SMILES: Cc1c(C(=O)N[C@@H](CC2CC2)C(=O)N2C[C@]3(C[C@H]2C#N)C(=O)Nc2ccc(F)cc23)sc2cccc(F)c12] | [M + H]$^+$ 534.950 | $^1$H NMR (400 MHz, Acetone-$d_6$) δ 9.71 (s, 1H), 7.79-7.68 (m, 2H), 7.46 (td, J = 8.0, 4.8 Hz, 1H), 7.19-7.06 (m, 2H), 7.06-6.96 (m, 2H), 5.26 (t, J = 8.2 Hz, 1H), 4.85 (q, J = 7.0 Hz, 1H), 4.45 (d, J = 10.5 Hz, 1H), 4.11 (d, J = 10.5 Hz, 1H), 2.71 (dd, J = 13.3, 8.0 Hz, 1H), 1.84 (t, J = 7.0 Hz, 2H), 0.93 (pd, J = 7.4, 3.8 Hz, 1H), 0.59-0.49 (m, 2H), 0.34-0.19 (m, 2H). |
| 522 | 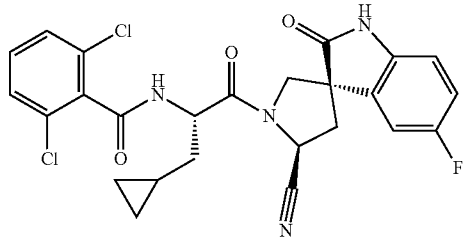 [SMILES: N#C[C@@H]1C[C@@]2(CN1C(=O)[C@H](CC1CC1)NC(=O)c1c(Cl)cccc1Cl)C(=O)Nc1ccc(F)cc12] | [M − H]$^+$ 512.804 | 1H NMR (500 MHz, Acetone-d6) δ 9.72 (s, 1H), 8.17-8.10 (m, 1H), 7.45-7.36 (m, 2H), 7.08-6.92 (m, 3H), 5.25 (t, J = 8.3 Hz, 1H), 4.99-4.90 (m, 1H), 4.49 (dd, J = 10.5, 1.2 Hz, 1H), 4.13 (d, J = 10.5 Hz, 1H), 2.84-2.77 (m, 2H), 2.72 (dd, J = 13.3, 8.4 Hz, 1H), 1.82 (td, J = 7.1, 2.6 Hz, 2H), 1.01-0.92 (m, 1H), 0.56-0.49 (m, 2H), 0.27-0.22 (m, 2H). |
| 523 | 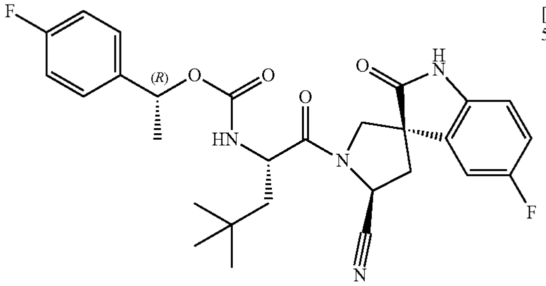 | [M + H]$^+$ 542.927 | 1H NMR (400 MHz, Acetone-d6) δ 9.71 (s, 1H), 7.45-7.30 (m, 2H), 7.18-7.07 (m, 2H), 7.06-6.96 (m, 2H), 6.91 (dd, J = 8.4, 2.4 Hz, 1H), 6.70 (d, J = 8.4 Hz, 1H), 5.68 (q, J = 6.6 Hz, 1H), 5.13 (t, J = 8.2 Hz, 1H), 4.48 (td, J = 8.6, 4.0 Hz, 1H), 4.26 (d, J = 10.3 Hz, 1H), 4.00 (d, J = 10.3 Hz, 1H), 2.84 (d, J = 12.7 Hz, 1H), 2.80-2.65 (m, 2H), 2.67 (dd, J = 13.3, 8.1 Hz, 1H), 1.81 (dd, J = 14.5, 4.1 Hz, 1H), 1.67 (dd, J = 14.5, 8.6 Hz, 1H), 1.45 (d, J = 6.6 Hz, 3H), 1.02 (s, 8H). |
| 524 | 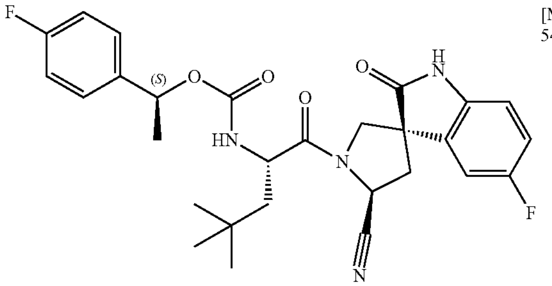 | [M + H]$^+$ 542.965 | 1H NMR (400 MHz, Acetone-d6) δ 9.73 (s, 1H), 7.41-7.32 (m, 2H), 7.08 (td, J = 9.1, 2.7 Hz, 3H), 7.01 (dd, J = 8.5, 4.5 Hz, 1H), 6.95 (dd, J = 8.4, 2.6 Hz, 1H), 6.74 (d, J = 8.6 Hz, 1H), 5.60 (q, J = 6.6 Hz, 1H), 5.22 (t, J = 8.4 Hz, 1H), 4.44 (td, J = 8.5, 4.2 Hz, 1H), 4.37 (d, J = 10.4 Hz, 1H), 3.98 (d, J = 10.3 Hz, 1H), 2.84-2.75 (m, 1H), 2.70 (dd, J = 13.2, 8.5 Hz, 1H), 1.80 (dd, J = 14.5, 4.2 Hz, 1H), 1.66 (dd, J = 14.5, 8.5 Hz, 1H), 1.41 (d, J = 6.6 Hz, 3H), 0.95 (s, 9H). |

-continued

| Example | Structure | MS | NMR |
|---|---|---|---|
| 525 | 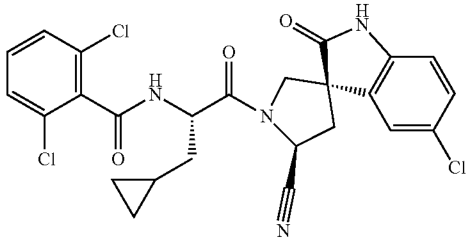 [SMILES: N#C[C@@H]1C[C@@]2(CN1C(=O)[C@H](CC1CC1)NC(=O)c1c(Cl)cccc1Cl)C(=O)Nc1ccc(Cl)cc12] | [M − H]⁻ 528.713 | 1H NMR (500 MHz, Acetone-d6) δ 9.81 (s, 1H), 8.12 (d, J = 7.7 Hz, 1H), 7.47-7.35 (m, 3H), 7.28 (dd, J = 8.3, 2.1 Hz, 1H), 7.18 (d, J = 2.1 Hz, 1H), 7.00 (d, J = 8.3 Hz, 1H), 5.27 (t, J = 8.3 Hz, 1H), 4.95 (q, J = 7.1 Hz, 1H), 4.47 (dd, J = 10.5, 1.1 Hz, 1H), 4.14 (d, J = 10.5 Hz, 1H), 2.83 (ddd, J = 13.2, 8.4, 1.1 Hz, 1H), 2.71 (dd, J = 13.3, 8.1 Hz, 1H), 1.82 (t, J = 7.0 Hz, 2H), 1.04-0.92 (m, 1H), 0.58-0.47 (m, 2H), 0.28 (d, J = 5.3 Hz, 2H). |
| 526 | 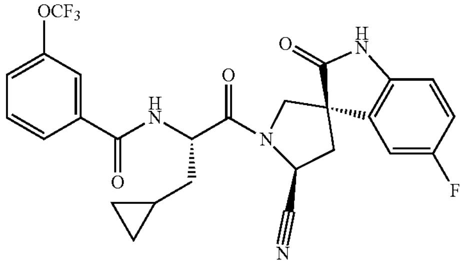 [SMILES: N#C[C@@H]1C[C@@]2(CN1C(=O)[C@H](CC1CC1)NC(=O)c1cccc(OC(F)(F)F)c1)C(=O)Nc1ccc(F)cc12] | $[M + H]^+$ 530.875 | 1H NMR (500 MHz, Acetone-d6) δ 9.87 (s, 1H), 8.27 (d, J = 7.2 Hz, 1H), 8.13 (s, 1H), 7.96-7.89 (m, 1H), 7.81 (d, J = 2.3 Hz, 1H), 7.61 (t, J = 8.0 Hz, 1H), 7.54-7.48 (m, 1H), 7.06-6.96 (m, 3H), 5.22 (t, J = 8.2 Hz, 1H), 4.86 (q, J = 7.3 Hz, 1H), 4.49 (d, J = 10.5 Hz, 1H), 4.09 (d, J = 10.5 Hz, 1H), 2.80 (dd, J = 13.3, 8.5 Hz, 1H), 2.69 (dd, J = 13.3, 7.9 Hz, 1H), 1.82 (td, J = 7.2, 2.8 Hz, 2H), 0.91 (tt, J = 7.6, 4.8 Hz, 1H), 0.51 (dd, J = 8.1, 4.0 Hz, 2H), 0.27-0.18 (m, 2H). |

Example 527

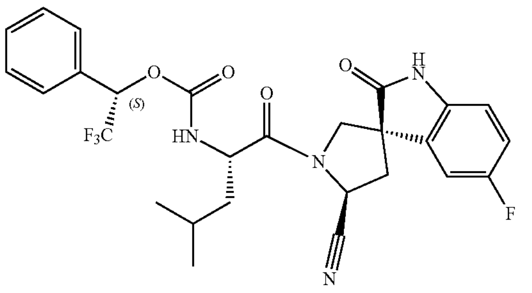

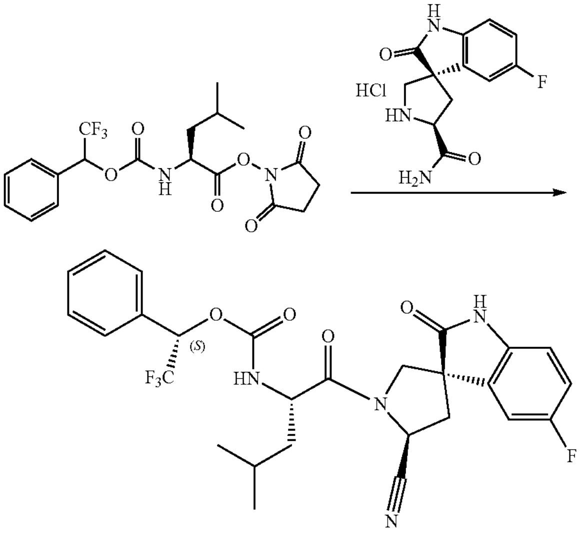

iPr2NEt (35.0 μl, 200 mmol) was added to a stirred mixture of 2,5-dioxopyrrolidin-1-yl (((S)-2,2,2-trifluoro-1-phenylethoxy)carbonyl)-L-leucinate (66.3 mg, 0.154 mmol), (3R,5'S)-5-fluoro-2-oxospiro[indoline-3,3'-pyrrolidine]-5'-carboxamide hydrochloride (44 mg, 0.154 mmol), and MeCN (0.380 ml). The resulting mixture was stirred at rt for 3 h, then warmed to 50° C. for 16 h. After this time, 15 uL iPr2NEt and 20 uL 2,5-dioxopyrrolidin-1-yl (((S)-2,2,2-trifluoro-1-phenylethoxy)carbonyl)-L-leucinate were added, and the mixture was warmed further to 65° C. After 24 h, palladium (II) trifluoroacetate (51 mg, 0.154 mmol), dichloroacetonitrile (0.38 mL), and water (0.38 mL) were added, and stirring continued at 65° C. After 25 min, the mixture was cooled to rt, filtered, and subjected to preparative HPLC to afford (S)-2,2,2-trifluoro-1-phenylethyl ((S)-1-((3R,5'S)-5'-cyano-5-fluoro-2-oxospiro[indoline-3,3'-pyrrolidin]-1'-yl)-4-methyl-1-oxopentan-2-yl)carbamate (0.96 mg, 0.0017 mmol, 1% yield). 1H NMR (500 MHz, Acetone-d6) δ 9.70 (s, 1H), 7.52 (dt, J=6.6, 3.8 Hz, 2H), 7.46 (dp, J=4.6, 1.7 Hz, 3H), 7.32 (d, J=8.0 Hz, 1H), 7.07 (ddd, J=9.4, 8.6, 2.6 Hz, 1H), 7.03-6.95 (m, 2H), 6.09 (q, J=7.1 Hz, 1H), 5.24 (t, J=8.2 Hz, 1H), 4.43 (ddd, J=9.7, 7.9, 4.6 Hz, 1H), 4.31-4.18 (m, 1H), 4.00 (d, J=10.4 Hz, 1H), 2.82 (ddd, J=13.3, 8.5, 1.0 Hz, 2H), 2.70 (dd, J=13.3, 7.9 Hz, 1H), 1.83-1.59 (m, 3H), 0.95 (d, J=6.6 Hz, 3H), 0.88 (d, J=6.5 Hz, 3H). $[M+H]^+$ 547.20.

Example 528

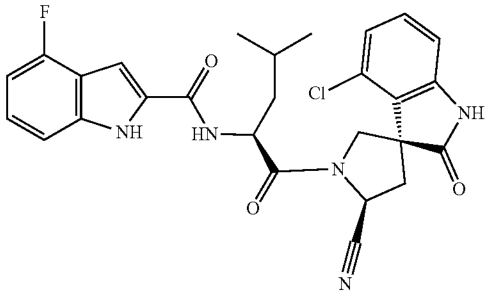

-continued

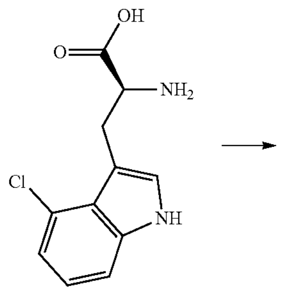

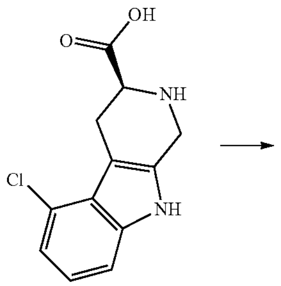

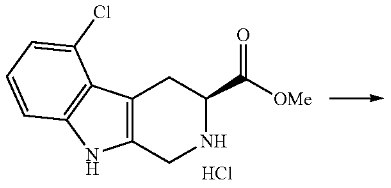

B-1

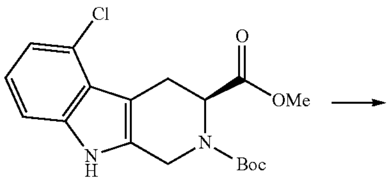

C-1

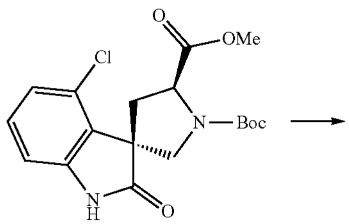

D-1

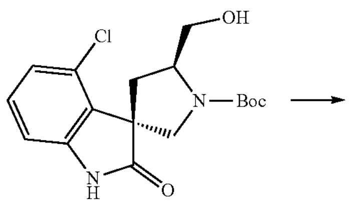

E-1

-continued

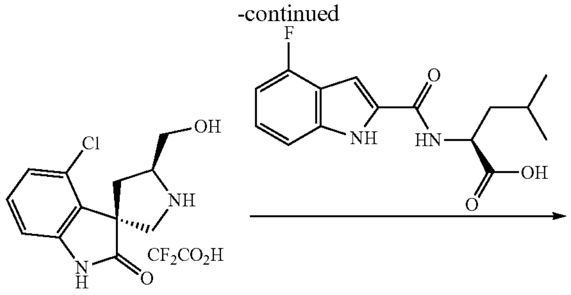

F-1

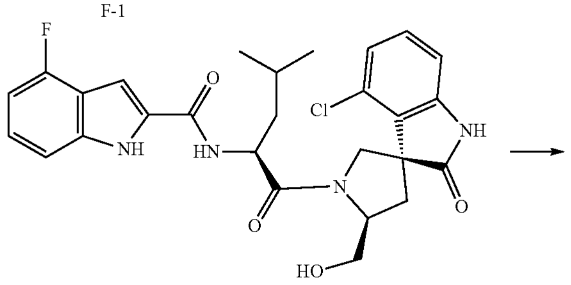

G-1

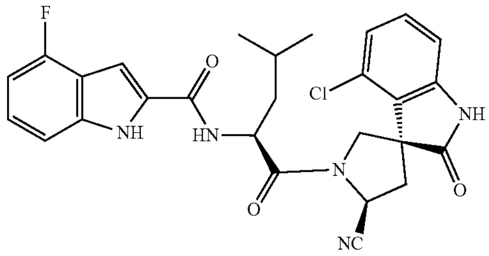

Example 528

Step 1

37% aqueous formaldehyde (0.312 ml, 4.19 mmol, 1.12 eq.) was added to a solution of (S)-2-amino-3-(4-chloro-1H-indol-3-yl)propanoic acid (892 mg, 3.74 mmol) and 0.5 N NaOH (1.1 eq. NaOH, 8.22 mL) at rt. The resulting mixture was stirred at rt for 2 h, then at 104° C. for 24 h. During this time, and as needed, the reaction was charged with additional formaldehyde solution (0.3 mL after 3 h in this case). The reaction mixture was then cooled to rt and acetic acid (0.449 ml, 7.85 mmol, 2.1 eq.) was added. The mixture was then filtered, rinsed sequentially with water and THF, affording crude A-1 which was used without further purification.

Step 2

A-1 (assumed 100% yield) was added to a solution of 0.44 M $SOCl_2$ in MeOH (15 mL, 0.25 M with respect to substrate). The resulting mixture was stirred at 40° C. for 5 d. When the SM was consumed by LCMS, the mixture was directly concentrated to afford crude B-1, which was used without further purification. [M+H] m/z 265.051.

Step 3

Compound B-1 (assumed 100% yield) was suspended in DCM (14 mL), then Hunig's base (1.25 mL, 7.2 mmol) was added, followed by a solution of di-tert-butyl dicarbonate (1.2 g, 5.5 mmol) in DCM (2.5 mL). When TLC (10:1 DCM/MeOH) indicated consumption of the SM, the reaction mixture was directly concentrated. The residue was subjected to silica gel chromatography, eluting with 0-35% EtOAc in hexanes, to afford C-1 (404 mg, 1.16 mmol, 31% yield over 3 steps).

Step 4

At 0° C. NBS (177 mg, 0.997 mmol, 0.9 eq.) was added to a vigorously stirred mixture of C-1 (404 mg, 1.107 mmol) in 2-MeTHF/water/acetic acid (63:28:9 ratio, 7.7 mL total volume, 0.114 M). The reaction was stirred at 0° C. for 90 min, then slowly warmed to rt. When TLC indicated consumption of the SM, the reaction was quenched with sat. aq. $NaHCO_3$, then extracted with $Et_2O$. The organic phase was dried over magnesium sulfate, filtered, and concentrated. The residue was subjected to silica gel chromatography, eluting with 0-50% EtOAc in hexanes, to afford D-1 (251 mg, 0.66 mmol, 60% yield).

Step 5

D-1 (251 mg, 0.659 mmol) was dissolved in THF (3.30 ml, 0.2 M) and cooled to 0° C. Lithium borohydride (2.0 M in THF, 1.98 mL, 6 eq.) was then added. When TLC (1:1 hexanes/EtOAc) indicated full conversion of the SM, the reaction was poured into ice-cold aqueous saturated ammonium chloride. The mixture was extracted with EtOAc and diethyl ether, then the pooled organic fractions were washed with brine, dried over magnesium sulfate, filtered, and concentrated, to afford crude E-1 (228 mg), which was used without further purification.

Step 6

Crude E-1 (50 mg, 0.142 mmol) was dissolved in DCM/TFA (4 mL, 1:1 ratio) and stirred at rt. After 45 min, the mixture was concentrated directly. The residue was redissolved in MeOH and reconcentrated. Then the residue was redissolved in EtOAc and reconcentrated, affording F-1, which was used without further purification.

Step 7

Compound F-1 was dissolved in DMF (0.947 mL) and $iPr_2NEt$ (92 mg, 0.71 mmol), and then (4-fluoro-1H-indole-2-carbonyl)-L-leucine (50 mg, 0.17 mmol) was added. When the mixture was homogenous, HATU (65 mg, 0.17 mmol) was added. The mixture was stirred for 2.5 d at rt, then diluted with water and DCM. The organic phase was washed with sat. aq. $NaHCO_3$ solution and brine, then dried over magnesium sulfate, filtered, and concentrated, affording crude G-1 (assumed 100% yield). [M+H] m/z 526.913.

Step 8

Crude G-1 was dissolved in $CH_2Cl_2$ (1.42 mL) and cooled to 0° C. Dess-Martin periodinane (110 mg) was added and the mixture was stirred at 0° C. After 1 h, additional Dess-Martin periodinane (80 mg) was added. After 2 h, additional Dess-Martin periodinane (200 mg) was added. The reaction mixture was then quenched with sat. aq. $Na_2S_2O_3$, then the mixture was extracted with DCM. The organic phase was washed with sat. aq. $NaHCO_3$ solution and brine, then dried over magnesium sulfate, filtered, and concentrated.

The crude residue obtained above was dissolved in DCM (10 mL) and iPr2NEt (92 mg, 0.71 mmol) was added. Hydroxylamine hydrochloride (247 mg, 3.55 mmol) was then added, and the mixture was stirred for 16 h at rt. Water was added, the phases were separated, and the organic phase was dried over magnesium sulfate and concentrated.

The crude residue obtained above was dissolved in MeCN (3 mL) and copper (II) acetate (9 mg, 0.05 mmol) was added. The mixture was heated to 70° C. for 1 h. The mixture was then cooled to rt and subjected to preparative HPLC to afford Example 528 (0.70 mg). $^1$H NMR (500 MHz, Acetone-d6) δ 7.42-7.36 (m, 1H), 7.26-7.19 (m, 1H), 6.96 (m, 1H), 6.81 (m, 1H), 5.35 (m, 1H), 5.05 (m, 1H), 4.76 (mf, 1H), 4.69 (d, J=11.0 Hz, 1H), 4.13 (d, J=11.0 Hz, 1H), 3.12 (dd, J=14.1, 9.7 Hz, 1H), 2.69 (dd, J=14.1, 4.5 Hz, 1H), 1.83 (m, 2H), 1.78-1.68 (m, 1H), 1.06-0.93 (m, 6H). [M+H] m/z 521.835.

The following examples were prepared employing similar protocol as described above.

| Example | Structure | MS | NMR |
|---|---|---|---|
| 529 | 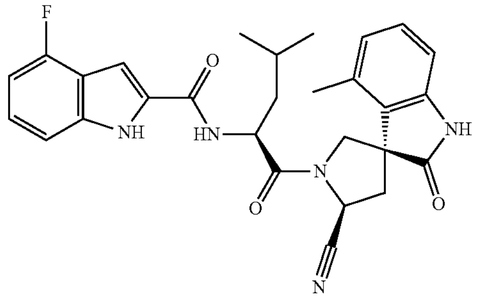 [SMILES: Cc1cccc2c1[C@@]1(C[C@@H](C#N)N(C(=O)[C@H](CC(C)C)NC(=O)c3cc4c(F)cccc4[nH]3)C1)C(=O)N2] | [M + H] m/z 501.956 | 1H NMR (500 MHz, Acetone-d6) δ 11.02 (s, lfH), 9.56 (s, 1H), 8.07 (d, J = 8.2 Hz, 1H), 7.41 - 7.33 (m, 2H), 7.21 (td, J = 8.0, 5.3 Hz, 1H), 7.14 (t, J = 7.7 Hz, 1H), 6.84 - 6.76 (m, 3H), 5.35 (dd, J = 9.9, 4.0 Hz, 1H), 4.98 (ddd, J = 10.0, 8.2, 4.6 Hz, 1H), 4.58 (d, J = 10.9 Hz, 1H), 4.11 (d, J= 10.9 Hz, 1H), 2.98 (dd, J = 14.3, 9.8 Hz, 1H), 2.65 (dd, J = 14.3, 4.0 Hz, 1H), 2.30 (s, 3H), 1.89-1.79 (m, 2H), 1.68 (m, 1H), 1.04 - 0.94 (m, 6H). |
| 530 | 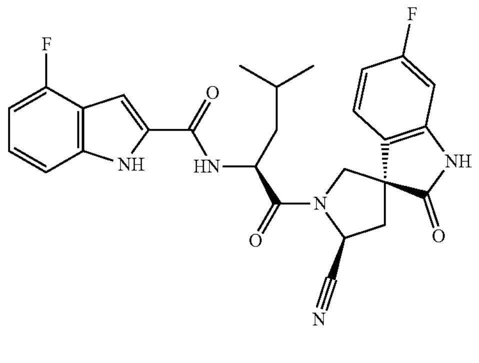 | [M + H] m/z 505.917. | 1H NMR (500 MHz, Acetone-d6) δ 10.94 (s, 1H), 9.83 (s, 1H), 8.03 (d, J = 8.2 Hz, 1H), 7.39-7.34 (m, 1H), 7.22 (m, 1H), 7.15 (dd, J = 8.3, 5.3 Hz, 1H), 6.85-6.73 (m, 2H), 6.62 (ddd, J = 9.9, 8.3, 2.4 Hz, 1H), 5.18 (t, J = 8.3 Hz, 1H), 4.93 (ddd, J = 9.8, 8.1, 4.7 Hz, 1H), 4.38 (dd, J = 10.5, 1.1 Hz, 1H), 4.05 (d, J = 10.4 Hz, 1H), 2.77 (ddd, J = 13.3, 8.4, 1.1 Hz, 1H), 2.69 (dd, J = 13.2, 8.1 Hz, 1H), 1.90-1.80 (m, 2H), 1.76-1.70 (m, 1H), 0.99 (m, 6H). |

-continued

| Example | Structure | MS | NMR |
|---|---|---|---|
| 531 | 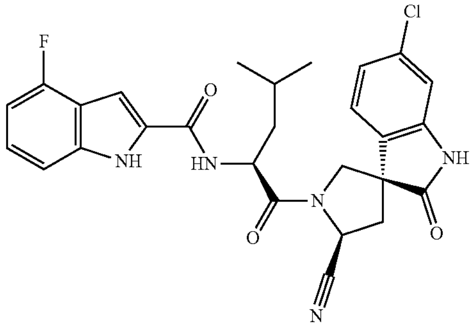 [SMILES: CC(C)C[C@H](NC(=O)c1cc2c(F)cccc2[nH]1)C(=O)N1C[C@]2(C[C@H]1C#N)C(=O)Nc1cc(Cl)ccc12] | [M + H] m/z 521.852 | 1H NMR (500 MHz, Acetone-d6) δ 10.92 (s, 1H), 9.83 (s, 1H), 8.03 (d, J = 8.1 Hz, 1H), 7.39-7.32 (m, 1H), 7.20 (td, J = 8.0, 5.2 Hz, 1H), 7.11 (d, J = 8.0 Hz, 1H), 6.98 (d, J = 1.9 Hz, 1H), 6.86 (dd, J = 8.0, 1.9 Hz, 1H), 6.82-6.77 (m, 1H), 5.17 (t, J = 8.3 Hz, 1H), 4.91 (ddd, J = 9.8, 8.1, 4.7 Hz, 1H), 4.40 (dd, J = 10.5, 1.2 Hz, 1H), 4.03 (d, J = 10.5 Hz, 1H), 2.76 (ddd, J = 13.4, 8.5, 1.2 Hz, 2H), 2.68 (dd, J = 13.2, 8.2 Hz, 1H), 1.87-1.78 (m, 2H), 1.71 (ddd, J = 13.7, 9.5, 5.1 Hz, 1H), 0.97 (m, 6H). |
| 532 | 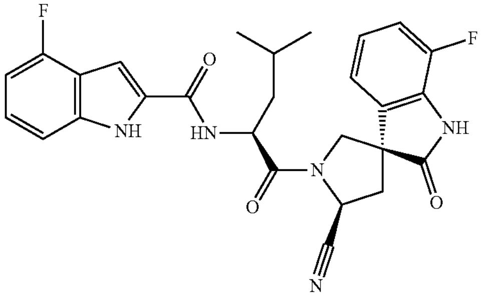 [SMILES: CC(C)C[C@H](NC(=O)c1cc2c(F)cccc2[nH]1)C(=O)N1C[C@]2(C[C@H]1C#N)C(=O)Nc1c(F)cccc12] | [M + H] m/z 505.941 | 1H NMR (500 MHz, Acetone-d6) δ 10.90 (s, 1H), 10.10 (s, 1H), 8.01 (d, J = 8.2 Hz, 1H), 7.37-7.34 (m, 1H), 7.21 (m, 1H), 7.03-6.97 (m, 1H), 6.95 (d, J = 7.4 Hz, 1H), 6.85 (m, 1H), 6.82-6.77 (m, 1H), 5.17 (t, J = 8.3 Hz, 1H), 4.93 (ddd, J = 9.6, 8.3, 4.7 Hz, 1H), 4.42 (dd, J = 10.6, 1.2 Hz, 1H), 4.06 (d, J = 10.5 Hz, 1H), 2.80-2.76 (m, 1H), 2.70 (dd, J = 13.3, 8.1Hz, 1H), 1.86-1.78 (m, 2H), 1.71 (m, 1H), 0.97 (m, 6H). |
| 533 | 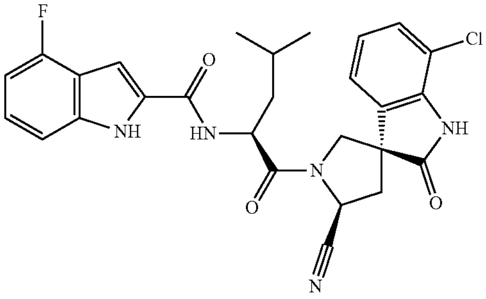 [SMILES: CC(C)C[C@H](NC(=O)c1cc2c(F)cccc2[nH]1)C(=O)N1C[C@]2(C[C@H]1C#N)C(=O)Nc1c(Cl)cccc12] | [M + H] m/z 521.892 | 1H NMR (500 MHz, Acetone-d6) δ 10.94 (s, 1H), 10.01 (d, J = 12.3 Hz, 1H), 8.05 (d, J = 8.4 Hz, 1H), 7.42-7.18 (m, 4H), 7.10-7.07 (m, 1H), 6.84-6.78 (m, 1H), 5.20 (td, J = 8.2, 4.4 Hz, 1H), 4.99-4.92 (m, 1H), 4.46 (dd, J = 10.6, 1.2 Hz, 1H), 4.08 (d, J = 10.6 Hz, 1H), 2.83-2.79 (m, 1H), 2.72 (ddd, J = 13.9, 7.9, 6.1 Hz, 1H), 1.85-1.80 (m, 1H), 1.76-1.71 (m, 1H), 1.03-0.95 (m, 6H). |
| 534 | 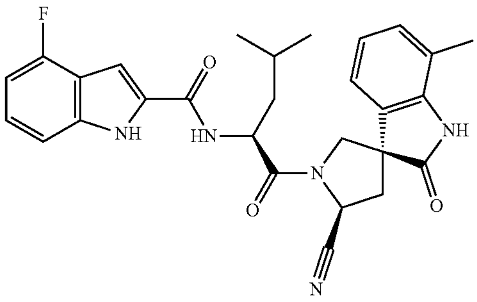 [SMILES: Cc1cccc2c1NC(=O)[C@]21C[C@@H](C#N)N(C(=O)[C@H](CC(C)C)NC(=O)c2cc3c(F)cccc3[nH]2)C1] | [M + H] m/z 501.972 | 1H NMR (500 MHz, Acetone-d6) δ 10.90 (s, 1H), 9.64 (d, J = 15.8 Hz, 1H), 7.99 (d, J = 8.3 Hz, 1H), 7.38-7.34 (m, 1H), 7.23-7.18 (m, 1H), 6.99-6.91 (m, 2H), 6.82-6.76 (m, 2H), 5.14 (t, J = 8.2 Hz, 1H), 4.97-4.90 (m, 1H), 4.31 (dd, J = 10.5, 1.0 Hz, 1H), 4.02 (d, J = 10.4 Hz, 1H), 3.72 (d, J = 17.2 Hz, 1H), 2.74-2.62 (m, 2H), 2.29 (s, 2H), 1.86-1.78 (m, 2H), 1.75-1.69 (m, 1H), 1.00-0.95 (m, 6H). |

Example 535

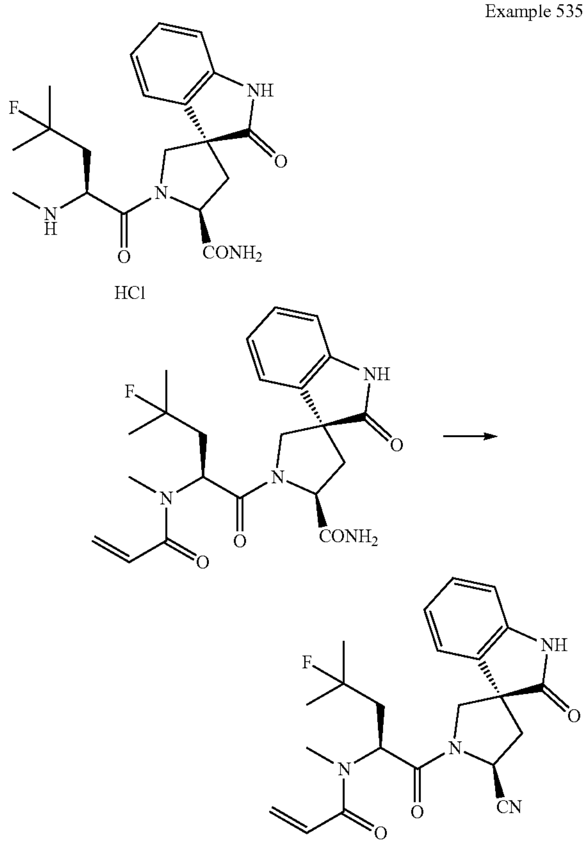

Step 1

(3R,5'S)-1'-((S)-4-fluoro-4-methyl-2-(methylamino)pentanoyl)-2-oxospiro[indoline-3,3'-pyrrolidine]-5'-carboxamide hydrochloride (198 mg, 0.48 mmol) was suspended in DCM (4.80 mL) and $Et_3N$ (334 uL, 2.40 mmol, 5 eq.) was added. The mixture was cooled to 0° C., then acryloyl chloride was added (42.9 µl, 0.528 mmol) dropwise. After 45 min at 0° C., MeOH (1 mL) was added and the mixture was concentrated directly. The residue was coevaporated with EtOAc and used immediately without further purification.

Step 2

The crude residue obtained from step 1 (assumed 100% yield) was suspended in DCM (3.43 mL), and Burgess reagent (0.343 g, 1.440 mmol) was added. The mixture was stirred overnight at rt, then concentrated directly. The residue was subjected to silica gel chromatography, eluting with 0-80% EtOAc in cyclohexane, to afford N—((S)-1-((3R,5'S)-5'-cyano-2-oxospiro[indoline-3,3'-pyrrolidin]-1'-yl)-4-fluoro-4-methyl-1-oxopentan-2-yl)-N-methylacrylamide (181 mg, 0.439 mmol, 91% yield over 2 steps). 1H NMR (400 MHz, Acetone-d6) δ 9.67 (s, 1H), 7.22 (td, J=7.6, 1.5 Hz, 1H), 7.03-6.91 (m, 3H), 6.48 (dd, J=16.7, 10.4 Hz, 1H), 5.85 (dd, J=16.7, 2.4 Hz, 1H), 5.70 (dd, J=7.5, 5.7 Hz, 1H), 5.49 (dd, J=10.4, 2.4 Hz, 1H), 5.16 (t, J=8.3 Hz, 1H), 4.27 (dd, J=10.7, 1.2 Hz, 1H), 3.89 (d, J=10.7 Hz, 1H), 2.77-2.58 (m, 2H), 2.36-2.23 (m, 1H), 2.23-2.08 (m, 1H), 1.41-1.35 (m, 6H). [M+Na] m/z 435.33.

The following examples were prepared employing a similar protocol as described above.

| Example | Structure | MS | NMR |
|---|---|---|---|
| 536 | 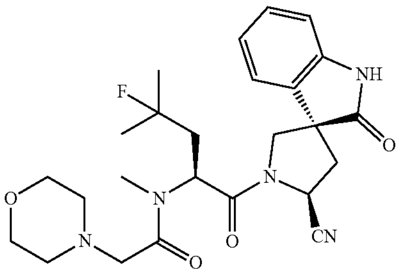 [SMILES: CN(C(=O)CN1CCOCC1)[C@@H](CC(C)(C)F)C(=O)N1C[C@]2(C[C@H]1C#N)C(=O)Nc1ccccc12] | $[M + H]^+$ 486.420 | 1H NMR (400 MHz, Acetone-d6) δ 9.71 (s, 1H), 8.11 (s, 1H), 7.33-7.25 (m, 1H), 7.07 (t, J = 7.4 Hz, 1H), 7.00 (dd, J = 13.9, 7.6 Hz, 2H), 5.63 (dd, J = 7.6, 5.6 Hz, 1H), 5.15 (t, J = 8.4 Hz, 1H), 4.18 (d, J = 10.7 Hz, 1H), 3.88 (d, J = 10.7 Hz, 1H), 3.47 (m, 4H), 2.80-2.62 (m, 4H), 2.26 (m, 5H), 2.12 (dt, J = 14.9, 7.5 Hz, 1H), 1.36 (m, 6H). |
| 537 | 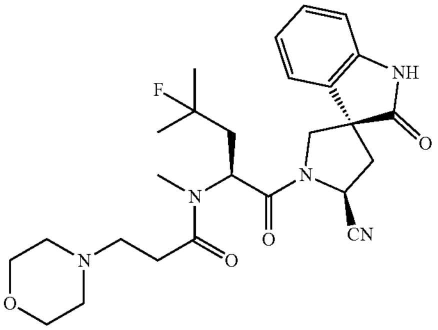 [SMILES: CN(C(=O)CCN1CCOCC1)[C@@H](CC(C)(C)F)C(=O)N1C[C@]2(C[C@H]1C#N)C(=O)Nc1ccccc12] | $[M + H]^+$ 500.400 | 1H NMR (400 MHz, DMSO-d6) δ 10.74 (s, 1H), 8.14 (s, 1H), 7.25 (td, J = 7.7, 1.3 Hz, 1H), 7.01 (td, J = 7.6, 1.0 Hz, 1H), 6.94-6.85 (m, 2H), 5.44 (dd, J = 7.4, 5.7 Hz, 1H), 5.17 (dd, J = 8.7, 7.4 Hz, 1H), 3.91 (d, J = 10.7 Hz, 1H), 3.74 (d, J = 10.7 Hz, 1H), 3.65 (d, J = 10.3 Hz, 1H), 3.62-3.51 (m, 4H), 3.35 (d, J = 19.4 Hz, 2H), 3.18 (d, J = 4.1 Hz, 1H), 2.89 (s, 3H), 2.62 (dd, J= 13.3, 8.8 Hz, 2H), 2.20 (ddd, J = 25.3, 14.9, 5.7 Hz, 2H), 2.02 (td, J = 15.4, 7.4 Hz, 1H), 1.30 (dd, J = 21.7, 12.1 Hz, 6H). |

-continued

| Example | Structure | MS | NMR |
|---|---|---|---|
| 538 | 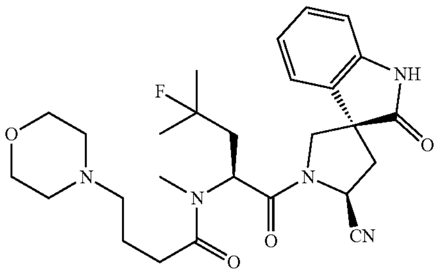 [SMILES: CN(C(=O)CCCN1CCOCC1)[C@@H](CC(C)(C)F)C(=O)N1C[C@]2(C[C@H]1C#N)C(=O)Nc1ccccc12] | [M + H]+ 514.448 | 1H NMR (400 MHz, Acetone-d6) δ 9.61 (s, 1H), 7.34-7.20 (m, 2H), 7.07-6.88 (m, 3H), 4.97-4.87 (m, 1H), 4.76 (dd, J = 9.7, 7.9 Hz, 1H), 4.23-4.15 (m, 1H), 3.94 (d, J = 9.9Hz, 1H), 3.71 (s, 3H), 3.06 (s, 2H), 2.56-2.30 (m, 3H), 2.13 (ddd, J = 19.5, 15.0, 7.0 Hz, 1H), 1.52 (dd, J = 21.6, 9.0 Hz, 1H), 1.42 (dd, J = 21.6, 7.0 Hz, 6H). |

Example 539

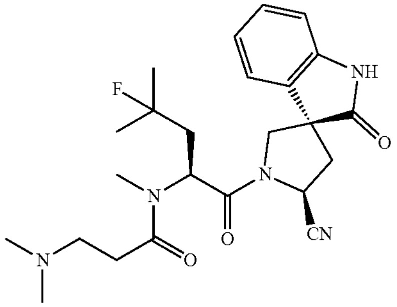

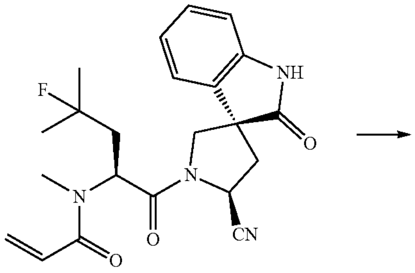

-continued

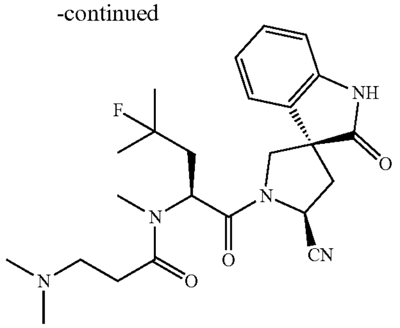

Triethylamine (47 uL, 7 eq.) was added to a solution of N—((S)-1-((3R,5'S)-5'-cyano-2-oxospiro[indoline-3,3'-pyrrolidin]-1'-yl)-4-fluoro-4-methyl-1-oxopentan-2-yl)-N-methylacrylamide (20 mg, 0.048 mmol) and dimethylamine hydrochloride (59 mg, 0.727 mmol) in MeOH (0.485 mL). When LCMS indicated product formation, the reaction mixture was subjected to preparative HPLC to afford N—((S)-1-((3R,5'S)-5'-cyano-2-oxospiro[indoline-3,3'-pyrrolidin]-1'-yl)-4-fluoro-4-methyl-1-oxopentan-2-yl)-3-(dimethylamino)-N-methylpropanamide (1.95 mg, 0.0043 mmol, 9% yield). 1H NMR (400 MHz, Acetone-d6) δ 7.32 (td, J=7.7, 1.2 Hz, 1H), 7.12 (td, J=7.5, 1.1 Hz, 1H), 7.04 (d, J=7.7 Hz, 1H), 6.97 (dt, J=7.4, 1.0 Hz, 1H), 5.68 (dd, J=7.2, 6.0 Hz, 1H), 5.19 (t, J=8.4 Hz, 1H), 4.28 (dd, J=10.8, 1.3 Hz, 1H), 3.86 (d, J=10.7 Hz, 1H), 3.01 (s, 3H), 2.79-2.62 (m, 3H), 2.62-2.44 (m, 2H), 2.44-2.24 (m, 4H), 2.16-2.10 (m, 1H), 1.37 (m, 6H). [M+H] m/z 458.488.

The following examples were prepared employing a similar protocol as described above.

| Example | Structure | MS | NMR |
|---|---|---|---|
| 540 | 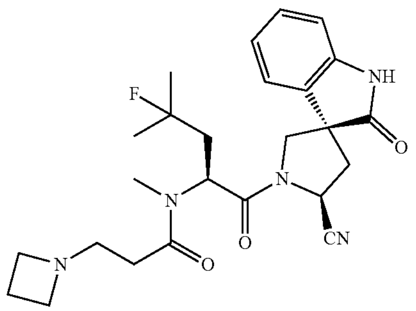 [SMILES: CN(C(=O)CCN1CCC1)[C@@H](CC(C)(C)F)C(=O)N1C[C@]2(C[C@H]1C#N)C(=O)Nc1ccccc12] | [M + H]+ 470.435 | 1H NMR (400 MHz, Acetone-d6) δ 7.32 (td, J = 7.7, 1.3 Hz, 1H), 7.11 (td, J = 7.6, 1.1 Hz, 1H), 7.05-6.94 (m, 2H), 5.65 (t, J = 6.6 Hz, 1H), 5.17 (t, J = 8.3 Hz, 1H), 4.24 (dd, J = 10.8, 1.3 Hz, 1H), 3.85 (d, J = 10.7 Hz, 1H), 3.77 (td, J = 7.7, 3.4 Hz, 4H), 2.97 (s, 4H), 2.79-2.69 (m, 2H), 2.65 (dd, J = 13.3, 7.8 Hz, 1H), 2.51 (ddd, J = 16.9, 8.4, 5.8 Hz, 1H), 2.42-2.34 (m, 1H), 2.33-2.23 (m, 3H), 1.34 (m, 6H). |

-continued

| Example | Structure | MS | NMR |
|---|---|---|---|
| 541 | 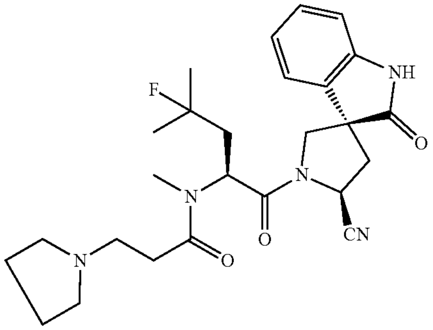 [SMILES: CN(C(=O)CCN1CCCC1)[C@@H](CC(C)(C)F)C(=O)N1C[C@]2(C[C@H]1C#N)C(=O)Nc1ccccc12] | [M + H]+ 484.437 | 1H NMR (400 MHz, Acetone-d6) δ 7.33 (td, J = 7.7, 1.2 Hz, 1H), 7.12 (td, J = 7.5, 1.1 Hz, 1H), 7.03 (d, J = 7.7 Hz, 1H), 6.99-6.92 (m, 1H), 5.65 (t, J = 6.5 Hz, 1H), 5.18 (t, J = 8.3 Hz, 1H), 4.26 (dd, J = 10.8, 1.3 Hz, 1H), 3.85 (d, J = 10.7 Hz, 1H), 3.07 (pd, J = 7.1, 6.0, 2.7 Hz, 5H), 2.99 (s, 3H), 2.82 -2.55 (m, 5H), 2.37-2.24 (m, 1H), 1.99-1.91 (m, 4H), 1.35 (m, 6H). |
| 542 | 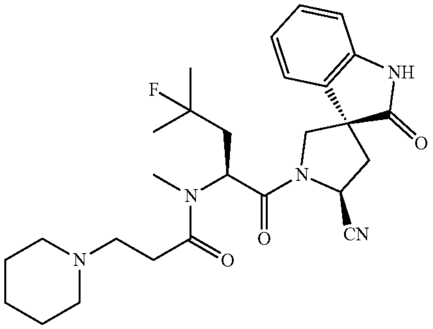 [SMILES: CN(C(=O)CCN1CCCCC1)[C@@H](CC(C)(C)F)C(=O)N1C[C@]2(C[C@H]1C#N)C(=O)Nc1ccccc12] | [M + H]+ 498.533 | 1H NMR (400 MHz, Acetone-d6) δ 7.32 (td, J = 7.7, 1.2 Hz, 1H), 7.12 (td, J = 7.5, 1.0 Hz, 1H), 7.06-6.94 (m, 2H), 5.67 (t, J = 6.6 Hz, 1H), 5.19 (t, J = 8.3 Hz, 1H), 4.29 (dd, J = 10.8, 1.3 Hz, 1H), 3.86 (d, J = 10.7 Hz, 1H), 3.01 (s, 3H), 2.87-2.57 (m, 7H), 2.57-2.21 (m, 3H), 1.69 (p, J = 5.7 Hz, 4H), 1.51 (p, J = 5.9, 5.5 Hz, 2H), 1.36 (m, 6H). |
| 543 | 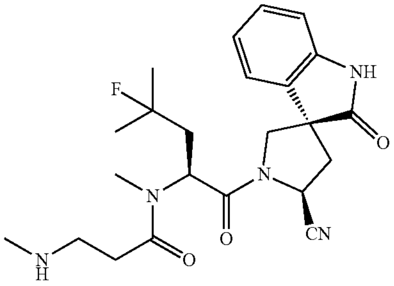 [SMILES: CNCCC(=O)N(C)[C@@H](CC(C)(C)F)C(=O)N1C[C@]2(C[C@H]1C#N)C(=O)Nc1ccccc12] | [M + H]+ 444.426 | 1H NMR (400 MHz, Acetone-d6) δ 7.32 (td, J = 7.7, 1.2Hz, 1H), 7.18-7.09 (m, 1H), 7.09-6.93 (m, 2H), 5.66 (t, J = 6.6 Hz, 1H), 5.20 (t, J = 8.3 Hz, 1H), 4.29 (dd, J = 10.6, 1.2 Hz, 1H), 3.88 (d, J = 10.7 Hz, 1H), 3.01 (s, 3H), 2.85-2.57 (m, 6H), 2.51 (s, 3H), 2.41-2.24 (m, 1H), 1.37 (m, 6H). |
| 544 | 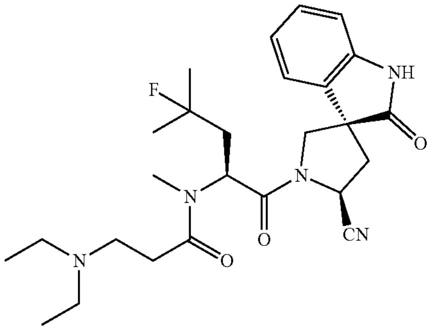 [SMILES: CCN(CC)CCC(=O)N(C)[C@@H](CC(C)(C)F)C(=O)N1C[C@]2(C[C@H]1C#N)C(=O)Nc1ccccc12] | [M + H]+ 486.516 | 1H NMR (400 MHz, Acetone-d6) δ 7.38-7.23 (m, 1H), 7.09 (t, J = 7.5 Hz, 1H), 7.01 (dd, J = 16.8, 7.6 Hz, 2H), 5.69 (t, J = 6.6 Hz, 1H), 5.17 (t, J = 8.3 Hz, 1H), 4.25 (d, J = 10.7 Hz, 1H), 3.88 (d, J = 10.8 Hz, 1H), 3.14 (m, 2H), 3.00 (s, 3H), 2.81-2.63 (m, 3H), 2.63-2.12 (m, 6H), 1.37 (m, 6H), 1.22-1.12 (m, 1H), 1.04 (dd, J = 6.7, 1.7 Hz, 9H). |

-continued

| Example | Structure | MS | NMR |
| --- | --- | --- | --- |
| 545 | 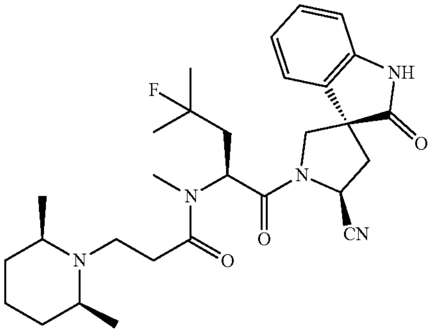 [SMILES: C[C@@H]1CCC[C@H](C)N1CCC(=O)N(C)[C@@H](CC(C)(C)F)C(=O)N1C[C@]2(C[C@H]1C#N)C(=O)Nc1ccccc12] | [M + H]+ 526.529 | 1H NMR (400 MHz, Acetone-d6) δ 7.30 (m, 1H), 7.14-7.06 (m, 1H), 7.06-6.94 (m, 2H), 5.68 (m, 1H), 5.18 (td, J = 8.4, 5.3 Hz, 1H), 4.25-4.17 (m, 1H), 3.89 (d, J = 10.9 Hz, 1H), 3.01 (s, 3H), 2.77-2.64 (m, 2H), 2.57 (m, 1H), 2.47-2.18 (m, 2H), 2.13 (m, 1H), 1.67 (m, 3H), 1.54-1.43 (m, 2H), 1.36 (m, 6H), 1.10 (m, 6H). |
| 546 | 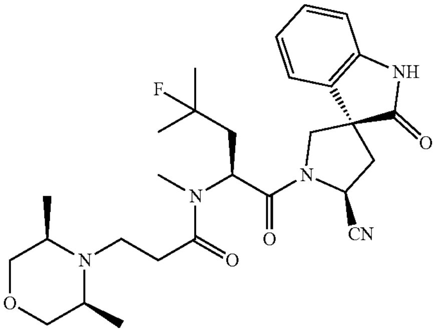 [SMILES: C[C@@H]1COC[C@H](C)N1CCC(=O)N(C)[C@@H](CC(C)(C)F)C(=O)N1C[C@]2(C[C@H]1C#N)C(=O)Nc1ccccc12] | [M + H]+ 528.682 | 1H NMR (400 MHz, Acetone-d6) δ 9.72 (s, 1H), 7.29 (td, J = 7.7, 1.3 Hz, 1H), 7.08 (td, J = 7.6, 1.1 Hz, 1H), 7.01 (d, J = 7.7 Hz, 1H), 6.95 (dd, J = 7.1, 1.0 Hz, 1H), 5.67 (dd, J = 7.3, 5.9 Hz, 1H), 5.16 (t, J = 8.5 Hz, 1H), 4.20 (dd, J = 10.8, 1.3 Hz, 1H), 3.86 (d, J = 10.8 Hz, 1H), 3.59-3.51 (m, 2H), 3.00 (s, 4H), 2.81-2.61 (m, 5H), 2.47 (ddt, J = 10.1, 6.5, 3.4 Hz, 1H), 2.40 (td, J = 6.4, 3.2 Hz, 1H), 2.34-2.21 (m, 2H), 2.15-2.07 (m, 1H), 1.99 (td, J = 10.3, 5.3 Hz, 1H), 1.38 (d, J = 8.3 Hz, 3H), 1.32 (d, J = 8.5 Hz, 3H), 0.80 (d, J = 6.3 Hz, 3H), 0.78 (d, J = 6.3 Hz, 3H). |
| 547 | 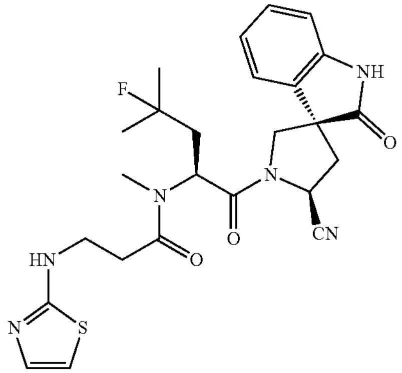 [SMILES: CN(C(=O)CCNc1nccs1)[C@@H](CC(C)(C)F)C(=O)N1C[C@]2(C[C@H]1C#N)C(=O)Nc1ccccc12] | [M + H]+ 513.489 | 1H NMR (400 MHz, DMSO-d6) δ 8.25 (s, 1H), 7.24 (td, J = 7.7, 1.3 Hz, 1H), 7.06-6.99 (m, 1H), 6.99-6.89 (m, 2H), 6.72 (d, J = 4.9 Hz, 1H), 6.11 (d, J = 4.9 Hz, 1H), 5.43 (dd, J = 7.3, 5.7 Hz, 1H), 5.16 (dd, J = 8.8, 7.0 Hz, 1H), 3.88 (d, J = 10.7 Hz, 2H), 3.76 (d, J = 10.7 Hz, 2H), 3.69 (dt, J = 13.9, 6.9 Hz, 2H), 3.62-3.53 (m, 2H), 2.88 (s, 3H), 2.71-2.58 (m, 2H), 2.38-2.11 (m, 2H), 2.11-1.95 (m, 1H), 1.28 (dd, J = 21.7, 9.4 Hz, 6H). |

Example 548

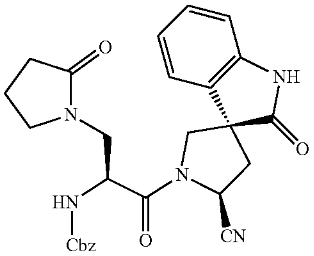

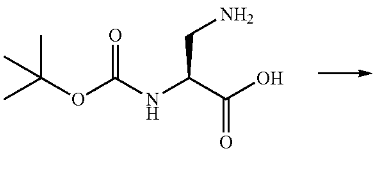

-continued

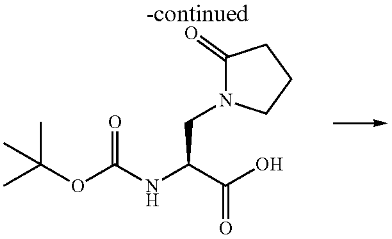

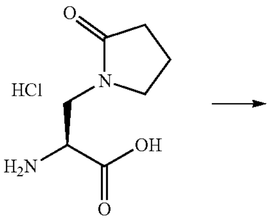

-continued

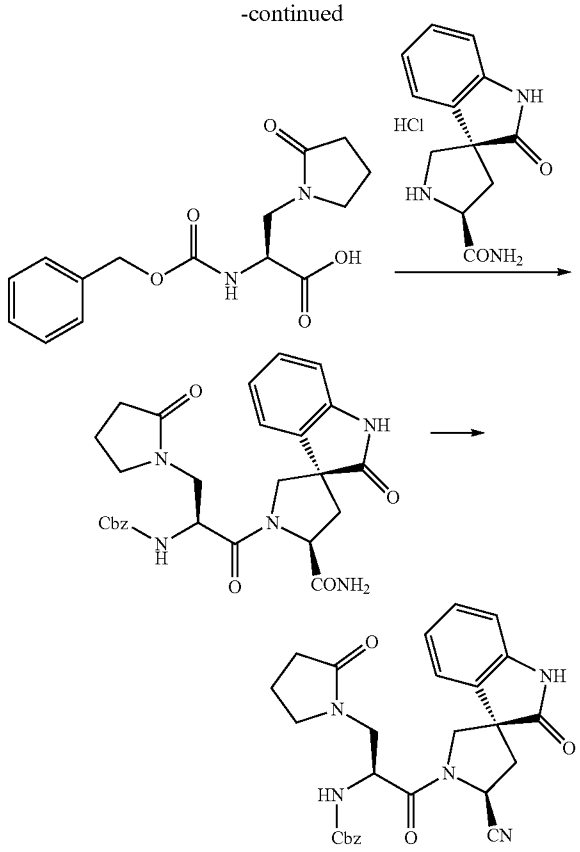

Step 1

Boc DAP OH (2 g, 9.79 mmol) was suspended in a mixture of THF (70.0 ml) and iPr2EtN (3.42 ml, 19.59 mmol), then cooled to 0° C. 4-chlorobutanoyl chloride (1.096 ml, 9.79 mmol) was then added at dropwise (10:25 am). After stirring at rt for 40 min, the reaction mixture was cooled to 0° C. KOtBu (4.40 g, 39.2 mmol) was then added in portions starting at 11:15 over 2 min. After 10 min, the reaction was titrated to pH 1 with 1 N HCl, then extracted with EtOAc. The organic phase was washed with brine, dried over magnesium sulfate, filtered, and concentrated. The residue was subjected to silica chromatography, eluting with 30-100% EtOAc in cyclohexane, to afford (S)-2-((tert-butoxycarbonyl)amino)-3-(2-oxopyrrolidin-1-yl)propanoic acid (1.42 g, 2.87 mmol, 29% yield). 1H NMR (400 MHz, DMSO-$d_6$) δ 12.73 (s, 1H), 7.09 (d, J=8.5 Hz, 1H), 4.15 (td, J=8.5, 5.4 Hz, 1H), 3.59 (dd, J=13.7, 5.4 Hz, 1H), 3.40-3.28 (m, 4H), 2.24-2.11 (m, 2H), 1.91-1.80 (m, 2H), 1.37 (s, 9H). [M+Na] m/z 295.326.

Step 2

(S)-2-((tert-butoxycarbonyl)amino)-3-(2-oxopyrrolidin-1-yl)propanoic acid (389 mg, 1.43 mmol) was added to a stirred solution of 4 N HCl in dioxane (4.3 mL, 12 eq. HCl) at rt. After 30 min at rt, the resulting white suspension was concentrated directly to afford (S)-2-amino-3-(2-oxopyrrolidin-1-yl)propanoic acid hydrochloride (408 mg, crude). The crude white solid was used without further purification. 1H NMR (400 MHz, Deuterium Oxide) δ 4.17 (dd, J=6.4, 4.2 Hz, 1H), 3.89 (dd, J=15.1, 4.2 Hz, 1H), 3.79 (d, J=6.4 Hz, 1H), 3.54 (td, J=7.3, 1.6 Hz, 2H), 2.45 (dd, J=9.1, 7.6 Hz, 2H), 2.08 (qd, J=8.2, 6.9 Hz, 2H).

Step 3

(S)-2-amino-3-(2-oxopyrrolidin-1-yl)propanoic acid hydrochloride (20 mg, crude) was dissolved in a mixture of THF (0.48 mL) and water (0.48 mL), then solid NaHCO3 (40 mg, 0.48 mmol) was added. The mixture was cooled to 0° C., then CbzCl (15 uL, 0.105 mmol) was added. The mixture was stirred for 3 d at rt, then partitioned between EtOAc and 1 N HCl. The organic phase was washed with brine, dried over magnesium sulfate, filtered, and concentrated to afford crude (S)-2-(((benzyloxy)carbonyl)amino)-3-(2-oxopyrrolidin-1-yl)propanoic acid, which was used without further purification (assumed 100% yield). [M+H] m/z 307.322.

Step 4

HATU (35 mg, 0.092 mmol) and iPr2NEt (74 uL, 0.424 mmol) were sequentially added to a stirred mixture of compound 1-4 (29.5 mg, 0.11 mmol) and (S)-2-(((benzyloxy)carbonyl)amino)-3-(2-oxopyrrolidin-1-yl)propanoic acid (crude, assumed 0.085 mmol) in DMF (0.42 mL) at −10° C. The mixture was then warmed to rt. The reaction was partitioned between EtOAc and water, then the organic phase was washed sequentially with sat. aq. $NaHCO_3$ and brine, then dried over magnesium sulfate, filtered, and concentrated. The crude residue (assumed 100% yield) was used without further purification. [M+H] m/z 520.468.

Step 5

Burgess reagent (122 mg, 0.51 mmol) was added to a stirred mixture of benzyl ((S)-1-((3R,5'S)-5'-carbamoyl-2-oxospiro[indoline-3,3'-pyrrolidin]-1'-yl)-1-oxo-3-(2-oxopyrrolidin-1-yl)propan-2-yl)carbamate (assumed 0.085 mmol) at rt. After 45 min, MeOH was added and the mixture was subjected to preparative HPLC purification to afford benzyl ((S)-1-((3R,5'S)-5'-cyano-2-oxospiro[indoline-3,3'-pyrrolidin]-1'-yl)-1-oxo-3-(2-oxopyrrolidin-1-yl)propan-2-yl)carbamate (1.28 mg). 1H NMR (400 MHz, Acetone-d6) δ 9.69 (s, 1H), 7.37-7.29 (m, 5H), 7.26 (td, J=7.7, 1.2 Hz, 1H), 7.18 (d, J=7.4 Hz, 1H), 7.00 (t, J=7.8 Hz, 2H), 6.82 (d, J=8.1 Hz, 1H), 5.16 (dd, J=8.7, 7.0 Hz, 1H), 5.03 (d, J=12.6 Hz, 1H), 4.95 (d, J=12.6 Hz, 1H), 4.77 (td, J=7.9, 4.9 Hz, 1H), 4.16 (q, J=10.6 Hz, 2H), 3.68 (dd, J=14.1, 7.8 Hz, 1H), 3.60-3.40 (m, 4H), 2.78 (dd, J=13.4, 8.8 Hz, 1H), 2.66 (dd, J=13.3, 7.1 Hz, 1H), 2.20 (td, J=8.2, 2.1 Hz, 2H), 2.09-2.00 (m, 4H), 2.00-1.87 (m, 2H). [M+H] m/z 502.481.

Example 549

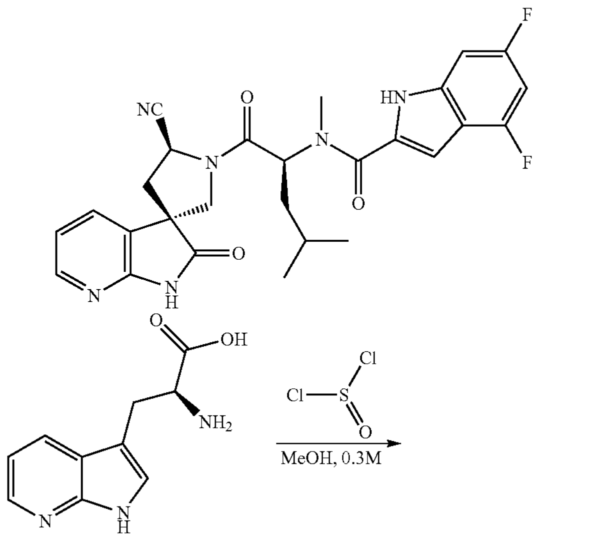

L-7-aza-tryptophan

-continued

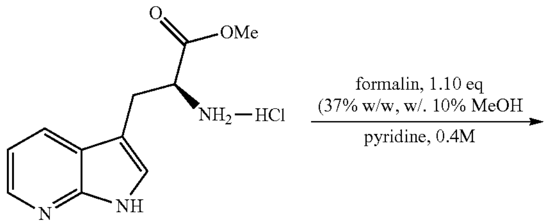

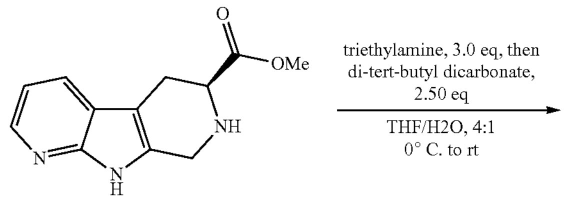

549-1

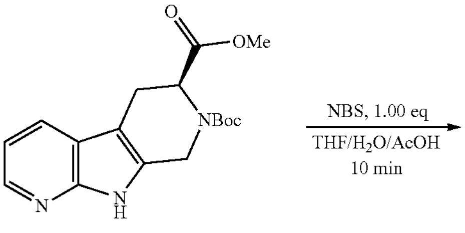

549-2

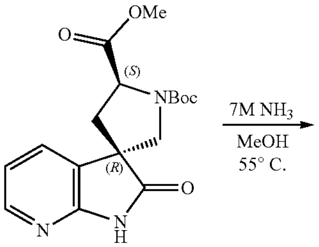

549-3

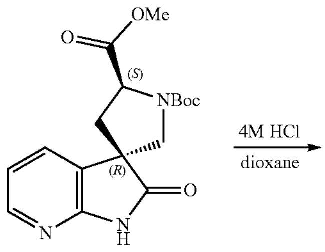

549-4

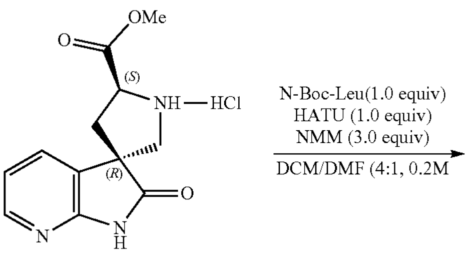

549-5

-continued

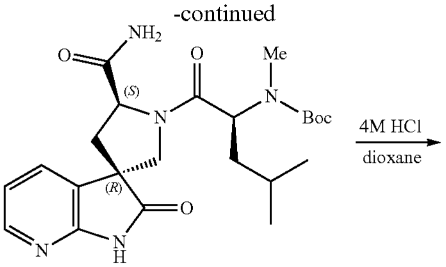

549-6

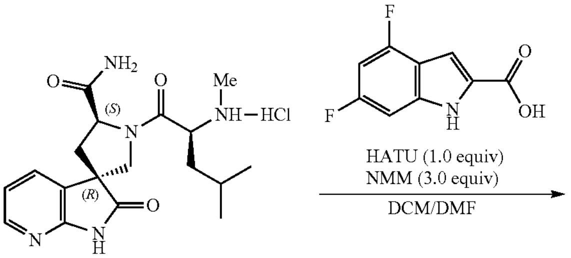

549-7

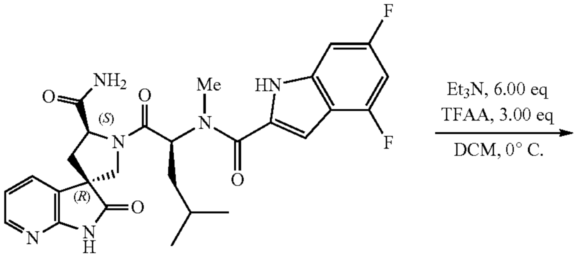

549-8

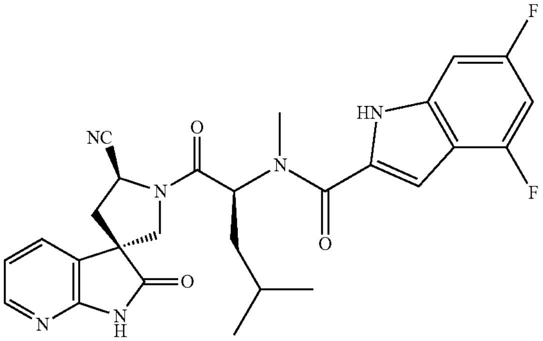

Example 549

Step 1

A 500-mL round bottom flask was charged with (S)-2-amino-3-(1H-pyrrolo[2,3-b]pyridin-3-yl)propanoic acid (3 g, 14.62 mmol) and a magnetic stir bar. Methanol (50 mL) was added, producing a white suspension. The flask was blown out with $N_2$, sealed with a rubber septum, and cooled to 0° C. Thionyl chloride (3.20 ml, 43.9 mmol) was added slowly against positive $N_2$ pressure as the flask was swirled in an ice bath. The resulting pale yellow solution was stirred 10 min as it warmed to near r.t., then heated to reflux for 2 h. Evaporation of the reaction solution yielded a white solid which was taken without further purification Step 2

To a 500-mL round bottom flask containing the crude 7-aza-tryptophan methyl ester was added a magnetic stir bar followed by pyridine (37 mL); a white gas evolved and a mild exotherm was noted. The mixture was then sonicated to provide a pale gold solution. Formaldehyde (1.197 ml, 37% w/w aq. solution containing 10% methanol, 16.08 mmol, 1.10 eq) was then added. The reaction vessel was equipped with a condense, heated to reflux and stirred 1 h, at which time the reaction was judged to be complete by LCMS. The reaction vessel was placed in an ice bath for 20 min, affording a thick, off-white slurry. This slurry was then filtered through a fritted funnel and the filter cake washed with pre-chilled pyridine (2×20 mL) followed by DCM (10 mL). The solids were then dried under a stream of nitrogen overnight, affording the beta-carboline 549-1 as a white solid that was taken on without further purification Step 3

A 250-mL round bottom flask containing crude beta-carboline 549-1 (3.38 g, 14.62 mmol) and a magnetic stir bar was charged with water (7.5 mL) and THF (30 mL), giving a cloudy solution. The reaction vessel was then cooled to 0° C. and triethylamine (6.11 ml, 43.9 mmol) was added, followed by di-tert-butyl dicarbonate (8.49 ml, 36.6 mmol). The reaction vessel was blown out with nitrogen and placed under positive nitrogen pressure. After stirring for 2 days, the reaction mixture was partitioned between EtOAc and water and the layers separated. The aqueous phase was then extracted with EtOAc (3×20 mL), and the combined organics dried over $Na_2SO_4$, filtered, and concentrated to give a yellow-tinted residue. Purification by flash chromatography on silica gel eluting with ethyl acetate in cyclohexane gave 549-2 as a colorless residue (1.61 g, 33% over three steps). $^1$H NMR (400 MHz, DMSO-$d_6$), mixture of rotamers: δ 11.40 (app. d, J=24.6 Hz, 1H), 8.13 (dd, J=4.8, 1.5 Hz, 1H), 7.85 (dd, J=7.8, 1.6 Hz, 1H), 7.02 (dd, J=7.8, 4.7 Hz, 1H), 5.31-5.13 (m, 1H), 4.75 (t, J=16.9 Hz, 1H), 4.49-4.27 (m, 1H), 3.57 (d, J=8.0 Hz, 3H), 3.27 (m, 1H), 3.00 (dd, J=15.5, 7.1 Hz, 1H), 1.46 (app. d, J=17.6 Hz, 9H).

Step 4

Compound 549-2 (1.60 g, 4.83 mmol) was added dissolved in THF (22.80 ml) and charged to a 1000-mL round bottom flask containing a magnetic stir bar. Water (2.85 ml) was added, and the resulting colorless, magnetically-stirred solution was then cooled to 0° C. N-bromosuccinimide (0.859 g, 4.83 mmol) was added portionwise over a few minutes, giving a yellow solution. The flask was then capped with a rubber septum and glacial acetic acid (1.935 ml, 33.8 mmol) was added. The color of the reaction deepened significantly to a rich orange-tinted yellow and stirring continued 30 min. Potassium carbonate (3.34 g, 24.14 mmol) and water were then added and the reaction mixture allowed to come to r.t. Layers were separated and the aqueous phase extracted with EtOAc. The combined organics were dried over $Na_2SO_4$, decanted, and concentrated under reduced pressure to give a tan-colored gum or foam. Purification by flash chromatography on silica gel eluting with ethyl acetate in cyclohexane afforded pure product 549-3 as a single diastereomer (220 mgs), as well as impure product obtained as a mixture of diastereomers (1.44 g, d.r. ~3:1 desired/undesired).

Step 5

To a 100-mL rbf containing 549-3 (220 mg, 0.633 mmol) and a magnetic stir bar was added methanolic ammonia (4.52 mL of a 7 M solution, 31.7 mmol). The flask was sealed with a plastic septum pierced with a needle, and the yellow reaction solution heated to 55° C. and stirred 6 days. The reaction mixture was then evaporated to reveal a tan solid 549-4.

Step 6

The crude amide 549-4 was suspended in a solution of HCl in dioxane (3 mL of a 4.0 M solution, 12 mmol). The suspension was stirred vigorously at r.t. overnight, then evaporated to reveal the amine hydrochloride 549-5 as an off-white solid (95 mg, 49% over three steps). $^1$H NMR (400 MHz, deuterium oxide) δ 8.19 (dd, J=5.7, 1.4 Hz, 1H), 8.01 (ddd, J=7.5, 1.5, 0.6 Hz, 1H), 7.30 (dd, J=7.7, 5.9 Hz, 1H), 4.94 (t, J=8.5 Hz, 1H), 3.94 (t, J=13.2 Hz, 1H), 3.81 (d, J=12.9 Hz, 1H), 2.92 (dd, J=14.1, 9.1 Hz, 1H), 2.73 (dd, J=14.1, 7.9 Hz, 1H).

Step 7

Compound 549-5 (181 mg, 0.593 mmol), N-(tert-butoxycarbonyl)-N-methyl-L-leucine (198 mg, 0.807 mmol), and a magnetic stir bar were combined in a 40-mL glass reaction vial. DCM (3 ml) and DMF (0.750 ml) were added, giving a white suspension. The mixture was cooled to 0° C.; N-methylmorpholine (0.261 ml, 2.373 mmol) was added followed by HATU (226 mg, 0.593 mmol). The vessel was blown out with nitrogen and the reaction mixture allowed to warm to r.t, stirring overnight. The reaction mixture was then evaporated onto Celite and the crude mixture purified by flash chromatography on silica gel (4 g) eluting with DCM/MeOH and affording a product of intermediate purity which was subsequently purified by reverse-phase HPLC to reveal the product 549-6 as a colorless solid.

Step 8

The above obtained 549-6 was charged to a glass scintillation containing a magnetic stir bar and treated with HCl in dioxane (2 mL of a 4.0 M solution, 8.00 mmol). The resulting heterogenous suspension was stirred 11 h; volatiles were then removed under reduced pressure, affording a white solid 549-7.

Step 9

Compound 549-7 obtained above was dissolved in DCM (0.8 ml) and DMF (0.200 ml), giving a white suspension. N-methylmorpholine (0.0717 ml, 0.652 mmol) was added; the mixture clarified immediately, giving a odorless solution. HATU (62.0 mg, 0.163 mmol) was added under a stream of nitrogen, followed by 4,6-difluoro-1H-indole-2-carboxylic acid (32.1 mg, 0.163 mmol). The vial was blown out again with nitrogen, capped, and the reaction mixture allowed to stir 3 h, at which time the reaction was quenched by partitioning between quarter-saturated aqueous $NaHCO_3$ and EtOAc. The layers were separated and the aqueous phase extracted with EtOAc (3×10 mL); the combined organics were then dried over sodium sulfate, filtered and concentrated under reduced pressure to reveal an off-white residue 549-8.

Step 10

To a 40-mL glass reaction vial containing crude amide product 549-8 and a magnetic stir bar was added DCM (1.25 ml). The vial was blown out with nitrogen, cooled to 0° C. and charged with triethylamine (0.1555 ml, 1.116 mmol). Trifluoroacetic anhydride (0.0787 ml, 0.557 mmol) was then added dropwise, giving a yellow-tinted reaction mixture that was allowed to warm to r.t. and stir for 1.25 h, at which time LCMS indicated consumption of starting material. The reaction was quenched with sat. aq. $NaHCO_3$; the layers were then separated and the organics dried with brine, then concentrated under reduced pressure to reveal a yellow gum. The crude product was purified by reverse-phase HPLC, giving a colorless film that was lyophilized to afford Example 549 as a free-flowing white powder (34 mgs, 11% yield over four steps). $^1$H NMR (400 MHz, Acetone-$d_6$) δ 10.87 (s, 1H), 10.26 (s, 1H), 7.93 (s, 1H), 7.36 (d, J=7.3 Hz, 1H), 7.12-7.00 (m, 2H), 6.81-6.67 (m, 2H), 5.55 (dd, J=9.7, 5.4 Hz, 1H), 5.21 (t, J=8.3 Hz, 1H), 4.43 (d, J=10.8 Hz, 1H), 4.03 (d, J=10.8 Hz, 1H), 3.47 (s, 3H), 2.83 (ddd, J=13.4, 8.6, 1.2 Hz, 1H), 2.72 (dd, J=13.4, 8.0 Hz, 1H), 1.96 (ddd, J=14.4, 9.7, 4.9 Hz, 1H), 1.76 (ddd, J=14.2, 8.8, 5.4 Hz, 1H), 1.62 (dtd, J=8.9, 6.6, 4.9 Hz, 1H), 1.00 (d, J=6.7 Hz, 3H), 0.94 (d, J=6.5 Hz, 3H). LCMS $[M+H]^+$ 521.0.

The following examples were prepared employing a similar protocol as described above.

| Example | Structure | MS | NMR |
|---|---|---|---|
| 550 | 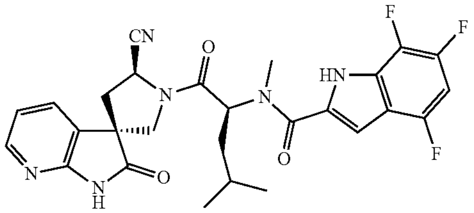 [SMILES: CC(C)C[C@@H](C(=O)N1C[C@]2(C[C@H]1C#N)C(=O)Nc1ncccc12)N(C)C(=O)c1cc2c(F)cc(F)c(F)c2[nH]1] | $[M + H]^+$ 538.9 | $^1$H NMR (400 MHz, Acetone-$d_6$) δ 11.28 (s, 1H), 10.38 (s, 1H), 8.03-7.84 (m, 1H), 7.49-7.32 (m, 1H), 7.06 (s, 1H), 6.98-6.86 (m, 1H), 6.80 (t, J = 6.4 Hz, 1H), 5.54 (dd, J = 9.7, 5.4 Hz, 1H), 5.22 (t, J = 8.3 Hz, 1H), 4.41 (d, J = 10.8 Hz, 1H), 4.05 (d, J = 10.8 Hz, 1H), 3.46 (s, 3H), 2.84 (ddd, J = 13.4, 8.5, 1.2 Hz, 1H), 2.72 (dd, J = 13.4, 8.0 Hz, 1H), 1.96 (ddd, J = 14.3, 9.9, 4.9 Hz, 1H), 1.78 (ddd, J = 14.2, 8.9, 5.4 Hz, 1H), 1.72-1.58 (m, 1H), 1.01 (d, J = 6.6 Hz, 3H), 0.95 (d, J = 8.5 Hz, 3H). |
| 551 | 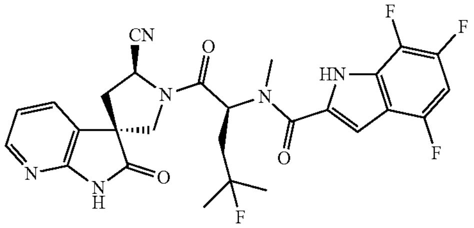 [SMILES: CN(C(=O)c1cc2c(F)cc(F)c(F)c2[nH]1)[C@@H](CC(C)(C)F)C(=O)N1C[C@]2(C[C@H]1C#N)C(=O)Nc1ncccc12] | $[M + H]^+$ 556.9 | $^1$H NMR (400 MHz, Acetone-d6), mixture of rotamers: δ 11.12 (s, 1H), 10.07 (s, 1H), 7.78 (d, J = 5.2 Hz, 1H), 7.27-7.17 (m, 1H), 6.92-6.87 (m, 1H), 6.80 (tdd, J = 9.5, 5.2, 2.4 Hz, 1H), 6.60 (t, J = 6.2 Hz, 1H), 5.66 (t, J = 6.6 Hz, 1H), 5.10 (t, J = 8.2 Hz, 1H), 4.29 (d, J = 11.0 Hz, 1H), 3.91 (d, J = 10.9 Hz, 1H), 3.33 (s, 3H), 2.60 (app. dd, J = 13.4, 7.9 Hz, 1H), 2.51-2.15 (m, 2H), 1.37-1.30 (m, 3H), 1.30-1.24 (m, 3H). |
| 552 | 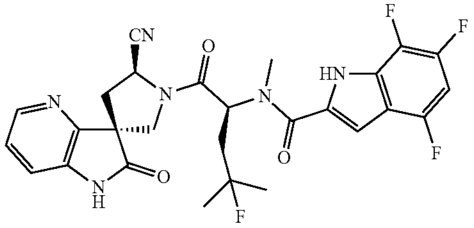 [SMILES: CN(C(=O)c1cc2c(F)cc(F)c(F)c2[nH]1)[C@@H](CC(C)(C)F)C(=O)N1C[C@]2(C[C@H]1C#N)C(=O)Nc1cccnc12] | $[M + H]^+$ 556.9 | $^1$H NMR (400 MHz, Acetone-$d_6$) δ 11.07 (s, 1H), 9.79 (s, 1H), 7.91 (d, J = 5.1 Hz, 1H), 7.21 (dd, 8.0, 1.4 Hz, 1H), 6.97-6.82 (m, 2H), 6.78 (d, J = 2.8 Hz, 1H), 5.79 (t, J = 6.5 Hz, 1H), 5.21 (t, J = 8.6 Hz, 1H), 4.39 (d, J = 10.9 Hz, 1H), 3.93 (d, 10.9 Hz, 1H), 3.84-3.58 (m, 1H), 3.37 (s, 3H), 2.66 (app. dd, J = 13.0, 9.1 Hz, 1H), 2.55-2.39 (m, 1H), 2.30-2.18 (m, 1H), 1.45 (d, J = 6.7 Hz, 3H), 1.40 (d, J = 7.0 Hz, 3H). |

Biological Activity

SARS-CoV-2 3C-Like (3CL) Protease Fluorescence Assay (FRET):

Recombinant SARS-CoV-2 3CL-protease was expressed and purified. TAMRA-SITSAVLQSGFRKMK-Dabcyl-OH peptide 3CLpro substrate was synthesized. Black, low volume, round-bottom, 384 well microplates were used. In a typical assay, 0.85 μL of test compound was dissolved in DMSO then incubated with SARS-CoV-2 3CL-protease (10 nM) in 10 μL assay buffer (50 mM HEPES [pH 7.5], 1 mM DTT, 0.01% BSA, 0.01% Triton-X 100) for 30 min at RT. Next, 10 μL of 3CL-protease substrate (40 μM) in assay buffer was added and the assays were monitored continuously for 1 h in an Envision multimode plate reader operating in fluorescence kinetics mode with excitation at 540 nm and emission at 580 nm at RT. No compound (DMSO only) and no enzyme controls were routinely included in each plate. All experiments were run in duplicate. Data Analysis: SARS-CoV-2 3CL-protease enzyme activity was measured as initial velocity of the linear phase (RFU/s) and normalized to controlled samples DMSO (100% activity) and no enzyme (0% activity) to determine percent residual activity at various concentrations of test compounds (0-10 μM). Data were fitted to normalized activity (variable slope) versus concentration fit in GraphPad Prism 7 to determine $IC_{50}$. All experiments were run in duplicate, and $IC_{50}$ ranges are reported as follows: A<0.1 μM; B 0.1-1 μM; C >1 μM.

TABLE 1

Summary of Activities

| Compound | FRET $IC_{50}$ | Compound | FRET $IC_{50}$ |
|---|---|---|---|
| 1 | B | 2 | A |
| 3 | C | 4 | A |
| 5 | A | 6 | C |
| 7 | A | 8 | A |
| 9 | B | 10 | B |
| 11 | A | 12 | C |
| 13 | A | 14 | B |
| 15 | A | 16 | B |
| 17 | A | 18 | C |
| 19 | A | 20 | A |
| 21 | A | 22 | B |
| 23 | A | 24 | B |
| 25 | A | 26 | B |
| 27 | A | 28 | A |
| 29 | A | 30 | A |
| 31 | B | 32 | A |
| 33 | A | 34 | C |
| 35 | C | 36 | B |
| 37 | B | 38 | C |
| 39 | A | 40 | A |
| 41 | A | 42 | A |
| 43 | B | 44 | A |
| 45 | A | 46 | A |
| 47 | A | 48 | B |
| 49 | A | 50 | A |
| 51 | A | 52 | A |
| 53 | A | 54 | A |

TABLE 1-continued

Summary of Activities

| Compound | FRET $IC_{50}$ | Compound | FRET $IC_{50}$ |
|---|---|---|---|
| 55 | A | 56 | A |
| 57 | A | 58 | A |
| 59 | A | 60 | A |
| 61 | A | 62 | A |
| 63 | A | 64 | A |
| 65 | A | 66 | A |
| 67 | A | 68 | A |
| 69 | A | 70 | A |
| 71 | A | 72 | A |
| 73 | A | 74 | A |
| 75 | A | 76 | A |
| 77 | B | 78 | A |
| 79 | A | 80 | A |
| 81 | A | 82 | A |
| 83 | A | 84 | A |
| 85 | A | 86 | A |
| 87 | A | 88 | A |
| 89 | A | 90 | A |
| 91 | A | 92 | A |
| 93 | A | 94 | A |
| 95 | A | 96 | A |
| 97 | A | 98 | A |
| 99 | A | 100 | A |
| 101 | A | 102 | A |
| 103 | A | 104 | A |
| 105 | A | 106 | A |
| 107 | A | 108 | A |
| 109 | A | 110 | A |
| 111 | A | 112 | A |
| 113 | A | 114 | A |
| 115 | A | 116 | A |
| 117 | — | 118 | — |
| 119 | A | 120 | B |
| 121 | A | 122 | A |
| 123 | A | 124 | A |
| 125 | A | 126 | A |
| 127 | A | 128 | C |
| 129 | C | 130 | B |
| 131 | A | 132 | A |
| 133 | A | 134 | B |
| 135 | A | 136 | A |
| 137 | A | 138 | A |
| 139 | A | 140 | B |
| 141 | A | 142 | B |
| 143 | A | 144 | A |
| 145 | A | 146 | A |
| 147 | A | 148 | A |
| 149 | A | 150 | A |
| 151 | C | 152 | A |
| 153 | A | 154 | A |
| 155 | C | 156 | C |
| 157 | C | 158 | C |
| 159 | C | 160 | C |
| 161 | C | 162 | A |
| 163 | B | 164 | A |
| 165 | B | 166 | A |
| 167 | A | 168 | A |
| 169 | A | 170 | A |
| 171 | A | 172 | A |
| 173 | A | 174 | A |
| 175 | A | 176 | A |
| 177 | A | 178 | A |
| 179 | A | 180 | A |
| 181 | A | 182 | A |
| 183 | B | 184 | A |
| 185 | A | 186 | A |
| 187 | A | 188 | A |
| 189 | B | 190 | B |
| 191 | A | 192 | B |
| 193 | B | 194 | B |
| 195 | A | 196 | A |
| 197 | B | 198 | B |
| 199 | B | 200 | A |
| 201 | B | 202 | B |
| 203 | A | 204 | B |

TABLE 1-continued

Summary of Activities

| Compound | FRET $IC_{50}$ | Compound | FRET $IC_{50}$ |
|---|---|---|---|
| 205 | A | 206 | B |
| 207 | A | 208 | A |
| 209 | A | 210 | A |
| 211 | B | 212 | A |
| 213 | A | 214 | A |
| 215 | A | 216 | A |
| 217 | B | 218 | B |
| 219 | B | 220 | A |
| 221 | A | 222 | B |
| 223 | B | 224 | A |
| 225 | C | 226 | A |
| 227 | A | 228 | A |
| 229 | A | 230 | B |
| 231 | B | 232 | B |
| 233 | B | 234 | A |
| 235 | A | 236 | B |
| 237 | A | 238 | A |
| 239 | B | 240 | A |
| 241 | A | 242 | A |
| 243 | B | 244 | B |
| 245 | A | 246 | B |
| 247 | B | 248 | B |
| 249 | A | 250 | A |
| 251 | B | 252 | A |
| 253 | A | 254 | A |
| 255 | A | 256 | A |
| 257 | B | 258 | B |
| 259 | B | 260 | B |
| 261 | B | 262 | B |
| 263 | B | 264 | B |
| 265 | B | 266 | B |
| 267 | A | 268 | B |
| 269 | A | 270 | A |
| 271 | B | 272 | B |
| 273 | B | 274 | A |
| 275 | A | 276 | A |
| 277 | B | 278 | A |
| 279 | B | 280 | A |
| 281 | A | 282 | B |
| 283 | A | 284 | A |
| 285 | B | 286 | A |
| 287 | A | 288 | B |
| 289 | A | 290 | B |
| 291 | A | 292 | A |
| 293 | A | 294 | A |
| 295 | A | 296 | B |
| 297 | B | 298 | B |
| 299 | A | 300 | B |
| 301 | A | 302 | B |
| 303 | A | 304 | A |
| 305 | A | 306 | A |
| 307 | B | 308 | A |
| 309 | A | 310 | A |
| 311 | B | 312 | A |
| 313 | B | 314 | B |
| 315 | A | 316 | A |
| 317 | A | 318 | A |
| 319 | A | 320 | A |
| 321 | A | 322 | A |
| 323 | A | 324 | B |
| 325 | A | 326 | A |
| 327 | A | 328 | A |
| 329 | A | 330 | A |
| 331 | A | 332 | A |
| 333 | A | 334 | A |
| 335 | B | 336 | A |
| 337 | A | 338 | A |
| 339 | B | 340 | B |
| 341 | B | 342 | A |
| 343 | A | 344 | B |
| 345 | A | 346 | A |
| 347 | A | 348 | A |
| 349 | A | 350 | A |
| 351 | A | 352 | A |
| 353 | A | 354 | A |

TABLE 1-continued

| Summary of Activities | | | |
|---|---|---|---|
| Compound | FRET $IC_{50}$ | Compound | FRET $IC_{50}$ |
| 355 | A | 356 | A |
| 357 | A | 358 | A |
| 359 | A | 360 | A |
| 361 | A | 362 | A |
| 363 | A | 364 | A |
| 365 | A | 366 | A |
| 367 | A | 368 | A |
| 369 | A | 370 | A |
| 371 | A | 372 | A |
| 373 | A | 374 | B |
| 375 | A | 376 | A |
| 377 | A | 378 | A |
| 379 | A | 380 | A |
| 381 | A | 382 | A |
| 383 | A | 384 | A |
| 385 | B | 386 | A |
| 387 | C | 388 | A |
| 389 | A | 390 | A |
| 391 | A | 392 | A |
| 393 | A | 394 | A |
| 395 | A | 396 | A |
| 397 | A | 398 | A |
| 399 | A | 400 | A |
| 401 | A | 402 | A |
| 403 | A | 404 | A |
| 405 | A | 406 | A |
| 407 | A | 408 | A |
| 409 | A | 410 | A |
| 411 | A | 412 | A |
| 413 | A | 414 | A |
| 415 | A | 416 | A |
| 417 | A | 418 | A |
| 419 | A | 420 | A |
| 421 | A | 422 | A |
| 423 | A | 424 | A |
| 425 | A | 426 | A |
| 427 | A | 428 | A |
| 429 | C | 430 | C |
| 431 | C | 432 | C |
| 433 | A | 434 | B |
| 435 | B | 436 | B |
| 437 | B | 438 | B |
| 439 | B | 440 | A |
| 441 | B | 442 | A |
| 443 | B | 444 | B |
| 445 | B | 446 | B |
| 447 | A | 448 | A |
| 449 | B | 450 | A |
| 451 | A | 452 | A |
| 453 | A | 454 | A |
| 455 | A | 456 | A |
| 457 | A | 458 | A |
| 459 | A | 460 | A |
| 461 | A | 462 | A |
| 463 | A | 464 | A |
| 465 | A | 466 | A |
| 467 | A | 468 | A |
| 469 | A | 470 | A |
| 471 | A | 472 | A |
| 473 | A | 474 | A |
| 475 | A | 476 | A |
| 477 | A | 478 | A |
| 479 | A | 480 | A |
| 481 | A | 482 | A |
| 483 | A | 484 | A |
| 485 | B | 486 | A |
| 487 | A | 488 | A |
| 489 | A | 490 | A |
| 491 | A | 492 | A |
| 493 | A | 494 | A |
| 495 | A | 496 | C |
| 497 | C | 498 | A |
| 499 | A | 500 | A |
| 501 | A | 502 | A |
| 503 | A | 504 | A |

TABLE 1-continued

| Summary of Activities | | | |
|---|---|---|---|
| Compound | FRET $IC_{50}$ | Compound | FRET $IC_{50}$ |
| 505 | A | 506 | A |
| 507 | A | 508 | A |
| 509 | A | 510 | A |
| 511 | A | 512 | A |
| 513 | A | 514 | A |
| 515 | A | 516 | A |
| 517 | A | 518 | A |
| 519 | A | 520 | A |
| 521 | A | 522 | B |
| 523 | A | 524 | A |
| 525 | A | 526 | A |
| 527 | A | 528 | B |
| 529 | B | 530 | A |
| 531 | A | 532 | A |
| 533 | A | 534 | A |
| 535 | B | 536 | B |
| 537 | A | 538 | C |
| 539 | A | 540 | A |
| 541 | A | 542 | A |
| 543 | A | 544 | A |
| 545 | A | 546 | A |
| 547 | A | 548 | B |
| 549 | A | 550 | A |
| 551 | A | 552 | A |

229E Assay Protocol

Viral Stock Preparation:

MRC-5 cells, (a diploid cell culture line composed of fibroblasts, originally developed from the lung tissue of a 14-week-old aborted Caucasian male fetus), were used for the culturing of 229E human corona virus (hCoV). Flasks were inoculated with hCoV-229E and viral stocks were collected once cytopathic effect (CPE) was greater than 70%. Viral stocks in Growth Media (EMEM, 1% Penn/Strep, 1% nonessential amino acids, 10% heat-inactivated FBS) plus 5% glycerol were snap frozen using liquid nitrogen and stored at −80° C. Viral stock titers were quantified by a $TCID_{50}$ (50% median tissue culture infectious dose) assay, as described elsewhere.

229E Live Virus Assay:

384-well black cell-culture-treated plastic clear-bottom plates are used in this assay. Using an ECHO liquid dispenser, 3-fold serial dilutions of control and test compounds suspended in DMSO are added to the plate wells in duplicate in a total volume of 125 nL per well. MRC-5 cells below passage 17 are seeded into the inner 240 wells of the 384-well plate at 1,500 cells per well in a volume of 12.5 μL using Growth Media. Viral stock is then added to the wells at a multiplicity of infection (MOI) of 0.05 in a volume of 12.5 μL per well, bringing the total volume of each well to ~25 μL. Each plate has a control row of 20 wells with cells plus DMSO and virus but no compound (positive control, max CPE, minimum ATPlite signal), and a row with cells plus DMSO but no compound or virus (negative control, minimum CPE, maximum ATPlite signal), and a row with no cells or virus or compound (background plate/reagent control). The control wells with cells but no virus are given an additional 12.5 μL of growth media containing an equal quantity of glycerol as those wells receiving the viral stock in order to keep consistent in media and volume conditions. The outer 2 rows/columns of wells are filled with 30 μL of moat media (DMEM, 1% Penn/Strep) to act as a thermal and evaporative barrier around the test wells. Following addition of all components, the sides of the plates are gently tapped by hand to promote even cell distribution across the wells.

Upon confirmation of cell distribution, plates are incubated at 34° C. in a $CO_2$ humidity-controlled incubator for 6 days. Following the 6-day incubation period, the plates are read using ATPlite (12.5 μL added per well), which quantifies the amount of ATP (a measure of cell health) present in each well. Assay plates are read using an Envision luminometer. These data are used to calculate the percent cell health per well relative to the negative control wells and the $EC_{50}$ of each compound is calculated using ExcelFit software and 4-parameter logistical curve fitting analysis.

All experiments were run in duplicate, and $EC_{50}$ ranges are reported as follows: A<0.1 μM; B 0.1-1 μM; C >1 μM.

TABLE 2

Summary of Activities

| Compound | 229E $EC_{50}$ | Compound | 229E $EC_{50}$ |
|---|---|---|---|
| 1 | B | 2 | B |
| 3 | C | 4 | B |
| 5 | B | 6 | — |
| 7 | — | 8 | — |
| 9 | — | 10 | — |
| 11 | A | 12 | B |
| 13 | A | 14 | A |
| 15 | A | 16 | B |
| 17 | A | 18 | B |
| 19 | A | 20 | A |
| 21 | A | 22 | — |
| 23 | A | 24 | A |
| 25 | A | 26 | A |
| 27 | A | 28 | A |
| 29 | A | 30 | A |
| 31 | B | 32 | B |
| 33 | C | 34 | C |
| 35 | C | 36 | B |
| 37 | B | 38 | — |
| 39 | C | 40 | B |
| 41 | C | 42 | A |
| 43 | A | 44 | A |
| 45 | A | 46 | A |
| 47 | B | 48 | B |
| 49 | A | 50 | A |
| 51 | A | 52 | A |
| 53 | — | 54 | — |
| 55 | — | 56 | — |
| 57 | — | 58 | B |
| 59 | C | 60 | B |
| 61 | C | 62 | C |
| 63 | C | 64 | C |
| 65 | A | 66 | A |
| 67 | — | 68 | — |
| 69 | — | 70 | — |
| 71 | — | 72 | — |
| 73 | — | 74 | — |
| 75 | — | 76 | — |
| 77 | — | 78 | — |
| 79 | — | 80 | — |
| 81 | A | 82 | A |
| 83 | — | 84 | — |
| 85 | A | 86 | A |
| 87 | A | 88 | A |
| 89 | B | 90 | B |
| 91 | A | 92 | A |
| 93 | A | 94 | — |
| 95 | B | 96 | B |
| 97 | C | 98 | B |
| 99 | — | 100 | B |
| 101 | — | 102 | C |
| 103 | B | 104 | A |
| 105 | A | 106 | — |
| 107 | — | 108 | — |
| 109 | — | 110 | — |
| 111 | — | 112 | — |
| 113 | A | 114 | A |
| 115 | A | 116 | A |
| 117 | — | 118 | — |

TABLE 2-continued

Summary of Activities

| Compound | 229E $EC_{50}$ | Compound | 229E $EC_{50}$ |
|---|---|---|---|
| 119 | B | 120 | C |
| 121 | B | 122 | B |
| 123 | A | 124 | A |
| 125 | B | 126 | A |
| 127 | A | 128 | C |
| 129 | C | 130 | — |
| 131 | — | 132 | — |
| 133 | — | 134 | A |
| 135 | A | 136 | A |
| 137 | A | 138 | A |
| 139 | A | 140 | A |
| 141 | A | 142 | A |
| 143 | A | 144 | A |
| 145 | A | 146 | A |
| 147 | A | 148 | A |
| 149 | A | 150 | A |
| 151 | — | 152 | — |
| 153 | A | 154 | A |
| 155 | C | 156 | C |
| 157 | B | 158 | B |
| 159 | C | 160 | C |
| 161 | C | 162 | — |
| 163 | — | 164 | — |
| 165 | — | 166 | — |
| 167 | A | 168 | — |
| 169 | A | 170 | — |
| 171 | A | 172 | A |
| 173 | A | 174 | A |
| 175 | A | 176 | A |
| 177 | A | 178 | A |
| 179 | A | 180 | A |
| 181 | A | 182 | A |
| 183 | A | 184 | A |
| 185 | A | 186 | A |
| 187 | A | 188 | A |
| 189 | A | 190 | A |
| 191 | A | 192 | A |
| 193 | A | 194 | A |
| 195 | A | 196 | A |
| 197 | A | 198 | A |
| 199 | A | 200 | A |
| 201 | A | 202 | A |
| 203 | A | 204 | A |
| 205 | A | 206 | A |
| 207 | A | 208 | A |
| 209 | A | 210 | A |
| 211 | A | 212 | A |
| 213 | A | 214 | A |
| 215 | A | 216 | A |
| 217 | A | 218 | A |
| 219 | A | 220 | A |
| 221 | A | 222 | A |
| 223 | A | 224 | A |
| 225 | B | 226 | A |
| 227 | A | 228 | A |
| 229 | A | 230 | A |
| 231 | A | 232 | A |
| 233 | A | 234 | A |
| 235 | A | 236 | A |
| 237 | A | 238 | A |
| 239 | A | 240 | A |
| 241 | A | 242 | A |
| 243 | A | 244 | A |
| 245 | A | 246 | A |
| 247 | A | 248 | A |
| 249 | A | 250 | A |
| 251 | A | 252 | A |
| 253 | A | 254 | A |
| 255 | A | 256 | A |
| 257 | A | 258 | A |
| 259 | A | 260 | A |
| 261 | B | 262 | B |
| 263 | A | 264 | A |
| 265 | B | 266 | A |
| 267 | A | 268 | A |

TABLE 2-continued

Summary of Activities

| Compound | 229E $EC_{50}$ | Compound | 229E $EC_{50}$ |
|---|---|---|---|
| 269 | A | 270 | A |
| 271 | A | 272 | A |
| 273 | A | 274 | A |
| 275 | A | 276 | A |
| 277 | A | 278 | A |
| 279 | A | 280 | A |
| 281 | A | 282 | A |
| 283 | A | 284 | A |
| 285 | A | 286 | A |
| 287 | A | 288 | A |
| 289 | — | 290 | — |
| 291 | — | 292 | — |
| 293 | — | 294 | — |
| 295 | — | 296 | — |
| 297 | — | 298 | — |
| 299 | — | 300 | — |
| 301 | — | 302 | — |
| 303 | — | 304 | — |
| 305 | — | 306 | — |
| 307 | B | 308 | B |
| 309 | A | 310 | B |
| 311 | A | 312 | B |
| 313 | C | 314 | A |
| 315 | B | 316 | A |
| 317 | B | 318 | A |
| 319 | A | 320 | B |
| 321 | B | 322 | A |
| 323 | B | 324 | B |
| 325 | — | 326 | — |
| 327 | — | 328 | — |
| 329 | — | 330 | — |
| 331 | — | 332 | — |
| 333 | — | 334 | — |
| 335 | — | 336 | — |
| 337 | — | 338 | — |
| 339 | — | 340 | — |
| 341 | — | 342 | B |
| 343 | B | 344 | B |
| 345 | A | 346 | A |
| 347 | A | 348 | B |
| 349 | B | 350 | B |
| 351 | B | 352 | A |
| 353 | A | 354 | A |
| 355 | A | 356 | A |
| 357 | — | 358 | — |
| 359 | — | 360 | — |
| 361 | — | 362 | — |
| 363 | — | 364 | — |
| 365 | — | 366 | — |
| 367 | — | 368 | — |
| 369 | — | 370 | A |
| 371 | A | 372 | A |
| 373 | B | 374 | B |
| 375 | A | 376 | A |
| 377 | A | 378 | A |
| 379 | A | 380 | A |
| 381 | A | 382 | A |
| 383 | A | 384 | — |
| 385 | — | 386 | — |
| 387 | — | 388 | — |
| 389 | — | 390 | — |
| 391 | — | 392 | — |
| 393 | — | 394 | — |
| 395 | — | 396 | — |
| 397 | — | 398 | — |
| 399 | — | 400 | — |
| 401 | — | 402 | A |
| 403 | — | 404 | — |
| 405 | — | 406 | — |
| 407 | — | 408 | — |
| 409 | — | 410 | — |
| 411 | — | 412 | A |
| 413 | A | 414 | A |
| 415 | A | 416 | A |
| 417 | A | 418 | B |

TABLE 2-continued

Summary of Activities

| Compound | 229E $EC_{50}$ | Compound | 229E $EC_{50}$ |
|---|---|---|---|
| 419 | B | 420 | — |
| 421 | — | 422 | A |
| 423 | A | 424 | A |
| 425 | — | 426 | — |
| 427 | A | 428 | A |
| 429 | — | 430 | — |
| 431 | — | 432 | C |
| 433 | — | 434 | — |
| 435 | A | 436 | A |
| 437 | A | 438 | A |
| 439 | A | 440 | A |
| 441 | A | 442 | A |
| 443 | B | 444 | B |
| 445 | B | 446 | B |
| 447 | B | 448 | A |
| 449 | B | 450 | A |
| 451 | B | 452 | B |
| 453 | — | 454 | A |
| 455 | A | 456 | — |
| 457 | — | 458 | — |
| 459 | — | 460 | — |
| 461 | — | 462 | — |
| 463 | — | 464 | — |
| 465 | — | 466 | — |
| 467 | — | 468 | — |
| 469 | — | 470 | — |
| 471 | — | 472 | A |
| 473 | B | 474 | B |
| 475 | B | 476 | B |
| 477 | B | 478 | B |
| 479 | B | 480 | A |
| 481 | B | 482 | A |
| 483 | B | 484 | B |
| 485 | B | 486 | B |
| 487 | B | 488 | — |
| 489 | — | 490 | — |
| 491 | — | 492 | B |
| 493 | B | 494 | B |
| 495 | B | 496 | C |
| 497 | C | 498 | A |
| 499 | A | 500 | A |
| 501 | A | 502 | A |
| 503 | A | 504 | A |
| 505 | A | 506 | — |

While this invention has been particularly shown and described with references to preferred embodiments thereof, it will be understood by those skilled in the art that various changes in form and details may be made therein without departing from the scope of the invention encompassed by the appended claims.

What is claimed:

1. A compound represented by Formula (Ia):

(Ia)

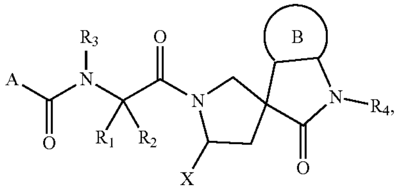

or a pharmaceutically acceptable salt thereof, wherein:

A is selected from:

1) $-R_{11}$;

2) $-OR_{12}$; and

3) $-NR_{13}R_{14}$;

B is an optionally substituted aryl or optionally substituted heteroaryl;

X is selected from:

1) —CN;
2) —C(O)$R_{15}$;
3) —CH(OH)$SO_3R_{16}$;
4) —C(O)$NR_{13}R_{14}$; and
5) —C(O)C(O)$NR_{13}R_{14}$;

$R_1$ and $R_2$ are each independently selected from:

1) Hydrogen;
2) Optionally substituted —$C_1$-$C_8$ alkyl;
3) Optionally substituted —$C_2$-$C_8$ alkenyl;
4) Optionally substituted —$C_2$-$C_8$ alkynyl;
5) Optionally substituted —$C_3$-$C_8$ cycloalkyl;
6) Optionally substituted 3- to 8-membered heterocycloalkyl;
7) Optionally substituted aryl;
8) Optionally substituted arylalkyl;
9) Optionally substituted heteroaryl; and
10) Optionally substituted heteroarylalkyl;

alternatively, $R_1$ and $R_2$ are taken together with the carbon atom to which they are attached to form an optionally substituted 3- to 8-membered carbocyclic ring or an optionally substituted 3- to 8-membered heterocyclic ring;

$R_3$ is hydrogen or optionally substituted —$C_1$-$C_6$ alkyl;

$R_4$ is hydrogen, optionally substituted —$C_1$-$C_4$ alkyl, optionally substituted —$C_2$-$C_4$ alkenyl, or optionally substituted —$C_3$-$C_6$ cycloalkyl;

$R_{11}$ and $R_{12}$ are each independently selected from:

1) Optionally substituted —$C_1$-$C_8$ alkyl;
2) Optionally substituted —$C_2$-$C_8$ alkenyl;
3) Optionally substituted —$C_2$-$C_8$ alkynyl;
4) Optionally substituted —$C_3$-$C_8$ cycloalkyl;
5) Optionally substituted 3- to 8-membered heterocycloalkyl;
6) Optionally substituted aryl;
7) Optionally substituted arylalkyl;
8) Optionally substituted heteroaryl; and
9) Optionally substituted heteroarylalkyl;

$R_{13}$ and $R_{14}$ each independently selected from:

1) Hydrogen;
2) Optionally substituted —$C_1$-$C_8$ alkyl;
3) Optionally substituted —$C_2$-$C_8$ alkenyl;
4) Optionally substituted —$C_2$-$C_8$ alkynyl;
5) Optionally substituted —$C_3$-$C_8$ cycloalkyl;
6) Optionally substituted 3- to 8-membered heterocycloalkyl;
7) Optionally substituted aryl;
8) Optionally substituted arylalkyl;
9) Optionally substituted heteroaryl; and
10) Optionally substituted heteroarylalkyl;

alternatively, $R_{13}$ and $R_{14}$ are taken together with the nitrogen atom to which they are attached to form an optionally substituted 3- to 8-membered heterocyclic ring;

$R_{15}$ is hydrogen, hydroxy, or optionally substituted —$C_1$-$C_8$alkyl; and $R_{16}$ is hydrogen or $Na^+$.

2. The compound of claim 1, wherein A is selected from the groups set forth below, and A is optionally substituted:

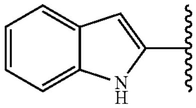 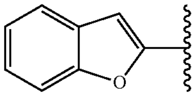

-continued

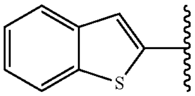 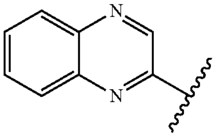

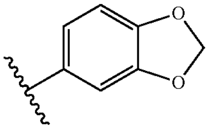 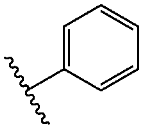

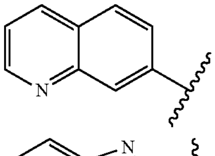 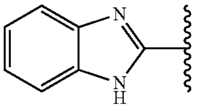

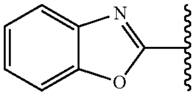 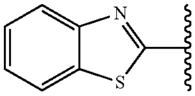

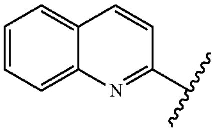 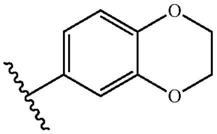

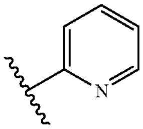 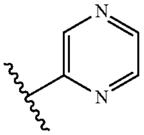 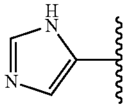

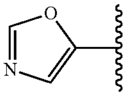 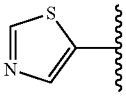 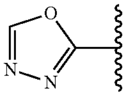

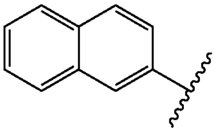 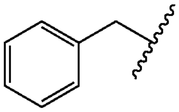

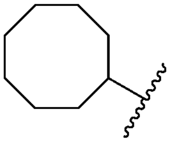 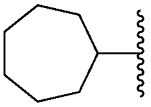 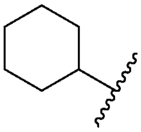

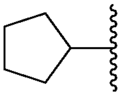 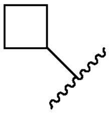 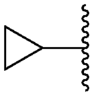 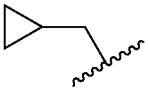

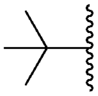 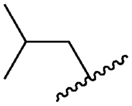 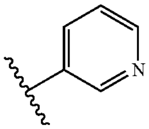

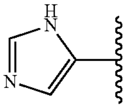 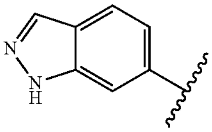

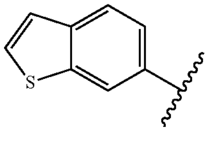 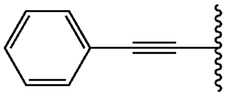

-continued

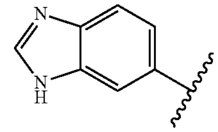 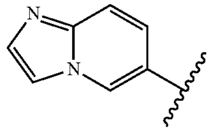
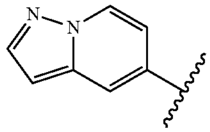 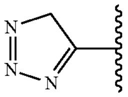 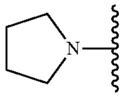
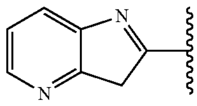 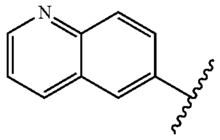
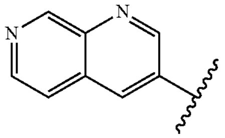 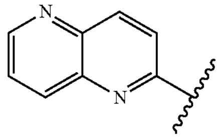
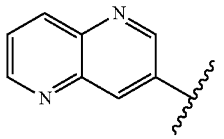 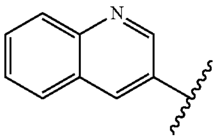
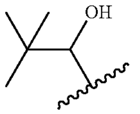 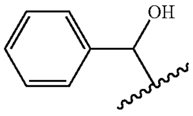
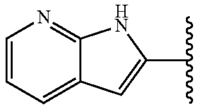 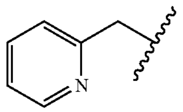
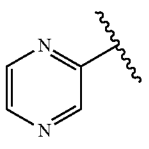 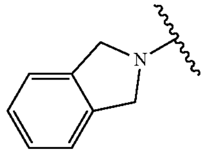
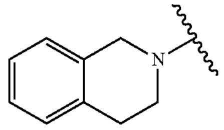 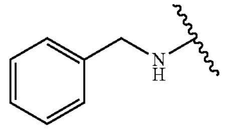
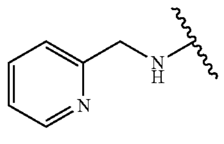 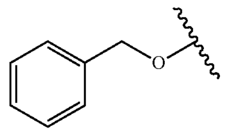
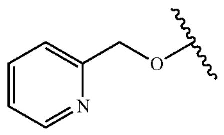 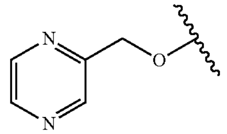
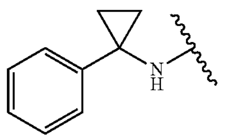 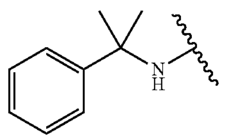

-continued

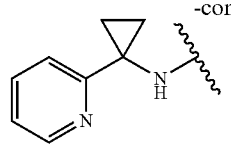 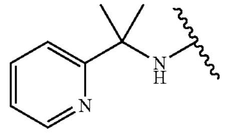
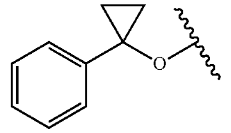 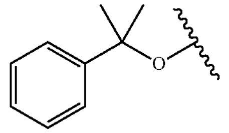
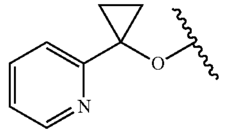 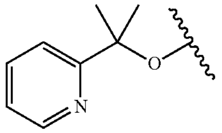 .

3. The compound of claim 1, wherein X is —CN, —C(O)$R_5$, or —C(O)C(O)$NR_{13}R_{14}$, and $R_{13}$, $R_{14}$, and $R_5$ are as defined in claim 1.

4. The compound of claim 1, represented by Formula (Ia-2), or a pharmaceutically acceptable salt thereof:

(Ia-2)

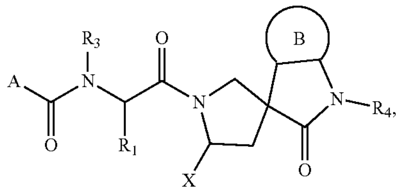

wherein A, B, $R_1$, $R_3$, $R_4$, and X are as defined in claim 1.

5. The compound of claim 1, represented by Formula (IIa), or a pharmaceutically acceptable salt thereof:

(II-a)

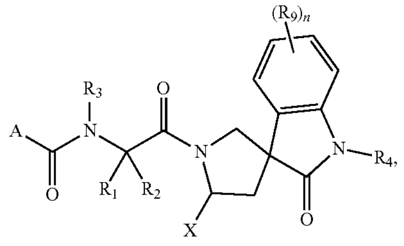

wherein n is 0, 1, 2, 3, or 4; each $R_9$ is independently selected from: halogen; —CN; —$OR_{11}$; —$SR_{11}$; —$NR_{13}R_{14}$; —OC(O)$NR_{13}R_{14}$; optionally substituted —$C_1$-$C_6$ alkyl; optionally substituted —$C_3$-$C_8$ cycloalkyl; optionally substituted 3- to 8-membered heterocycloalkyl; optionally substituted aryl; and optionally substituted heteroaryl; and A, $R_1$, $R_2$, $R_3$, $R_4$, $R_{11}$, $R_{13}$, $R_{14}$, and X are as defined in claim 1.

6. The compound of claim 1, represented by one of Formulas (VIII-1a) to (VIII-5a), or a pharmaceutically acceptable salt thereof;

(VIII-1a)

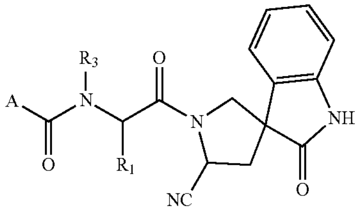

(VIII-2a)

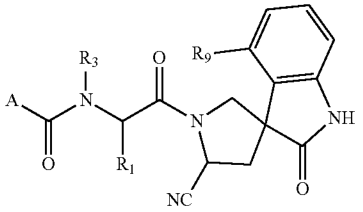

(VIII-3a)

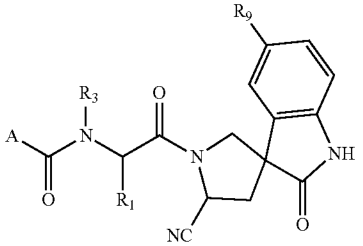

(VIII-4a)

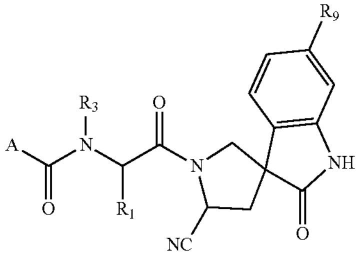

(VIII-5a)

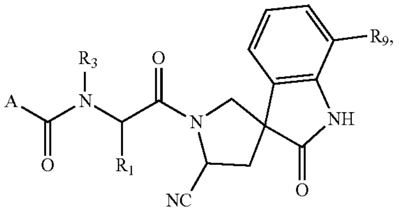

wherein $R_9$ is independently selected from: halogen; —CN; —$OR_{11}$; —$SR_{11}$; —$NR_{13}R_{14}$; —OC(O)$NR_{13}R_{14}$; optionally substituted —$C_1$-$C_6$ alkyl; optionally substituted —$C_3$-$C_8$ cycloalkyl; optionally substituted 3- to 8-membered heterocycloalkyl; optionally substituted aryl; and optionally substituted heteroaryl; $R_{11}$, $R_{13}$, $R_{14}$, A, $R_1$, and $R_3$ are as defined in claim 1.

7. The compound of claim 1, represented by one of Formulas (XIII-1) to (XIII-6), or a pharmaceutically acceptable salt thereof:

(XIII-1)

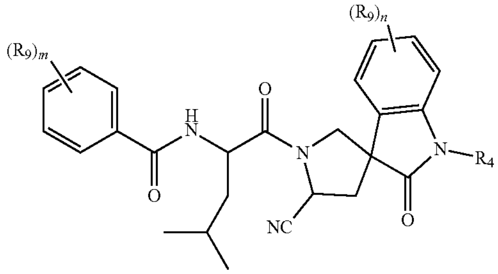

(XII-2)

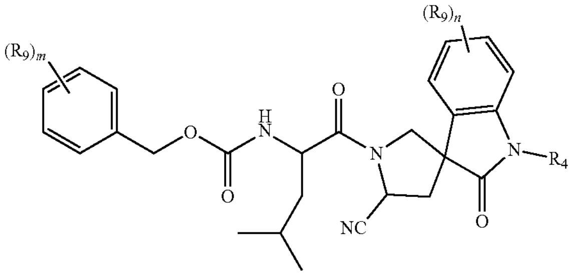

(XII-3)

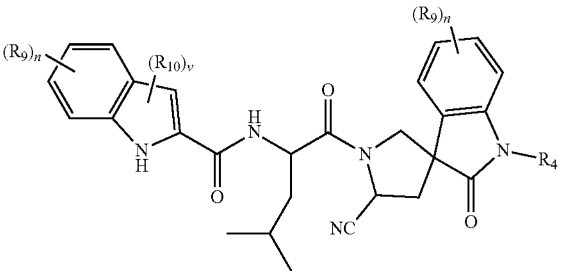

(XII-4)

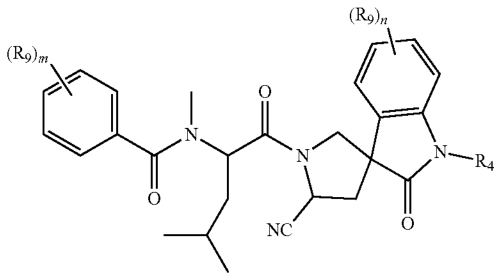

-continued (XII-5)

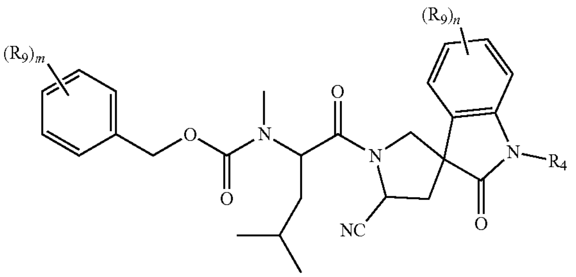

(XII-6)

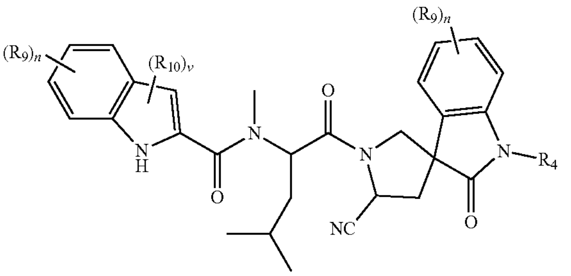

wherein each n is 0, 1, 2, 3, or 4; m is 0, 1, 2, 3, 4 or 5; v is 0, 1 or 2; each $R_9$ is independently selected from: halogen; —CN; —$OR_{11}$; —$SR_{11}$; —$NR_{13}R_{14}$; —OC(O)$NR_{13}R_{14}$; optionally substituted —$C_1$-$C_6$ alkyl; optionally substituted —$C_3$-$C_8$ cycloalkyl; optionally substituted 3- to 8-membered heterocycloalkyl; optionally substituted aryl; and optionally substituted heteroaryl; each $R_{10}$ is optionally substituted —$C_1$-$C_4$ alkyl or optionally substituted —$C_3$-$C_6$ cycloalkyl; and $R_4$, $R_{11}$, $R_{13}$, and $R_{14}$ are as defined in claim 1.

8. The compound of claim 1 represented by Formula (XVIII-1) or Formula (XVIII-2):

(XVIII-1)

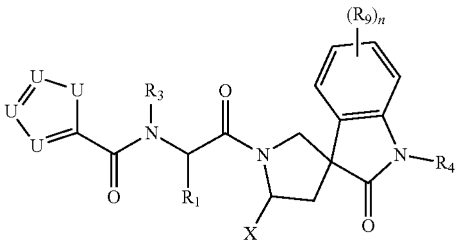

(XVIII-2)

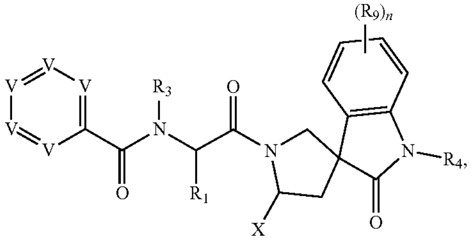

wherein n is 0, 1, 2, 3, or 4; $R_9$ is independently selected from: halogen; —CN; —$OR_{11}$; —$SR_{11}$; —$NR_{13}R_{14}$; —OC(O)$NR_{13}R_{14}$; optionally substituted —$C_1$-$C_6$ alkyl; optionally substituted —$C_3$-$C_8$ cycloalkyl; optionally substituted 3- to 8-membered heterocycloalkyl; optionally substituted aryl; and optionally substituted heteroaryl; one U is N or $NR_{13}$, another U is N, $NR_{13}$, or $CR_{13}$, another U is N, $NR_{13}$, or $CR_{13}$, and the fourth U is O, S, N, $NR_{13}$, or $CR_{13}$; each Vis independently $CR_{13}$ or N; and $R_1$, $R_3$, $R_4$, $R_9$, $R_{13}$, $R_{14}$, and X are as defined in claim 1.

9. A compound selected from the compounds set forth below or a pharmaceutically acceptable salt thereof:

| Compound | Structure |
|---|---|
| 1 | 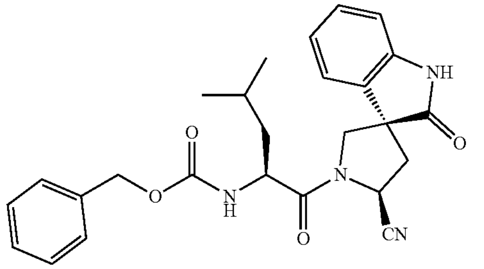 [SMILES: CC(C)C[C@H](NC(=O)OCc1ccccc1)C(=O)N1C[C@]2(C[C@H]1C#N)C(=O)Nc1ccccc12] |
| 2 | 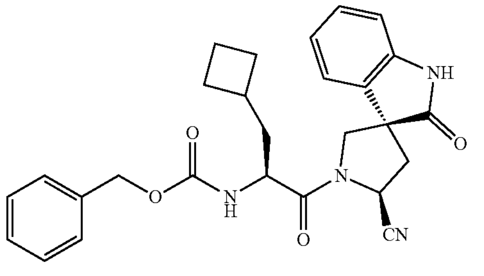 [SMILES: N#C[C@@H]1C[C@@]2(CN1C(=O)[C@H](CC1CCC1)NC(=O)OCc1ccccc1)C(=O)Nc1ccccc12] |

-continued
| Compound | Structure |
| --- | --- |
| 3 | 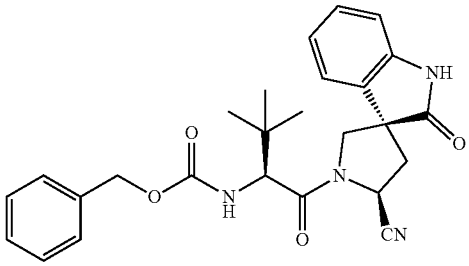 [SMILES: CC(C)(C)[C@H](NC(=O)OCc1ccccc1)C(=O)N1C[C@]2(C[C@H]1C#N)C(=O)Nc1ccccc12] |
| 4 | 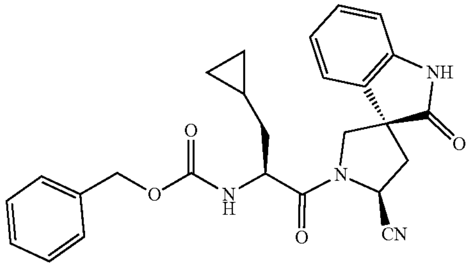 [SMILES: N#C[C@@H]1C[C@@]2(CN1C(=O)[C@H](CC1CC1)NC(=O)OCc1ccccc1)C(=O)Nc1ccccc12] |
| 5 | 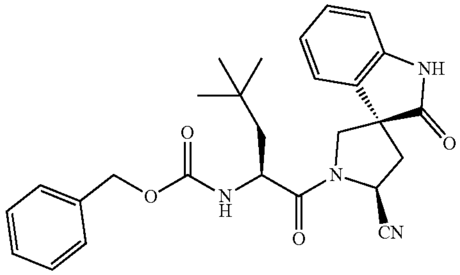 |
| 6 | 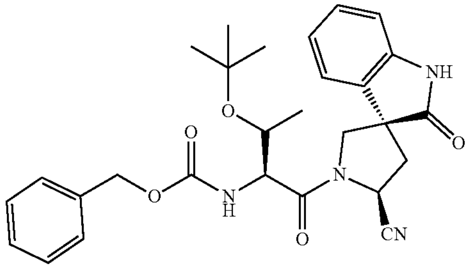 [SMILES: CC(OC(C)(C)C)[C@H](NC(=O)OCc1ccccc1)C(=O)N1C[C@]2(C[C@H]1C#N)C(=O)Nc1ccccc12] |
| 7 | 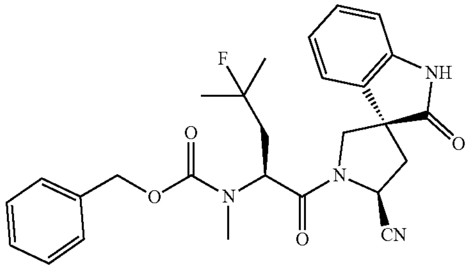 [SMILES: CN(C(=O)OCc1ccccc1)[C@@H](CC(C)(C)F)C(=O)N1C[C@]2(C[C@H]1C#N)C(=O)Nc1ccccc12] |

-continued
| Compound | Structure |
|---|---|
| 8 | 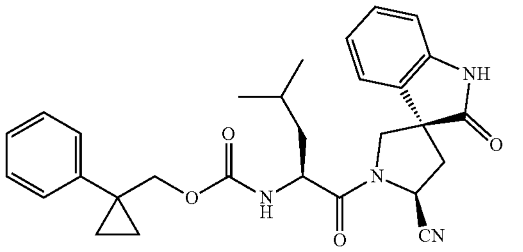 [SMILES: CC(C)C[C@H](NC(=O)OCC1(c2ccccc2)CC1)C(=O)N1C[C@]2(C[C@H]1C#N)C(=O)Nc1ccccc12] |
| 9 | 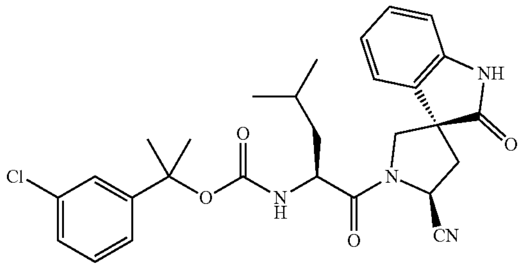 [SMILES: CC(C)C[C@H](NC(=O)OC(C)(C)c1cccc(Cl)c1)C(=O)N1C[C@]2(C[C@H]1C#N)C(=O)Nc1ccccc12] |
| 10 | 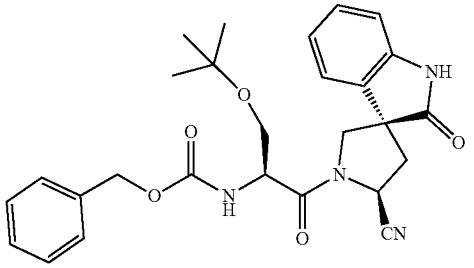 [SMILES: CC(C)(C)OC[C@H](NC(=O)OCc1ccccc1)C(=O)N1C[C@]2(C[C@H]1C#N)C(=O)Nc1ccccc12] |
| 11 | 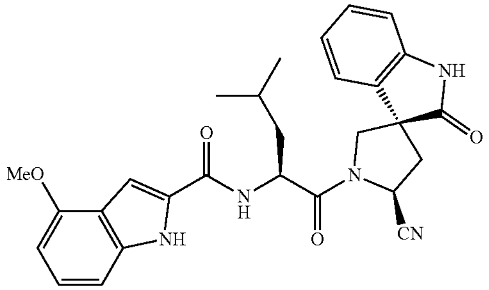 [SMILES: COc1cccc2[nH]c(C(=O)N[C@@H](CC(C)C)C(=O)N3C[C@]4(C[C@H]3C#N)C(=O)Nc3ccccc34)cc12] |
| 12 | 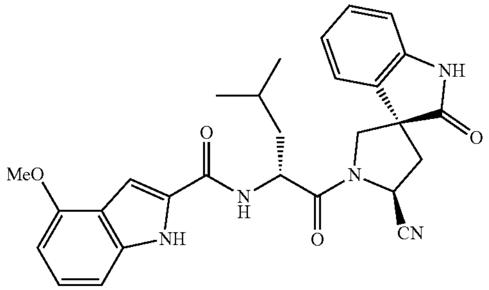 [SMILES: COc1cccc2[nH]c(C(=O)N[C@H](CC(C)C)C(=O)N3C[C@]4(C[C@H]3C#N)C(=O)Nc3ccccc34)cc12] |

-continued
| Compound | Structure |
|---|---|
| 13 | 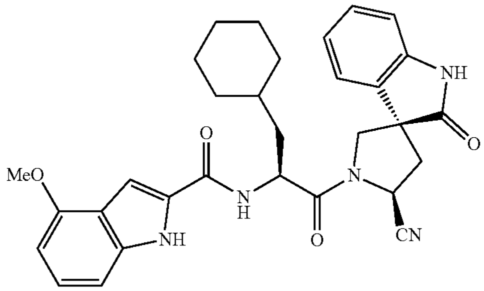 [SMILES: COc1cccc2[nH]c(C(=O)N[C@@H](CC3CCCCC3)C(=O)N3C[C@]4(C[C@H]3C#N)C(=O)Nc3ccccc34)cc12] |
| 14 | 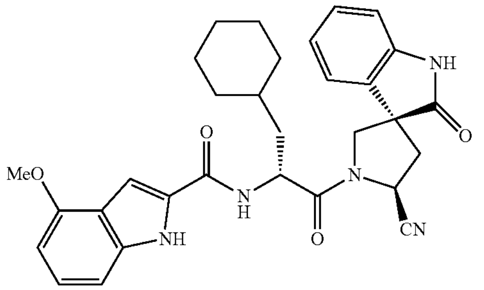 [SMILES: COc1cccc2[nH]c(C(=O)N[C@H](CC3CCCCC3)C(=O)N3C[C@]4(C[C@H]3C#N)C(=O)Nc3ccccc34)cc12] |
| 15 | 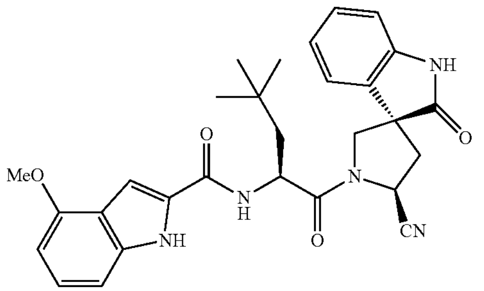 [SMILES: COc1cccc2[nH]c(C(=O)N[C@@H](CC(C)(C)C)C(=O)N3C[C@]4(C[C@H]3C#N)C(=O)Nc3ccccc34)cc12] |
| 16 | 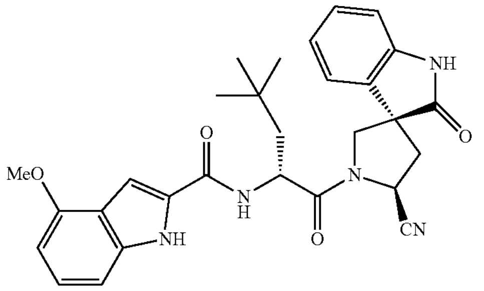 [SMILES: COc1cccc2[nH]c(C(=O)N[C@H](CC(C)(C)C)C(=O)N3C[C@]4(C[C@H]3C#N)C(=O)Nc3ccccc34)cc12] |
| 17 | 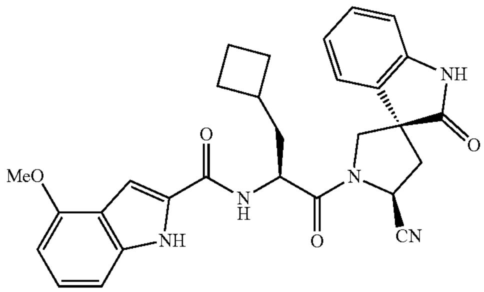 [SMILES: COc1cccc2[nH]c(C(=O)N[C@@H](CC3CCC3)C(=O)N3C[C@]4(C[C@H]3C#N)C(=O)Nc3ccccc34)cc12] |

-continued
| Compound | Structure |
|---|---|
| 18 | 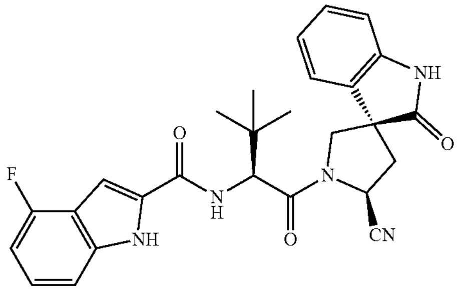 [SMILES: CC(C)(C)[C@H](NC(=O)c1cc2c(F)cccc2[nH]1)C(=O)N1C[C@]2(C[C@H]1C#N)C(=O)Nc1ccccc12] |
| 19 | 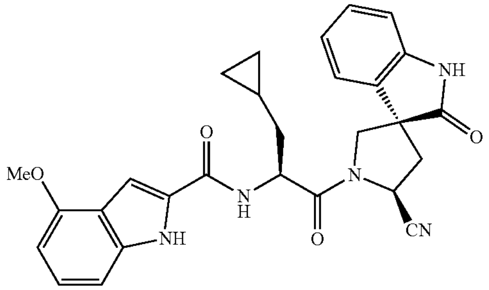 [SMILES: COc1cccc2[nH]c(C(=O)N[C@@H](CC3CC3)C(=O)N3C[C@]4(C[C@H]3C#N)C(=O)Nc3ccccc34)cc12] |
| 20 | 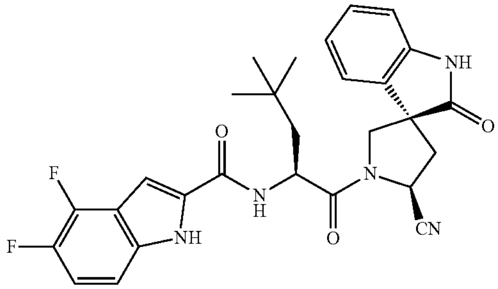 [SMILES: CC(C)(C)C[C@H](NC(=O)c1cc2c(F)c(F)ccc2[nH]1)C(=O)N1C[C@]2(C[C@H]1C#N)C(=O)Nc1ccccc12] |
| 21 | 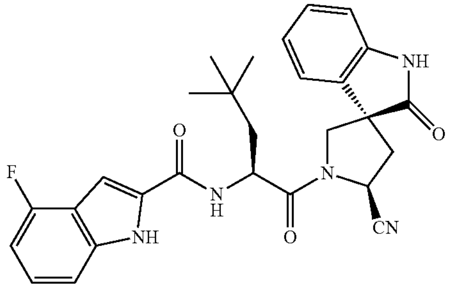 [SMILES: CC(C)(C)C[C@H](NC(=O)c1cc2c(F)cccc2[nH]1)C(=O)N1C[C@]2(C[C@H]1C#N)C(=O)Nc1ccccc12] |
| 22 | 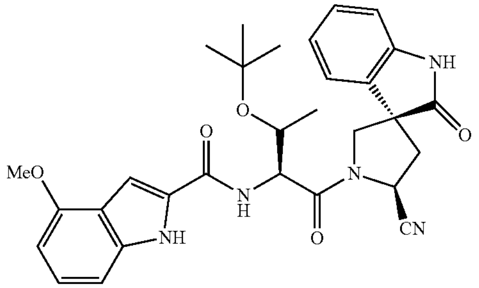 [SMILES: COc1cccc2[nH]c(C(=O)N[C@H](C(=O)N3C[C@]4(C[C@H]3C#N)C(=O)Nc3ccccc34)C(C)OC(C)(C)C)cc12] |

-continued
| Compound | Structure |
|---|---|
| 23 | 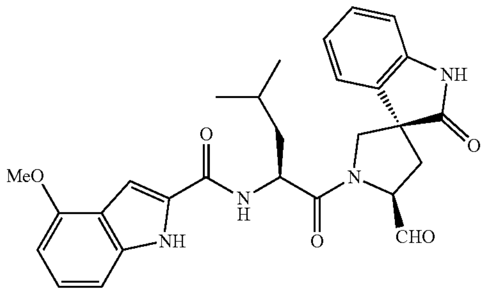 [SMILES: COc1cccc2[nH]c(C(=O)N[C@@H](CC(C)C)C(=O)N3C[C@]4(C[C@H]3C=O)C(=O)Nc3ccccc34)cc12] |
| 24 | 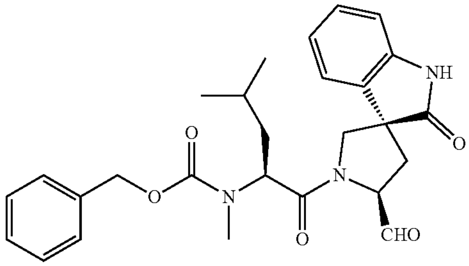 [SMILES: CC(C)C[C@@H](C(=O)N1C[C@]2(C[C@H]1C=O)C(=O)Nc1ccccc12)N(C)C(=O)OCc1ccccc1] |
| 25 | 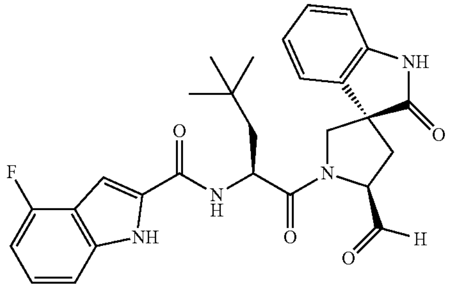 [SMILES: CC(C)(C)C[C@H](NC(=O)c1cc2c(F)cccc2[nH]1)C(=O)N1C[C@]2(C[C@H]1C=O)C(=O)Nc1ccccc12] |
| 26 | 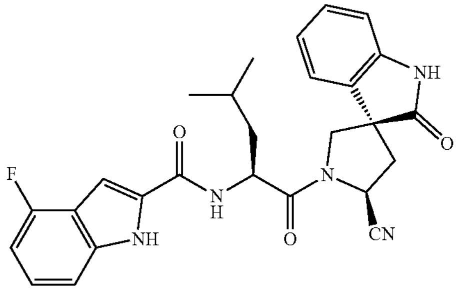 |
| 27 | 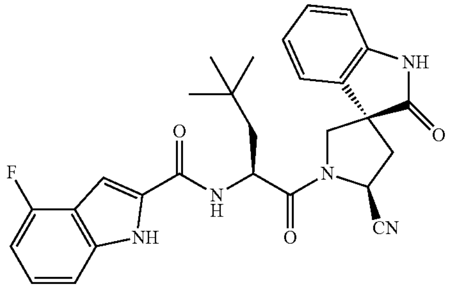 [SMILES: CC(C)(C)C[C@H](NC(=O)c1cc2c(F)cccc2[nH]1)C(=O)N1C[C@]2(C[C@H]1C#N)C(=O)Nc1ccccc12] |

-continued
| Compound | Structure |
|---|---|
| 28 | 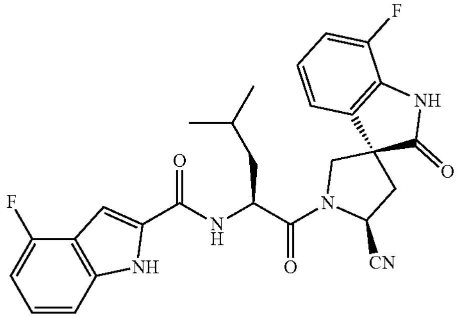 [SMILES: CC(C)C[C@H](NC(=O)c1cc2c(F)cccc2[nH]1)C(=O)N1C[C@]2(C[C@H]1C#N)C(=O)Nc1c(F)cccc12] |
| 29 | 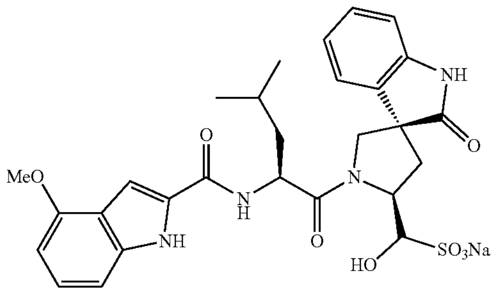 |
| 30 | 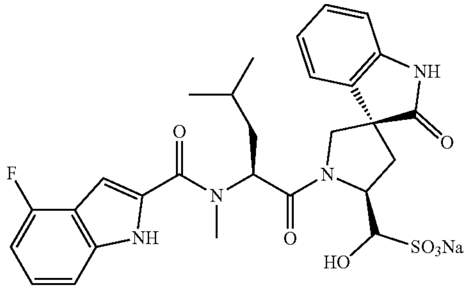 |
| 31 | 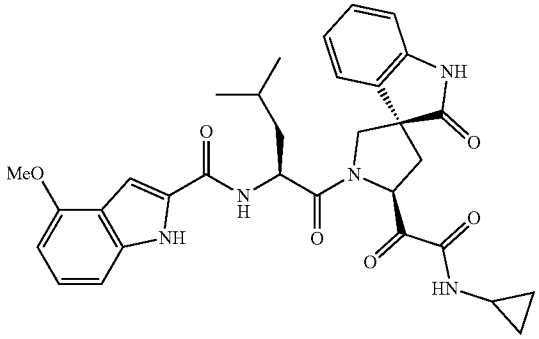 [SMILES: COc1cccc2[nH]c(C(=O)N[C@@H](CC(C)C)C(=O)N3C[C@]4(C[C@H]3C(=O)C(=O)NC3CC3)C(=O)Nc3ccccc34)cc12] |

-continued
| Compound | Structure |
| --- | --- |
| 32 | 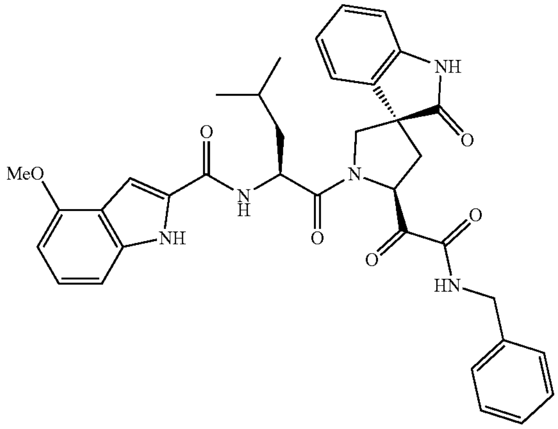 [SMILES: COc1cccc2[nH]c(C(=O)N[C@@H](CC(C)C)C(=O)N3C[C@]4(C[C@H]3C(=O)C(=O)NCc3ccccc3)C(=O)Nc3ccccc34)cc12] |
| 33 | 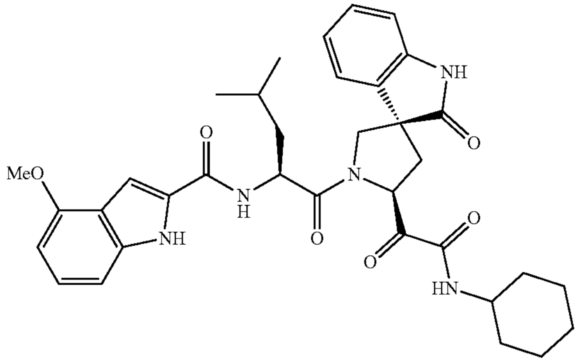 |
| 34 | 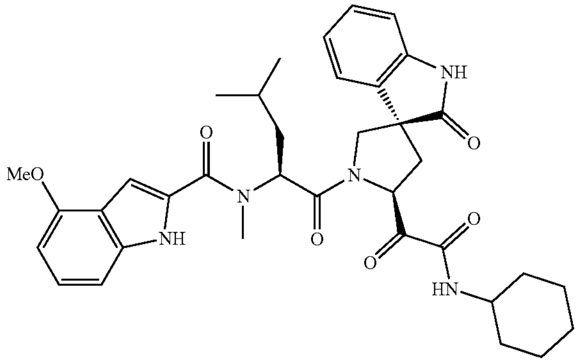 |
| 35 | 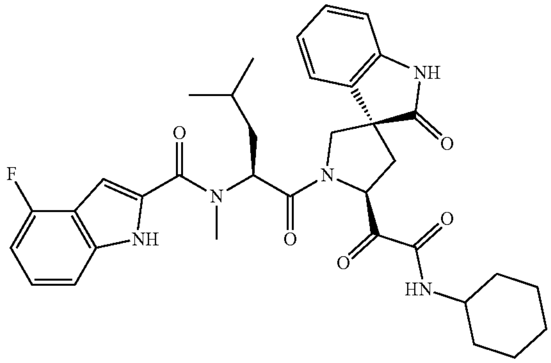 [SMILES: CC(C)C[C@@H](C(=O)N1C[C@]2(C[C@H]1C(=O)C(=O)NC1CCCCC1)C(=O)Nc1ccccc12)N(C)C(=O)c1cc2c(F)cccc2[nH]1] |

-continued
| Compound | Structure |
|---|---|
| 36 | 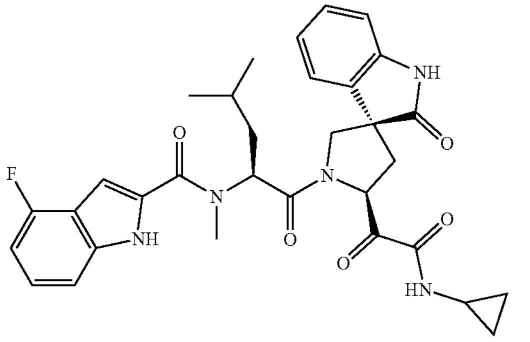 [SMILES: CC(C)C[C@@H](C(=O)N1C[C@]2(C[C@H]1C(=O)C(=O)NC1CC1)C(=O)Nc1ccccc12)N(C)C(=O)c1cc2c(F)cccc2[nH]1] |
| 37 | 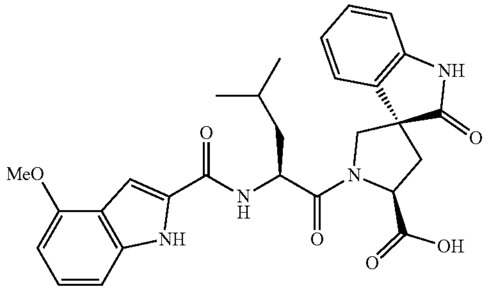 [SMILES: COc1cccc2[nH]c(C(=O)N[C@@H](CC(C)C)C(=O)N3C[C@]4(C[C@H]3C(=O)O)C(=O)Nc3ccccc34)cc12] |
| 38 | 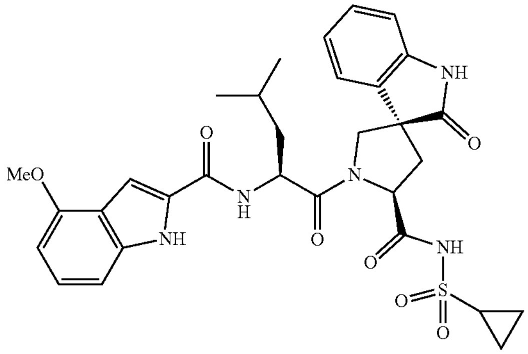 [SMILES: COc1cccc2[nH]c(C(=O)N[C@@H](CC(C)C)C(=O)N3C[C@]4(C[C@H]3C(=O)NS(=O)(=O)C3CC3)C(=O)Nc3ccccc34)cc12] |
| 39 | 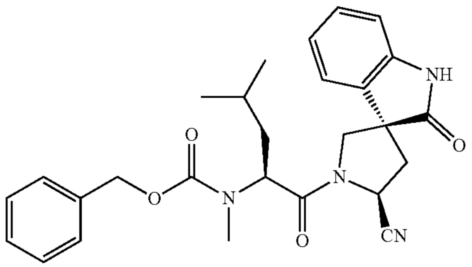 [SMILES: CC(C)C[C@@H](C(=O)N1C[C@]2(C[C@H]1C#N)C(=O)Nc1ccccc12)N(C)C(=O)OCc1ccccc1] |
| 40 | 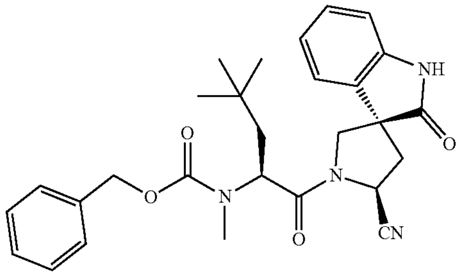 [SMILES: CN(C(=O)OCc1ccccc1)[C@@H](CC(C)(C)C)C(=O)N1C[C@]2(C[C@H]1C#N)C(=O)Nc1ccccc12] |

-continued
| Compound | Structure |
| --- | --- |
| 41 | 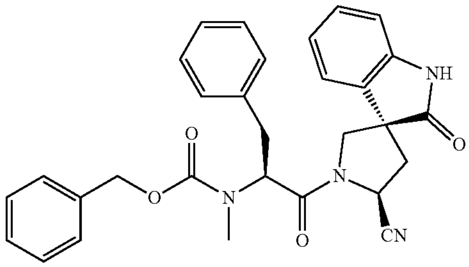 [SMILES: CN(C(=O)OCc1ccccc1)[C@@H](Cc1ccccc1)C(=O)N1C[C@]2(C[C@H]1C#N)C(=O)Nc1ccccc12] |
| 42 | 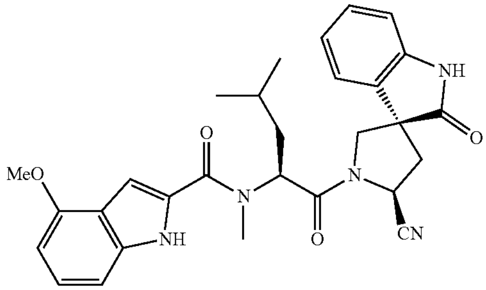 [SMILES: COc1cccc2[nH]c(C(=O)N(C)[C@@H](CC(C)C)C(=O)N3C[C@]4(C[C@H]3C#N)C(=O)Nc3ccccc34)cc12] |
| 43 | 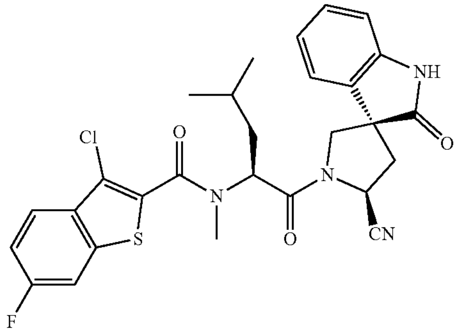 [SMILES: CC(C)C[C@@H](C(=O)N1C[C@]2(C[C@H]1C#N)C(=O)Nc1ccccc12)N(C)C(=O)c1sc2cc(F)ccc2c1Cl] |
| 44 | 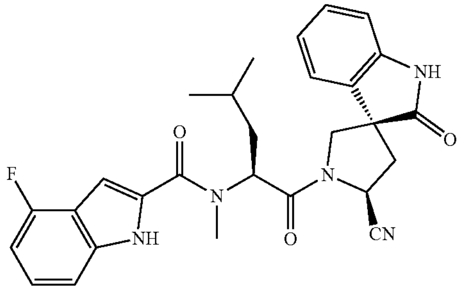 [SMILES: CC(C)C[C@@H](C(=O)N1C[C@]2(C[C@H]1C#N)C(=O)Nc1ccccc12)N(C)C(=O)c1cc2c(F)cccc2[nH]1] |
| 45 | 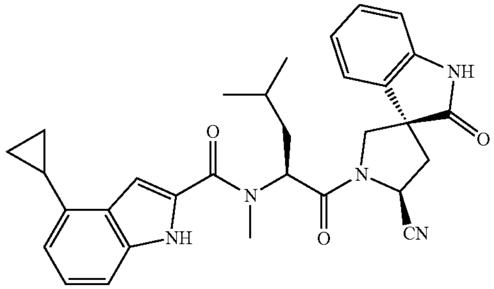 [SMILES: CC(C)C[C@@H](C(=O)N1C[C@]2(C[C@H]1C#N)C(=O)Nc1ccccc12)N(C)C(=O)c1cc2c(C3CC3)cccc2[nH]1] |

-continued
| Compound | Structure |
|---|---|
| 46 | 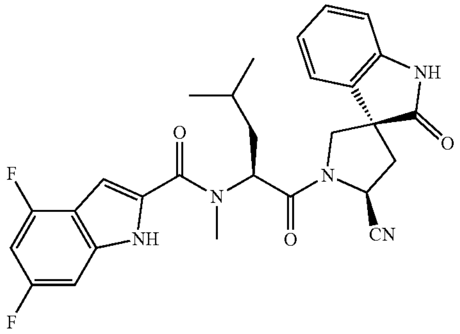 |
| 47 | 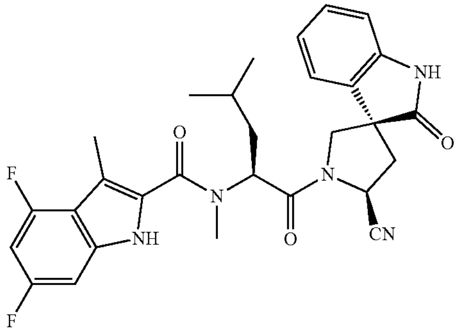 |
| 48 | 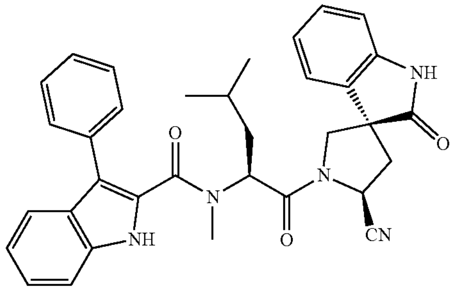 [SMILES: CC(C)C[C@@H](C(=O)N1C[C@]2(C[C@H]1C#N)C(=O)Nc1ccccc12)N(C)C(=O)c1[nH]c2ccccc2c1-c1ccccc1] |
| 49 | 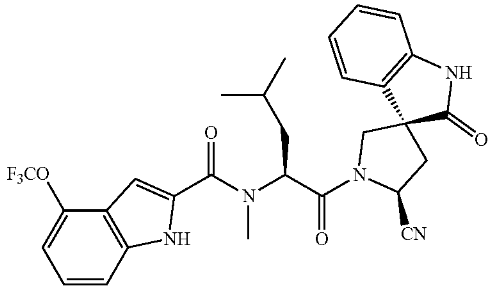 [SMILES: CC(C)C[C@@H](C(=O)N1C[C@]2(C[C@H]1C#N)C(=O)Nc1ccccc12)N(C)C(=O)c1cc2c(OC(F)(F)F)cccc2[nH]1] |
| 50 | 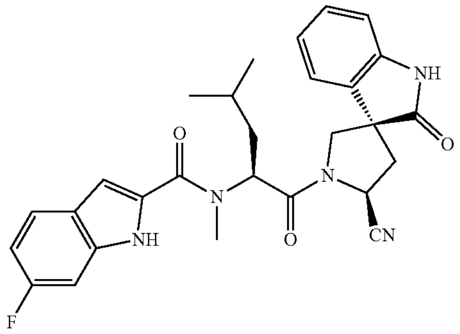 |

-continued
| Compound | Structure |
|---|---|
| 51 | 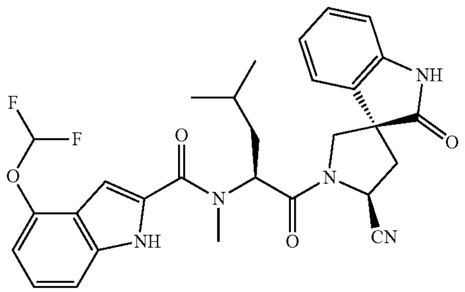 [SMILES: CC(C)C[C@@H](C(=O)N1C[C@]2(C[C@H]1C#N)C(=O)Nc1ccccc12)N(C)C(=O)c1cc2c(OC(F)F)cccc2[nH]1] |
| 52 | 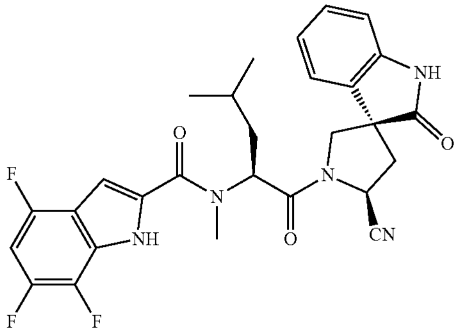 |
| 53 | 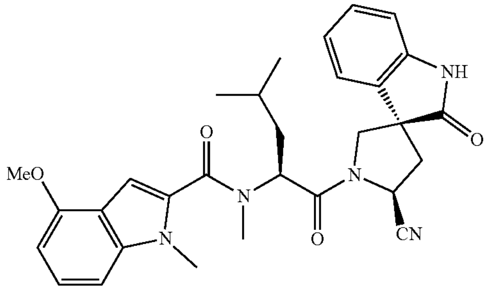 [SMILES: COc1cccc2c1cc(C(=O)N(C)[C@@H](CC(C)C)C(=O)N1C[C@]3(C[C@H]1C#N)C(=O)Nc1ccccc13)n2C] |
| 54 | 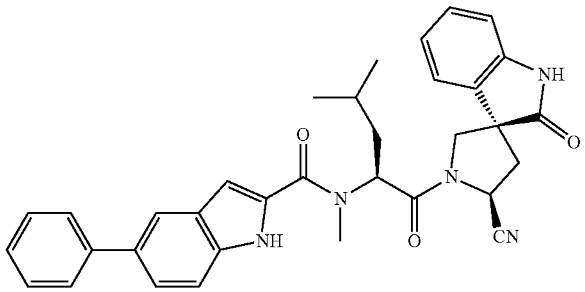 [SMILES: CC(C)C[C@@H](C(=O)N1C[C@]2(C[C@H]1C#N)C(=O)Nc1ccccc12)N(C)C(=O)c1cc2cc(-c3ccccc3)ccc2[nH]1] |

-continued
| Compound | Structure |
|---|---|
| 55 | 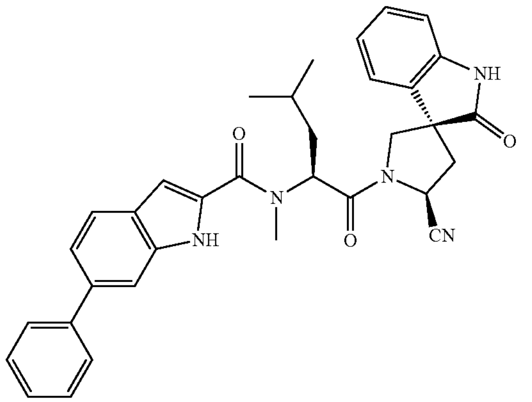 [SMILES: CC(C)C[C@@H](C(=O)N1C[C@]2(C[C@H]1C#N)C(=O)Nc1ccccc12)N(C)C(=O)c1cc2ccc(-c3ccccc3)cc2[nH]1] |
| 56 | 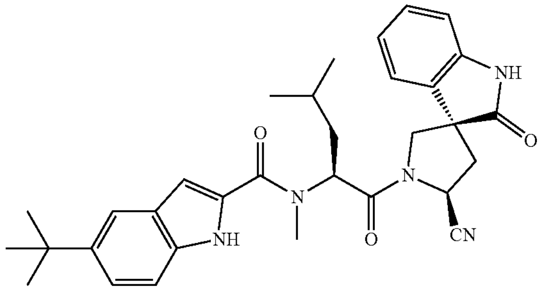 [SMILES: CC(C)C[C@@H](C(=O)N1C[C@]2(C[C@H]1C#N)C(=O)Nc1ccccc12)N(C)C(=O)c1cc2cc(C(C)(C)C)ccc2[nH]1] |
| 57 | 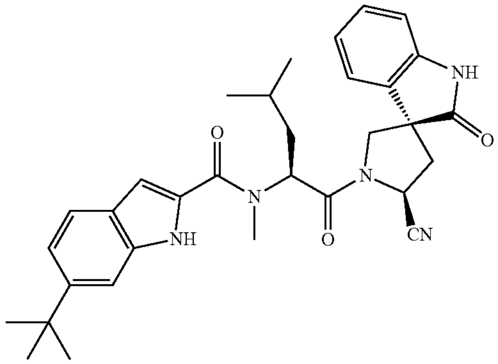 [SMILES: CC(C)C[C@@H](C(=O)N1C[C@]2(C[C@H]1C#N)C(=O)Nc1ccccc12)N(C)C(=O)c1cc2ccc(C(C)(C)C)cc2[nH]1] |
| 58 | 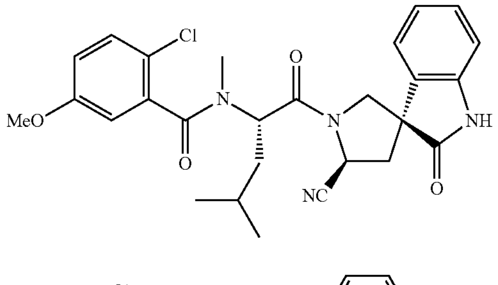 |
| 59 | 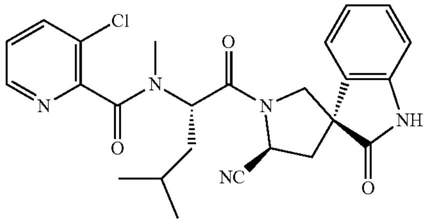 [SMILES: CC(C)C[C@@H](C(=O)N1C[C@]2(C[C@H]1C#N)C(=O)Nc1ccccc12)N(C)C(=O)c1ncccc1Cl] |

-continued
| Compound | Structure |
|---|---|
| 60 | 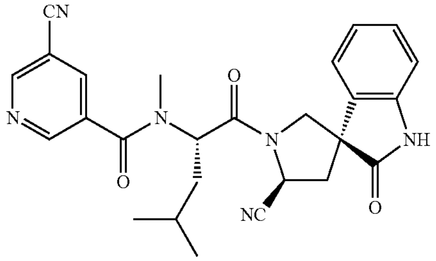 [SMILES: CC(C)C[C@@H](C(=O)N1C[C@]2(C[C@H]1C#N)C(=O)Nc1ccccc12)N(C)C(=O)c1cncc(C#N)c1] |
| 61 | 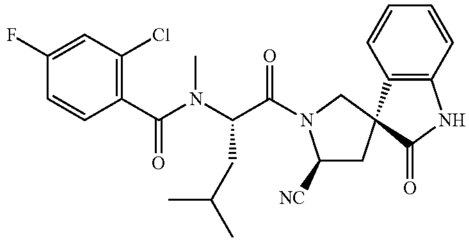 [SMILES: CC(C)C[C@@H](C(=O)N1C[C@]2(C[C@H]1C#N)C(=O)Nc1ccccc12)N(C)C(=O)c1ccc(F)cc1Cl] |
| 62 | 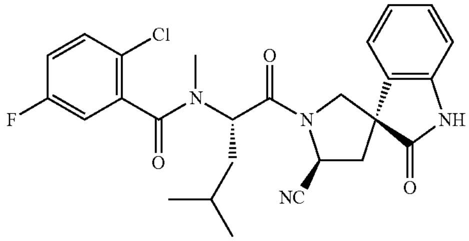 [SMILES: CC(C)C[C@@H](C(=O)N1C[C@]2(C[C@H]1C#N)C(=O)Nc1ccccc12)N(C)C(=O)c1cc(F)ccc1Cl] |
| 63 | 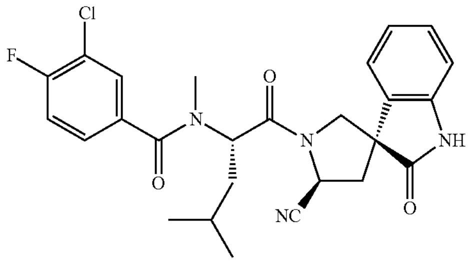 |
| 64 | 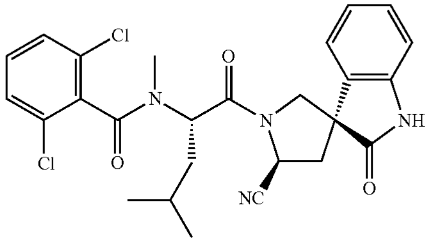 [SMILES: CC(C)C[C@@H](C(=O)N1C[C@]2(C[C@H]1C#N)C(=O)Nc1ccccc12)N(C)C(=O)c1c(Cl)cccc1Cl] |
| 65 | 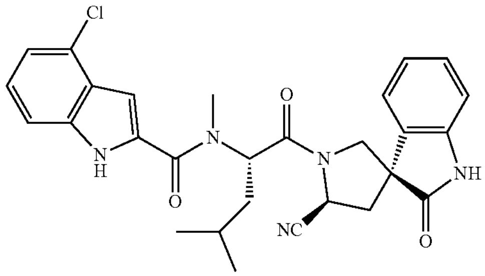 |

-continued
| Compound | Structure |
|---|---|
| 66 | 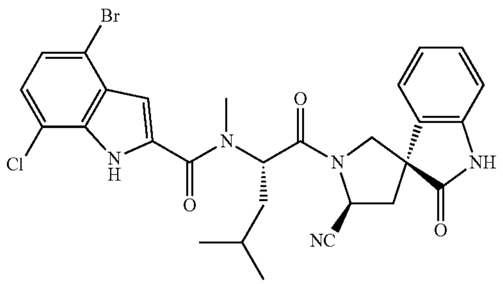 [SMILES: CC(C)C[C@@H](C(=O)N1C[C@]2(C[C@H]1C#N)C(=O)Nc1ccccc12)N(C)C(=O)c1cc2c(Br)ccc(Cl)c2[nH]1] |
| 67 | 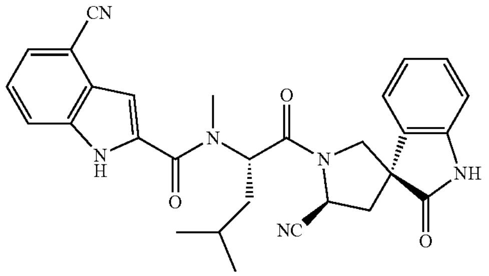 [SMILES: CC(C)C[C@@H](C(=O)N1C[C@]2(C[C@H]1C#N)C(=O)Nc1ccccc12)N(C)C(=O)c1cc2c(C#N)cccc2[nH]1] |
| 68 | 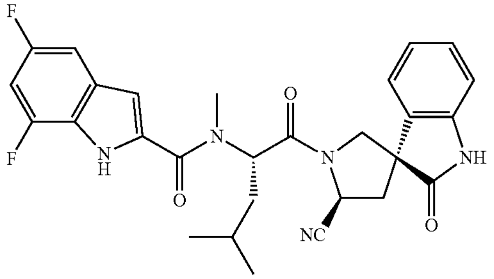 [SMILES: CC(C)C[C@@H](C(=O)N1C[C@]2(C[C@H]1C#N)C(=O)Nc1ccccc12)N(C)C(=O)c1cc2cc(F)cc(F)c2[nH]1] |
| 69 | 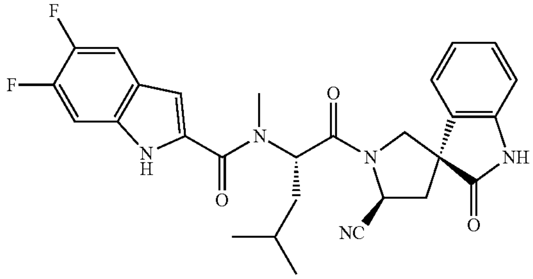 [SMILES: CC(C)C[C@@H](C(=O)N1C[C@]2(C[C@H]1C#N)C(=O)Nc1ccccc12)N(C)C(=O)c1cc2cc(F)c(F)cc2[nH]1] |
| 70 | 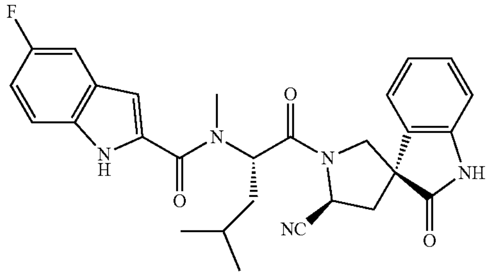 [SMILES: CC(C)C[C@@H](C(=O)N1C[C@]2(C[C@H]1C#N)C(=O)Nc1ccccc12)N(C)C(=O)c1cc2cc(F)ccc2[nH]1] |

-continued
| Compound | Structure |
|---|---|
| 71 | 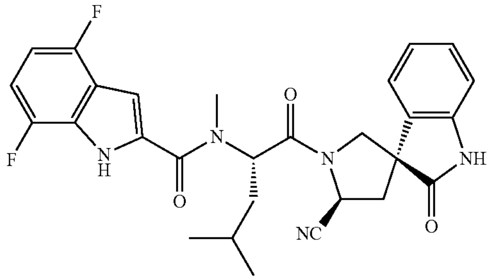 [SMILES: CC(C)C[C@@H](C(=O)N1C[C@]2(C[C@H]1C#N)C(=O)Nc1ccccc12)N(C)C(=O)c1cc2c(F)ccc(F)c2[nH]1] |
| 72 | 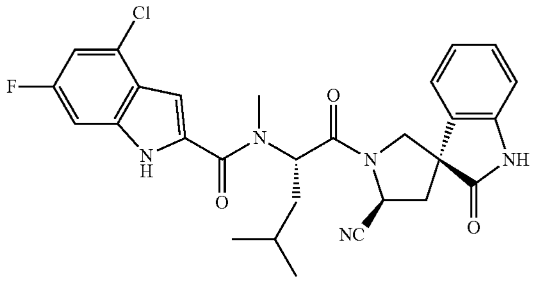 [SMILES: CC(C)C[C@@H](C(=O)N1C[C@]2(C[C@H]1C#N)C(=O)Nc1ccccc12)N(C)C(=O)c1cc2c(Cl)cc(F)cc2[nH]1] |
| 73 | 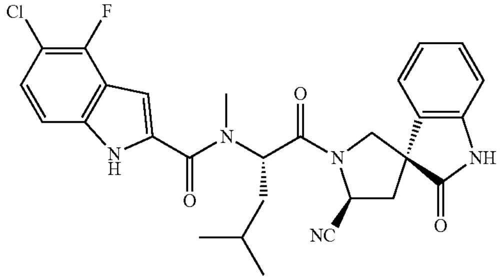 [SMILES: CC(C)C[C@@H](C(=O)N1C[C@]2(C[C@H]1C#N)C(=O)Nc1ccccc12)N(C)C(=O)c1cc2c(F)c(Cl)ccc2[nH]1] |
| 74 | 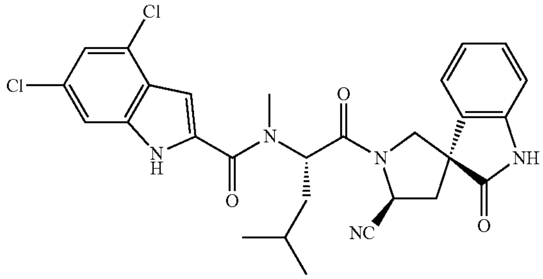 [SMILES: CC(C)C[C@@H](C(=O)N1C[C@]2(C[C@H]1C#N)C(=O)Nc1ccccc12)N(C)C(=O)c1cc2c(Cl)cc(Cl)cc2[nH]1] |
| 75 | 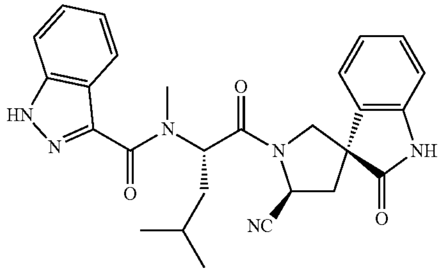 [SMILES: CC(C)C[C@@H](C(=O)N1C[C@]2(C[C@H]1C#N)C(=O)Nc1ccccc12)N(C)C(=O)c1n[nH]c2ccccc12] |

-continued
| Compound | Structure |
|---|---|
| 76 | 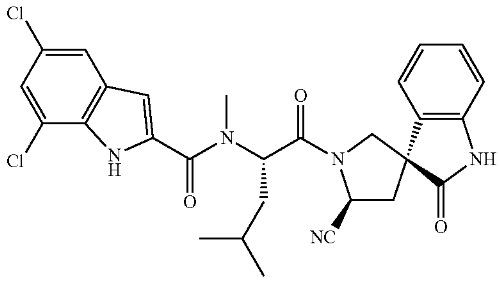 [SMILES: CC(C)C[C@@H](C(=O)N1C[C@]2(C[C@H]1C#N)C(=O)Nc1ccccc12)N(C)C(=O)c1cc2cc(Cl)cc(Cl)c2[nH]1] |
| 77 | 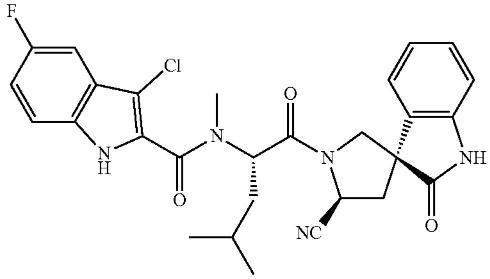 [SMILES: CC(C)C[C@@H](C(=O)N1C[C@]2(C[C@H]1C#N)C(=O)Nc1ccccc12)N(C)C(=O)c1[nH]c2ccc(F)cc2c1Cl] |
| 78 | 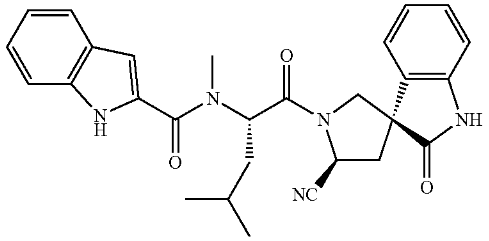 [SMILES: CC(C)C[C@@H](C(=O)N1C[C@]2(C[C@H]1C#N)C(=O)Nc1ccccc12)N(C)C(=O)c1cc2ccccc2[nH]1] |
| 79 | 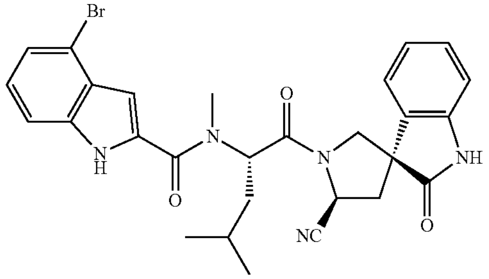 [SMILES: CC(C)C[C@@H](C(=O)N1C[C@]2(C[C@H]1C#N)C(=O)Nc1ccccc12)N(C)C(=O)c1cc2c(Br)cccc2[nH]1] |
| 80 | 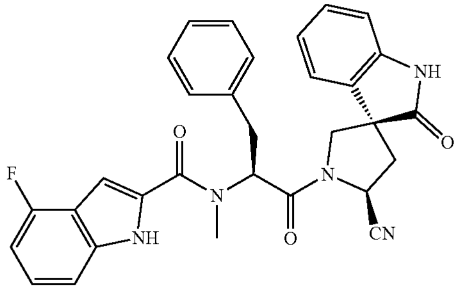 [SMILES: CN(C(=O)c1cc2c(F)cccc2[nH]1)[C@@H](Cc1ccccc1)C(=O)N1C[C@]2(C[C@H]1C#N)C(=O)Nc1ccccc12] |

-continued
| Compound | Structure |
|---|---|
| 81 | 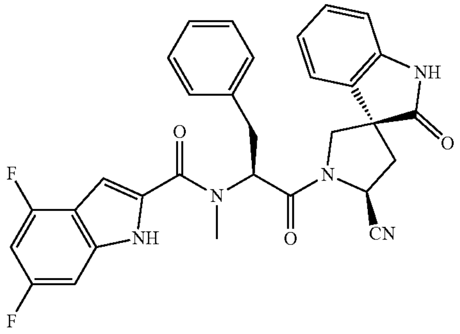 [SMILES: CN(C(=O)c1cc2c(F)cc(F)cc2[nH]1)[C@@H](Cc1ccccc1)C(=O)N1C[C@]2(C[C@H]1C#N)C(=O)Nc1ccccc12] |
| 82 | 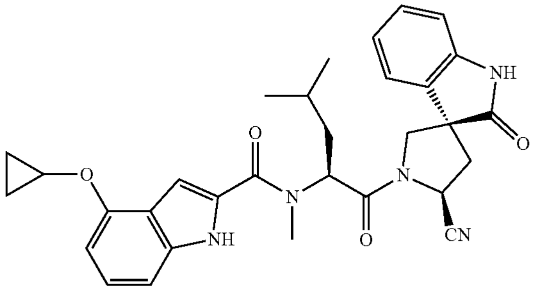 [SMILES: CC(C)C[C@@H](C(=O)N1C[C@]2(C[C@H]1C#N)C(=O)Nc1ccccc12)N(C)C(=O)c1cc2c(OC3CC3)cccc2[nH]1] |
| 83 | 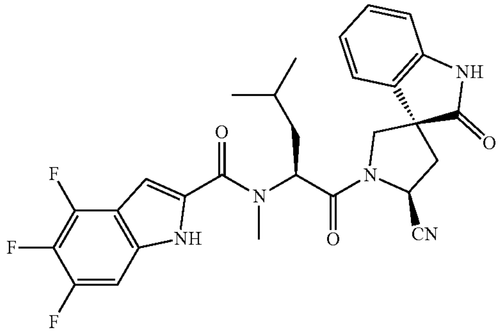 [SMILES: CC(C)C[C@@H](C(=O)N1C[C@]2(C[C@H]1C#N)C(=O)Nc1ccccc12)N(C)C(=O)c1cc2c(F)c(F)c(F)cc2[nH]1] |
| 84 | 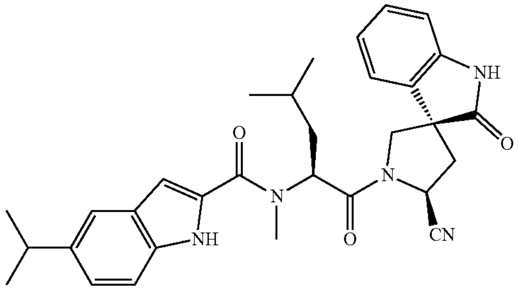 [SMILES: CC(C)C[C@@H](C(=O)N1C[C@]2(C[C@H]1C#N)C(=O)Nc1ccccc12)N(C)C(=O)c1cc2cc(C(C)C)ccc2[nH]1] |
| 85 | 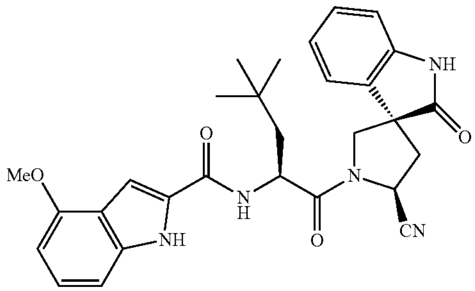 [SMILES: COc1cccc2[nH]c(C(=O)N[C@@H](CC(C)(C)C)C(=O)N3C[C@]4(C[C@H]3C#N)C(=O)Nc3ccccc34)cc12] |

-continued
| Compound | Structure |
|---|---|
| 86 | 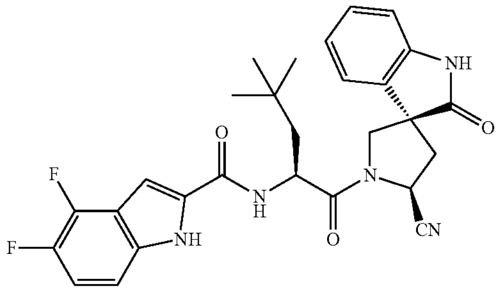 [SMILES: CC(C)(C)C[C@H](NC(=O)c1cc2c(F)c(F)ccc2[nH]1)C(=O)N1C[C@]2(C[C@H]1C#N)C(=O)Nc1ccccc12] |
| 87 | 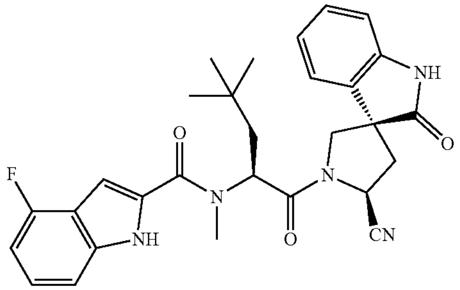 [SMILES: CN(C(=O)c1cc2c(F)cccc2[nH]1)[C@@H](CC(C)(C)C)C(=O)N1C[C@]2(C[C@H]1C#N)C(=O)Nc1ccccc12] |
| 88 | 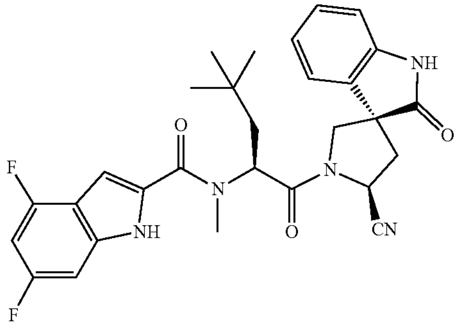 [SMILES: CN(C(=O)c1cc2c(F)cc(F)cc2[nH]1)[C@@H](CC(C)(C)C)C(=O)N1C[C@]2(C[C@H]1C#N)C(=O)Nc1ccccc12] |
| 89 | 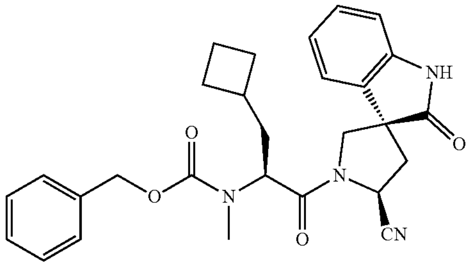 [SMILES: CN(C(=O)OCc1ccccc1)[C@@H](CC1CCC1)C(=O)N1C[C@]2(C[C@H]1C#N)C(=O)Nc1ccccc12] |
| 90 | 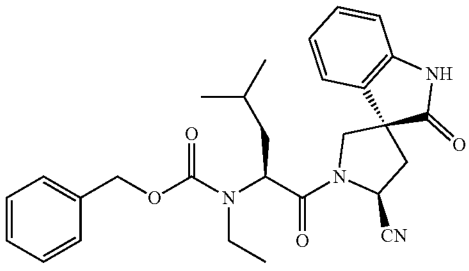 [SMILES: CCN(C(=O)OCc1ccccc1)[C@@H](CC(C)C)C(=O)N1C[C@]2(C[C@H]1C#N)C(=O)Nc1ccccc12] |

-continued
| Compound | Structure |
|---|---|
| 91 | 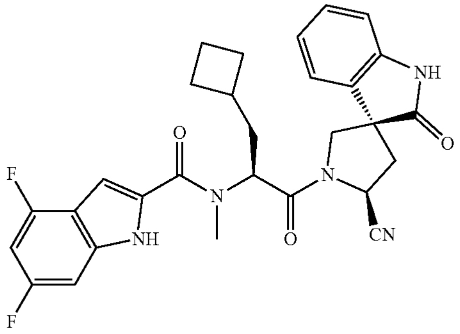 [SMILES: CN(C(=O)c1cc2c(F)cc(F)cc2[nH]1)[C@@H](CC1CCC1)C(=O)N1C[C@]2(C[C@H]1C#N)C(=O)Nc1ccccc12] |
| 92 | 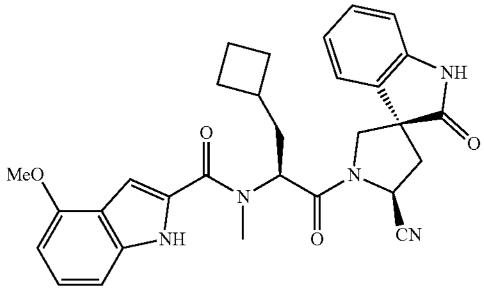 [SMILES: COc1cccc2[nH]c(C(=O)N(C)[C@@H](CC3CCC3)C(=O)N3C[C@]4(C[C@H]3C#N)C(=O)Nc3ccccc34)cc12] |
| 93 | 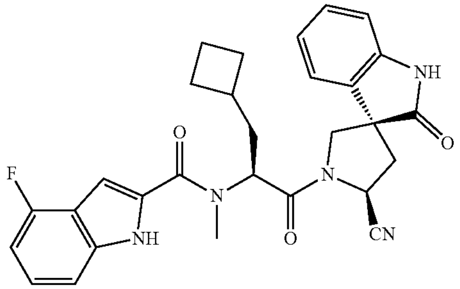 [SMILES: CN(C(=O)c1cc2c(F)cccc2[nH]1)[C@@H](CC1CCC1)C(=O)N1C[C@]2(C[C@H]1C#N)C(=O)Nc1ccccc12] |
| 94 | 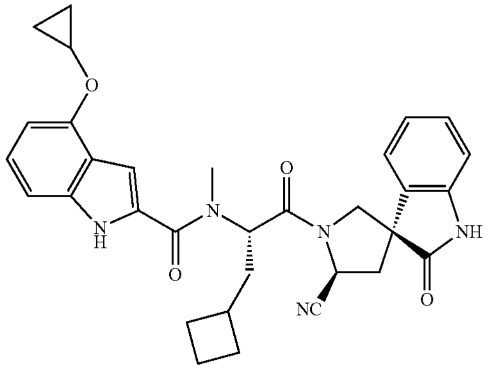 [SMILES: CN(C(=O)c1cc2c(OC3CC3)cccc2[nH]1)[C@@H](CC1CCC1)C(=O)N1C[C@]2(C[C@H]1C#N)C(=O)Nc1ccccc12] |
| 95 | 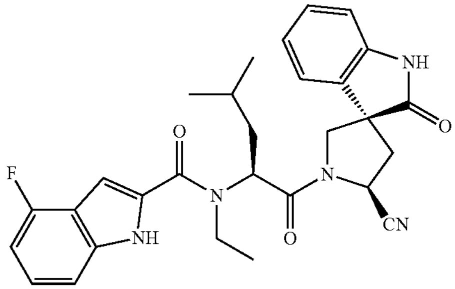 [SMILES: CCN(C(=O)c1cc2c(F)cccc2[nH]1)[C@@H](CC(C)C)C(=O)N1C[C@]2(C[C@H]1C#N)C(=O)Nc1ccccc12] |

-continued
| Compound | Structure |
|---|---|
| 96 | 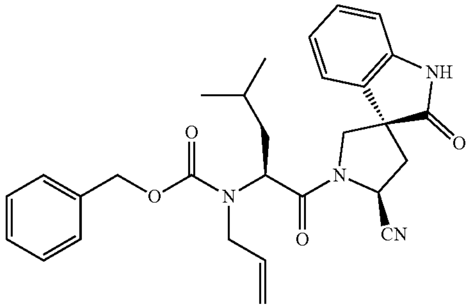 [SMILES: C=CCN(C(=O)OCc1ccccc1)[C@@H](CC(C)C)C(=O)N1C[C@]2(C[C@H]1C#N)C(=O)Nc1ccccc12] |
| 97 | 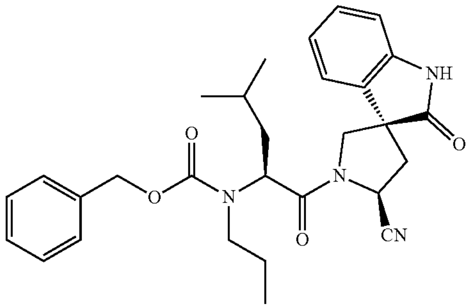 [SMILES: CCCN(C(=O)OCc1ccccc1)[C@@H](CC(C)C)C(=O)N1C[C@]2(C[C@H]1C#N)C(=O)Nc1ccccc12] |
| 98 | 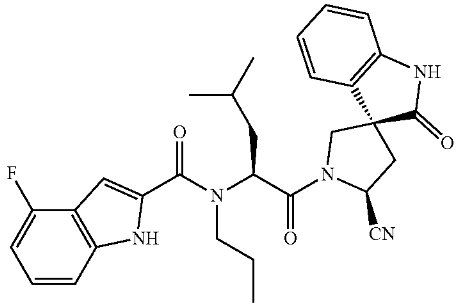 [SMILES: CCCN(C(=O)c1cc2c(F)cccc2[nH]1)[C@@H](CC(C)C)C(=O)N1C[C@]2(C[C@H]1C#N)C(=O)Nc1ccccc12] |
| 99 | 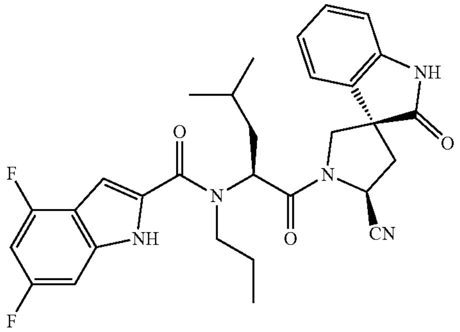 [SMILES: CCCN(C(=O)c1cc2c(F)cc(F)cc2[nH]1)[C@@H](CC(C)C)C(=O)N1C[C@]2(C[C@H]1C#N)C(=O)Nc1ccccc12] |
| 100 | 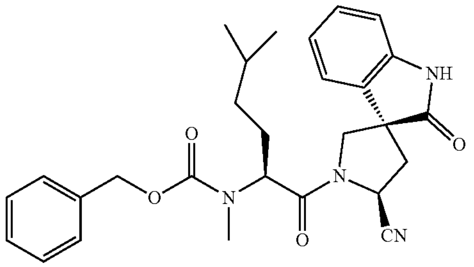 [SMILES: CC(C)CC[C@@H](C(=O)N1C[C@]2(C[C@H]1C#N)C(=O)Nc1ccccc12)N(C)C(=O)OCc1ccccc1] |

-continued
| Compound | Structure |
| --- | --- |
| 101 | 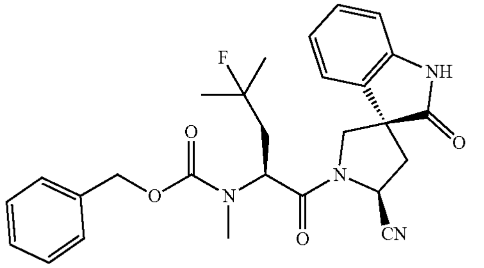 [SMILES: CN(C(=O)OCc1ccccc1)[C@@H](CC(C)(C)F)C(=O)N1C[C@]2(C[C@H]1C#N)C(=O)Nc1ccccc12] |
| 102 | 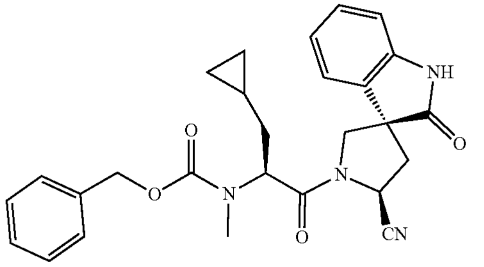 [SMILES: CN(C(=O)OCc1ccccc1)[C@@H](CC1CC1)C(=O)N1C[C@]2(C[C@H]1C#N)C(=O)Nc1ccccc12] |
| 103 | 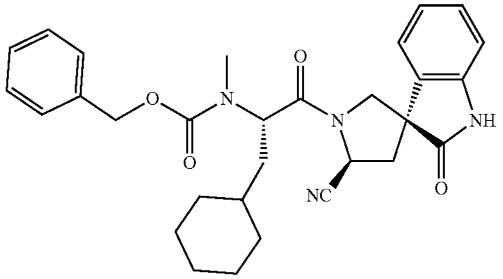 [SMILES: CN(C(=O)OCc1ccccc1)[C@@H](CC1CCCCC1)C(=O)N1C[C@]2(C[C@H]1C#N)C(=O)Nc1ccccc12] |
| 104 | 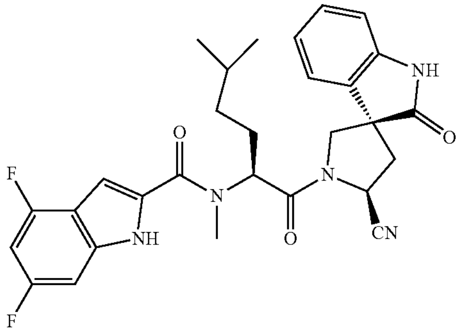 [SMILES: CC(C)CC[C@@H](C(=O)N1C[C@]2(C[C@H]1C#N)C(=O)Nc1ccccc12)N(C)C(=O)c1cc2c(F)cc(F)cc2[nH]1] |
| 105 | 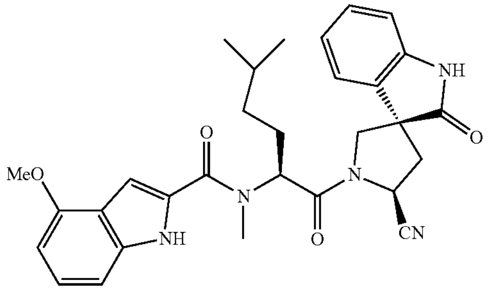 [SMILES: COc1cccc2[nH]c(C(=O)N(C)[C@@H](CCC(C)C)C(=O)N3C[C@]4(C[C@H]3C#N)C(=O)Nc3ccccc34)cc12] |

-continued
| Compound | Structure |
|---|---|
| 106 | 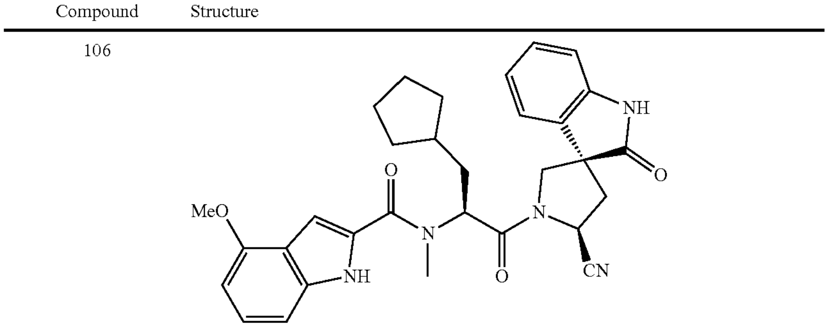 |
| 107 | 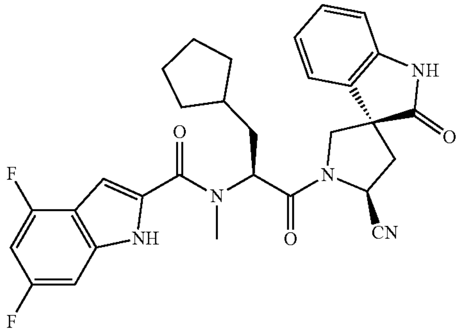 [SMILES: CN(C(=O)c1cc2c(F)cc(F)cc2[nH]1)[C@@H](CC1CCCC1)C(=O)N1C[C@]2(C[C@H]1C#N)C(=O)Nc1ccccc12] |
| 108 | 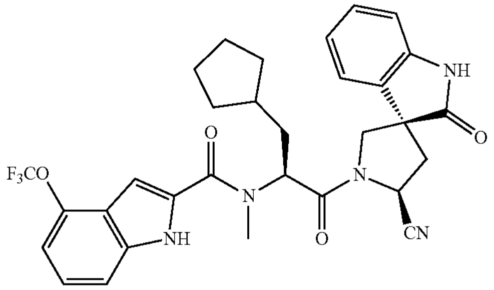 [SMILES: CN(C(=O)c1cc2c(OC(F)(F)F)cccc2[nH]1)[C@@H](CC1CCCC1)C(=O)N1C[C@]2(C[C@H]1C#N)C(=O)Nc1ccccc12] |
| 109 | 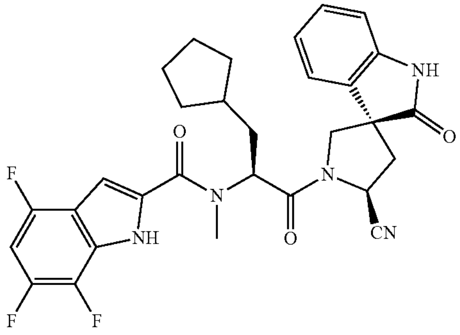 [SMILES: CN(C(=O)c1cc2c(F)cc(F)c(F)c2[nH]1)[C@@H](CC1CCCC1)C(=O)N1C[C@]2(C[C@H]1C#N)C(=O)Nc1ccccc12] |
| 110 | 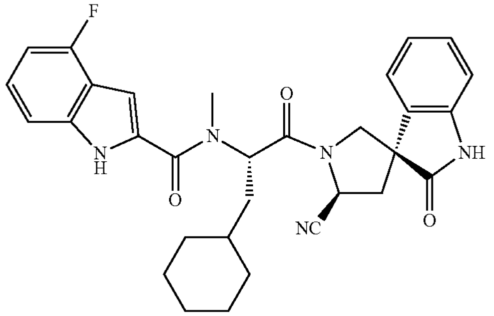 [SMILES: CN(C(=O)c1cc2c(F)cccc2[nH]1)[C@@H](CC1CCCCC1)C(=O)N1C[C@]2(C[C@H]1C#N)C(=O)Nc1ccccc12] |

-continued
| Compound | Structure |
|---|---|
| 111 | 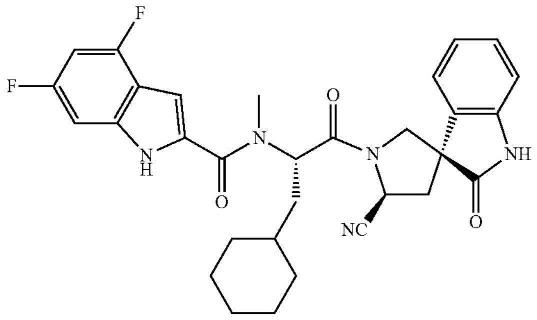 [SMILES: CN(C(=O)c1cc2c(F)cc(F)cc2[nH]1)[C@@H](CC1CCCCC1)C(=O)N1C[C@]2(C[C@H]1C#N)C(=O)Nc1ccccc12] |
| 112 | 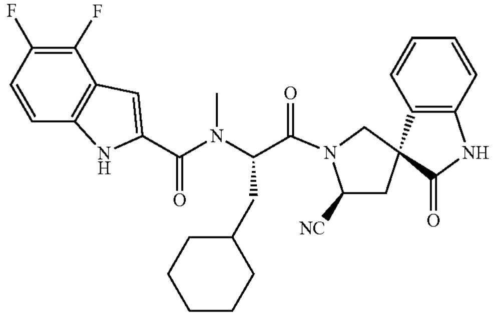 [SMILES: CN(C(=O)c1cc2c(F)c(F)ccc2[nH]1)[C@@H](CC1CCCCC1)C(=O)N1C[C@]2(C[C@H]1C#N)C(=O)Nc1ccccc12] |
| 113 | 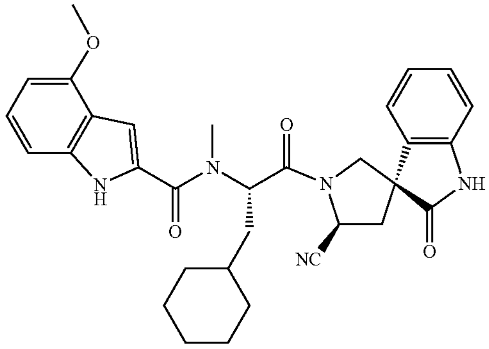 [SMILES: COc1cccc2[nH]c(C(=O)N(C)[C@@H](CC3CCCCC3)C(=O)N3C[C@]4(C[C@H]3C#N)C(=O)Nc3ccccc34)cc12] |
| 114 | 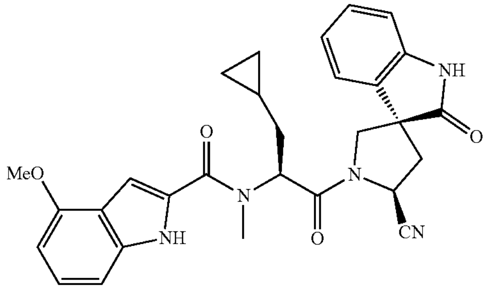 [SMILES: COc1cccc2[nH]c(C(=O)N(C)[C@@H](CC3CC3)C(=O)N3C[C@]4(C[C@H]3C#N)C(=O)Nc3ccccc34)cc12] |

-continued
| Compound | Structure |
|---|---|
| 115 | 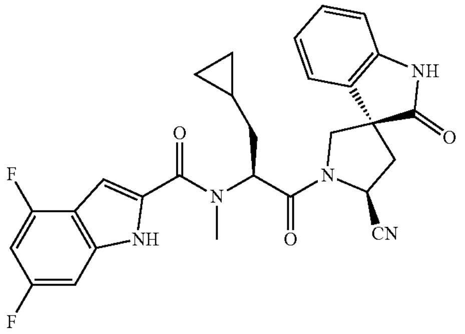 [SMILES: CN(C(=O)c1cc2c(F)cc(F)cc2[nH]1)[C@@H](CC1CC1)C(=O)N1C[C@]2(C[C@H]1C#N)C(=O)Nc1ccccc12] |
| 116 | 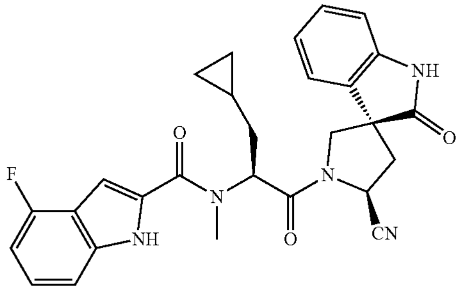 [SMILES: CN(C(=O)c1cc2c(F)cccc2[nH]1)[C@@H](CC1CC1)C(=O)N1C[C@]2(C[C@H]1C#N)C(=O)Nc1ccccc12] |
| 117 | 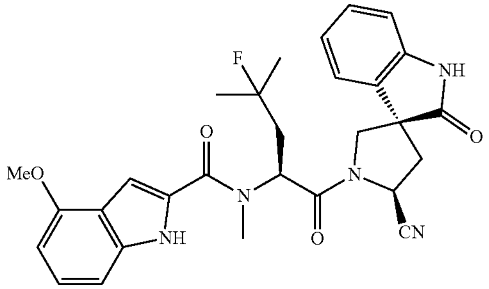 [SMILES: COc1cccc2[nH]c(C(=O)N(C)[C@@H](CC(C)(C)F)C(=O)N3C[C@]4(C[C@H]3C#N)C(=O)Nc3ccccc34)cc12] |
| 118 | 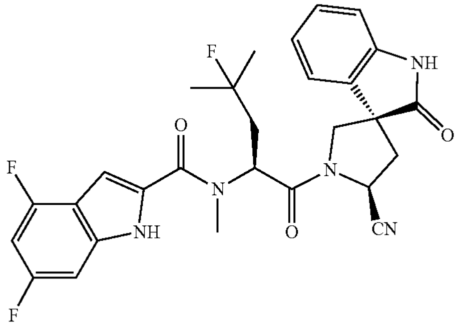 |
| 119 | 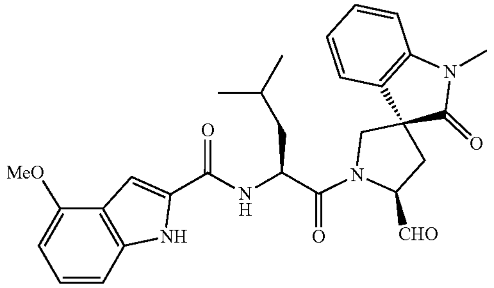 [SMILES: COc1cccc2[nH]c(C(=O)N[C@@H](CC(C)C)C(=O)N3C[C@]4(C[C@H]3C=O)C(=O)N(C)c3ccccc34)cc12] |

-continued
| Compound | Structure |
| --- | --- |
| 120 | 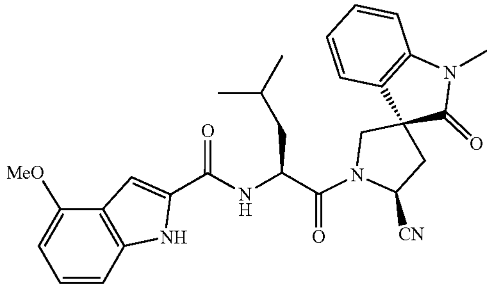 [SMILES: COc1cccc2[nH]c(C(=O)N[C@@H](CC(C)C)C(=O)N3C[C@]4(C[C@H]3C#N)C(=O)N(C)c3ccccc34)cc12] |
| 121 | 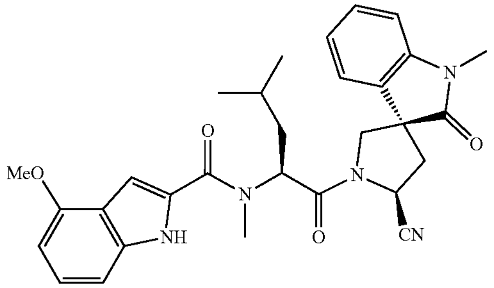 [SMILES: COc1cccc2[nH]c(C(=O)N(C)[C@@H](CC(C)C)C(=O)N3C[C@]4(C[C@H]3C#N)C(=O)N(C)c3ccccc34)cc12] |
| 122 | 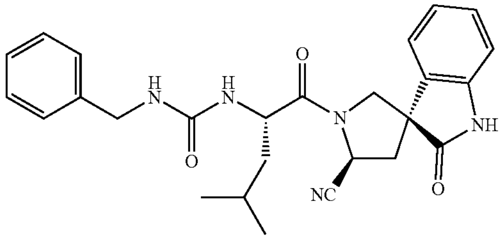 [SMILES: CC(C)C[C@H](NC(=O)NCc1ccccc1)C(=O)N1C[C@]2(C[C@H]1C#N)C(=O)Nc1ccccc12] |
| 123 | 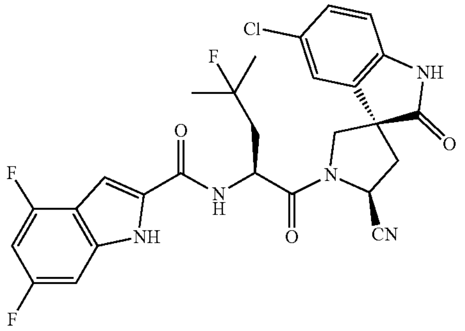 [SMILES: CC(C)(F)C[C@H](NC(=O)c1cc2c(F)cc(F)cc2[nH]1)C(=O)N1C[C@]2(C[C@H]1C#N)C(=O)Nc1ccc(Cl)cc12] |
| 124 | 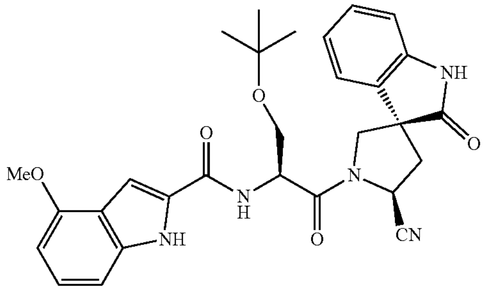 [SMILES: COc1cccc2[nH]c(C(=O)N[C@@H](COC(C)(C)C)C(=O)N3C[C@]4(C[C@H]3C#N)C(=O)Nc3ccccc34)cc12] |

-continued
| Compound | Structure |
|---|---|
| 125 | 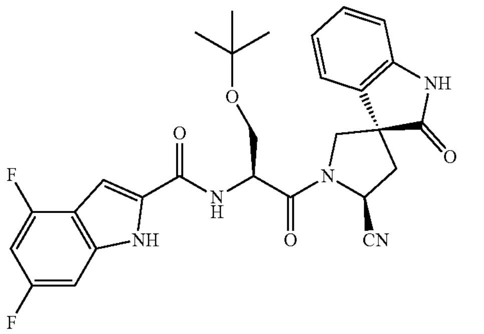 [SMILES: CC(C)(C)OC[C@H](NC(=O)c1cc2c(F)cc(F)cc2[nH]1)C(=O)N1C[C@]2(C[C@H]1C#N)C(=O)Nc1ccccc12] |
| 126 | 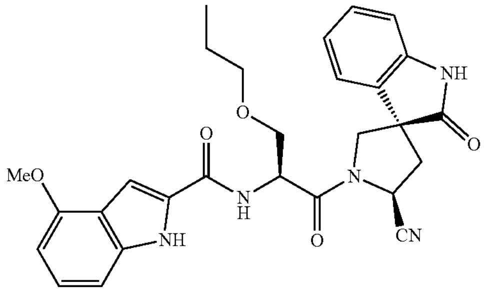 [SMILES: CCCOC[C@H](NC(=O)c1cc2c(OC)cccc2[nH]1)C(=O)N1C[C@]2(C[C@H]1C#N)C(=O)Nc1ccccc12] |
| 127 | 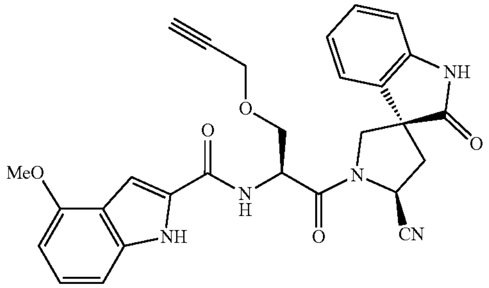 [SMILES: C#CCOC[C@H](NC(=O)c1cc2c(OC)cccc2[nH]1)C(=O)N1C[C@]2(C[C@H]1C#N)C(=O)Nc1ccccc12] |
| 128 | 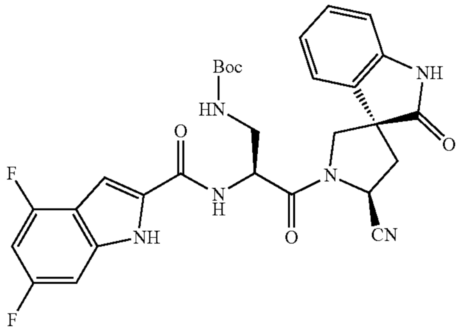 [SMILES: CC(C)(C)OC(=O)NC[C@H](NC(=O)c1cc2c(F)cc(F)cc2[nH]1)C(=O)N1C[C@]2(C[C@H]1C#N)C(=O)Nc1ccccc12] |

-continued
| Compound | Structure |
| --- | --- |
| 129 | 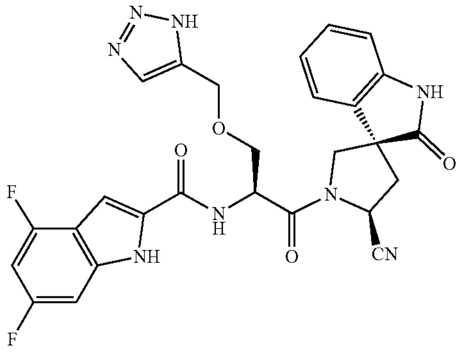 [SMILES: N#C[C@@H]1C[C@@]2(CN1C(=O)[C@H](COCc1cnn[nH]1)NC(=O)c1cc3c(F)cc(F)cc3[nH]1)C(=O)Nc1ccccc12] |
| 130 | 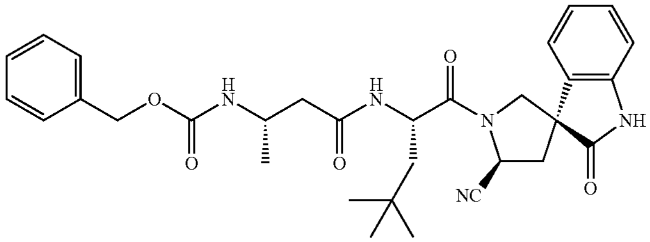 [SMILES: C[C@@H](CC(=O)N[C@@H](CC(C)(C)C)C(=O)N1C[C@]2(C[C@H]1C#N)C(=O)Nc1ccccc12)NC(=O)OCc1ccccc1] |
| 131 | 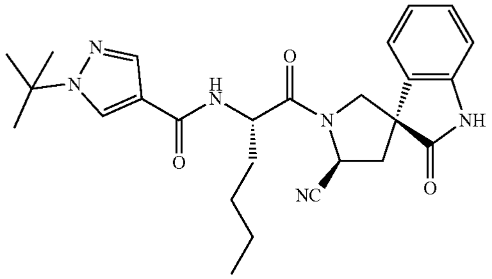 [SMILES: CCCC[C@H](NC(=O)c1cnn(C(C)(C)C)c1)C(=O)N1C[C@]2(C[C@H]1C#N)C(=O)Nc1ccccc12] |
| 132 | 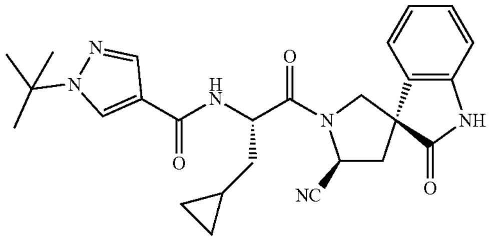 [SMILES: CC(C)(C)n1cc(C(=O)N[C@@H](CC2CC2)C(=O)N2C[C@]3(C[C@H]2C#N)C(=O)Nc2ccccc23)cn1] |
| 133 | 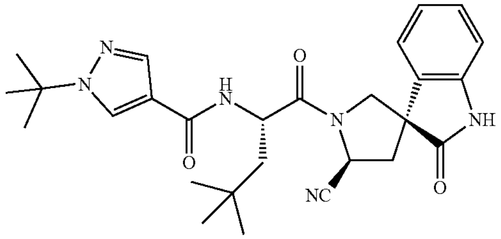 [SMILES: CC(C)(C)C[C@H](NC(=O)c1cnn(C(C)(C)C)c1)C(=O)N1C[C@]2(C[C@H]1C#N)C(=O)Nc1ccccc12] |

-continued
| Compound | Structure |
| --- | --- |
| 134 | 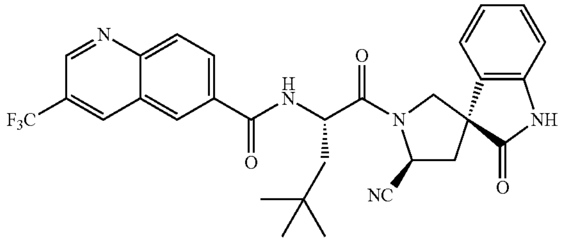 [SMILES: CC(C)(C)C[C@H](NC(=O)c1ccc2ncc(C(F)(F)F)cc2c1)C(=O)N1C[C@]2(C[C@H]1C#N)C(=O)Nc1ccccc12] |
| 135 | 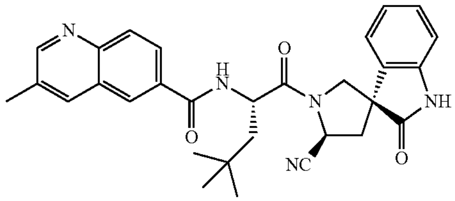 [SMILES: Cc1cnc2ccc(C(=O)N[C@@H](CC(C)(C)C)C(=O)N3C[C@]4(C[C@H]3C#N)C(=O)Nc3ccccc34)cc2c1] |
| 136 | 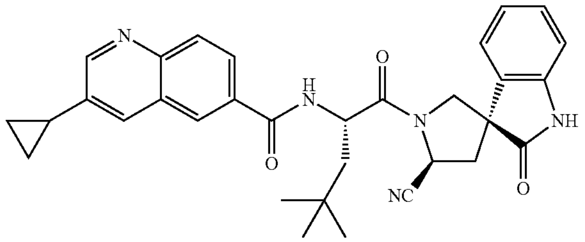 [SMILES: CC(C)(C)C[C@H](NC(=O)c1ccc2ncc(C3CC3)cc2c1)C(=O)N1C[C@]2(C[C@H]1C#N)C(=O)Nc1ccccc12] |
| 137 | 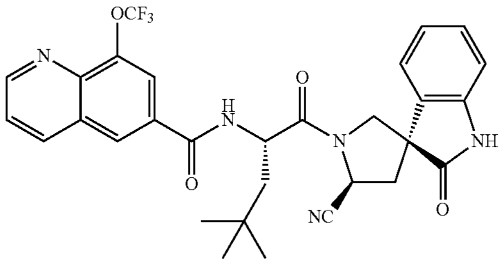 [SMILES: CC(C)(C)C[C@H](NC(=O)c1cc(OC(F)(F)F)c2ncccc2c1)C(=O)N1C[C@]2(C[C@H]1C#N)C(=O)Nc1ccccc12] |
| 138 | 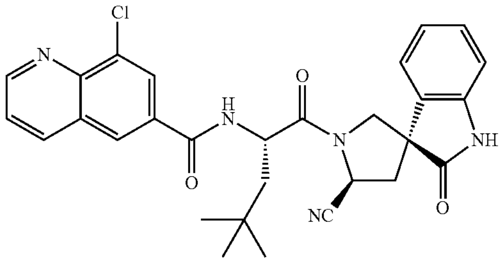 [SMILES: CC(C)(C)C[C@H](NC(=O)c1cc(Cl)c2ncccc2c1)C(=O)N1C[C@]2(C[C@H]1C#N)C(=O)Nc1ccccc12] |
| 139 | 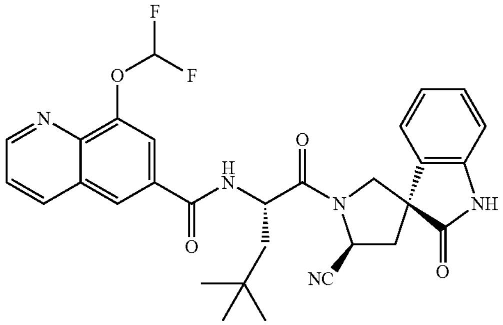 [SMILES: CC(C)(C)C[C@H](NC(=O)c1cc(OC(F)F)c2ncccc2c1)C(=O)N1C[C@]2(C[C@H]1C#N)C(=O)Nc1ccccc12] |

-continued
| Compound | Structure |
| --- | --- |
| 140 | 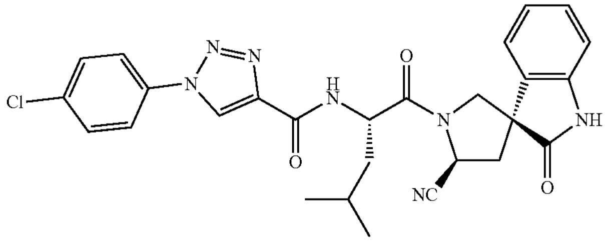 [SMILES: CC(C)C[C@H](NC(=O)c1cn(-c2ccc(Cl)cc2)nn1)C(=O)N1C[C@]2(C[C@H]1C#N)C(=O)Nc1ccccc12] |
| 141 | 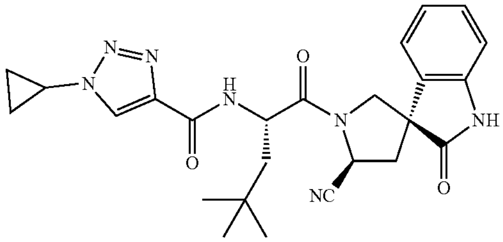 [SMILES: CC(C)(C)C[C@H](NC(=O)c1cn(C2CC2)nn1)C(=O)N1C[C@]2(C[C@H]1C#N)C(=O)Nc1ccccc12] |
| 142 | 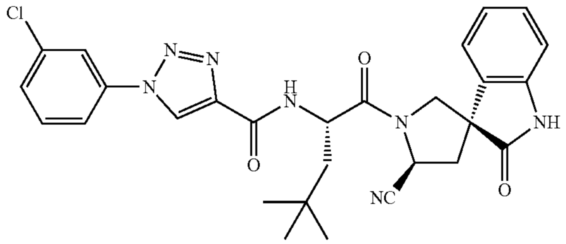 [SMILES: CC(C)(C)C[C@H](NC(=O)c1cn(-c2cccc(Cl)c2)nn1)C(=O)N1C[C@]2(C[C@H]1C#N)C(=O)Nc1ccccc12] |
| 143 | 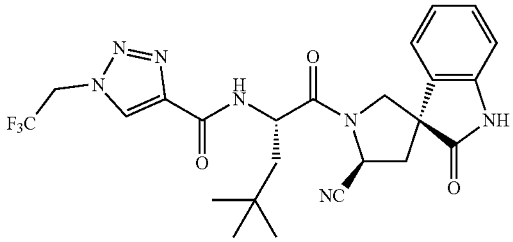 [SMILES: CC(C)(C)C[C@H](NC(=O)c1cn(CC(F)(F)F)nn1)C(=O)N1C[C@]2(C[C@H]1C#N)C(=O)Nc1ccccc12] |
| 144 | 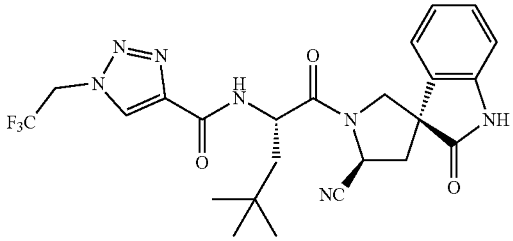 [SMILES: CC(C)(C)C[C@H](NC(=O)c1cn(CC(F)(F)F)nn1)C(=O)N1C[C@]2(C[C@H]1C#N)C(=O)Nc1ccccc12] |
| 145 | 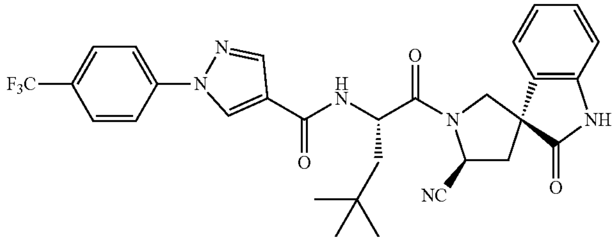 [SMILES: CC(C)(C)C[C@H](NC(=O)c1cnn(-c2ccc(C(F)(F)F)cc2)c1)C(=O)N1C[C@]2(C[C@H]1C#N)C(=O)Nc1ccccc12] |

-continued
| Compound | Structure |
|---|---|
| 146 | 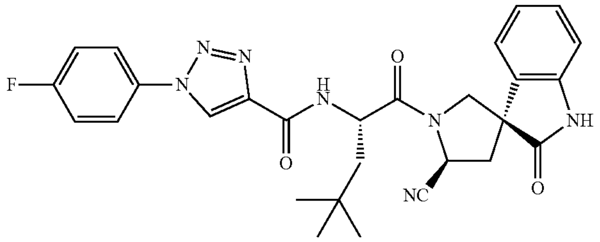 [SMILES: CC(C)(C)C[C@H](NC(=O)c1cn(-c2ccc(F)cc2)nn1)C(=O)N1C[C@]2(C[C@H]1C#N)C(=O)Nc1ccccc12] |
| 147 | 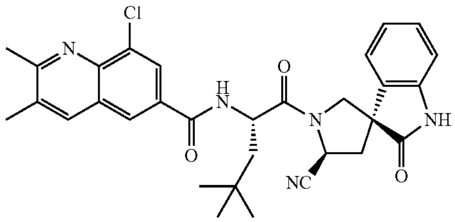 [SMILES: Cc1cc2cc(C(=O)N[C@@H](CC(C)(C)C)C(=O)N3C[C@]4(C[C@H]3C#N)C(=O)Nc3ccccc34)cc(Cl)c2nc1C] |
| 148 | 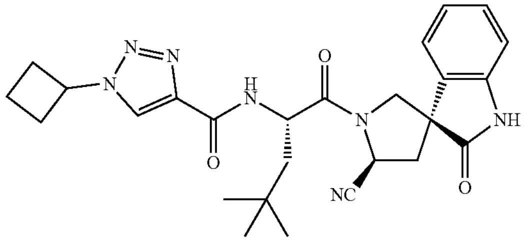 [SMILES: CC(C)(C)C[C@H](NC(=O)c1cn(C2CCC2)nn1)C(=O)N1C[C@]2(C[C@H]1C#N)C(=O)Nc1ccccc12] |
| 149 | 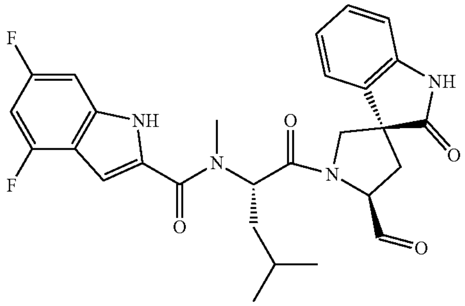 [SMILES: CC(C)C[C@@H](C(=O)N1C[C@]2(C[C@H]1C=O)C(=O)Nc1ccccc12)N(C)C(=O)c1cc2c(F)cc(F)cc2[nH]1] |
| 150 | 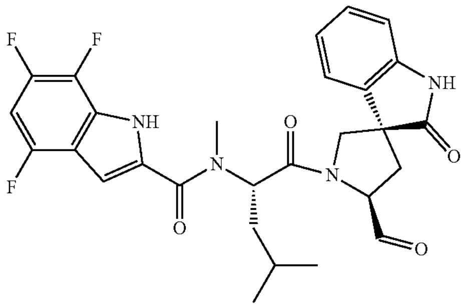 [SMILES: CC(C)C[C@@H](C(=O)N1C[C@]2(C[C@H]1C=O)C(=O)Nc1ccccc12)N(C)C(=O)c1cc2c(F)cc(F)c(F)c2[nH]1] |

-continued
| Compound | Structure |
|---|---|
| 151 | 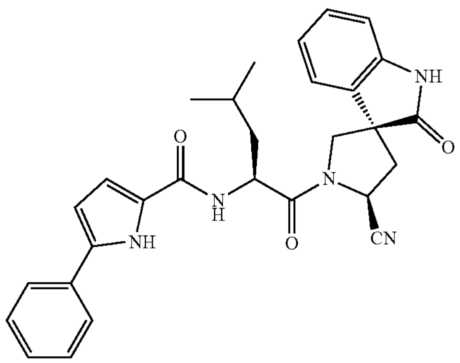 [SMILES: CC(C)C[C@H](NC(=O)c1ccc(-c2ccccc2)[nH]1)C(=O)N1C[C@]2(C[C@H]1C#N)C(=O)Nc1ccccc12] |
| 152 | 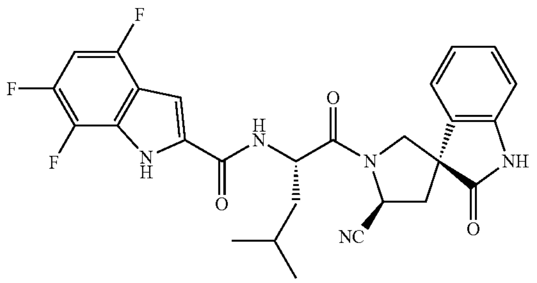 [SMILES: CC(C)C[C@H](NC(=O)c1cc2c(F)cc(F)c(F)c2[nH]1)C(=O)N1C[C@]2(C[C@H]1C#N)C(=O)Nc1ccccc12] |
| 153 | 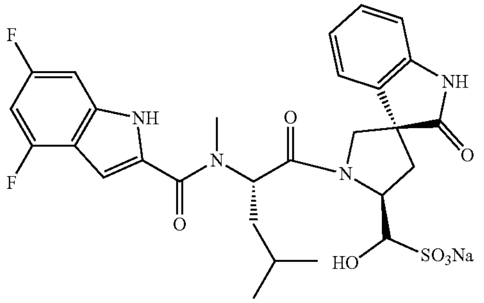 |
| 154 | 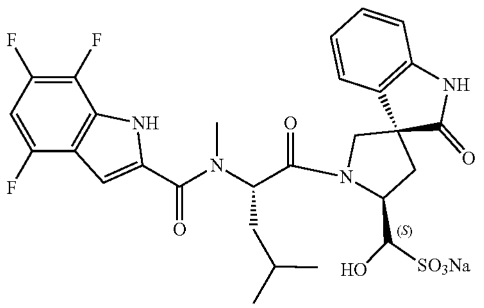 |

-continued
| Compound | Structure |
|---|---|
| 155 | 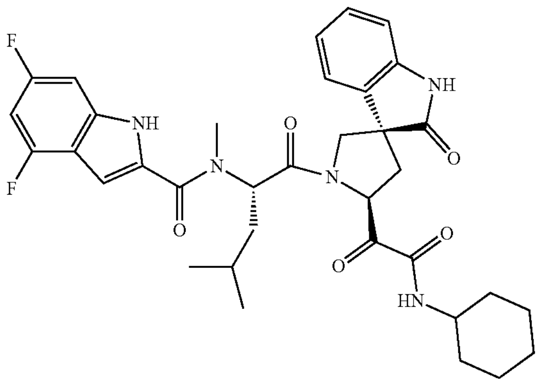 [SMILES: CC(C)C[C@@H](C(=O)N1C[C@]2(C[C@H]1C(=O)C(=O)NC1CCCCC1)C(=O)Nc1ccccc12)N(C)C(=O)c1cc2c(F)cc(F)cc2[nH]1] |
| 156 | 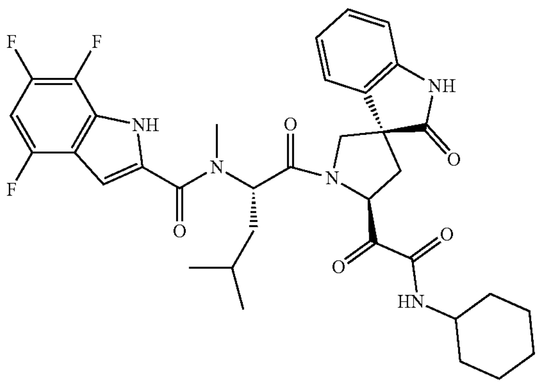 [SMILES: CC(C)C[C@@H](C(=O)N1C[C@]2(C[C@H]1C(=O)C(=O)NC1CCCCC1)C(=O)Nc1ccccc12)N(C)C(=O)c1cc2c(F)cc(F)c(F)c2[nH]1] |
| 157 | 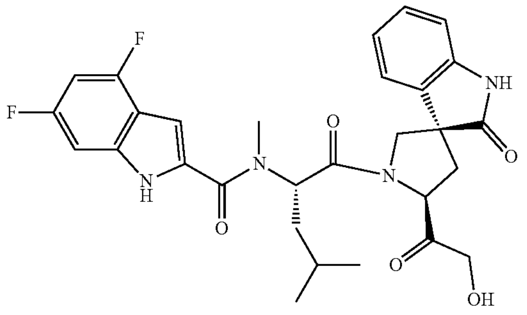 [SMILES: CC(C)C[C@@H](C(=O)N1C[C@]2(C[C@H]1C(=O)CO)C(=O)Nc1ccccc12)N(C)C(=O)c1cc2c(F)cc(F)cc2[nH]1] |
| 158 | 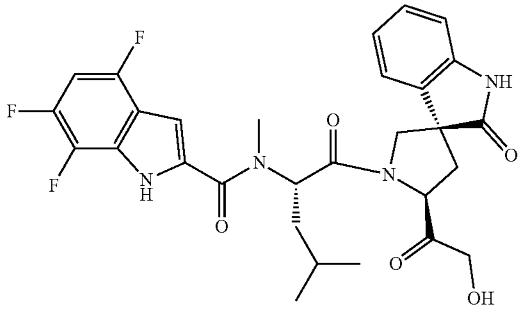 |

-continued
| Compound | Structure |
|---|---|
| 159 | 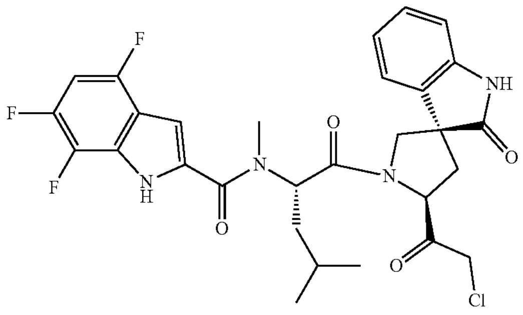 [SMILES: CC(C)C[C@@H](C(=O)N1C[C@]2(C[C@H]1C(=O)CCl)C(=O)Nc1ccccc12)N(C)C(=O)c1cc2c(F)cc(F)c(F)c2[nH]1] |
| 160 | 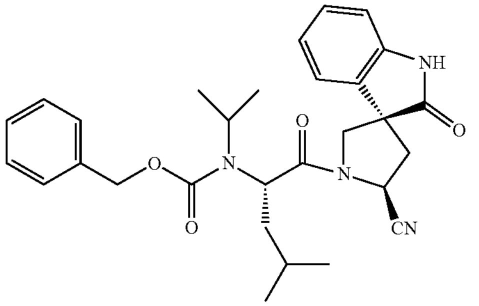 [SMILES: CC(C)C[C@@H](C(=O)N1C[C@]2(C[C@H]1C#N)C(=O)Nc1ccccc12)N(C(=O)OCc1ccccc1)C(C)C] |
| 161 | 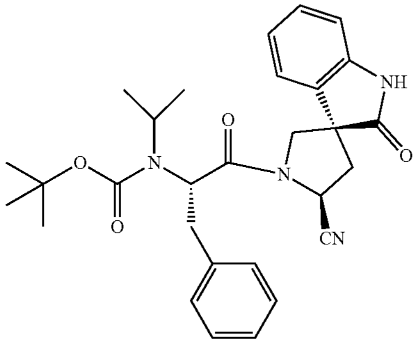 [SMILES: CC(C)N(C(=O)OC(C)(C)C)[C@@H](Cc1ccccc1)C(=O)N1C[C@]2(C[C@H]1C#N)C(=O)Nc1ccccc12] |
| 162 | 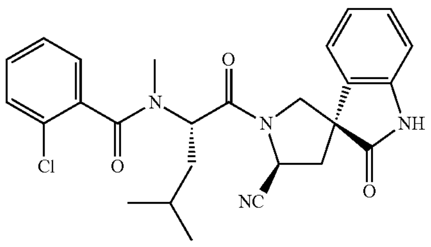 [SMILES: CC(C)C[C@@H](C(=O)N1C[C@]2(C[C@H]1C#N)C(=O)Nc1ccccc12)N(C)C(=O)c1ccccc1Cl] |
| 163 | 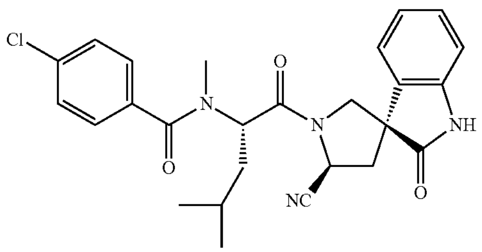 [SMILES: CC(C)C[C@@H](C(=O)N1C[C@]2(C[C@H]1C#N)C(=O)Nc1ccccc12)N(C)C(=O)c1ccc(Cl)cc1] |

-continued
| Compound | Structure |
| --- | --- |
| 164 | 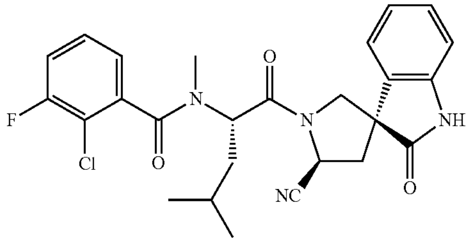 [SMILES: CC(C)C[C@@H](C(=O)N1C[C@]2(C[C@H]1C#N)C(=O)Nc1ccccc12)N(C)C(=O)c1cccc(F)c1Cl] |
| 165 | 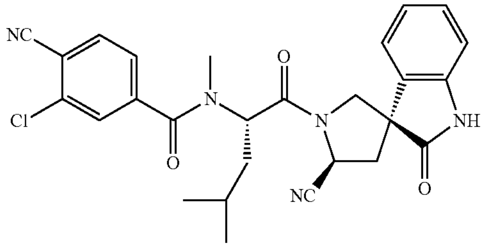 [SMILES: CC(C)C[C@@H](C(=O)N1C[C@]2(C[C@H]1C#N)C(=O)Nc1ccccc12)N(C)C(=O)c1ccc(C#N)c(Cl)c1] |
| 166 | 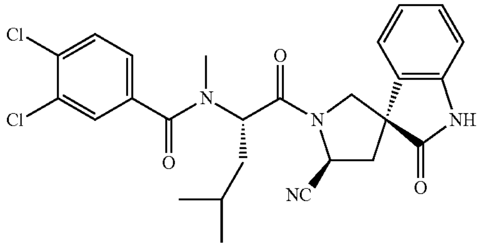 [SMILES: CC(C)C[C@@H](C(=O)N1C[C@]2(C[C@H]1C#N)C(=O)Nc1ccccc12)N(C)C(=O)c1ccc(Cl)c(Cl)c1] |
| 167 | 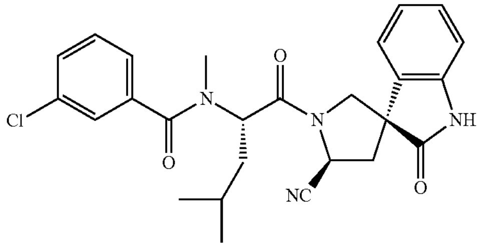 [SMILES: CC(C)C[C@@H](C(=O)N1C[C@]2(C[C@H]1C#N)C(=O)Nc1ccccc12)N(C)C(=O)c1cccc(Cl)c1] |
| 168 | 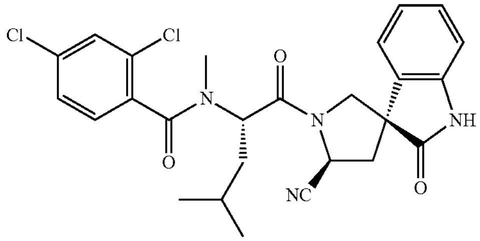 [SMILES: CC(C)C[C@@H](C(=O)N1C[C@]2(C[C@H]1C#N)C(=O)Nc1ccccc12)N(C)C(=O)c1ccc(Cl)cc1Cl] |
| 169 | 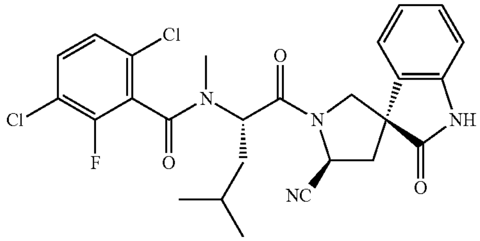 [SMILES: CC(C)C[C@@H](C(=O)N1C[C@]2(C[C@H]1C#N)C(=O)Nc1ccccc12)N(C)C(=O)c1c(Cl)ccc(Cl)c1F] |

-continued
| Compound | Structure |
|---|---|
| 170 | 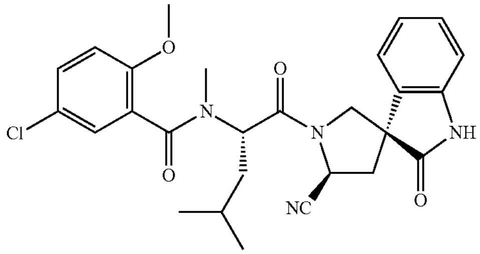 [SMILES: COc1ccc(Cl)cc1C(=O)N(C)[C@@H](CC(C)C)C(=O)N1C[C@]2(C[C@H]1C#N)C(=O)Nc1ccccc12] |
| 171 | 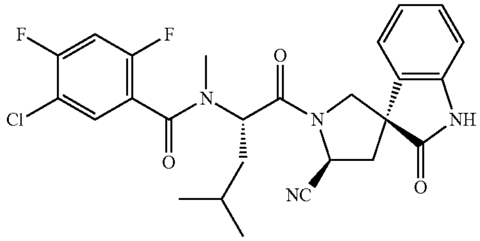 [SMILES: CC(C)C[C@@H](C(=O)N1C[C@]2(C[C@H]1C#N)C(=O)Nc1ccccc12)N(C)C(=O)c1cc(Cl)c(F)cc1F] |
| 172 | 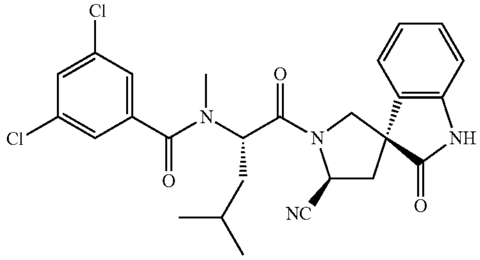 [SMILES: CC(C)C[C@@H](C(=O)N1C[C@]2(C[C@H]1C#N)C(=O)Nc1ccccc12)N(C)C(=O)c1cc(Cl)cc(Cl)c1] |
| 173 | 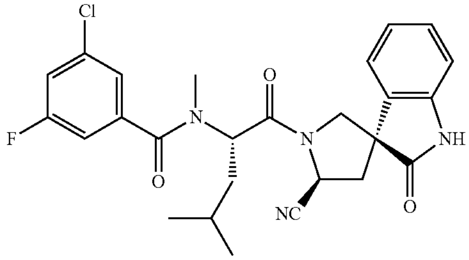 [SMILES: CC(C)C[C@@H](C(=O)N1C[C@]2(C[C@H]1C#N)C(=O)Nc1ccccc12)N(C)C(=O)c1cc(F)cc(Cl)c1] |
| 174 | 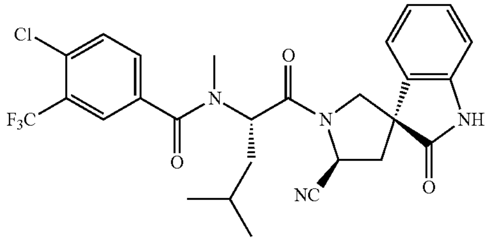 [SMILES: CC(C)C[C@@H](C(=O)N1C[C@]2(C[C@H]1C#N)C(=O)Nc1ccccc12)N(C)C(=O)c1ccc(Cl)c(C(F)(F)F)c1] |
| 175 | 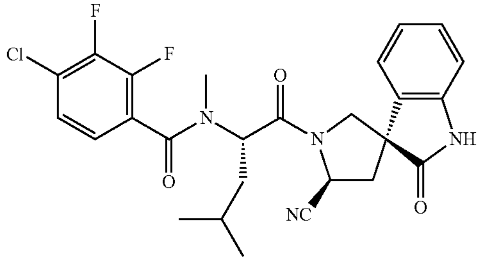 [SMILES: CC(C)C[C@@H](C(=O)N1C[C@]2(C[C@H]1C#N)C(=O)Nc1ccccc12)N(C)C(=O)c1ccc(Cl)c(F)c1F] |

-continued
| Compound | Structure |
|---|---|
| 176 | 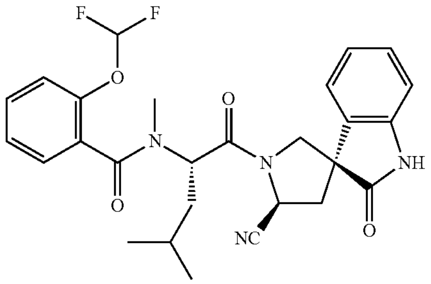 [SMILES: CC(C)C[C@@H](C(=O)N1C[C@]2(C[C@H]1C#N)C(=O)Nc1ccccc12)N(C)C(=O)c1ccccc1OC(F)F] |
| 177 | 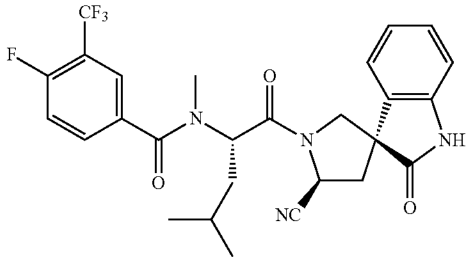 [SMILES: CC(C)C[C@@H](C(=O)N1C[C@]2(C[C@H]1C#N)C(=O)Nc1ccccc12)N(C)C(=O)c1ccc(F)c(C(F)(F)F)c1] |
| 178 | 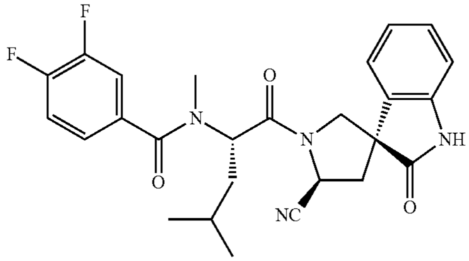 [SMILES: CC(C)C[C@@H](C(=O)N1C[C@]2(C[C@H]1C#N)C(=O)Nc1ccccc12)N(C)C(=O)c1ccc(F)c(F)c1] |
| 179 | 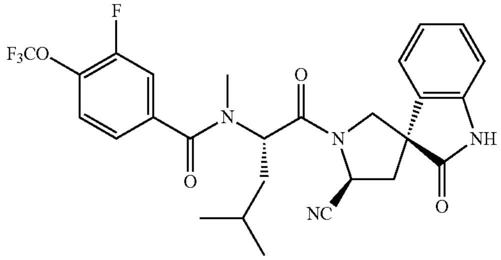 [SMILES: CC(C)C[C@@H](C(=O)N1C[C@]2(C[C@H]1C#N)C(=O)Nc1ccccc12)N(C)C(=O)c1ccc(OC(F)(F)F)c(F)c1] |
| 180 | 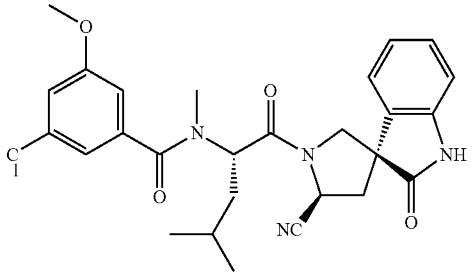 [SMILES: COc1cc(Cl)cc(C(=O)N(C)[C@@H](CC(C)C)C(=O)N2C[C@]3(C[C@H]2C#N)C(=O)Nc2ccccc23)c1] |

-continued
| Compound | Structure |
| --- | --- |
| 181 | 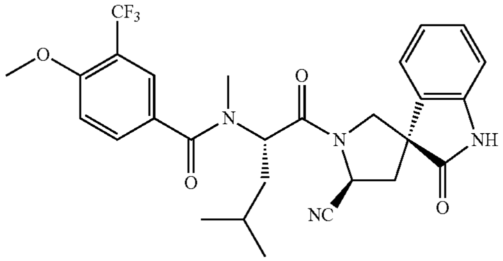 [SMILES: COc1ccc(C(=O)N(C)[C@@H](CC(C)C)C(=O)N2C[C@]3(C[C@H]2C#N)C(=O)Nc2ccccc23)cc1C(F)(F)F] |
| 182 | 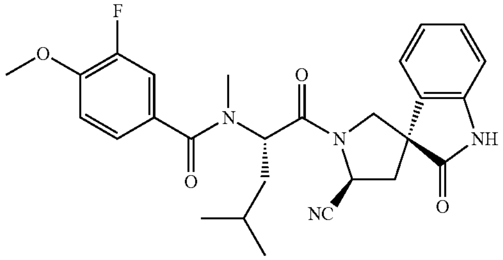 [SMILES: COc1ccc(C(=O)N(C)[C@@H](CC(C)C)C(=O)N2C[C@]3(C[C@H]2C#N)C(=O)Nc2ccccc23)cc1F] |
| 183 | 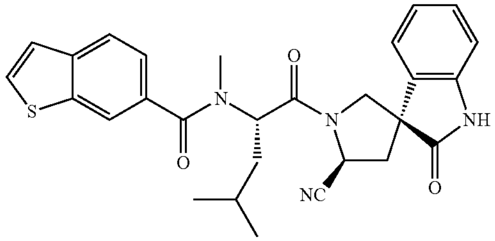 [SMILES: CC(C)C[C@@H](C(=O)N1C[C@]2(C[C@H]1C#N)C(=O)Nc1ccccc12)N(C)C(=O)c1ccc2ccsc2c1] |
| 184 | 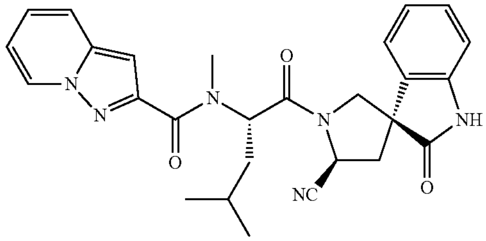 [SMILES: CC(C)C[C@@H](C(=O)N1C[C@]2(C[C@H]1C#N)C(=O)Nc1ccccc12)N(C)C(=O)c1cc2ccccn2n1] |
| 185 | 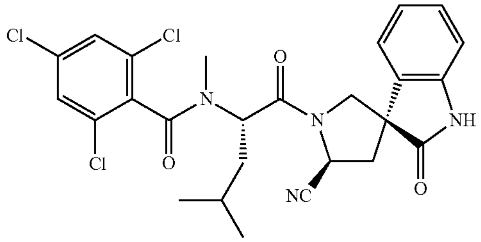 [SMILES: CC(C)C[C@@H](C(=O)N1C[C@]2(C[C@H]1C#N)C(=O)Nc1ccccc12)N(C)C(=O)c1c(Cl)cc(Cl)cc1Cl] |
| 186 | 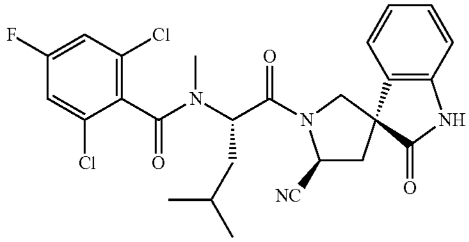 [SMILES: CC(C)C[C@@H](C(=O)N1C[C@]2(C[C@H]1C#N)C(=O)Nc1ccccc12)N(C)C(=O)c1c(Cl)cc(F)cc1Cl] |

-continued
| Compound | Structure |
| --- | --- |
| 187 | 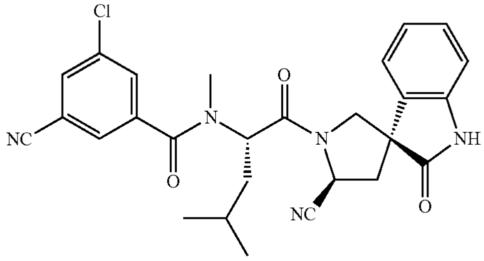 [SMILES: CC(C)C[C@@H](C(=O)N1C[C@]2(C[C@H]1C#N)C(=O)Nc1ccccc12)N(C)C(=O)c1cc(Cl)cc(C#N)c1] |
| 188 | 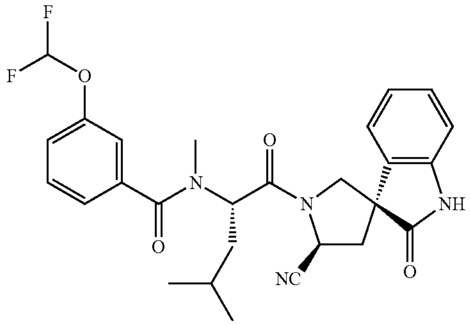 [SMILES: CC(C)C[C@@H](C(=O)N1C[C@]2(C[C@H]1C#N)C(=O)Nc1ccccc12)N(C)C(=O)c1cccc(OC(F)F)c1] |
| 189 | 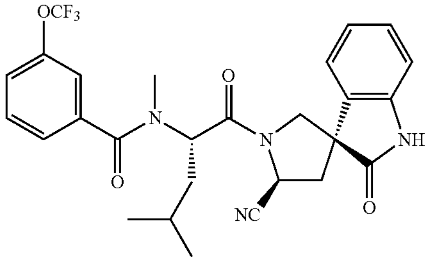 [SMILES: CC(C)C[C@@H](C(=O)N1C[C@]2(C[C@H]1C#N)C(=O)Nc1ccccc12)N(C)C(=O)c1cccc(OC(F)(F)F)c1] |
| 190 | 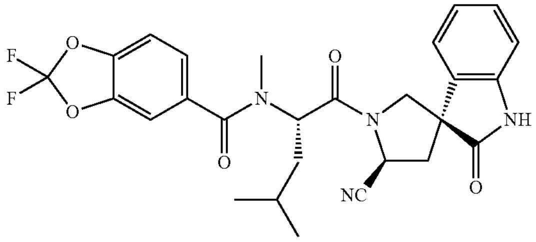 [SMILES: CC(C)C[C@@H](C(=O)N1C[C@]2(C[C@H]1C#N)C(=O)Nc1ccccc12)N(C)C(=O)c1ccc2c(c1)OC(F)(F)O2] |
| 191 | 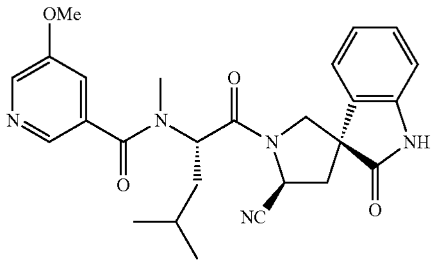 |

-continued
| Compound | Structure |
|---|---|
| 192 | 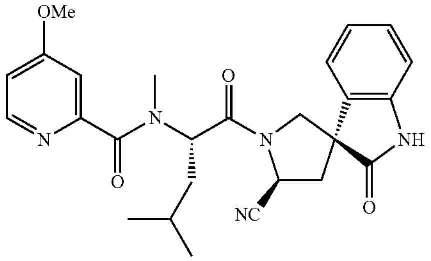 |
| 193 | 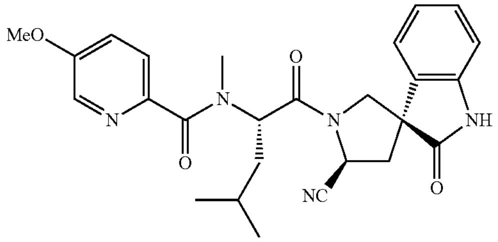 [SMILES: COc1ccc(C(=O)N(C)[C@@H](CC(C)C)C(=O)N2C[C@]3(C[C@H]2C#N)C(=O)Nc2ccccc23)nc1] |
| 194 | 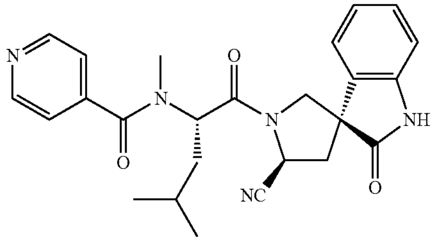 [SMILES: CC(C)C[C@@H](C(=O)N1C[C@]2(C[C@H]1C#N)C(=O)Nc1ccccc12)N(C)C(=O)c1ccncc1] |
| 195 | 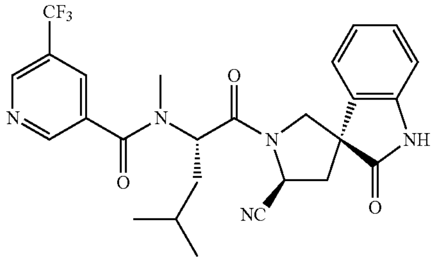 |
| 196 | 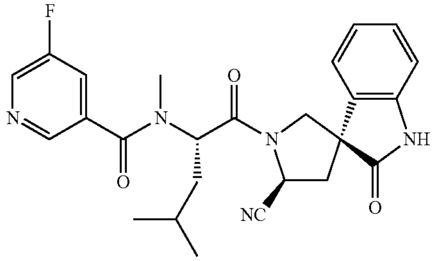 [SMILES: CC(C)C[C@@H](C(=O)N1C[C@]2(C[C@H]1C#N)C(=O)Nc1ccccc12)N(C)C(=O)c1cncc(F)c1] |
| 197 | 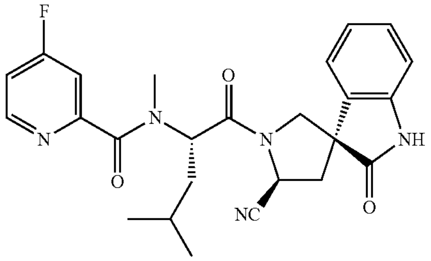 [SMILES: CC(C)C[C@@H](C(=O)N1C[C@]2(C[C@H]1C#N)C(=O)Nc1ccccc12)N(C)C(=O)c1cc(F)ccn1] |

-continued
| Compound | Structure |
|---|---|
| 198 | 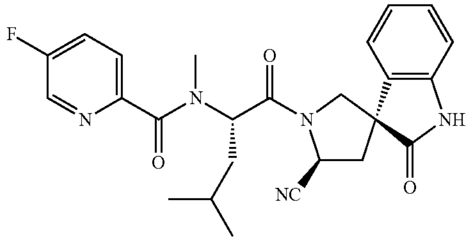 [SMILES: CC(C)C[C@@H](C(=O)N1C[C@]2(C[C@H]1C#N)C(=O)Nc1ccccc12)N(C)C(=O)c1ccc(F)cn1] |
| 199 | 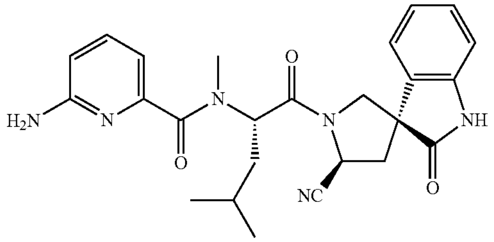 [SMILES: CC(C)C[C@@H](C(=O)N1C[C@]2(C[C@H]1C#N)C(=O)Nc1ccccc12)N(C)C(=O)c1cccc(N)n1] |
| 200 | 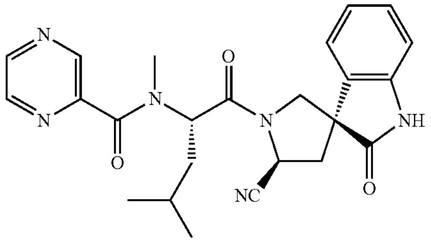 [SMILES: CC(C)C[C@@H](C(=O)N1C[C@]2(C[C@H]1C#N)C(=O)Nc1ccccc12)N(C)C(=O)c1cnccn1] |
| 201 | 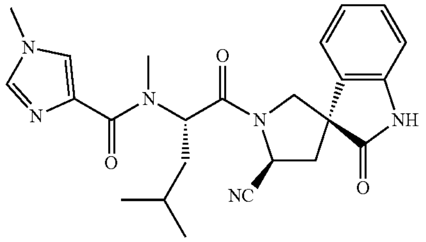 [SMILES: CC(C)C[C@@H](C(=O)N1C[C@]2(C[C@H]1C#N)C(=O)Nc1ccccc12)N(C)C(=O)c1cn(C)cn1] |
| 202 | 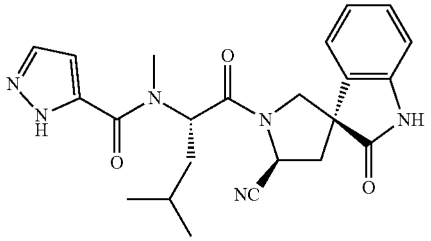 [SMILES: CC(C)C[C@@H](C(=O)N1C[C@]2(C[C@H]1C#N)C(=O)Nc1ccccc12)N(C)C(=O)c1ccn[nH]1] |
| 203 | 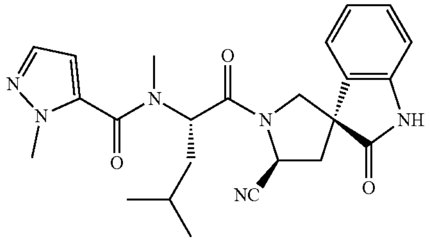 |

-continued
| Compound | Structure |
|---|---|
| 204 | 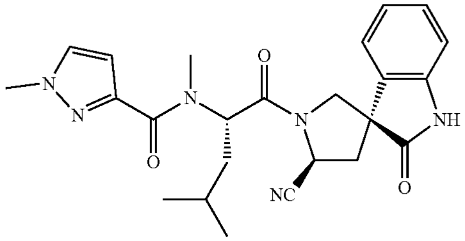 [SMILES: CC(C)C[C@@H](C(=O)N1C[C@]2(C[C@H]1C#N)C(=O)Nc1ccccc12)N(C)C(=O)c1ccn(C)n1] |
| 205 | 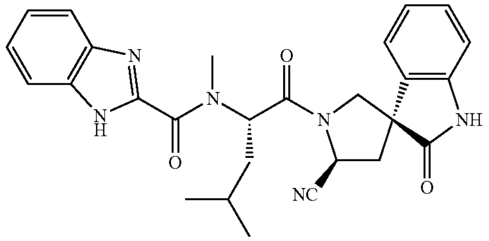 [SMILES: CC(C)C[C@@H](C(=O)N1C[C@]2(C[C@H]1C#N)C(=O)Nc1ccccc12)N(C)C(=O)c1nc2ccccc2[nH]1] |
| 206 | 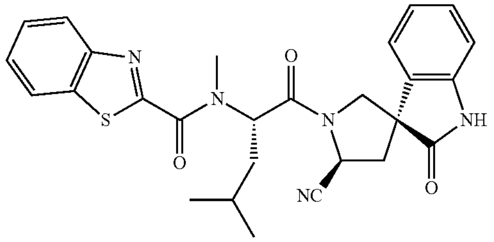 [SMILES: CC(C)C[C@@H](C(=O)N1C[C@]2(C[C@H]1C#N)C(=O)Nc1ccccc12)N(C)C(=O)c1nc2ccccc2s1] |
| 207 | 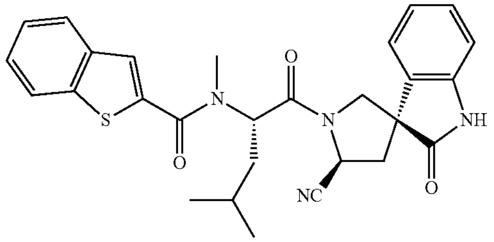 |
| 208 | 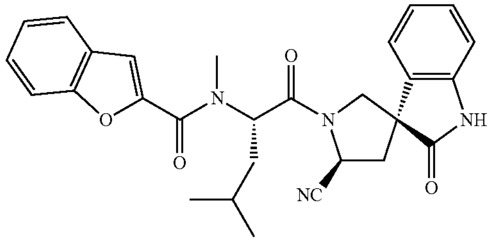 [SMILES: CC(C)C[C@@H](C(=O)N1C[C@]2(C[C@H]1C#N)C(=O)Nc1ccccc12)N(C)C(=O)c1cc2ccccc2s1] |
| 209 | 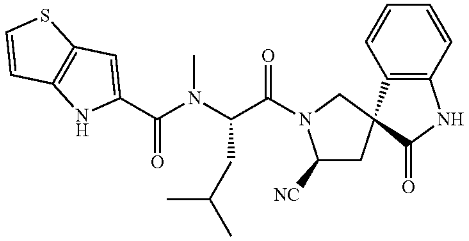 [SMILES: CC(C)C[C@@H](C(=O)N1C[C@]2(C[C@H]1C#N)C(=O)Nc1ccccc12)N(C)C(=O)c1cc2sccc2[nH]1] |

-continued
| Compound | Structure |
| --- | --- |
| 210 | 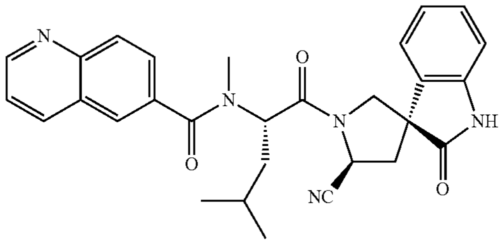 [SMILES: CC(C)C[C@@H](C(=O)N1C[C@]2(C[C@H]1C#N)C(=O)Nc1ccccc12)N(C)C(=O)c1ccc2ncccc2c1] |
| 211 | 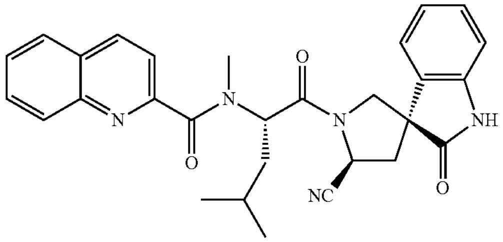 [SMILES: CC(C)C[C@@H](C(=O)N1C[C@]2(C[C@H]1C#N)C(=O)Nc1ccccc12)N(C)C(=O)c1ccc2ccccc2n1] |
| 212 | 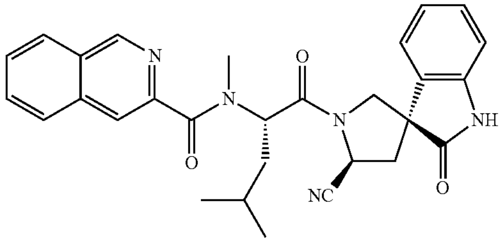 |
| 213 | 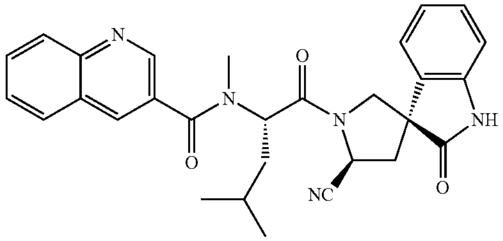 [SMILES: CC(C)C[C@@H](C(=O)N1C[C@]2(C[C@H]1C#N)C(=O)Nc1ccccc12)N(C)C(=O)c1cnc2ccccc2c1] |
| 214 | 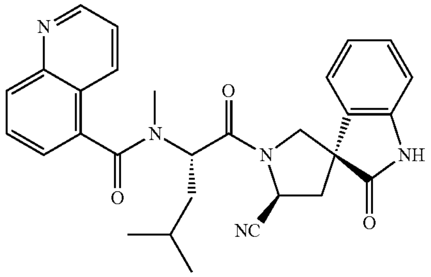 [SMILES: CC(C)C[C@@H](C(=O)N1C[C@]2(C[C@H]1C#N)C(=O)Nc1ccccc12)N(C)C(=O)c1cccc2ncccc12] |
| 215 | 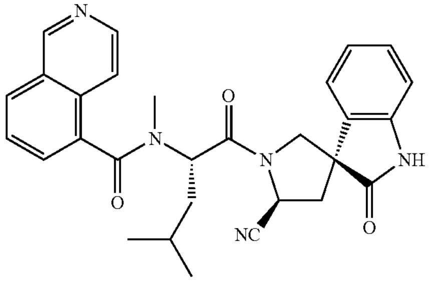 [SMILES: CC(C)C[C@@H](C(=O)N1C[C@]2(C[C@H]1C#N)C(=O)Nc1ccccc12)N(C)C(=O)c1cccc2cnccc12] |

-continued
| Compound | Structure |
| --- | --- |
| 216 | 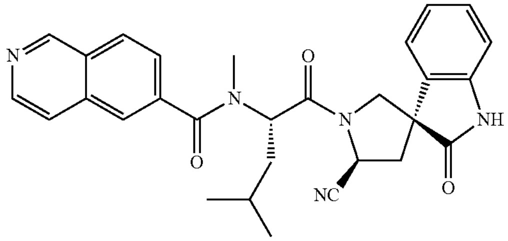 [SMILES: CC(C)C[C@@H](C(=O)N1C[C@]2(C[C@H]1C#N)C(=O)Nc1ccccc12)N(C)C(=O)c1ccc2cnccc2c1] |
| 217 | 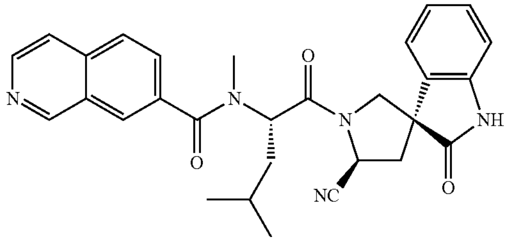 [SMILES: CC(C)C[C@@H](C(=O)N1C[C@]2(C[C@H]1C#N)C(=O)Nc1ccccc12)N(C)C(=O)c1ccc2ccncc2c1] |
| 218 | 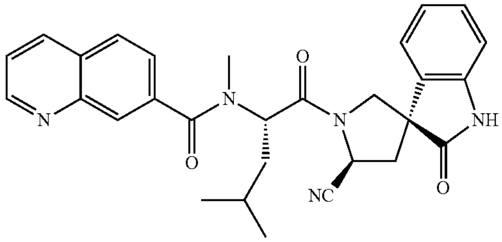 |
| 219 | 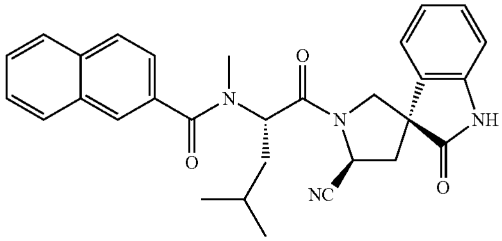 [SMILES: CC(C)C[C@@H](C(=O)N1C[C@]2(C[C@H]1C#N)C(=O)Nc1ccccc12)N(C)C(=O)c1ccc2ccccc2c1] |
| 220 | 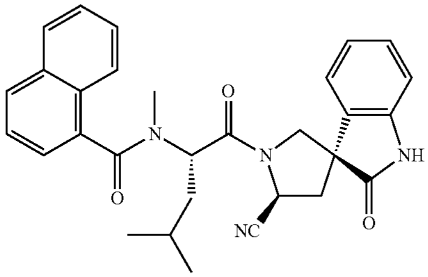 [SMILES: CC(C)C[C@@H](C(=O)N1C[C@]2(C[C@H]1C#N)C(=O)Nc1ccccc12)N(C)C(=O)c1cccc2ccccc12] |
| 221 | 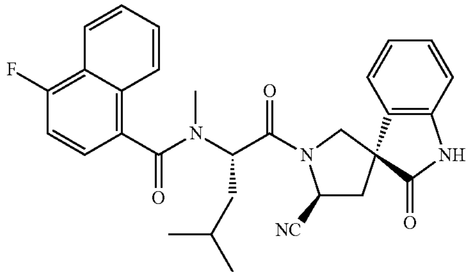 [SMILES: CC(C)C[C@@H](C(=O)N1C[C@]2(C[C@H]1C#N)C(=O)Nc1ccccc12)N(C)C(=O)c1ccc(F)c2ccccc12] |

-continued
| Compound | Structure |
|---|---|
| 222 | 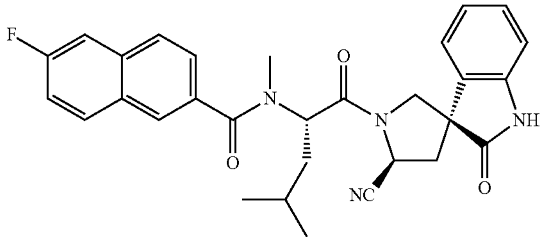 [SMILES: CC(C)C[C@@H](C(=O)N1C[C@]2(C[C@H]1C#N)C(=O)Nc1ccccc12)N(C)C(=O)c1ccc2cc(F)ccc2c1] |
| 223 | 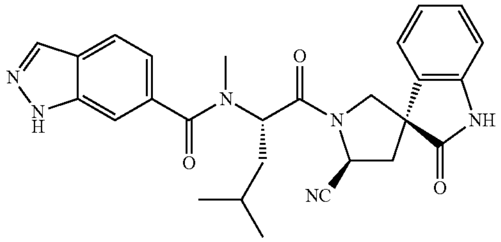 [SMILES: CC(C)C[C@@H](C(=O)N1C[C@]2(C[C@H]1C#N)C(=O)Nc1ccccc12)N(C)C(=O)c1ccc2cn[nH]c2c1] |
| 224 | 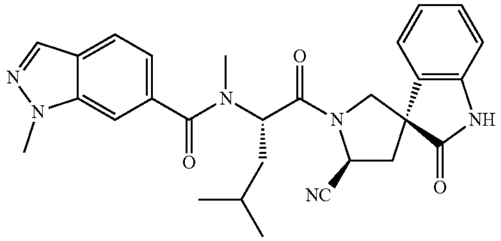 [SMILES: CC(C)C[C@@H](C(=O)N1C[C@]2(C[C@H]1C#N)C(=O)Nc1ccccc12)N(C)C(=O)c1ccc2cnn(C)c2c1] |
| 225 | 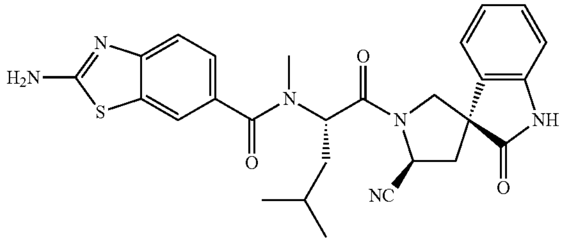 [SMILES: CC(C)C[C@@H](C(=O)N1C[C@]2(C[C@H]1C#N)C(=O)Nc1ccccc12)N(C)C(=O)c1ccc2nc(N)sc2c1] |
| 226 | 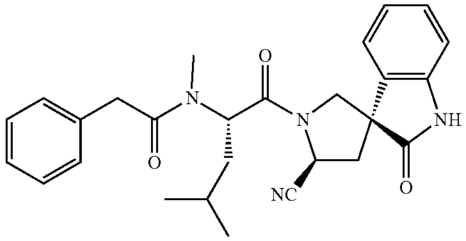 [SMILES: CC(C)C[C@@H](C(=O)N1C[C@]2(C[C@H]1C#N)C(=O)Nc1ccccc12)N(C)C(=O)Cc1ccccc1] |
| 227 | 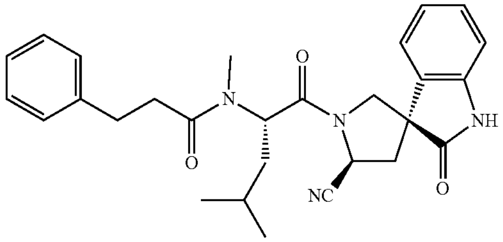 [SMILES: CC(C)C[C@@H](C(=O)N1C[C@]2(C[C@H]1C#N)C(=O)Nc1ccccc12)N(C)C(=O)CCc1ccccc1] |

-continued
| Compound | Structure |
| --- | --- |
| 228 | 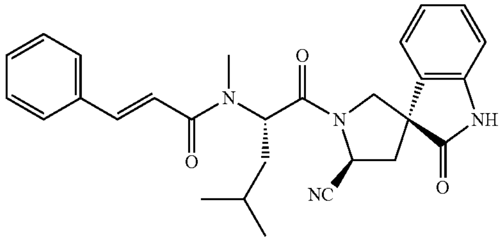 [SMILES: CC(C)C[C@@H](C(=O)N1C[C@]2(C[C@H]1C#N)C(=O)Nc1ccccc12)N(C)C(=O)/C=C/c1ccccc1] |
| 229 | 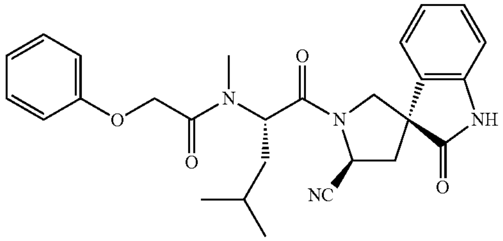 [SMILES: CC(C)C[C@@H](C(=O)N1C[C@]2(C[C@H]1C#N)C(=O)Nc1ccccc12)N(C)C(=O)COc1ccccc1] |
| 230 | 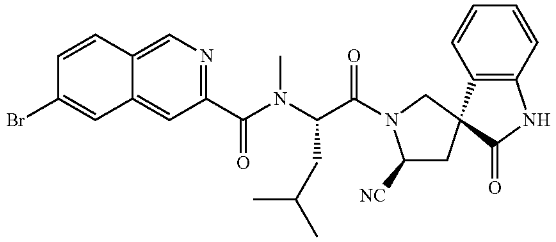 [SMILES: CC(C)C[C@@H](C(=O)N1C[C@]2(C[C@H]1C#N)C(=O)Nc1ccccc12)N(C)C(=O)c1cc2cc(Br)ccc2cn1] |
| 231 | 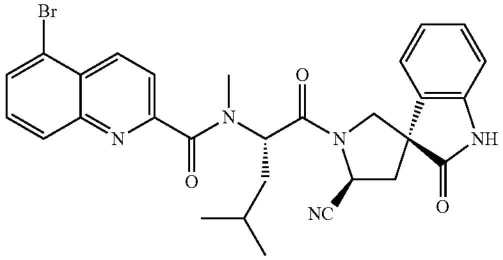 [SMILES: CC(C)C[C@@H](C(=O)N1C[C@]2(C[C@H]1C#N)C(=O)Nc1ccccc12)N(C)C(=O)c1ccc2c(Br)cccc2n1] |
| 232 | 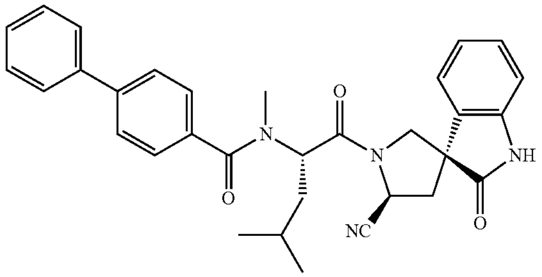 |
| 233 | 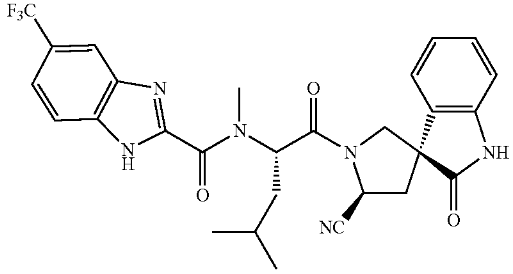 [SMILES: CC(C)C[C@@H](C(=O)N1C[C@]2(C[C@H]1C#N)C(=O)Nc1ccccc12)N(C)C(=O)c1nc2cc(C(F)(F)F)ccc2[nH]1] |

-continued
| Compound | Structure |
|---|---|
| 234 | 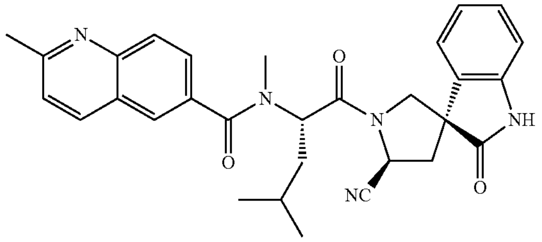 [SMILES: Cc1ccc2cc(C(=O)N(C)[C@@H](CC(C)C)C(=O)N3C[C@]4(C[C@H]3C#N)C(=O)Nc3ccccc34)ccc2n1] |
| 235 | 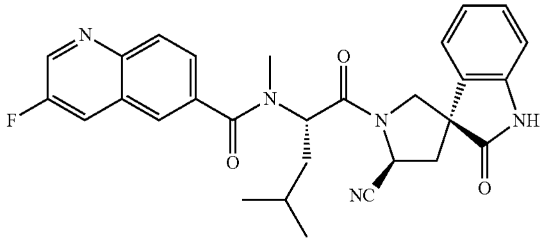 [SMILES: CC(C)C[C@@H](C(=O)N1C[C@]2(C[C@H]1C#N)C(=O)Nc1ccccc12)N(C)C(=O)c1ccc2ncc(F)cc2c1] |
| 236 | 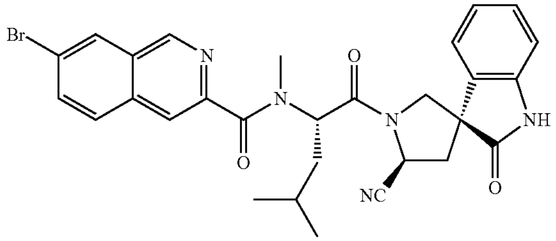 [SMILES: CC(C)C[C@@H](C(=O)N1C[C@]2(C[C@H]1C#N)C(=O)Nc1ccccc12)N(C)C(=O)c1cc2ccc(Br)cc2cn1] |
| 237 | 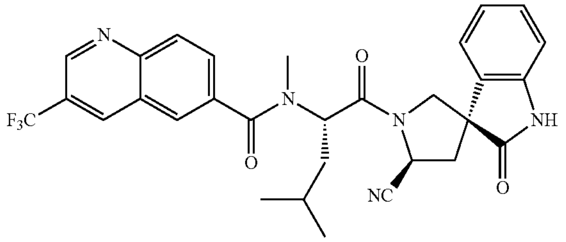 [SMILES: CC(C)C[C@@H](C(=O)N1C[C@]2(C[C@H]1C#N)C(=O)Nc1ccccc12)N(C)C(=O)c1ccc2ncc(C(F)(F)F)cc2c1] |
| 238 | 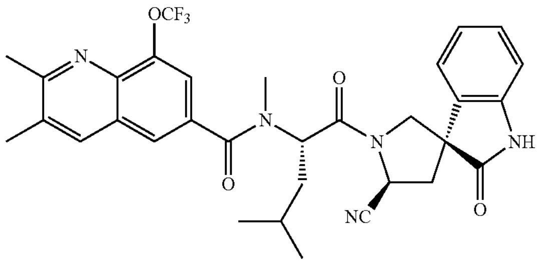 [SMILES: Cc1cc2cc(C(=O)N(C)[C@@H](CC(C)C)C(=O)N3C[C@]4(C[C@H]3C#N)C(=O)Nc3ccccc34)cc(OC(F)(F)F)c2nc1C] |
| 239 | 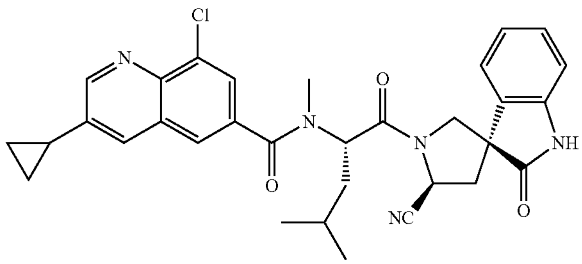 [SMILES: CC(C)C[C@@H](C(=O)N1C[C@]2(C[C@H]1C#N)C(=O)Nc1ccccc12)N(C)C(=O)c1cc(Cl)c2ncc(C3CC3)cc2c1] |

-continued
| Compound | Structure |
|---|---|
| 240 | 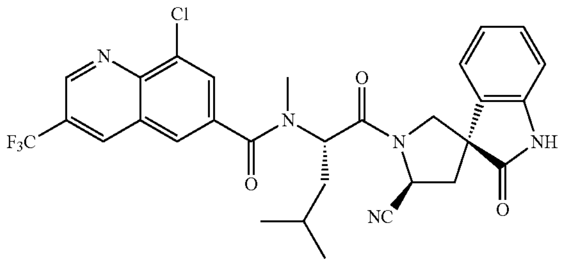 [SMILES: CC(C)C[C@@H](C(=O)N1C[C@]2(C[C@H]1C#N)C(=O)Nc1ccccc12)N(C)C(=O)c1cc(Cl)c2ncc(C(F)(F)F)cc2c1] |
| 241 | 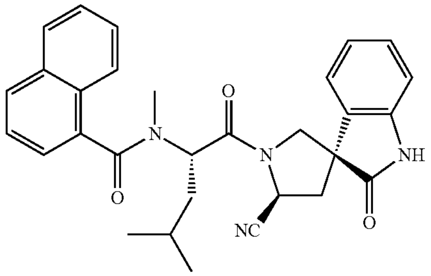 |
| 242 | 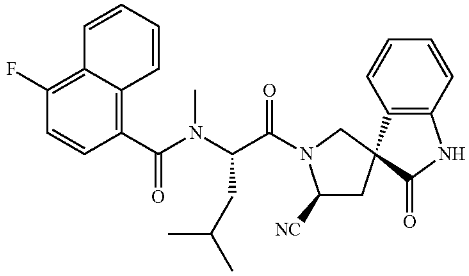 [SMILES: CC(C)C[C@@H](C(=O)N1C[C@]2(C[C@H]1C#N)C(=O)Nc1ccccc12)N(C)C(=O)c1ccc(F)c2ccccc12] |
| 243 | 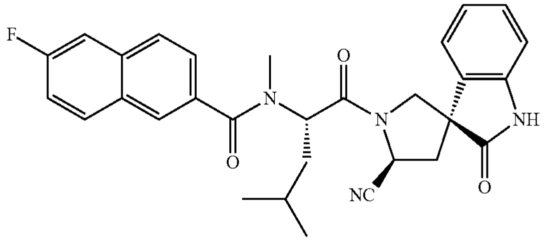 [SMILES: CC(C)C[C@@H](C(=O)N1C[C@]2(C[C@H]1C#N)C(=O)Nc1ccccc12)N(C)C(=O)c1ccc2cc(F)ccc2c1] |
| 244 | 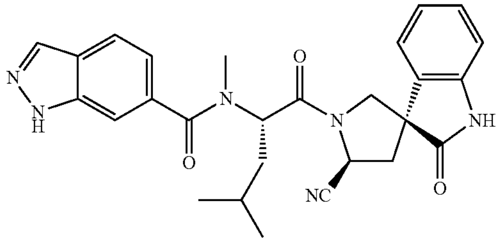 |
| 245 | 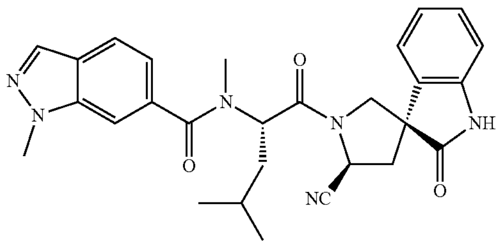 |

-continued
| Compound | Structure |
| --- | --- |
| 246 | 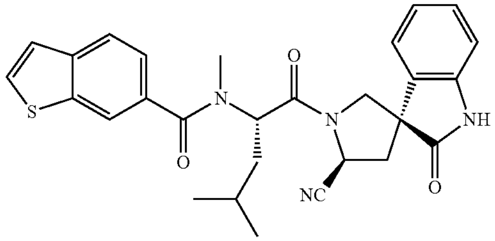 [SMILES: CC(C)C[C@@H](C(=O)N1C[C@]2(C[C@H]1C#N)C(=O)Nc1ccccc12)N(C)C(=O)c1ccc2ccsc2c1] |
| 247 | 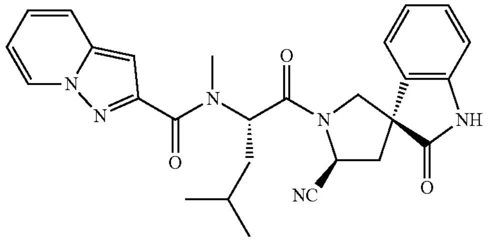 [SMILES: CC(C)C[C@@H](C(=O)N1C[C@]2(C[C@H]1C#N)C(=O)Nc1ccccc12)N(C)C(=O)c1cc2ccccn2n1] |
| 248 | 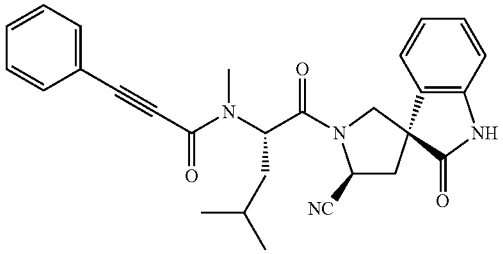 [SMILES: CC(C)C[C@@H](C(=O)N1C[C@]2(C[C@H]1C#N)C(=O)Nc1ccccc12)N(C)C(=O)C#Cc1ccccc1] |
| 249 | 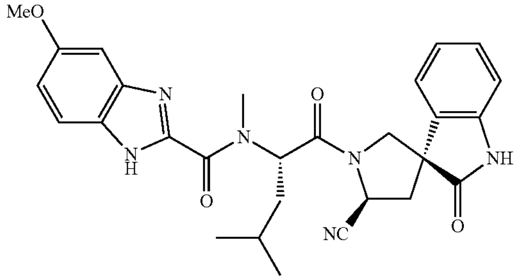 [SMILES: COc1ccc2[nH]c(C(=O)N(C)[C@@H](CC(C)C)C(=O)N3C[C@]4(C[C@H]3C#N)C(=O)Nc3ccccc34)nc2c1] |
| 250 | 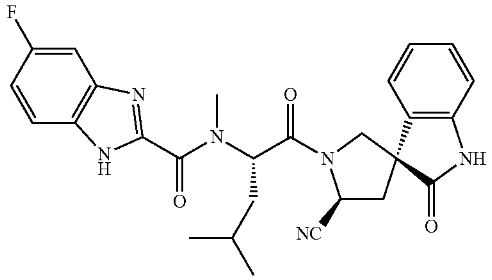 [SMILES: CC(C)C[C@@H](C(=O)N1C[C@]2(C[C@H]1C#N)C(=O)Nc1ccccc12)N(C)C(=O)c1nc2cc(F)ccc2[nH]1] |

-continued
| Compound | Structure |
|---|---|
| 251 | 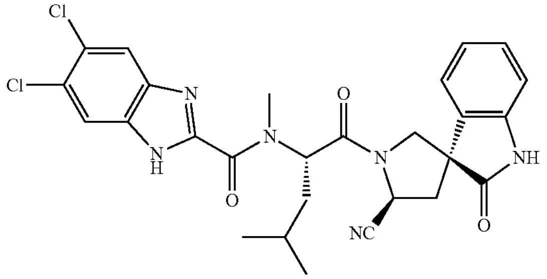 [SMILES: CC(C)C[C@@H](C(=O)N1C[C@]2(C[C@H]1C#N)C(=O)Nc1ccccc12)N(C)C(=O)c1nc2cc(Cl)c(Cl)cc2[nH]1] |
| 252 | 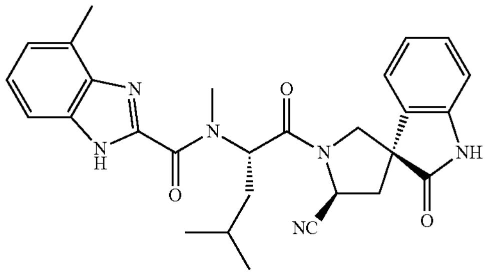 [SMILES: Cc1cccc2[nH]c(C(=O)N(C)[C@@H](CC(C)C)C(=O)N3C[C@]4(C[C@H]3C#N)C(=O)Nc3ccccc34)nc12] |
| 253 | 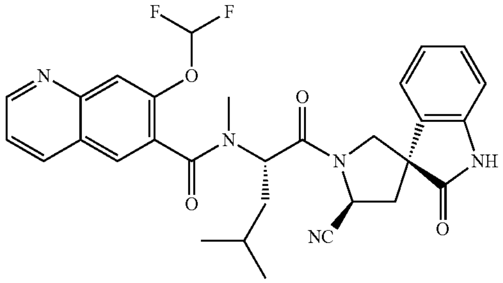 [SMILES: CC(C)C[C@@H](C(=O)N1C[C@]2(C[C@H]1C#N)C(=O)Nc1ccccc12)N(C)C(=O)c1cc2cccnc2cc1OC(F)F] |
| 254 | 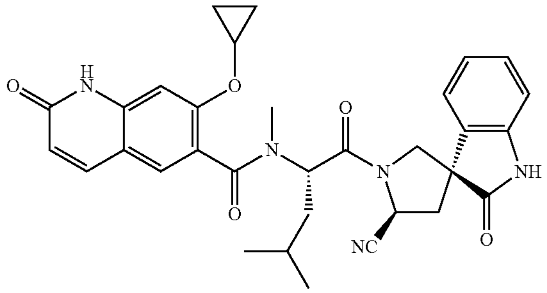 [SMILES: CC(C)C[C@@H](C(=O)N1C[C@]2(C[C@H]1C#N)C(=O)Nc1ccccc12)N(C)C(=O)c1cc2ccc(=O)[nH]c2cc1OC1CC1] |
| 255 | 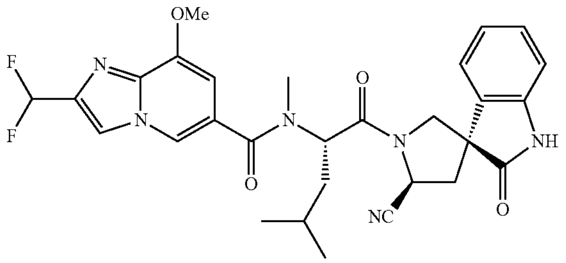 [SMILES: COc1cc(C(=O)N(C)[C@@H](CC(C)C)C(=O)N2C[C@]3(C[C@H]2C#N)C(=O)Nc2ccccc23)cn2cc(C(F)F)nc12] |

-continued
| Compound | Structure |
|---|---|
| 256 | 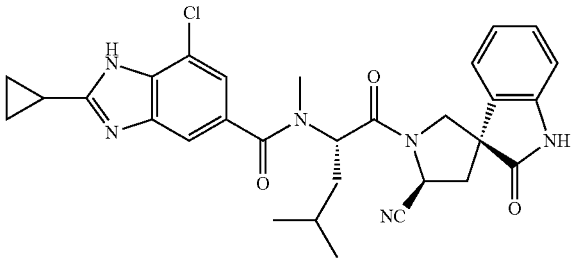 [SMILES: CC(C)C[C@@H](C(=O)N1C[C@]2(C[C@H]1C#N)C(=O)Nc1ccccc12)N(C)C(=O)c1cc(Cl)c2[nH]c(C3CC3)nc2c1] |
| 257 | 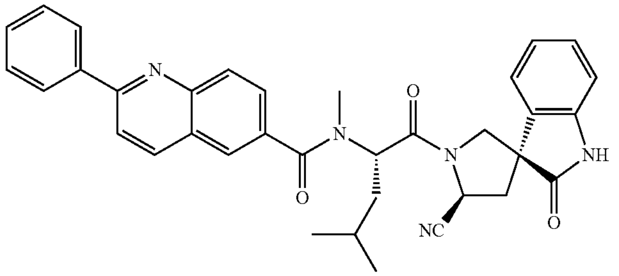 [SMILES: CC(C)C[C@@H](C(=O)N1C[C@]2(C[C@H]1C#N)C(=O)Nc1ccccc12)N(C)C(=O)c1ccc2nc(-c3ccccc3)ccc2c1] |
| 258 | 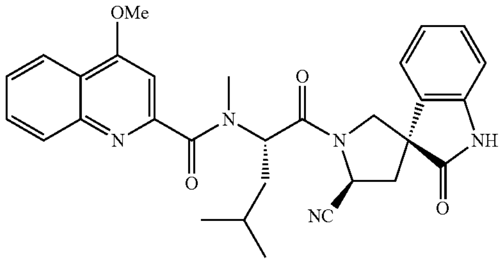 [SMILES: COc1cc(C(=O)N(C)[C@@H](CC(C)C)C(=O)N2C[C@]3(C[C@H]2C#N)C(=O)Nc2ccccc23)nc2ccccc12] |
| 259 | 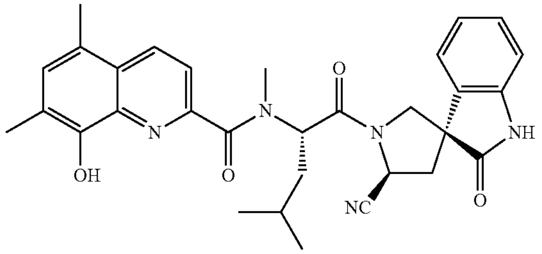 [SMILES: Cc1cc(C)c2ccc(C(=O)N(C)[C@@H](CC(C)C)C(=O)N3C[C@]4(C[C@H]3C#N)C(=O)Nc3ccccc34)nc2c1O] |
| 260 | 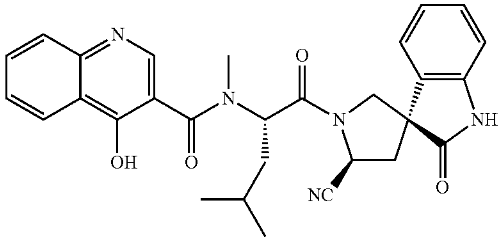 [SMILES: CC(C)C[C@@H](C(=O)N1C[C@]2(C[C@H]1C#N)C(=O)Nc1ccccc12)N(C)C(=O)c1cnc2ccccc2c1O] |
| 261 | 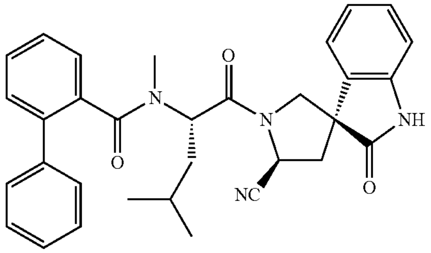 [SMILES: CC(C)C[C@@H](C(=O)N1C[C@]2(C[C@H]1C#N)C(=O)Nc1ccccc12)N(C)C(=O)c1ccccc1-c1ccccc1] |

-continued
| Compound | Structure |
|---|---|
| 262 | 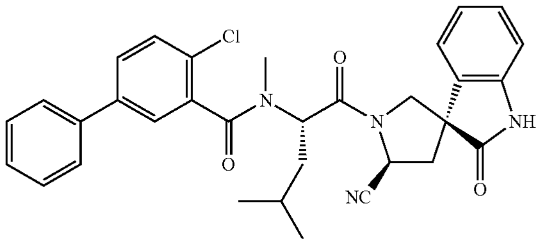 [SMILES: CC(C)C[C@@H](C(=O)N1C[C@]2(C[C@H]1C#N)C(=O)Nc1ccccc12)N(C)C(=O)c1cc(-c2ccccc2)ccc1Cl] |
| 263 | 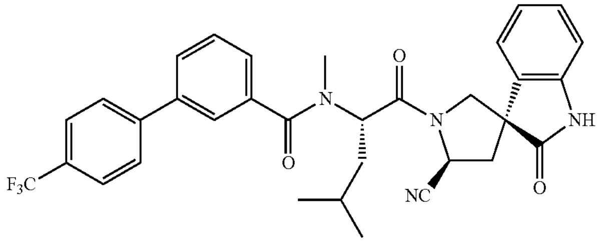 [SMILES: CC(C)C[C@@H](C(=O)N1C[C@]2(C[C@H]1C#N)C(=O)Nc1ccccc12)N(C)C(=O)c1cccc(-c2ccc(C(F)(F)F)cc2)c1] |
| 264 | 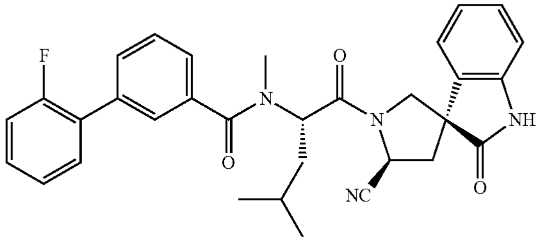 [SMILES: CC(C)C[C@@H](C(=O)N1C[C@]2(C[C@H]1C#N)C(=O)Nc1ccccc12)N(C)C(=O)c1cccc(-c2ccccc2F)c1] |
| 265 | 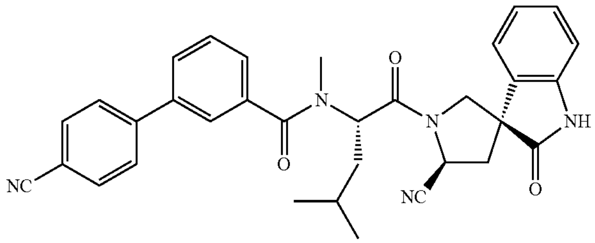 [SMILES: CC(C)C[C@@H](C(=O)N1C[C@]2(C[C@H]1C#N)C(=O)Nc1ccccc12)N(C)C(=O)c1cccc(-c2ccc(C#N)cc2)c1] |
| 266 | 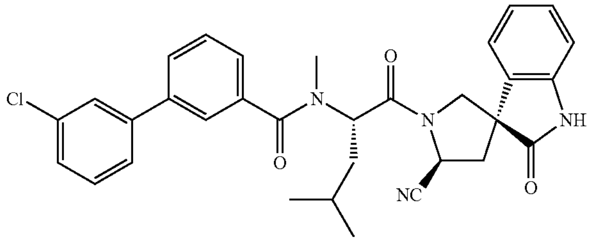 [SMILES: CC(C)C[C@@H](C(=O)N1C[C@]2(C[C@H]1C#N)C(=O)Nc1ccccc12)N(C)C(=O)c1cccc(-c2cccc(Cl)c2)c1] |
| 267 | 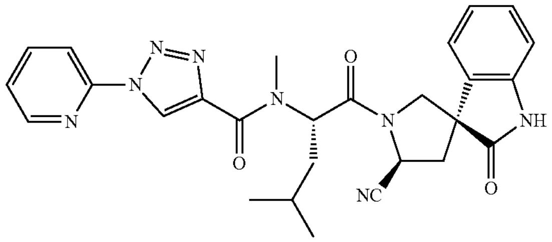 [SMILES: CC(C)C[C@@H](C(=O)N1C[C@]2(C[C@H]1C#N)C(=O)Nc1ccccc12)N(C)C(=O)c1cn(-c2ccccn2)nn1] |

-continued
| Compound | Structure |
| --- | --- |
| 268 | 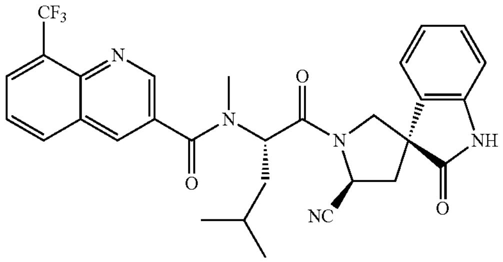 [SMILES: CC(C)C[C@@H](C(=O)N1C[C@]2(C[C@H]1C#N)C(=O)Nc1ccccc12)N(C)C(=O)c1cnc2c(C(F)(F)F)cccc2c1] |
| 269 | 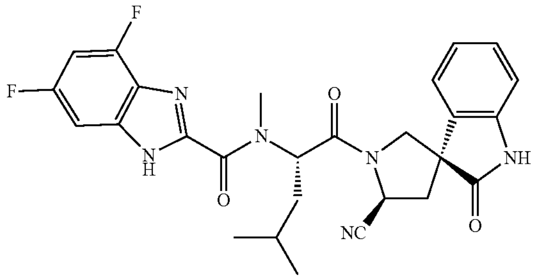 [SMILES: CC(C)C[C@@H](C(=O)N1C[C@]2(C[C@H]1C#N)C(=O)Nc1ccccc12)N(C)C(=O)c1nc2c(F)cc(F)cc2[nH]1] |
| 270 | 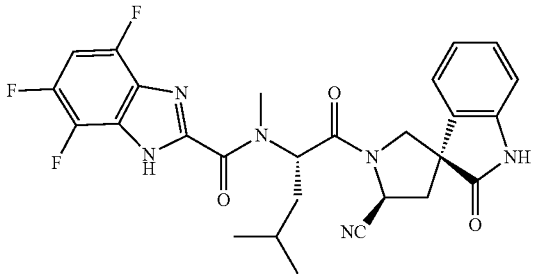 [SMILES: CC(C)C[C@@H](C(=O)N1C[C@]2(C[C@H]1C#N)C(=O)Nc1ccccc12)N(C)C(=O)c1nc2c(F)cc(F)c(F)c2[nH]1] |
| 271 | 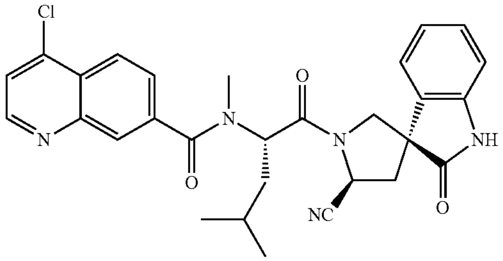 [SMILES: CC(C)C[C@@H](C(=O)N1C[C@]2(C[C@H]1C#N)C(=O)Nc1ccccc12)N(C)C(=O)c1ccc2c(Cl)ccnc2c1] |
| 272 | 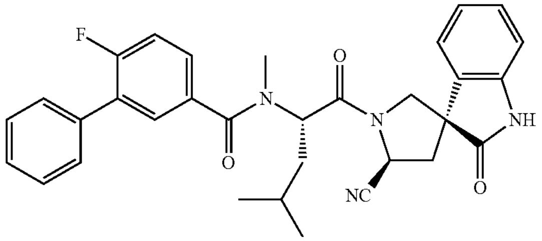 [SMILES: CC(C)C[C@@H](C(=O)N1C[C@]2(C[C@H]1C#N)C(=O)Nc1ccccc12)N(C)C(=O)c1ccc(F)c(-c2ccccc2)c1] |

-continued
| Compound | Structure |
|---|---|
| 273 | 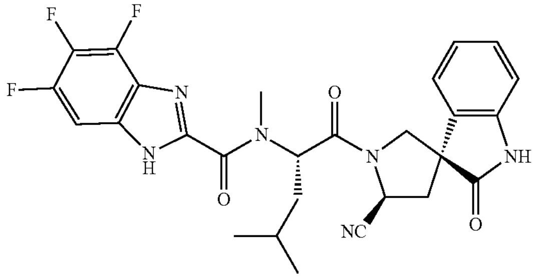 [SMILES: CC(C)C[C@@H](C(=O)N1C[C@]2(C[C@H]1C#N)C(=O)Nc1ccccc12)N(C)C(=O)c1nc2c(F)c(F)c(F)cc2[nH]1] |
| 274 | 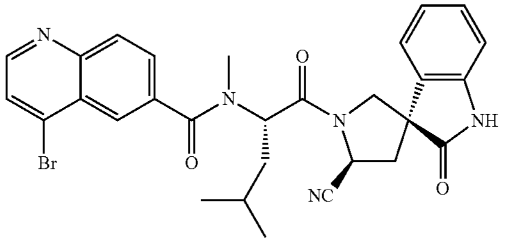 [SMILES: CC(C)C[C@@H](C(=O)N1C[C@]2(C[C@H]1C#N)C(=O)Nc1ccccc12)N(C)C(=O)c1ccc2nccc(Br)c2c1] |
| 275 | 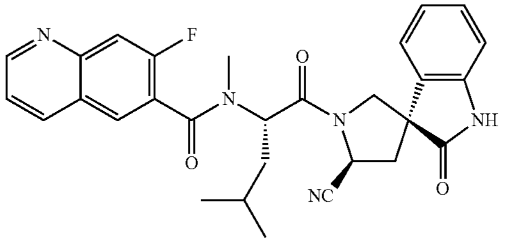 [SMILES: CC(C)C[C@@H](C(=O)N1C[C@]2(C[C@H]1C#N)C(=O)Nc1ccccc12)N(C)C(=O)c1cc2cccnc2cc1F] |
| 276 | 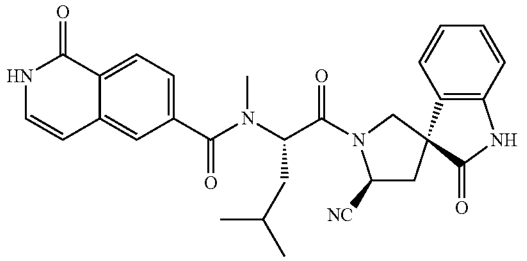 [SMILES: CC(C)C[C@@H](C(=O)N1C[C@]2(C[C@H]1C#N)C(=O)Nc1ccccc12)N(C)C(=O)c1ccc2c(=O)[nH]ccc2c1] |
| 277 | 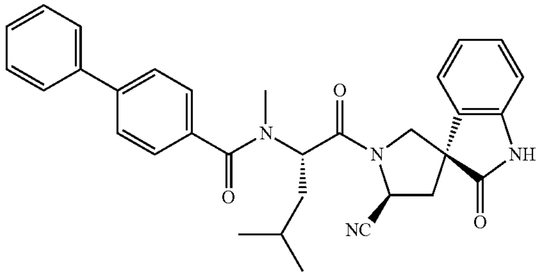 [SMILES: CC(C)C[C@@H](C(=O)N1C[C@]2(C[C@H]1C#N)C(=O)Nc1ccccc12)N(C)C(=O)c1ccc(-c2ccccc2)cc1] |
| 278 | 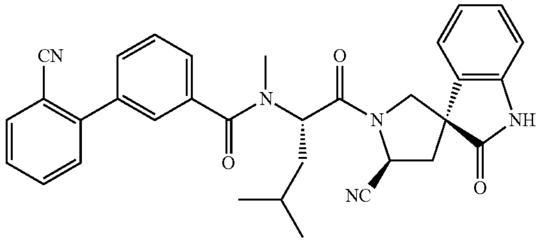 [SMILES: CC(C)C[C@@H](C(=O)N1C[C@]2(C[C@H]1C#N)C(=O)Nc1ccccc12)N(C)C(=O)c1cccc(-c2ccccc2C#N)c1] |

-continued
| Compound | Structure |
| --- | --- |
| 279 | 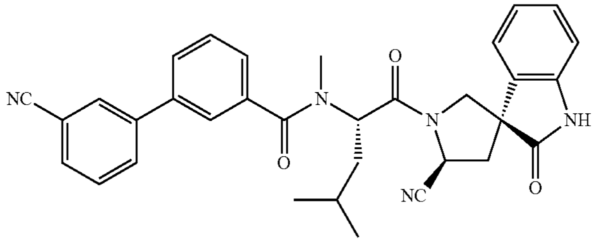 [SMILES: CC(C)C[C@@H](C(=O)N1C[C@]2(C[C@H]1C#N)C(=O)Nc1ccccc12)N(C)C(=O)c1cccc(-c2cccc(C#N)c2)c1] |
| 280 | 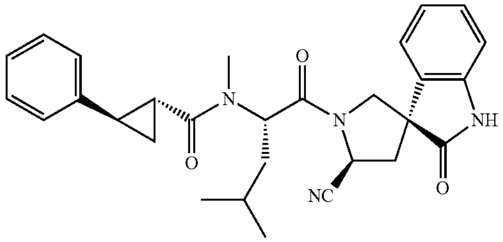 [SMILES: CC(C)C[C@@H](C(=O)N1C[C@]2(C[C@H]1C#N)C(=O)Nc1ccccc12)N(C)C(=O)[C@@H]1C[C@H]1c1ccccc1] |
| 281 | 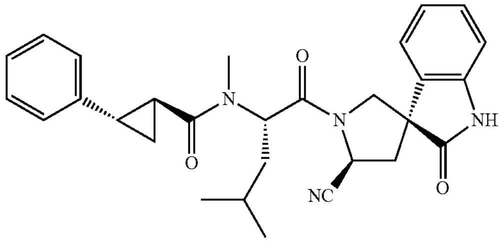 [SMILES: CC(C)C[C@@H](C(=O)N1C[C@]2(C[C@H]1C#N)C(=O)Nc1ccccc12)N(C)C(=O)[C@H]1C[C@@H]1c1ccccc1] |
| 282 | 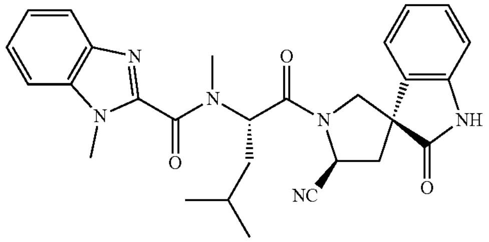 [SMILES: CC(C)C[C@@H](C(=O)N1C[C@]2(C[C@H]1C#N)C(=O)Nc1ccccc12)N(C)C(=O)c1nc2ccccc2n1C] |
| 283 | 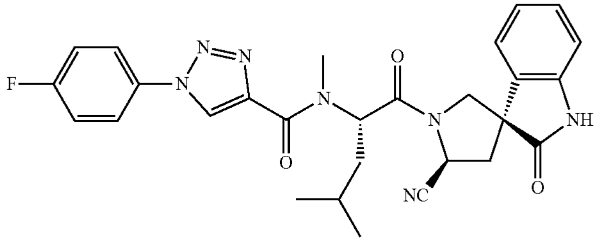 [SMILES: CC(C)C[C@@H](C(=O)N1C[C@]2(C[C@H]1C#N)C(=O)Nc1ccccc12)N(C)C(=O)c1cn(-c2ccc(F)cc2)nn1] |
| 284 | 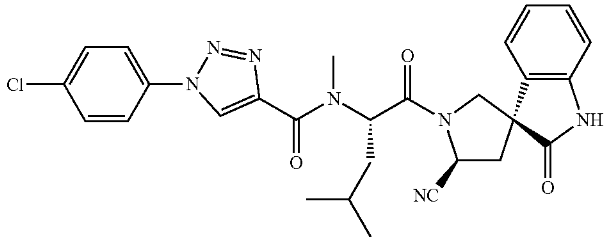 [SMILES: CC(C)C[C@@H](C(=O)N1C[C@]2(C[C@H]1C#N)C(=O)Nc1ccccc12)N(C)C(=O)c1cn(-c2ccc(Cl)cc2)nn1] |

-continued
| Compound | Structure |
| --- | --- |
| 285 | 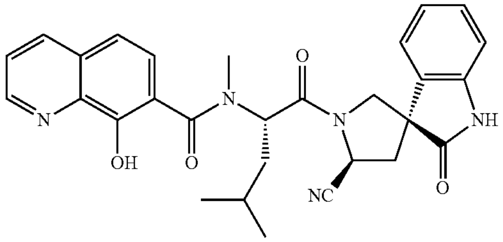 [SMILES: CC(C)C[C@@H](C(=O)N1C[C@]2(C[C@H]1C#N)C(=O)Nc1ccccc12)N(C)C(=O)c1ccc2cccnc2c1O] |
| 286 | 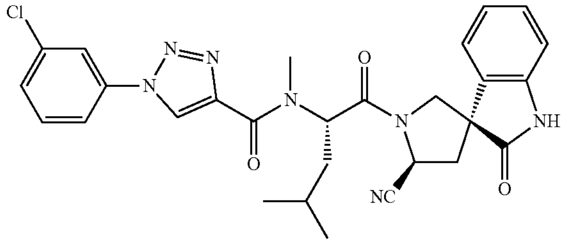 [SMILES: CC(C)C[C@@H](C(=O)N1C[C@]2(C[C@H]1C#N)C(=O)Nc1ccccc12)N(C)C(=O)c1cn(-c2cccc(Cl)c2)nn1] |
| 287 | 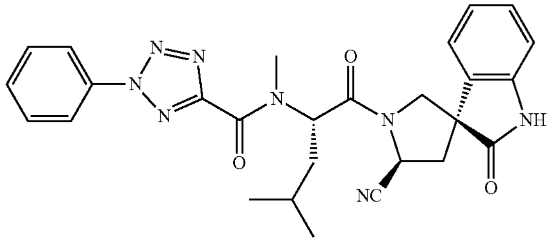 [SMILES: CC(C)C[C@@H](C(=O)N1C[C@]2(C[C@H]1C#N)C(=O)Nc1ccccc12)N(C)C(=O)c1nnn(-c2ccccc2)n1] |
| 288 | 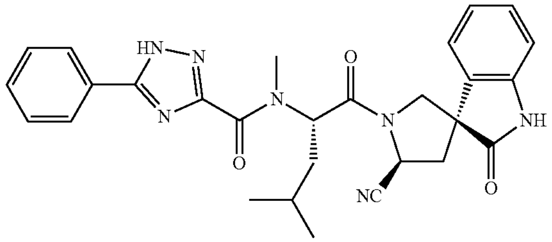 [SMILES: CC(C)C[C@@H](C(=O)N1C[C@]2(C[C@H]1C#N)C(=O)Nc1ccccc12)N(C)C(=O)c1n[nH]c(-c2ccccc2)n1] |
| 289 | 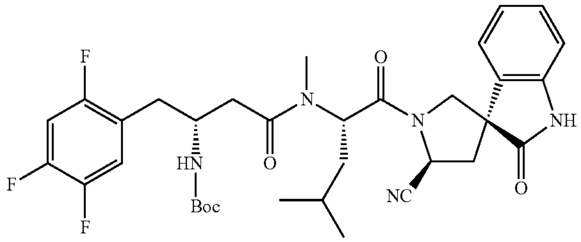 [SMILES: CC(C)C[C@@H](C(=O)N1C[C@]2(C[C@H]1C#N)C(=O)Nc1ccccc12)N(C)C(=O)C[C@@H](Cc1cc(F)c(F)cc1F)NC(=O)OC(C)(C)C] |
| 290 | 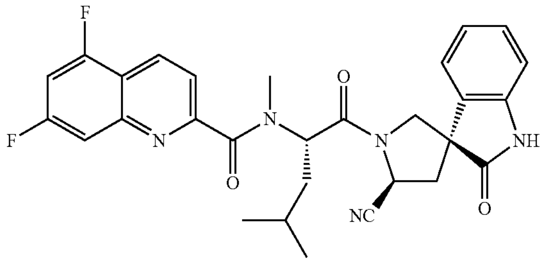 [SMILES: CC(C)C[C@@H](C(=O)N1C[C@]2(C[C@H]1C#N)C(=O)Nc1ccccc12)N(C)C(=O)c1ccc2c(F)cc(F)cc2n1] |

-continued
| Compound | Structure |
|---|---|
| 291 | 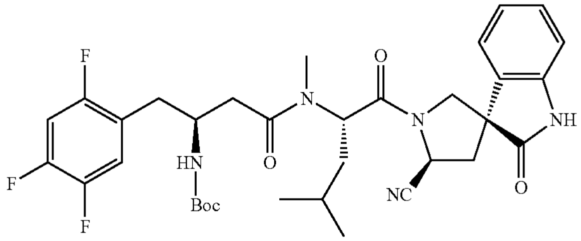 [SMILES: CC(C)C[C@@H](C(=O)N1C[C@]2(C[C@H]1C#N)C(=O)Nc1ccccc12)N(C)C(=O)C[C@H](Cc1cc(F)c(F)cc1F)NC(=O)OC(C)(C)C] |
| 292 | 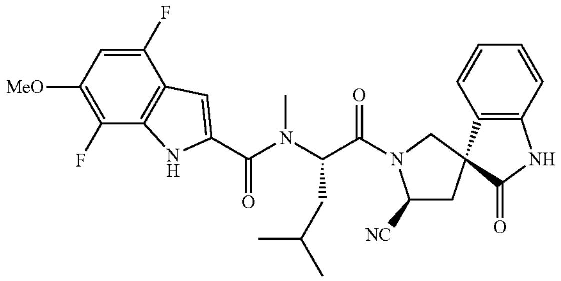 [SMILES: COc1cc(F)c2cc(C(=O)N(C)[C@@H](CC(C)C)C(=O)N3C[C@]4(C[C@H]3C#N)C(=O)Nc3ccccc34)[nH]c2c1F] |
| 293 | 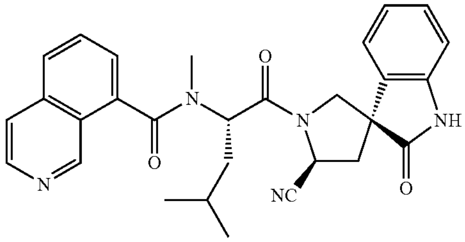 [SMILES: CC(C)C[C@@H](C(=O)N1C[C@]2(C[C@H]1C#N)C(=O)Nc1ccccc12)N(C)C(=O)c1cccc2ccncc12] |
| 294 | 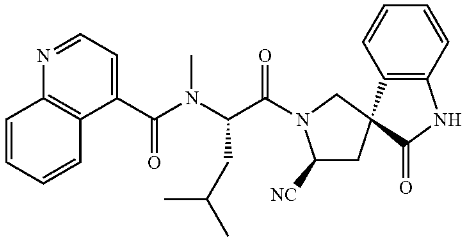 [SMILES: CC(C)C[C@@H](C(=O)N1C[C@]2(C[C@H]1C#N)C(=O)Nc1ccccc12)N(C)C(=O)c1ccnc2ccccc12] |
| 295 | 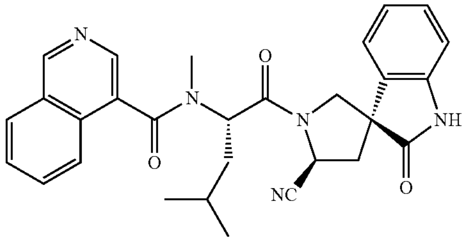 [SMILES: CC(C)C[C@@H](C(=O)N1C[C@]2(C[C@H]1C#N)C(=O)Nc1ccccc12)N(C)C(=O)c1cncc2ccccc12] |
| 296 | 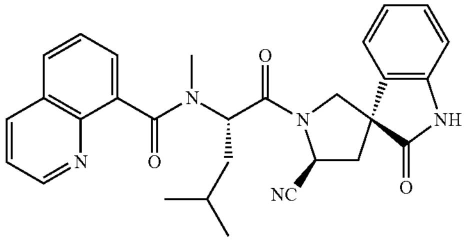 [SMILES: CC(C)C[C@@H](C(=O)N1C[C@]2(C[C@H]1C#N)C(=O)Nc1ccccc12)N(C)C(=O)c1cccc2cccnc12] |

-continued
| Compound | Structure |
|---|---|
| 297 | 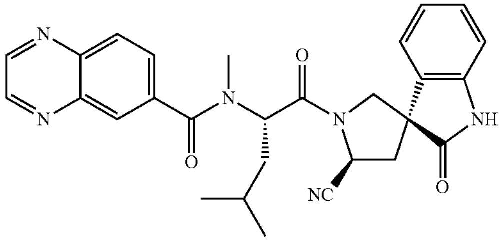 [SMILES: CC(C)C[C@@H](C(=O)N1C[C@]2(C[C@H]1C#N)C(=O)Nc1ccccc12)N(C)C(=O)c1ccc2nccnc2c1] |
| 298 | 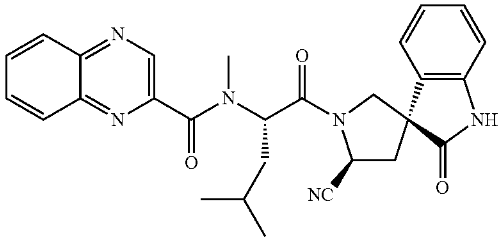 |
| 299 | 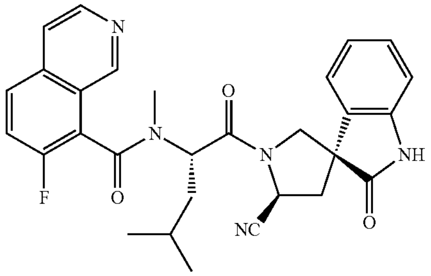 [SMILES: CC(C)C[C@@H](C(=O)N1C[C@]2(C[C@H]1C#N)C(=O)Nc1ccccc12)N(C)C(=O)c1c(F)ccc2ccncc12] |
| 300 | 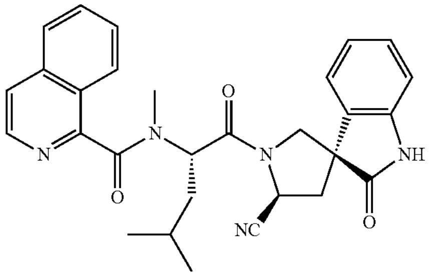 [SMILES: CC(C)C[C@@H](C(=O)N1C[C@]2(C[C@H]1C#N)C(=O)Nc1ccccc12)N(C)C(=O)c1nccc2ccccc12] |
| 301 | 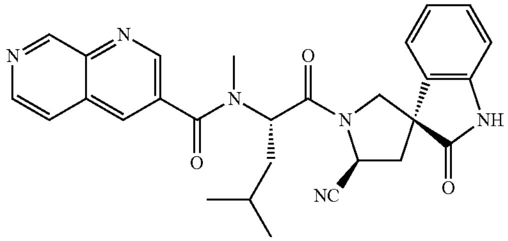 |
| 302 | 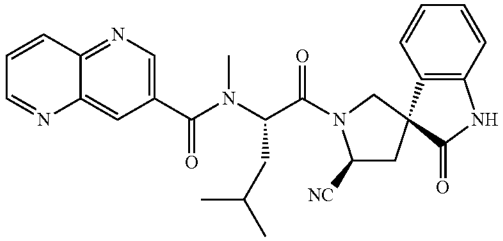 [SMILES: CC(C)C[C@@H](C(=O)N1C[C@]2(C[C@H]1C#N)C(=O)Nc1ccccc12)N(C)C(=O)c1cnc2cccnc2c1] |

-continued
| Compound | Structure |
|---|---|
| 303 | 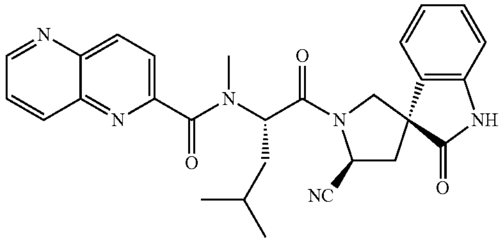 |
| 304 | 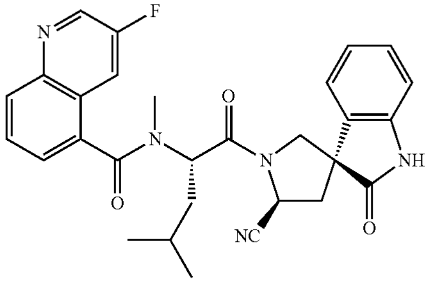 [SMILES: CC(C)C[C@@H](C(=O)N1C[C@]2(C[C@H]1C#N)C(=O)Nc1ccccc12)N(C)C(=O)c1cccc2ncc(F)cc12] |
| 305 | 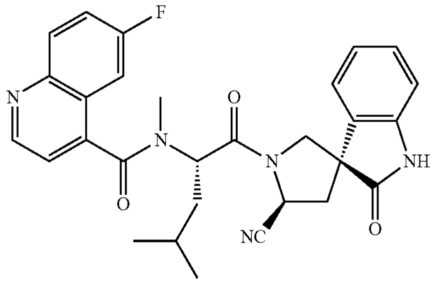 [SMILES: CC(C)C[C@@H](C(=O)N1C[C@]2(C[C@H]1C#N)C(=O)Nc1ccccc12)N(C)C(=O)c1ccnc2ccc(F)cc12] |
| 306 | 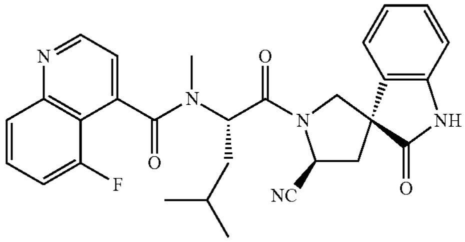 [SMILES: CC(C)C[C@@H](C(=O)N1C[C@]2(C[C@H]1C#N)C(=O)Nc1ccccc12)N(C)C(=O)c1ccnc2cccc(F)c12] |
| 307 | 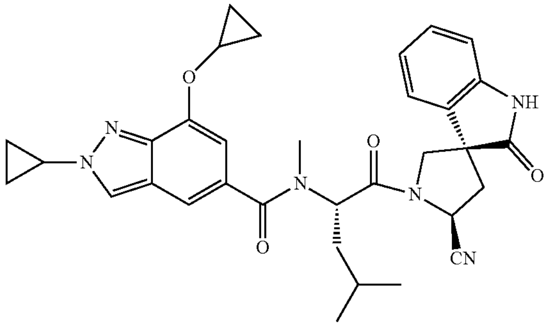 [SMILES: CC(C)C[C@@H](C(=O)N1C[C@]2(C[C@H]1C#N)C(=O)Nc1ccccc12)N(C)C(=O)c1cc(OC2CC2)c2nn(C3CC3)cc2c1] |

-continued
| Compound | Structure |
|---|---|
| 308 | 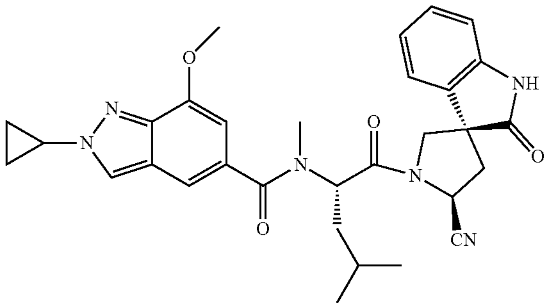 [SMILES: COc1cc(C(=O)N(C)[C@@H](CC(C)C)C(=O)N2C[C@]3(C[C@H]2C#N)C(=O)Nc2ccccc23)cc2cn(C3CC3)nc12] |
| 309 | 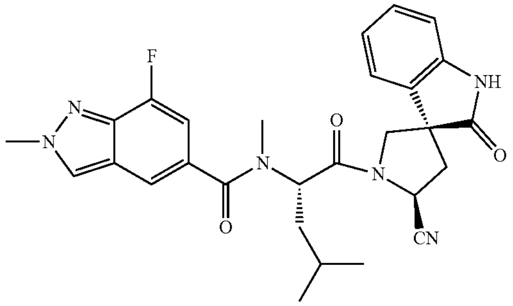 [SMILES: CC(C)C[C@@H](C(=O)N1C[C@]2(C[C@H]1C#N)C(=O)Nc1ccccc12)N(C)C(=O)c1cc(F)c2nn(C)cc2c1] |
| 310 | 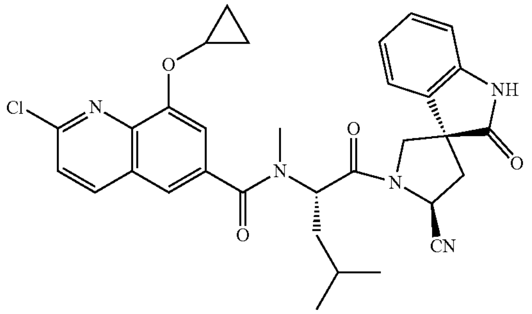 [SMILES: CC(C)C[C@@H](C(=O)N1C[C@]2(C[C@H]1C#N)C(=O)Nc1ccccc12)N(C)C(=O)c1cc(OC2CC2)c2nc(Cl)ccc2c1] |
| 311 | 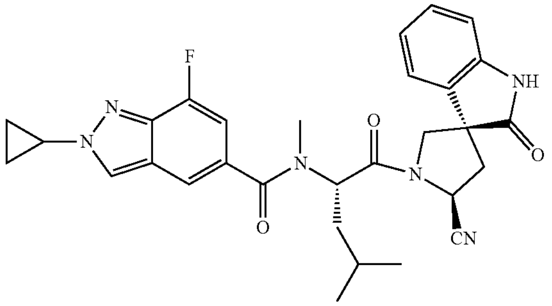 [SMILES: CC(C)C[C@@H](C(=O)N1C[C@]2(C[C@H]1C#N)C(=O)Nc1ccccc12)N(C)C(=O)c1cc(F)c2nn(C3CC3)cc2c1] |
| 312 | 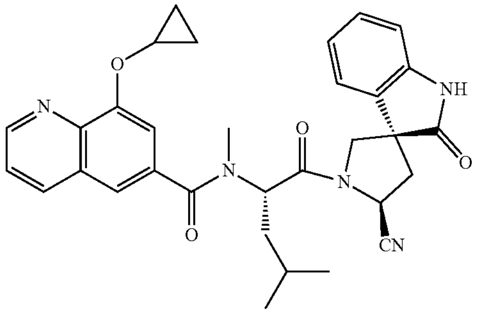 [SMILES: CC(C)C[C@@H](C(=O)N1C[C@]2(C[C@H]1C#N)C(=O)Nc1ccccc12)N(C)C(=O)c1cc(OC2CC2)c2ncccc2c1] |

-continued
| Compound | Structure |
| --- | --- |
| 313 | 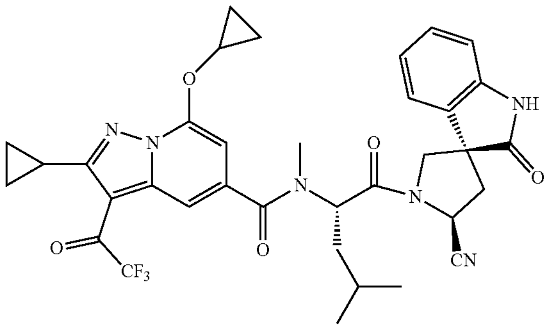 [SMILES: CC(C)C[C@@H](C(=O)N1C[C@]2(C[C@H]1C#N)C(=O)Nc1ccccc12)N(C)C(=O)c1cc(OC2CC2)n2nc(C3CC3)c(C(=O)C(F)(F)F)c2c1] |
| 314 | 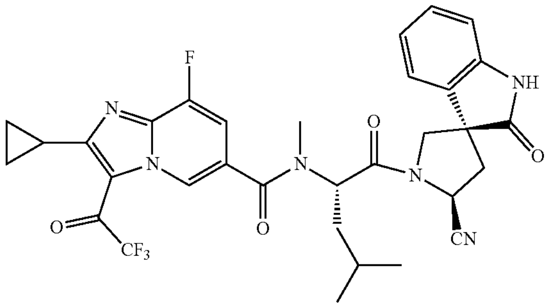 [SMILES: CC(C)C[C@@H](C(=O)N1C[C@]2(C[C@H]1C#N)C(=O)Nc1ccccc12)N(C)C(=O)c1cc(F)c2nc(C3CC3)c(C(=O)C(F)(F)F)n2c1] |
| 315 | 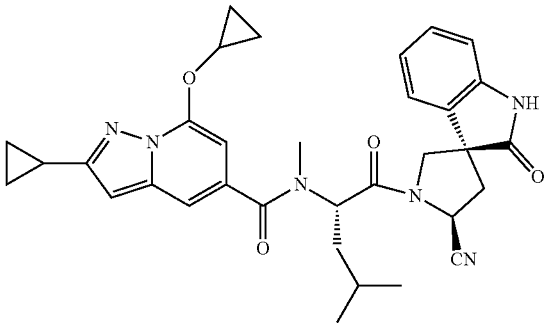 [SMILES: CC(C)C[C@@H](C(=O)N1C[C@]2(C[C@H]1C#N)C(=O)Nc1ccccc12)N(C)C(=O)c1cc(OC2CC2)n2nc(C3CC3)cc2c1] |
| 316 | 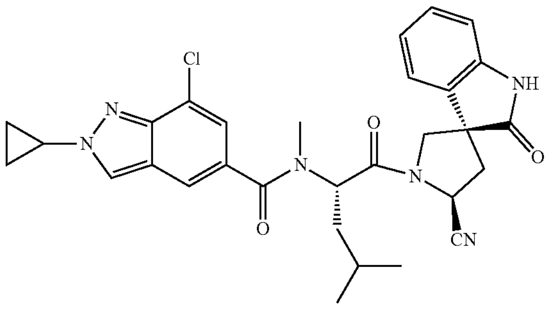 |

-continued
| Compound | Structure |
|---|---|
| 317 | 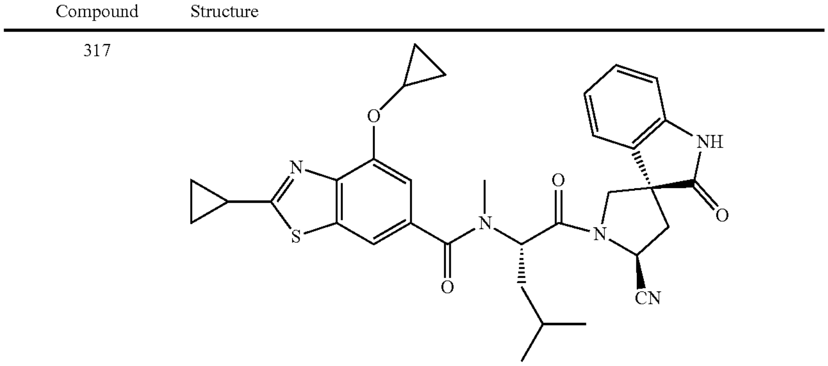 |
| 318 | 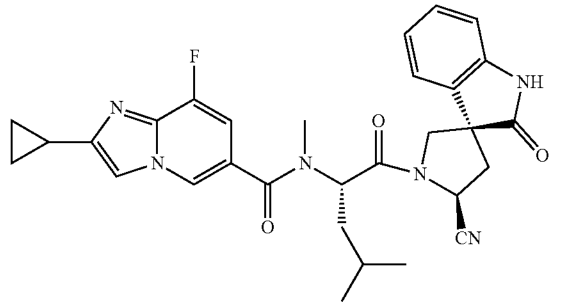 [SMILES: CC(C)C[C@@H](C(=O)N1C[C@]2(C[C@H]1C#N)C(=O)Nc1ccccc12)N(C)C(=O)c1cc(F)c2nc(C3CC3)cn2c1] |
| 319 | 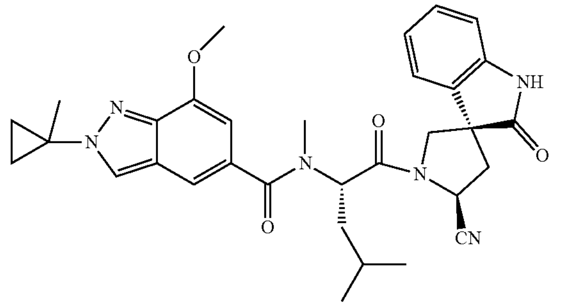 [SMILES: COc1cc(C(=O)N(C)[C@@H](CC(C)C)C(=O)N2C[C@]3(C[C@H]2C#N)C(=O)Nc2ccccc23)cc2cn(C3(C)CC3)nc12] |
| 320 | 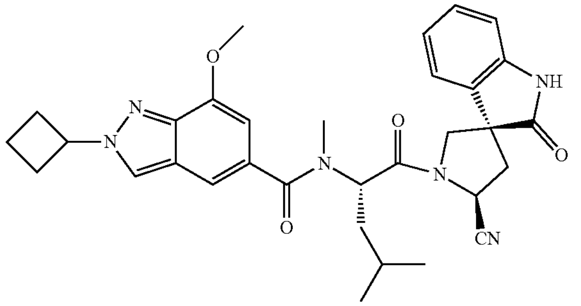 [SMILES: COc1cc(C(=O)N(C)[C@@H](CC(C)C)C(=O)N2C[C@]3(C[C@H]2C#N)C(=O)Nc2ccccc23)cc2cn(C3CCC3)nc12] |
| 321 | 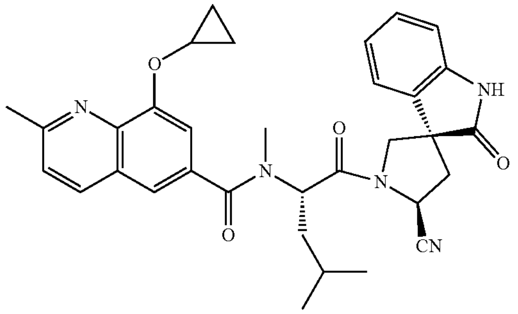 |

-continued
| Compound | Structure |
| --- | --- |
| 322 | 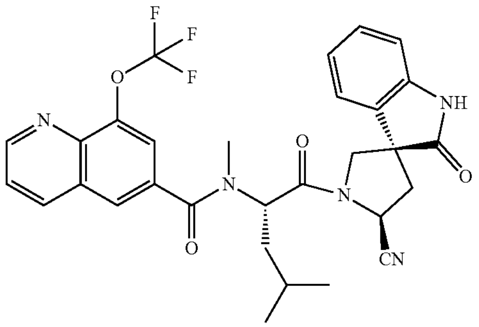 [SMILES: CC(C)C[C@@H](C(=O)N1C[C@]2(C[C@H]1C#N)C(=O)Nc1ccccc12)N(C)C(=O)c1cc(OC(F)(F)F)c2ncccc2c1] |
| 323 | 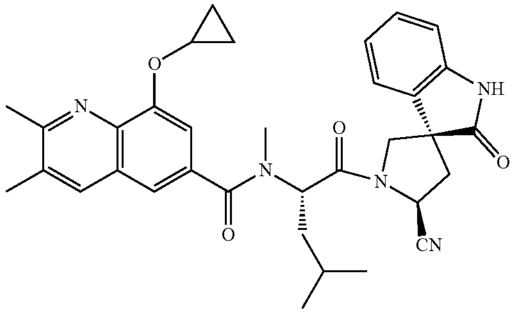 [SMILES: Cc1cc2cc(C(=O)N(C)[C@@H](CC(C)C)C(=O)N3C[C@]4(C[C@H]3C#N)C(=O)Nc3ccccc34)cc(OC3CC3)c2nc1C] |
| 324 | 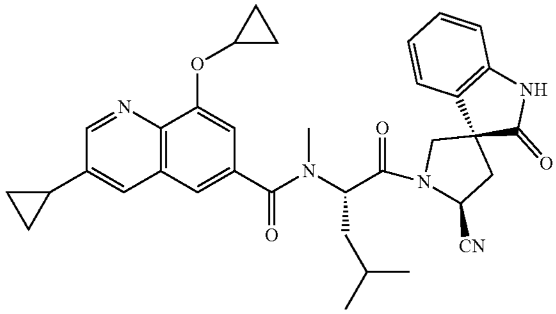 [SMILES: CC(C)C[C@@H](C(=O)N1C[C@]2(C[C@H]1C#N)C(=O)Nc1ccccc12)N(C)C(=O)c1cc(OC2CC2)c2ncc(C3CC3)cc2c1] |
| 325 | 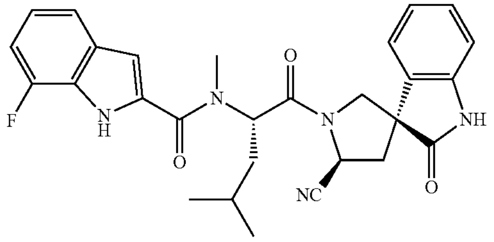 [SMILES: CC(C)C[C@@H](C(=O)N1C[C@]2(C[C@H]1C#N)C(=O)Nc1ccccc12)N(C)C(=O)c1cc2cccc(F)c2[nH]1] |
| 326 | 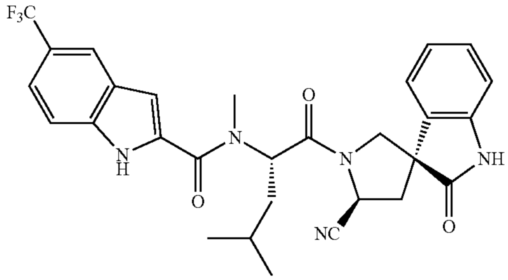 |

-continued
| Compound | Structure |
| --- | --- |
| 327 | 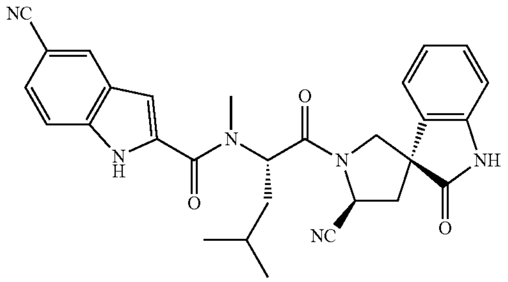 [SMILES: CC(C)C[C@@H](C(=O)N1C[C@]2(C[C@H]1C#N)C(=O)Nc1ccccc12)N(C)C(=O)c1cc2cc(C#N)ccc2[nH]1] |
| 328 | 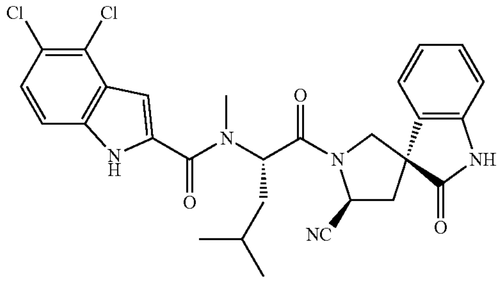 [SMILES: CC(C)C[C@@H](C(=O)N1C[C@]2(C[C@H]1C#N)C(=O)Nc1ccccc12)N(C)C(=O)c1cc2c(Cl)c(Cl)ccc2[nH]1] |
| 329 | 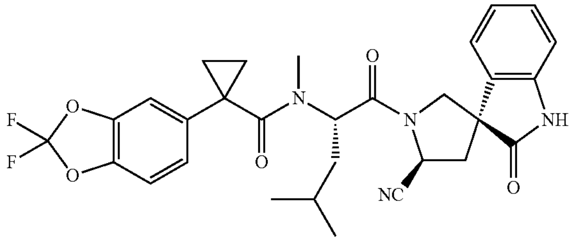 [SMILES: CC(C)C[C@@H](C(=O)N1C[C@]2(C[C@H]1C#N)C(=O)Nc1ccccc12)N(C)C(=O)C1(c2ccc3c(c2)OC(F)(F)O3)CC1] |
| 330 | 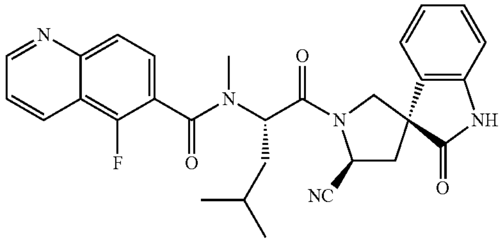 |
| 331 | 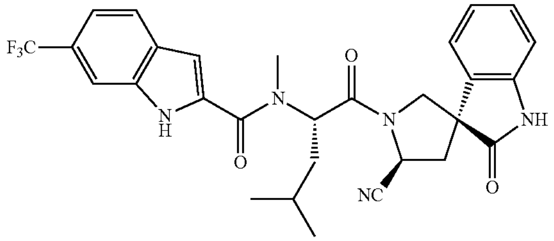 [SMILES: CC(C)C[C@@H](C(=O)N1C[C@]2(C[C@H]1C#N)C(=O)Nc1ccccc12)N(C)C(=O)c1cc2ccc(C(F)(F)F)cc2[nH]1] |
| 332 | 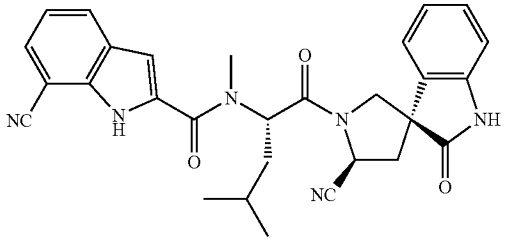 [SMILES: CC(C)C[C@@H](C(=O)N1C[C@]2(C[C@H]1C#N)C(=O)Nc1ccccc12)N(C)C(=O)c1cc2cccc(C#N)c2[nH]1]

-continued
| Compound | Structure |
|---|---|
| 333 | 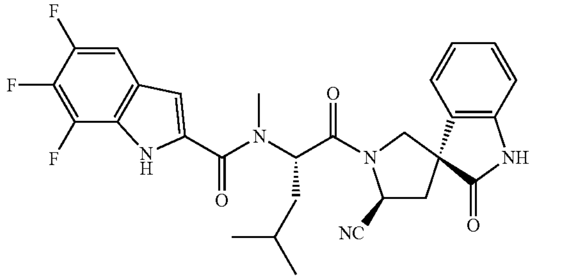 [SMILES: CC(C)C[C@@H](C(=O)N1C[C@]2(C[C@H]1C#N)C(=O)Nc1ccccc12)N(C)C(=O)c1cc2cc(F)c(F)c(F)c2[nH]1] |
| 334 | 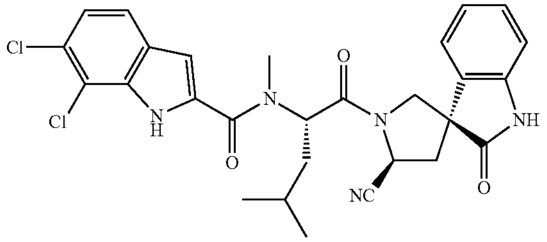 [SMILES: CC(C)C[C@@H](C(=O)N1C[C@]2(C[C@H]1C#N)C(=O)Nc1ccccc12)N(C)C(=O)c1cc2ccc(Cl)c(Cl)c2[nH]1] |
| 335 | 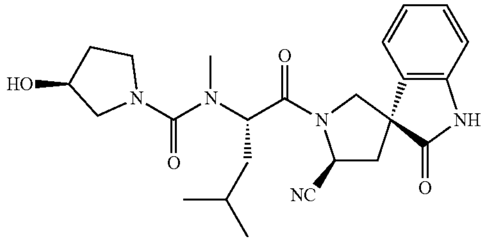 [SMILES: CC(C)C[C@@H](C(=O)N1C[C@]2(C[C@H]1C#N)C(=O)Nc1ccccc12)N(C)C(=O)N1CC[C@H](O)C1] |
| 336 | 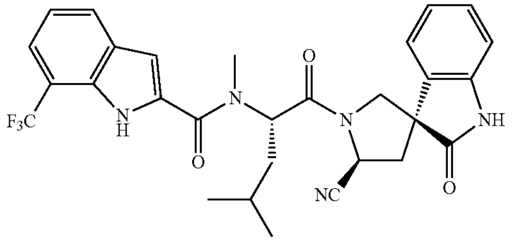 |
| 337 | 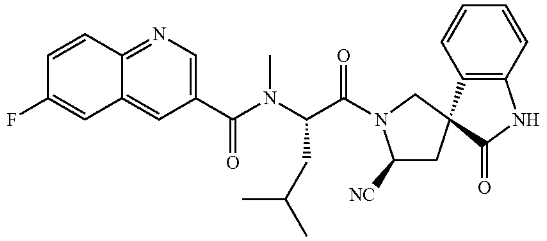 [SMILES: CC(C)C[C@@H](C(=O)N1C[C@]2(C[C@H]1C#N)C(=O)Nc1ccccc12)N(C)C(=O)c1cnc2ccc(F)cc2c1] |
| 338 | 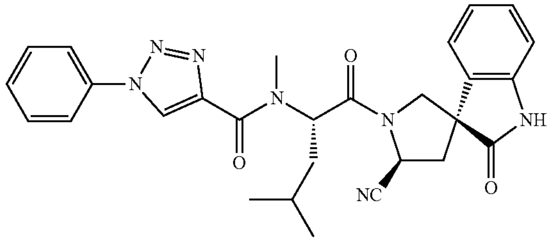 [SMILES: CC(C)C[C@@H](C(=O)N1C[C@]2(C[C@H]1C#N)C(=O)Nc1ccccc12)N(C)C(=O)c1cn(-c2ccccc2)nn1] |

-continued
| Compound | Structure |
|---|---|
| 339 | 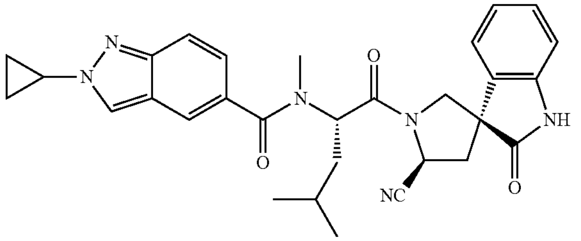 [SMILES: CC(C)C[C@@H](C(=O)N1C[C@]2(C[C@H]1C#N)C(=O)Nc1ccccc12)N(C)C(=O)c1ccc2nn(C3CC3)cc2c1] |
| 340 | 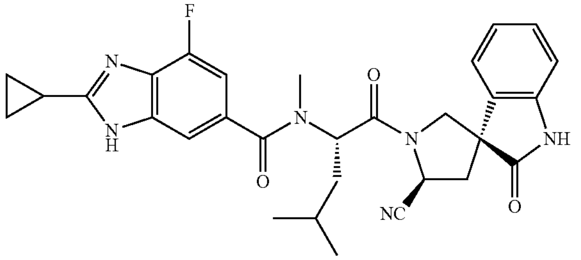 [SMILES: CC(C)C[C@@H](C(=O)N1C[C@]2(C[C@H]1C#N)C(=O)Nc1ccccc12)N(C)C(=O)c1cc(F)c2nc(C3CC3)[nH]c2c1] |
| 341 | 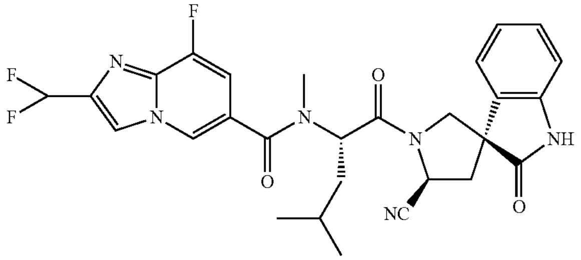 [SMILES: CC(C)C[C@@H](C(=O)N1C[C@]2(C[C@H]1C#N)C(=O)Nc1ccccc12)N(C)C(=O)c1cc(F)c2nc(C(F)F)cn2c1] |
| 342 | 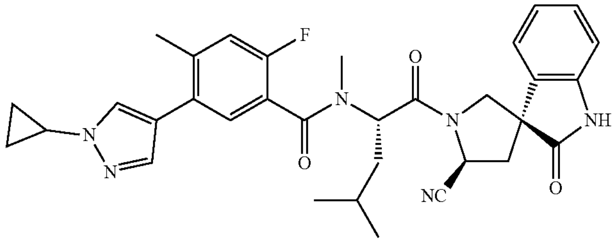 [SMILES: Cc1cc(F)c(C(=O)N(C)[C@@H](CC(C)C)C(=O)N2C[C@]3(C[C@H]2C#N)C(=O)Nc2ccccc23)cc1-c1cnn(C2CC2)c1] |
| 343 | 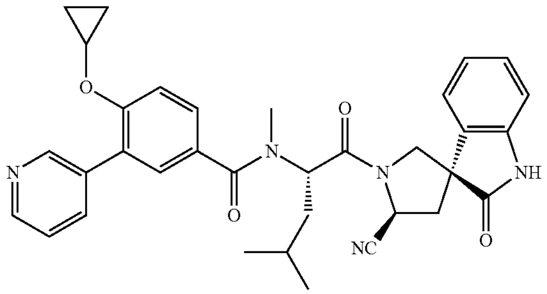 [SMILES: CC(C)C[C@@H](C(=O)N1C[C@]2(C[C@H]1C#N)C(=O)Nc1ccccc12)N(C)C(=O)c1ccc(OC2CC2)c(-c2cccnc2)c1] |
| 344 | 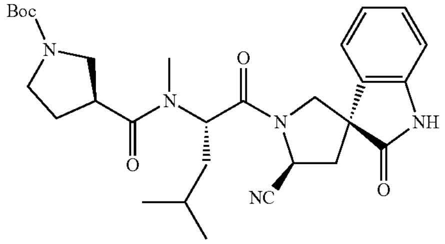 [SMILES: CC(C)C[C@@H](C(=O)N1C[C@]2(C[C@H]1C#N)C(=O)Nc1ccccc12)N(C)C(=O)[C@H]1CCN(C(=O)OC(C)(C)C)C1] |

-continued
| Compound | Structure |
| --- | --- |
| 345 | 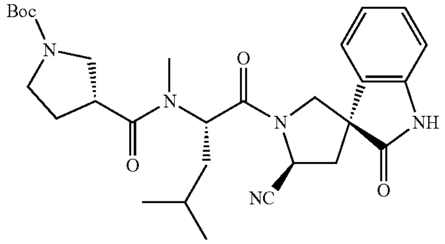 [SMILES: CC(C)C[C@@H](C(=O)N1C[C@]2(C[C@H]1C#N)C(=O)Nc1ccccc12)N(C)C(=O)[C@@H]1CCN(C(=O)OC(C)(C)C)C1] |
| 346 | 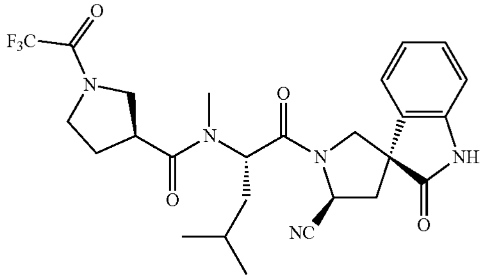 [SMILES: CC(C)C[C@@H](C(=O)N1C[C@]2(C[C@H]1C#N)C(=O)Nc1ccccc12)N(C)C(=O)[C@H]1CCN(C(=O)C(F)(F)F)C1] |
| 347 | 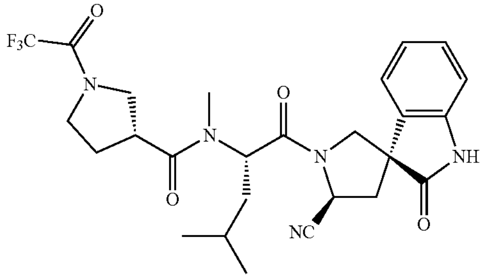 [SMILES: CC(C)C[C@@H](C(=O)N1C[C@]2(C[C@H]1C#N)C(=O)Nc1ccccc12)N(C)C(=O)[C@@H]1CCN(C(=O)C(F)(F)F)C1] |
| 348 | 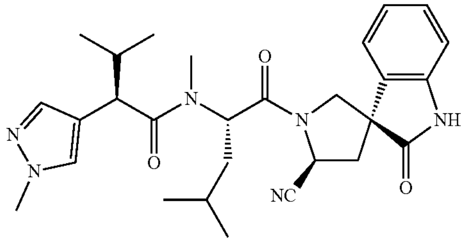 [SMILES: CC(C)C[C@@H](C(=O)N1C[C@]2(C[C@H]1C#N)C(=O)Nc1ccccc12)N(C)C(=O)[C@@H](c1cnn(C)c1)C(C)C] |
| 349 | 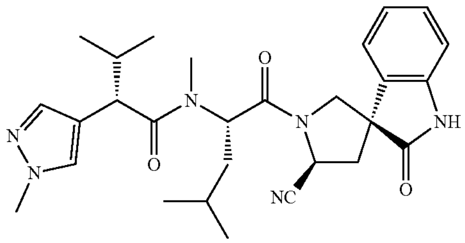 [SMILES: CC(C)C[C@@H](C(=O)N1C[C@]2(C[C@H]1C#N)C(=O)Nc1ccccc12)N(C)C(=O)[C@H](c1cnn(C)c1)C(C)C] |
| 350 | 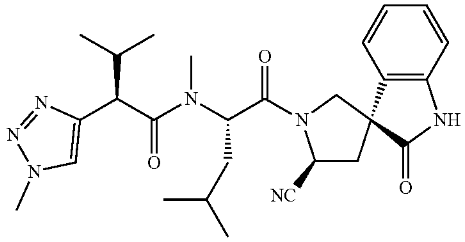 [SMILES: CC(C)C[C@@H](C(=O)N1C[C@]2(C[C@H]1C#N)C(=O)Nc1ccccc12)N(C)C(=O)[C@@H](c1cn(C)nn1)C(C)C] |

-continued
| Compound | Structure |
|---|---|
| 351 | 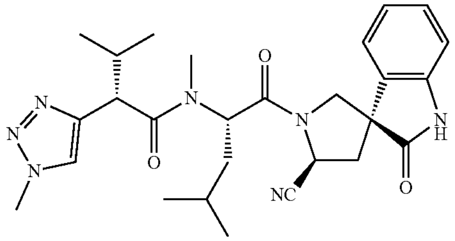 [SMILES: CC(C)C[C@@H](C(=O)N1C[C@]2(C[C@H]1C#N)C(=O)Nc1ccccc12)N(C)C(=O)[C@H](c1cn(C)nn1)C(C)C] |
| 352 | 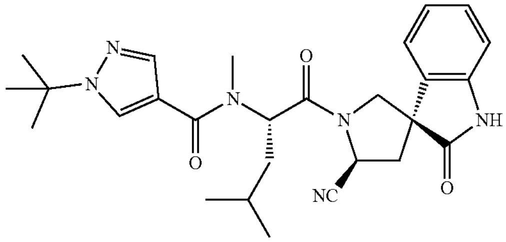 [SMILES: CC(C)C[C@@H](C(=O)N1C[C@]2(C[C@H]1C#N)C(=O)Nc1ccccc12)N(C)C(=O)c1cnn(C(C)(C)C)c1] |
| 353 | 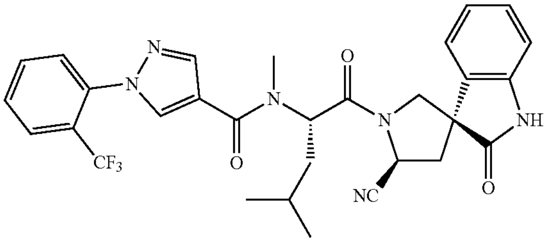 [SMILES: CC(C)C[C@@H](C(=O)N1C[C@]2(C[C@H]1C#N)C(=O)Nc1ccccc12)N(C)C(=O)c1cnn(-c2ccccc2C(F)(F)F)c1] |
| 354 | 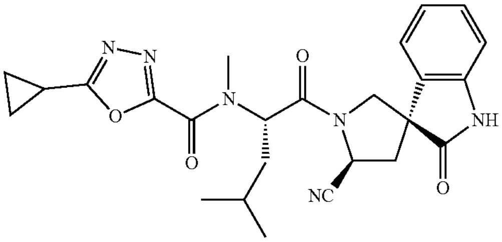 [SMILES: CC(C)C[C@@H](C(=O)N1C[C@]2(C[C@H]1C#N)C(=O)Nc1ccccc12)N(C)C(=O)c1nnc(C2CC2)o1] |
| 355 | 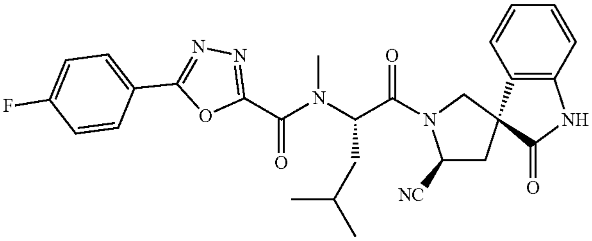 [SMILES: CC(C)C[C@@H](C(=O)N1C[C@]2(C[C@H]1C#N)C(=O)Nc1ccccc12)N(C)C(=O)c1nnc(-c2ccc(F)cc2)o1] |
| 356 | 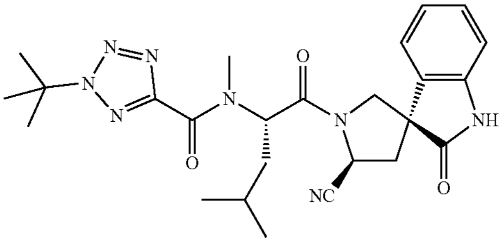 [SMILES: CC(C)C[C@@H](C(=O)N1C[C@]2(C[C@H]1C#N)C(=O)Nc1ccccc12)N(C)C(=O)c1nnn(C(C)(C)C)n1] |

-continued
| Compound | Structure |
| --- | --- |
| 357 | 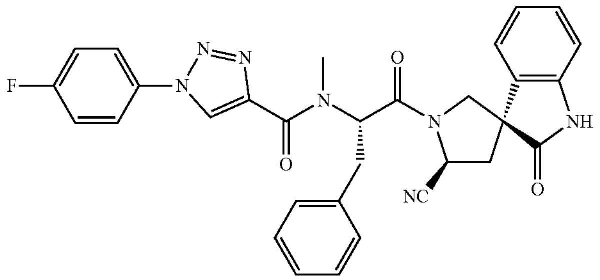 [SMILES: CN(C(=O)c1cn(-c2ccc(F)cc2)nn1)[C@@H](Cc1ccccc1)C(=O)N1C[C@]2(C[C@H]1C#N)C(=O)Nc1ccccc12] |
| 358 | 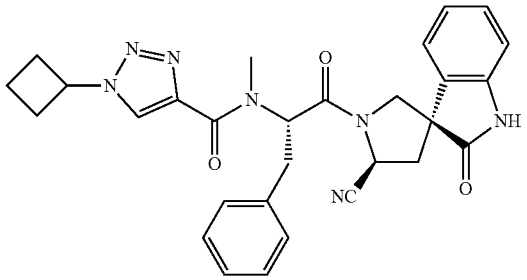 [SMILES: CN(C(=O)c1cn(C2CCC2)nn1)[C@@H](Cc1ccccc1)C(=O)N1C[C@]2(C[C@H]1C#N)C(=O)Nc1ccccc12] |
| 359 | 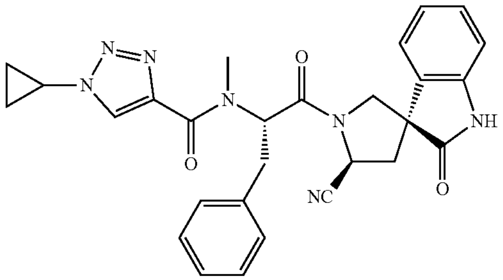 [SMILES: CN(C(=O)c1cn(C2CC2)nn1)[C@@H](Cc1ccccc1)C(=O)N1C[C@]2(C[C@H]1C#N)C(=O)Nc1ccccc12] |
| 360 | 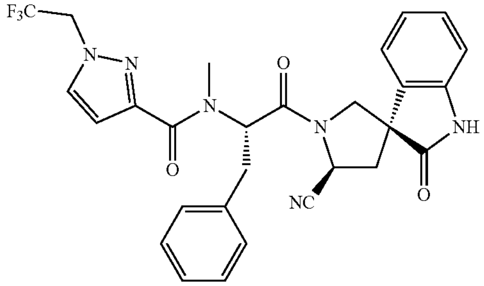 [SMILES: CN(C(=O)c1ccn(CC(F)(F)F)n1)[C@@H](Cc1ccccc1)C(=O)N1C[C@]2(C[C@H]1C#N)C(=O)Nc1ccccc12] |
| 361 | 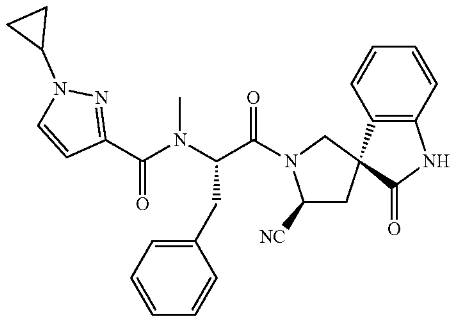 [SMILES: CN(C(=O)c1ccn(C2CC2)n1)[C@@H](Cc1ccccc1)C(=O)N1C[C@]2(C[C@H]1C#N)C(=O)Nc1ccccc12] |

-continued
| Compound | Structure |
|---|---|
| 362 | 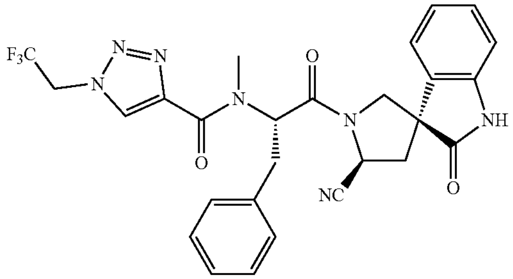 [SMILES: CN(C(=O)c1cn(CC(F)(F)F)nn1)[C@@H](Cc1ccccc1)C(=O)N1C[C@]2(C[C@H]1C#N)C(=O)Nc1ccccc12] |
| 363 | 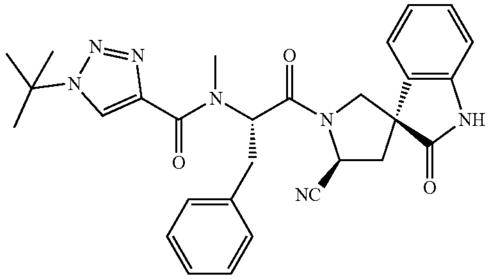 [SMILES: CN(C(=O)c1cn(C(C)(C)C)nn1)[C@@H](Cc1ccccc1)C(=O)N1C[C@]2(C[C@H]1C#N)C(=O)Nc1ccccc12] |
| 364 | 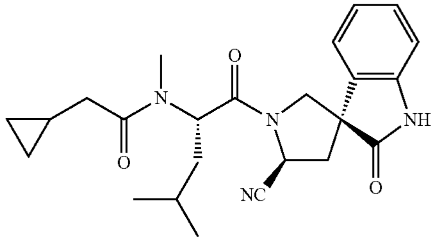 [SMILES: CC(C)C[C@@H](C(=O)N1C[C@]2(C[C@H]1C#N)C(=O)Nc1ccccc12)N(C)C(=O)CC1CC1] |
| 365 | 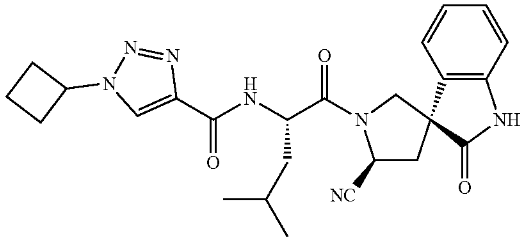 [SMILES: CC(C)C[C@H](NC(=O)c1cn(C2CCC2)nn1)C(=O)N1C[C@]2(C[C@H]1C#N)C(=O)Nc1ccccc12] |
| 366 | 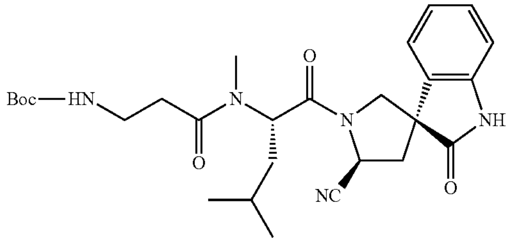 [SMILES: CC(C)C[C@@H](C(=O)N1C[C@]2(C[C@H]1C#N)C(=O)Nc1ccccc12)N(C)C(=O)CCNC(=O)OC(C)(C)C] |
| 367 | 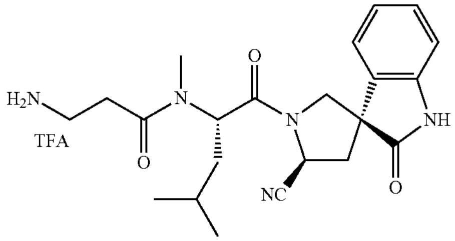 [SMILES: CC(C)C[C@@H](C(=O)N1C[C@]2(C[C@H]1C#N)C(=O)Nc1ccccc12)N(C)C(=O)CCN] |

-continued
| Compound | Structure |
|---|---|
| 368 | 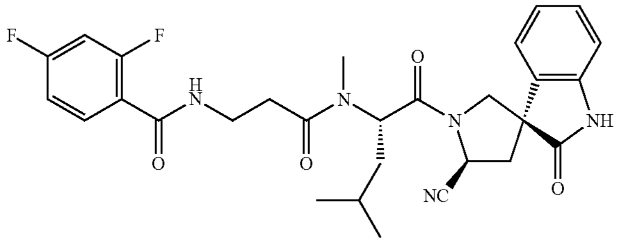 [SMILES: CC(C)C[C@@H](C(=O)N1C[C@]2(C[C@H]1C#N)C(=O)Nc1ccccc12)N(C)C(=O)CCNC(=O)c1ccc(F)cc1F] |
| 369 | 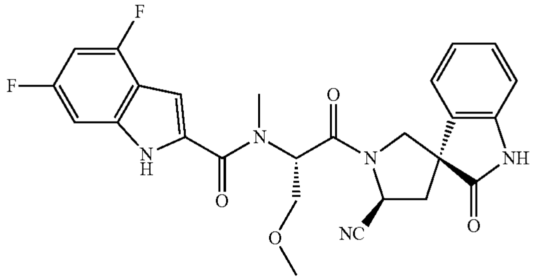 [SMILES: COC[C@@H](C(=O)N1C[C@]2(C[C@H]1C#N)C(=O)Nc1ccccc12)N(C)C(=O)c1cc2c(F)cc(F)cc2[nH]1] |
| 370 | 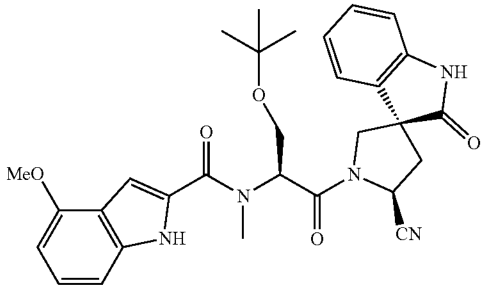 [SMILES: COc1cccc2[nH]c(C(=O)N(C)[C@@H](COC(C)(C)C)C(=O)N3C[C@]4(C[C@H]3C#N)C(=O)Nc3ccccc34)cc12] |
| 371 | 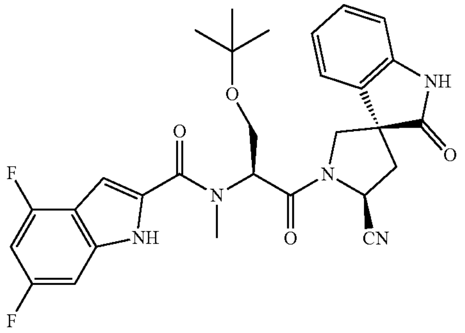 [SMILES: CN(C(=O)c1cc2c(F)cc(F)cc2[nH]1)[C@@H](COC(C)(C)C)C(=O)N1C[C@]2(C[C@H]1C#N)C(=O)Nc1ccccc12] |
| 372 | 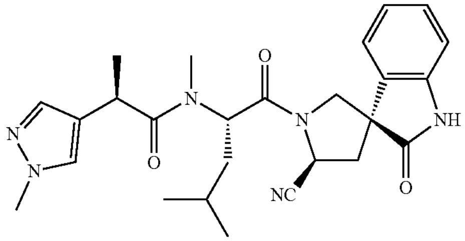 [SMILES: CC(C)C[C@@H](C(=O)N1C[C@]2(C[C@H]1C#N)C(=O)Nc1ccccc12)N(C)C(=O)[C@H](C)c1cnn(C)c1] |

-continued
| Compound | Structure |
| --- | --- |
| 373 | 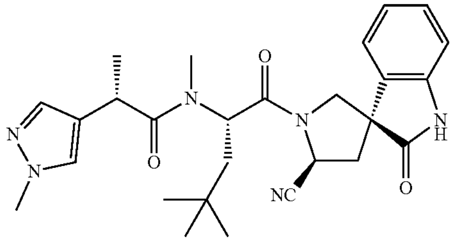 [SMILES: C[C@H](C(=O)N(C)[C@@H](CC(C)(C)C)C(=O)N1C[C@]2(C[C@H]1C#N)C(=O)Nc1ccccc12)c1cnn(C)c1] |
| 374 | 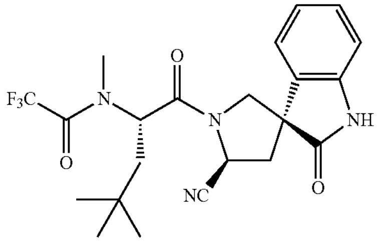 [SMILES: CN(C(=O)C(F)(F)F)[C@@H](CC(C)(C)C)C(=O)N1C[C@]2(C[C@H]1C#N)C(=O)Nc1ccccc12] |
| 375 | 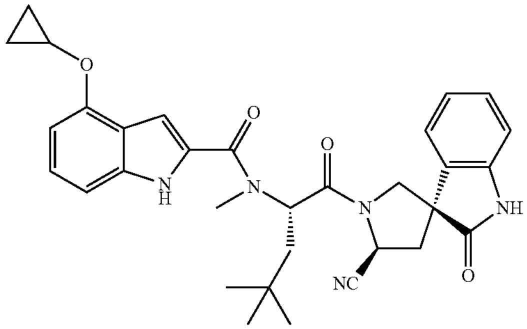 [SMILES: CN(C(=O)c1cc2c(OC3CC3)cccc2[nH]1)[C@@H](CC(C)(C)C)C(=O)N1C[C@]2(C[C@H]1C#N)C(=O)Nc1ccccc12] |
| 376 | 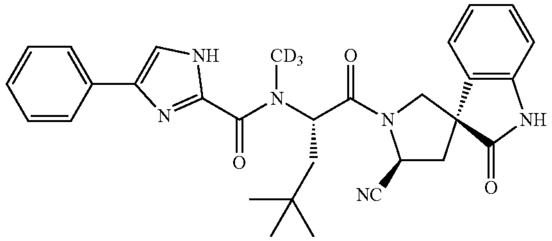 [SMILES: [2H]C([2H])([2H])N(C(=O)c1nc(-c2ccccc2)c[nH]1)[C@@H](CC(C)(C)C)C(=O)N1C[C@]2(C[C@H]1C#N)C(=O)Nc1ccccc12] |
| 377 | 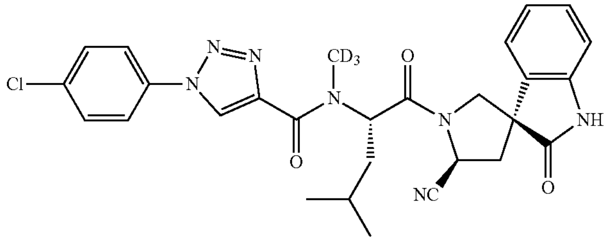 [SMILES: [2H]C([2H])([2H])N(C(=O)c1cn(-c2ccc(Cl)cc2)nn1)[C@@H](CC(C)C)C(=O)N1C[C@]2(C[C@H]1C#N)C(=O)Nc1ccccc12] |
| 378 | 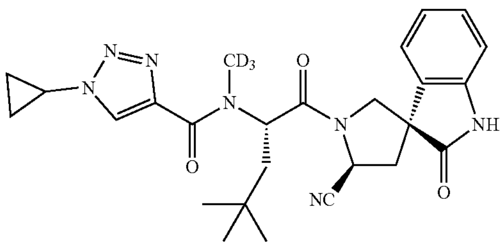 [SMILES: [2H]C([2H])([2H])N(C(=O)c1cn(C2CC2)nn1)[C@@H](CC(C)(C)C)C(=O)N1C[C@]2(C[C@H]1C#N)C(=O)Nc1ccccc12] |

-continued
| Compound | Structure |
|---|---|
| 379 | 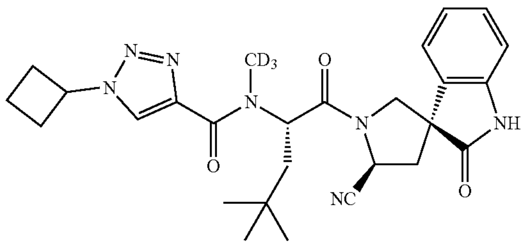 [SMILES: [2H]C([2H])([2H])N(C(=O)c1cn(C2CCC2)nn1)[C@@H](CC(C)(C)C)C(=O)N1C[C@]2(C[C@H]1C#N)C(=O)Nc1ccccc12] |
| 380 | 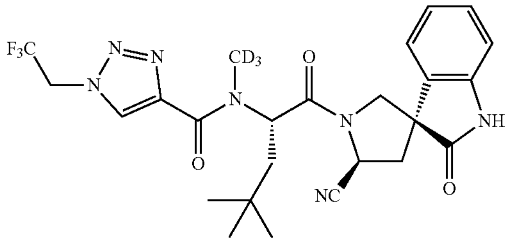 [SMILES: [2H]C([2H])([2H])N(C(=O)c1cn(CC(F)(F)F)nn1)[C@@H](CC(C)(C)C)C(=O)N1C[C@]2(C[C@H]1C#N)C(=O)Nc1ccccc12] |
| 381 | 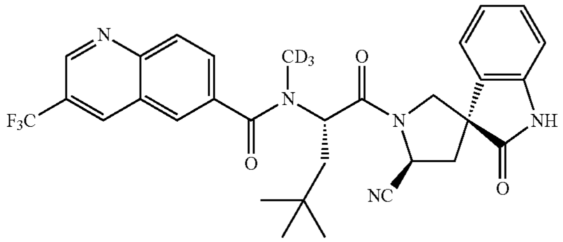 [SMILES: [2H]C([2H])([2H])N(C(=O)c1ccc2ncc(C(F)(F)F)cc2c1)[C@@H](CC(C)(C)C)C(=O)N1C[C@]2(C[C@H]1C#N)C(=O)Nc1ccccc12] |
| 382 | 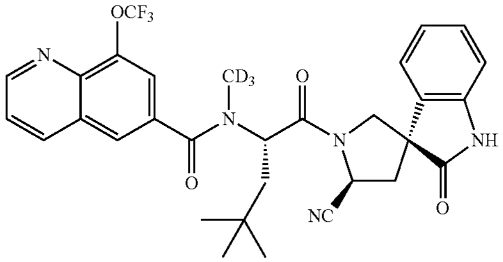 [SMILES: [2H]C([2H])([2H])N(C(=O)c1cc(OC(F)(F)F)c2ncccc2c1)[C@@H](CC(C)(C)C)C(=O)N1C[C@]2(C[C@H]1C#N)C(=O)Nc1ccccc12] |
| 383 | 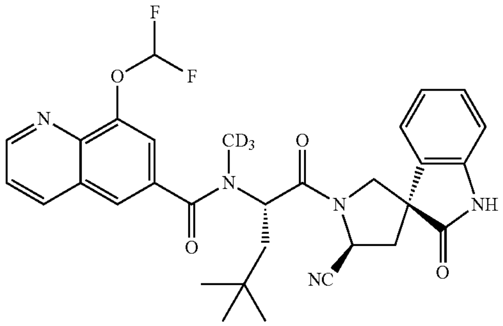 [SMILES: [2H]C([2H])([2H])N(C(=O)c1cc(OC(F)F)c2ncccc2c1)[C@@H](CC(C)(C)C)C(=O)N1C[C@]2(C[C@H]1C#N)C(=O)Nc1ccccc12] |

-continued
| Compound | Structure |
|---|---|
| 384 | 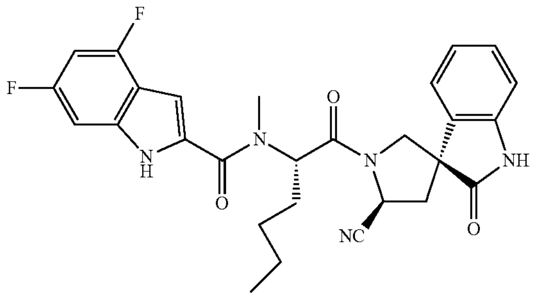 [SMILES: CCCC[C@@H](C(=O)N1C[C@]2(C[C@H]1C#N)C(=O)Nc1ccccc12)N(C)C(=O)c1cc2c(F)cc(F)cc2[nH]1] |
| 385 | 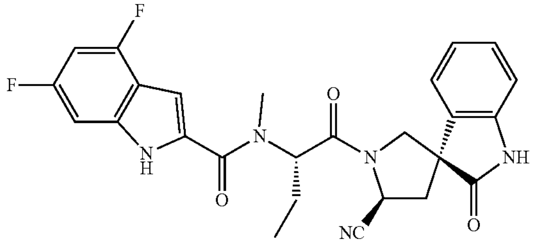 [SMILES: CC[C@@H](C(=O)N1C[C@]2(C[C@H]1C#N)C(=O)Nc1ccccc12)N(C)C(=O)c1cc2c(F)cc(F)cc2[nH]1] |
| 386 | 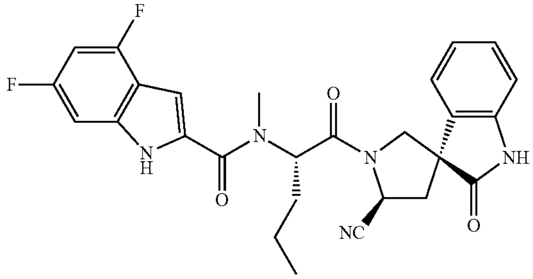 [SMILES: CCC[C@@H](C(=O)N1C[C@]2(C[C@H]1C#N)C(=O)Nc1ccccc12)N(C)C(=O)c1cc2c(F)cc(F)cc2[nH]1] |
| 387 | 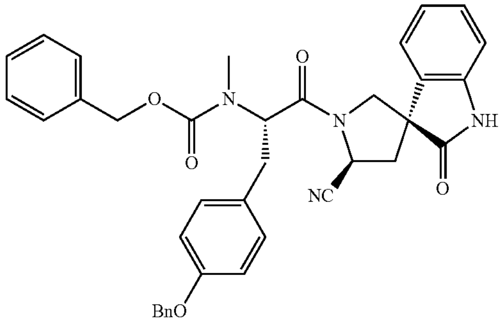 [SMILES: CN(C(=O)OCc1ccccc1)[C@@H](Cc1ccc(OCc2ccccc2)cc1)C(=O)N1C[C@]2(C[C@H]1C#N)C(=O)Nc1ccccc12] |
| 388 | 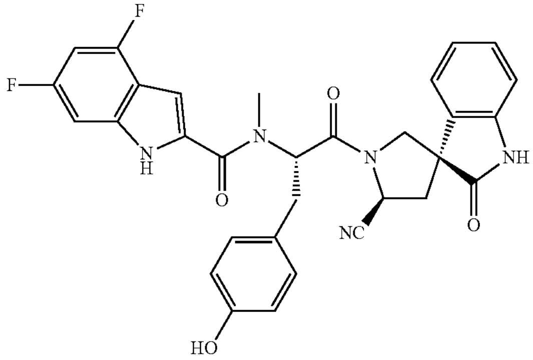 [SMILES: CN(C(=O)c1cc2c(F)cc(F)cc2[nH]1)[C@@H](Cc1ccc(O)cc1)C(=O)N1C[C@]2(C[C@H]1C#N)C(=O)Nc1ccccc12] |

-continued
| Compound | Structure |
| --- | --- |
| 389 | 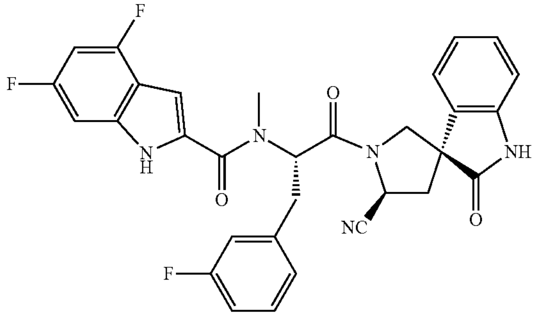 [SMILES: CN(C(=O)c1cc2c(F)cc(F)cc2[nH]1)[C@@H](Cc1cccc(F)c1)C(=O)N1C[C@]2(C[C@H]1C#N)C(=O)Nc1ccccc12] |
| 390 | 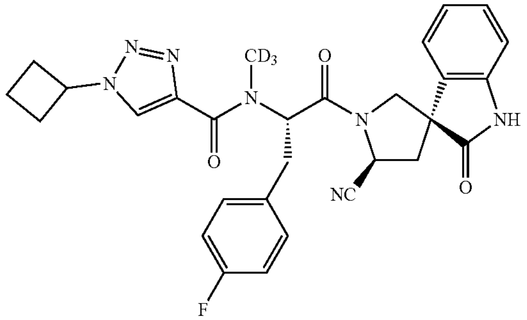 [SMILES: [2H]C([2H])([2H])N(C(=O)c1cn(C2CCC2)nn1)[C@@H](Cc1ccc(F)cc1)C(=O)N1C[C@]2(C[C@H]1C#N)C(=O)Nc1ccccc12] |
| 391 | 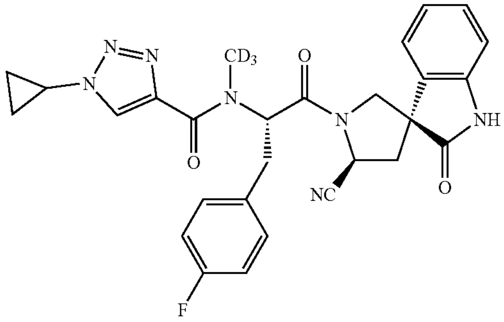 [SMILES: [2H]C([2H])([2H])N(C(=O)c1cn(C2CC2)nn1)[C@@H](Cc1ccc(F)cc1)C(=O)N1C[C@]2(C[C@H]1C#N)C(=O)Nc1ccccc12] |
| 392 | 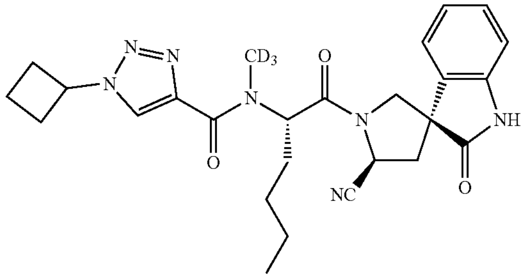 [SMILES: [2H]C([2H])([2H])N(C(=O)c1cn(C2CCC2)nn1)[C@@H](CCCC)C(=O)N1C[C@]2(C[C@H]1C#N)C(=O)Nc1ccccc12] |
| 393 | 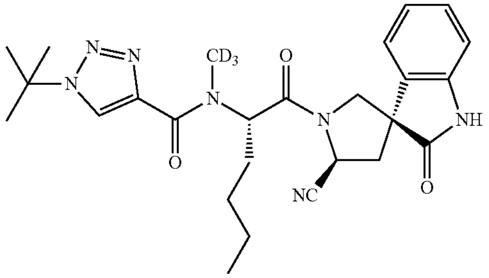 [SMILES: [2H]C([2H])([2H])N(C(=O)c1cn(C(C)(C)C)nn1)[C@@H](CCCC)C(=O)N1C[C@]2(C[C@H]1C#N)C(=O)Nc1ccccc12] |

-continued
| Compound | Structure |
|---|---|
| 394 | 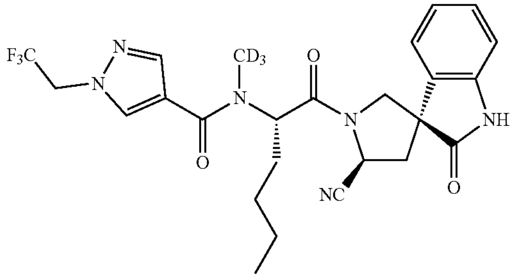 [SMILES: [2H]C([2H])([2H])N(C(=O)c1cnn(CC(F)(F)F)c1)[C@@H](CCCC)C(=O)N1C[C@]2(C[C@H]1C#N)C(=O)Nc1ccccc12] |
| 395 | 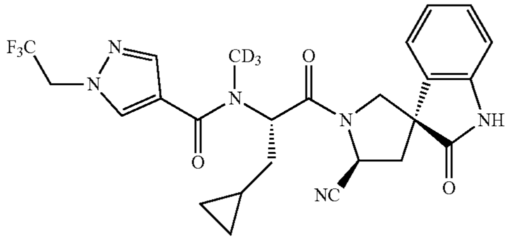 [SMILES: [2H]C([2H])([2H])N(C(=O)c1cnn(CC(F)(F)F)c1)[C@@H](CC1CC1)C(=O)N1C[C@]2(C[C@H]1C#N)C(=O)Nc1ccccc12] |
| 396 | 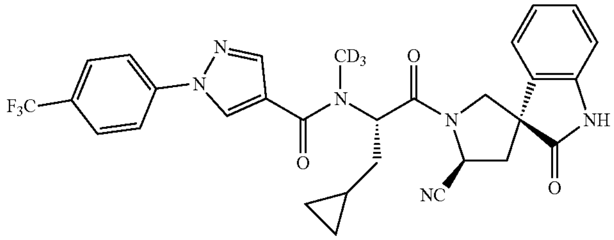 [SMILES: [2H]C([2H])([2H])N(C(=O)c1cnn(-c2ccc(C(F)(F)F)cc2)c1)[C@@H](CC1CC1)C(=O)N1C[C@]2(C[C@H]1C#N)C(=O)Nc1ccccc12] |
| 397 | 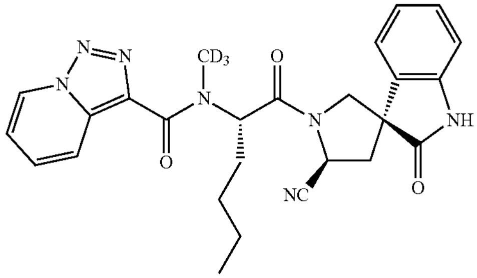 [SMILES: [2H]C([2H])([2H])N(C(=O)c1nnn2ccccc12)[C@@H](CCCC)C(=O)N1C[C@]2(C[C@H]1C#N)C(=O)Nc1ccccc12] |
| 398 | 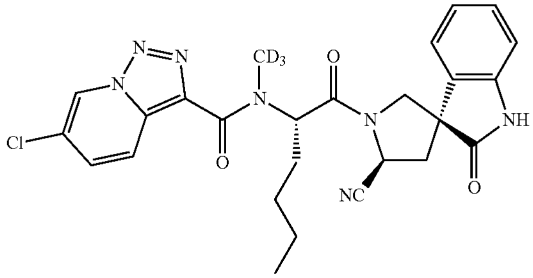 |
| 399 | 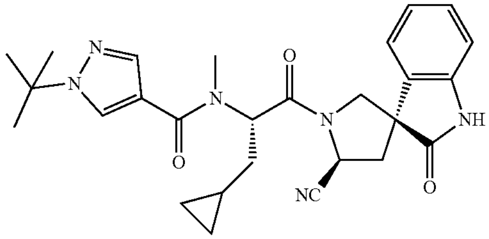 [SMILES: CN(C(=O)c1cnn(C(C)(C)C)c1)[C@@H](CC1CC1)C(=O)N1C[C@]2(C[C@H]1C#N)C(=O)Nc1ccccc12] |

-continued
| Compound | Structure |
| --- | --- |
| 400 | 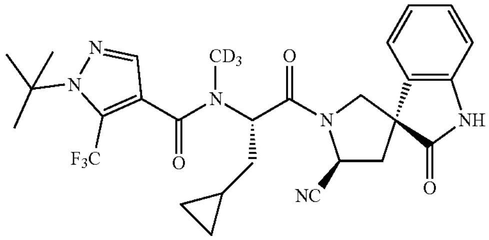 [SMILES: [2H]C([2H])([2H])N(C(=O)c1cnn(C(C)(C)C)c1C(F)(F)F)[C@@H](CC1CC1)C(=O)N1C[C@]2(C[C@H]1C#N)C(=O)Nc1ccccc12] |
| 401 | 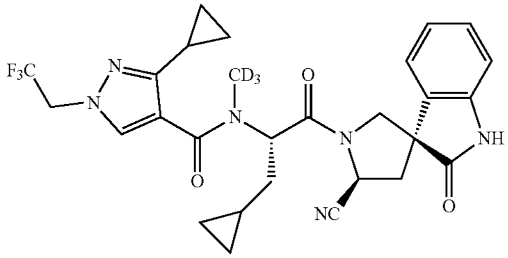 [SMILES: [2H]C([2H])([2H])N(C(=O)c1cn(CC(F)(F)F)nc1C1CC1)[C@@H](CC1CC1)C(=O)N1C[C@]2(C[C@H]1C#N)C(=O)Nc1ccccc12] |
| 402 | 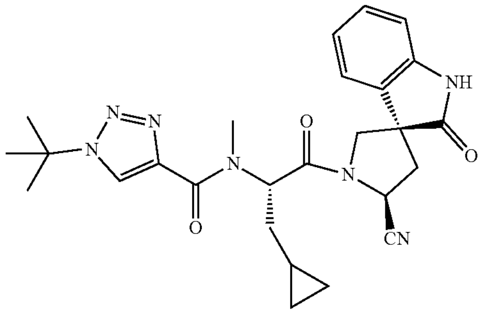 [SMILES: CN(C(=O)c1cn(C(C)(C)C)nn1)[C@@H](CC1CC1)C(=O)N1C[C@]2(C[C@H]1C#N)C(=O)Nc1ccccc12] |
| 403 | 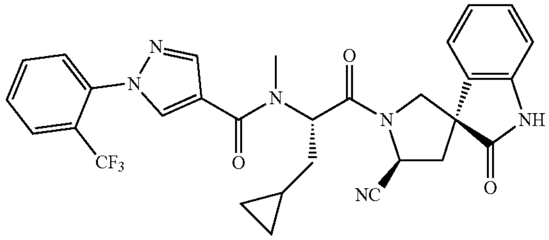 [SMILES: CN(C(=O)c1cnn(-c2ccccc2C(F)(F)F)c1)[C@@H](CC1CC1)C(=O)N1C[C@]2(C[C@H]1C#N)C(=O)Nc1ccccc12] |
| 404 | 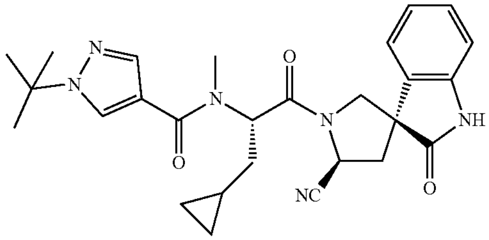 [SMILES: CN(C(=O)c1cnn(C(C)(C)C)c1)[C@@H](CC1CC1)C(=O)N1C[C@]2(C[C@H]1C#N)C(=O)Nc1ccccc12] |
| 405 | 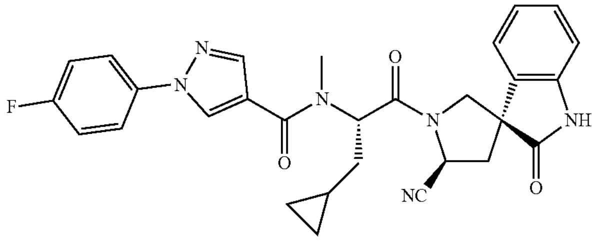 [SMILES: CN(C(=O)c1cnn(-c2ccc(F)cc2)c1)[C@@H](CC1CC1)C(=O)N1C[C@]2(C[C@H]1C#N)C(=O)Nc1ccccc12] |

-continued
| Compound | Structure |
|---|---|
| 406 | 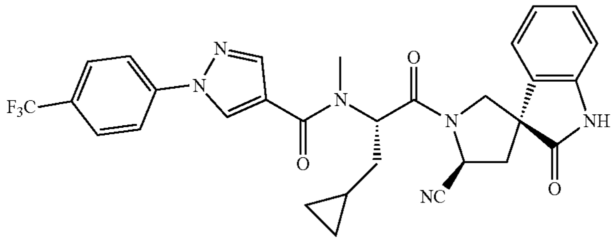 [SMILES: CN(C(=O)c1cnn(-c2ccc(C(F)(F)F)cc2)c1)[C@@H](CC1CC1)C(=O)N1C[C@]2(C[C@H]1C#N)C(=O)Nc1ccccc12] |
| 407 | 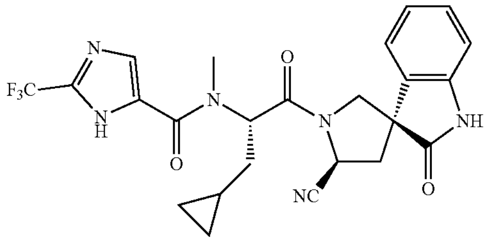 [SMILES: CN(C(=O)c1cnc(C(F)(F)F)[nH]1)[C@@H](CC1CC1)C(=O)N1C[C@]2(C[C@H]1C#N)C(=O)Nc1ccccc12] |
| 408 | 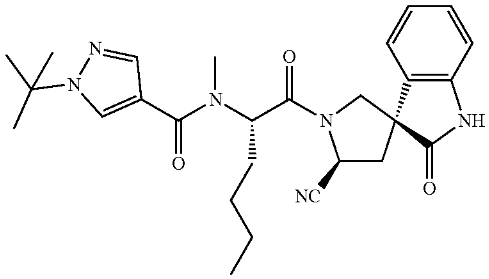 [SMILES: CCCC[C@@H](C(=O)N1C[C@]2(C[C@H]1C#N)C(=O)Nc1ccccc12)N(C)C(=O)c1cnn(C(C)(C)C)c1] |
| 409 | 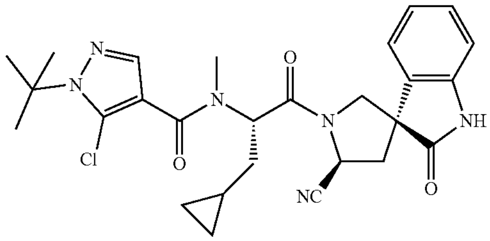 [SMILES: CN(C(=O)c1cnn(C(C)(C)C)c1Cl)[C@@H](CC1CC1)C(=O)N1C[C@]2(C[C@H]1C#N)C(=O)Nc1ccccc12] |
| 410 | 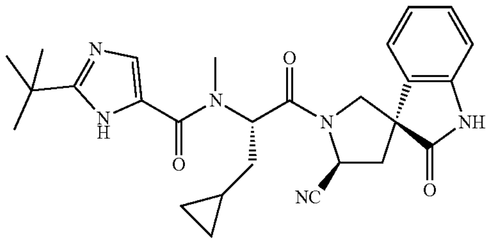 [SMILES: CN(C(=O)c1cnc(C(C)(C)C)[nH]1)[C@@H](CC1CC1)C(=O)N1C[C@]2(C[C@H]1C#N)C(=O)Nc1ccccc12] |
| 411 | 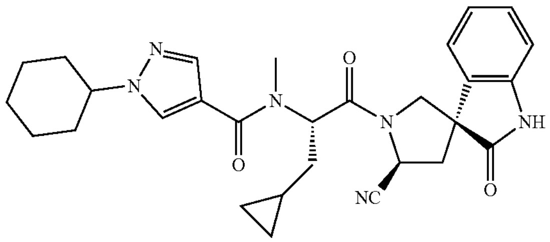 [SMILES: CN(C(=O)c1cnn(C2CCCCC2)c1)[C@@H](CC1CC1)C(=O)N1C[C@]2(C[C@H]1C#N)C(=O)Nc1ccccc12] |

-continued
| Compound | Structure |
|---|---|
| 412 | 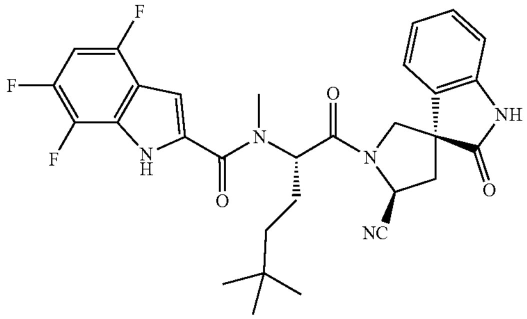 [SMILES: CN(C(=O)c1cc2c(F)cc(F)c(F)c2[nH]1)[C@@H](CCC(C)(C)C)C(=O)N1C[C@]2(C[C@H]1C#N)C(=O)Nc1ccccc12] |
| 413 | 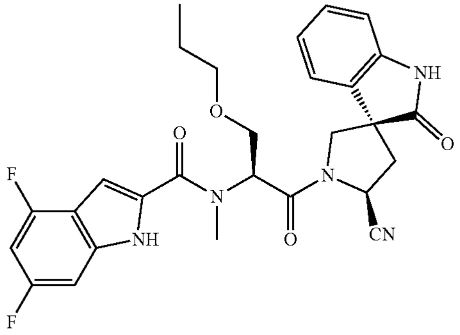 [SMILES: CCCOC[C@@H](C(=O)N1C[C@]2(C[C@H]1C#N)C(=O)Nc1ccccc12)N(C)C(=O)c1cc2c(F)cc(F)cc2[nH]1] |
| 414 | 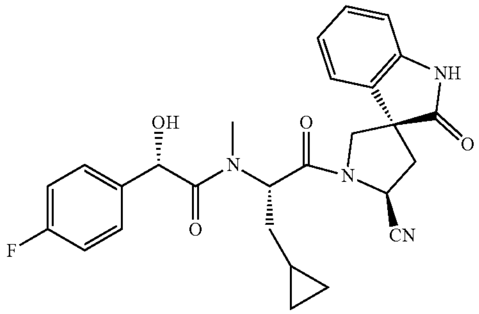 [SMILES: CN(C(=O)[C@@H](O)c1ccc(F)cc1)[C@@H](CC1CC1)C(=O)N1C[C@]2(C[C@H]1C#N)C(=O)Nc1ccccc12] |
| 415 | 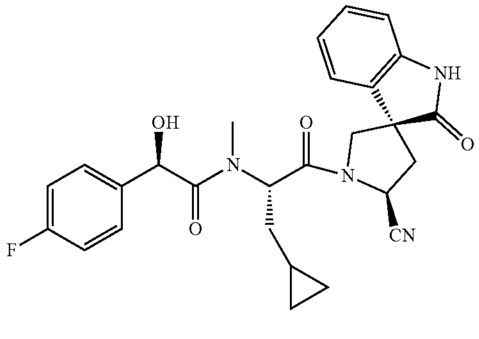 [SMILES: CN(C(=O)[C@H](O)c1ccc(F)cc1)[C@@H](CC1CC1)C(=O)N1C[C@]2(C[C@H]1C#N)C(=O)Nc1ccccc12] |

-continued
| Compound | Structure |
| --- | --- |
| 416 | 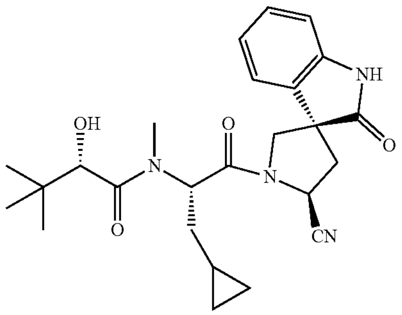 [SMILES: CN(C(=O)[C@@H](O)C(C)(C)C)[C@@H](CC1CC1)C(=O)N1C[C@]2(C[C@H]1C#N)C(=O)Nc1ccccc12] |
| 417 | 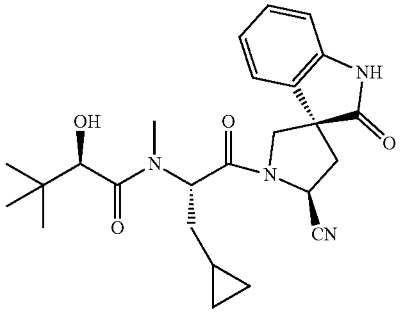 [SMILES: CN(C(=O)[C@H](O)C(C)(C)C)[C@@H](CC1CC1)C(=O)N1C[C@]2(C[C@H]1C#N)C(=O)Nc1ccccc12] |
| 418 | 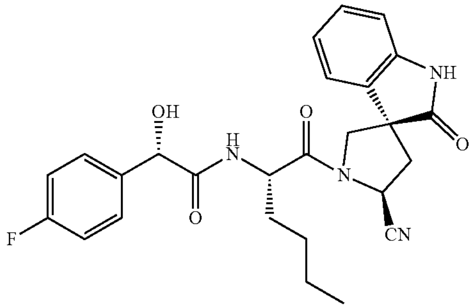 [SMILES: CCCC[C@H](NC(=O)[C@@H](O)c1ccc(F)cc1)C(=O)N1C[C@]2(C[C@H]1C#N)C(=O)Nc1ccccc12] |
| 419 | 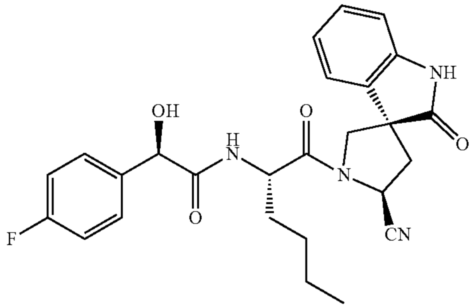 [SMILES: CCCC[C@H](NC(=O)[C@H](O)c1ccc(F)cc1)C(=O)N1C[C@]2(C[C@H]1C#N)C(=O)Nc1ccccc12] |
| 420 | 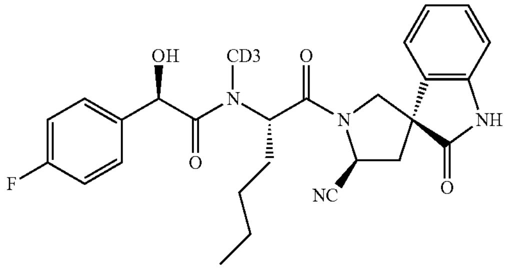 [SMILES: [2H]C([2H])([2H])N(C(=O)[C@H](O)c1ccc(F)cc1)[C@@H](CCCC)C(=O)N1C[C@]2(C[C@H]1C#N)C(=O)Nc1ccccc12] |

-continued
| Compound | Structure |
| --- | --- |
| 421 | 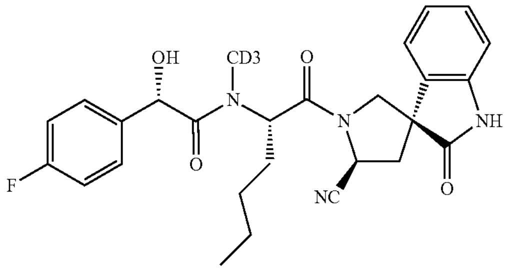 [SMILES: [2H]C([2H])([2H])N(C(=O)[C@@H](O)c1ccc(F)cc1)[C@@H](CCCC)C(=O)N1C[C@]2(C[C@H]1C#N)C(=O)Nc1ccccc12] |
| 422 | 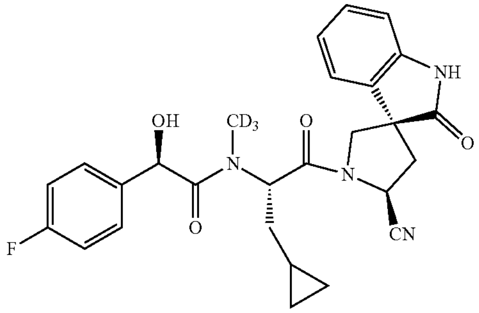 [SMILES: [2H]C([2H])([2H])N(C(=O)[C@H](O)c1ccc(F)cc1)[C@@H](CC1CC1)C(=O)N1C[C@]2(C[C@H]1C#N)C(=O)Nc1ccccc12] |
| 423 | 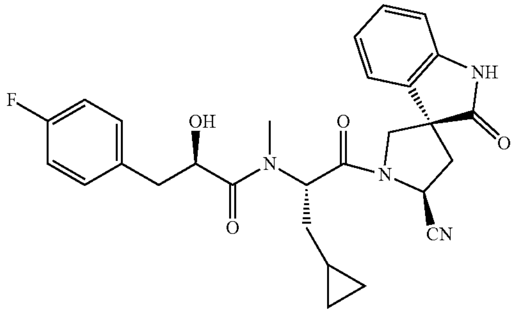 [SMILES: CN(C(=O)[C@H](O)Cc1ccc(F)cc1)[C@@H](CC1CC1)C(=O)N1C[C@]2(C[C@H]1C#N)C(=O)Nc1ccccc12] |
| 424 | 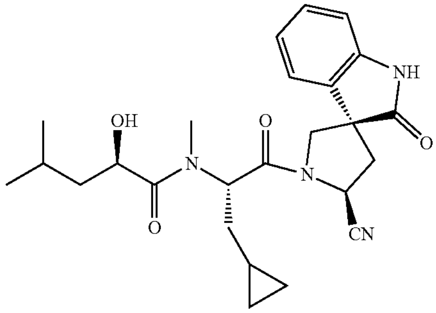 [SMILES: CC(C)C[C@@H](O)C(=O)N(C)[C@@H](CC1CC1)C(=O)N1C[C@]2(C[C@H]1C#N)C(=O)Nc1ccccc12] |
| 425 | 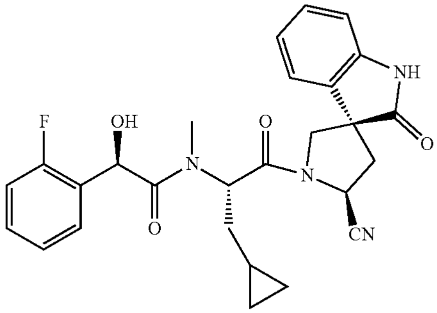 [SMILES: CN(C(=O)[C@H](O)c1ccccc1F)[C@@H](CC1CC1)C(=O)N1C[C@]2(C[C@H]1C#N)C(=O)Nc1ccccc12] |

-continued
| Compound | Structure |
|---|---|
| 426 | 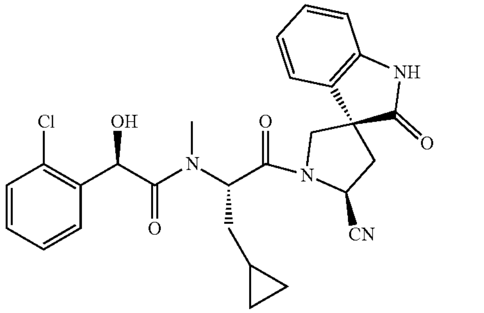 [SMILES: CN(C(=O)[C@H](O)c1ccccc1Cl)[C@@H](CC1CC1)C(=O)N1C[C@]2(C[C@H]1C#N)C(=O)Nc1ccccc12] |
| 427 | 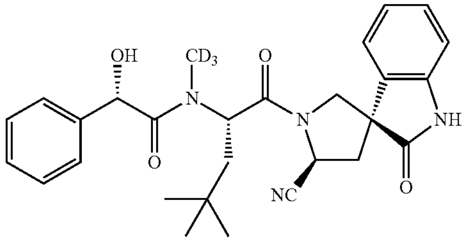 [SMILES: [2H]C([2H])([2H])N(C(=O)[C@@H](O)c1ccccc1)[C@@H](CC(C)(C)C)C(=O)N1C[C@]2(C[C@H]1C#N)C(=O)Nc1ccccc12] |
| 428 | 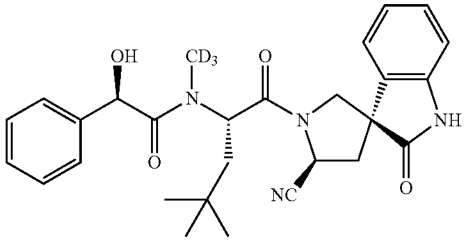 [SMILES: [2H]C([2H])([2H])N(C(=O)[C@H](O)c1ccccc1)[C@@H](CC(C)(C)C)C(=O)N1C[C@]2(C[C@H]1C#N)C(=O)Nc1ccccc12] |
| 429 | 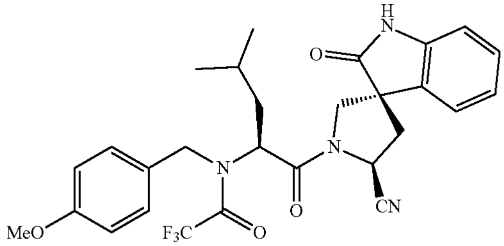 [SMILES: COc1ccc(CN(C(=O)C(F)(F)F)[C@@H](CC(C)C)C(=O)N2C[C@]3(C[C@H]2C#N)C(=O)Nc2ccccc23)cc1] |
| 430 | 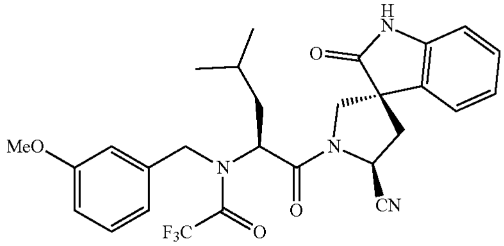 [SMILES: COc1cccc(CN(C(=O)C(F)(F)F)[C@@H](CC(C)C)C(=O)N2C[C@]3(C[C@H]2C#N)C(=O)Nc2ccccc23)c1] |
| 431 | 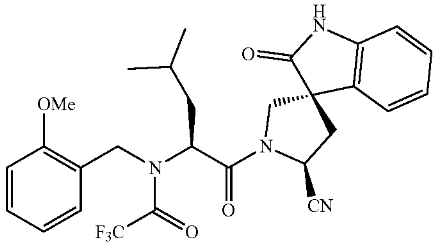 [SMILES: COc1ccccc1CN(C(=O)C(F)(F)F)[C@@H](CC(C)C)C(=O)N1C[C@]2(C[C@H]1C#N)C(=O)Nc1ccccc12] |

-continued
| Compound | Structure |
| --- | --- |
| 432 | 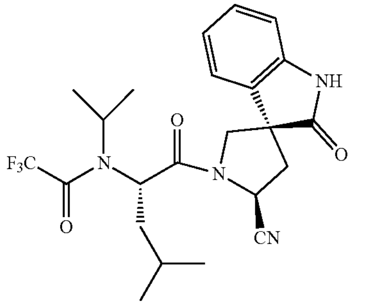 [SMILES: CC(C)C[C@@H](C(=O)N1C[C@]2(C[C@H]1C#N)C(=O)Nc1ccccc12)N(C(=O)C(F)(F)F)C(C)C] |
| 433 | 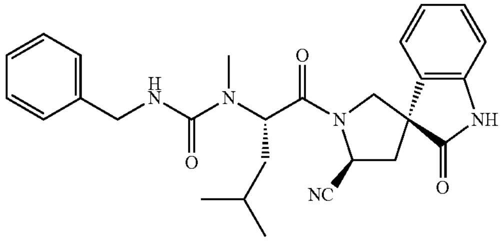 [SMILES: CC(C)C[C@@H](C(=O)N1C[C@]2(C[C@H]1C#N)C(=O)Nc1ccccc12)N(C)C(=O)NCc1ccccc1] |
| 434 | 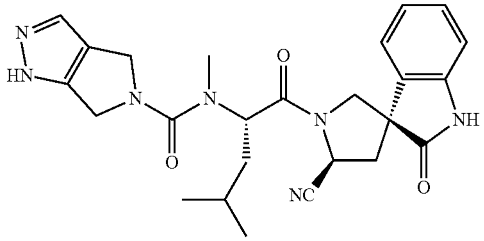 [SMILES: CC(C)C[C@@H](C(=O)N1C[C@]2(C[C@H]1C#N)C(=O)Nc1ccccc12)N(C)C(=O)N1Cc2cn[nH]c2C1] |
| 435 | 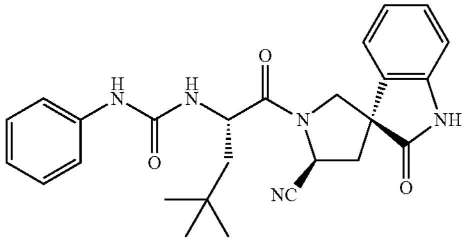 [SMILES: CC(C)(C)C[C@H](NC(=O)Nc1ccccc1)C(=O)N1C[C@]2(C[C@H]1C#N)C(=O)Nc1ccccc12] |
| 436 | 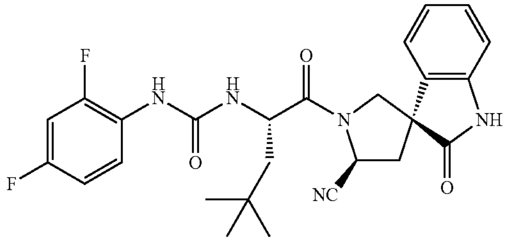 [SMILES: CC(C)(C)C[C@H](NC(=O)Nc1ccc(F)cc1F)C(=O)N1C[C@]2(C[C@H]1C#N)C(=O)Nc1ccccc12] |
| 437 | 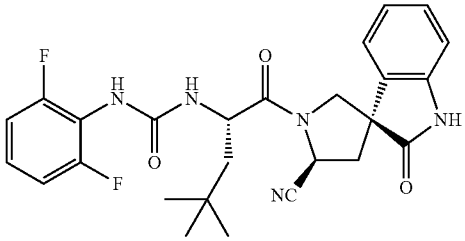 [SMILES: CC(C)(C)C[C@H](NC(=O)Nc1c(F)cccc1F)C(=O)N1C[C@]2(C[C@H]1C#N)C(=O)Nc1ccccc12] |

-continued
| Compound | Structure |
|---|---|
| 438 | 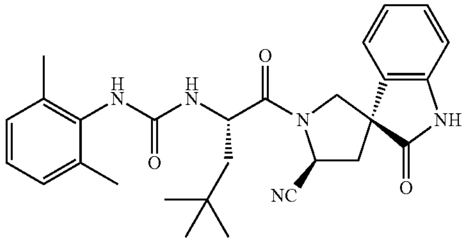 [SMILES: Cc1cccc(C)c1NC(=O)N[C@@H](CC(C)(C)C)C(=O)N1C[C@]2(C[C@H]1C#N)C(=O)Nc1ccccc12] |
| 439 | 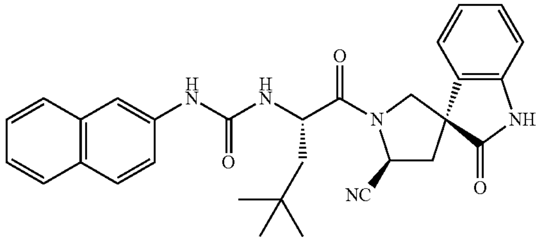 [SMILES: CC(C)(C)C[C@H](NC(=O)Nc1ccc2ccccc2c1)C(=O)N1C[C@]2(C[C@H]1C#N)C(=O)Nc1ccccc12] |
| 440 | 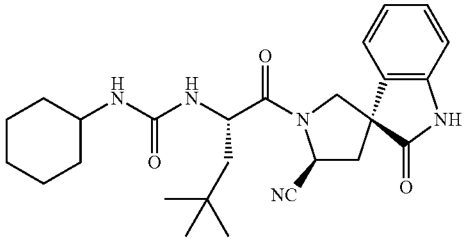 [SMILES: CC(C)(C)C[C@H](NC(=O)NC1CCCCC1)C(=O)N1C[C@]2(C[C@H]1C#N)C(=O)Nc1ccccc12] |
| 441 | 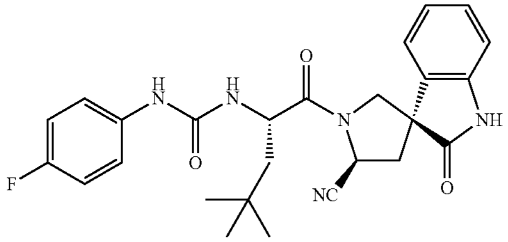 |
| 442 | 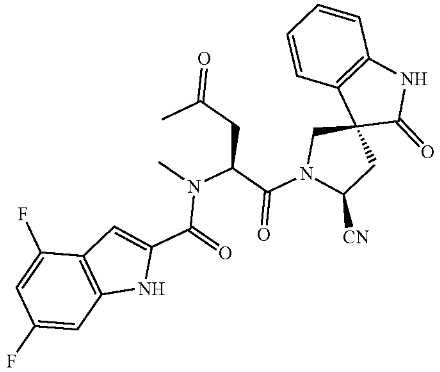 [SMILES: CC(=O)C[C@@H](C(=O)N1C[C@]2(C[C@H]1C#N)C(=O)Nc1ccccc12)N(C)C(=O)c1cc2c(F)cc(F)cc2[nH]1] |

-continued
| Compound | Structure |
| --- | --- |
| 443 | 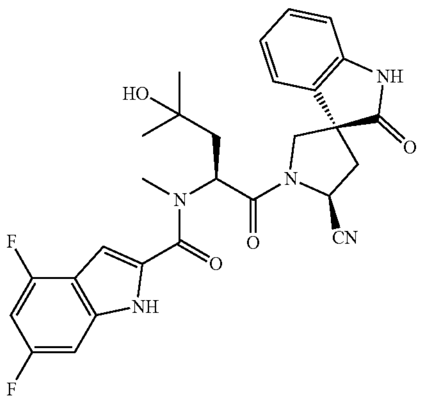 [SMILES: CN(C(=O)c1cc2c(F)cc(F)cc2[nH]1)[C@@H](CC(C)(C)O)C(=O)N1C[C@]2(C[C@H]1C#N)C(=O)Nc1ccccc12] |
| 444 | 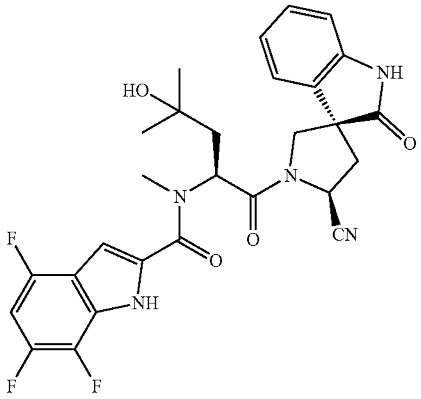 [SMILES: CN(C(=O)c1cc2c(F)cc(F)c(F)c2[nH]1)[C@@H](CC(C)(C)O)C(=O)N1C[C@]2(C[C@H]1C#N)C(=O)Nc1ccccc12] |
| 445 | 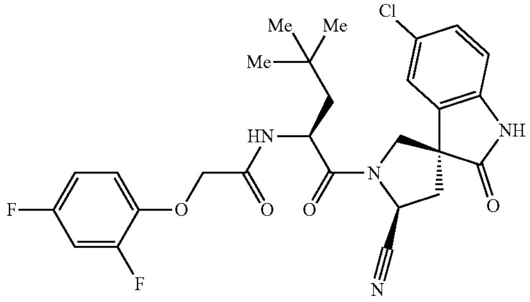 [SMILES: CC(C)(C)C[C@H](NC(=O)COc1ccc(F)cc1F)C(=O)N1C[C@]2(C[C@H]1C#N)C(=O)Nc1ccc(Cl)cc12] |
| 446 | 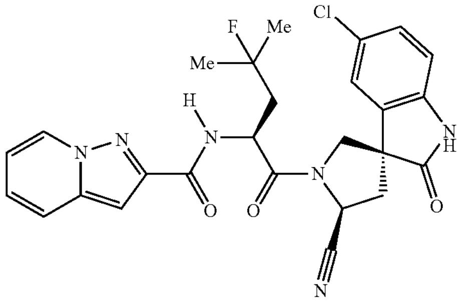 [SMILES: CC(C)(F)C[C@H](NC(=O)c1cc2ccccn2n1)C(=O)N1C[C@]2(C[C@H]1C#N)C(=O)Nc1ccc(Cl)cc12] |

-continued
| Compound | Structure |
|---|---|
| 447 | 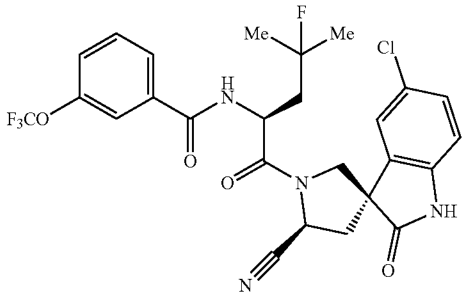 [SMILES: CC(C)(F)C[C@H](NC(=O)c1cccc(OC(F)(F)F)c1)C(=O)N1C[C@]2(C[C@H]1C#N)C(=O)Nc1ccc(Cl)cc12] |
| 448 | 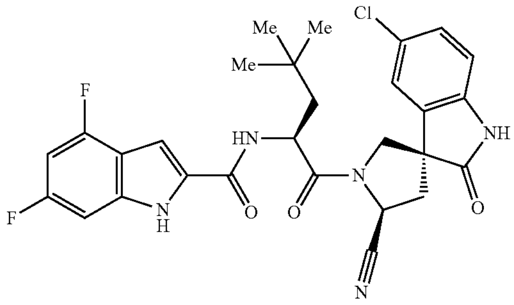 [SMILES: CC(C)(C)C[C@H](NC(=O)c1cc2c(F)cc(F)cc2[nH]1)C(=O)N1C[C@]2(C[C@H]1C#N)C(=O)Nc1ccc(Cl)cc12] |
| 449 | 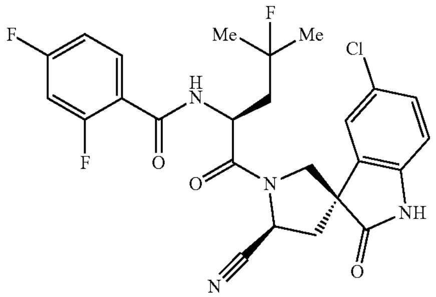 [SMILES: CC(C)(F)C[C@H](NC(=O)c1ccc(F)cc1F)C(=O)N1C[C@]2(C[C@H]1C#N)C(=O)Nc1ccc(Cl)cc12] |
| 450 | 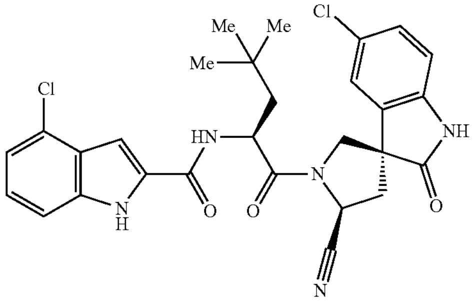 [SMILES: CC(C)(C)C[C@H](NC(=O)c1cc2c(Cl)cccc2[nH]1)C(=O)N1C[C@]2(C[C@H]1C#N)C(=O)Nc1ccc(Cl)cc12] |
| 451 | 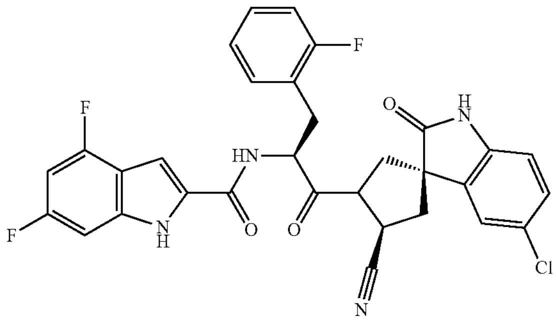 |

-continued
| Compound | Structure |
|---|---|
| 452 | 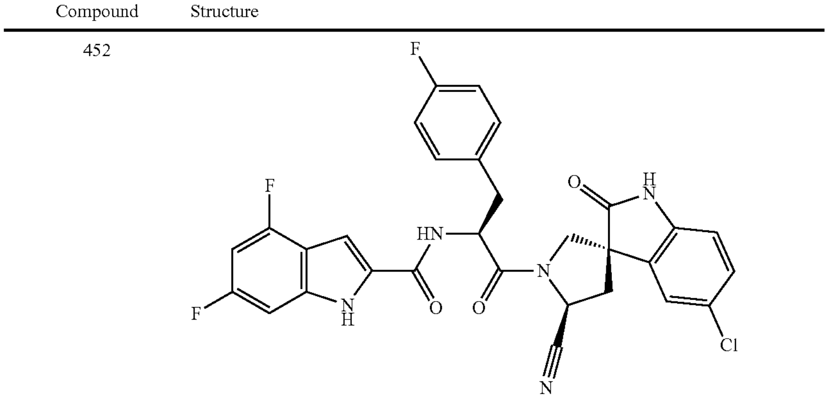 |
| 453 | 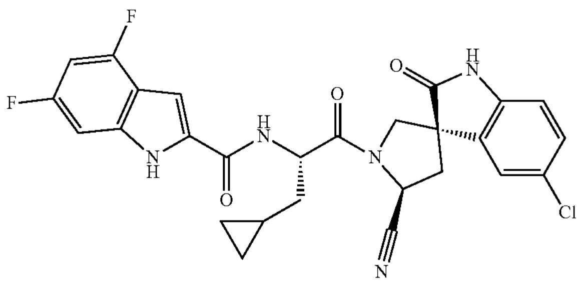 [SMILES: N#C[C@@H]1C[C@@]2(CN1C(=O)[C@H](CC1CC1)NC(=O)c1cc3c(F)cc(F)cc3[nH]1)C(=O)Nc1ccc(Cl)cc12] |
| 454 | 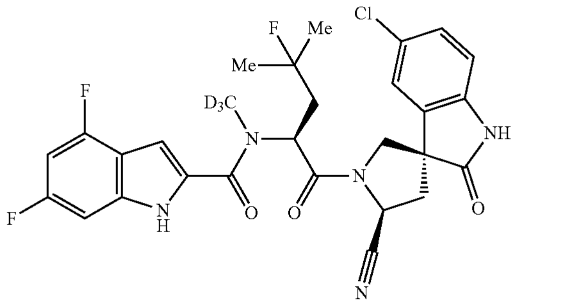 [SMILES: [2H]C([2H])([2H])N(C(=O)c1cc2c(F)cc(F)cc2[nH]1)[C@@H](CC(C)(C)F)C(=O)N1C[C@]2(C[C@H]1C#N)C(=O)Nc1ccc(Cl)cc12] |
| 455 | 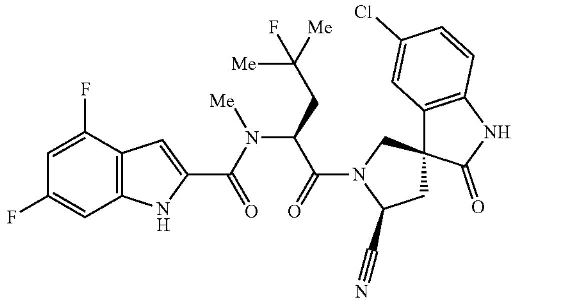 [SMILES: CN(C(=O)c1cc2c(F)cc(F)cc2[nH]1)[C@@H](CC(C)(C)F)C(=O)N1C[C@]2(C[C@H]1C#N)C(=O)Nc1ccc(Cl)cc12] |

-continued
| Compound | Structure |
|---|---|
| 456 | 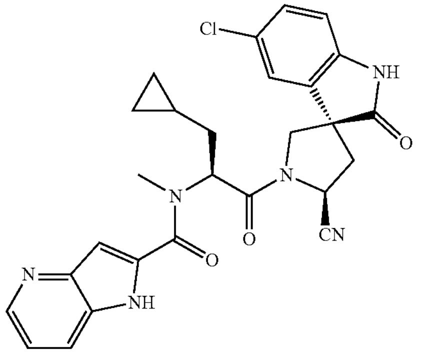 [SMILES: CN(C(=O)c1cc2ncccc2[nH]1)[C@@H](CC1CC1)C(=O)N1C[C@]2(C[C@H]1C#N)C(=O)Nc1ccc(Cl)cc12] |
| 457 | 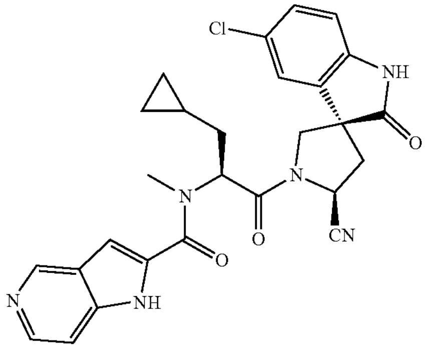 [SMILES: CN(C(=O)c1cc2cnccc2[nH]1)[C@@H](CC1CC1)C(=O)N1C[C@]2(C[C@H]1C#N)C(=O)Nc1ccc(Cl)cc12] |
| 458 | 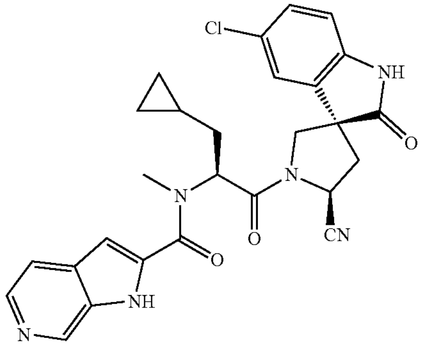 [SMILES: CN(C(=O)c1cc2ccncc2[nH]1)[C@@H](CC1CC1)C(=O)N1C[C@]2(C[C@H]1C#N)C(=O)Nc1ccc(Cl)cc12] |
| 459 | 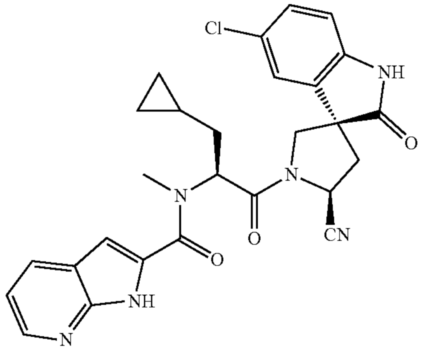 [SMILES: CN(C(=O)c1cc2cccnc2[nH]1)[C@@H](CC1CC1)C(=O)N1C[C@]2(C[C@H]1C#N)C(=O)Nc1ccc(Cl)cc12] |

-continued
| Compound | Structure |
|---|---|
| 460 | 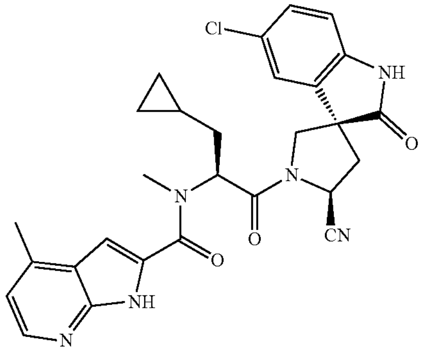 [SMILES: Cc1ccnc2[nH]c(C(=O)N(C)[C@@H](CC3CC3)C(=O)N3C[C@]4(C[C@H]3C#N)C(=O)Nc3ccc(Cl)cc34)cc12] |
| 461 | 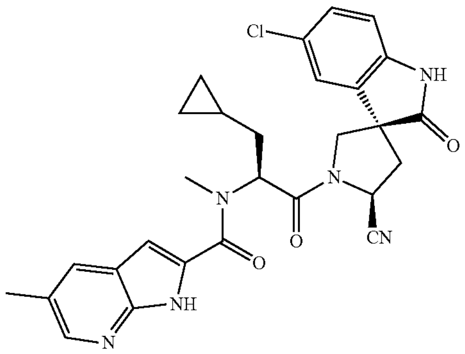 [SMILES: Cc1cnc2[nH]c(C(=O)N(C)[C@@H](CC3CC3)C(=O)N3C[C@]4(C[C@H]3C#N)C(=O)Nc3ccc(Cl)cc34)cc2c1] |
| 462 | 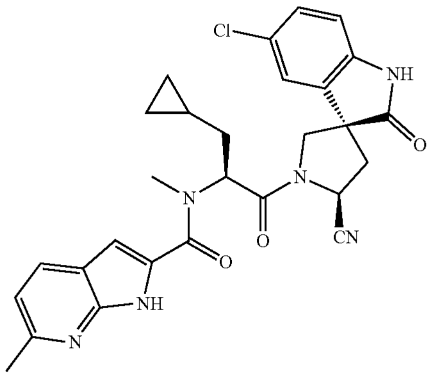 [SMILES: Cc1ccc2cc(C(=O)N(C)[C@@H](CC3CC3)C(=O)N3C[C@]4(C[C@H]3C#N)C(=O)Nc3ccc(Cl)cc34)[nH]c2n1] |
| 463 | 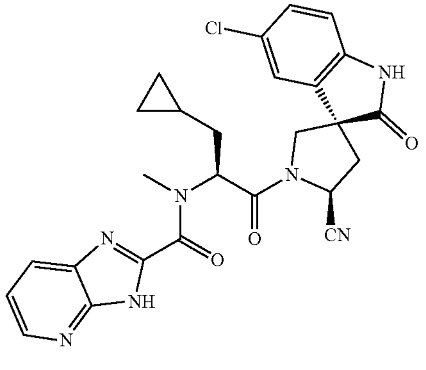 [SMILES: CN(C(=O)c1nc2cccnc2[nH]1)[C@@H](CC1CC1)C(=O)N1C[C@]2(C[C@H]1C#N)C(=O)Nc1ccc(Cl)cc12] |

-continued
| Compound | Structure |
|---|---|
| 464 | 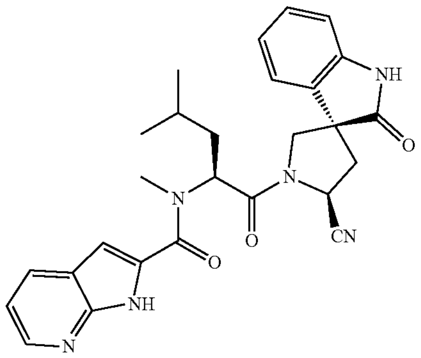 [SMILES: CC(C)C[C@@H](C(=O)N1C[C@]2(C[C@H]1C#N)C(=O)Nc1ccccc12)N(C)C(=O)c1cc2cccnc2[nH]1] |
| 465 | 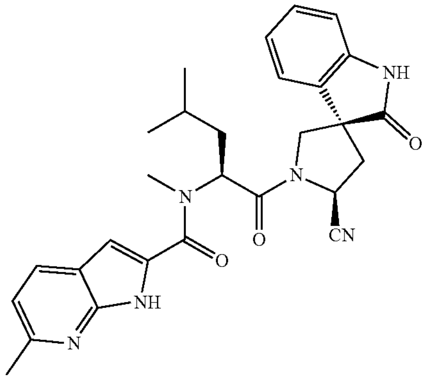 [SMILES: Cc1ccc2cc(C(=O)N(C)[C@@H](CC(C)C)C(=O)N3C[C@]4(C[C@H]3C#N)C(=O)Nc3ccccc34)[nH]c2n1] |
| 466 | 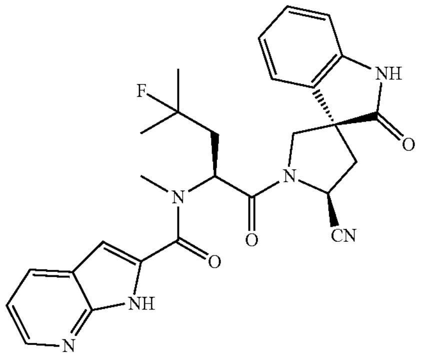 [SMILES: CN(C(=O)c1cc2cccnc2[nH]1)[C@@H](CC(C)(C)F)C(=O)N1C[C@]2(C[C@H]1C#N)C(=O)Nc1ccccc12] |
| 467 | 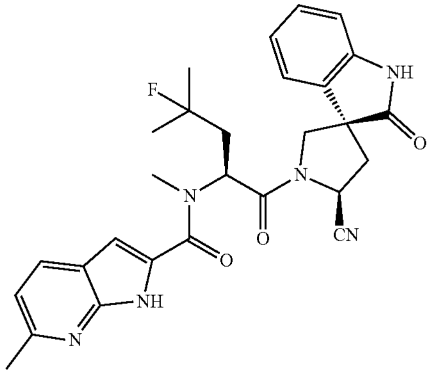 [SMILES: Cc1ccc2cc(C(=O)N(C)[C@@H](CC(C)(C)F)C(=O)N3C[C@]4(C[C@H]3C#N)C(=O)Nc3ccccc34)[nH]c2n1] |

-continued
| Compound | Structure |
|---|---|
| 468 | 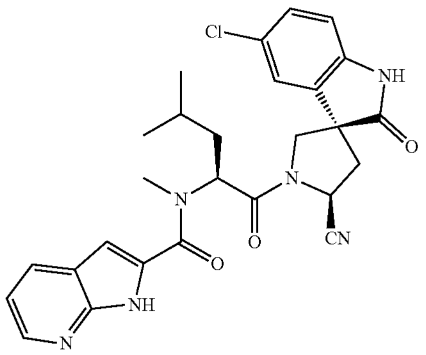 [SMILES: CC(C)C[C@@H](C(=O)N1C[C@]2(C[C@H]1C#N)C(=O)Nc1ccc(Cl)cc12)N(C)C(=O)c1cc2cccnc2[nH]1] |
| 469 | 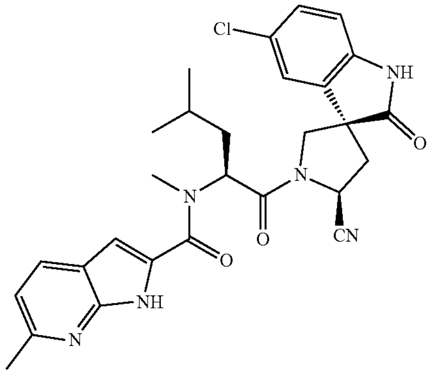 [SMILES: Cc1ccc2cc(C(=O)N(C)[C@@H](CC(C)C)C(=O)N3C[C@]4(C[C@H]3C#N)C(=O)Nc3ccc(Cl)cc34)[nH]c2n1] |
| 470 | 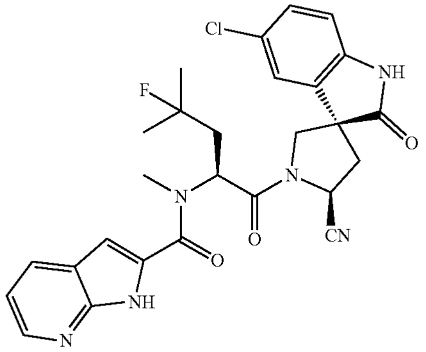 [SMILES: CN(C(=O)c1cc2cccnc2[nH]1)[C@@H](CC(C)(C)F)C(=O)N1C[C@]2(C[C@H]1C#N)C(=O)Nc1ccc(Cl)cc12] |
| 471 | 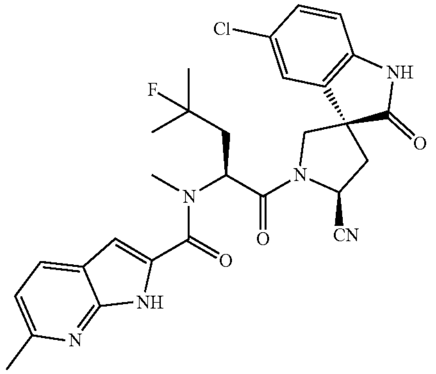 [SMILES: Cc1ccc2cc(C(=O)N(C)[C@@H](CC(C)(C)F)C(=O)N3C[C@]4(C[C@H]3C#N)C(=O)Nc3ccc(Cl)cc34)[nH]c2n1] |

-continued
| Compound | Structure |
|---|---|
| 472 | 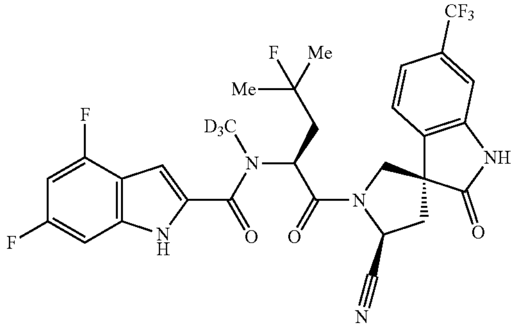 [SMILES: [2H]C([2H])([2H])N(C(=O)c1cc2c(F)cc(F)cc2[nH]1)[C@@H](CC(C)(C)F)C(=O)N1C[C@]2(C[C@H]1C#N)C(=O)Nc1cc(C(F)(F)F)ccc12] |
| 473 | 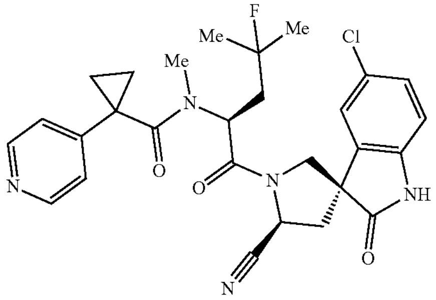 [SMILES: CN(C(=O)C1(c2ccncc2)CC1)[C@@H](CC(C)(C)F)C(=O)N1C[C@]2(C[C@H]1C#N)C(=O)Nc1ccc(Cl)cc12] |
| 474 | 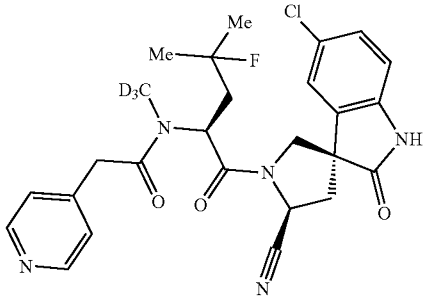 [SMILES: [2H]C([2H])([2H])N(C(=O)Cc1ccncc1)[C@@H](CC(C)(C)F)C(=O)N1C[C@]2(C[C@H]1C#N)C(=O)Nc1ccc(Cl)cc12] |
| 475 | 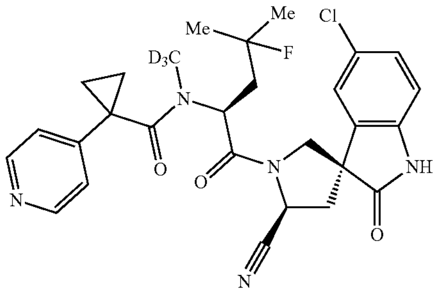 [SMILES: [2H]C([2H])([2H])N(C(=O)C1(c2ccncc2)CC1)[C@@H](CC(C)(C)F)C(=O)N1C[C@]2(C[C@H]1C#N)C(=O)Nc1ccc(Cl)cc12] |
| 476 | 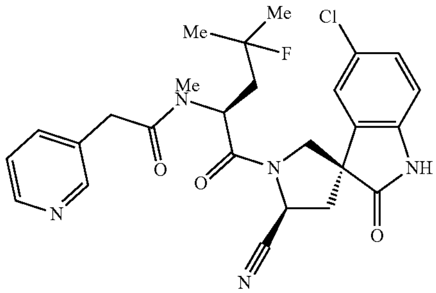 [SMILES: CN(C(=O)Cc1cccnc1)[C@@H](CC(C)(C)F)C(=O)N1C[C@]2(C[C@H]1C#N)C(=O)Nc1ccc(Cl)cc12] |

-continued
| Compound | Structure |
| --- | --- |
| 477 | 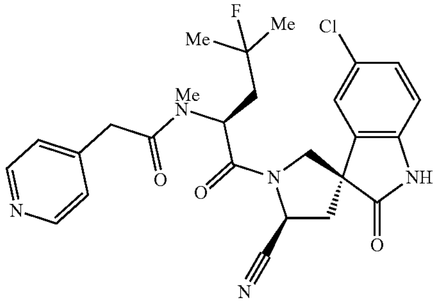 [SMILES: CN(C(=O)Cc1ccncc1)[C@@H](CC(C)(C)F)C(=O)N1C[C@]2(C[C@H]1C#N)C(=O)Nc1ccc(Cl)cc12] |
| 478 | 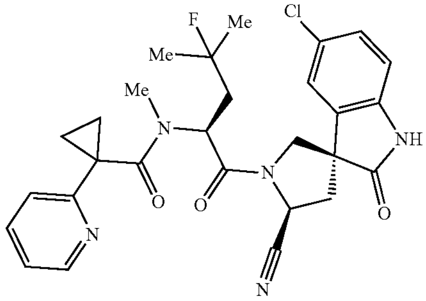 [SMILES: CN(C(=O)C1(c2ccccn2)CC1)[C@@H](CC(C)(C)F)C(=O)N1C[C@]2(C[C@H]1C#N)C(=O)Nc1ccc(Cl)cc12] |
| 479 | 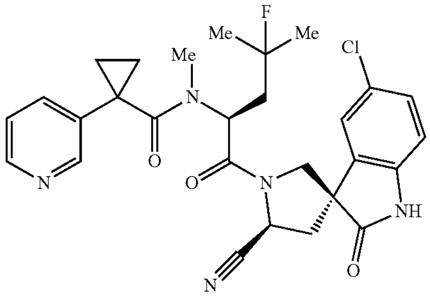 [SMILES: CN(C(=O)C1(c2cccnc2)CC1)[C@@H](CC(C)(C)F)C(=O)N1C[C@]2(C[C@H]1C#N)C(=O)Nc1ccc(Cl)cc12] |
| 480 | 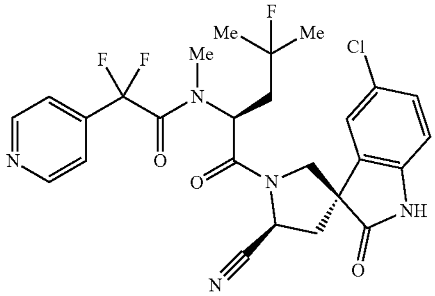 [SMILES: CN(C(=O)C(F)(F)c1ccncc1)[C@@H](CC(C)(C)F)C(=O)N1C[C@]2(C[C@H]1C#N)C(=O)Nc1ccc(Cl)cc12] |
| 481 | 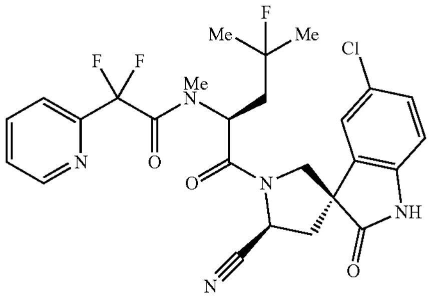 [SMILES: CN(C(=O)C(F)(F)c1ccccn1)[C@@H](CC(C)(C)F)C(=O)N1C[C@]2(C[C@H]1C#N)C(=O)Nc1ccc(Cl)cc12] |

-continued
| Compound | Structure |
|---|---|
| 482 | 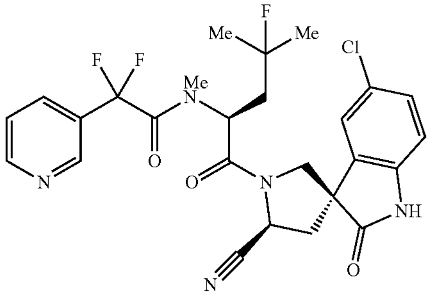 [SMILES: CN(C(=O)C(F)(F)c1cccnc1)[C@@H](CC(C)(C)F)C(=O)N1C[C@]2(C[C@H]1C#N)C(=O)Nc1ccc(Cl)cc12] |
| 483 | 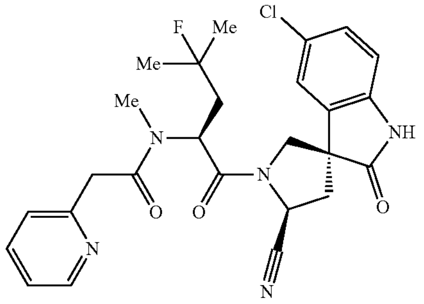 [SMILES: CN(C(=O)Cc1ccccn1)[C@@H](CC(C)(C)F)C(=O)N1C[C@]2(C[C@H]1C#N)C(=O)Nc1ccc(Cl)cc12] |
| 484 | 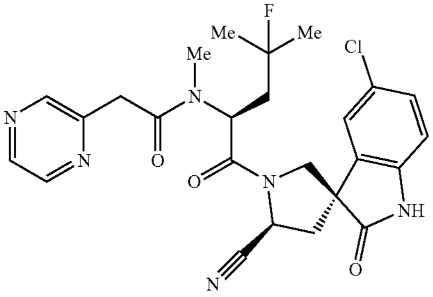 [SMILES: CN(C(=O)Cc1cnccn1)[C@@H](CC(C)(C)F)C(=O)N1C[C@]2(C[C@H]1C#N)C(=O)Nc1ccc(Cl)cc12] |
| 485 | 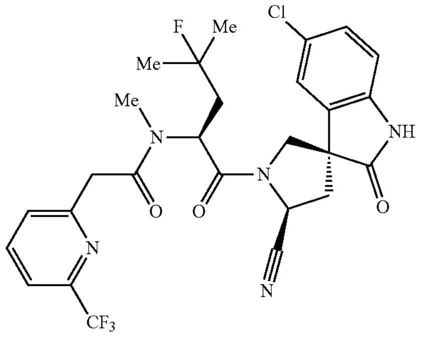 [SMILES: CN(C(=O)Cc1cccc(C(F)(F)F)n1)[C@@H](CC(C)(C)F)C(=O)N1C[C@]2(C[C@H]1C#N)C(=O)Nc1ccc(Cl)cc12] |
| 486 | 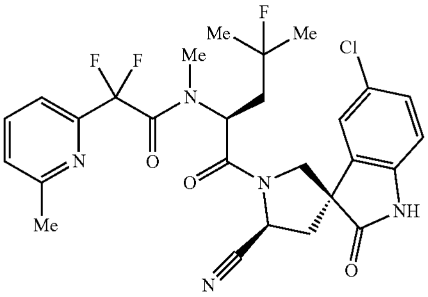 [SMILES: Cc1cccc(C(F)(F)C(=O)N(C)[C@@H](CC(C)(C)F)C(=O)N2C[C@]3(C[C@H]2C#N)C(=O)Nc2ccc(Cl)cc23)n1] |

-continued
| Compound | Structure |
|---|---|
| 487 | 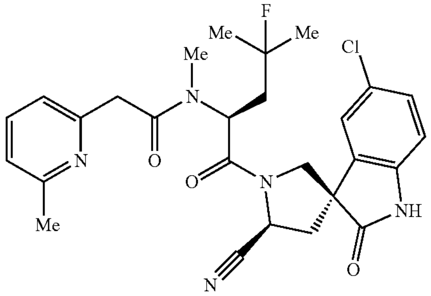 [SMILES: Cc1cccc(CC(=O)N(C)[C@@H](CC(C)(C)F)C(=O)N2C[C@]3(C[C@H]2C#N)C(=O)Nc2ccc(Cl)cc23)n1] |
| 488 | 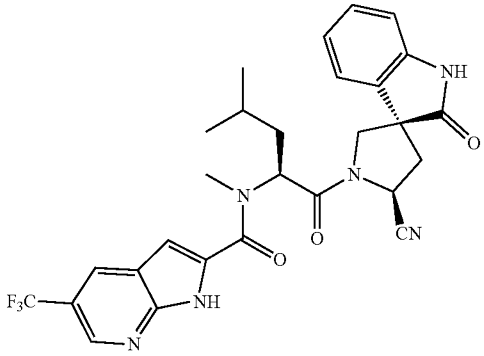 [SMILES: CC(C)C[C@@H](C(=O)N1C[C@]2(C[C@H]1C#N)C(=O)Nc1ccccc12)N(C)C(=O)c1cc2cc(C(F)(F)F)cnc2[nH]1] |
| 489 | 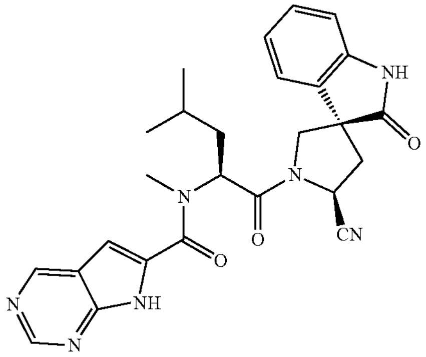 [SMILES: CC(C)C[C@@H](C(=O)N1C[C@]2(C[C@H]1C#N)C(=O)Nc1ccccc12)N(C)C(=O)c1cc2cncnc2[nH]1] |
| 490 | 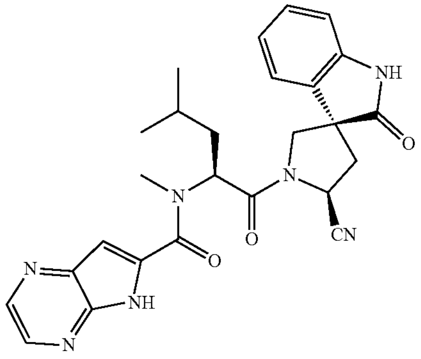 [SMILES: CC(C)C[C@@H](C(=O)N1C[C@]2(C[C@H]1C#N)C(=O)Nc1ccccc12)N(C)C(=O)c1cc2nccnc2[nH]1] |

-continued
| Compound | Structure |
|---|---|
| 491 | 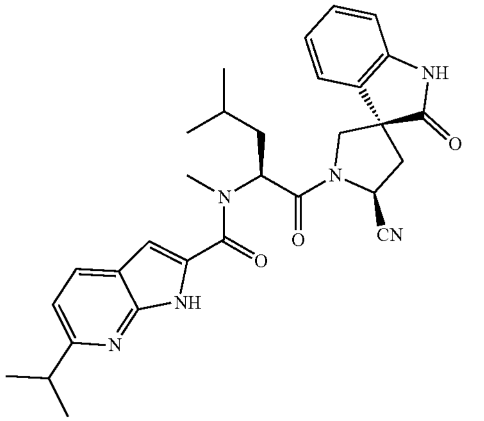 [SMILES: CC(C)C[C@@H](C(=O)N1C[C@]2(C[C@H]1C#N)C(=O)Nc1ccccc12)N(C)C(=O)c1cc2ccc(C(C)C)nc2[nH]1] |
| 492 | 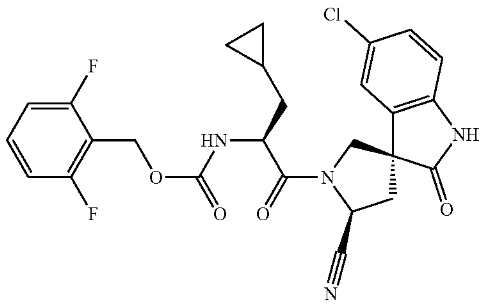 [SMILES: N#C[C@@H]1C[C@@]2(CN1C(=O)[C@H](CC1CC1)NC(=O)OCc1c(F)cccc1F)C(=O)Nc1ccc(Cl)cc12] |
| 493 | 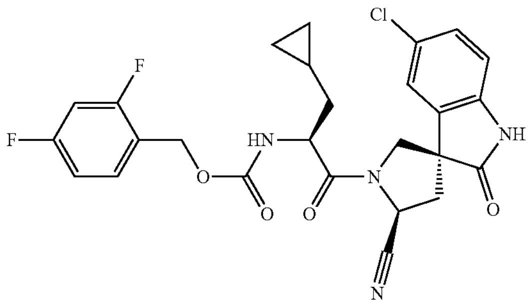 [SMILES: N#C[C@@H]1C[C@@]2(CN1C(=O)[C@H](CC1CC1)NC(=O)OCc1ccc(F)cc1F)C(=O)Nc1ccc(Cl)cc12] |
| 494 | 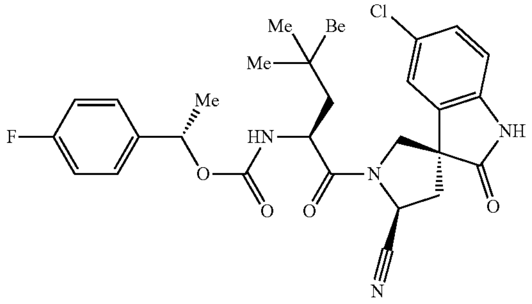 |

-continued
| Compound | Structure |
| --- | --- |
| 495 | 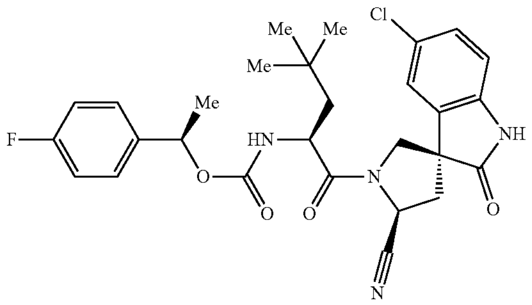 [SMILES: C[C@@H](OC(=O)N[C@@H](CC(C)(C)C)C(=O)N1C[C@]2(C[C@H]1C#N)C(=O)Nc1ccc(Cl)cc12)c1ccc(F)cc1] |
| 496 | 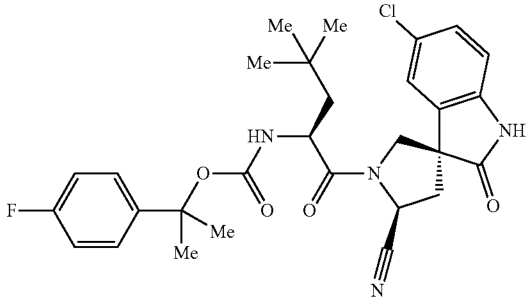 [SMILES: CC(C)(C)C[C@H](NC(=O)OC(C)(C)c1ccc(F)cc1)C(=O)N1C[C@]2(C[C@H]1C#N)C(=O)Nc1ccc(Cl)cc12] |
| 497 | 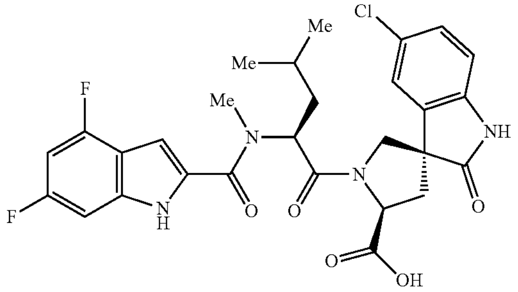 [SMILES: CC(C)C[C@@H](C(=O)N1C[C@]2(C[C@H]1C(=O)O)C(=O)Nc1ccc(Cl)cc12)N(C)C(=O)c1cc2c(F)cc(F)cc2[nH]1] |
| 498 | 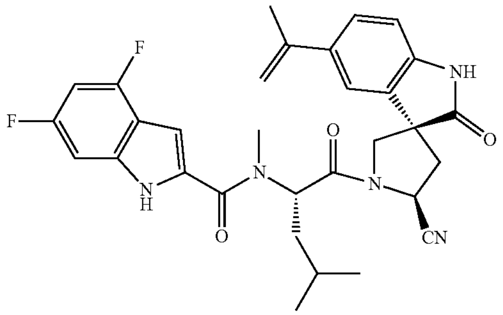 [SMILES: C=C(C)c1ccc2c(c1)[C@@]1(C[C@@H](C#N)N(C(=O)[C@H](CC(C)C)N(C)C(=O)c3cc4c(F)cc(F)cc4[nH]3)C1)C(=O)N2] |
| 499 | 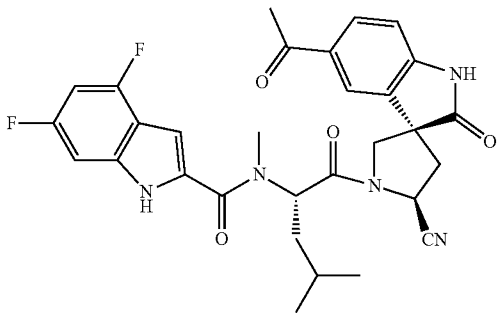 [SMILES: CC(=O)c1ccc2c(c1)[C@@]1(C[C@@H](C#N)N(C(=O)[C@H](CC(C)C)N(C)C(=O)c3cc4c(F)cc(F)cc4[nH]3)C1)C(=O)N2] |

-continued
| Compound | Structure |
|---|---|
| 500 | 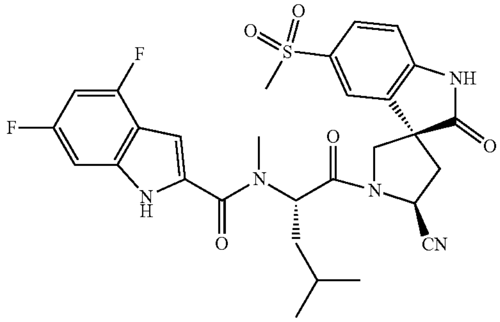 [SMILES: CC(C)C[C@@H](C(=O)N1C[C@]2(C[C@H]1C#N)C(=O)Nc1ccc(S(C)(=O)=O)cc12)N(C)C(=O)c1cc2c(F)cc(F)cc2[nH]1] |
| 501 | 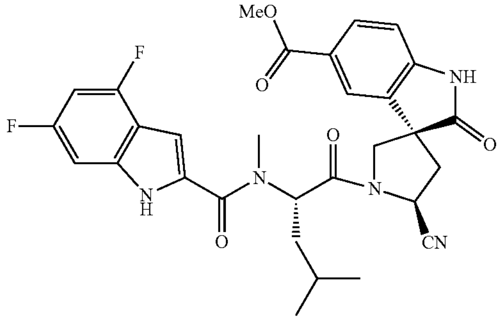 [SMILES: COC(=O)c1ccc2c(c1)[C@@]1(C[C@@H](C#N)N(C(=O)[C@H](CC(C)C)N(C)C(=O)c3cc4c(F)cc(F)cc4[nH]3)C1)C(=O)N2] |
| 502 | 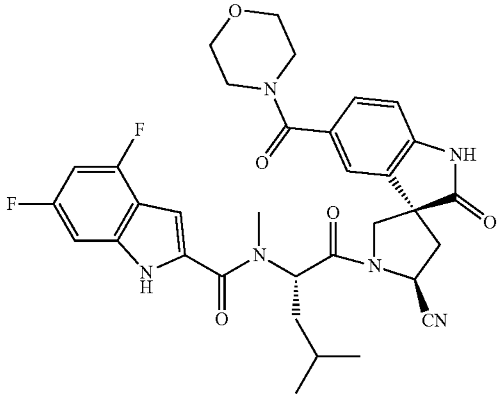 [SMILES: CC(C)C[C@@H](C(=O)N1C[C@]2(C[C@H]1C#N)C(=O)Nc1ccc(C(=O)N3CCOCC3)cc12)N(C)C(=O)c1cc2c(F)cc(F)cc2[nH]1] |
| 503 | 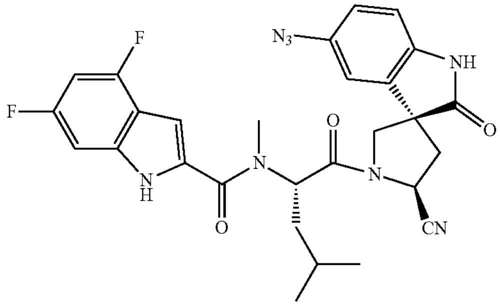 [SMILES: CC(C)C[C@@H](C(=O)N1C[C@]2(C[C@H]1C#N)C(=O)Nc1ccc(N=[N+]=[N-])cc12)N(C)C(=O)c1cc2c(F)cc(F)cc2[nH]1] |

-continued
| Compound | Structure |
| --- | --- |
| 504 | 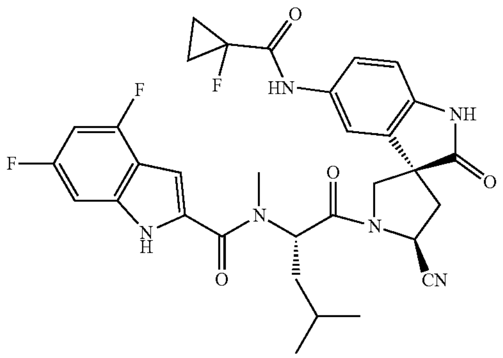 [SMILES: CC(C)C[C@@H](C(=O)N1C[C@]2(C[C@H]1C#N)C(=O)Nc1ccc(NC(=O)C3(F)CC3)cc12)N(C)C(=O)c1cc2c(F)cc(F)cc2[nH]1] |
| 505 | 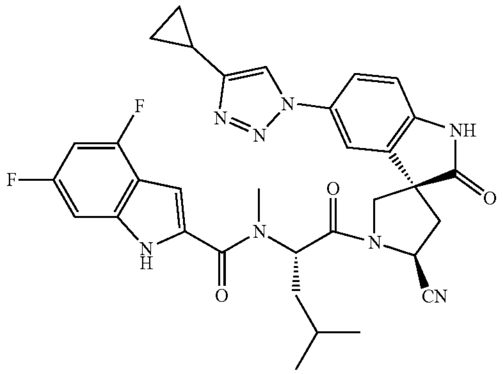 [SMILES: CC(C)C[C@@H](C(=O)N1C[C@]2(C[C@H]1C#N)C(=O)Nc1ccc(-n3cc(C4CC4)nn3)cc12)N(C)C(=O)c1cc2c(F)cc(F)cc2[nH]1] |
| 506 | 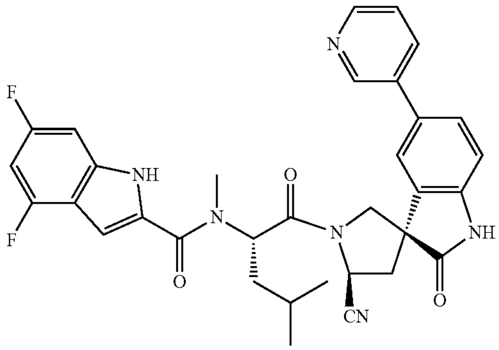 [SMILES: CC(C)C[C@@H](C(=O)N1C[C@]2(C[C@H]1C#N)C(=O)Nc1ccc(-c3cccnc3)cc12)N(C)C(=O)c1cc2c(F)cc(F)cc2[nH]1] |
| 507 | 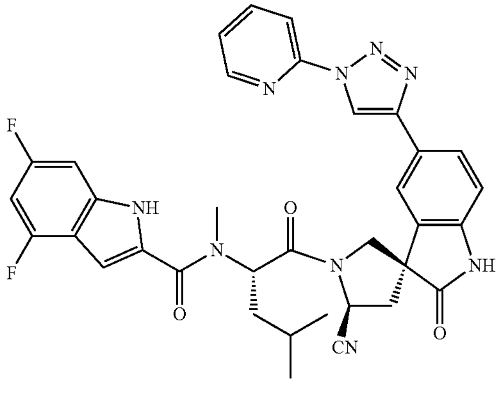 [SMILES: CC(C)C[C@@H](C(=O)N1C[C@]2(C[C@H]1C#N)C(=O)Nc1ccc(-c3cn(-c4ccccn4)nn3)cc12)N(C)C(=O)c1cc2c(F)cc(F)cc2[nH]1] |

-continued
| Compound | Structure |
| --- | --- |
| 508 | 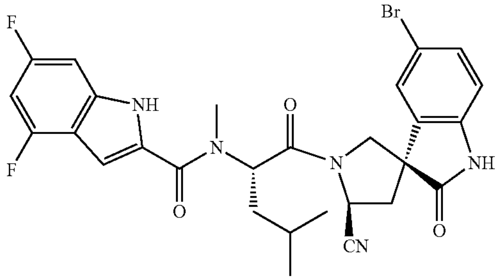 [SMILES: CC(C)C[C@@H](C(=O)N1C[C@]2(C[C@H]1C#N)C(=O)Nc1ccc(Br)cc12)N(C)C(=O)c1cc2c(F)cc(F)cc2[nH]1] |
| 509 | 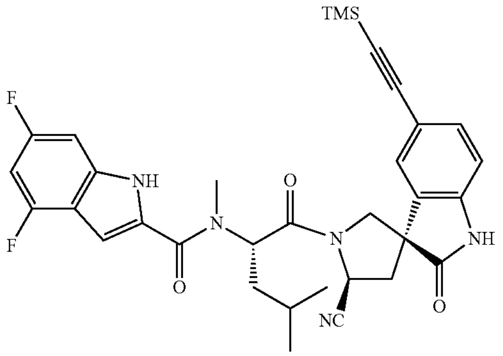 [SMILES: CC(C)C[C@@H](C(=O)N1C[C@]2(C[C@H]1C#N)C(=O)Nc1ccc(C#C[Si](C)(C)C)cc12)N(C)C(=O)c1cc2c(F)cc(F)cc2[nH]1] |
| 510 | 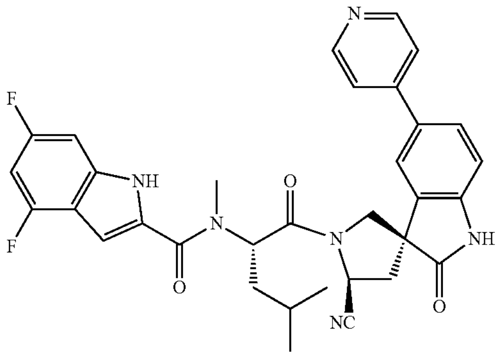 [SMILES: CC(C)C[C@@H](C(=O)N1C[C@]2(C[C@H]1C#N)C(=O)Nc1ccc(-c3ccncc3)cc12)N(C)C(=O)c1cc2c(F)cc(F)cc2[nH]1] |
| 511 | 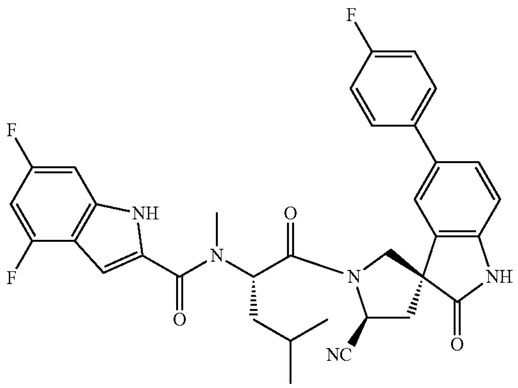 [SMILES: CC(C)C[C@@H](C(=O)N1C[C@]2(C[C@H]1C#N)C(=O)Nc1ccc(-c3ccc(F)cc3)cc12)N(C)C(=O)c1cc2c(F)cc(F)cc2[nH]1] |

-continued
| Compound | Structure |
|---|---|
| 512 | 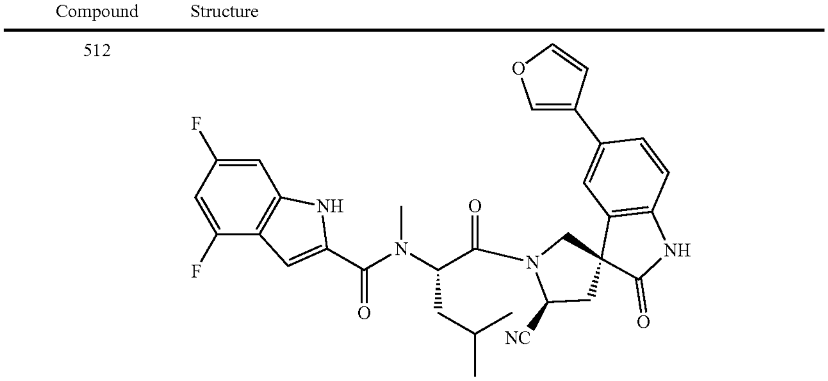 |
| 513 | 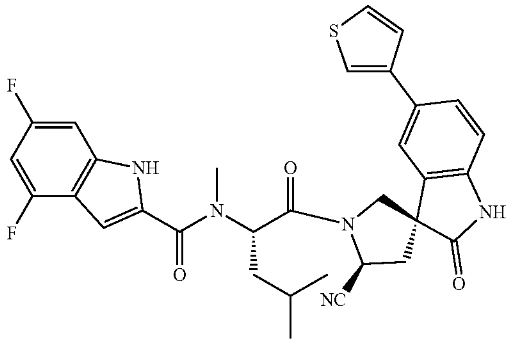 [SMILES: CC(C)C[C@@H](C(=O)N1C[C@]2(C[C@H]1C#N)C(=O)Nc1ccc(-c3ccoc3)cc12)N(C)C(=O)c1cc2c(F)cc(F)cc2[nH]1] |
| 514 | 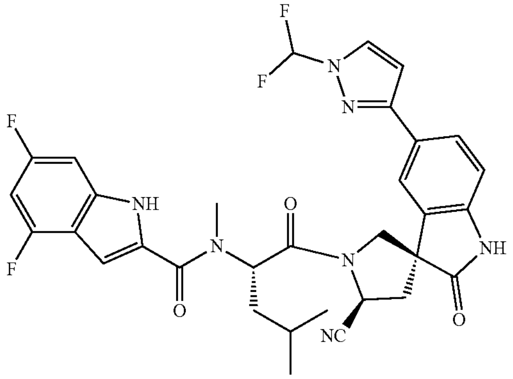 [SMILES: CC(C)C[C@@H](C(=O)N1C[C@]2(C[C@H]1C#N)C(=O)Nc1ccc(-c3ccn(C(F)F)n3)cc12)N(C)C(=O)c1cc2c(F)cc(F)cc2[nH]1] |
| 515 | 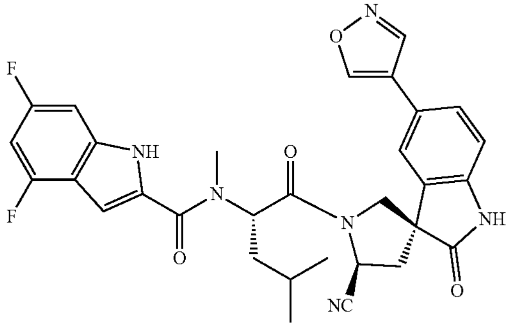 [SMILES: CC(C)C[C@@H](C(=O)N1C[C@]2(C[C@H]1C#N)C(=O)Nc1ccc(-c3cnoc3)cc12)N(C)C(=O)c1cc2c(F)cc(F)cc2[nH]1] |

-continued
| Compound | Structure |
|---|---|
| 516 | 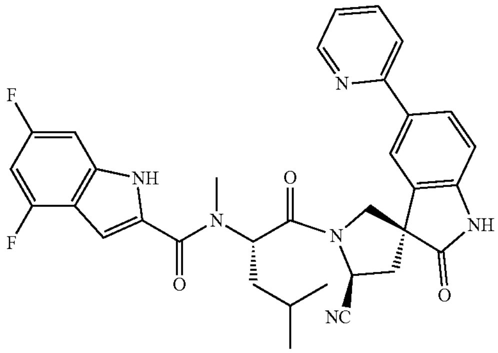 [SMILES: CC(C)C[C@@H](C(=O)N1C[C@]2(C[C@H]1C#N)C(=O)Nc1ccc(-c3ccccn3)cc12)N(C)C(=O)c1cc2c(F)cc(F)cc2[nH]1] |
| 517 | 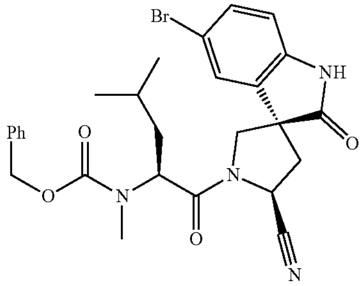 [SMILES: CC(C)C[C@@H](C(=O)N1C[C@]2(C[C@H]1C#N)C(=O)Nc1ccc(Br)cc12)N(C)C(=O)OCc1ccccc1] |
| 518 | 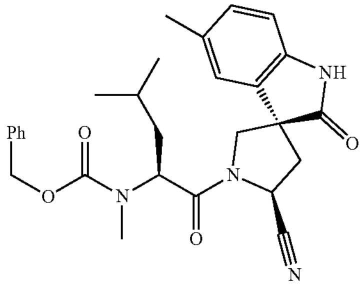 [SMILES: Cc1ccc2c(c1)[C@@]1(C[C@@H](C#N)N(C(=O)[C@H](CC(C)C)N(C)C(=O)OCc3ccccc3)C1)C(=O)N2] |
| 519 | 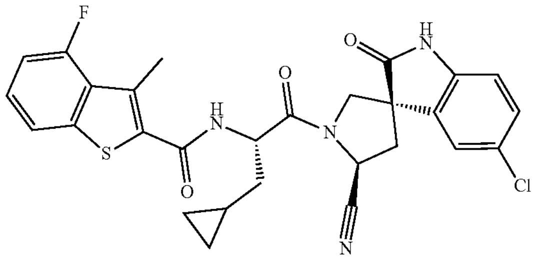 [SMILES: Cc1c(C(=O)N[C@@H](CC2CC2)C(=O)N2C[C@]3(C[C@H]2C#N)C(=O)Nc2ccc(Cl)cc23)sc2cccc(F)c12] |
| 520 | 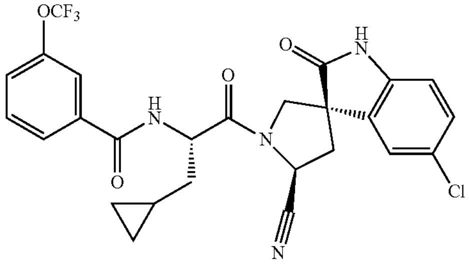 [SMILES: N#C[C@@H]1C[C@@]2(CN1C(=O)[C@H](CC1CC1)NC(=O)c1cccc(OC(F)(F)F)c1)C(=O)Nc1ccc(Cl)cc12] |

-continued
| Compound | Structure |
|---|---|
| 521 | 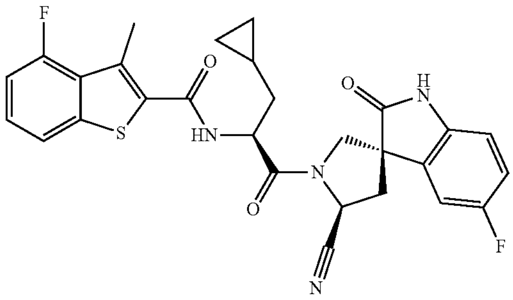 [SMILES: Cc1c(C(=O)N[C@@H](CC2CC2)C(=O)N2C[C@]3(C[C@H]2C#N)C(=O)Nc2ccc(F)cc23)sc2cccc(F)c12] |
| 522 | 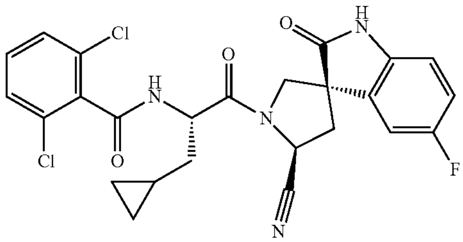 [SMILES: N#C[C@@H]1C[C@@]2(CN1C(=O)[C@H](CC1CC1)NC(=O)c1c(Cl)cccc1Cl)C(=O)Nc1ccc(F)cc12] |
| 523 | 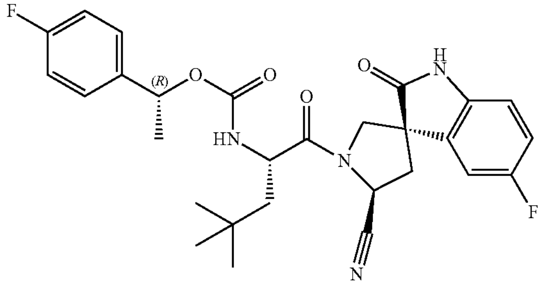 |
| 524 | 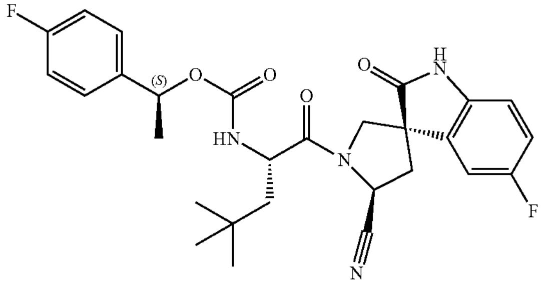 |
| 525 | 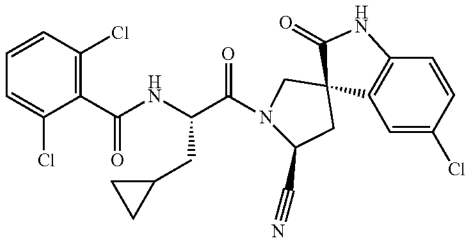 [SMILES: N#C[C@@H]1C[C@@]2(CN1C(=O)[C@H](CC1CC1)NC(=O)c1c(Cl)cccc1Cl)C(=O)Nc1ccc(Cl)cc12] |

-continued
| Compound | Structure |
| --- | --- |
| 526 | 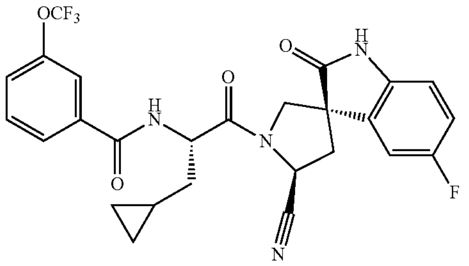 [SMILES: N#C[C@@H]1C[C@@]2(CN1C(=O)[C@H](CC1CC1)NC(=O)c1cccc(OC(F)(F)F)c1)C(=O)Nc1ccc(F)cc12] |
| 527 | 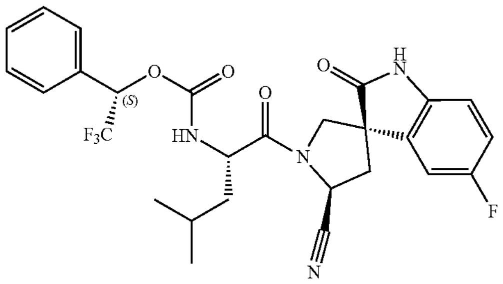 |
| 528 | 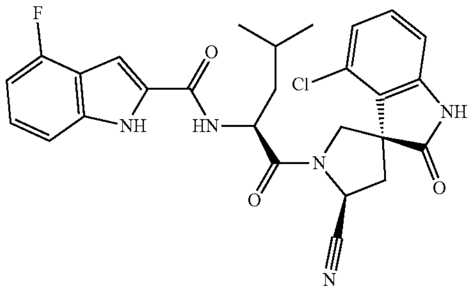 [SMILES: CC(C)C[C@H](NC(=O)c1cc2c(F)cccc2[nH]1)C(=O)N1C[C@]2(C[C@H]1C#N)C(=O)Nc1cccc(Cl)c12] |
| 529 | 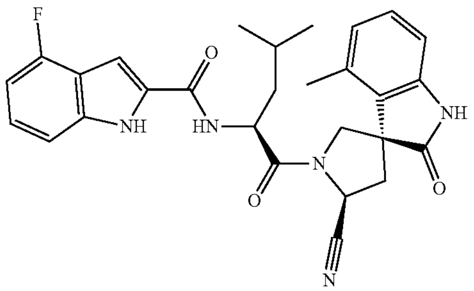 [SMILES: Cc1cccc2c1[C@@]1(C[C@@H](C#N)N(C(=O)[C@H](CC(C)C)NC(=O)c3cc4c(F)cccc4[nH]3)C1)C(=O)N2] |
| 530 | 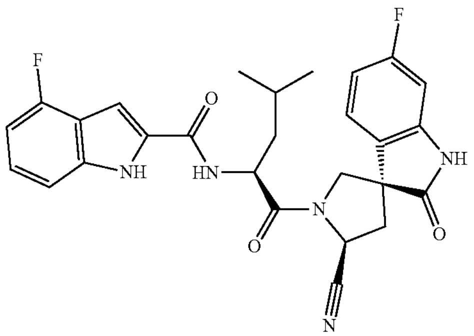 [SMILES: CC(C)C[C@H](NC(=O)c1cc2c(F)cccc2[nH]1)C(=O)N1C[C@]2(C[C@H]1C#N)C(=O)Nc1cc(F)ccc12] |

-continued
| Compound | Structure |
|---|---|
| 531 | 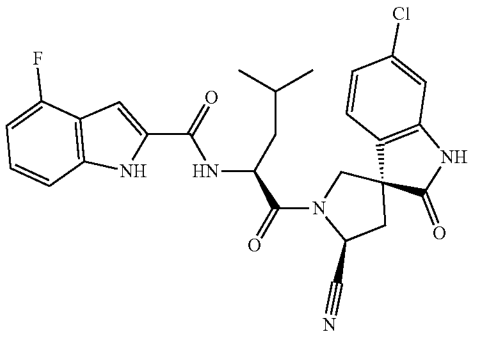 |
| 532 | 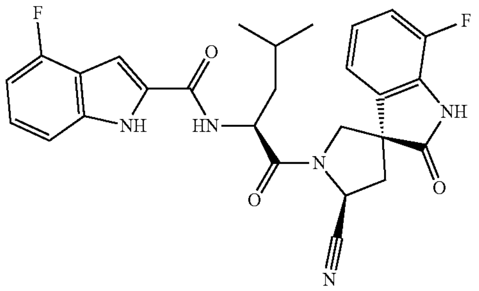 [SMILES: CC(C)C[C@H](NC(=O)c1cc2c(F)cccc2[nH]1)C(=O)N1C[C@]2(C[C@H]1C#N)C(=O)Nc1c(F)cccc12] |
| 533 | 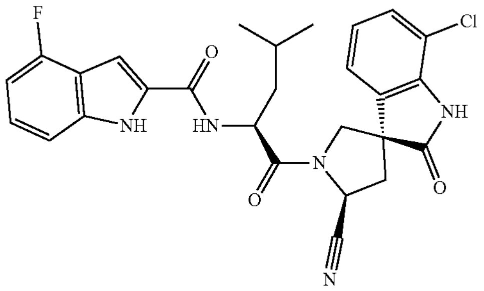 [SMILES: CC(C)C[C@H](NC(=O)c1cc2c(F)cccc2[nH]1)C(=O)N1C[C@]2(C[C@H]1C#N)C(=O)Nc1c(Cl)cccc12] |
| 534 | 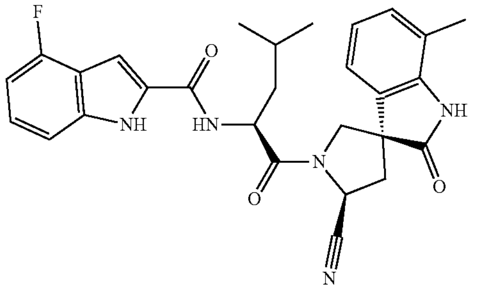 [SMILES: Cc1cccc2c1NC(=O)[C@]21C[C@@H](C#N)N(C(=O)[C@H](CC(C)C)NC(=O)c2cc3c(F)cccc3[nH]2)C1] |
| 535 | 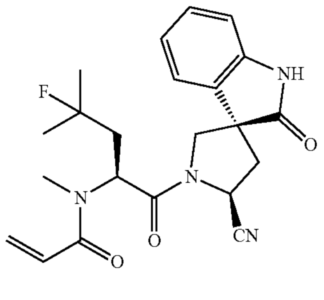 [SMILES: C=CC(=O)N(C)[C@@H](CC(C)(C)F)C(=O)N1C[C@]2(C[C@H]1C#N)C(=O)Nc1ccccc12] |

-continued
| Compound | Structure |
| --- | --- |
| 536 | 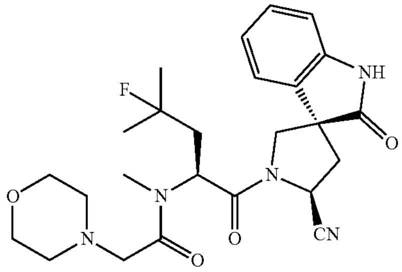 [SMILES: CN(C(=O)CN1CCOCC1)[C@@H](CC(C)(C)F)C(=O)N1C[C@]2(C[C@H]1C#N)C(=O)Nc1ccccc12] |
| 537 | 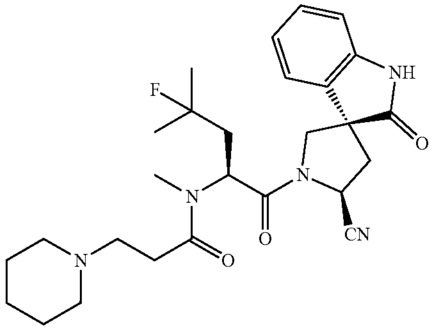 [SMILES: CN(C(=O)CCN1CCCCC1)[C@@H](CC(C)(C)F)C(=O)N1C[C@]2(C[C@H]1C#N)C(=O)Nc1ccccc12] |
| 538 | 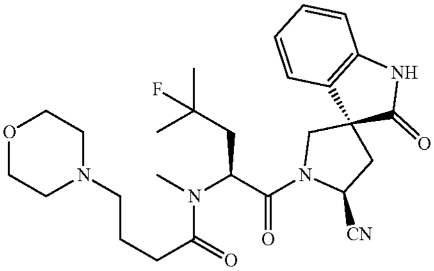 [SMILES: CN(C(=O)CCCN1CCOCC1)[C@@H](CC(C)(C)F)C(=O)N1C[C@]2(C[C@H]1C#N)C(=O)Nc1ccccc12] |
| 539 | 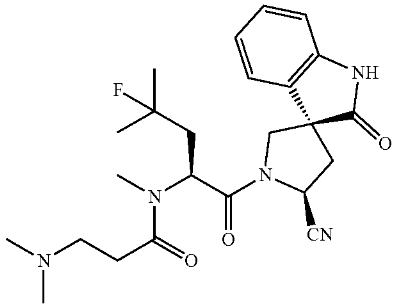 [SMILES: CN(C)CCC(=O)N(C)[C@@H](CC(C)(C)F)C(=O)N1C[C@]2(C[C@H]1C#N)C(=O)Nc1ccccc12] |
| 540 | 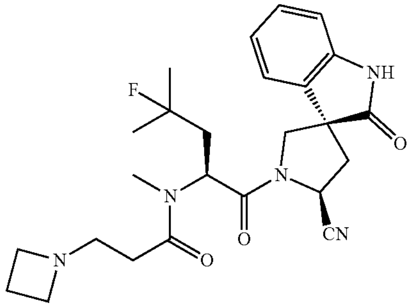 [SMILES: CN(C(=O)CCN1CCC1)[C@@H](CC(C)(C)F)C(=O)N1C[C@]2(C[C@H]1C#N)C(=O)Nc1ccccc12] |

-continued
| Compound | Structure |
|---|---|
| 541 | 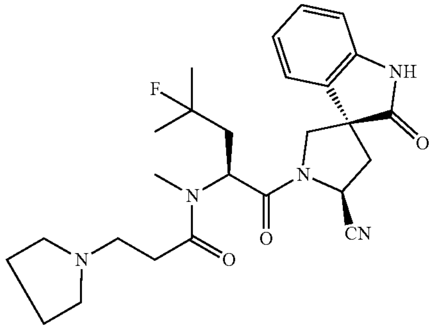 [SMILES: CN(C(=O)CCN1CCCC1)[C@@H](CC(C)(C)F)C(=O)N1C[C@]2(C[C@H]1C#N)C(=O)Nc1ccccc12] |
| 542 | 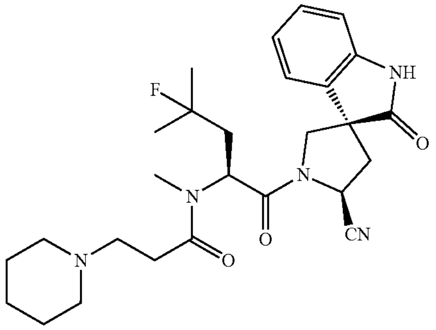 [SMILES: CN(C(=O)CCN1CCCCC1)[C@@H](CC(C)(C)F)C(=O)N1C[C@]2(C[C@H]1C#N)C(=O)Nc1ccccc12] |
| 543 | 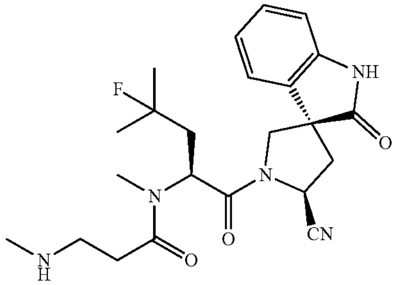 [SMILES: CNCCC(=O)N(C)[C@@H](CC(C)(C)F)C(=O)N1C[C@]2(C[C@H]1C#N)C(=O)Nc1ccccc12] |
| 544 | 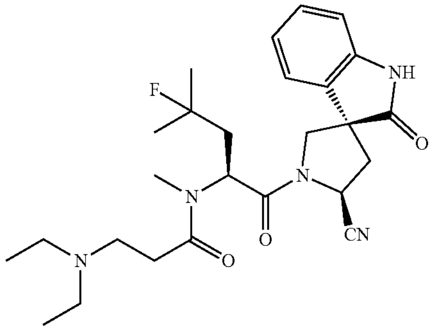 [SMILES: CCN(CC)CCC(=O)N(C)[C@@H](CC(C)(C)F)C(=O)N1C[C@]2(C[C@H]1C#N)C(=O)Nc1ccccc12] |

-continued
| Compound | Structure |
| --- | --- |
| 545 | 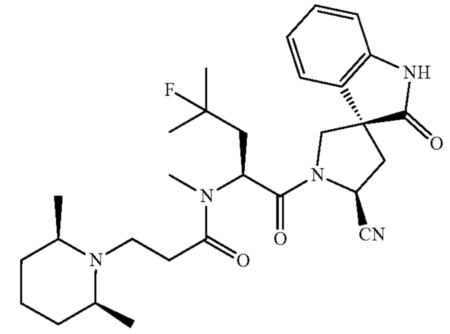 [SMILES: C[C@@H]1CCC[C@H](C)N1CCC(=O)N(C)[C@@H](CC(C)(C)F)C(=O)N1C[C@]2(C[C@H]1C#N)C(=O)Nc1ccccc12] |
| 546 | 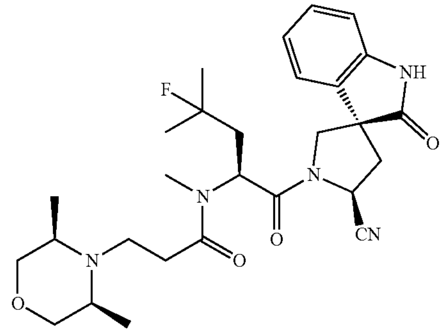 [SMILES: C[C@@H]1COC[C@H](C)N1CCC(=O)N(C)[C@@H](CC(C)(C)F)C(=O)N1C[C@]2(C[C@H]1C#N)C(=O)Nc1ccccc12] |
| 547 | 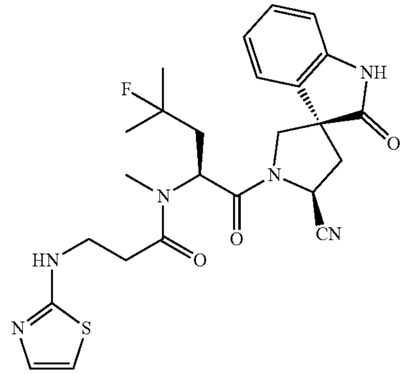 [SMILES: CN(C(=O)CCNc1nccs1)[C@@H](CC(C)(C)F)C(=O)N1C[C@]2(C[C@H]1C#N)C(=O)Nc1ccccc12] |
| 548 | 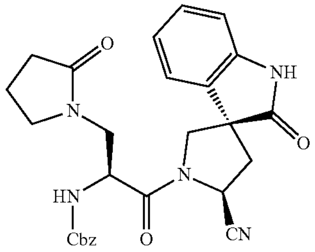 [SMILES: N#C[C@@H]1C[C@@]2(CN1C(=O)[C@H](CN1CCCC1=O)NC(=O)OCc1ccccc1)C(=O)Nc1ccccc12] |

-continued
| Compound | Structure |
| --- | --- |
| 549 | 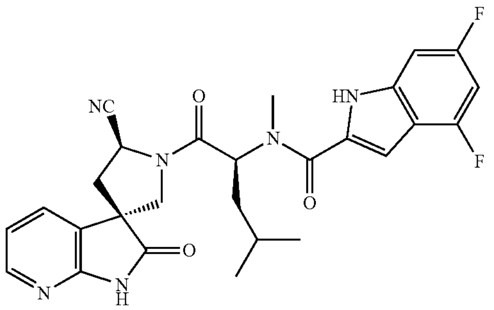 [SMILES: CC(C)C[C@@H](C(=O)N1C[C@]2(C[C@H]1C#N)C(=O)Nc1ncccc12)N(C)C(=O)c1cc2c(F)cc(F)cc2[nH]1] |
| 550 | 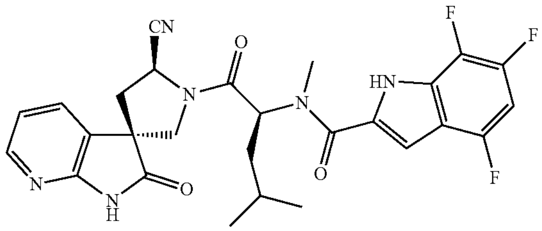 [SMILES: CC(C)C[C@@H](C(=O)N1C[C@]2(C[C@H]1C#N)C(=O)Nc1ncccc12)N(C)C(=O)c1cc2c(F)cc(F)c(F)c2[nH]1] |
| 551 | 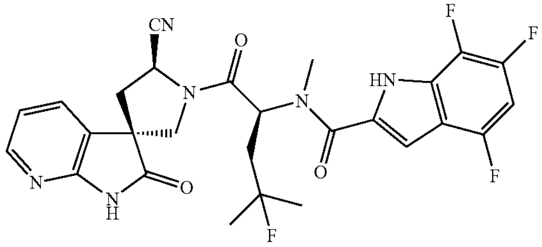 [SMILES: CN(C(=O)c1cc2c(F)cc(F)c(F)c2[nH]1)[C@@H](CC(C)(C)F)C(=O)N1C[C@]2(C[C@H]1C#N)C(=O)Nc1ncccc12] |
| 552 | 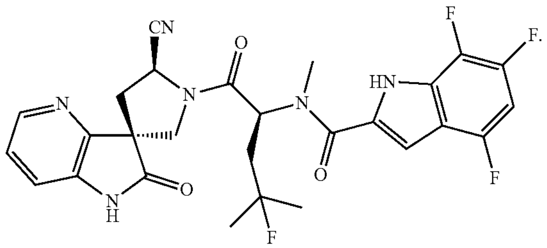 [SMILES: CN(C(=O)c1cc2c(F)cc(F)c(F)c2[nH]1)[C@@H](CC(C)(C)F)C(=O)N1C[C@]2(C[C@H]1C#N)C(=O)Nc1cccnc12] |

10. A pharmaceutical composition comprising a compound according to claim 1, or a pharmaceutically acceptable salt thereof, and a pharmaceutically acceptable carrier or excipient.

11. A method of treating a coronavirus infection in a subject in need thereof, comprising administering to the subject a therapeutically effective amount of the compound according to claim 1, or a pharmaceutically acceptable salt thereof.

12. The method according to claim 11, wherein the coronavirus is selected from a 229E, NL63, OC43, HKU1, SARS-COV or MERS coronavirus.

13. The method of claim 12, wherein the coronavirus is SARS-COV-2.

* * * * *